United States Patent
Qiao et al.

(10) Patent No.: US 7,312,214 B2
(45) Date of Patent: Dec. 25, 2007

(54) 1, 1-DISUBSTITUTED CYCLOALKYL DERIVATIVES AS FACTOR XA INHIBITORS

(75) Inventors: Jennifer X. Qiao, Princeton, NJ (US); Donald J. Pinto, Kennett Square, PA (US); Michael J. Orwat, New Hope, PA (US); Sarah R. Friedrich, Blue Bell, PA (US); Wei Han, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 487 days.

(21) Appl. No.: 10/430,024

(22) Filed: May 5, 2003

(65) Prior Publication Data

US 2004/0254158 A1 Dec. 16, 2004

Related U.S. Application Data

(60) Provisional application No. 60/415,367, filed on Oct. 2, 2002, provisional application No. 60/379,357, filed on May 10, 2002.

(51) Int. Cl.
  *A61K 31/535* (2006.01)
  *A61K 31/50* (2006.01)
  *A61K 31/495* (2006.01)
  *A01N 43/58* (2006.01)
  *A01N 43/60* (2006.01)

(52) U.S. Cl. .................. 514/230.5; 546/113; 514/248; 514/266; 514/303; 544/63; 544/237; 544/284

(58) Field of Classification Search ............. 514/225.5; 546/119
See application file for complete search history.

(56) References Cited

U.S. PATENT DOCUMENTS

| | | |
|---|---|---|
| 3,340,269 A | 9/1967 | Blatter et al. |
| 3,365,459 A | 1/1968 | Blatter et al. |
| 3,423,414 A | 1/1969 | Blatter et al. |
| 5,342,851 A | 8/1994 | Sanfilippo et al. |
| 5,998,424 A | 12/1999 | Galemmo et al. |
| 6,020,357 A | 2/2000 | Pinto et al. |
| 6,060,491 A | 5/2000 | Pruitt et al. |
| 6,191,159 B1 | 2/2001 | Pinto et al. |
| 6,271,237 B1 | 8/2001 | Galemmo et al. |
| 6,465,656 B2 | 10/2002 | Zhou et al. |

FOREIGN PATENT DOCUMENTS

| | | |
|---|---|---|
| WO | WO 98/33496 | 6/1998 |
| WO | WO98/28269 | 7/1998 |
| WO | WO98/28282 | 7/1998 |
| WO | WO98/57934 | 12/1998 |
| WO | WO98/57937 | 12/1998 |
| WO | WO98/57951 | 12/1998 |
| WO | WO99/32454 | 7/1999 |
| WO | WO99/32477 | 7/1999 |
| WO | WO99/50255 | 10/1999 |
| WO | WO 00/39108 | 7/2000 |
| WO | WO 00/39131 | 7/2000 |
| WO | WO 00/59902 | 10/2000 |
| WO | WO 01/05784 | 1/2001 |
| WO | WO 01/19798 | 3/2001 |
| WO | WO 01/32628 | 5/2001 |
| WO | WO 02/00655 * | 1/2002 |

OTHER PUBLICATIONS

Elodi et al., "Optimization of Conditions for the Catalytic Effect of The Factor IXa - Factor VIII Complex: Probable role of the complex in the amplification of blood coagulation", Thrombosis Research, vol. 15, pp. 617-623, 1979.
Gresele et al., "Novel approaches to the treatment of thrombosis", TRENDS in Pharmacological Sciences, vol. 23, No. 1, pp. 25-32, Jan. 2002.
Linkins et al., "New Anticoagulants", Seminars in Thrombosis and Hemostasis, vol. 29, No. 6, pp. 619-631, 2003.
Rauch et al., "Thrombus Formation on Atherosclerotic Plaques: Pathogenesis and Clinical Consequences", Annals of Internal Medicine, vol. 134, No. 3., pp. 224-238, Feb. 6, 2001.
Ruef et al., "New antithrombotic drugs on the horizon", Expert Opin. Investig. Drug, vol. 12, No. 5, pp. 781-797, 2003.
Wang et al., "Inhibition of Factor Xa Reduces Ischemic Brain Damage After Thromboembolic Stroke in Rats", Stroke, pp. 468-474, Feb. 2003.
Wong et al., "Nonpeptide Factor Xa Inhibitors III: Effects of DPC423, an Orally-Active Pyrazole Antithrombotic Agent, on Arterial Thrombosis in Rabbits", vol. 303, No. 3, pp. 993-1000, 2002.

* cited by examiner

*Primary Examiner*—Zachary C Tucker
(74) *Attorney, Agent, or Firm*—Jing G. Sun; David H. Vance

(57) ABSTRACT

The present application describes 1,1-disubstituted cycloalkyl compounds and derivatives thereof, or pharmaceutically acceptable salt forms thereof, which are useful as inhibitors of factor Xa.

31 Claims, No Drawings

1,1-DISUBSTITUTED CYCLOALKYL DERIVATIVES AS FACTOR XA INHIBITORS

CROSS-REFERENCE TO RELATED APPLICATIONS

The present application claims the priority benefits of U.S. Provisional Application No. 60/379,357, filed May 10, 2002 and U.S. Provisional Application No. 60/415,367, filed Oct. 2, 2002, all of which are fully incorporated herein by reference.

FIELD OF THE INVENTION

This invention relates generally to 1,1-disubstituted cycloalkyl compounds, which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

U.S. Pat. Nos. 3,365,459, 3,340,269, and 3,423,414 illustrate anti-inflammatory inhibitors of the following formula:

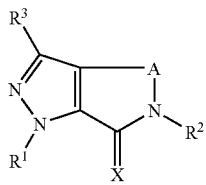

wherein A is 2–3 carbon atoms, X can be O, and $R^1$ and $R^3$ can be substituted or unsubstituted aromatic groups. None of these patents, however, exemplify or suggest compounds of the present invention.

U.S. Pat. No. 5,342,851 depicts thiazole platelet aggregation inhibitors including those of the following formula:

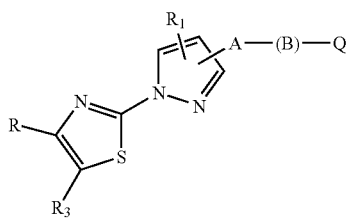

wherein A is a linker, B can be a linker or a ring, Q is a ring or an amino group, R, $R_1$, and $R_3$ are a variety of groups. This patent, however, does not exemplify or suggest compounds of the present invention.

WO00/39131 describes heterobicyclic Factor Xa inhibitors of which the following is an example formula:

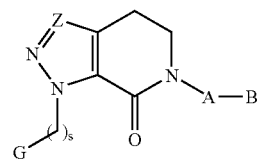

wherein Z is C or N, G is a mono- or bicyclic group, A is a cyclic moiety and B is a basic group or a cyclic moiety. Compounds specifically described in WO00/39131 are not considered to be part of the present invention.

WO98/28269, WO98/28282, WO99/32454, U.S. Pat. No. 6,020,357, and U.S. Pat. No. 6,271,237 describe Factor Xa inhibitors of the following formula:

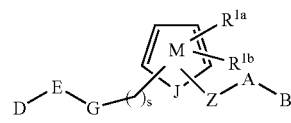

wherein ring M is a heterocycle, Z is a linker, A is a ring, B is a basic or cyclic group, D is a basic moiety, and E is a ring. Compounds specifically described in WO98/28269, WO98/28282, WO99/32454, U.S. Pat. No. 6,020,357, and U.S. Pat. No. 6,271,237 are not considered to be part of the present invention.

WO98/57951 describes Factor Xa inhibitors of the following formula:

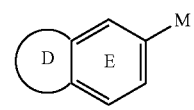

wherein ring M can be a variety of heterocycles and rings D-E represent a heterobicyclic group. Compounds specifically described in WO98/57951 are not considered to be part of the present invention.

WO98/57934 and U.S. Pat. No. 6,060,491 describe Factor Xa inhibitors of the following formula:

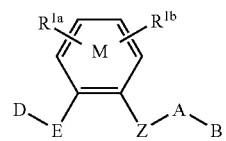

wherein ring M is a 6-membered heteroaryl, Z is a linker, A is a ring, B is a basic or cyclic group, D is a basic moiety, and E is a ring. Compounds specifically described in WO98/57934 and U.S. Pat. No. 6,060,491 are not considered to be part of the present invention.

WO98/57937 and U.S. Pat. No. 5,998,424 describe Factor Xa inhibitors of the following formula:

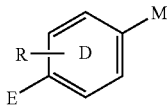

wherein ring M is a variety of rings, ring D is an aromatic ring, and R and E are non-basic groups. Compounds specifically described in WO98/57937 and U.S. Pat. No. 5,998,424 are not considered to be part of the present invention.

WO99/50255 and U.S. Pat. No. 6,191,159 describe pyrazoline and triazoline Factor Xa inhibitors of the following formulas:

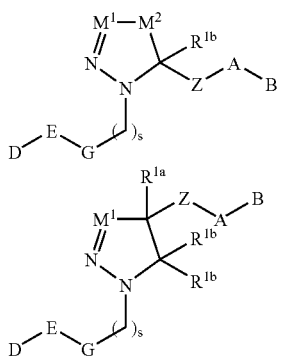

Compounds specifically described in WO99/50255 and U.S. Pat. No. 6,191,159 are not considered to be part of the present invention.

WO00/59902 describes Factor Xa inhibitors of the following formula:

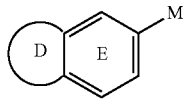

wherein ring M can be a variety of rings all of which are substituted with Z-A-B, Z is a linker, A is a ring, B is a sulfonyl-containing heterobicycle, and rings D-E represent a heterobicyclic group or a 6-membered ring. Compounds specifically described in WO00/59902 are not considered to be part of the present invention.

WO01/32628 describes cyano-pyrroles, cyano-imidazoles, cyano-pyrazoles, and cyano-triazoles that are Factor Xa inhibitors. Compounds specifically described in WO01/32628 are not considered to be part of the present invention.

WO01/05784 describes Factor Xa inhibitors of the following formulas:

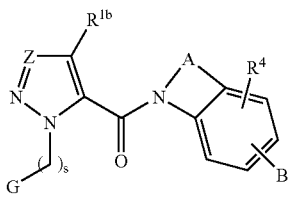

-continued

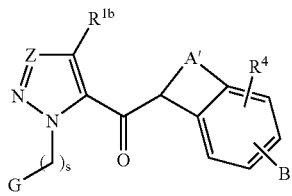

wherein Z is C or N, G is a mono- or bicyclic ring M, A is a linker, B is a basic or cyclic group. Compounds specifically described in WO01/05784 are not considered to be part of the present invention.

WO00/39108 describes Factor Xa inhibitors of the following formula:

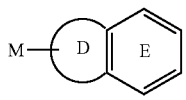

wherein ring M can be a variety of heterocycles and rings D–E represent a heterobicyclic group. Compounds specifically described in WO00/39108 are not considered to be part of the present invention.

WO01/19798 describes factor Xa inhibitors of the following formula:

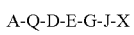

A-Q-D-E-G-J-X wherein A, D, G, and X can be phenyl or heterocycle. However, none of the presently claimed compounds are exemplified or suggested in WO01/19798.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. Thromb. Res. 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors. In addition, it is also desirable to find new compounds with improved pharmacological characteristics compared with known factor Xa inhibitors. For example, it is preferred to find new compounds with improved factor Xa inhibitory activity and selectivity for factor Xa versus other serine proteases (i.e., trypsin). It is also desirable and preferable to find compounds with advantageous and improved characteristics in one or more of the following categories, but are not limited to: (a) pharmaceutical properties; (b) dosage requirements; (c) factors which decrease blood concentration peak-totrough characteristics; (d) factors that increase the concentration of active drug at the receptor; (e) factors that decrease the liability for clinical drug-drug interactions; (f) factors that decrease the potential for adverse side-effects; and, (g) factors that improve manufacturing costs or feasibility.

SUMMARY OF THE INVENTION

Accordingly, the present invention provides novel 1,1-disubstituted cycloalkyl compounds that are useful as factor Xa inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating thromboembolic disorders comprising administering to a host in need of such treatment a therapeutically effective amount of at least one of the compounds of the present invention or a pharmaceutically acceptable salt or prodrug form thereof.

The present invention provides a novel method of treating a patient in need of thromboembolic disorder treatment, comprising: administering a compound of the present invention or a pharmaceutically acceptable salt thereof in an amount effective to treat a thromboembolic disorder.

The present invention provides a novel method, comprising: administering a compound of the present invention or a pharmaceutically acceptable salt thereof in an amount effective to treat a thromboembolic disorder.

The present invention provides novel compounds for use in therapy.

The present invention provides the use of novel compounds for the manufacture of a medicament for the treatment of a thromboembolic disorder.

These and other objects, which will become apparent during the following detailed description, have been achieved by the inventors' discovery that the presently claimed 1,1-disubstituted cycloalkyl compounds, or pharmaceutically acceptable salt or prodrug forms thereof, are effective factor Xa inhibitors.

DETAILED DESCRIPTION OF PREFERRED EMBODIMENTS

[1] In an embodiment, the present invention provides a novel compound of formula I:

$$P_4\text{-}P\text{-}M\text{-}M_4 \quad (I)$$

or a stereoisomer or pharmaceutically acceptable salt thereof, wherein;

M is a 3–10 membered carbocycle or a 4–10 membered heterocycle, consisting of: carbon atoms and 1–3 heteroatoms selected from O, $S(O)_p$, N, and $NZ^2$;

ring M is substituted with 0–3 $R^{1a}$ and 0–2 carbonyl groups, and there are 0–3 ring double bonds;

P is fused onto ring M and is a 5, 6, or 7 membered carbocycle or a 5, 6, or 7 membered heterocycle, consisting of: carbon atoms and 1–3 heteroatoms selected from O, $S(O)_p$, and N;

ring P is substituted with 0–3 $R^{1a}$ and 0–2 carbonyl groups, and there are 0–3 ring double bonds;

alternatively, ring P is absent and $P_4$ is directly attached to ring M, provided that when ring P is absent, $P_4$ and $M_4$ are attached to the 1,2, 1,3, or 1,4 positions of ring M;

one of $P_4$ and $M_4$ is -Z-A-B and the other -$G_1$-G, provided that $P_4$ and $M_4$ are attached to different rings when ring P is present;

G is a group of formula IIa or IIb:

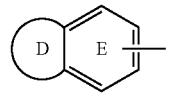

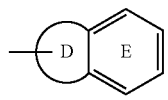

ring D, including the two atoms of Ring E to which it is attached, is a 5–6 membered ring consisting of carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–3 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–3 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5–6 membered heterocycle consisting of: carbon atoms and 1–4 heteroatoms selected from the group consisting of N, O, and $S(O)_p$, wherein the 5–6 membered heterocycle is substituted with 0–2 carbonyls and 1–3 R and there are 0–3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $ONHC(=NR^8)NR^7R^9$, $NR^8CH(=NR^7)$, $NH_2$, $NH(C_{1-3}$ alkyl), $N(C_{1-3}$ alkyl)$_2$, $C(=NH)NH_2$, $CH_2NH_2$, $CH_2NH(C_{1-3}$ alkyl), $CH_2N(C_{1-3}$ alkyl)$_2$, $CH_2CH_2NH_2$, $CH_2CH_2NH(C_{1-3}$ alkyl), $CH_2CH_2N(C_{1-3}$ alkyl)$_2$, $(CR^8R^9)_tC(O)H$, $(CR^8R^9)_tC(O)R^{2c}$, $(CR^8R^9)_tNR^7R^8$, $(CR^8R^9)_tC(O)NR^7R^8$, $(CR^8R^9)_tNR^7C(O)R^7$, $(CR^8R^9)_tOR^3$, $(CR^8R^9)_tS(O)_pNR^7R^8$, $(CR^8R^9)_tNR^7S(O)_pR^7$, $(CR^8R^9)_tSR^3$, $(CR^8R^9)_tS(O)R^3$, $(CR^8R^9)_tS(O)_2R^3$, and $OCF_3$, provided that $S(O)_pR^7$ forms other than $S(O)_2H$ or $S(O)H$;

alternatively, when 2 R groups are attached to adjacent atoms, they combine to form methylenedioxy or ethylenedioxy;

A is selected from:
$C_{3-10}$ carbocycle substituted with 0–2 $R^4$, and
5–12 membered heterocycle substituted with 0–2 $R^4$ and consisting of: carbon atoms and 1–4 heteroatoms selected from the group consisting of N, O, and $S(O)_p$;

B is $Y-R^{4a}$ or $X-Y-R^{4a}$, provided that Z and B are attached to different atoms on A and A and $R^{4a}$ or X and $R^{4a}$ are attached to the same atom on Y;

X is selected from $-(CR^2R^{2a})_{1-4}-$, $-CR^2(CR^2R^{2b})(CH_2)_t-$, $-C(O)-$, $-C(=NR^{1b})-$, $-CR^2(NR^{1b}R^2)-$, $-CR^2(OR^2)-$, $-CR^2(SR^2)-$, $-C(O)$ $CR^2R^{2a}$—, —$CR^2R^{2a}C(O)$—, —$S(O)$—, —$S(O)_2$—, —$SCR^2R^{2a}$—, —$S(O)CR^2R^{2a}$—, —$S(O)_2CR^2R^{2a}$—, —$CR^2R^{2a}S$—, —$CR^2R^{2a}S(O)$—, —$CR^2R^{2a}S(O)_2$—, —$S(O)_2NR^2$—, —$S(O)_2NR^2CR^2R^{2a}$—, —$CR^2R^{2a}S(O)_2NR^2$—, —$NR^2S(O)_2$—, —$CR^2R^{2a}NR^2S(O)_2$—, —$NR^2S(O)_2CR^2R^{2a}$—, —$NR^2C(O)$—, —$C(O)NR^2$—, —$NR^2C(O)CR^2R^{2a}$—, —$C(O)NR^2CR^2R^{2a}$—, —$CR^2R^{2a}NR^2C(O)$—, —$CR^2R^{2a}C(O)NR^2$—, $NR^2$, —$NR^2CR^2R^{2a}$—, —$CR^2R^{2a}NR^2$—, O, —$OCR^2R^{2a}$—, and —$CR^2R^{2a}O$—;

Y is a $C_{3-10}$ carbocycle or 3–10 membered heterocycle, wherein the carobocycle or heterocycle consists of carbon atoms and 0–4 heteroatoms selected from N, O, and $S(O)_p$, the carbocycle or heterocycle further comprises 0–4 double bonds and 0–2 carbonyl groups, and the carbocycle or heterocycle is substituted with 0–2 $R^4$, provided that Y is other than a 1,3-dioxolanyl group;

alternatively, Y is $CY^1Y^2$, and $Y^1$ and $Y^2$ are independently $C_{1-4}$ alkyl substituted with 0–2 $R^4$;

$G_1$ is absent or is selected from $(CR^3R^{3a})_{1-5}$, $(CR^3R^{3a})_{0-2}CR^3=CR^3(CR^3R^{3a})_{0-2}$, $(CR^3R^{3a})_{0-2}C≡C(CR^3R^{3a})_{0-2}$, $(CR^3R^{3a})_uC(O)(CR^3R^{3a})_w$, $(CR^3R^{3a})_uC(O)O(CR^3R^{3a})_w$, $(CR^3R^{3a})_uOC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uC(O)NR^{3b}(CR^3R^{3a})_w$, $(CR^3R^{3a})_uNR^{3b}C(O)O(CR^3R^{3a})_w$, $(CR^3R^{3a})_uNR^{3b}C(O)NR^{3b}(CR^3R^{3a})_w$, $(CR^3R^{3a})_uNR^{3b}C(S)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, $(CR^3R^{3a})_uNR^{3b}S(O)_2NR^{3b}(CR^3R^{3a})_w$, $(CR^3R^{3a})_uNR^{3e}(CR^3R^{3a})_w$, $(CR^3R^{3a})_uC(O)(CR^3R^{3a})_uC(O)(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uC(O)(CR^3R^{3a})_uC(O)NR^{3b}(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uNR^{3b}C(S)(CR^3R^{3a})_uC(O)NR^{3b}(CR^3R^{3a})_w$, $(CR^3R^{3a})_uNR^{3b}C(O)(CR^3R^{3a})_uC(S)NR^{3b}(CR^3R^{3a})_w$, $(CR^3R^{3a})_uS(O)NR^{3b}C(O)(CR^3R^{3a})_w$, $(CR^3R^{3a})_uC(O)NR^{3b}S(O)_2(CR^3R^{3a})_w$, and $(CR^3R^{3a})_uS(O)_2NR^{3b}C(O)NR^{3b}(CR^3R^{3a})_w$, wherein u+w total 0, 1, 2, 3, or 4, provided that $G_1$ does not form a N—S, $NCH_2N$, $NCH_2O$, or $NCH_2S$ bond with either group to which it is attached;

Z is selected from a bond, —$(CR^3R^{3e})_{1-4}$—, $(CR^3R^{3e})_qO(CR^3R^{3e})_{q1}$, $(CR^3R^{3e})_qNR^{3b}(CR^3R^{3e})_{q1}$, $(CR^3R^{3e})_qC(O)(CR^3R^{3e})_{q1}$, $(CR^3R^{3e})_qC(O)O(CR^3R^{3e})_{q1}$, $(CR^3R^{3e})_qOC(O)(CR^3R^{3e})_{q1}$, $(CR^3R^{3e})_qC(O)NR^{3b}(CR^3R^{3e})_{q1}$, $(CR^3R^{3e})_qNR^{3b}C(O)(CR^3R^{3e})_{q1}$, $(CR^3R^{3e})_qOC(O)O(CR^3R^{3e})_{q1}$, $(CR^3R^{3e})_qOC(O)NR^{3b}(CR^3R^{3e})_{q1}$, $(CR^3R^{3e})_qNR^{3b}C(O)O(CR^3R^{3e})_{q1}$, $(CR^3R^{3e})_qNR^{3b}C(O)NR^{3b}(CR^3R^{3e})_{q1}$, $(CR^3R^{3e})_qC(O)(CR^3R^{3e})_qC(O)(CR^3R^{3e})_{q1}$, $(CR^3R^{3e})_qNR^{3b}(CR^3R^{3e})_qC(O)NR^{3b}(CR^3R^{3e})_{q1}$, $(CR^3R^{3e})_qNR^{3b}C(O)(CR^3R^{3e})_qC(O)(CR^3R^{3e})_{q1}$, $(CR^3R^{3e})_qC(O)(CR^3R^{3e})_qC(O)NR^{3b}(CR^3R^{3e})_{q1}$, $(CR^3R^{3e})_qNR^{3b}C(O)(CR^3R^{3e})_qC(O)NR^{3b}(CR^3R^{3e})_{q1}$, $(CR^3R^{3e})_qS(CR^3R^{3e})_{q1}$, $(CR^3R^{3e})_qS(O)(CR^3R^{3e})_{q1}$, $(CR^3R^{3e})_qS(O)_2(CR^3R^{3e})_{q1}$, $(CR^3R^{3e})_qSO_2NR^{3b}(CR^3R^{3e})_{q1}$, $(CR^3R^{3e})_qNR^{3b}SO_2(CR^3R^{3e})_{q1}$, $(CR^3R^{3e})_qS(O)NR^{3b}C(O)(CR^3R^{3e})_{q1}$, $(CR^3R^{3e})_qC(O)NR^{3b}S(O)_2(CR^3R^{3e})_{q1}$, and $(CR^3R^{3e})_qNR^{3b}SO_2NR^{3b}(CR^3R^{3e})_{q1}$, wherein q+q1 total 0, 1, 2, 3, or 4, provided that Z does not form a N—S, $NCH_2N$, $NCH_2O$, or $NCH_2S$ bond with either group to which it is attached;

provided that:
(a) when ring P is absent and ring M is a pyridyl ring, then Z is other than $C(O)NHCH_2$; and,
(b) when ring P is absent and ring M is a piperazinyl ring, then either Z is other than alkylene or A is other than phenyl;

$Z^2$ is selected from H, $S(O)_2NHR^{3b}$, $C(O)R^{3b}$, $C(O)NHR^{3b}$, $C(O)OR^{3f}$, $S(O)R^{3f}$, $S(O)_2R^{3f}$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —$(C_{0-4}$ alkyl$)$-$C_{3-10}$ carbocycle substituted with 0–3 $R^{1a}$, and —$(C_{0-4}$ alkyl$)$-5–10 membered heterocycle substituted with 0–3 $R^{1a}$ and consisting of: carbon atoms and 1–4 heteroatoms selected from the group consisting of N, O, and $S(O)_p$;

$R^{1a}$, at each occurrence, is selected from H, —$(CR^3R^{3a})_r$—$R^{1b}$, —$(CR^3R^{3a})_r$—$CR^3R^{1b}R^{1b}$, —$(CR^3R^{3a})_r$—O—$(CR^3R^{3a})_r$—$R^{1b}$, —$(CR^3R^{3a})_r$—$NR^2$—$(CR^3R^{3a})_r$—$R^{1b}$, —$(CR^3R^{3a})_r$—$S(O)_p$—$(CR^3R^{3a})_r$—$R^{1b}$, —$(CR^3R^{3a})_r$—$CO_2$—$(CR^3R^{3a})_r$—$R^{1b}$, —$(CR^3R^{3a})_r$—$C(O)NR^2$—$(CR^3R^{3a})_r$—$R^{1b}$, —$(CR^3R^{3a})_r$—$C(O)$—$(CR^3R^{3a})_r$—$R^{1b}$, —$C_{2-6}$ alkenylene-$R^{1b}$, —$C_{2-6}$ alkynylene-$R^{1b}$, and —$(CR^3R^{3a})_r$—$C(=NR^{1b})NR^3R^{1b}$, provided that $R^{1a}$ forms other than an N-halo, N—S, O—O, or N—CN bond;

alternatively, when two $R^{1a}$ groups are attached to adjacent atoms or to the same carbon atom, together with the atoms to which they are attached, they form a 5–7 membered ring consisting of: carbon atoms and 0–2 heteroatoms selected from the group consisting of N, O, and $S(O)_p$, this ring being substituted with 0–2 $R^{4b}$ and comprising: 0–3 double bonds;

$R^{1b}$ is selected from H, $C_{1-3}$ alkyl, F, Cl, Br, I, —CN, —$NO_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $CH(CH_2OR^2)_2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NR^2R^{2a}$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C(O)NR^2SO_2R^2$, $C_{3-6}$ carbocycle substituted with 0–2 $R^{4b}$, and 5–10 membered heterocycle substituted with 0–2 $R^{4b}$ and consisting of carbon atoms and from 1–4 heteroatoms selected from the group consisting of N, O, and $S(O)_p$, provided that $R^{1b}$ forms other than an O—O, N-halo, N—S, or N—CN bond and provided that $S(O)_pR^2$ forms other than $S(O)_2H$ or $S(O)H$;

$R^2$, at each occurrence, is selected from H, $CF_3$, $C_{1-6}$ alkyl, benzyl, —$(CH_2)_r$—$C_{3-10}$ carbocycle substituted with 0–2 $R^{4b}$, and —$(CH_2)_r$-5–10 membered heterocycle substituted with 0–2 $R^{4b}$ and consisting of: carbon atoms and 1–4 heteroatoms selected from the group consisting of N, O, and $S(O)_p$;

$R^{2a}$, at each occurrence, is selected from H, $CF_3$, $C_{1-6}$ alkyl, benzyl, —$(CH_2)_r$—$C_{3-10}$ carbocycle substituted with 0–2 $R^{4b}$, and —$(CH_2)_r$-5–10 membered heterocycle substituted with 0–2 $R^{4b}$ and consisting of: carbon atoms and 1–4 heteroatoms selected from the group consisting of N, O, and $S(O)_p$;

alternatively, $R^2$ and $R^{2a}$, together with the nitrogen atom to which they are attached, combine to form a 3–6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy substituted with 0–2 $R^{4b}$, $C_{1-6}$ alkyl substituted with 0–3 $R^{4b}$, —$(CH_2)_r$—$C_{3-10}$ carbocycle substituted with 0–2 $R^{4b}$, and —$(CH_2)_r$-5–10 membered heterocycle substituted with 0–2 $R^{4b}$ and consisting of: carbon atoms and 1–4 heteroatoms selected from the group consisting of N, O, and $S(O)_p$;

$R^{2c}$, at each occurrence, is selected from $CF_3$, OH, $C_{1-4}$ alkoxy, $C_{1-6}$ alkyl, $—(CH_2)_r—C_{3-10}$ carbocycle substituted with 0–2 $R^{4b}$, and $—(CH_2)_r$-5–10 membered heterocycle substituted with 0–2 $R^{4b}$ and consisting of carbon atoms and from 1–4 heteroatoms selected from the group consisting of N, O, and $S(O)_p$;

$R^{2d}$, at each occurrence, is selected from H, $R^{4c}$, $C_{1-6}$ alkyl substituted with 0–2 $R^{4c}$, $—(CR^3R^{3a})_r—C_{3-10}$ carbocycle substituted with 0–2 $R^{4c}$, and $—(CR^3R^{3a})_r$-5–10 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, when two $R^{2d}$'s are attached to the same nitrogen atom, then $R^{2d}$ and $R^{2d}$, together with the nitrogen atom to which they are attached, combine to form a 5–10 membered saturated, partially saturated or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-6}$ alkyl substituted with 0–2 $R^{4c}$, $—(CR^3R^{3a})_r—C_{3-10}$ carbocycle substituted with 0–2 $R^{4c}$, and $—(CR^3R^{3a})_r$-5–10 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^3$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms, the nitrogen atom to which $R^3$ and $R^{3a}$ are attached, and 0–1 additional heteroatoms selected from the group consisting of N, O, and $S(O)_p$;

$R^{3b}$, at each occurrence, is selected from H, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $—(C_{0-4}$ alkyl)-5–10 membered carbocycle substituted with 0–3 $R^{1a}$, and $—(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{3e}$, at each occurrence, is selected from H, $S(O)_2NHR^3$, $C(O)R^3$, $C(O)NHR^3$, $C(O)OR^{3f}$, $S(O)R^{3f}$, $S(O)_2R^{3f}$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $—(C_{0-4}$ alkyl)-5–10 membered carbocycle substituted with 0–3 $R^{1a}$, and $—(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3f}$, at each occurrence, is selected from: $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $—(C_{0-4}$ alkyl)-5–10 membered carbocycle substituted with 0–3 $R^{1a}$, and $—(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3g}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $—(CH_2)_r$-3–6 membered carbocycle, and $—(CH_2)_r$-5–6 membered heterocycle consisting of: carbon atoms and 1–4 heteroatoms selected from the group consisting of N, O, and $S(O)_p$;

alternatively, when $R^3$ and $R^{3g}$ are attached to the same carbon atom, they combine with the attached carbon atom to form a cyclopropyl group;

$R^4$, at each occurrence, is selected from H, =O, $(CR^3R^{3a})_r$ $OR^2$, F, Cl, Br, I, $C_{1-4}$ alkyl, $(CR^3R^{3a})_r CN$, $(CR^3R^{3a})_r NO_2$, $(CR^3R^{3a})_r NR^2R^{2a}$, $(CR^3R^{3a})_r C(O)R^{2c}$, $(CR^3R^{3a})_r NR^2C(O)R^{2b}$, $(CR^3R^{3a})_r C(O)NR^2R^{2a}$, $(CR^3R^{3a})_r NR^2C(O)NR^2R^{2a}$, $(CR^3R^{3a})_r C(=NR^2)NR^2R^{2a}$, $(CR^3R^{3a})_r C(=NS(O)_2R^{5a})NR^2R^{2a}$, $(CR^3R^{3a})_r NR^2C(=NR^2)NR^2R^{2a}$, $(CR^3R^{3a})_r C(O)NR^2C(=NR^2)NR^2R^{2a}$, $(CR^3R^{3a})_r SO_2NR^2R^{2a}$, $(CR^3R^{3a})_r NR^2SO_2NR^2R^{2a}$, $(CR_3R^{3a})_r NR^2SO_2—C_{1-4}$ alkyl, $(CR^3R^{3a})_r NR^2SO_2R^{5a}$, $(CR^3R^{3a})_r S(O)_p R^{5a}$, $(CR^3R^{3a})_r (CF_2)_r CF_3$, $N(CH_2)_r R^{1b}$, $O(CH_2)_r R^{1b}$, $S(CH_2)_r R^{1b}$, $(CR^3R^{3a})_r$-5–6 membered carbocycle substituted with 0–1 $R^5$, and a $(CR^3R^{3a})_r$-5–6 membered heterocycle substituted with 0–1 $R^5$ and consisting of: carbon atoms and 1–4 heteroatoms selected from the group consisting of N, O, and $S(O)_p$;

$R^{4a}$ is selected from $C_{1-6}$ alkyl substituted with 0–2 $R^{4c}$, $C_{2-6}$ alkenyl substituted with 0–2 $R^{4c}$, $C_{2-6}$ alkynyl substituted with 0–2 $R^{4c}$, $—(CR^3R^{3a})_r—C_{5-10}$ membered carbocycle substituted with 0–3 $R^{4c}$, $—(CR^3R^{3g})_r$-5–10 membered heterocycle substituted with 0–3 $R^{4c}$ and consisting of: carbon atoms and 1–4 heteroatoms selected from the group consisting of N, O, and $S(O)_p$, $(CR^3R^{3g})_r CN$, $(CR^3R^{3g})_r C(=NR^{2d})NR^{2d}R^{2d}$, $(CR^3R^{3g})_r NR^{2d}C(=NR^{2d})NR^{2d}R^{2d}$, $(CR^3R^{3g})_r NR^{2d}C(R^{2e})(=NR^{2d})$, $(CR^3R^{3g})_r NR^{2d}R^{2d}$, $(CR^3R^{3g})_r N(\rightarrow O)R^{2d}R^{2d}$, $(CR^3R^{3g})_r OR^{2d}$, $(CR^3R^{3g})_r —NR^{2d}C(O)R^{2e}$, $(CR^3R^{3g})_r —C(O)R^{2e}$, $(CR^3R^{3g})_r —OC(O)R^{2e}$, $(CR^3R^{3g})_r —C(O)NR^{2d}R^{2d}$, $(CR^3R^{3g})_r —C(O)OR^{2d}$, $(CR^3R^{3g})_r —NR^{2d}C(O)NR^{2d}R^{2d}$, $(CR^3R^{3g})_r —OC(O)NR^{2d}R^{2d}$, $(CR^3R^{3g})_r —NR^{2d}C(O)OR^{2d}$, $(CR^3R^{3g})_r —SO_2NR^{2d}R^{2d}$, $(CR^3R^{3g})_r —NR^{2d}SO_2NR^{2d}R^{2d}$, $(CR^3R^{3g})_r —C(O)NR^{2d}SO_2R^{2d}$, $(CR^3R^{3g})_r —NR^{2d}SO_2R^{2d}$, and $(CR^3R^{3g})_r —S(O)_p R^{2d}$, provided that $S(O)_p R^{2d}$ forms other than $S(O)_2H$ or $S(O)H$ and further provided that $R^{4a}$ is other than a hydroxamic acid;

$R^{4b}$, at each occurrence, is selected from H, =O, $(CH_2)_r OR^3$, $(CH_2)_r F$, $(CH_2)_r Cl$, $(CH_2)_r Br$, $(CH_2)_r I$, $C_{1-4}$ alkyl, $(CH_2)_r CN$, $(CH_2)_r NO_2$, $(CH_2)_r NR^3R^{3a}$, $(CH_2)_r C(O)R^3$, $(CH_2)_r C(O)OR^{3c}$, $(CH_2)_r NR^3C(O)R^{3a}$, $(CH_2)_r —C(O)NR^3R^{3a}$, $(CH_2)_r NR^3C(O)NR^3R^{3a}$, $(CH_2)_r —C(=NR^3)NR^3R^{3a}$, $(CH_2)_r NR^3C(=NR^3)NR^3R^{3a}$, $(CH_2)_r SO_2NR^3R^{3a}$, $(CH_2)_r NR^3SO_2NR^3R^{3a}$, $(CH_2)_r NR^3SO_2—C_{1-4}$ alkyl, $(CH_2)_r NR^3SO_2CF_3$, $(CH_2)_r NR^3SO_2$-phenyl, $(CH_2)_r S(O)_p CF_3$, $(CH_2)_r S(O)_p—C_{1-4}$ alkyl, $(CH_2)_r S(O)_p$-phenyl, and $(CH_2)_r (CF_2)_r CF_3$;

$R^{4c}$, at each occurrence, is selected from =O, $(CR^3R^{3a})_r OR^2$, $(CR^3R^{3a})_r F$, $(CR^3R^{3a})_r Br$, $(CR^3R^{3a})_r Cl$, $(CR^3R^{3a})_r CF_3$, $C_{1-4}$ alkyl, $C_{2-6}$ alkenyl, $C_{2-6}$ alkynyl, $(CR^3R^{3a})_r CN$, $(CR^3R^{3a})_r NO_2$, $(CR^3R^{3a})_r NR^2R^{2a}$, $(CR^3R^{3a})_r N(\rightarrow O)R^2R^{2a}$, $(CR^3R^{3a})_r C(O)R^{2c}$, $(CR^3R^{3a})_r NR^2C(O)R^{2b}$, $(CR^3R^{3a})_rC(O)NR^2R^{2a}$, $(CR^3R^{3a})_rN=CHOR^3$, $(CR^3R^{3a})_rC(O)NR^2(CH_2)_2NR^2R^{2a}$, $(CR^3R^{3a})_rNR^2C(O)$ $NR^2R^{2a}$, $(CR^3R^{3a})_rC(=NR^2)NR^2R^{2a}$, $(CR^3R^{3a})_rNR^2C$ $(=NR^2)NR^2R^{2a}$, $(CR^3R^{3a})_rSO_2NR^2R^{2a}$, $(CR^3R^{3a})_r$ $NR^2SO_2NR^2R^{2a}$, $(CR^3R^{3a})_rC(O)NR^2SO_2$—$C_{1-4}$ alkyl, $(CR^3R^{3a})_rNR^2SO_2R^{5a}$, $(CR^3R^{3a})_rS(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$4–10 membered heterocycle substituted with 0–2 $R^{4b}$ and consisting of carbon atoms and from 1–4 heteroatoms selected from the group consisting of N, O, and $S(O)_p$;

$R^5$, at each occurrence, is selected from H, $C_{1-6}$ alkyl, =O, $(CH_2)_rOR^3$, F, Cl, Br, I, —CN, $NO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CH_2)_rNR^3C(O)NR^3R^{3a}$, $(CH_2)_rCH$ $(=NOR^{3d})$, $(CH_2)_rC(=NR^3)NR^3R^{3a}$, $(CH_2)_rNR^3C$ $(=NR^3)NR^3R^{3a}$, $(CH_2)_rSO_2NR^3R^{3a}$, $(CH_2)_r$ $NR^3SO_2NR^3R^{3a}$, $(CH_2)_rNR^3SO_2$—$C_{1-4}$ alkyl, $(CH_2)_r$ $NR^3SO_2CF_3$, $(CH_2)_rNR^3SO_2$-phenyl, $(CH_2)_rS(O)_pCF_3$, $(CH_2)_rS(O)_p$—$C_{1-4}$ alkyl, $(CH_2)_rS(O)_p$-phenyl, $(CH_2)_r$ $CF_3$, phenyl substituted with 0–2 $R^6$, naphthyl substituted with 0–2 $R^6$, and benzyl substituted with 0–2 $R^6$;

$R^{5a}$, at each occurrence, is selected from $C_{1-6}$ alkyl, $(CH_2)_r$ $OR^3$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CF_2)_rCF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—C(O) bond;

$R^6$, at each occurrence, is selected from H, OH, $(CH_2)_rOR^2$, halo, $C_{1-4}$ alkyl, —CN, $NO_2$, $(CH_2)_rNR^2R^{2a}$, $(CH_2)_rC(O)$ $R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkyl-C(O)—, $C_{1-6}$ alkyl-O—, $(CH_2)_n$-phenyl, $C_{1-4}$ alkyl-OC(O)—, $C_{6-10}$ aryl-O—, $C_{6-10}$ aryl-OC(O)—, $C_{6-10}$ aryl-$CH_2$—C(O)—, $C_{1-4}$ alkyl-C(O)O—$C_{1-4}$ alkyl-OC (O)—, $C_{6-10}$ aryl-C(O)O—$C_{1-4}$ alkyl-OC(O)—, $C_{1-6}$ alkyl-$NH_2$—C(O)—, phenyl-$NH_2$—C(O)—, and phenyl $C_{1-4}$ alkyl-C(O)—;

$R^8$, at each occurrence, is selected from H, $C_{1-6}$ alkyl, and $(CH_2)_n$-phenyl;

alternatively, $R^7$ and $R^8$, when attached to the same nitrogen, combine to form a 5–10 membered heterocyclic ring consisting of carbon atoms and 0–2 additional heteroatoms selected from the group consisting of N, O, and $S(O)_p$;

$R^9$, at each occurrence, is selected from H, $C_{1-6}$ alkyl, and $(CH_2)_n$-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6; and, t, at each occurrence, is selected from 0, 1, 2, and 3.

[2] In a preferred embodiment, the present invention provides a novel compound of Formula II:

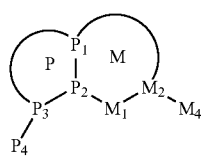

II or a stereoisomer or pharmaceutically acceptable salt thereof, wherein;

ring M, including $P_1$, $P_2$, $M_1$, and $M_2$, is a 5, 6, or 7 membered carbocycle or a 5, 6, or 7 membered heterocycle, consisting of: carbon atoms and 1–3 heteroatoms selected from O, $S(O)_p$, N, and $NZ^2$;

ring M is substituted with 0–2 $R^{1a}$ and 0–2 carbonyl groups, and there are 0–3 ring double bonds;

ring P, including $P_1$, $P_2$, and $P_3$, is a 5 or 6 membered aromatic heterocycle, consisting of: carbon atoms and 1–3 heteroatoms selected from O, $S(O)_p$, and N;

alternatively, ring P, including $P_1$, $P_2$, and $P_3$, is a 5 or 6 membered dihydro-aromatic heterocycle, consisting of: carbon atoms and 1–3 heteroatoms selected from O, $S(O)_p$, and N;

ring P is substituted with 0–2 $R^{1a}$;

one of $P_4$ and $M_4$ is -Z-A-B and the other -$G_1$-G;

G is a group of formula IIa or IIb:

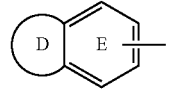

IIa

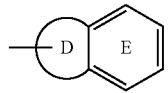

IIb ring D, including the two atoms of Ring E to which it is attached, is a 5–6 membered ring consisting of carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–3 R;

alternatively, ring D is absent, and ring E is selected from phenyl, pyridyl, pyrimidyl, and thienyl, and ring E is substituted with 1–3 R;

alternatively, ring D is absent, ring E is selected from phenyl, pyridyl, and thienyl, and ring E is substituted with 1 R and substituted with a 5–6 membered heterocycle consisting of: carbon atoms and 1–4 heteroatoms selected from the group consisting of N, O, and $S(O)_p$, wherein the 5–6 membered heterocycle is substituted with 0–2 carbonyls and 1–3 R and there are 0–3 ring double bonds;

R is selected from H, $C_{1-4}$ alkyl, F, Cl, OH, $OCH_3$, $OCH_2CH_3$, $OCH(CH_3)_2$, CN, $C(=NH)NH_2$, $C(=NH)$ NHOH, $C(=NH)NHOCH_3$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $(CR^8R^9)_tNR^7R^8$, $C(O)NR^7R^8$, $CH_2C$ $(O)NR^7R^8$, $S(O)_pNR^7R^8$, $CH_2S(O)_pNR^7R^8$, $SO_2R^3$, and $OCF_3$;

alternatively, when 2 R groups are attached to adjacent atoms, they combine to form methylenedioxy or ethylenedioxy;

A is selected from:

$C_{5-10}$ carbocycle substituted with 0–2 $R^4$, and

5–10 membered heterocycle substituted with 0–2 $R^4$ and consisting of: carbon atoms and 1–4 heteroatoms selected from the group consisting of N, O, and $S(O)_p$;

X is selected from —$(CR^2R^{2a})_{1-4}$—, —C(O)—, —C(O) $CR^2R^{2a}$—, —$CR^2R^{2a}$C(O), —$S(O)_2$—, —$S(O)_2$ $CR^2R^{2a}$—, —$CR^2R^{2a}S(O)_2$, —$NR^2S(O)_2$—, —$S(O)_2$ $NR^2$—, —$NR^2C(O)$—, —$C(O)NR^2$—, $NR^2$, —$NR^2CR^2R^{2a}$—, —$CR^2R^{2a}NR^2$—, O, —$OCR^2R^{2a}$—, and —$CR^2R^{2a}O$—;

Y is a $C_{3-7}$ monocyclic carbocycle or 3–7 membered monocyclic heterocycle, wherein the carobocycle or heterocycle consists of: carbon atoms and 0–2 heteroatoms selected from N, O, and $S(O)_p$, the carbocycle or heterocycle further comprises 0–2 double bonds and 0–2 carbonyl groups, and the carbocycle or heterocycle is substituted with 0–2 $R^4$;

alternatively, Y is $CY^1Y^2$, and $Y^1$ and $Y^2$ are independently $C_{1-3}$ alkyl substituted with 0–1 $R^4$;

Z is selected from a bond, $CH_2$, $CH_2CH_2$, $CH_2O$, $OCH_2$, $C(O)$, NH, $CH_2NH$, $NHCH_2$, $CH_2C(O)$, $C(O)CH_2$, $C(O)NH$, $NHC(O)$, $NHC(O)CH_2C(O)NH$, $S(O)_2$, $CH_2S(O)_2$, $S(O)_2(CH_2)$, $SO_2NH$, and $NHSO_2$, provided that Z does not form a N—S, $NCH_2N$, $NCH_2O$, or $NCH_2S$ bond with either group to which it is attached;

$Z^2$ is selected from H, $C_{1-4}$ alkyl, phenyl, benzyl, $C(O)R^{3b}$, $S(O)R^{3f}$, and $S(O)_2R^{3f}$;

$R^{1a}$, at each occurrence, is selected from H, —$(CH_2)_r$—$R^{1b}$, —$(CH(CH_3))_r$—$R^{1b}$, —$(C(CH_3)_2)_r$—$R^{1b}$, —O—$(CR^3R^{3a})_r$—$R^{1b}$, —$NR^2$—$(CR^3R^{3a})_r$—$R^{1b}$, and —S—$(CR^3R^{3a})_r$—$R^{1b}$, provided that $R^{1a}$ forms other than an N-halo, N—S, O—O, or N—CN bond;

alternatively, when two $R^{1a}$ groups are attached to adjacent atoms or to the same carbon atom, together with the atoms to which they are attached, they form a 5–7 membered ring consisting of: carbon atoms and 0–2 heteroatoms selected from the group consisting of N, O, and $S(O)_p$, this ring being substituted with 0–2 $R^{4b}$ and comprising: 0–3 double ring bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_p$$R^{2b}$, $NR^2(CH_2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C_{5-6}$ carbocycle substituted with 0–2 $R^{4b}$, and 5–6 membered heterocycle substituted with 0–2 $R^{4b}$ and consisting of carbon atoms and from 1–4 heteroatoms selected from the group consisting of N, O, and $S(O)_p$, provided that $R^{1b}$ forms other than an O—O, N-halo, N—S, or N—CN bond and provided that $S(O)_pR^2$ forms other than $S(O)_2H$ or $S(O)H$;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, a $C_{5-6}$ carbocycle-$CH_2$-substituted with 0–2 $R^{4b}$, and 5–6 membered heterocycle substituted with 0–2 $R^{4b}$ and consisting of: carbon atoms and 1–4 heteroatoms selected from the group consisting of N, O, and $S(O)_p$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle substituted with 0–2 $R^{4b}$ and consisting of: carbon atoms and 1–4 heteroatoms selected from the group consisting of N, O, and $S(O)_p$;

alternatively, $R^2$ and $R^{2a}$, together with the nitrogen atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle substituted with 0–2 $R^{4b}$ and consisting of: carbon atoms and 1–4 heteroatoms selected from the group consisting of N, O, and $S(O)_p$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle substituted with 0–2 $R^{4b}$ and consisting of carbon atoms and from 1–4 heteroatoms selected from the group consisting of N, O, and $S(O)_p$;

$R^{2d}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N-C-halo, $S(O)_p$-halo, O-halo, N—S, S—N, $S(O)_p$—$S(O)_p$, S—O, O—N, O—S, or O—O moiety;

alternatively, when two $R^{2d}$'s are attached to the same nitrogen atom, then $R^{2d}$ and $R^{2d}$, together with the nitrogen atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^{3g}$, at each occurrence, is selected from H, $CH_3$, $CH_2CH_3$, $CH_2CH_2CH_3$, $CH(CH_3)_2$, cyclopropyl, cyclopropyl-methyl, benzyl, and phenyl;

alternatively, when $R^3$ and $R^{3g}$ are attached to the same carbon atom, they combine with the attached carbon atom to form a cyclopropyl group;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^{5a}$, $CF_3$, $CF_2CF_3$, 5–6 membered carbocycle substituted with 0–1 $R^5$, and a 5–6 membered heterocycle substituted with 0–1 $R^5$ and consisting of: carbon atoms and 1–4 heteroatoms selected from the group consisting of N, O, and $S(O)_p$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, C(CH₃)₃, —CN, NO₂, NR³R³ᵃ, CH₂NR³R³ᵃ, C(O)R³, CH₂—C(O)R³, C(O)OR³ᶜ, CH₂C(O)OR³ᶜ, NR³C(O)R³ᵃ, CH₂NR³C(O)R³ᵃ, C(O)NR³R³ᵃ, CH₂C(O)NR³R³ᵃ, NR³C(O)NR³R³ᵃ, CH₂NR³C(O)NR³R³ᵃ, C(=NR³)NR³R³ᵃ, CH₂C(=NR³)NR³R³ᵃ, NR³C(=NR³)NR³R³ᵃ, CH₂NR³C(=NR³)NR³R³ᵃ, SO₂NR³R³ᵃ, CH₂SO₂NR³R³ᵃ, NR³SO₂NR³R³ᵃ, CH₂NR³SO₂NR³R³ᵃ, NR³SO₂—C₁₋₄ alkyl, CH₂NR³SO₂—C₁₋₄ alkyl, NR³SO₂CF₃, CH₂NR³SO₂CF₃, NR³SO₂-phenyl, CH₂NR³SO₂-phenyl, S(O)ₚCF₃, CH₂S(O)ₚCF₃, S(O)ₚ—C₁₋₄ alkyl, CH₂S(O)ₚ—C₁₋₄ alkyl, S(O)ₚ-phenyl, CH₂S(O)ₚ-phenyl, CF₃, and CH₂—CF₃;

R⁴ᶜ, at each occurrence, is selected from =O, (CR³R³ᵃ)ᵣOR², (CR³R³ᵃ)ᵣF, (CR³R³ᵃ)ᵣBr, (CR³R³ᵃ)ᵣCl, (CR³R³ᵃ)ᵣCF₃, C₁₋₄ alkyl, C₂₋₄ alkenyl, C₂₋₄ alkynyl, (CR³R³ᵃ)ᵣCN, (CR³R³ᵃ)ᵣNO₂, (CR³R³ᵃ)ᵣNR²R²ᵃ, (CR³R³ᵃ)ᵣN(→O)R²R²ᵃ, (CR³R³ᵃ)ᵣC(O)R²ᶜ, (CR³R³ᵃ)ᵣNR²C(O)R²ᵇ, (CR³R³ᵃ)ᵣC(O)ᵣR²R²ᵃ, (CR³R³ᵃ)ᵣNR²C(O)ᵣNR²R²ᵃ, (CR³R³ᵃ)ᵣSO₂NR²R²ᵃ, (CR³R³ᵃ)ᵣNR²SO₂NR²R²ᵃ, (CR³R³ᵃ)ᵣNR²SO₂R⁵ᵃ, (CR³R³ᵃ)ᵣS(O)ᵣR⁵ᵃ, (CF₂)ᵣCF₃, (CR³R³ᵃ)ᵣC₃₋₁₀ carbocycle substituted with 0–2 R⁴ᵇ, and (CR³R³ᵃ)ᵣ5–10 membered heterocycle substituted with 0–2 R⁴ᵇ and consisting of carbon atoms and from 1–4 heteroatoms selected from the group consisting of N, O, and S(O)ₚ;

R⁵, at each occurrence, is selected from H, =O, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, OR³, CH₂OR³, F, Cl, —CN, NO₂, NR³R³ᵃ, CH₂NR³R³ᵃ, C(O)R³, CH₂C(O)R³, C(O)OR³ᶜ, CH₂C(O)OR³ᶜ, NR³C(O)R³ᵃ, C(O)NR³R³ᵃ, NR³C(O)NR³R³ᵃ, CH(=NOR³ᵈ), C(=NR³)NR³R³ᵃ, NR³C(=NR³)NR³R³ᵃ, SO₂NR³R³ᵃ, NR³SO₂NR³R³ᵃ, NR³SO₂—C₁₋₄ alkyl, NR³SO₂CF₃, NR³SO₂-phenyl, S(O)ₚCF₃, S(O)ₚ—C₁₋₄ alkyl, S(O)ₚ-phenyl, CF₃, phenyl substituted with 0–2 R⁶, naphthyl substituted with 0–2 R⁶, and benzyl substituted with 0–2 R⁶;

R⁶, at each occurrence, is selected from H, OH, OR², F, Cl, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, —CN, NO₂, NR²R²ᵃ, CH₂NR²R²ᵃ, C(O)R²ᵇ, CH₂C(O)R²ᵇ, NR²C(O)R²ᵇ, NR²C(O)NR²R²ᵃ, C(=NH)NH₂, NHC(=NH)NH₂, SO₂NR²R²ᵃ, NR²SO₂NR²R²ᵃ, and NR²SO₂C₁₋₄ alkyl; and, r, at each occurrence, is selected from 0, 1, 2, and 3.

[3] In another preferred embodiment, the present invention provides a novel compound, wherein:

ring M is substituted with 0–2 R¹ᵃ and is selected from the group:

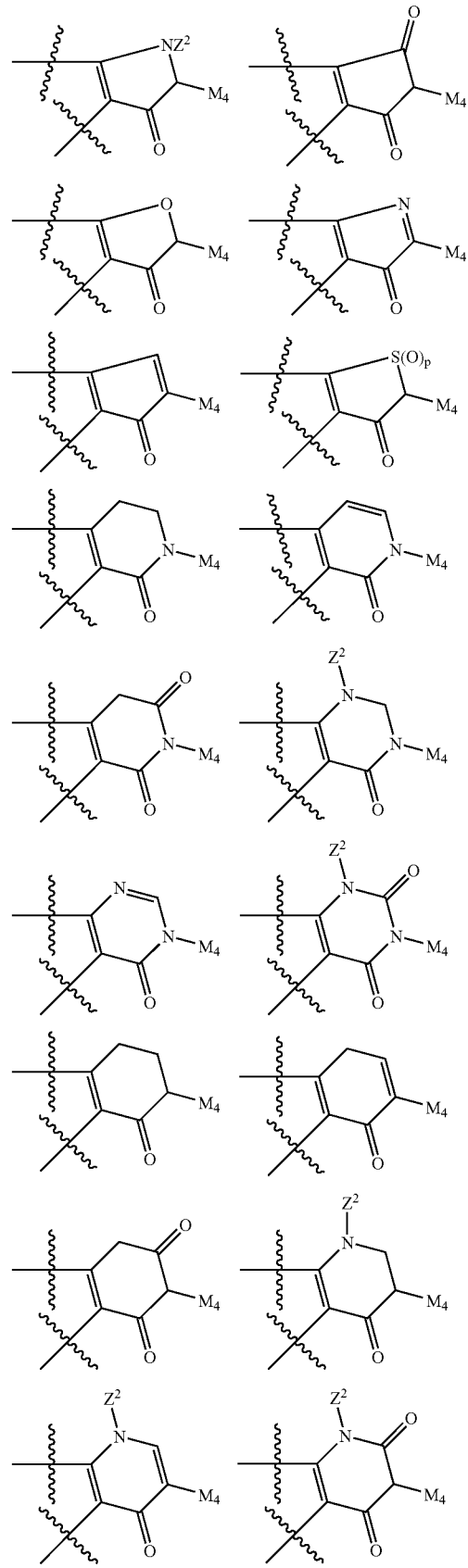

-continued
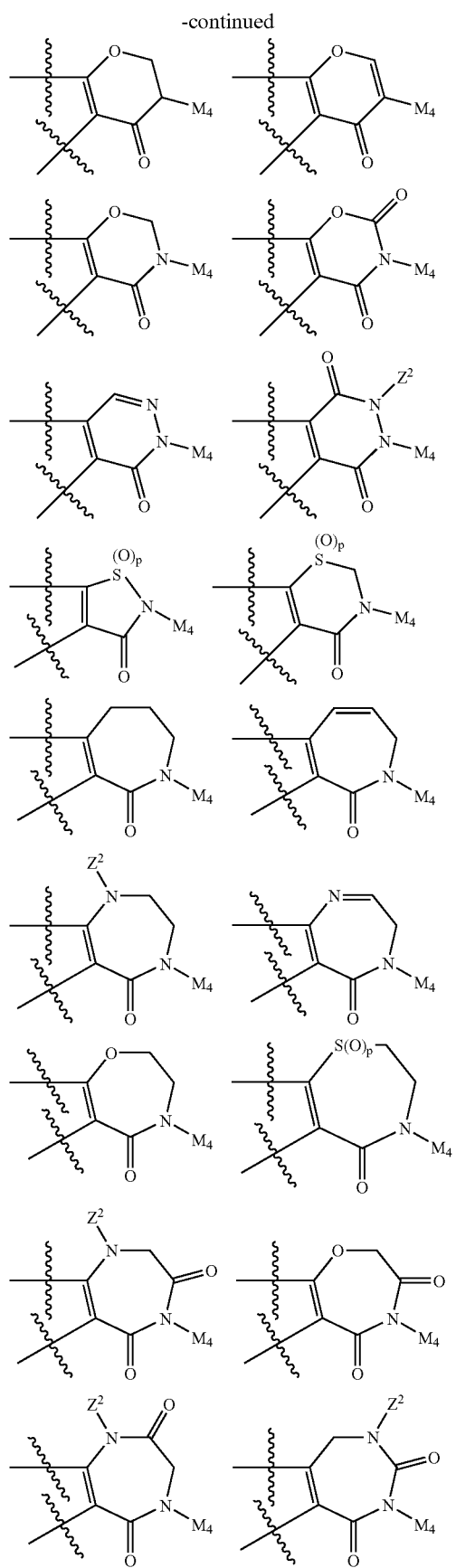
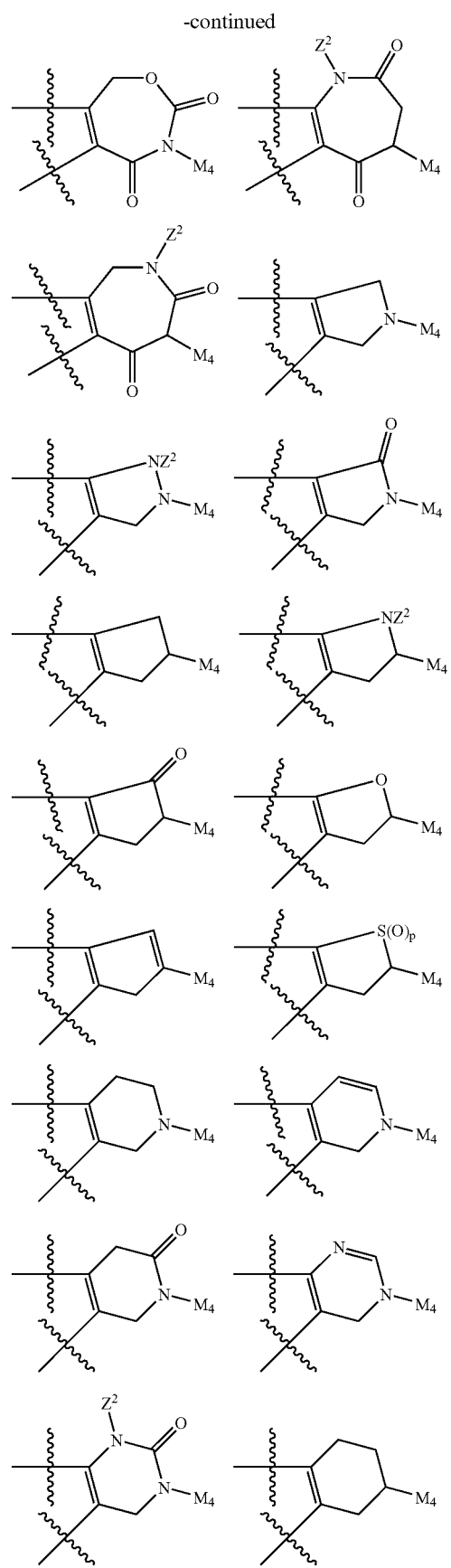

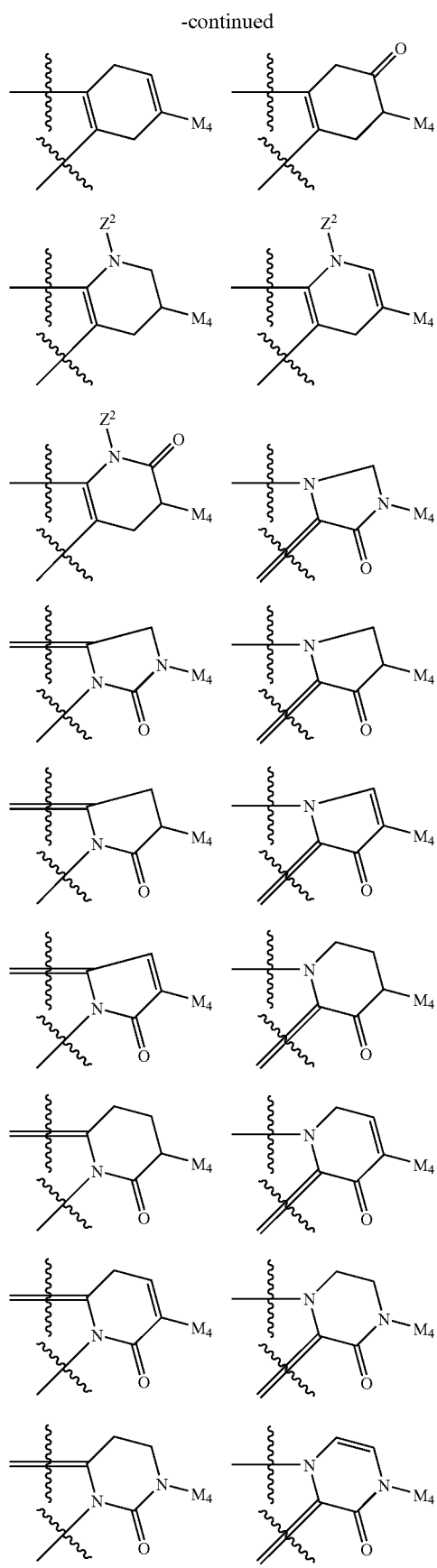
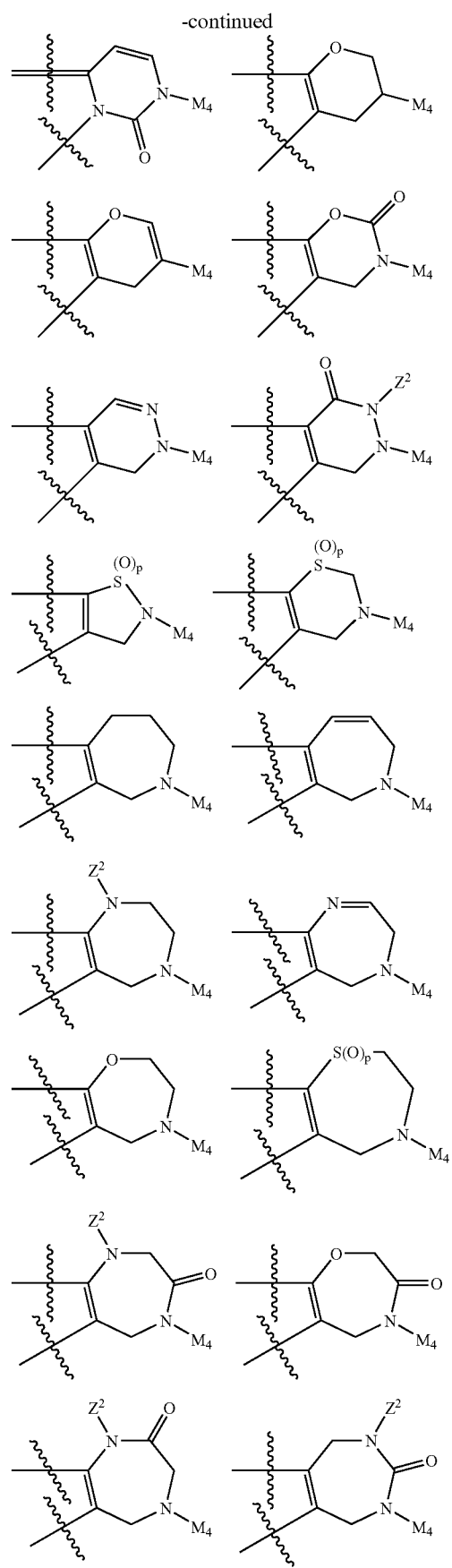

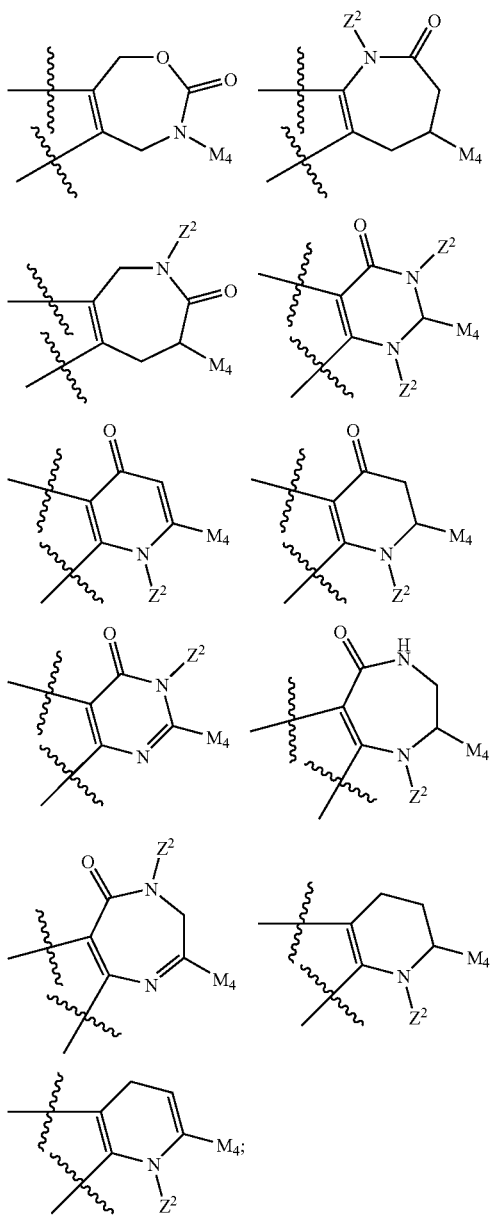
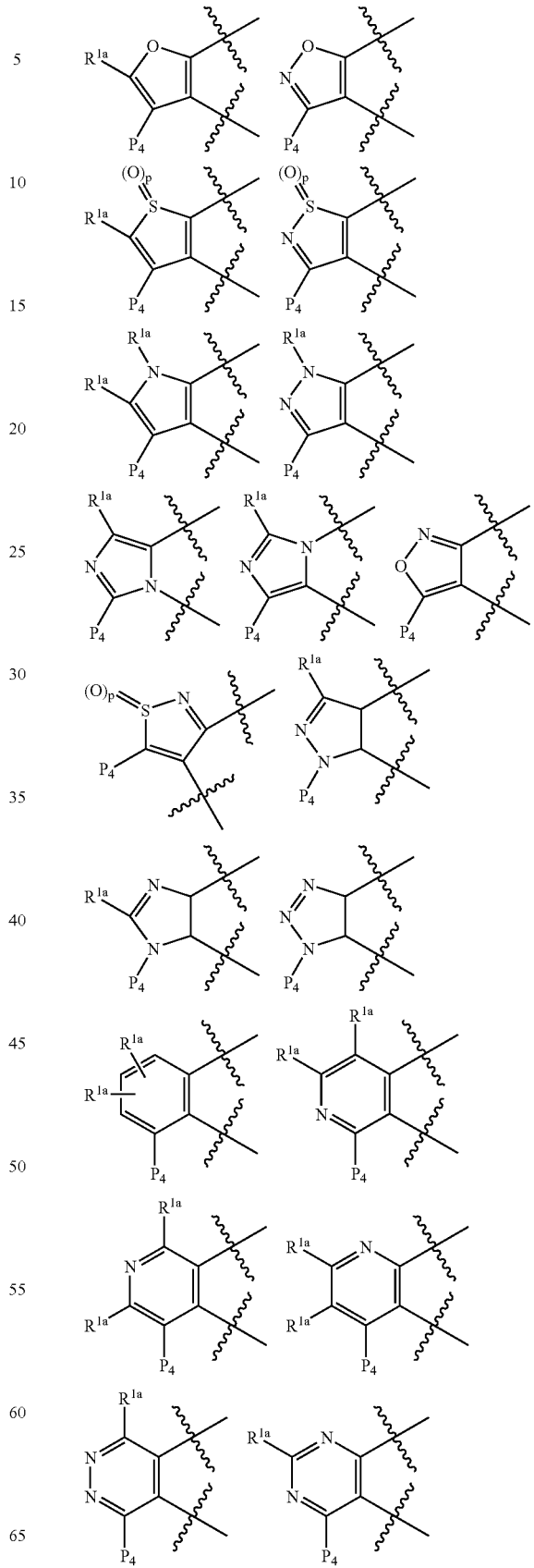
ring P, including $P_1$, $P_2$, $P_3$, and $P_4$ is selected from group:

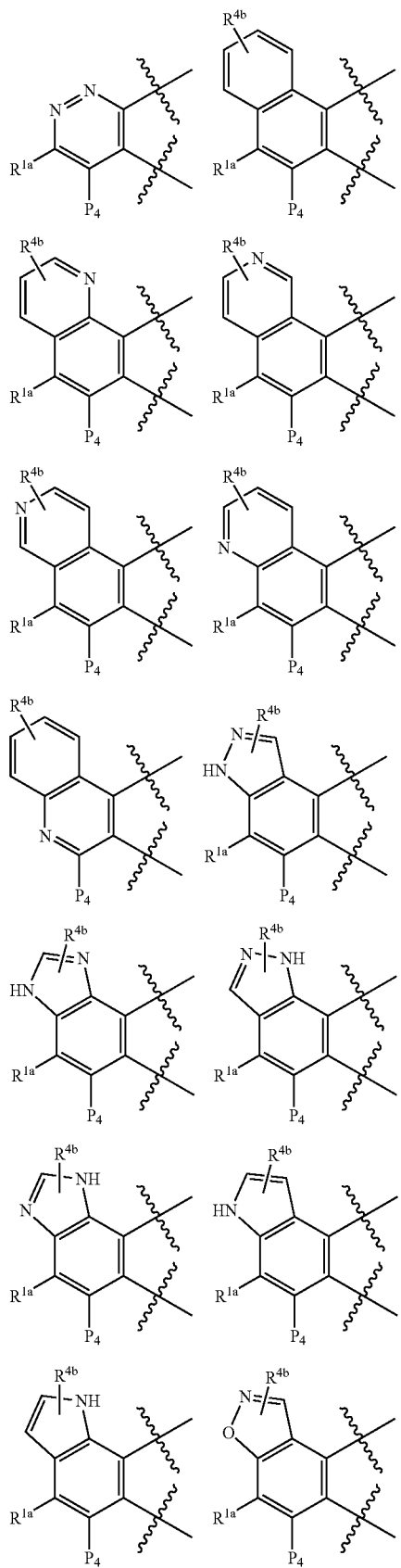
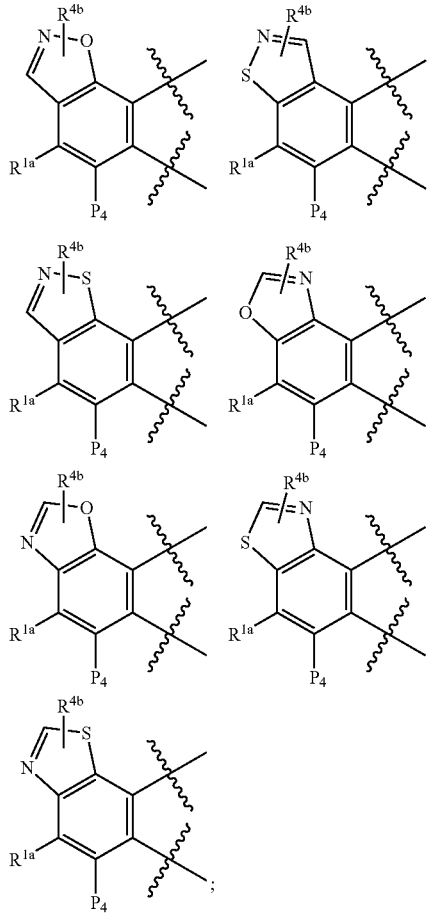

G is selected from the group:
phenyl; 2,5-bis-aminomethyl-phenyl; 2-amido-4-methoxy-phenyl; 2-amido-5-chloro-phenyl; 2-amido-phenyl; 2-aminomethyl-3-fluoro-phenyl; 2-aminomethyl-3-methoxy-phenyl; 2-aminomethyl-4-fluoro-phenyl; 2-aminomethyl-4-methoxy-phenyl; 2-aminomethyl-5-fluoro-phenyl; 2-aminomethyl-5-methoxy-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 2-aminomethyl-4-ethyl-phenyl; 2-aminosulfonyl-4-ethyl-phenyl; 2-amido-4-ethyl-phenyl; 2-hydroxy-4-methoxy-phenyl; 2-methylsulfonyl-phenyl; 3-(N,N-dimethylamino)-4-chloro-phenyl; 3-(N,N-dimethylamino)-phenyl; 3-(N-hydroxy-amidino)-phenyl; 3-(N-methoxy-amidino)-phenyl; 3-(N-methylamino)-4-chloro-phenyl; 3-(N-methylamino)-phenyl; 3-amidino-phenyl; 3-amido-6-hydroxy-phenyl; 3-amido-phenyl; 3-amino-4-chloro-phenyl; 3-aminomethyl-phenyl; 3-amino-phenyl; 3-chloro-4-fluoro-phenyl; 3-chloro-phenyl; 3-hydroxy-4-methoxy-phenyl; 4-(N,N-dimethylamino)-5-chloro-thien-2-yl; 4-(N-methylamino)-5-chloro-thien-2-yl; 4-amino-5-chloro-thien-2-yl; 4-amino-pyrid-2-yl; 4-chloro-3-fluoro-phenyl; 4-chloro-phenyl; 4-chloro-pyrid-2-yl; 4-ethyl-phenyl; 4-ethyl-2-methylsulfonyl-phenyl; 4-ethyl-2-methoxy-phenyl; 4-methoxy-2-methylsulfonyl-phenyl; 4-methoxy-phenyl; 2-methoxy-pyrid-5-yl; 5-(N,N-dimethylamino)-4-chloro-thien-2-yl; 5-(N-methylamino)-4- chloro-thien-2-yl; 5-amino-4-chloro-thien-2-yl; 5-chloro-2-aminosulfonyl-phenyl; 5-chloro-2-methyl-sulfonyl-phenyl; 5-chloro-pyrid-2-yl; 5-chloro-thien-2-yl; 5-methoxy-thien-2-yl; 5-methyl-thien-2-yl; 5-fluoro-thien-2-yl; 6-amino-5-chloro-pyrid-2-yl; 6-amino-pyrid-2-yl;
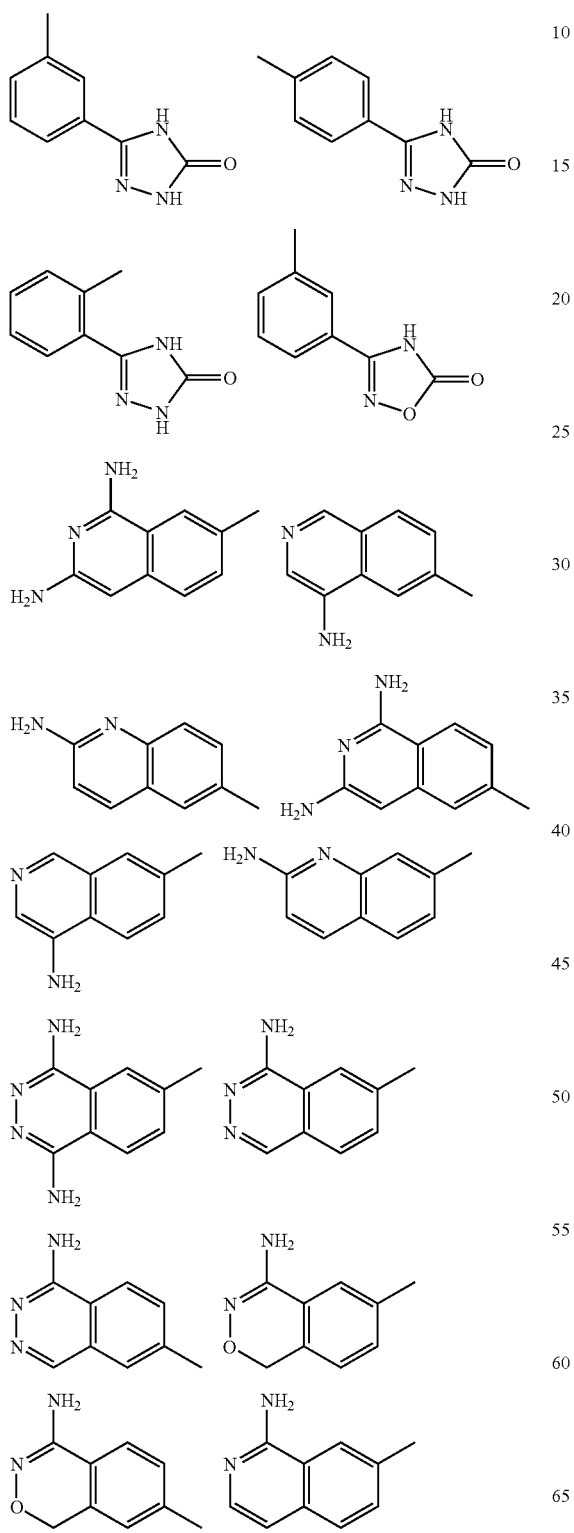
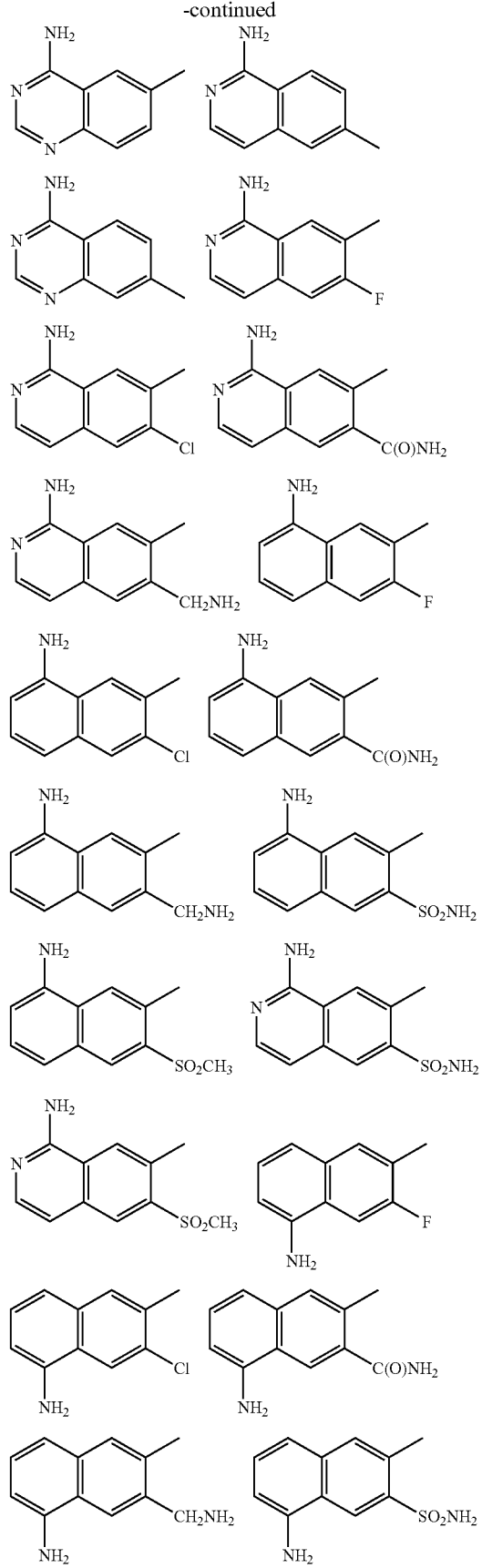

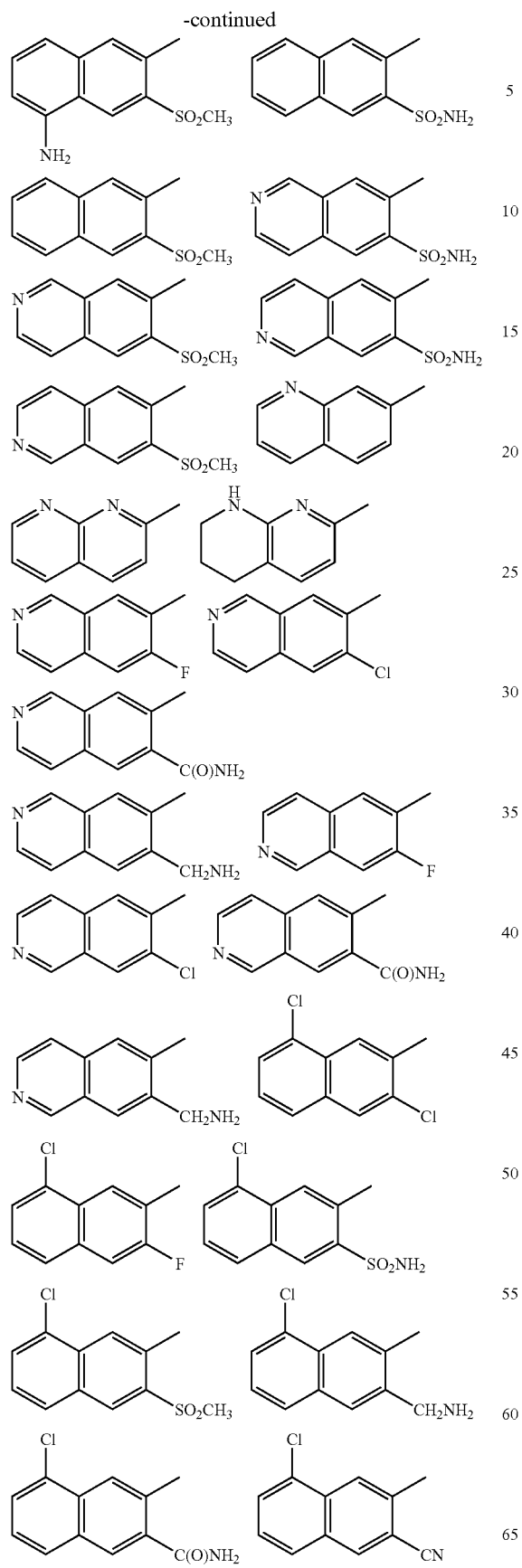
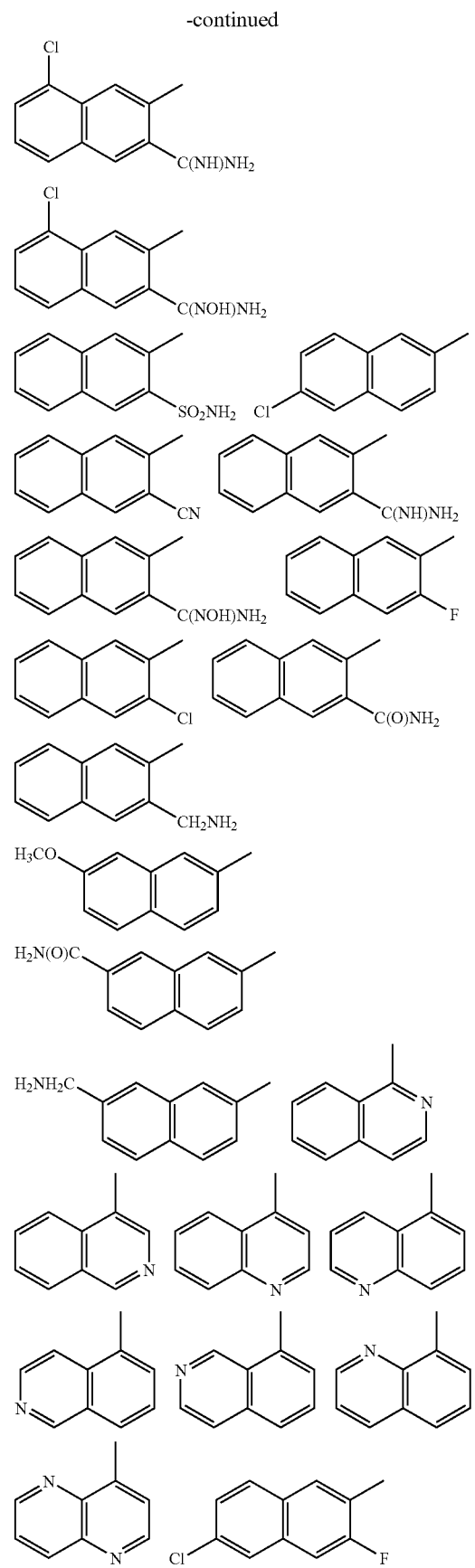

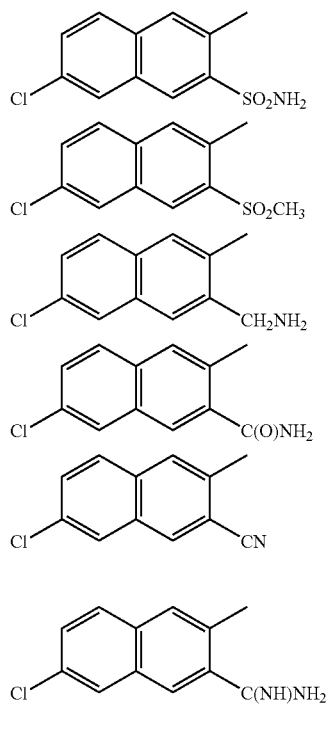
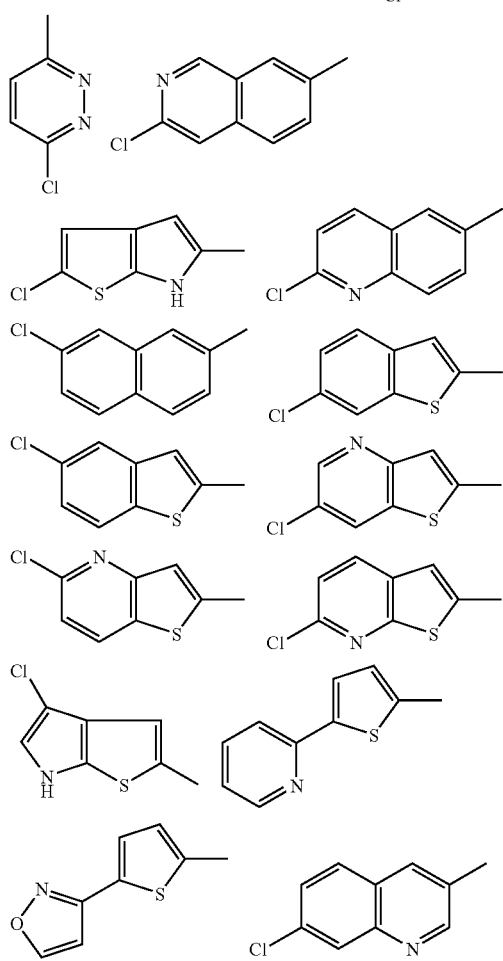
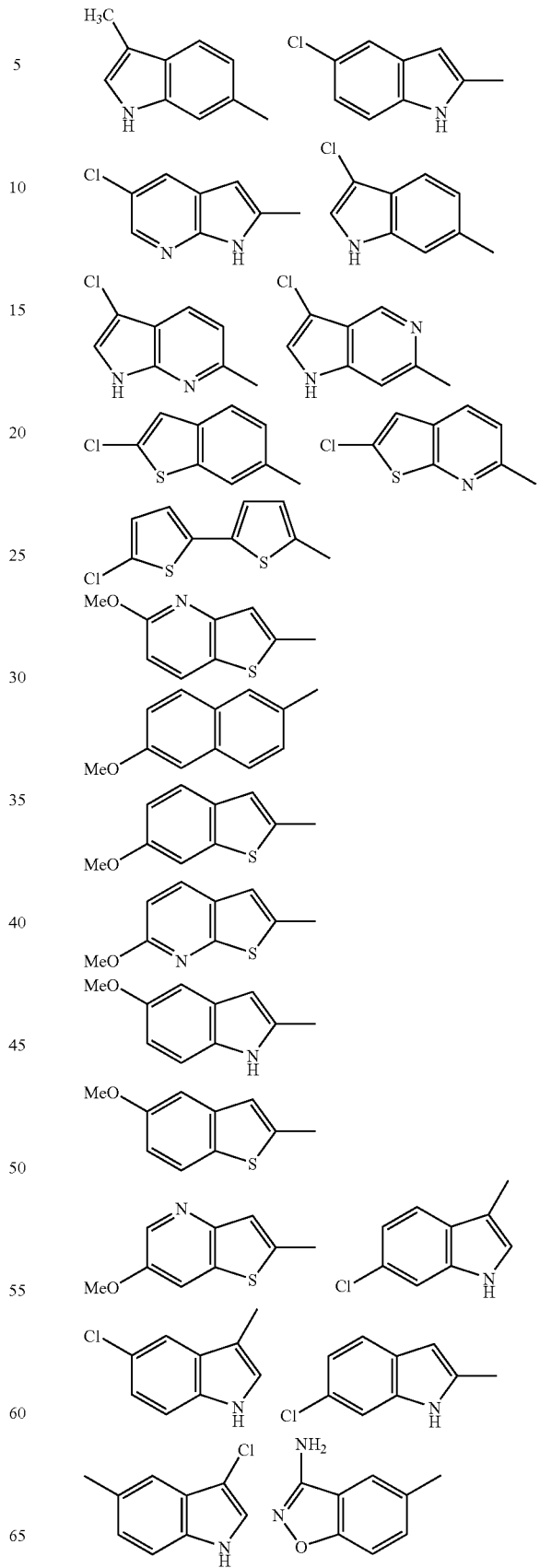

-continued
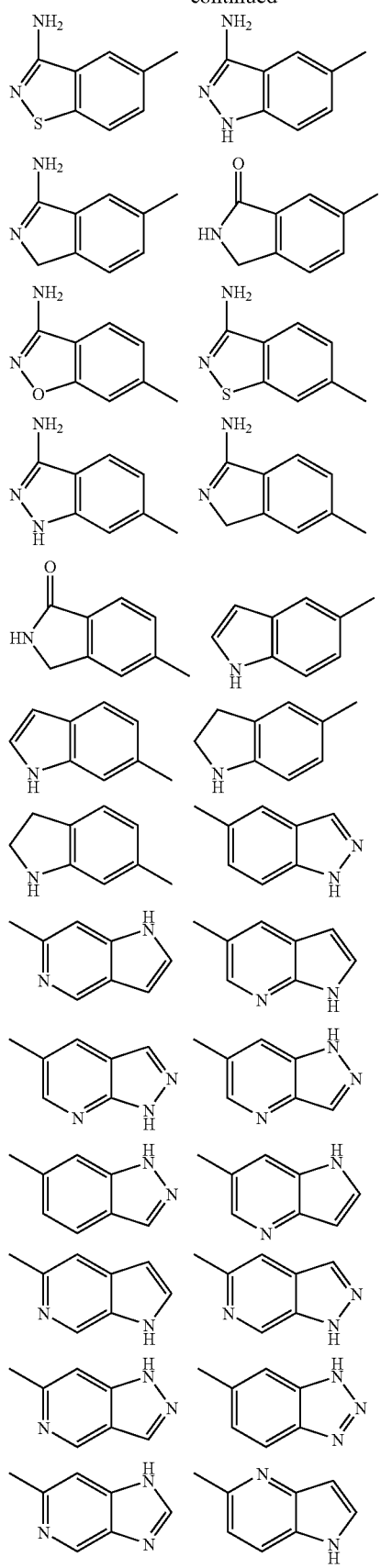
-continued
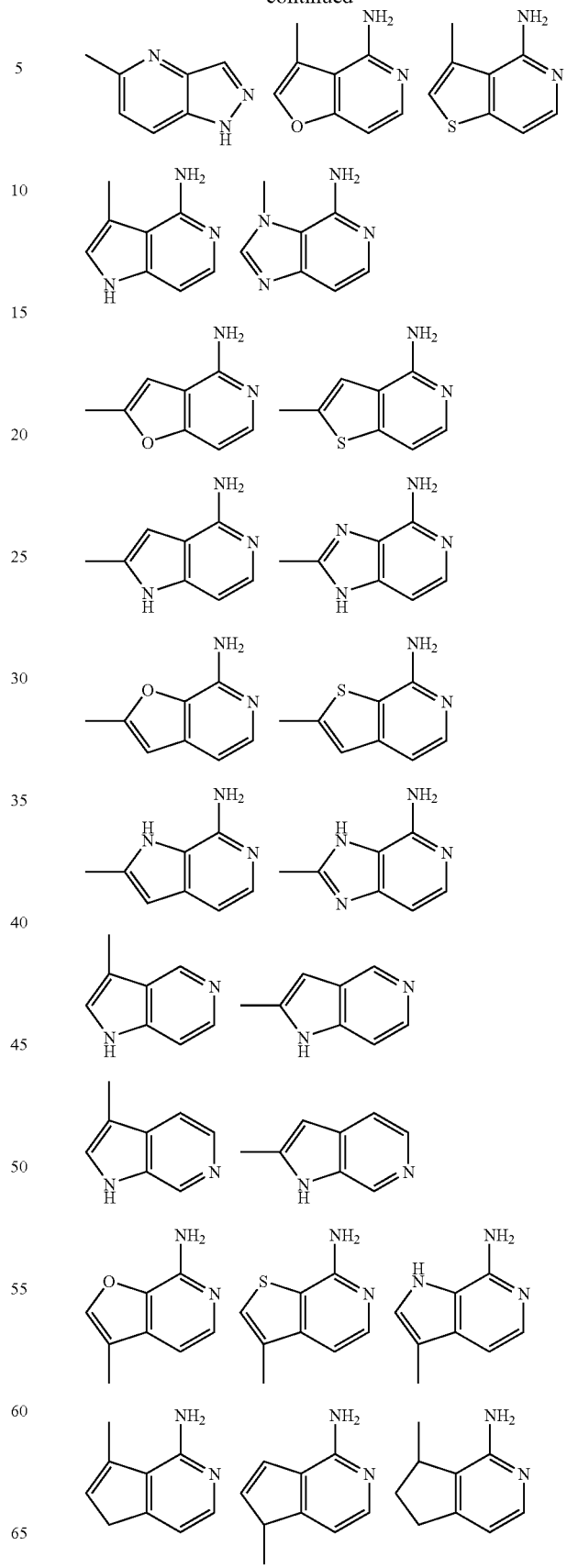

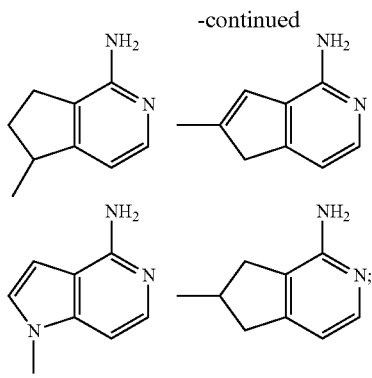

G$_1$ is absent or is selected from (CR$^3$R$^{3a}$)$_{1-3}$, CR$^3$=CR$^3$, (CR$^3$R$^{3a}$)$_u$C(O)(CR$^3$R$^{3a}$)$_w$, (CR$^3$R$^{3a}$)$_u$O(CR$^3$R$^{3a}$)$_w$, (CR$^3$R$^{3a}$)$_u$NR$^{3b}$(CR$^3$R$^{3a}$)$_w$, (CR$^3$R$^{3a}$)$_u$C(O)NR$^{3b}$ (CR$^3$R$^{3a}$)$_w$, (CR$^3$R$^{3a}$)$_u$NR$^{3b}$C(O)(CR$^3$R$^{3a}$)$_w$, (CR$^3$R$^{3a}$)$_u$ NR$^{3b}$C(O)(CR$^3$R$^{3a}$)$_u$C(O)NR$^{3b}$(CR$^3$R$^{3a}$)$_w$, (CR$^3$R$^{3a}$)$_u$S (CR$^3$R$^{3a}$)$_w$, (CR$^3$R$^{3a}$)$_u$S(O)(CR$^3$R$^{3a}$)$_w$, (CR$^3$R$^{3a}$)$_u$S(O)$_2$ (CR$^3$R$^{3a}$)$_w$, (CR$^3$R$^{3a}$)$_u$S(O)NR$^{3b}$(CR$^3$R$^{3a}$)$_w$, (CR$^3$R$^{3a}$)$_u$ NR$^{3b}$S(O)$_2$(CR$^3$R$^{3a}$)$_w$, and (CR$^3$R$^{3a}$)$_u$S(O)$_2$NR$^{3b}$ (CR$^3$R$^{3a}$)$_w$, wherein u+w total 0, 1, or 2, provided that G$_1$ does not form a N—S, NCH$_2$N, NCH$_2$O, or NCH$_2$S bond with either group to which it is attached;

A is selected from one of the following carbocycles and heterocycles which are substituted with 0–2 R$^4$;
  cyclohexyl, phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

X is selected from —(CR$^2$R$^{2a}$)$_{1-2}$—, —C(O)—, —S(O)$_2$—, —NR$^2$S(O)$_2$—, —NR$^2$S(O)$_2$NR$^2$—, —NR$^2$C(O)—, —C(O)NR$^2$—, NR$^2$, —NR$^2$CR$^2$R$^{2a}$—, —CR$^2$R$^{2a}$NR$^2$—, O, OCR$^2$R$^{2a}$—, and —CR$^2$R$^{2a}$O—;

Y is a C$_{3-6}$ monocyclic carbocycle or 5–6 membered monocyclic heterocycle, wherein the carobocycle or heterocycle consists of carbon atoms and 0–2 heteroatoms selected from N, O, and S(O)$_p$, the carbocycle or heterocycle further comprises 0–1 double bonds and 0–1 carbonyl groups, and the carbocycle or heterocycle is substituted with 0–2 R$^4$;
alternatively, Y is CY$^1$Y$^2$, and Y$^1$ and Y$^2$ are independently C$_{1-2}$ alkyl substituted with 0–1 R$^4$;

R$^{1a}$, at each occurrence, is selected from H, R$^{1b}$, CH(CH$_3$) R$^{1b}$, C(CH$_3$)$_2$R$^{1b}$, CH$_2$R$^{1b}$, and CH$_2$CH$_2$R$^{1b}$, provided that R$^{1a}$ forms other than an N-halo, N—S, or N—CN bond;

alternatively, when two R$^{1a}$ groups are attached to adjacent atoms or to the same carbon atom, together with the atoms to which they are attached they form a 5–6 membered ring consisting of: carbon atoms and 0–2 heteroatoms selected from the group consisting of N, O, and S(O)$_p$, this ring being substituted with 0–2 R$^{4b}$ and 0–3 ring double bonds;

R$^{1b}$ is selected from H, CH$_3$, CH$_2$CH$_3$, F, Cl, Br, —CN, —CHO, CF$_3$, OR$^2$, NR$^2$R$^{2a}$, C(O)R$^{2b}$, CO$_2$R$^{2b}$, OC(O) R$^2$, CO$_2$R$^{2a}$, S(O)$_p$R$^2$, NR$^2$(CH$_2$)$_r$OR$^2$, NR$^2$C(O)R$^{2b}$, C(O)NR$^2$R$^{2a}$, SO$_2$NR$^2$R$^{2a}$, NR$^2$SO$_2$R$^2$, phenyl substituted with 0–2 R$^{4b}$, and 5–6 membered aromatic heterocycle consisting of carbon atoms and from 1–4 heteroatoms selected from the group consisting of N, O, and S(O)$_p$ and substituted with 0–2 R$^{4b}$, provided that R$^{1b}$ forms other than an O—O, N-halo, N—S, or N—CN bond;

R$^2$, at each occurrence, is selected from H, CF$_3$, CH$_3$, CH$_2$CH$_3$, CH$_2$CH$_2$CH$_3$, CH(CH$_3$)$_2$, phenyl substituted with 0–2 R$^{4b}$, benzyl substituted with 0–2 R$^{4b}$, and 5–6 membered aromatic heterocycle substituted with 0–2 R$^{4b}$ and consisting of: carbon atoms and 1–4 heteroatoms selected from the group consisting of N, O, and S(O)$_p$;

R$^{2a}$, at each occurrence, is selected from H, CF$_3$, CH$_3$, CH$_2$CH$_3$, CH$_2$CH$_2$CH$_3$, CH(CH$_3$)$_2$, benzyl, phenyl substituted with 0–2 R$^{4b}$, and 5–6 membered aromatic heterocycle substituted with 0–2 R$^{4b}$ and consisting of: carbon atoms and 1–4 heteroatoms selected from the group consisting of N, O, and S(O)$_p$;

alternatively, R$^2$ and R$^{2a}$, together with the nitrogen atom to which they are attached, combine to form a 5 or 6 membered saturated, partially saturated or unsaturated ring substituted with 0–2 R$^{4b}$ and consisting of: 0–1 additional heteroatoms selected from the group consisting of N, O, and S(O)$_p$;

R$^{2b}$, at each occurrence, is selected from CF$_3$, C$_{1-4}$ alkoxy, CH$_3$, CH$_2$CH$_3$, CH$_2$CH$_2$CH$_3$, CH(CH$_3$)$_2$, benzyl, phenyl substituted with 0–2 R$^{4b}$, and 5–6 membered aromatic heterocycle substituted with 0–2 R$^{4b}$ and consisting of: carbon atoms and 1–4 heteroatoms selected from the group consisting of N, O, and S(O)$_p$;

R$^{2c}$, at each occurrence, is selected from CF$_3$, OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl, phenyl substituted with 0–2 R$^{4b}$, and 5–6 membered aromatic heterocycle substituted with 0–2 R$^{4b}$ and consisting of carbon atoms and from 1–4 heteroatoms selected from the group consisting of N, O, and S(O)$_p$;

R$^{2d}$, at each occurrence, is selected from H, R$^{4c}$, C$_{1-4}$ alkyl substituted with 0–2 R$^{4c}$, C$_{3-6}$ carbocycle substituted with 0–2 R$^{4c}$, —(CR$^3$R$^{3a}$)—C$_{3-6}$ carbocycle substituted with 0–2 R$^{4c}$, 5–6 membered heterocycle substituted with 0–2 R$^{4c}$ and consisting of: carbon atoms and 1–4 heteroatoms selected from the group consisting of N, O, and S(O)$_p$, and —(CR$^3$R$^{3a}$)-5–6 membered heterocycle substituted with 0–2 R$^{4c}$ and consisting of: carbon atoms and 1–4 heteroatoms selected from the group consisting of N, O, and S(O)$_p$, provided that R$^{2d}$ forms other than a N-halo, N—C-halo, S(O)$_p$-halo, O-halo, N—S, S—N, S(O)$_p$—S (O)$_p$, S—O, O—N, O—S, or O—O moiety;

R$^{2e}$, at each occurrence, is selected from H, R$^{4c}$, C$_{1-4}$ alkyl substituted with 0–2 R$^{4c}$, C$_{3-6}$ carbocycle substituted with 0–2 R$^{4c}$, —(CR$^3$R$^{3a}$)—C$_{3-6}$ carbocycle substituted with 0–2 R$^{4c}$, 5–6 membered heterocycle substituted with 0–2 R$^{4c}$ and consisting of: carbon atoms and 1–4 heteroatoms selected from the group consisting of N, O, and S(O)$_p$, and —(CR$^3$R$^{3a}$)-5–6 membered heterocycle substituted with 0–2 R$^{4c}$ and consisting of: carbon atoms and 1–4 heteroatoms selected from the group consisting of N, O, and S(O)$_p$, provided that R$^{2e}$ forms other than a C(O)-halo or C(O)—S(O)$_p$ moiety;

R$^4$, at each occurrence, is selected from H, (CH$_2$)$_2$OR$^2$, CH$_2$OR$^2$, OR$^2$, F, Cl, Br, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$) CH$_2$CH$_3$, C(CH$_3$)$_3$, —CN, NO$_2$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, SO$_2$NR$^2$R$^{2a}$, CF$_3$, and CF$_2$CF$_3$;

$R^{4a}$ is selected from —$(CR^3R^{3g})_r$-5–6 membered carbocycle substituted with 0–3 $R^{4c}$, —$(CR^3R^{3g})_r$-5–6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r$—$NR^{2d}C(O)R^{2e}$, $(CR^3R^{3g})_r$—$C(O)R^{2e}$, $(CR^3R^{3g})_r$—$OC(O)R^{2e}$, $(CR^3R^{3g})_r$—$C(O)NR^{2d}R^{2d}$, $(CR^3R^{3g})_r$—$C(O)OR^{2d}$, $(CR^3R^{3g})_r$—$NR^{2d}C(O)NR^{2d}R^{2d}$, $(CR^3R^{3g})_r$—$NR^{2d}C(O)OR^{2d}$, $(CR^3R^{3g})_r$—$SO_2NR^{2d}R^{2d}$, $(CR^3R^{3g})_r$—$NR^{2d}SO_2R^{2d}$, and $(CR^3R^{3g})_r$—$S(O)_pR^{2d}$, provided that $S(O)^pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2$—$C(O)R^3$, $C(O)OR^{3c}$, $CH_2$—$C(O)OR^{3c}$, $NR^3C(O)R^{3a}$, $CH_2NR^3C(O)R^{3a}$, $C(O)NR^3R^{3a}$, $CH_2$—$C(O)NR^3R^{3a}$, $SO_2NR^3R^{3a}$, $CH_2SO_2NR^3R^{3a}$, $NR^3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})F$, Br, $(CR^3R^{3a})Br$, Cl, $(CR^3R^{3a})Cl$, $CF_3$, $(CR^3R^{3a})CF_3$, $C_{1-4}$ alkyl, $C_{2-3}$ alkenyl, $C_{2-3}$ alkynyl, —CN, $(CR^3R^{3a})CN$, $NO_2$, $(CR^3R^{3a})NO_2$, $NR^2R^{2a}$, $(CR^3R^{3a})NR^2R^{2a}$, $N(\rightarrow O)R^2R^{2a}$, $(CR^3R^{3a})N(\rightarrow O)R^2R^{2a}$, $C(O)R^{2c}$, $(CR^3R^{3a})C(O)R^{2c}$, $NR^2C(O)R^{2b}$, $(CR^3R^{3a})NR^2C(O)R^{2b}$, $C(O)NR^2R^{2a}$, $(CR^3R^{3a})C(O)NR^2R^{2a}$, $NR^2C(O)NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})NR^2SO_2NR^2R^{2a}$, $NR^2SO_2R^{5a}$, $(CR^3R^{3a})NR^2SO_2R^{5a}$, $S(O)_pR^{5a}$, $(CR^3R^{3a})S(O)_pR^{5a}$, $CF_3$, $CF_2CF_3$, $C_{3-10}$ carbocycle substituted with 0–2 $R^{4b}$, $(CR_3R^{3a})$—$C_{3-10}$ carbocycle substituted with 0–2 $R^{4b}$, 5–10 membered heterocycle substituted with 0–2 $R^{4b}$ and consisting of carbon atoms and from 1–4 heteroatoms selected from the group consisting of N, O, and $S(O)_p$, and $(CR^3R^{3a})$-5–10 membered heterocycle substituted with 0–2 $R^{4b}$ and consisting of carbon atoms and from 1–4 heteroatoms selected from the group consisting of N, O, and $S(O)_p$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.

[4] In another preferred embodiment, the present invention provides a novel compound, wherein:
ring M is substituted with 0–2 $R^{1a}$ and is selected from the group:

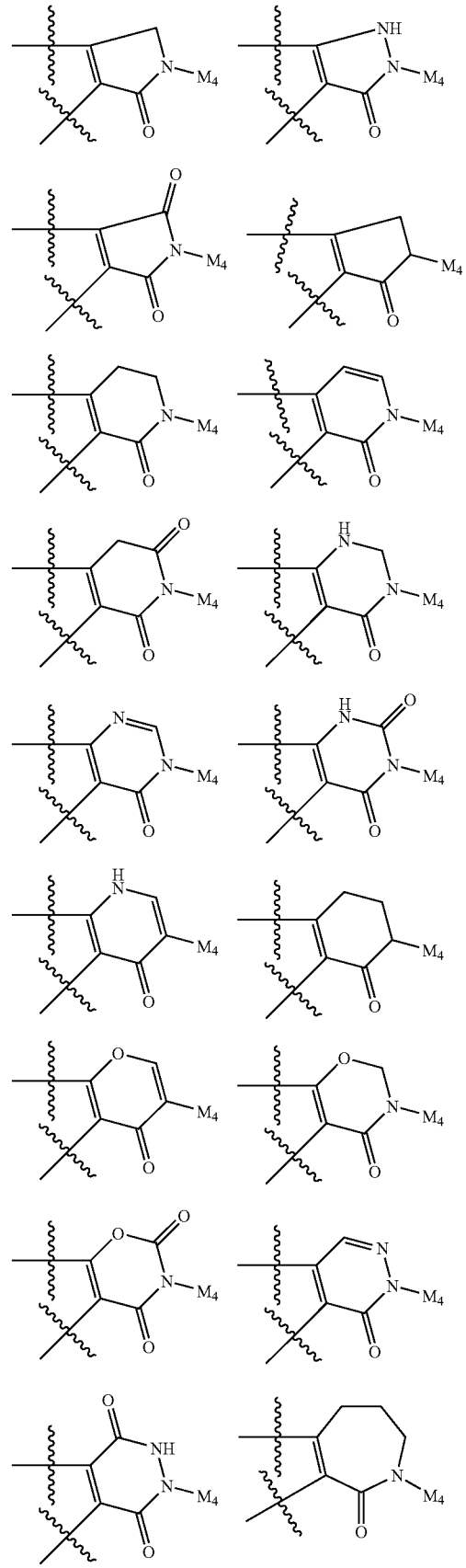

-continued
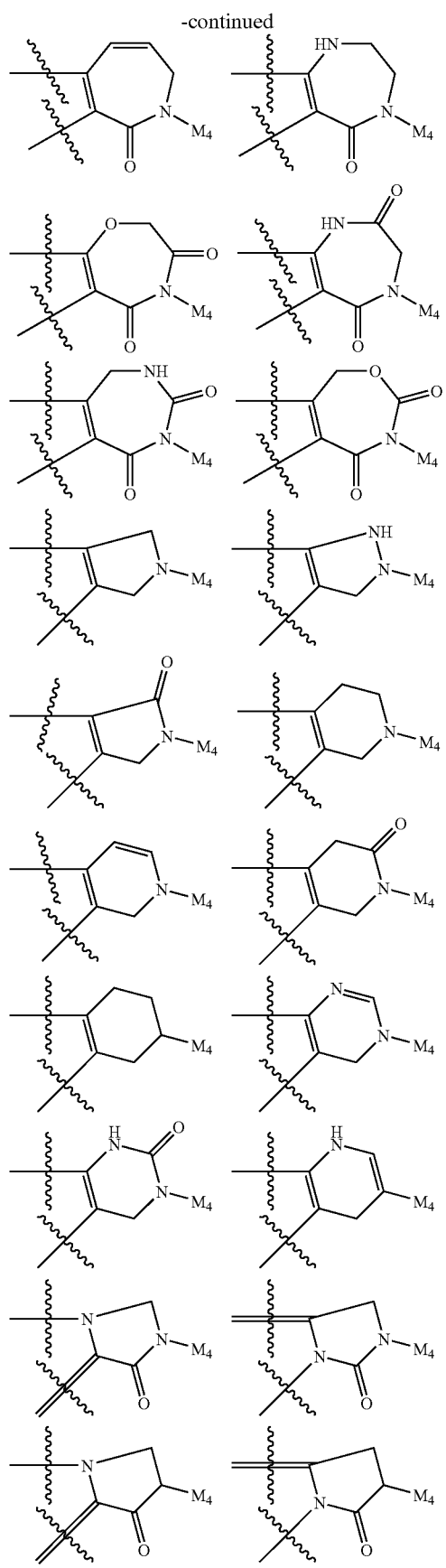
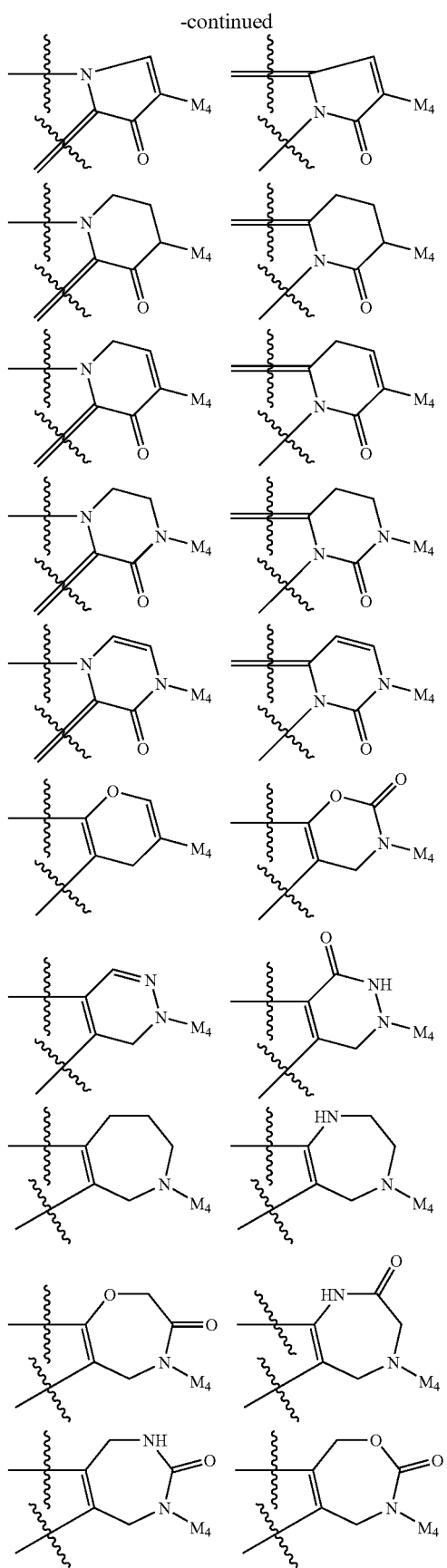

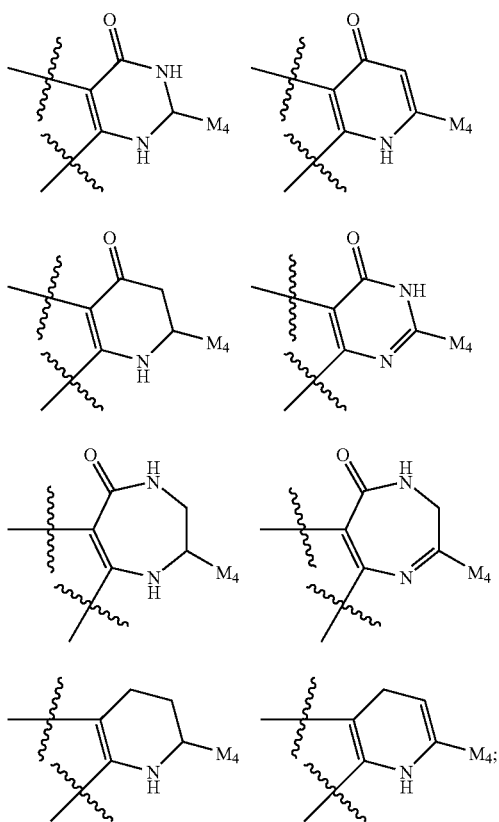
ring P, including $P_1$, $P_2$, $P_3$, and $P_4$ is selected from group:
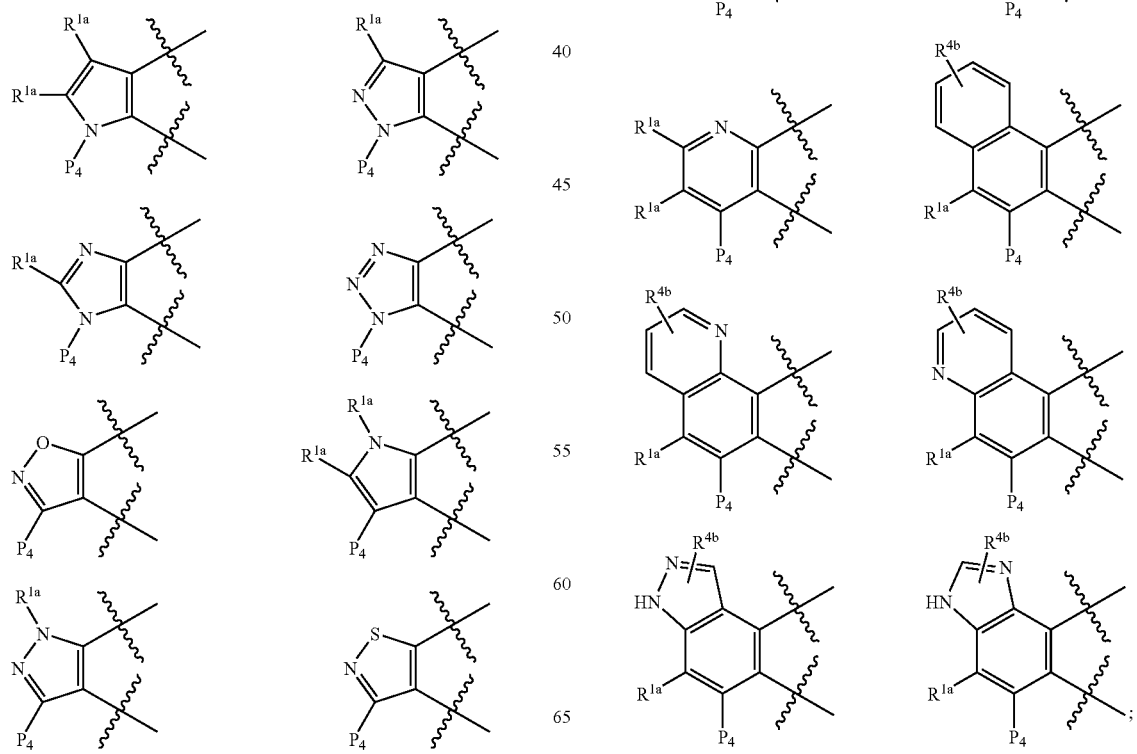
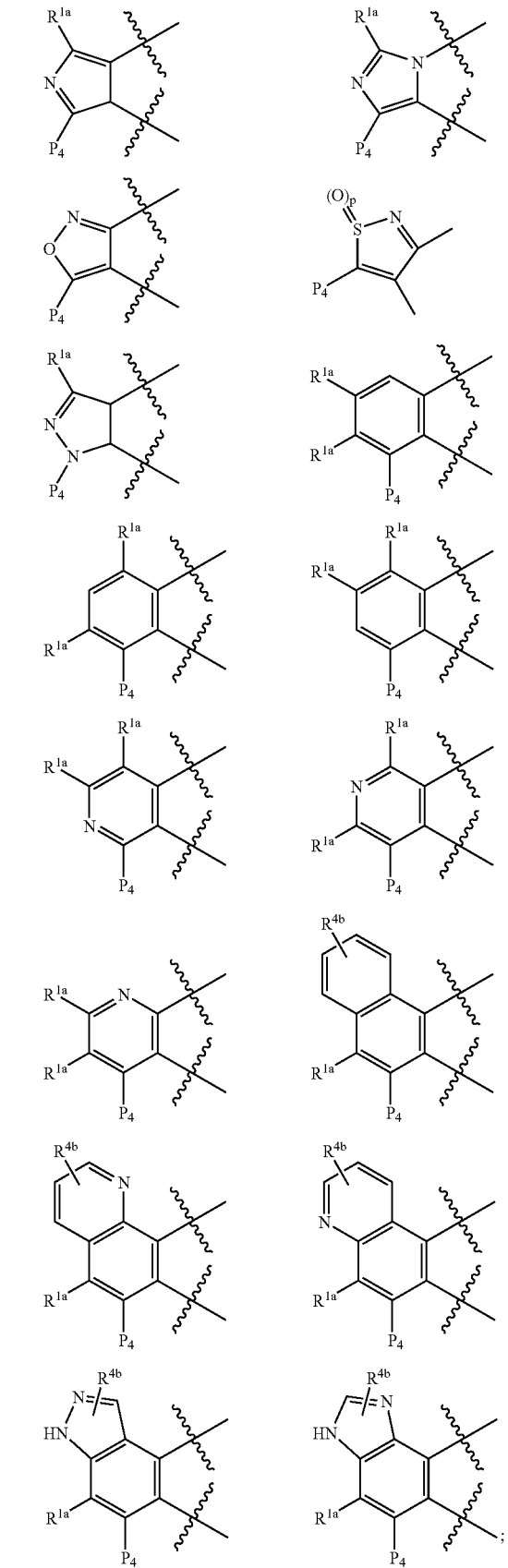

G is selected from the group:

phenyl; 2-amido-4-methoxy-phenyl; 2-amido-phenyl; 2-aminomethyl-3-fluoro-phenyl; 2-aminomethyl-4-fluoro-phenyl; 2-aminomethyl-4-methoxy-phenyl; 2-aminomethyl-5-fluoro-phenyl; 2-aminomethyl-5-methoxy-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 2-methylsulfonyl-phenyl; 2-aminomethyl-4-ethyl-phenyl; 2-aminosulfonyl-4-ethyl-phenyl; 2-amido-4-ethyl-phenyl; 3-(N,N-dimethylamino)-4-chloro-phenyl; 3-(N,N-dimethylamino)-phenyl; 3-(N-methylamino)-4-chloro-phenyl; 3-(N-methylamino)-phenyl; 3-amido-phenyl; 3-amino-4-chloro-phenyl; 3-aminomethyl-phenyl; 3-amino-phenyl; 3-chloro-phenyl; 4-(N,N-dimethylamino)-5-chloro-thien-2-yl; 4-(N-methylamino)-5-chloro-thien-2-yl; 4-amino-5-chloro-thien-2-yl; 4-chloro-phenyl; 4-ethyl-phenyl; 4-ethyl-2-methylsulfonyl-phenyl; 4-ethyl-2-methoxy-phenyl; 4-methoxy-2-methylsulfonyl-phenyl; 4-methoxy-phenyl; 5-(N,N-dimethylamino)-4-chloro-thien-2-yl; 5-(N-methylamino)-4-chloro-thien-2-yl; 5-amino-4-chloro-thien-2-yl; 5-chloro-pyrid-2-yl; 5-chloro-thien-2-yl; 5-methoxy-thien-2-yl; 5-methyl-thien-2-yl; 5-fluoro-thien-2-yl; 6-amino-5-chloro-pyrid-2-yl; 6-amino-pyrid-2-yl;

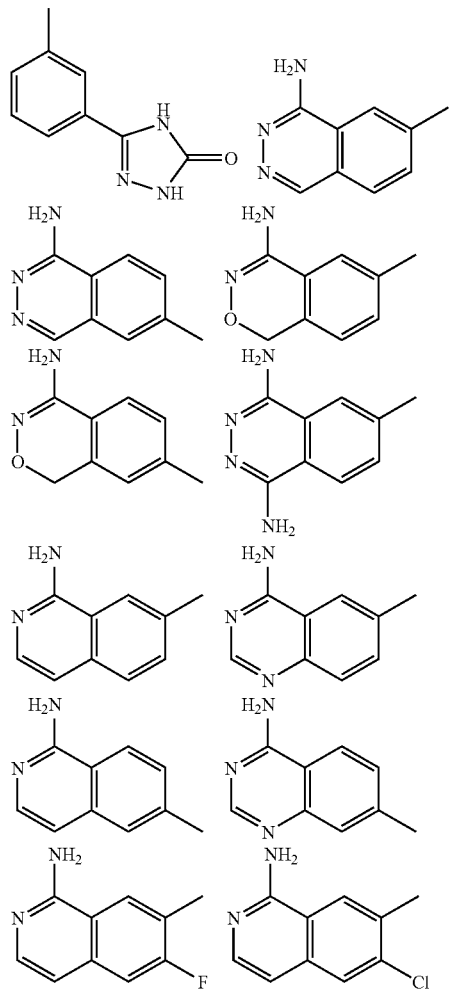

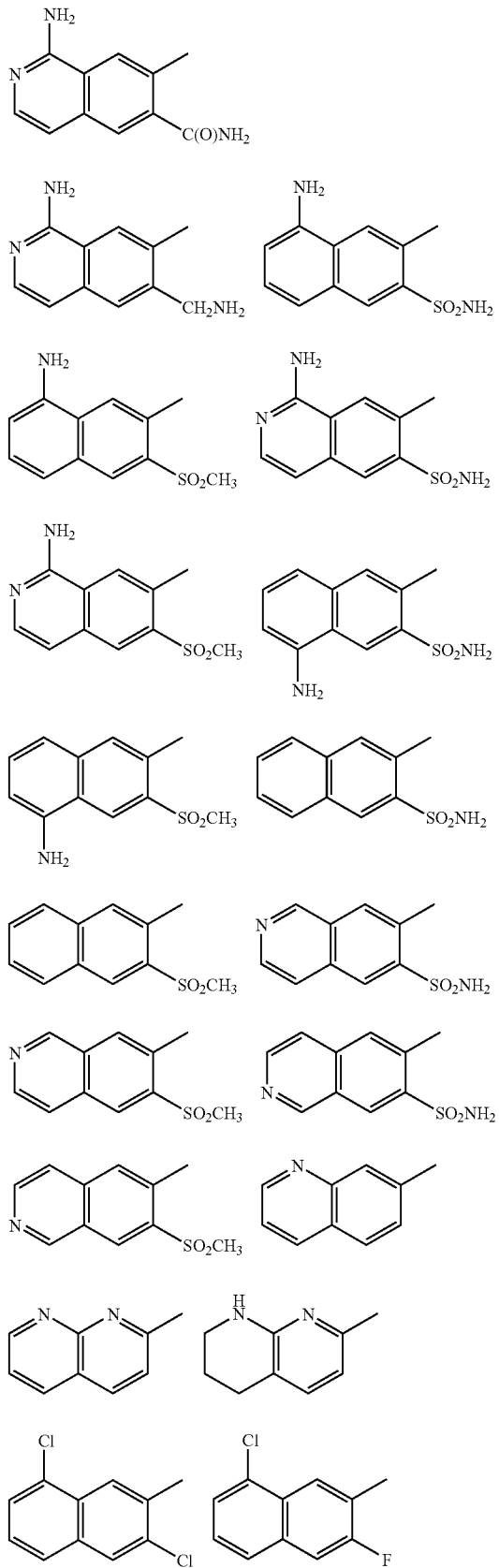

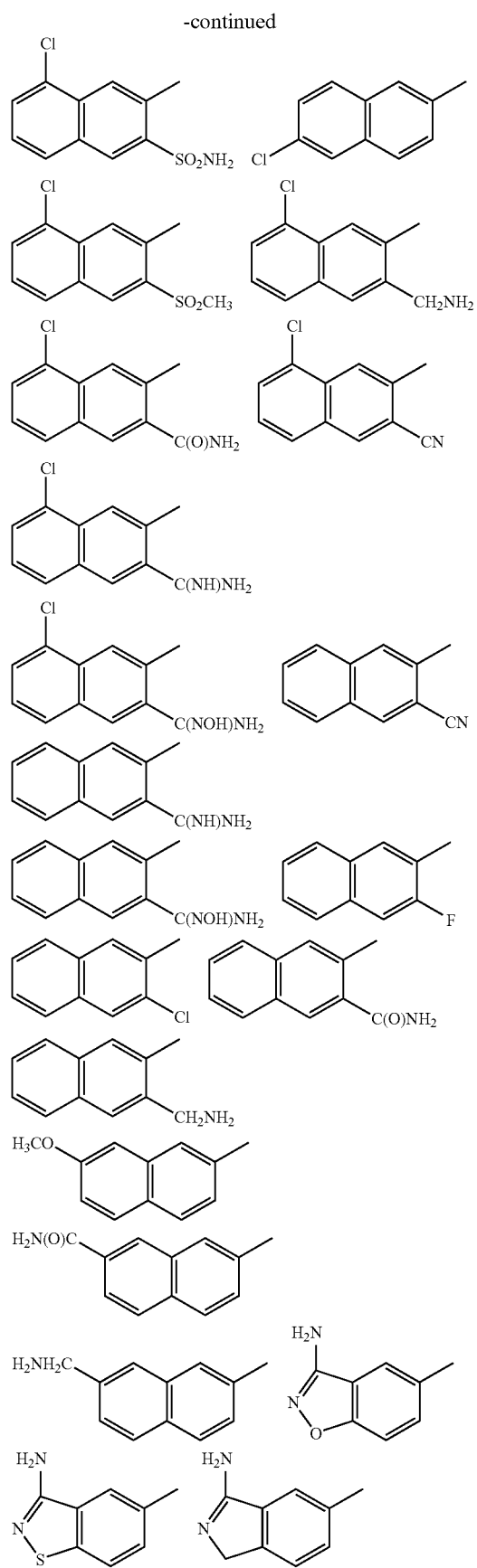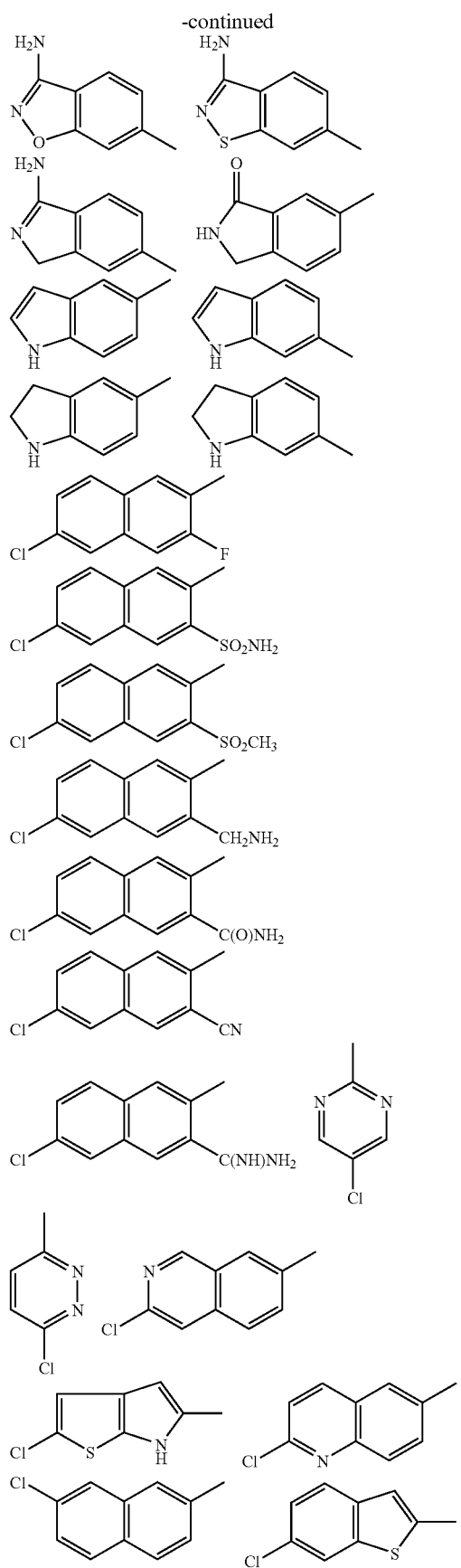

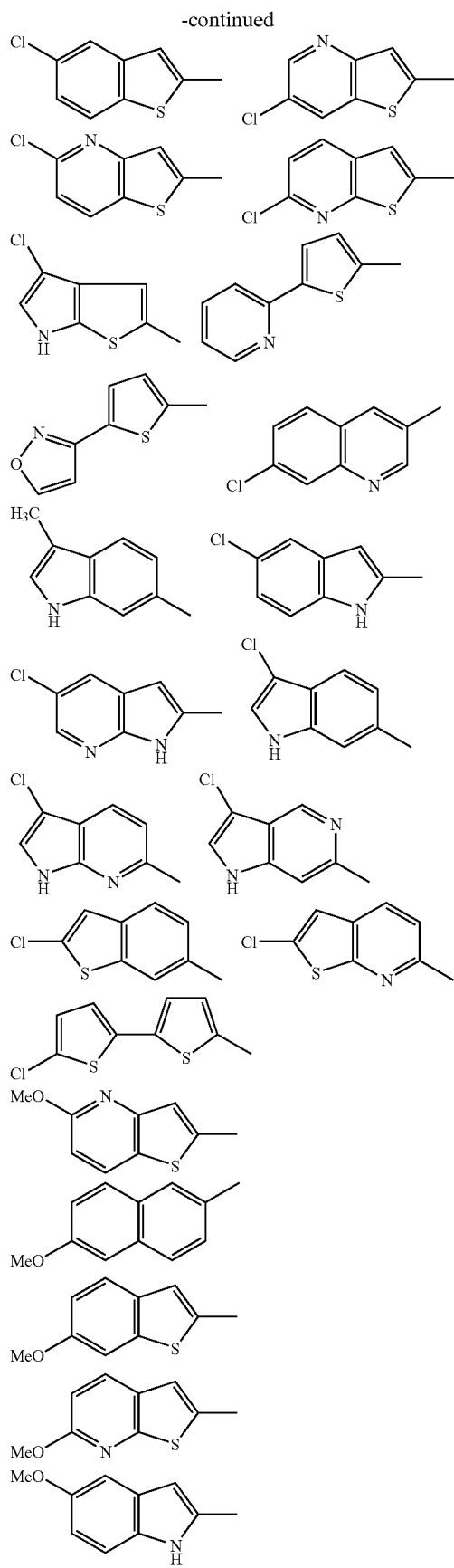
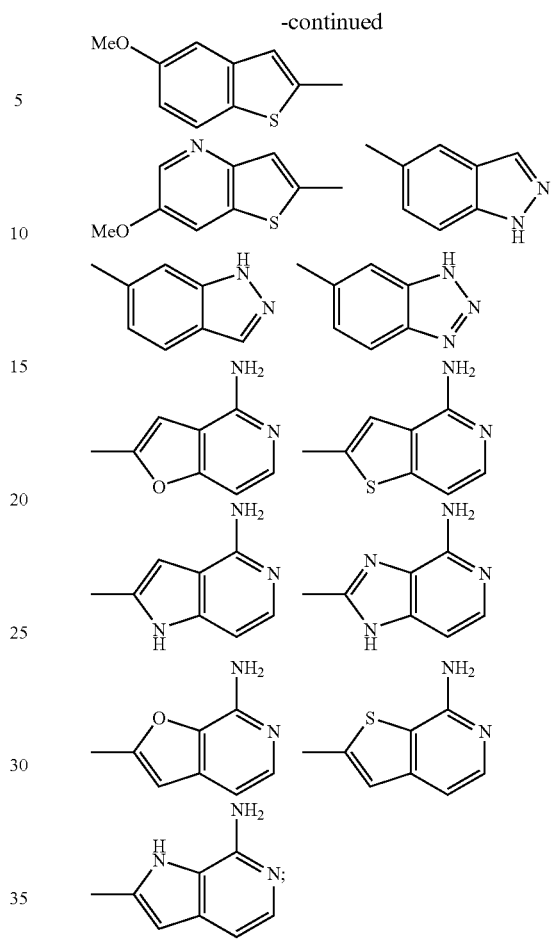

$G_1$ is absent or is selected from $CH_2$, $CH_2CH_2$, $CH=CH$, $CH_2O$, $OCH_2$, $NH$, $CH_2NH$, $NHCH_2$, $CH_2C(O)$, $C(O)CH_2$, $C(O)NH$, $NHC(O)$, $CH_2S(O)_2$, $S(O)_2(CH_2)$, $SO_2NH$, and $NHSO_2$, provided that $G_1$ does not form a N—S, $NCH_2N$, $NCH_2O$, or $NCH_2S$ bond with either group to which it is attached;

A is selected from cyclohexyl, piperidinyl, phenyl, pyridyl, and pyrimidyl, and is substituted with 0–2 $R^4$;

X is selected from $CH_2$, $C(O)$, —$S(O)_2$—, —$NHC(O)$—, —$C(O)NH$—, —$CH_2NH$—, O, and —$CH_2O$—;

Y is selected from $C(CH_3)_2$, $C(CH_2CH_3)_2$, cyclopropyl, cyclobutyl, cyclopentyl, cyclopentanonyl, cyclohexyl, cyclohexanonyl, pyrrolidinyl, pyrrolidinonyl, piperidinyl, piperidinonyl, tetrahydrofuranyl, and tetrahydropyranyl, and, when Y is a ring, Y is substituted with 0–1 $R^4$;

$R^{1a}$, at each occurrence, is selected from H, $R^{1b}$, $CH(CH_3)R^{1b}$, $C(CH_3)_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^2$, $C(O)NR^2R^{2a}$, $SO_2NR^2R^{2a}$, $NR^2SO_2R^2$, and 5–6 membered aromatic heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5–6 membered aromatic heterocycle substituted with 0–1 $R^{4b}$ and consisting of: carbon atoms and 1–4 heteroatoms selected from the group consisting of N, O, and $S(O)_p$;

$R^{2a}$, at each occurrence, is selected from H, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle substituted with 0–1 $R^{4b}$ and consisting of: carbon atoms and 1–4 heteroatoms selected from the group consisting of N, O, and $S(O)_p$;

alternatively, $R^2$ and $R^{2a}$, together with the nitrogen atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle substituted with 0–1 $R^{4b}$ and consisting of: carbon atoms and 1–4 heteroatoms selected from the group consisting of N, O, and $S(O)_p$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle substituted with 0–1 $R^{4b}$ and consisting of carbon atoms and from 1–4 heteroatoms selected from the group consisting of N, O, and $S(O)_p$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—S$(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^4$, at each occurrence, is selected from OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $CF_3$, and $CF_2CF_3$;

$R^{4a}$ is selected from —$(CR^3R^{3g})_r$-5–6 membered carbocycle substituted with 0–3 $R^{4c}$, —$(CR^3R^{3g})_r$-5–6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r$—$C(O)NR^{2d}R^{2d}$, $(CR^3R^{3g})_r$—$NR^{2d}C(O)R^{2e}$, $(CR^3R^{3g})_r$—$C(O)R^{2e}$, $(CR^3R^{3g})_rNR^{2d}C(O)NR^{2d}R^{2d}$, $(CR^3R^{3g})_r$—$NR^{2d}C(O)OR^{2d}$, $(CR^3R^{3g})_r$—$NR^{2d}SO_2R^{2d}$, and $(CR^3R^{3g})_r$—$S(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, and $CF_3$;

$R^{4c}$, at each occurrence, is selected from =O, $OR^2$, $CH_2OR^2$, F, Br, Cl, $CF_3$, $CH_3$, $CH_2CH_3$, $CH_2CH_2CH_3$, $CH(CH_3)_2$, $C_{2-3}$ alkenyl, $C_{2-3}$ alkynyl, —CN, $NO_2$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, $CF_2CF_3$, $C_{3-6}$ carbocycle substituted with 0–2 $R^{4b}$, $(CH_2)$—$C_{3-6}$ carbocycle substituted with 0–2 $R^{4b}$, 5–6 membered heterocycle substituted with 0–2 $R^{4b}$ and consisting of carbon atoms and from 1–4 heteroatoms selected from the group consisting of N, O, and $S(O)_p$, and $(CH_2)$-5–6 membered heterocycle substituted with 0–2 $R^{4b}$ and consisting of carbon atoms and from 1–4 heteroatoms selected from the group consisting of N, O, and $S(O)_p$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$; and, r, at each occurrence, is selected from 0, 1, and 2.

[5] In another preferred embodiment, the present invention provides a novel compound, wherein:

ring M is substituted with 0–1 $R^{1a}$ and is selected from the group:

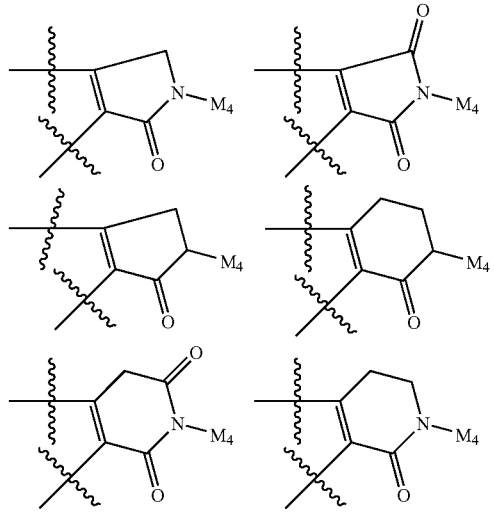

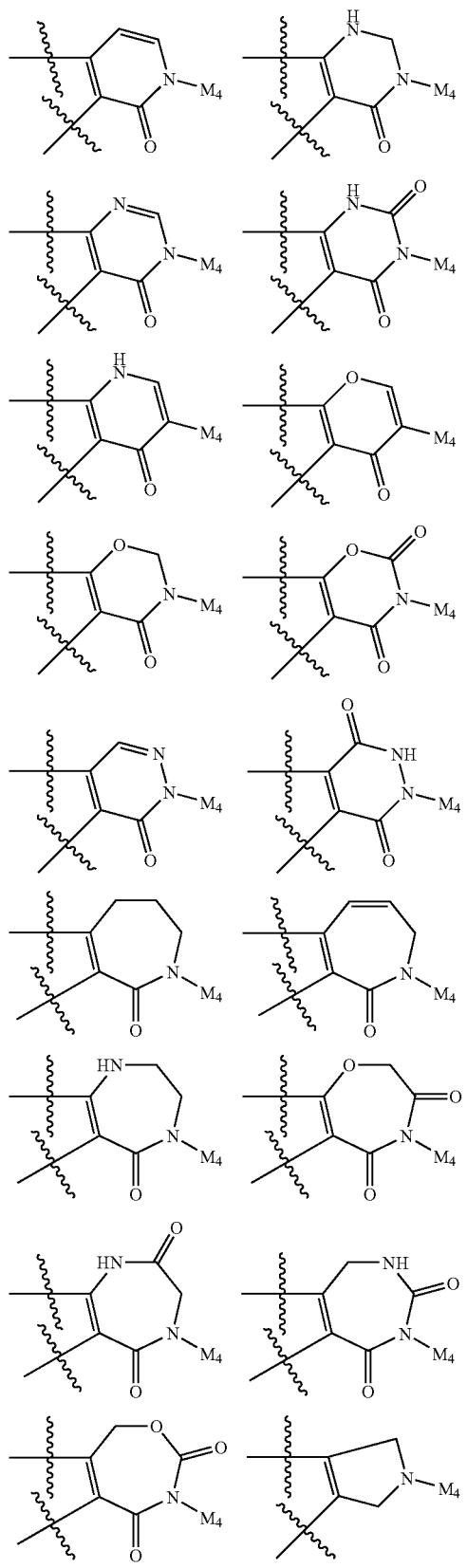
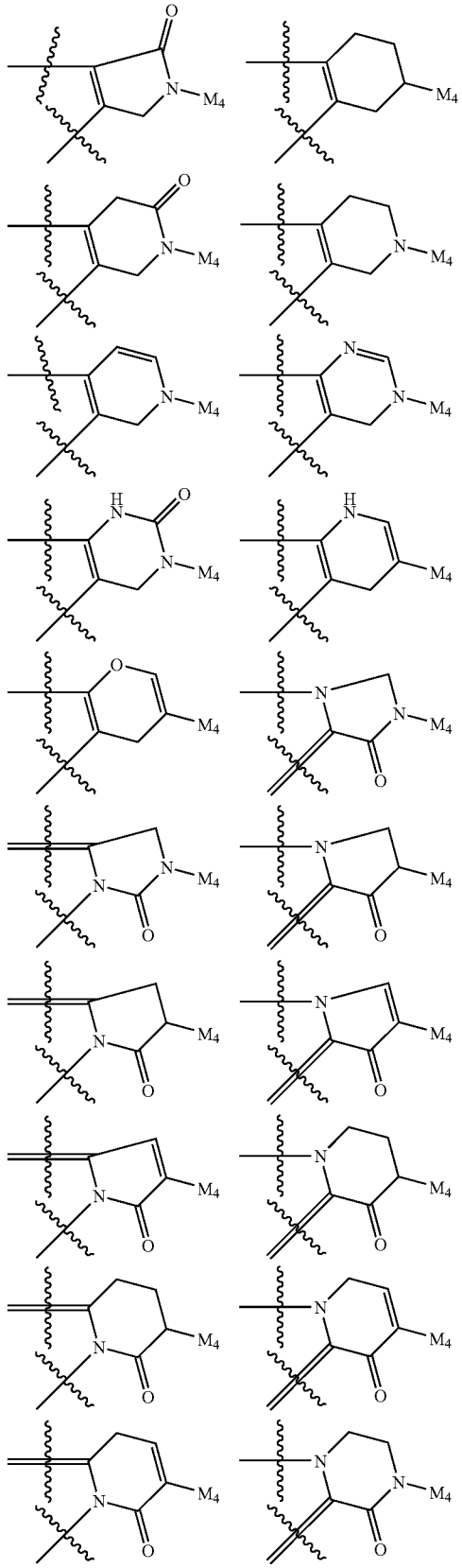

-continued

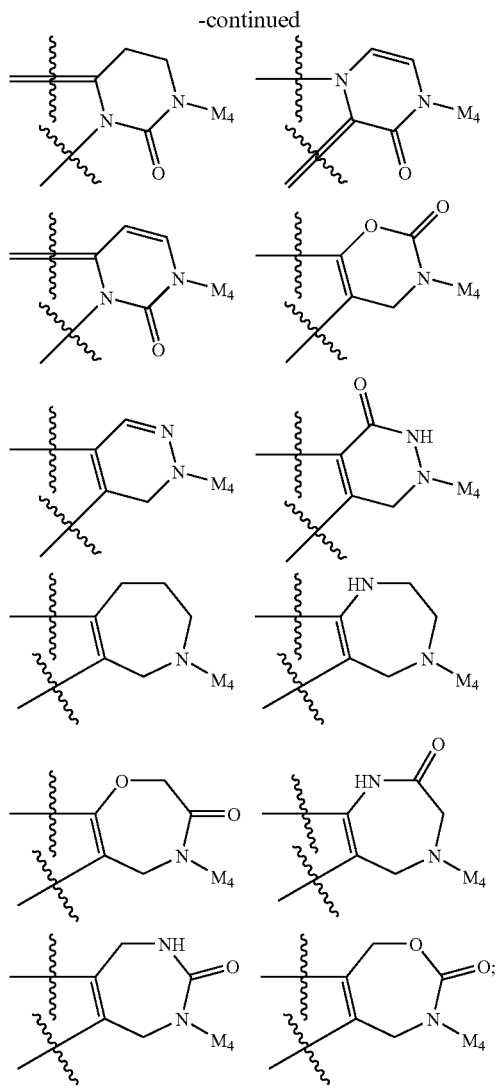

ring P, including P₁, P₂, P₃, and P₄ is selected from group:

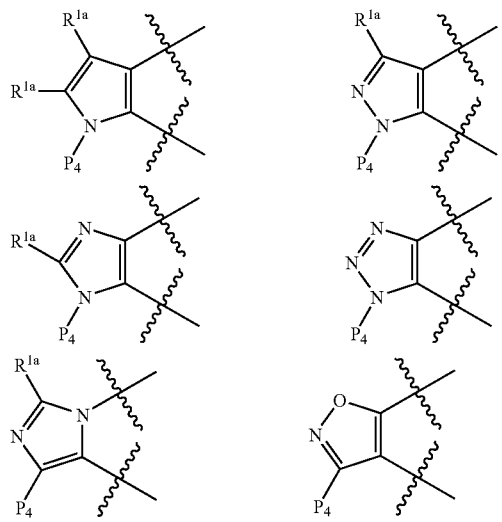

-continued

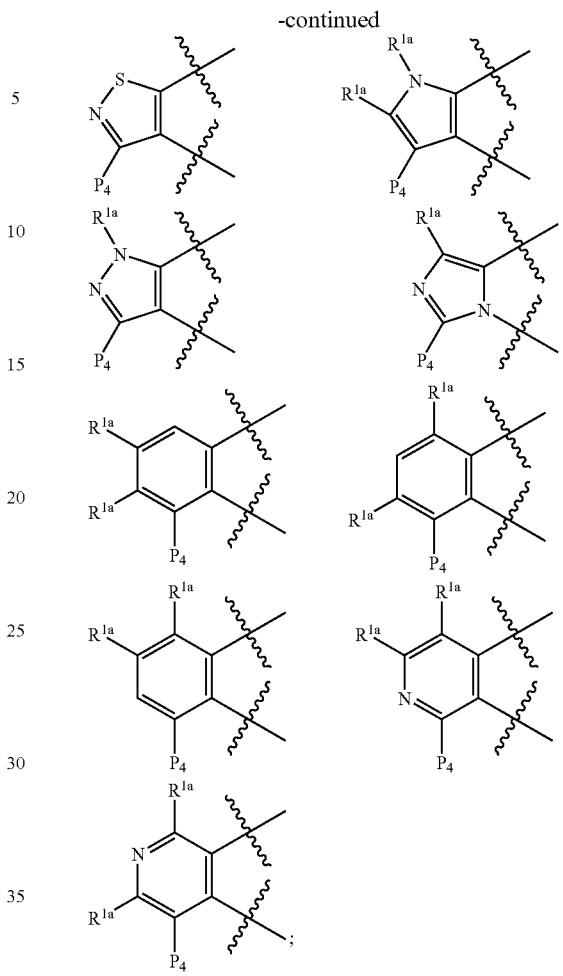

-G is selected from:
2-amido-4-methoxy-phenyl; 2-amido-phenyl; 2-aminomethyl-3-fluoro-phenyl; 2-aminomethyl-4-fluoro-phenyl; 2-aminomethyl-5-fluoro-phenyl; 2-aminomethyl-6-fluoro-phenyl; 2-aminomethyl-phenyl; 2-aminopyrid-4-yl; 2-aminosulfonyl-4-methoxy-phenyl; 2-aminosulfonyl-phenyl; 3-amido-phenyl; 3-amino-4-chloro-phenyl; 3-aminomethyl-phenyl; 3-chloro-phenyl; 4-chloro-phenyl; 4-ethyl-phenyl; 4-methoxy-phenyl; 5-chloro-pyrid-2-yl; 5-chloro-thien-2-yl; 6-amino-5-chloro-pyrid-2-yl; 6-amino-pyrid-2-yl;

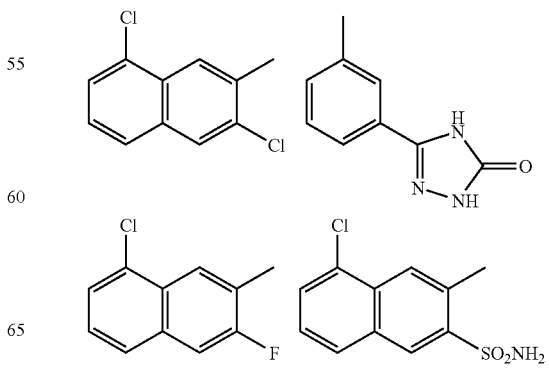

-continued
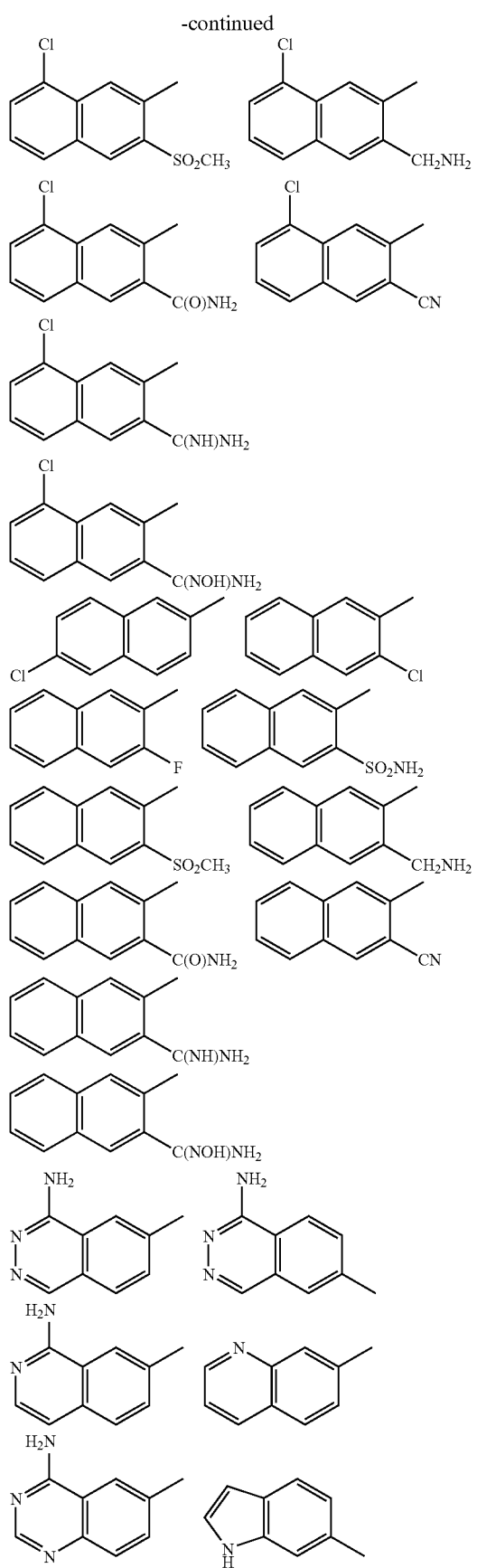
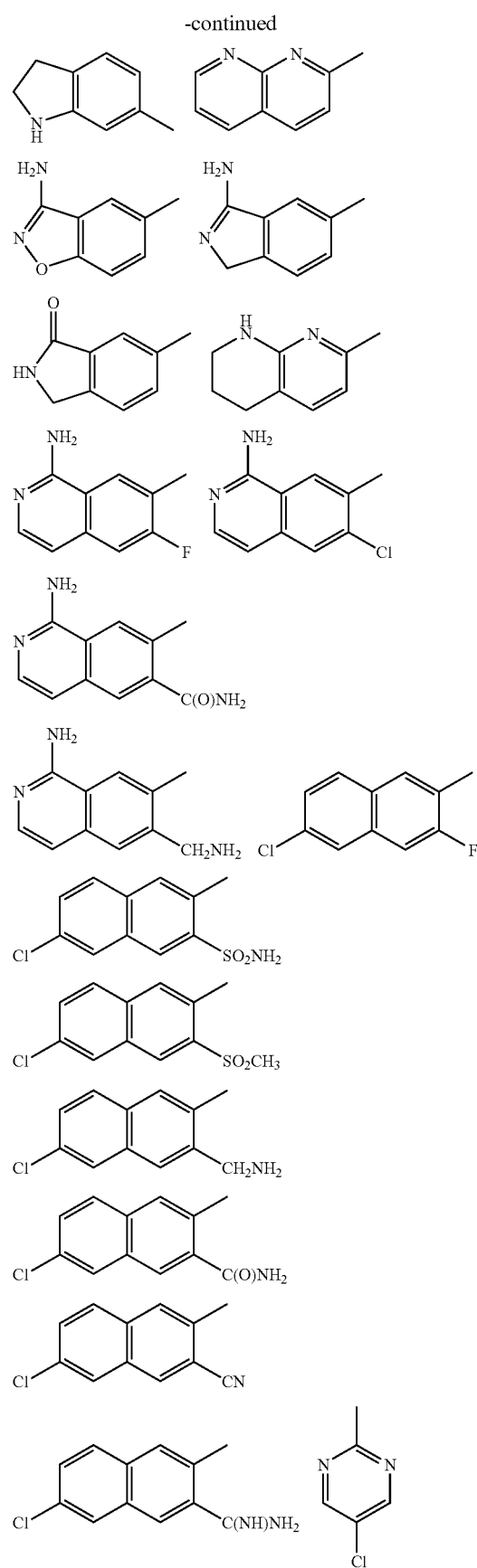

-continued

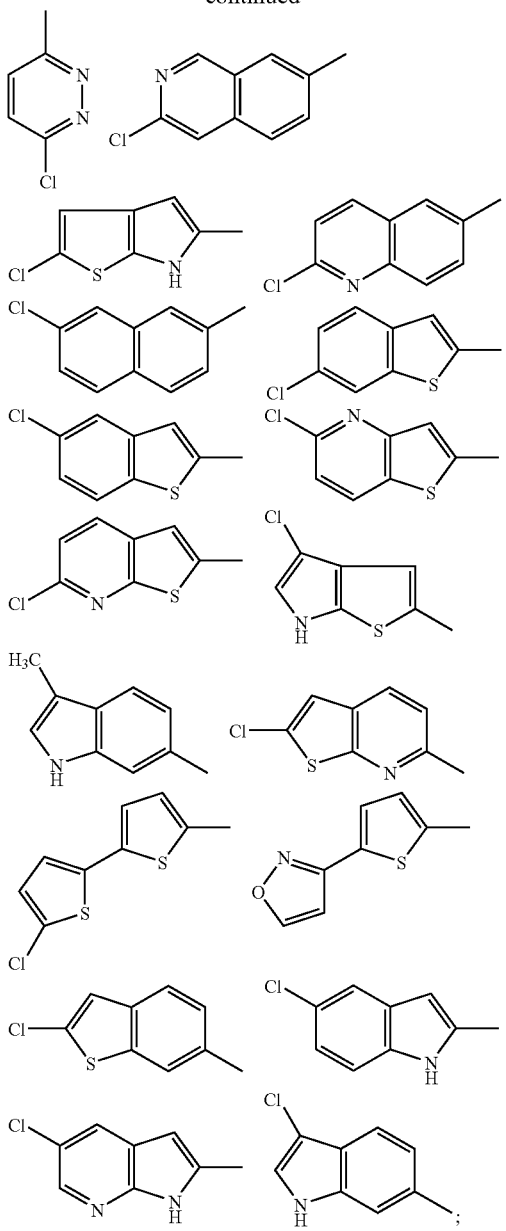

A is selected from the group: cyclohexyl, piperidinyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

Y is selected from $C(CH_3)_2$, $C(CH_2CH_3)_2$, cyclopropyl, cyclobutyl, cyclopentyl, 2-cyclopentanonyl, cyclohexyl, 2-cyclohexanonyl, pyrrolidinyl (attached to A and $R^{4a}$ at the 2-position), pyrrolidinyl (attached to A and $R^{4a}$ at the 3-position), 2-pyrrolidinonyl (attached to A and $R^{4a}$ at the 3-position), piperidinyl (attached to A and $R^{4a}$ at the 4-position), 4-piperidinonyl (attached to A and $R^{4a}$ at the 3-position), tetrahydrofuranyl, and tetrahydropyranyl (attached to A and $R^{4a}$ at the 4-position);

$R^{1a}$, at each occurrence, is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N$ $(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5 membered aromatic heterocycle substituted with 0–1 $R^{4b}$ and consisting of: carbon atoms and 1–4 heteroatoms selected from the group consisting of N, O, and $S(O)_p$;

$R^{2a}$, at each occurrence, is selected from H, $CH_3$, and $CH_2CH_3$;

alternatively, $R^2$ and $R^{2a}$, together with the nitrogen atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from OH, $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from —$(CH_2)_r$-5–6 membered carbocycle substituted with 0–3 $R^{4c}$, —$(CH_2)_r$-5–6 membered heterocycle substituted with 0–3 $R^{4c}$ and consisting of: carbon atoms and 1–4 heteroatoms selected from the group consisting of N, O, and $S(O)_p$, $(CH_2)_rNR^{2d}R^{2d}$, $(CH_2)_rN(\rightarrow O)R^{2d}R^{2d}$, $(CH_2)_rOR^{2d}$, $(CH_2)_r$—$C(O)$ $NR^{2d}R^{2d}$, $(CH_2)_r$—$NR^{2d}C(O)R^{2e}$, $(CH_2)_r$—$C(O)R^{2e}$, $(CH_2)_r$—$NR^{2d}C(O)NR^{2d}R^{2d}$, $(CH_2)_r$—$NR^{2d}C(O)OR^{2d}$, $(CH_2)_r$—$NR^{2d}SO_2R^{2d}$, and $(CH_2)_r$—$S(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$;

$R^{4c}$, at each occurrence, is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $C_{2-3}$ alkenyl, $C_{2-3}$ alkynyl, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, cyclopropyl substituted with 0–1 $R^{4b}$, cyclobutyl substituted with 0–1 $R^{4b}$, cyclopentyl substituted with 0–1 $R^{4b}$, phenyl substituted with 0–1 $R^{4b}$, —$CH_2$-cyclopropyl substituted with 0–1 $R^{4b}$, —$CH_2$-cyclobutyl substituted with 0–1 $R^{4b}$, —$CH_2$-cyclopentyl substituted with 0–1 $R^{4b}$, benzyl substituted with 0–2 $R^{4b}$, 5–6 membered aromatic heterocycle substituted with 0–2 $R^{4b}$ and consisting of carbon atoms and from 1–4 heteroatoms selected from the group consisting of N, O, and $S(O)_p$, and $(CH_2)$5–6 membered aromatic heterocycle substituted with 0–2 $R^{4b}$ and consisting of carbon atoms and from 1–4 heteroatoms selected from the group consisting of N, O, and $S(O)_p$;

$R^5$, at each occurrence, is selected from H, =O, $CH_3$, $CH_2CH_3$, $OR^3$, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_2$—$CH_3$, $S(O)_2$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

[6] In another preferred embodiment, the present invention provides a novel compound, wherein the compound is selected from:

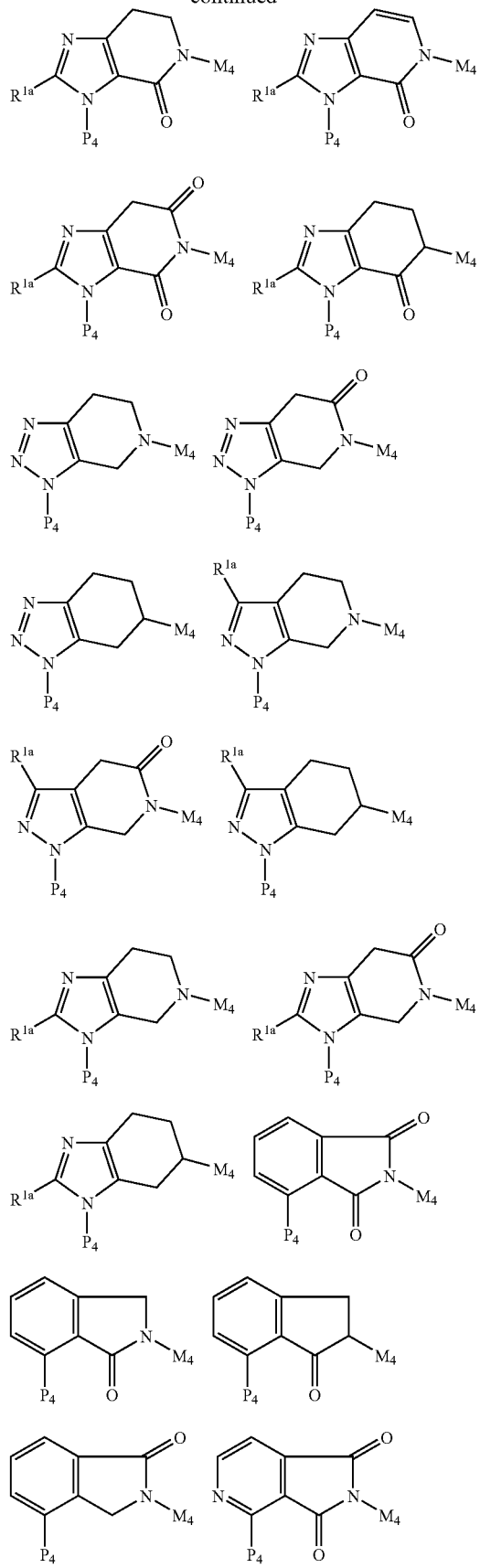

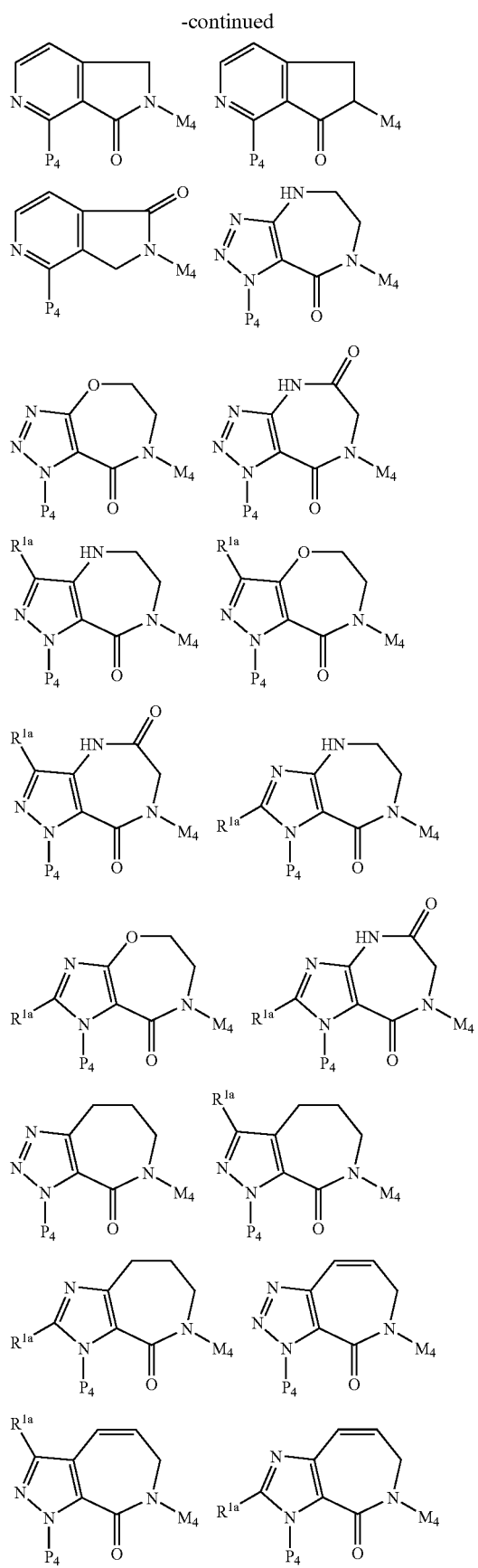
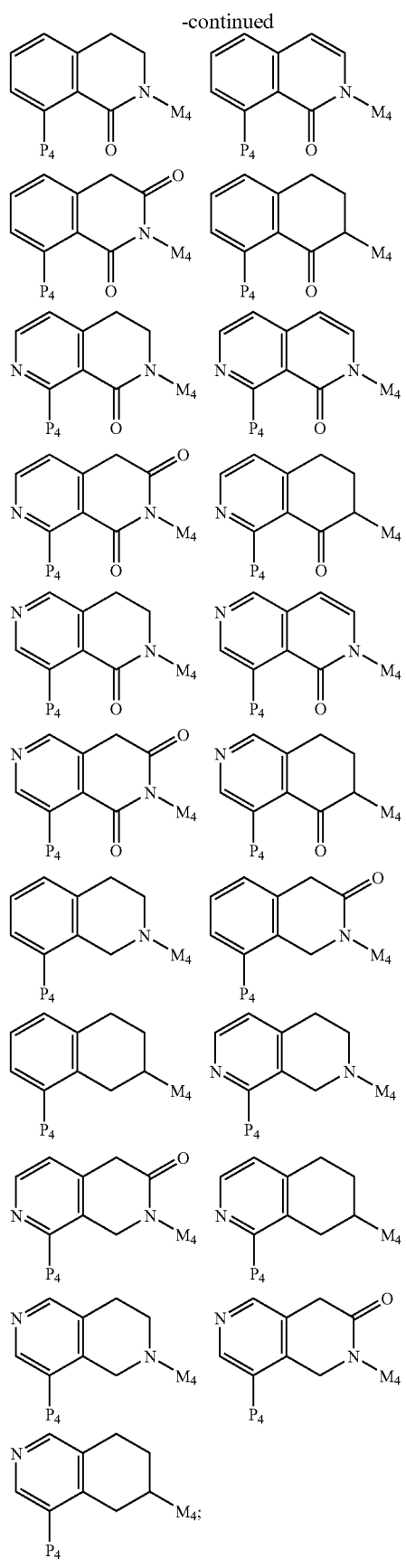

P₄ is -G₁-G;
M₄ is -A-B;
-G is selected from:
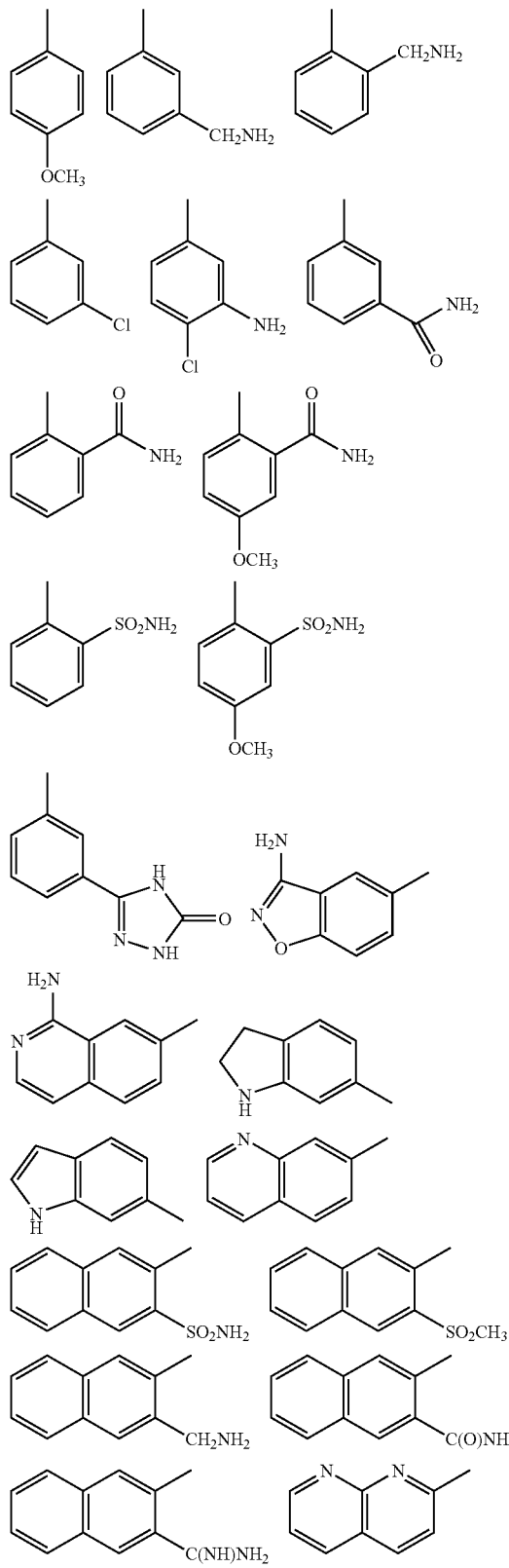
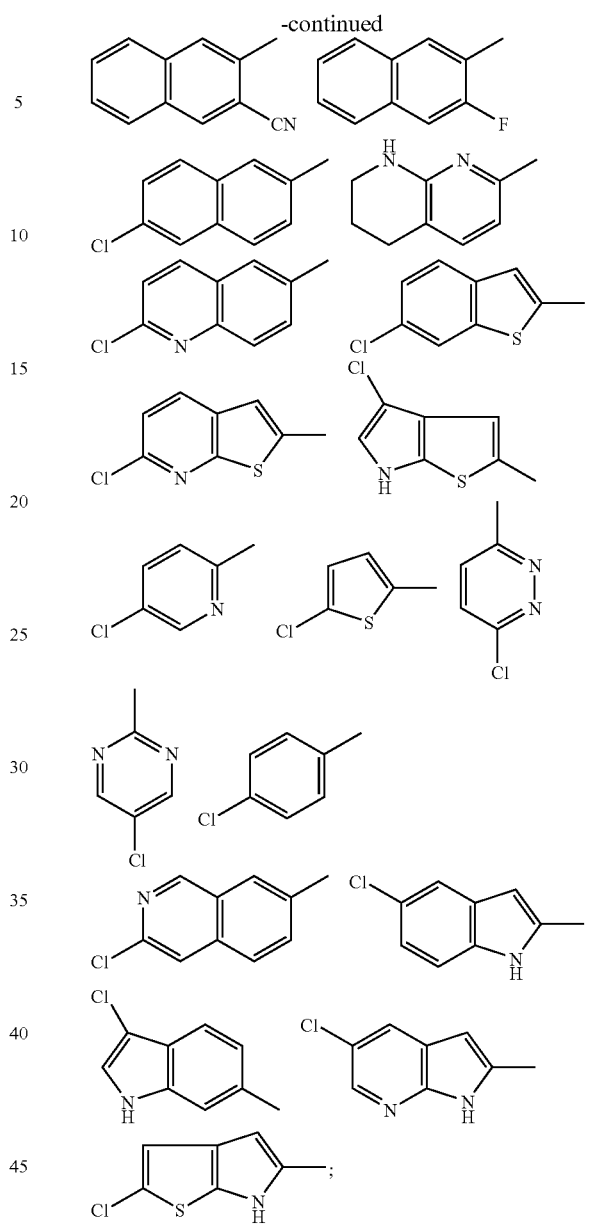
G₁ is absent or is selected from C(O)NH, NHC(O), and NHSO₂;
A-B is selected from:
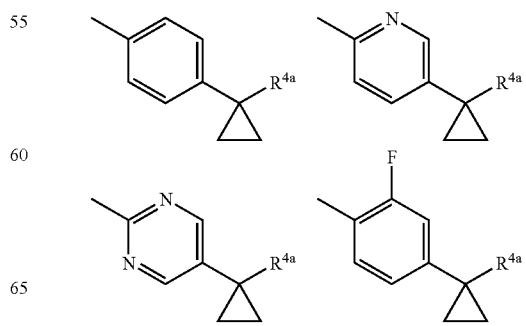

-continued

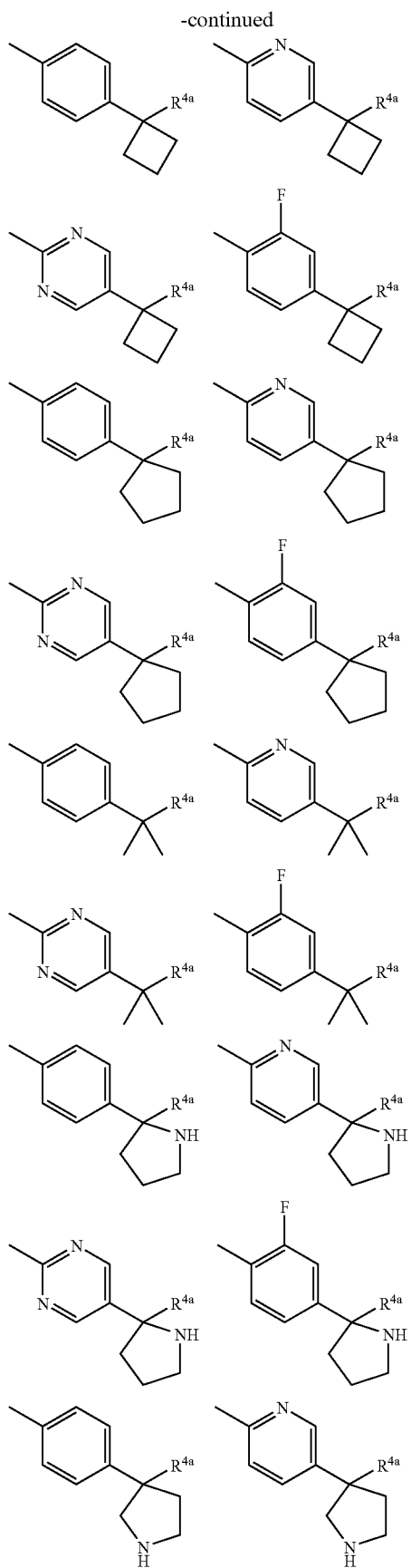

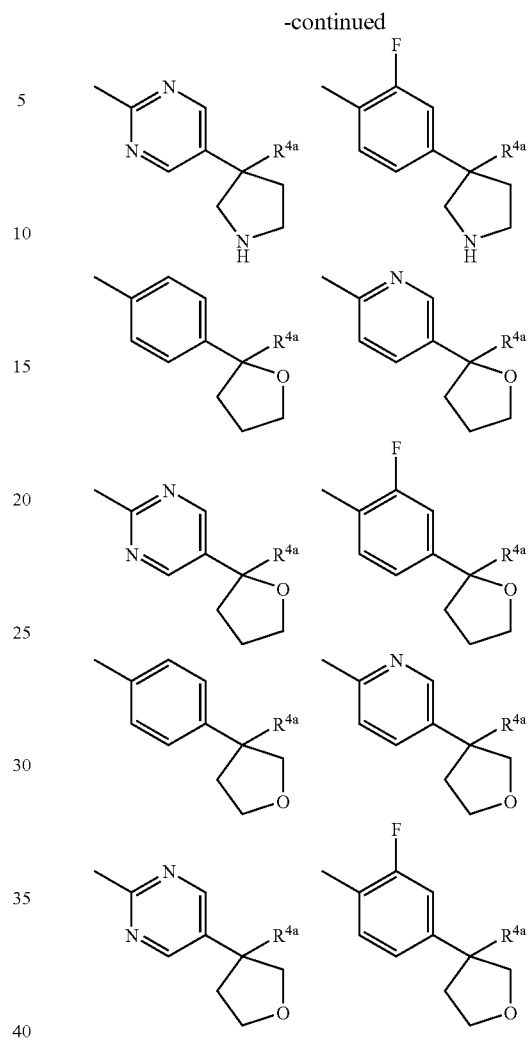

Z is selected from a bond, $CH_2$, and $CH_2CH_2$;

$R^{2d}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $C_{1-4}$ alkyl substituted with 0–1 $R^{4c}$, $C_{3-6}$ cycloalkyl substituted with 0–2 $R^{4c}$, phenyl, substituted with 0–2 $R^{4c}$, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from $NR^{2d}R^{2d}$, $CH_2NR^{2d}R^{2d}$, $CH_2CH_2NR^{2d}R^{2d}$, $N(\rightarrow O)R^{2d}R^{2d}$, $CH_2N(\rightarrow O)R^{2d}R^{2d}$, $CH_2OR^{2d}$, $C(O)R^{2e}$, $C(O)NR^{2d}R^{2d}$, $CH_2C(O)NR^{2d}R^{2d}$, $NR^{2d}C(O)R^{2e}$, $CH_2NR^{2d}C(O)R^{2e}$, $NR^{2d}C(O)NR^{2d}R^{2d}$, $CH_2NR^{2d}C(O)NR^{2d}R^{2d}$, $NR^{2d}C(O)OR^{2d}$, $CH_2NR^{2d}C(O)OR^{2d}$, $NR^{2d}SO_2R^{2d}$, $CH_2NR^{2d}SO_2R^{2d}$, $S(O)_pR^{2d}$, $CH_2S(O)_pR^{2d}$, 5–6 membered carbocycle substituted with 0–2 $R^{4c}$, —$(CH_2)$-5–6 membered carbocycle substituted with 0–2 $R^{4c}$, —$(CH_2)_2$-5–6 membered carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, —$(CH_2)$-5–6 membered heterocycle substituted with 0–2 $R^{4c}$ and consisting of: carbon atoms and 1–4 heteroatoms selected from the group consisting of N, O, and $S(O)_p$, and —$(CH_2)_2$-5–6 membered heterocycle substituted with 0–2 $R^{4c}$ and consisting of: carbon atoms and 1–4 heteroatoms selected from the group consisting of N, O, and $S(O)_p$ provided that $S(O)_p R^{2d}$ forms other than $S(O)_2H$ or $S(O)H$; and, $R^{4c}$ is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH=CH_2$, $CH\equiv CH$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_p R^{5a}$, and $CH_2S(O)_p R^{5a}$.

[7] In another preferred embodiment, the present invention provides a novel compound, wherein the compound is selected from:

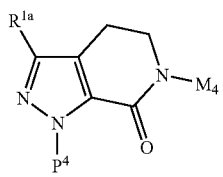 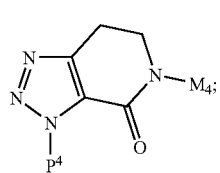

$P_4$ is -G;
$M_4$ is -A-B;
A-B is selected from:

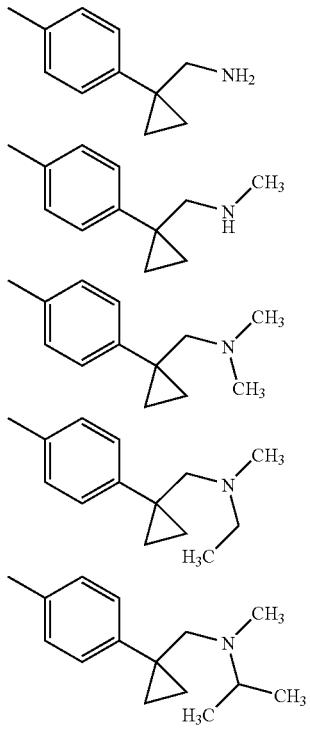

-continued

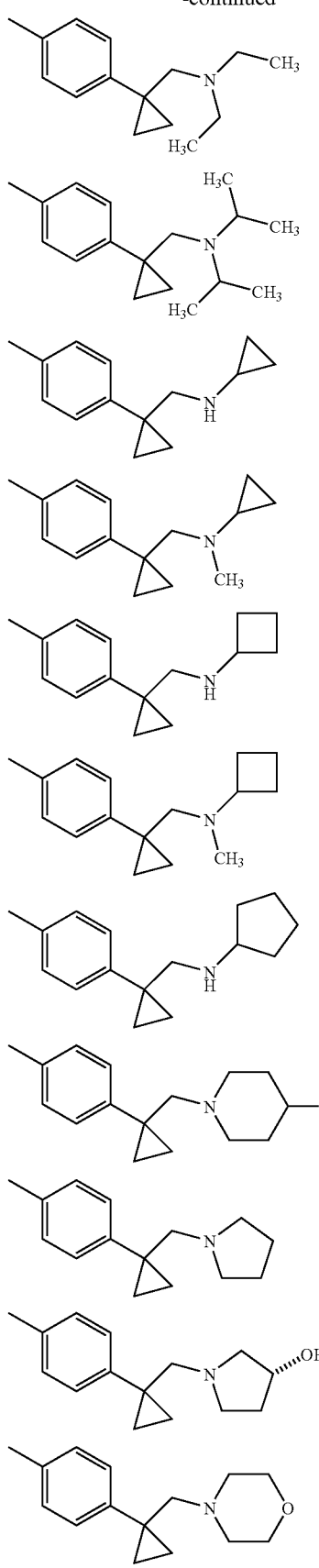

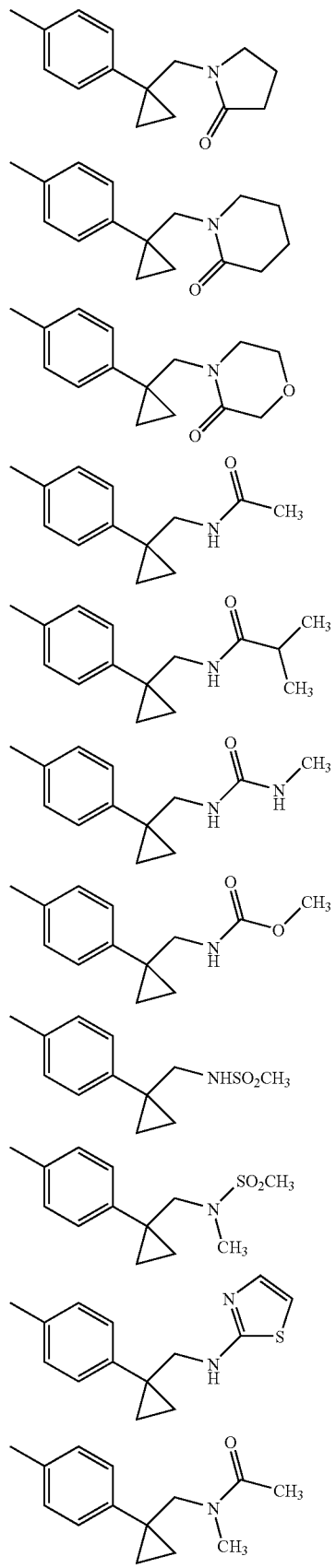
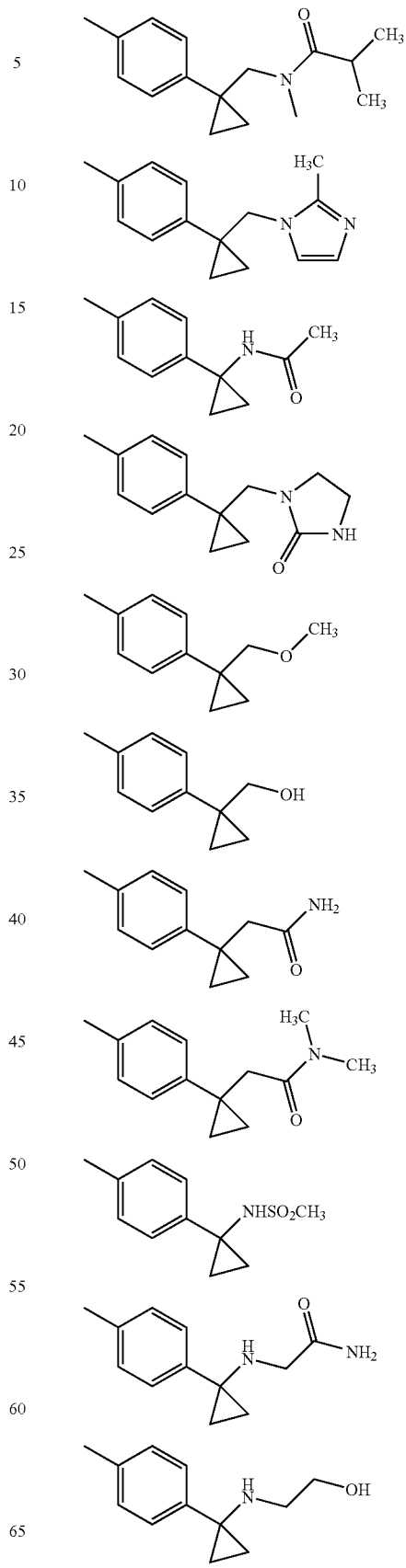

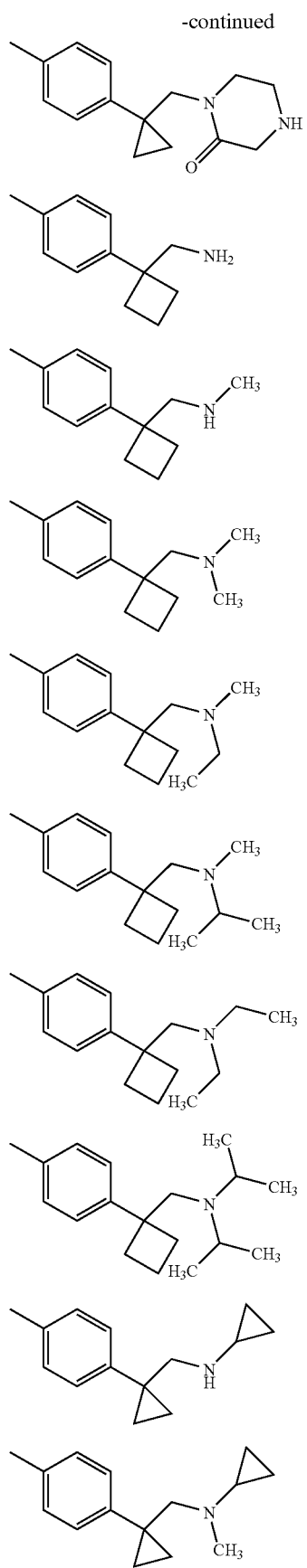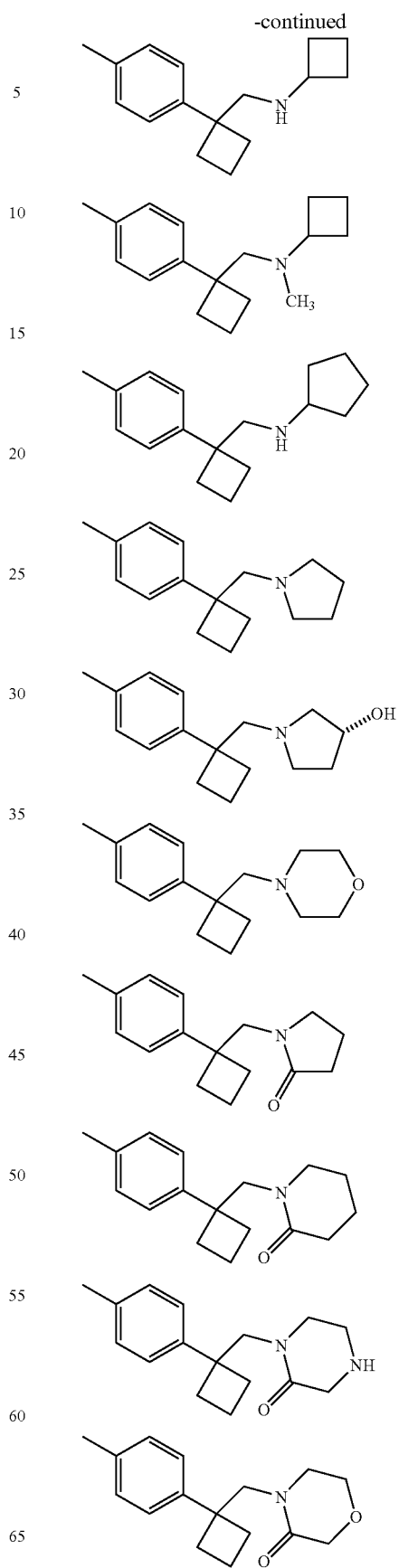

-continued
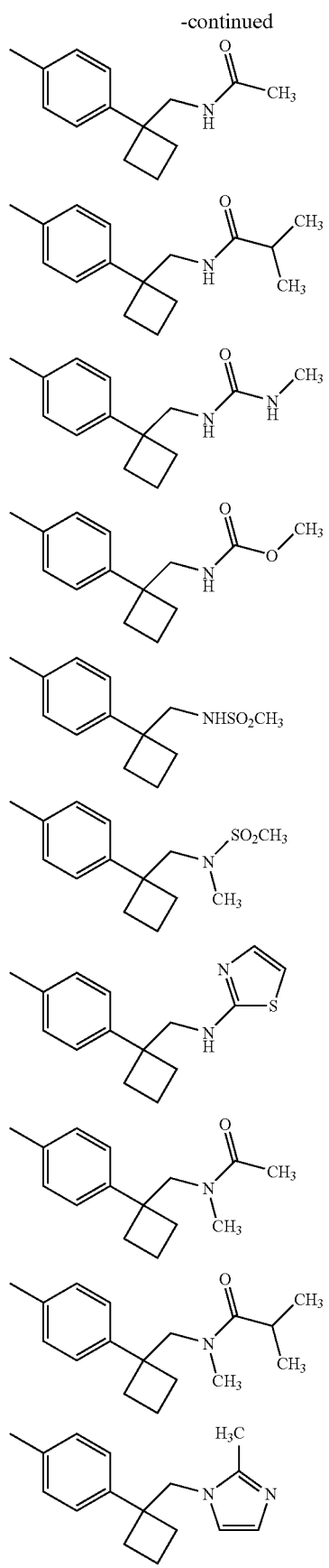
-continued
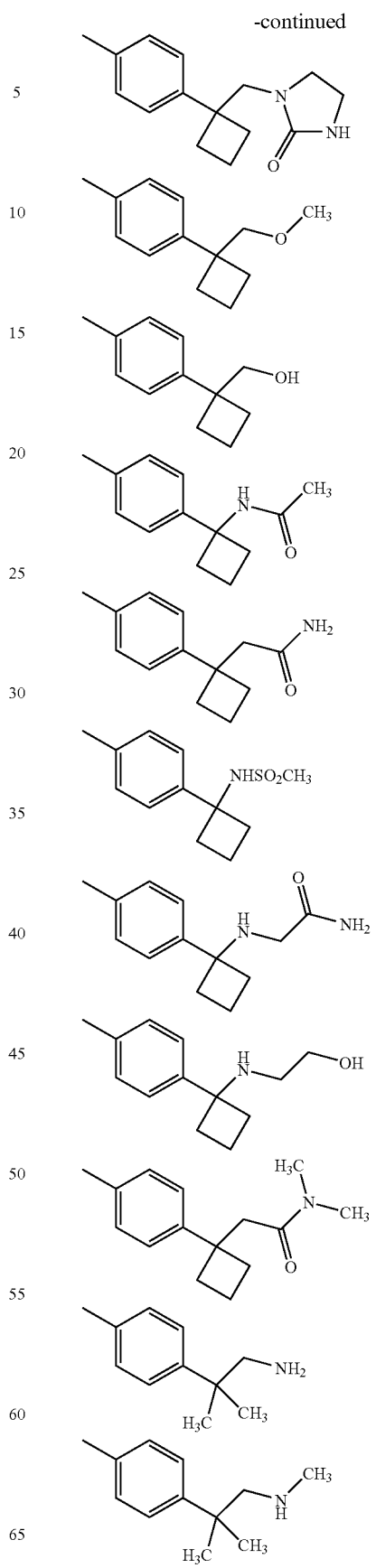

-continued
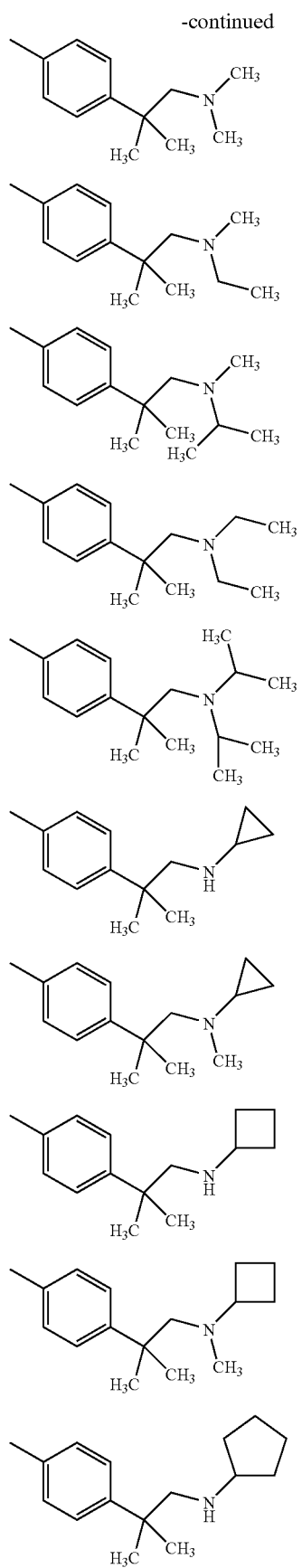
-continued
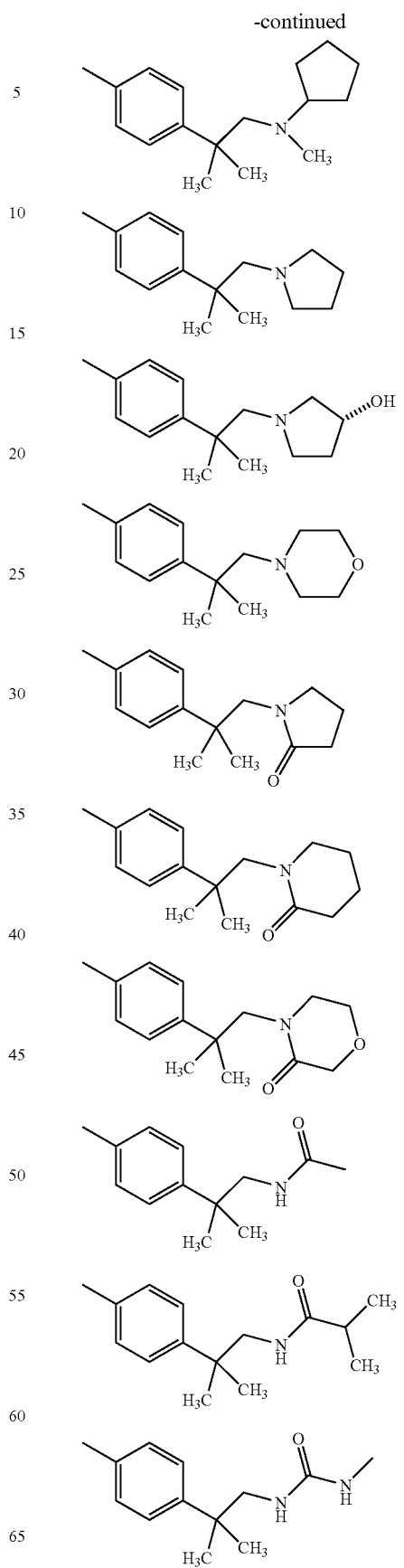

-continued
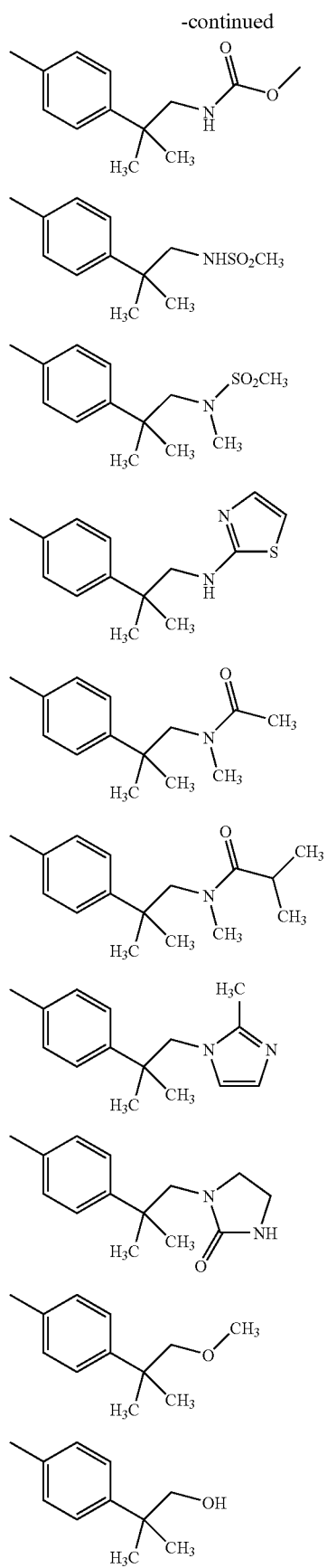
-continued
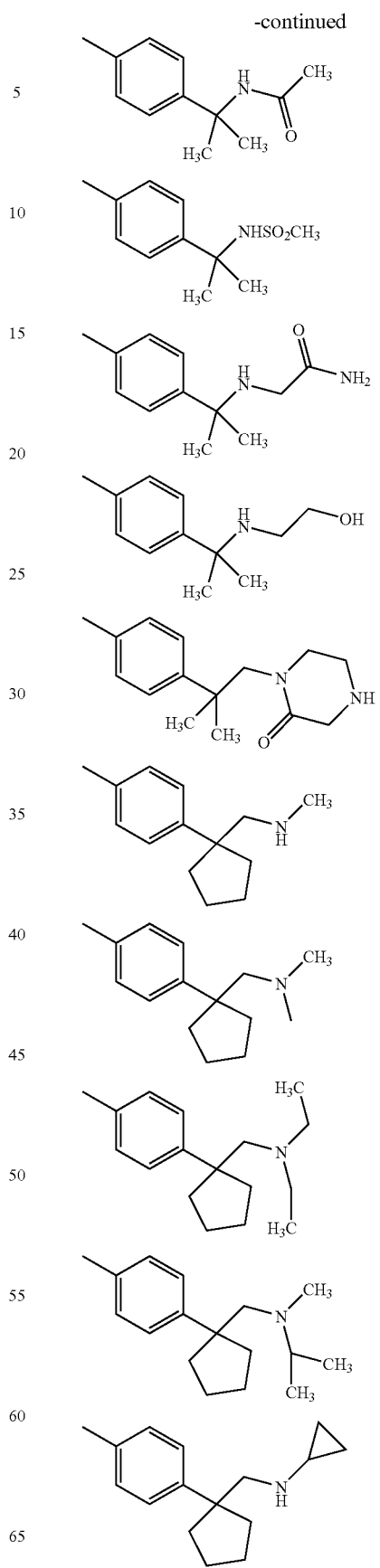

-continued
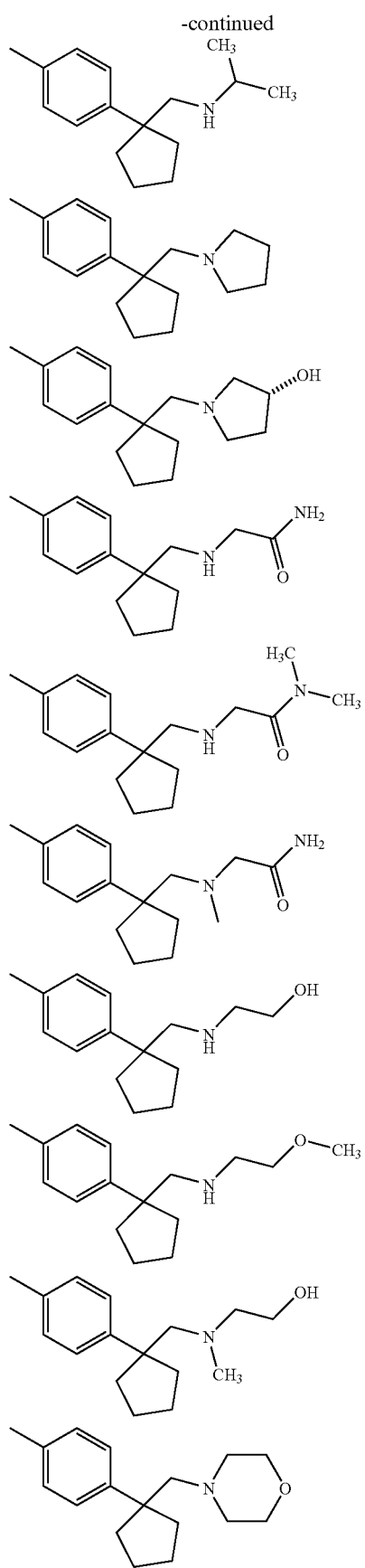
-continued
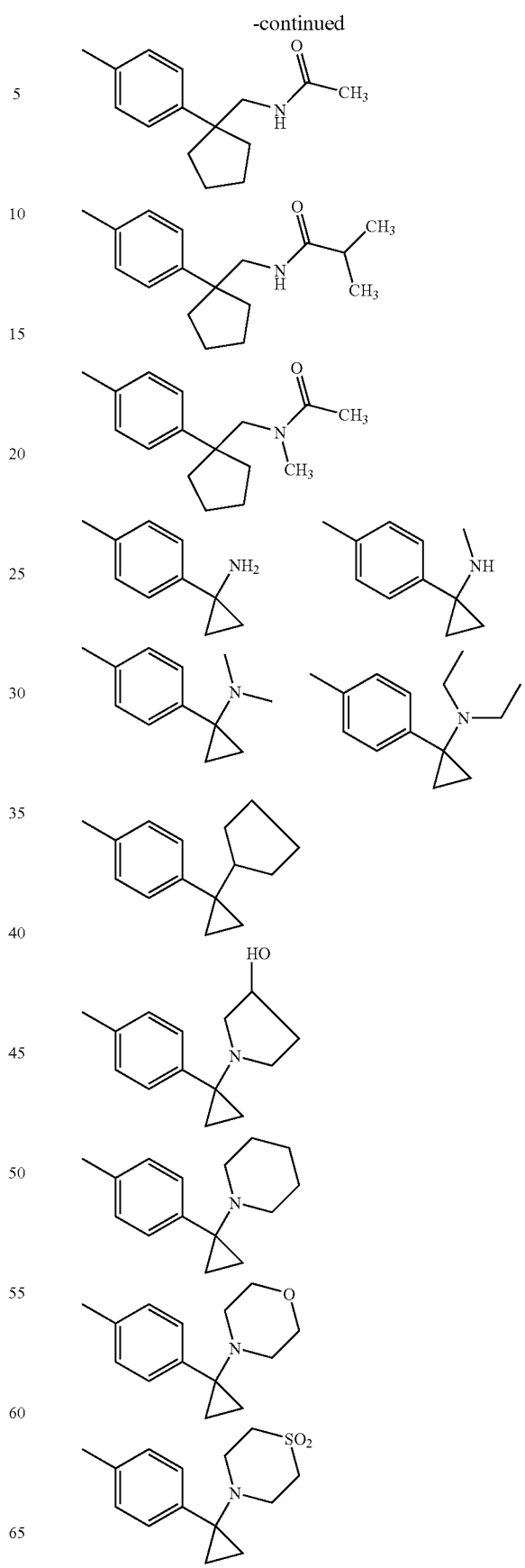

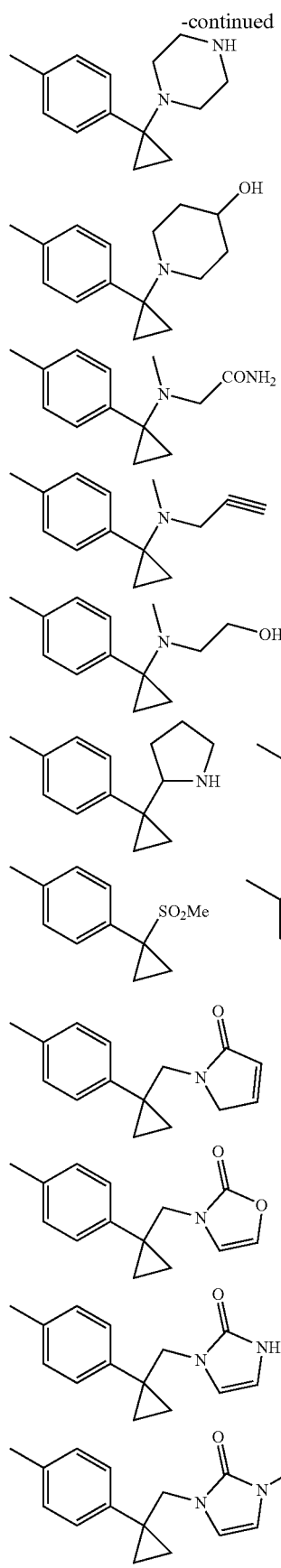
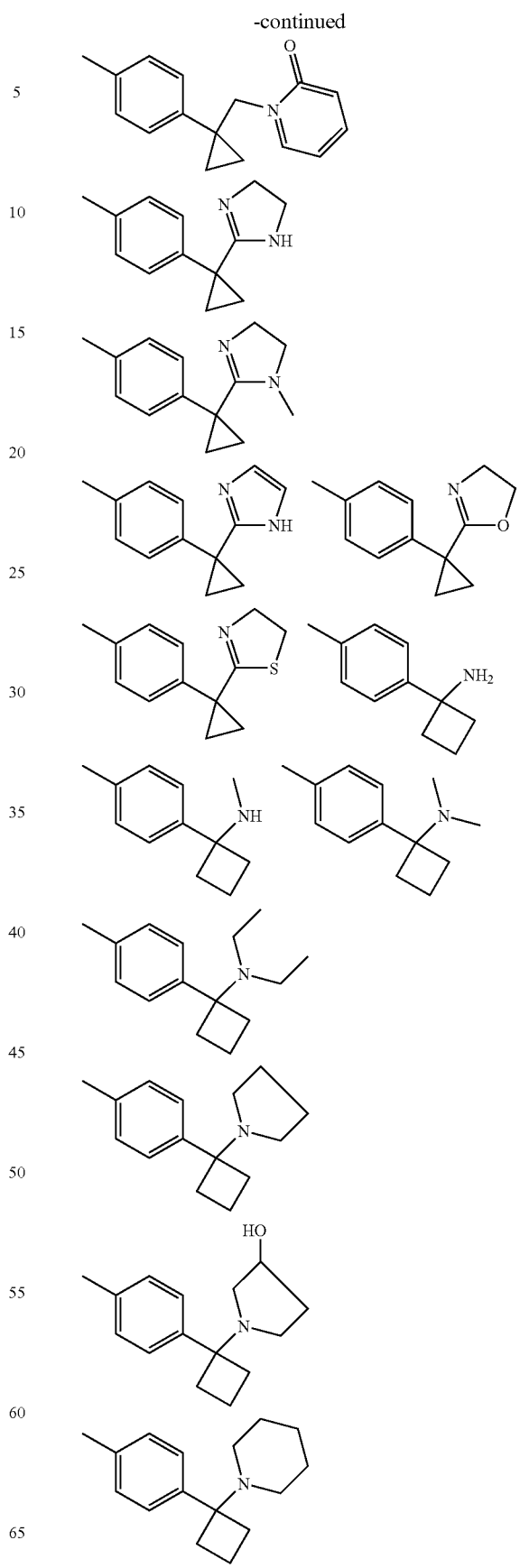

-continued
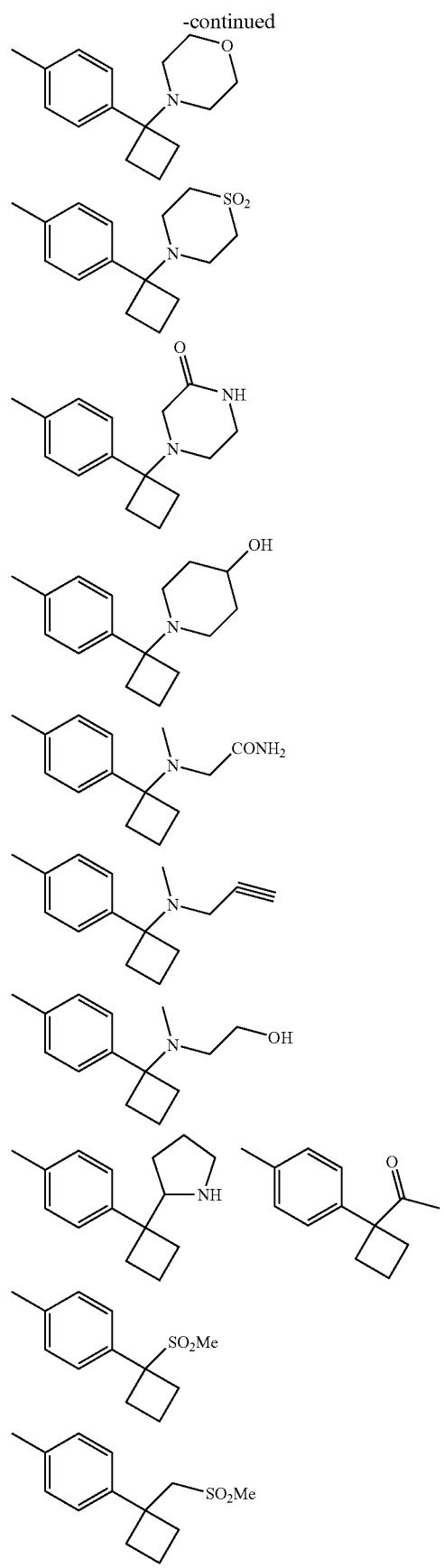
-continued
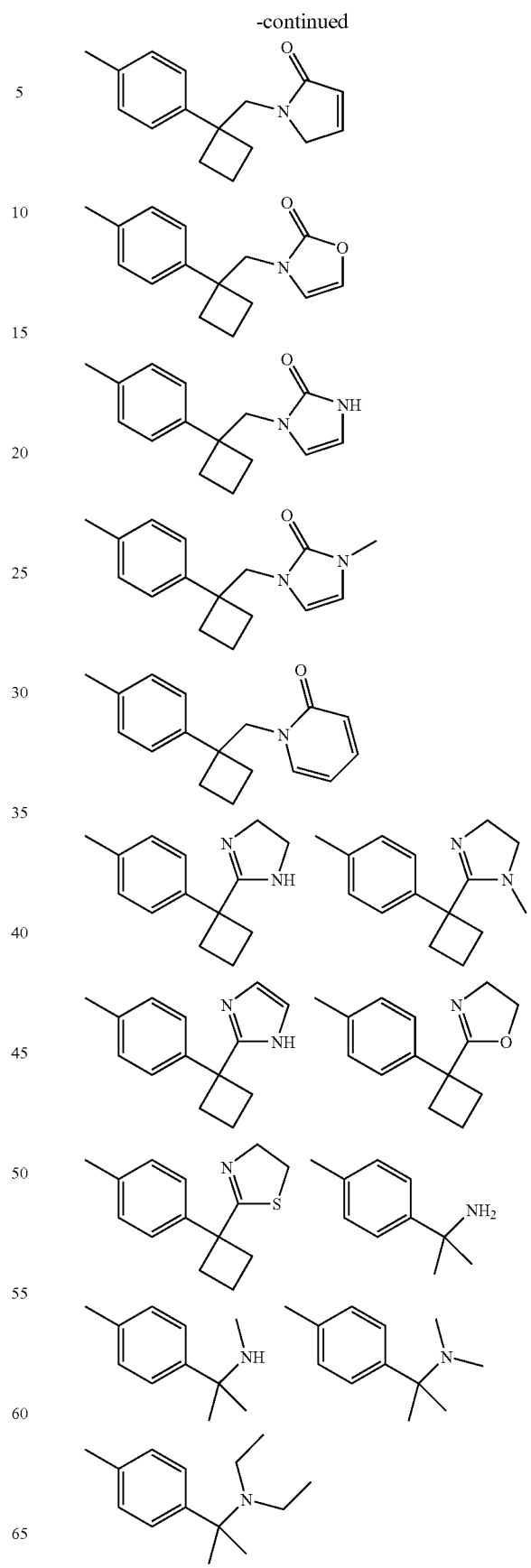

-continued
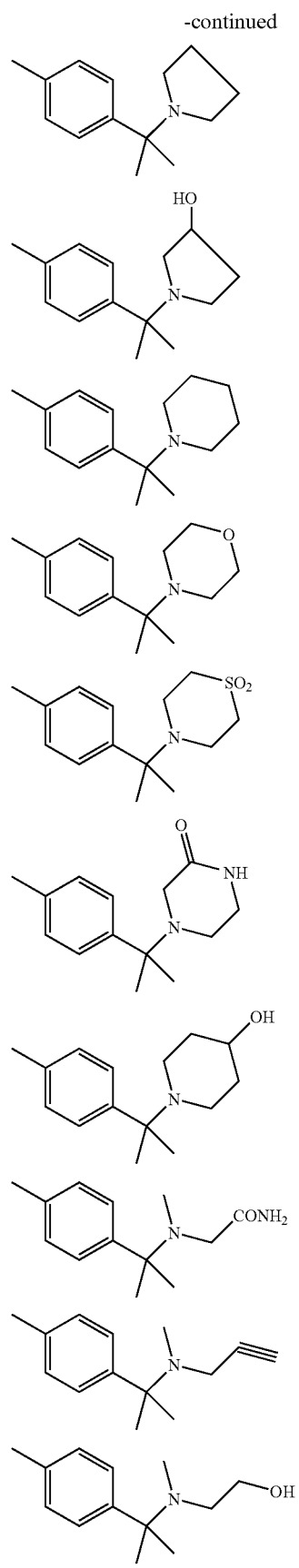
-continued
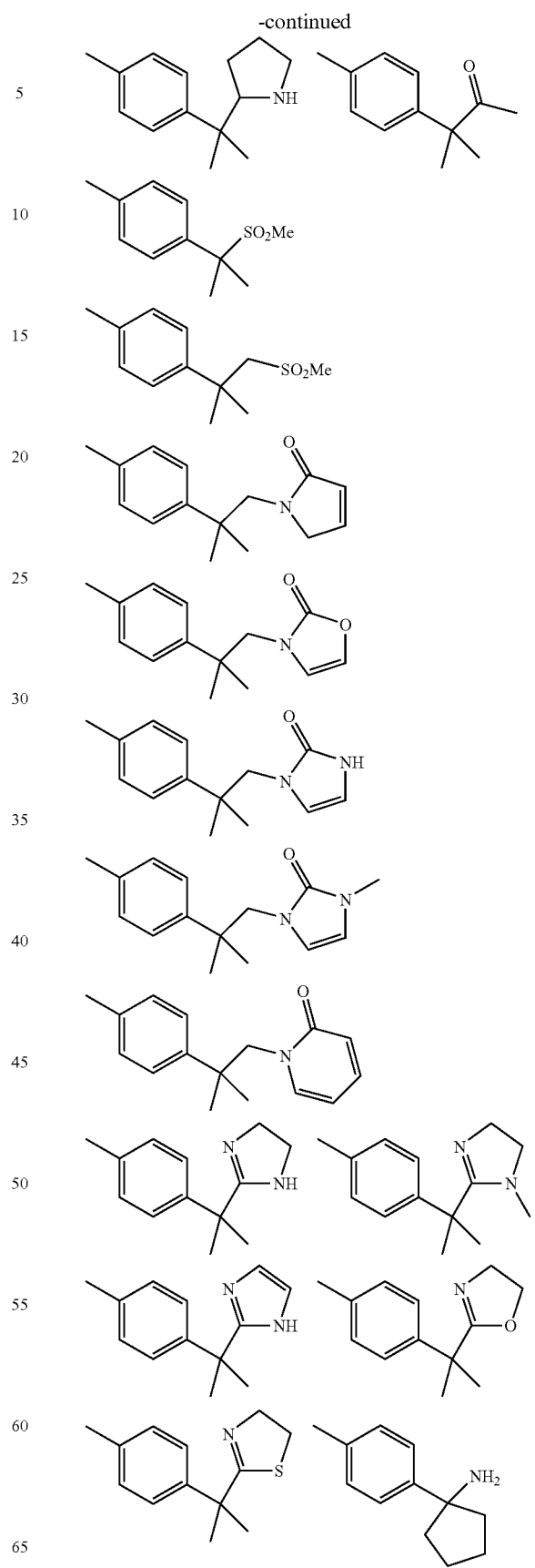

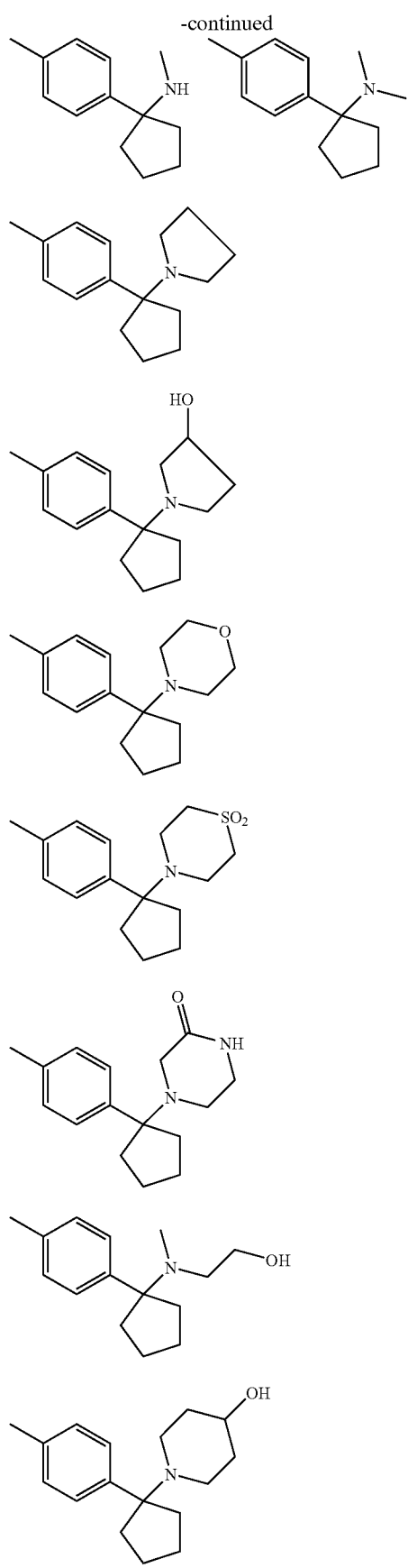
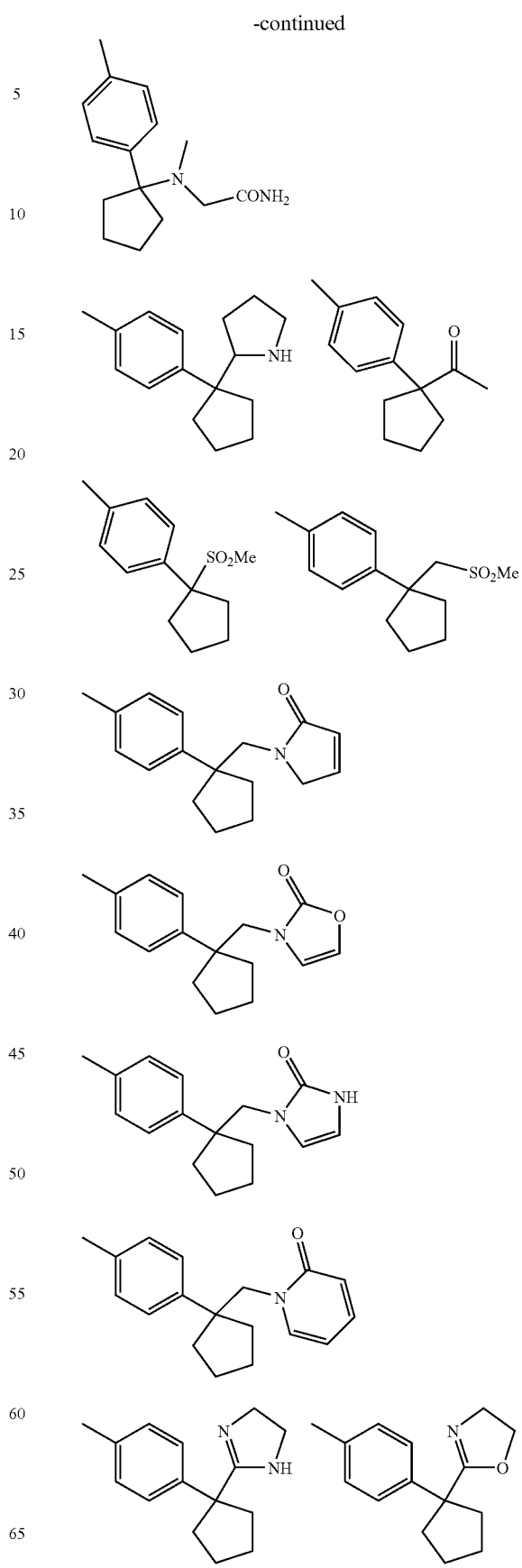

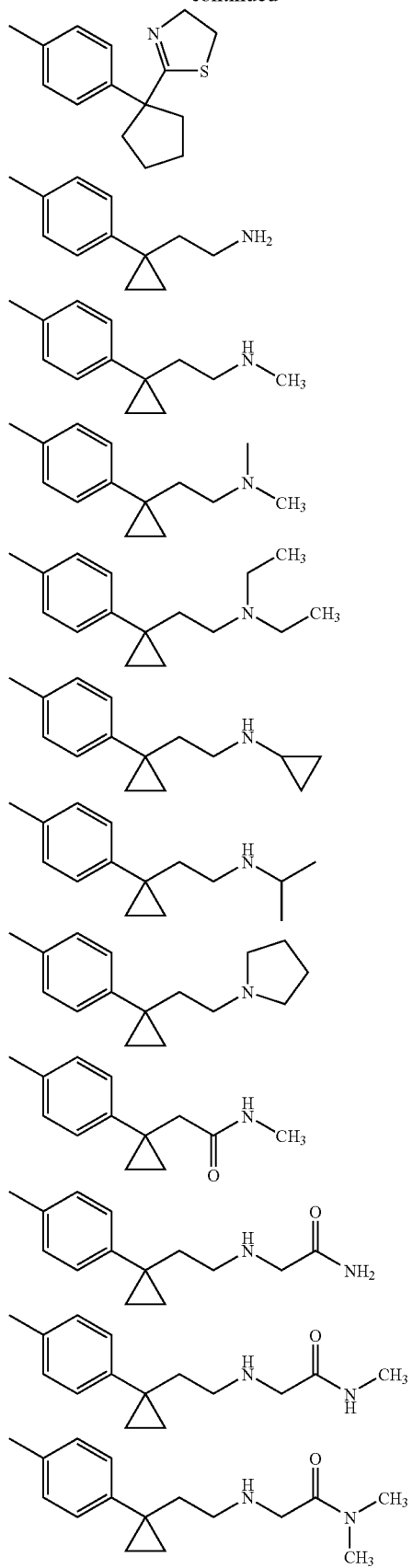
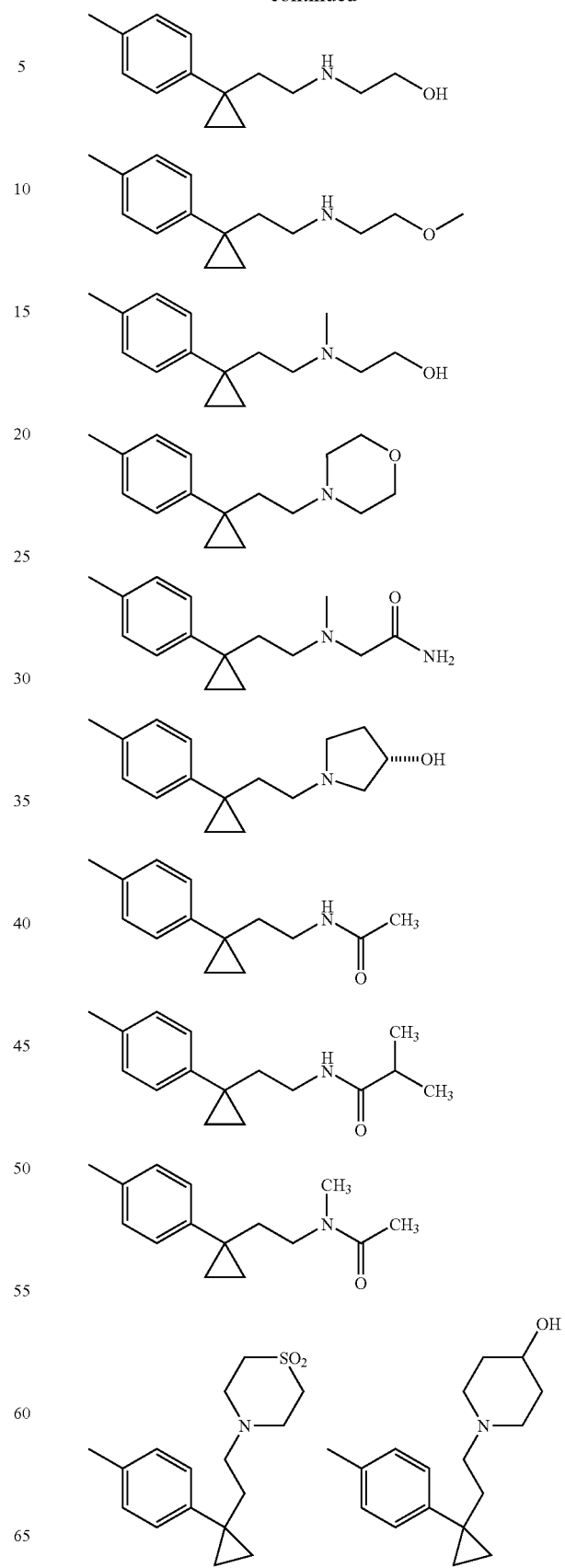

-continued
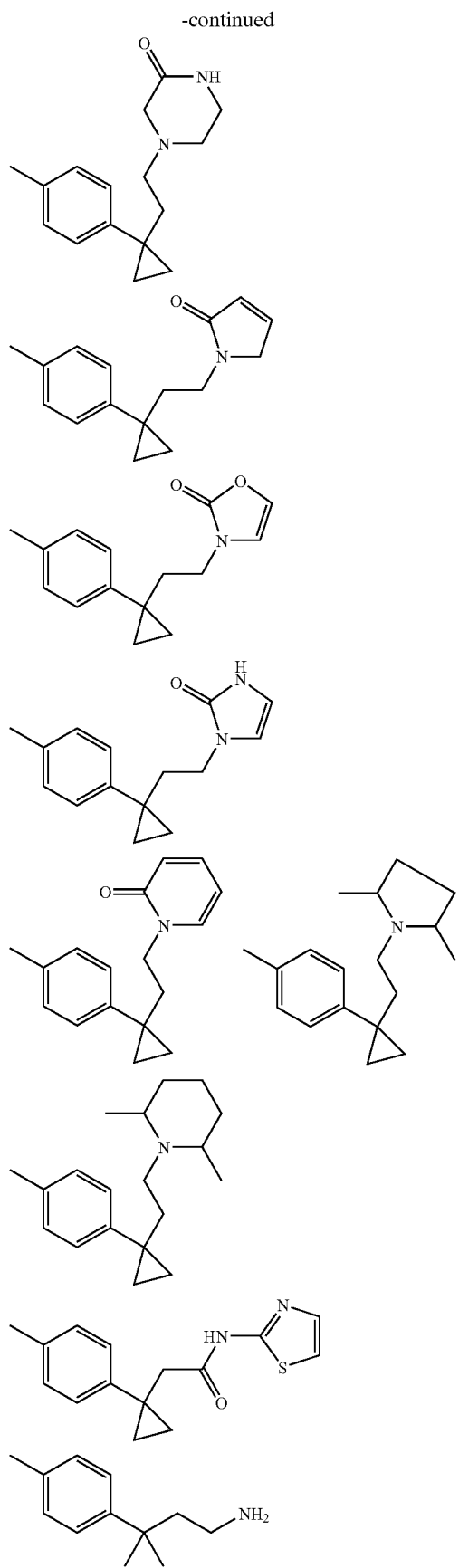
-continued
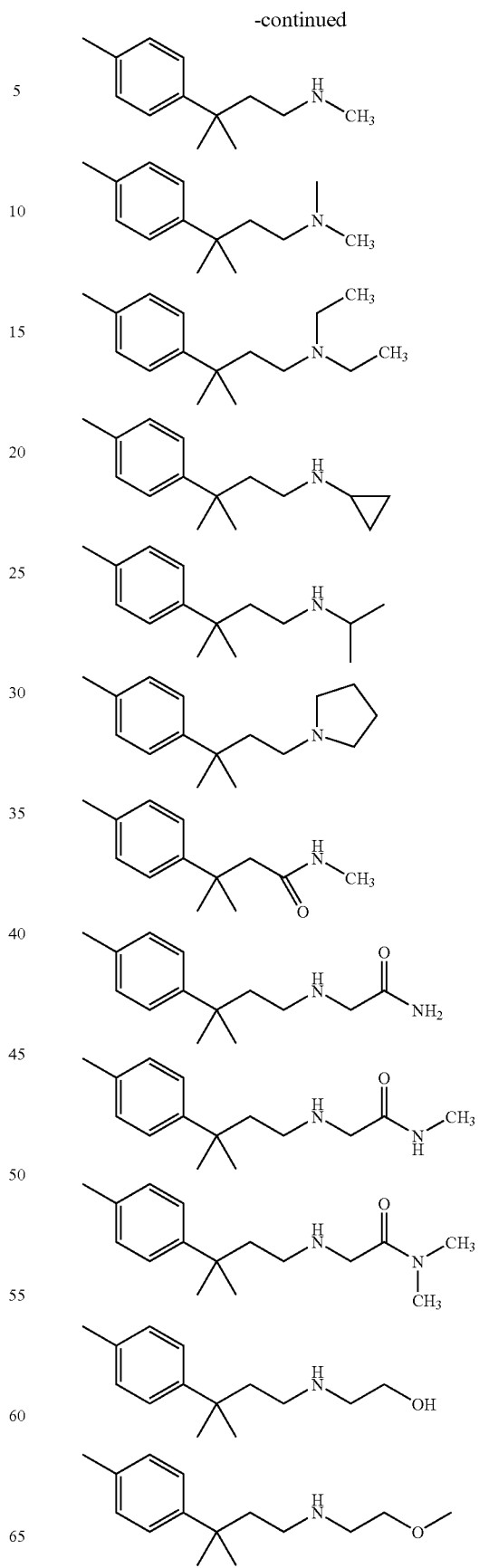

-continued
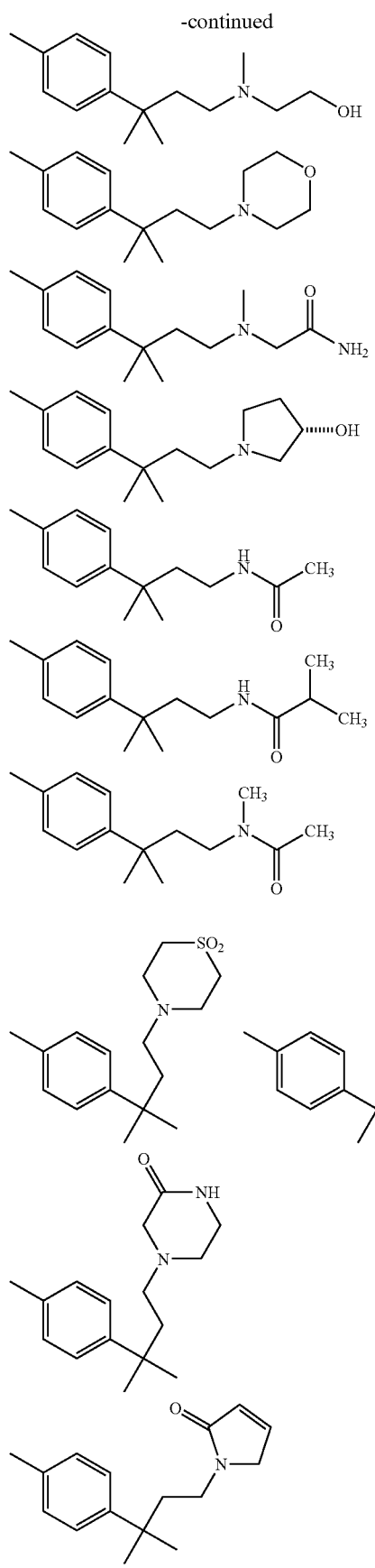
-continued
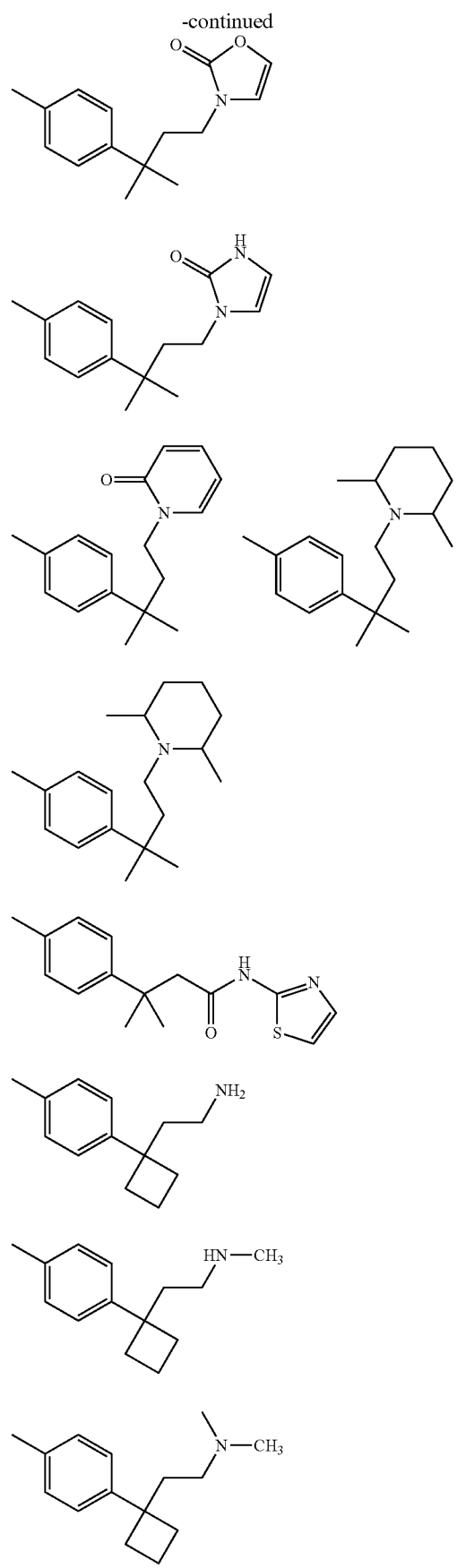

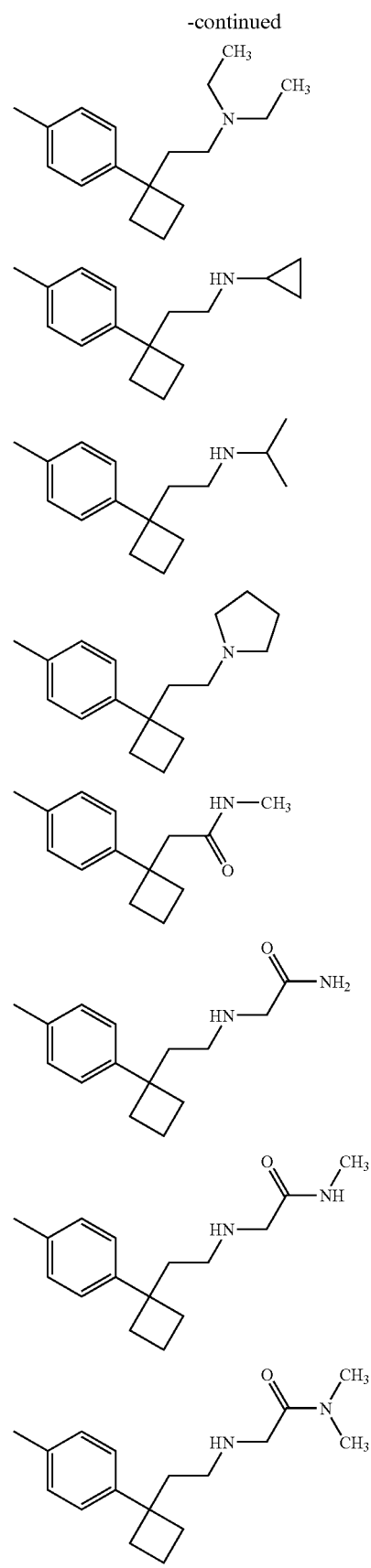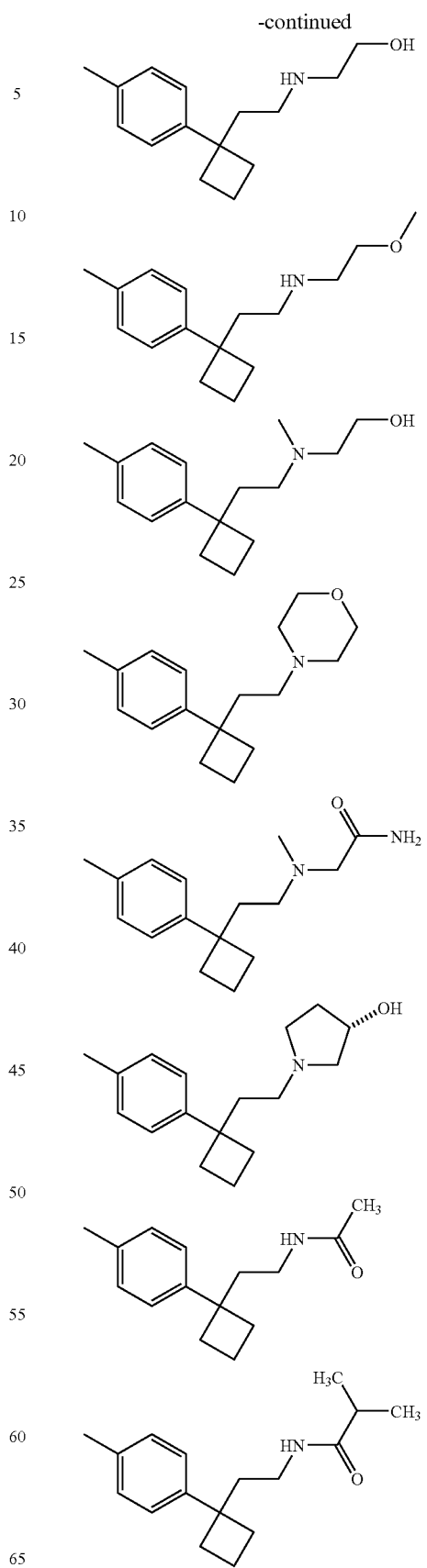

-continued
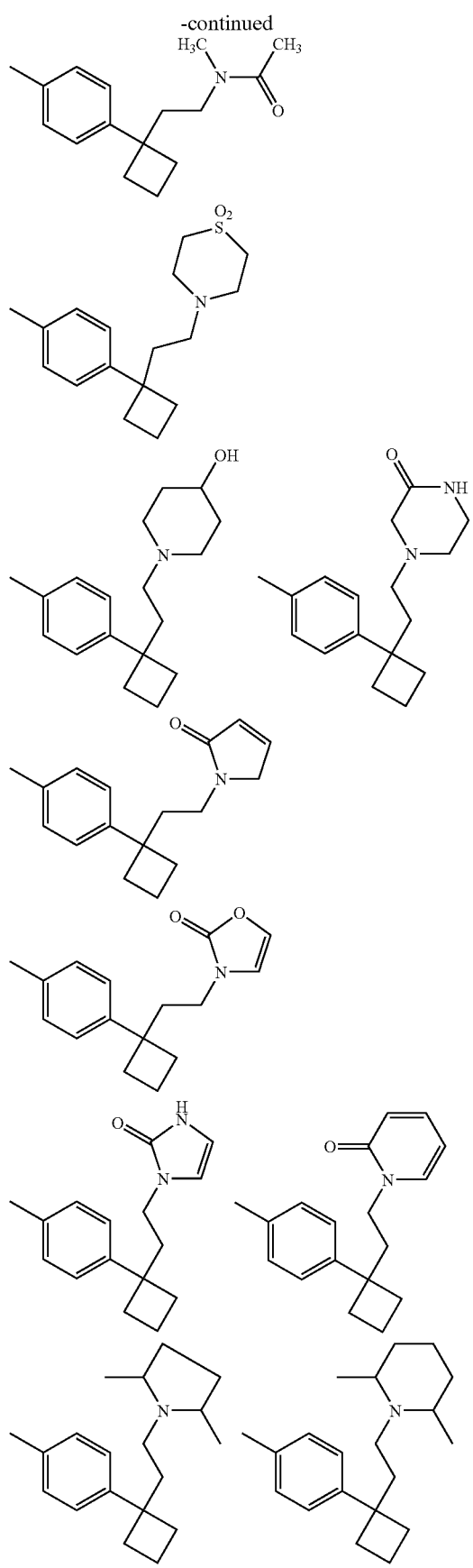
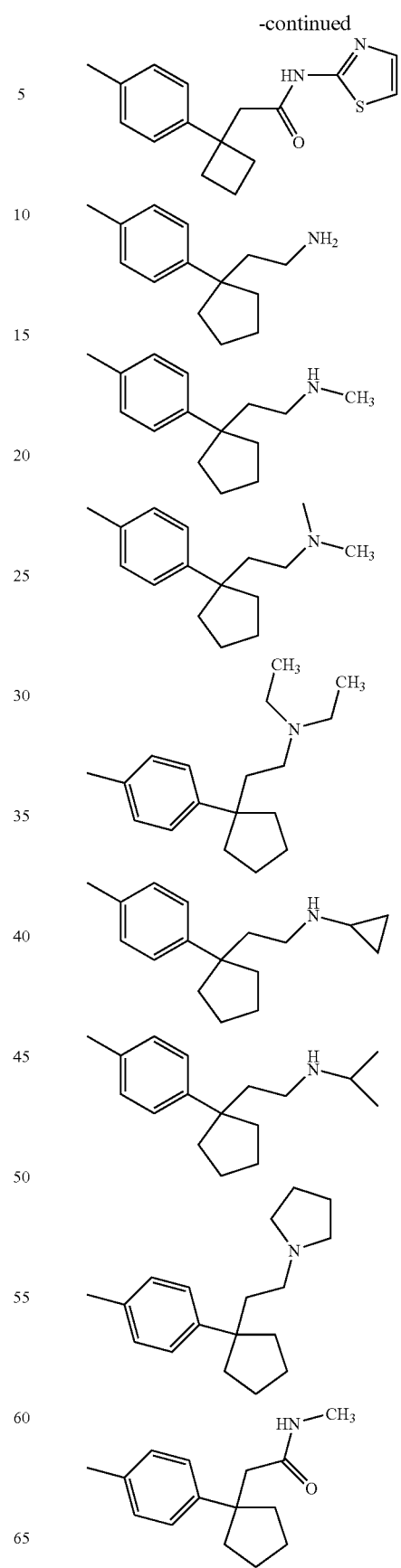

-continued
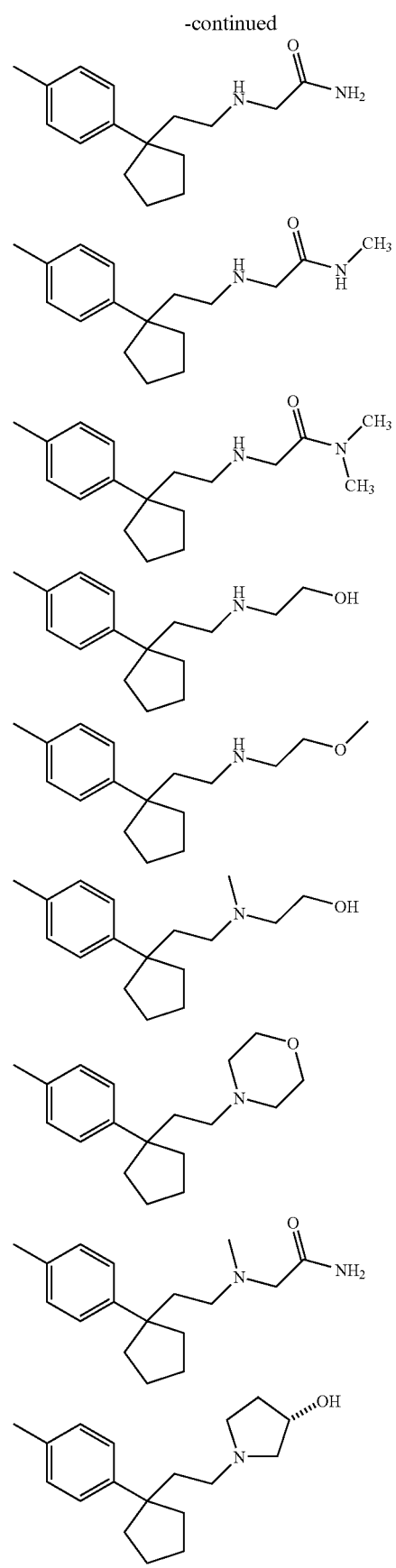
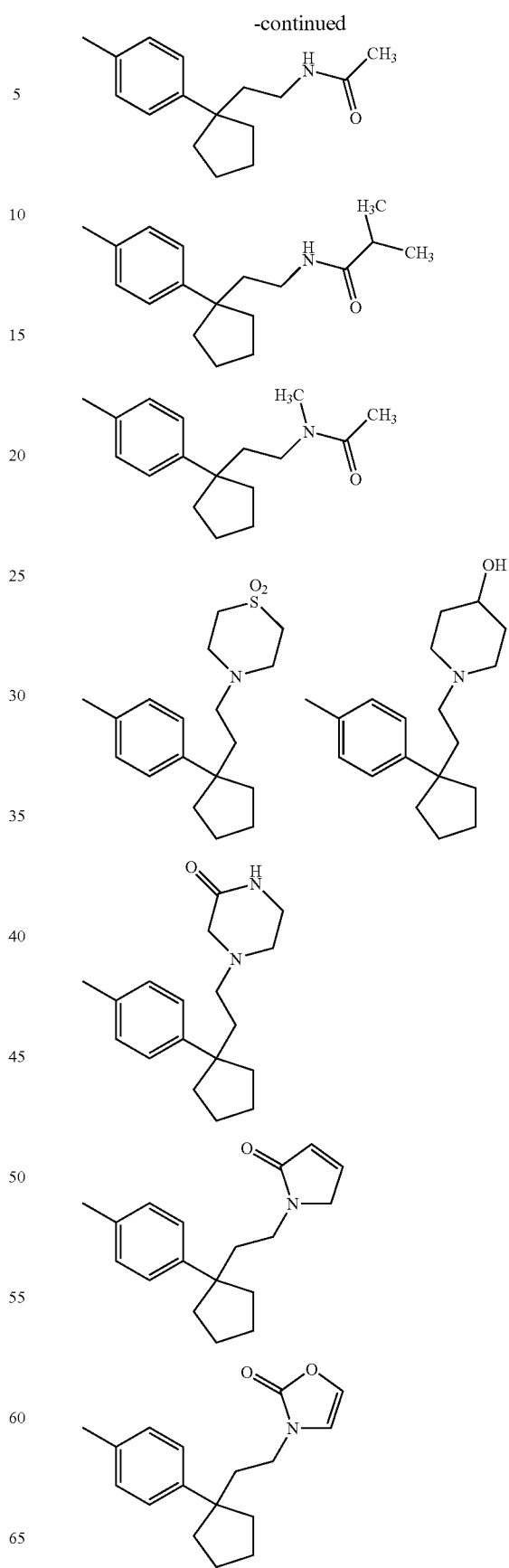

-continued
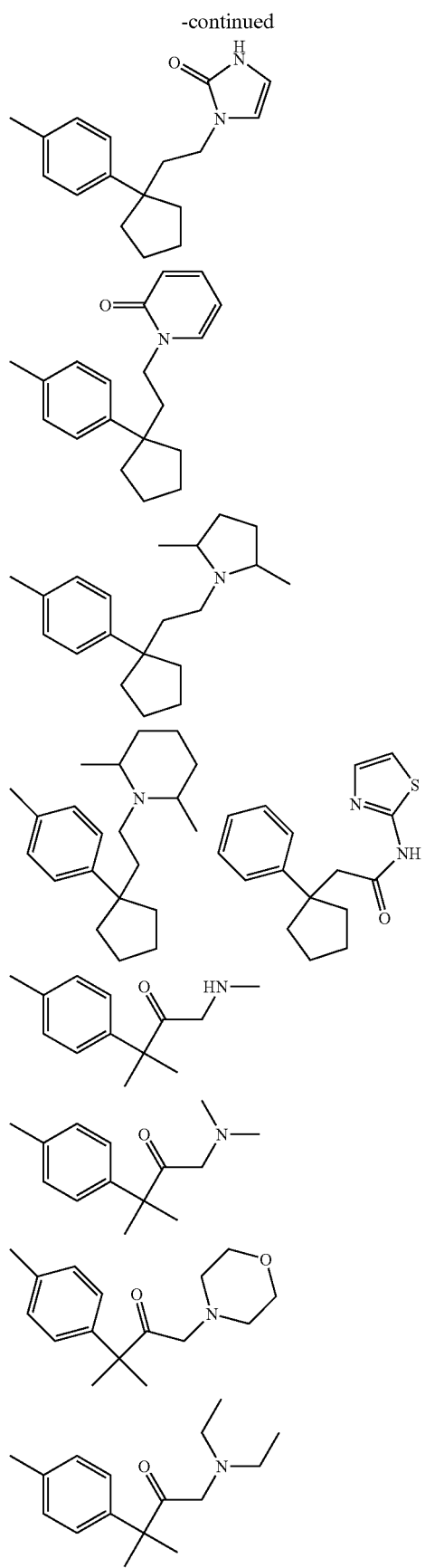
-continued
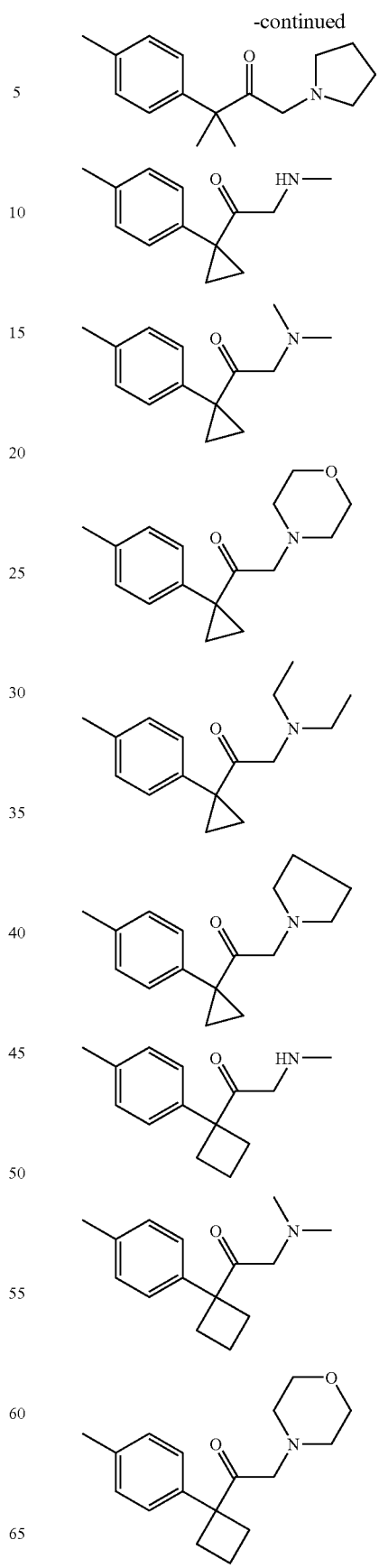

101

-continued

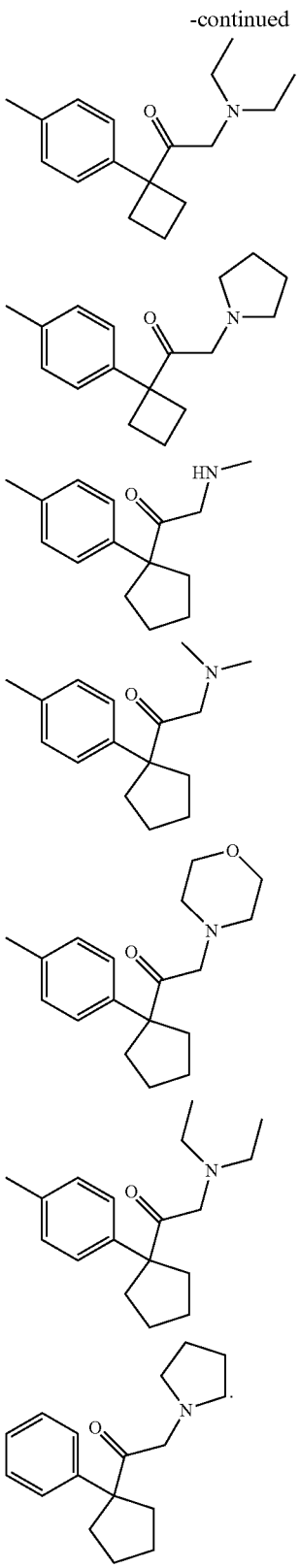

[8] In another preferred embodiment, the present invention provides a novel compound, wherein the compound is selected from the group:

102

1-(4-methoxyphenyl)-6-(4-{1-[(methylamino)methyl]
cyclopropyl}phenyl)-3-(trifluoromethyl)-1,4,5,6-tetrahydro-7H-pyrazolo[3,4-c]pyridin-7-one;

6-(4-{1-[(dimethylamino)methyl]cyclopropyl}phenyl)-1-(4-methoxyphenyl)-3-(trifluoromethyl)-1,4,5,6-tetrahydro-7H-pyrazolo[3,4-c]pyridin-7-one;

6-(4-{1-[(diethylamino)methyl]cyclopropyl}phenyl)-1-(4-methoxyphenyl)-3-(trifluoromethyl)-1,4,5,6-tetrahydro-7H-pyrazolo[3,4-c]pyridin-7-one;

6-(4-{1-[(isopropylamino)methyl]cyclopropyl}phenyl)-1-(4-methoxyphenyl)-3-(trifluoromethyl)-1,4,5,6-tetrahydro-7H-pyrazolo[3,4-c]pyridin-7-one;

6-(4-{1-[(cyclopentylamino)methyl]cyclopropyl}phenyl)-1-(4-methoxyphenyl)-3-(trifluoromethyl)-1,4,5,6-tetrahydro-7H-pyrazolo[3,4-c]pyridin-7-one;

1-(4-methoxyphenyl)-6-{4-[1-(1-pyrrolidinylmethyl)cyclopropyl]phenyl}-3-(trifluoromethyl)-1,4,5,6-tetrahydro-7H-pyrazolo[3,4-c]pyridin-7-one;

6-[4-(1-{[(3R)-3-hydroxy-1-pyrrolidinyl]methyl}cyclopropyl)phenyl]-1-(4-methoxyphenyl)-3-(trifluoromethyl)-1,4,5,6-tetrahydro-7H-pyrazolo[3,4-c]pyridin-7-one;

6-(4-{1-[(4-hydroxy-1-piperidinyl)methyl]cyclopropyl}phenyl)-1-(4-methoxyphenyl)-3-(trifluoromethyl)-1,4,5,6-tetrahydro-7H-pyrazolo[3,4-c]pyridin-7-one;

1-(4-methoxyphenyl)-6-{4-[1-(4-morpholinylmethyl)cyclopropyl]phenyl}-3-(trifluoromethyl)-1,4,5,6-tetrahydro-7H-pyrazolo[3,4-c]pyridin-7-one;

1-(4-methoxyphenyl)-6-{4-[1-(1-pyrrolidinylcarbonyl)cyclopropyl]phenyl}-3-(trifluoromethyl)-1,4,5,6-tetrahydro-7H-pyrazolo[3,4-c]pyridin-7-one;

1-{4-[1-(4-methoxyphenyl)-7-oxo-3-(trifluoromethyl)-1,4,5,7-tetrahydro-6H-pyrazolo[3,4-c]pyridin-6-yl]phenyl}-N,N-dimethylcyclopropanecarboxamide;

1-(4-methoxyphenyl)-6-(4-{1-[(4-methyl-1-piperazinyl)carbonyl]cyclopropyl}phenyl)-3-(trifluoromethyl)-1,4,5,6-tetrahydro-7H-pyrazolo[3,4-c]pyridin-7-one;

6-{4-[1-(4-hydroxypiperidine-1-carbonyl)cyclopropyl]phenyl}-1-(4-methoxyphenyl)-3-(trifluoromethyl)-1,4,5,6-tetrahydro-7H-pyrazolo[3,4-c]pyridin-7-one;

1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropanecarboxamide;

1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropanecarboxylic acid cyclopentylamide;

1-{4-[1-(4-methoxyphenyl)-7-oxo-3-(trifluoromethyl)-1,4,5,7-tetrahydro-6H-pyrazolo[3,4-c]pyridin-6-yl]phenyl}-N-(1,3,4-thiadiazol-2-yl)cyclopropanecarboxamide;

1-{4-[1-(4-methoxyphenyl)-7-oxo-3-(trifluoromethyl)-1,4,5,7-tetrahydro-6H-pyrazolo[3,4-c]pyridin-6-yl]phenyl}-N-(1H-tetrazol-5-yl)cyclopropanecarboxamide;

methyl 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropanecarboxylate;

1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropanecarbonitrile;

6-{4-[1-(aminomethyl)cyclopropyl]phenyl}-1-(4-methoxyphenyl)-3-(trifluoromethyl)-1,4,5,6-tetrahydro-7H-pyrazolo[3,4-c]pyridin-7-one;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropyl)methyl]-N-methylacetamide;

N'-ethyl-N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropyl)methyl]-N-methylurea;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropyl)methyl]-N-methylmethanesulfonamide;

1-(4-methoxyphenyl)-6-{4-[1-(2-methylimidazol-1-ylmethyl)cyclopropyl]phenyl}-3-trifluoromethyl-1,4,5,6-tetrahydro-pyrazolo[3,4-c]pyridin-7-one;

1-(4-methoxyphenyl)-6-{4-[1-(thiazol-2-ylaminomethyl)cyclopropyl]phenyl}-3-trifluoromethyl-1,4,5,6-tetrahydro-pyrazolo[3,4-c]pyridin-7-one;

methyl 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopentanecarboxylate;

1-(4-methoxyphenyl)-6-(4-{1-[(methylamino)methyl]cyclopentyl}phenyl)-3-(trifluoromethyl)-1,4,5,6-tetrahydro-7H-pyrazolo[3,4-c]pyridin-7-one;

6-(4-{1-[(dimethylamino)methyl]cyclopentyl}phenyl)-1-(4-methoxyphenyl)-3-(trifluoromethyl)-1,4,5,6-tetrahydro-7H-pyrazolo[3,4-c]pyridin-7-one;

1-(4-methoxyphenyl)-6-{4-[1-(1-pyrrolidinylmethyl)cyclopentyl]phenyl}-3-(trifluoromethyl)-1,4,5,6-tetrahydro-7H-pyrazolo[3,4-c]pyridin-7-one;

6-[4-(1-{[(3R)-3-hydroxy-1-pyrrolidinyl]methyl}cyclopentyl)phenyl]-1-(4-methoxyphenyl)-3-(trifluoromethyl)-1,4,5,6-tetrahydro-7H-pyrazolo[3,4-c]pyridin-7-one;

1-(4-methoxyphenyl)-6-{4-[1-(4-morpholinylmethyl)cyclopentyl]phenyl}-3-(trifluoromethyl)-1,4,5,6-tetrahydro-7H-pyrazolo[3,4-c]pyridin-7-one;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopentyl)methyl]-N-methylacetamide;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopentyl)methyl]-N-methylmethanesulfonamide;

methyl 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclobutanecarboxylate;

1-(4-methoxyphenyl)-6-(4-{1-[(methylamino)methyl]cyclobutyl}phenyl)-3-(trifluoromethyl)-1,4,5,6-tetrahydro-7H-pyrazolo[3,4-c]pyridin-7-one;

6-(4-{1-[(dimethylamino)methyl]cyclobutyl}phenyl)-1-(4-methoxyphenyl)-3-(trifluoromethyl)-1,4,5,6-tetrahydro-7H-pyrazolo[3,4-c]pyridin-7-one;

6-(4-{1-[(diethylamino)methyl]cyclobutyl}phenyl)-1-(4-methoxyphenyl)-3-(trifluoromethyl)-1,4,5,6-tetrahydro-7H-pyrazolo[3,4-c]pyridin-7-one;

1-(4-methoxyphenyl)-6-{4-[1-(1-pyrrolidinylmethyl)cyclobutyl]phenyl}-3-(trifluoromethyl)-1,4,5,6-tetrahydro-7H-pyrazolo[3,4-c]pyridin-7-one;

6-[4-(1-{[(3R)-3-hydroxy-1-pyrrolidinyl]methyl}cyclobutyl)phenyl]-1-(4-methoxyphenyl)-3-(trifluoromethyl)-1,4,5,6-tetrahydro-7H-pyrazolo[3,4-c]pyridin-7-one;

1-(4-methoxyphenyl)-6-{4-[1-(4-morpholinylmethyl)cyclobutyl]phenyl}-3-(trifluoromethyl)-1,4,5,6-tetrahydro-7H-pyrazolo[3,4-c]pyridin-7-one;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclobutyl)methyl]-N-methylacetamide;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclobutyl)methyl]-N-methylmethanesulfonamide;

1-{4-[1-(4-Methoxyphenyl)-7-oxo-3-trifluoromethyl-1,4,5,7-tetrahydro-pyrazolo[3,4-c]pyridin-6-yl]-phenyl}cyclohexanecarboxylic acid methyl ester;

1-(4-methoxyphenyl)-6-(4-{1-[(methylamino)methyl]cyclohexyl}phenyl)-3-(trifluoromethyl)-1,4,5,6-tetrahydro-7H-pyrazolo[3,4-c]pyridin-7-one;

6-(4-{1-[(dimethylamino)methyl]cyclohexyl}phenyl)-1-(4-methoxyphenyl)-3-(trifluoromethyl)-1,4,5,6-tetrahydro-7H-pyrazolo[3,4-c]pyridin-7-one;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclohexyl)methyl]-N-methylacetamide;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclohexyl)methyl]-N-methylmethanesulfonamide;

1-(4-methoxyphenyl)-6-(4-{1-[(methylamino)methyl]cyclopropyl}phenyl)-3-(methylsulfonyl)-1,4,5,6-tetrahydro 7H-pyrazolo[3,4-c]pyridin-7-one;

6-(4-{1-[(dimethylamino)methyl]cyclopropyl}phenyl)-1-(4-methoxyphenyl)-3-(methylsulfonyl)-1,4,5,6-tetrahydro-7H-pyrazolo[3,4-c]pyridin-7-one;

6-(4-{1-[(isopropylamino)methyl]cyclopropyl}phenyl)-1-(4-methoxyphenyl)-3-(methylsulfonyl)-1,4,5,6-tetrahydro-7H-pyrazolo[3,4-c]pyridin-7-one;

6-(4-{1-[(cyclopentylamino)methyl]cyclopropyl}phenyl)-1-(4-methoxyphenyl)-3-(methylsulfonyl)-1,4,5,6-tetrahydro-7H-pyrazolo[3,4-c]pyridin-7-one;

1-(4-methoxyphenyl)-3-(methylsulfonyl)-6-{4-[1-(1-pyrrolidinylmethyl)cyclopropyl]phenyl}-1,4,5,6-tetrahydro-7H-pyrazolo[3,4-c]pyridin-7-one;

6-[4-(1-{[(3R)-3-hydroxy-1-pyrrolidinyl]methyl}cyclopropyl)phenyl]-1-(4-methoxyphenyl)-3-(methylsulfonyl)-1,4,5,6-tetrahydro-7H-pyrazolo[3,4-c]pyridin-7-one;

6-(4-{1-[(diethylamino)methyl]cyclopropyl}phenyl)-1-(4-methoxyphenyl)-3-(methylsulfonyl)-1,4,5,6-tetrahydro-7H-pyrazolo[3,4-c]pyridin-7-one;

1-(4-methoxyphenyl)-3-(methylsulfonyl)-6-{4-[1-(4-morpholinylmethyl)cyclopropyl]phenyl}-1,4,5,6-tetrahydro-7H-pyrazolo[3,4-c]pyridin-7-one;

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}cyclopropyl)methyl]-N-methylacetamide;

3-methanesulfonyl-1-(4-methoxyphenyl)-6-{4-[1-(2-methylimidazol-1-ylmethyl)cyclopropyl]phenyl}-1,4,5,6-tetrahydro-pyrazolo[3,4-c]pyridin-7-one;

3-methanesulfonyl-1-(4-methoxyphenyl)-6-{4-[1-(thiazol-2-ylaminomethyl)cyclopropyl]phenyl}-1,4,5,6-tetrahydro-pyrazolo[3,4-c]pyridin-7-one;

1-(4-methoxyphenyl)-6-(4-{1-[(methylamino)methyl]cyclobutyl}phenyl)-3-(methylsulfonyl)-1,4,5,6-tetrahydro 7H-pyrazolo[3,4-c]pyridin-7-one;

6-(4-{1-[(dimethylamino)methyl]cyclobutyl}phenyl)-1-(4-methoxyphenyl)-3-(methylsulfonyl)-1,4,5,6-tetrahydro-7H-pyrazolo[3,4-c]pyridin-7-one;

6-(4-{1-[(isopropylamino)methyl]cyclobutyl}phenyl)-1-(4-methoxyphenyl)-3-(methylsulfonyl)-1,4,5,6-tetrahydro-7H-pyrazolo[3,4-c]pyridin-7-one;

1-(4-methoxyphenyl)-3-(methylsulfonyl)-6-{4-[1-(1-pyrrolidinylmethyl)cyclobutyl]phenyl}-1,4,5,6-tetrahydro-7H-pyrazolo[3,4-c]pyridin-7-one;

6-[4-(1-{[(3R)-3-hydroxy-1-pyrrolidinyl]
methyl}cyclobutyl)phenyl]-1-(4-methoxyphenyl)-3-(methylsulfonyl)-1,4,5,6-tetrahydro-7H-pyrazolo[3,4-c]pyridin-7-one;

6-(4-{1-[(diethylamino)methyl]cyclobutyl}phenyl)-1-(4-methoxyphenyl)-3-(methylsulfonyl)-1,4,5,6-tetrahydro-7H-pyrazolo[3,4-c]pyridin-7-one;

1-(4-methoxyphenyl)-3-(methylsulfonyl)-6-{4-[1-(4-morpholinylmethyl)cyclobutyl]phenyl}-1,4,5,6-tetrahydro-7H-pyrazolo[3,4-c]pyridin-7-one;

N-[(1-{4-[1-(4-methoxyphenyl)-3-(methylsulfonyl)-7-oxo-1,4,5,7-tetrahydro-6H-pyrazolo[3,4-c]pyridin-6-yl]
phenyl}cyclopropyl)methyl]-N-methylacetamide;

1-(4-methoxyphenyl)-6-(4-{1-[(methylamino)methyl]
cyclopropyl}phenyl)-7-oxo-4,5,6,7-tetrahydro-1H-pyrazolo[3,4-c]pyridine-3-carboxamide;

6-(4-{1-[(dimethylamino)methyl]cyclopropyl}phenyl)-1-(4-methoxyphenyl)-7-oxo-4,5,6,7-tetrahydro-1H-pyrazolo[3,4-c]pyridine-3-carboxamide;

6-(4-{1-[(diethylamino)methyl]cyclopropyl}phenyl)-1-(4-methoxyphenyl)-7-oxo-4,5,6,7-tetrahydro-1H-pyrazolo[3,4-c]pyridine-3-carboxamide;

1-(4-methoxyphenyl)-7-oxo-6-{4-[1-(1-pyrrolidinylmethyl)cyclopropyl]phenyl}-4,5,6,7-tetrahydro-1H-pyrazolo[3,4-c]pyridine-3-carboxamide;

1-(4-methoxyphenyl)-6-{4-[1-(4-morpholinylmethyl)cyclopropyl]phenyl}-7-oxo-4,5,6,7-tetrahydro-1H-pyrazolo[3,4-c]pyridine-3-carboxamide;

6-(4-{1-[(isopropylamino)methyl]cyclopropyl}phenyl)-1-(4-methoxyphenyl)-7-oxo-4,5,6,7-tetrahydro-1H-pyrazolo[3,4-c]pyridine-3-carboxamide;

6-[4-(1-{[(3R)-3-hydroxy-1-pyrrolidinyl]
methyl}cyclopropyl)phenyl]-1-(4-methoxyphenyl)-7-oxo-4,5,6,7-tetrahydro-1H-pyrazolo[3,4-c]pyridine-3-carboxamide;

1-(4-methoxyphenyl)-6-(4-{1-[(methylamino)methyl]
cyclopropyl}phenyl)-7-oxo-4,5,6,7-tetrahydro-1H-pyrazolo[3,4-c]pyridine-3-carbonitrile;

6-(4-{1-[(dimethylamino)methyl]cyclopropyl}phenyl)-1-(4-methoxyphenyl)-7-oxo-4,5,6,7-tetrahydro-1H-pyrazolo[3,4-c]pyridine-3-carbonitrile;

6-(4-{1-[(diethylamino)methyl]cyclopropyl}phenyl)-1-(4-methoxyphenyl)-7-oxo-4,5,6,7-tetrahydro-1H-pyrazolo[3,4-c]pyridine-3-carbonitrile;

1-(4-methoxyphenyl)-7-oxo-6-{4-[1-(1-pyrrolidinylmethyl)cyclopropyl]phenyl}-4,5,6,7-tetrahydro-1H-pyrazolo[3,4-c]pyridine-3-carbonitrile;

6-(4-{1-[(isopropylamino)methyl]cyclopropyl}phenyl)-1-(4-methoxyphenyl)-7-oxo-4,5,6,7-tetrahydro-1H-pyrazolo[3,4-c]pyridine-3-carbonitrile;

6-[4-(1-{[(3R)-3-hydroxy-1-pyrrolidinyl]
methyl}cyclopropyl)phenyl]-1-(4-methoxyphenyl)-7-oxo-4,5,6,7-tetrahydro-1H-pyrazolo[3,4-c]pyridine-3-carbonitrile;

1-(4-methoxyphenyl)-6-{4-[1-(4-morpholinylmethyl)cyclopropyl]phenyl}-7-oxo-4,5,6,7-tetrahydro-1H-pyrazolo[3,4-c]pyridine-3-carbonitrile;

1-(3-chlorophenyl)-6-{4-[1-(isopropylamino)methyl]cyclopropyl]phenyl}-7-oxo-4,5,6,7-tetrahydro-1H-pyrazolo[3,4-c]pyridine-3-carboxamide;

1-(3-chlorophenyl)-6-{4-[1-(4-morpholinylmethyl)cyclopropyl]phenyl}-7-oxo-4,5,6,7-tetrahydro-1H-pyrazolo[3,4-c]pyridine-3-carboxamide;

6-(4-{1-[(isopropylamino)methyl]cyclopropyl}phenyl)-1-(4-methoxyphenyl)-7-oxo-4,5,6,7-tetrahydro-1H-pyrazolo[3,4-c]pyridine-3-carbonitrile;

1-(4-methoxyphenyl)-6-{4-[1-(4-morpholinylmethyl)cyclopropyl]phenyl}-7-oxo-4,5,6,7-tetrahydro-1H-pyrazolo[3,4-c]pyridine-3-carbonitrile;

1-(3-chlorophenyl)-6-(4-{1-[(methylamino)methyl]
cyclopropyl}phenyl)-7-oxo-4,5,6,7-tetrahydro-1H-pyrazolo[3,4-c]pyridine-3-carboxamide;

1-(3-chlorophenyl)-6-(4-{1-[(dimethylamino)methyl]
cyclopropyl}phenyl)-7-oxo-4,5,6,7-tetrahydro-1H-pyrazolo[3,4-c]pyridine-3-carboxamide;

1-(3-chlorophenyl)-6-(4-{1-[(diethylamino)methyl]
cyclopropyl}phenyl)-7-oxo-4,5,6,7-tetrahydro-1H-pyrazolo[3,4-c]pyridine-3-carboxamide;

1-(3-chlorophenyl)-6-(4-{1-[(diisopropylamino)methyl]
cyclopropyl}phenyl)-7-oxo-4,5,6,7-tetrahydro-1H-pyrazolo[3,4-c]pyridine-3-carboxamide;

1-(3-chlorophenyl)-6-(4-{1-[(cyclopropylamino)methyl]
cyclopropyl}phenyl)-7-oxo-4,5,6,7-tetrahydro-1H-pyrazolo[3,4-c]pyridine-3-carboxamide;

1-(3-chlorophenyl)-6-(4-{1-[(cyclobutylamino)methyl]
cyclopropyl}phenyl)-7-oxo-4,5,6,7-tetrahydro-1H-pyrazolo[3,4-c]pyridine-3-carboxamide;

1-(3-chlorophenyl)-7-oxo-6-(4-{1-[(2-oxo-1-pyrrolidinyl)
methyl]cyclopropyl}phenyl)-4,5,6,7-tetrahydro-1H-pyrazolo[3,4-c]pyridine-3-carboxamide;

1-(3-chlorophenyl)-6-[4-(1-{[(2-hydroxyethyl)(methyl)
amino]methyl}cyclopropyl)phenyl]-7-oxo-4,5,6,7-tetrahydro-1H-pyrazolo[3,4-c]pyridine-3-carboxamide;

1-(3-chlorophenyl)-6-(4-{1-[2-(dimethylamino)-2-oxoethyl]cyclopropyl}phenyl)-7-oxo-4,5,6,7-tetrahydro-1H-pyrazolo[3,4-c]pyridine-3-carboxamide;

1-(3-chlorophenyl)-6-{4-[1-(methoxymethyl)cyclopropyl]
phenyl}-7-oxo-4,5,6,7-tetrahydro-1H-pyrazolo[3,4-c]pyridine-3-carboxamide;

1-(3-chlorophenyl)-6-{4-[1-(methoxymethyl)cyclopropyl]
phenyl}-7-oxo-4,5,6,7-tetrahydro-1H-pyrazolo[3,4-c]pyridine-3-carbonitrile;

1-(3-chlorophenyl)-6-(4-{1-[(methylamino)methyl]
cyclopropyl}phenyl)-7-oxo-4,5,6,7-tetrahydro-1H-pyrazolo[3,4-c]pyridine-3-carbonitrile;

1-(3-chlorophenyl)-6-(4-{1-[(dimethylamino)methyl]
cyclopropyl}phenyl)-7-oxo-4,5,6,7-tetrahydro-1H-pyrazolo[3,4-c]pyridine-3-carbonitrile;

1-(3-chlorophenyl)-6-[4-(1-{[(2-hydroxyethyl)(methyl)
amino]methyl}cyclopropyl)phenyl]-7-oxo-4,5,6,7-tetrahydro-1H-pyrazolo[3,4-c]pyridine-3-carbonitrile;

1-(4-methoxyphenyl)-7-oxo-6-(4-{1-[(2-oxo-1-pyrrolidinyl)methyl]cyclopropyl}phenyl)-4,5,6,7-tetrahydro-1H-pyrazolo[3,4-c]pyridine-3-carbonitrile;

N-[(1-{4-[3-cyano-1-(4-methoxyphenyl)-7-oxo-1,4,5,7-tetrahydro-6H-pyrazolo[3,4-c]pyridin-6-yl]
phenyl}cyclopropyl)methyl]-N-methylacetamide;

6-(4-{1-[(cyclopropylamino)methyl]cyclopropyl}phenyl)-1-(4-methoxyphenyl)-7-oxo-4,5,6,7-tetrahydro-1H-pyrazolo[3,4-c]pyridine-3-carbonitrile;

6-(4-{1-[(cyclobutylamino)methyl]cyclopropyl}phenyl)-1-(4-methoxyphenyl)-7-oxo-4,5,6,7-tetrahydro-1H-pyrazolo[3,4-c]pyridine-3-carbonitrile;

6-[4-(1-{[(2-hydroxyethyl)amino]methyl}cyclopropyl)phenyl]-1-(4-methoxyphenyl)-7-oxo-4,5,6,7-tetrahydro-1H-pyrazolo[3,4-c]pyridine-3-carbonitrile;

6-[4-(1-{[(2-hydroxyethyl)(methyl)amino]
methyl}cyclopropyl)phenyl]-1-(4-methoxyphenyl)-7-oxo-4,5,6,7-tetrahydro-1H-pyrazolo[3,4-c]pyridine-3-carbonitrile;

6-(4-{1-[(diisopropylamino)methyl]cyclopropyl}phenyl)-1-(4-methoxyphenyl)-7-oxo-4,5,6,7-tetrahydro-1H-pyrazolo[3,4-c]pyridine-3-carbonitrile;

5-(4-{1-[(diisopropylamino)methyl]cyclopropyl}phenyl)-3-(4-methoxyphenyl)-3,5,6,7-tetrahydro-4H-[1,2,3]triazolo[4,5-c]pyridin-4-one;

5-(4-{1-[(isopropylamino)methyl]cyclopropyl}phenyl)-3-(4-methoxyphenyl)-3,5,6,7-tetrahydro-4H-[1,2,3]triazolo[4,5-c]pyridin-4-one;

3-(4-methoxyphenyl)-5-(4-{1-[(methylamino)methyl]cyclopropyl}phenyl)-3,5,6,7-tetrahydro-4H-[1,2,3]triazolo[4,5-c]pyridin-4-one;

3-(4-methoxyphenyl)-5-{4-[1-(1-pyrrolidinylmethyl)cyclopropyl]phenyl}-3,5,6,7-tetrahydro-4H-[1,2,3]triazolo[4,5-c]pyridin-4-one;

3-(4-methoxyphenyl)-5-(4-{1-[(2-oxo-1-pyrrolidinyl)methyl]cyclopropyl}phenyl)-3,5,6,7-tetrahydro-4H-[1,2,3]triazolo[4,5-c]pyridin-4-one;

5-[4-(1-{[(2-hydroxyethyl)amino]methyl}cyclopropyl)phenyl]-3-(4-methoxyphenyl)-3,5,6,7-tetrahydro-4H-[1,2,3]triazolo[4,5-c]pyridin-4-one;

3-(3-chlorophenyl)-5-[4-(1-{[(2-hydroxyethyl)amino]methyl}cyclopropyl)phenyl]-3,5,6,7-tetrahydro-4H-[1,2,3]triazolo[4,5-c]pyridin-4-one;

3-(3-chlorophenyl)-5-[4-(1-{[(2-hydroxyethyl)(methyl)amino]methyl}cyclopropyl)phenyl]-3,5,6,7-tetrahydro-4H-[1,2,3]triazolo[4,5-c]pyridin-4-one;

3-(3-chlorophenyl)-5-{4-[1-(1-pyrrolidinylmethyl)cyclopropyl]phenyl}-3,5,6,7-tetrahydro-4H-[1,2,3]triazolo[4,5-c]pyridin-4-one;

3-(3-chlorophenyl)-5-(4-{1-[(3-hydroxy-1-pyrrolidinyl)methyl]cyclopropyl}phenyl)-3,5,6,7-tetrahydro-4H-[1,2,3]triazolo[4,5-c]pyridin-4-one;

6-[4-(1-{[(2-hydroxyethyl)(methyl)amino]methyl}cyclopropyl)phenyl]-1-(4-methoxyphenyl)-7-oxo-4,5,6,7-tetrahydro-1H-pyrazolo[3,4-c]pyridine-3-carboxamide;

6-{4-[1-(dimethylamino)cyclopropyl]phenyl}-1-(4-methoxyphenyl)-7-oxo-4,5,6,7-tetrahydro-1H-pyrazolo[3,4-c]pyridine-3-carboxamide;

6-(4-{1-[(2-hydroxyethyl)(methyl)amino]cyclopropyl}phenyl)-1-(4-methoxyphenyl)-7-oxo-4,5,6,7-tetrahydro-1H-pyrazolo[3,4-c]pyridine-3-carboxamide;

2-(1-{4-[1-(4-methoxyphenyl)-3-(methylsulfonyl)-7-oxo-1,4,5,7-tetrahydro-6H-pyrazolo[3,4-c]pyridin-6-yl]phenyl}cyclopropyl)-N,N-dimethylacetamide;

6-(4-{1-[2-(dimethylamino)-2-oxoethyl]cyclopropyl}phenyl)-1-(4-methoxyphenyl)-7-oxo-4,5,6,7-tetrahydro-1H-pyrazolo[3,4-c]pyridine-3-carboxamide;

2-(1-{4-[3-cyano-1-(4-methoxyphenyl)-7-oxo-1,4,5,7-tetrahydro-6H-pyrazolo[3,4-c]pyridin-6-yl]phenyl}cyclopropyl)-N,N-dimethylacetamide;

2-(1-{4-[3-cyano-1-(4-methoxyphenyl)-7-oxo-1,4,5,7-tetrahydro-6H-pyrazolo[3,4-c]pyridin-6-yl]phenyl}cyclopropyl)acetamide;

2-(1-{4-[1-(3-chlorophenyl)-3-cyano-7-oxo-1,4,5,7-tetrahydro-6H-pyrazolo[3,4-c]pyridin-6-yl]phenyl}cyclopropyl)acetamide;

1-(3-chlorophenyl)-6-(4-{1-[2-(dimethylamino)-2-oxoethyl]cyclopropyl}phenyl)-7-oxo-4,5,6,7-tetrahydro-1H-pyrazolo[3,4-c]pyridine-3-carboxamide;

2-(1-{4-[1-(3-chlorophenyl)-3-(methylsulfonyl)-7-oxo-1,4,5,7-tetrahydro-6H-pyrazolo[3,4-c]pyridin-6-yl]phenyl}cyclopropyl)-N,N-dimethylacetamide;

2-(1-{4-[3-(3-chlorophenyl)-4-oxo-3,4,6,7-tetrahydro-5H-[1,2,3]triazolo[4,5-c]pyridin-5-yl]phenyl}cyclopropyl)-N,N-dimethylacetamide;

2-(1-{4-[3-(4-methoxyphenyl)-4-oxo-3,4,6,7-tetrahydro-5H-[1,2,3]triazolo[4,5-c]pyridin-5-yl]phenyl}cyclopropyl)-N,N-dimethylacetamide;

2-(1-{4-[3-(4-methoxyphenyl)-4-oxo-3,4,6,7-tetrahydro-5H-[1,2,3]triazolo[4,5-c]pyridin-5-yl]phenyl}cyclopropyl)acetamide;

1-(4-methoxyphenyl)-7-oxo-6-(4-{1-[(2-oxo-1-imidazolidinyl)methyl]cyclopropyl}phenyl)-4,5,6,7-tetrahydro-1H-pyrazolo[3,4-c]pyridine-3-carbonitrile;

1-(4-methoxyphenyl)-7-oxo-6-(4-{1-[(2-oxo-1-piperazinyl)methyl]cyclopropyl}phenyl)-4,5,6,7-tetrahydro-1H-pyrazolo[3,4-c]pyridine-3-carbonitrile;

1-(4-methoxyphenyl)-7-oxo-6-(4-{1-[(3-oxo-4-morpholinyl)methyl]cyclopropyl}phenyl)-4,5,6,7-tetrahydro-1H-pyrazolo[3,4-c]pyridine-3-carbonitrile;

1-(4-methoxyphenyl)-7-oxo-6-(4-{1-[(2-oxo-1-piperidinyl)methyl]cyclopropyl}phenyl)-4,5,6,7-tetrahydro-1H-pyrazolo[3,4-c]pyridine-3-carbonitrile;

2-[(1-{4-[3-cyano-1-(4-methoxyphenyl)-7-oxo-1,4,5,7-tetrahydro-6H-pyrazolo[3,4-c]pyridin-6-yl]phenyl}cyclopropyl)oxy]acetamide;

1-{4-[3-cyano-1-(4-methoxyphenyl)-7-oxo-1,4,5,7-tetrahydro-6H-pyrazolo[3,4-c]pyridin-6-yl]phenyl}cyclopropyl carbamate;

2-(1-{4-[3-cyano-1-(4-methoxyphenyl)-7-oxo-1,4,5,7-tetrahydro-6H-pyrazolo[3,4-c]pyridin-6-yl]phenyl}cyclopropyl)acetamide;

2-(1-{4-[3-cyano-1-(4-methoxyphenyl)-7-oxo-1,4,5,7-tetrahydro-6H-pyrazolo[3,4-c]pyridin-6-yl]phenyl}cyclopropyl)-N,N-dimethylacetamide;

1-(4-methoxyphenyl)-6-{4-[1-(methylamino)cyclopropyl]phenyl}-7-oxo-4,5,6,7-tetrahydro-1H-pyrazolo[3,4-c]pyridine-3-carbonitrile;

6-{4-[1-(dimethylamino)cyclopropyl]phenyl}-1-(4-methoxyphenyl)-7-oxo-4,5,6,7-tetrahydro-1H-pyrazolo[3,4-c]pyridine-3-carbonitrile;

1-(4-methoxyphenyl)-7-oxo-6-{4-[1-(1,3-thiazol-2-ylamino)cyclopropyl]phenyl}-4,5,6,7-tetrahydro-1H-pyrazolo[3,4-c]pyridine-3-carbonitrile;

N-(1-{4-[3-cyano-1-(4-methoxyphenyl)-7-oxo-1,4,5,7-tetrahydro-6H-pyrazolo[3,4-c]pyridin-6-yl]phenyl}cyclopropyl)urea;

N-(1-{4-[3-cyano-1-(4-methoxyphenyl)-7-oxo-1,4,5,7-tetrahydro-6H-pyrazolo[3,4-c]pyridin-6-yl]phenyl}cyclopropyl)-N'-methylurea;

N-(1-{4-[3-cyano-1-(4-methoxyphenyl)-7-oxo-1,4,5,7-tetrahydro-6H-pyrazolo[3,4-c]pyridin-6-yl]phenyl}cyclopropyl)-2-methylpropanamide;

6-(4-{1-[(4-hydroxy-1-piperidinyl)methyl]cyclopropyl}phenyl)-1-(4-methoxyphenyl)-7-oxo-4,5,6,7-tetrahydro-1H-pyrazolo[3,4-c]pyridine-3-carbonitrile;

1-(4-methoxyphenyl)-6-(4-{1-[(2-methyl-5,6-dihydro-1-(4H)-pyrimidinyl)methyl]cyclopropyl}phenyl)-7-oxo-4,5,6,7-tetrahydro-1H-pyrazolo[3,4-c]pyridine-3-carbonitrile;

1-(4-methoxyphenyl)-6-(4-{1-[(2-methyl-4,5-dihydro-1H-imidazol-1-yl)methyl]cyclopropyl}phenyl)-7-oxo-4,5,6,7-tetrahydro-1H-pyrazolo[3,4-c]pyridine-3-carbonitrile;

6-{4-[1-(4,5-dihydro-1,3-oxazol-2-ylmethyl)cyclopropyl]phenyl}-1-(4-methoxyphenyl)-7-oxo-4,5,6,7-tetrahydro-1H-pyrazolo[3,4-c]pyridine-3-carbonitrile;

6-{4-[1-(4,5-dihydro-1H-imidazol-2-ylmethyl)cyclopropyl]phenyl}-1-(4-methoxyphenyl)-7-oxo-4,5,6,7-tetrahydro-1H-pyrazolo[3,4-c]pyridine-3-carbonitrile;

1-(4-methoxyphenyl)-6-(4-{1-[(1-methyl-4,5-dihydro-1H-imidazol-2-yl)methyl]cyclopropyl}phenyl)-7-oxo-4,5,6,7-tetrahydro-1H-pyrazolo[3,4-c]pyridine-3-carbonitrile;

1-(4-methoxyphenyl)-7-oxo-6-(4-{1-[(1,3-thiazol-2-ylamino)methyl]cyclopropyl}phenyl)-4,5,6,7-tetrahydro-1H-pyrazolo[3,4-c]pyridine-3-carbonitrile;

1-(4-methoxyphenyl)-6-(4-{1-[(2-methyl-1H-imidazol-1-yl)methyl]cyclopropyl}phenyl)-7-oxo-4,5,6,7-tetrahydro-1H-pyrazolo[3,4-c]pyridine-3-carbonitrile;

1-(4-methoxyphenyl)-6-{4-[1-methyl-1-(2-oxo-1-pyrrolidinyl)ethyl]phenyl}-7-oxo-4,5,6,7-tetrahydro-1H-pyrazolo[3,4-c]pyridine-3-carboxamide;

1-(4-methoxyphenyl)-6-{4-[1-methyl-1-(2-oxo-1-piperidinyl)ethyl]phenyl}-7-oxo-4,5,6,7-tetrahydro-1H-pyrazolo[3,4-c]pyridine-3-carboxamide;

6-{4-[1,1-dimethyl-2-(2-oxo-1-piperidinyl)ethyl]phenyl}-1-(4-methoxyphenyl)-7-oxo-4,5,6,7-tetrahydro-1H-pyrazolo[3,4-c]pyridine-3-carboxamide;

6-{4-[1,1-dimethyl-2-(2-oxo-1-pyrrolidinyl)ethyl]phenyl}-1-(4-methoxyphenyl)-7-oxo-4,5,6,7-tetrahydro-1H-pyrazolo[3,4-c]pyridine-3-carboxamide;

6-{4-[1,1-dimethyl-2-(3-oxo-4-morpholinyl)ethyl]phenyl}-1-(4-methoxyphenyl)-7-oxo-4,5,6,7-tetrahydro-1H-pyrazolo[3,4-c]pyridine-3-carboxamide;

6-{4-[1,1-dimethyl-2-(2-oxo-1-piperazinyl)ethyl]phenyl}-1-(4-methoxyphenyl)-7-oxo-4,5,6,7-tetrahydro-1H-pyrazolo[3,4-c]pyridine-3-carboxamide;

6-{4-[1,1-dimethyl-2-(2-oxotetrahydro-1(2H)-pyrimidinyl)ethyl]phenyl}-1-(4-methoxyphenyl)-7-oxo-4,5,6,7-tetrahydro-1H-pyrazolo[3,4-c]pyridine-3-carboxamide;

6-{4-[1,1-dimethyl-2-(2-oxodihydro-2H-1,3-oxazin-3(4H)-yl)ethyl]phenyl}-1-(4-methoxyphenyl)-7-oxo-4,5,6,7-tetrahydro-1H-pyrazolo[3,4-c]pyridine-3-carboxamide;

1-{4-[3-(aminocarbonyl)-1-(4-methoxyphenyl)-7-oxo-1,4,5,7-tetrahydro-6H-pyrazolo[3,4-c]pyridin-6-yl]phenyl}-1-methylethyl methylcarbamate;

1-{4-[3-(aminocarbonyl)-1-(4-methoxyphenyl)-7-oxo-1,4,5,7-tetrahydro-6H-pyrazolo[3,4-c]pyridin-6-yl]phenyl}-1-methylethyl 3-pyrrolidinylcarbamate;

6-{4-[1-ethyl-1-(1-pyrrolidinylmethyl)propyl]phenyl}-1-(4-methoxyphenyl)-7-oxo-4,5,6,7-tetrahydro-1H-pyrazolo[3,4-c]pyridine-3-carboxamide;

6-(4-{1-[(dimethylamino)methyl]-1-ethylpropyl}phenyl)-1-(4-methoxyphenyl)-7-oxo-4,5,6,7-tetrahydro-1H-pyrazolo[3,4-c]pyridine-3-carboxamide;

1-[3-(aminomethyl)phenyl]-6-{4-[1,1-dimethyl-2-(1-pyrrolidinyl)ethyl]phenyl}-7-oxo-4,5,6,7-tetrahydro-1H-pyrazolo[3,4-c]pyridine-3-carboxamide;

1-[3-(aminomethyl)phenyl]-6-{4-[2-(dimethylamino)-1,1-dimethylethyl]phenyl}-7-oxo-4,5,6,7-tetrahydro-1H-pyrazolo[3,4-c]pyridine-3-carboxamide;

1-[3-(aminocarbonyl)phenyl]-6-{4-[2-(dimethylamino)-1,1-dimethylethyl]phenyl}-7-oxo-4,5,6,7-tetrahydro-1H-pyrazolo[3,4-c]pyridine-3-carboxamide;

1-[3-(aminocarbonyl)phenyl]-6-{4-[1,1-dimethyl-2-(1-pyrrolidinyl)ethyl]phenyl}-7-oxo-4,5,6,7-tetrahydro-1H-pyrazolo[3,4-c]pyridine-3-carboxamide;

1-(3-amino-1,2-benzisoxazol-5-yl)-6-{4-[1,1-dimethyl-2-(1-pyrrolidinyl)ethyl]phenyl}-7-oxo-4,5,6,7-tetrahydro-1H-pyrazolo[3,4-c]pyridine-3-carboxamide;

1-(3-amino-1,2-benzisoxazol-5-yl)-6-{4-[1,1-dimethyl-2-(1-pyrrolidinyl)ethyl]phenyl}-3-(trifluoromethyl)-1,4,5,6-tetrahydro-7H-pyrazolo[3,4-c]pyridin-7-one;

1-(1-amino-7-isoquinolinyl)-6-{4-[1,1-dimethyl-2-(1-pyrrolidinyl)ethyl]phenyl}-7-oxo-4,5,6,7-tetrahydro-1H-pyrazolo[3,4-c]pyridine-3-carboxamide;

1-(1-amino-7-isoquinolinyl)-6-{4-[2-(dimethylamino)-1,1-dimethylethyl]phenyl}-7-oxo-4,5,6,7-tetrahydro-1H-pyrazolo[3,4-c]pyridine-3-carboxamide;

1-(1-amino-7-isoquinolinyl)-6-(4-{1-[(dimethylamino)methyl]cyclopropyl}phenyl)-7-oxo-4,5,6,7-tetrahydro-1H-pyrazolo[3,4-c]pyridine-3-carboxamide;

1-(1-amino-7-isoquinolinyl)-7-oxo-6-{4-[1-(1-pyrrolidinylmethyl)cyclopropyl]phenyl}-4,5,6,7-tetrahydro-1H-pyrazolo[3,4-c]pyridine-3-carboxamide;

1-(3-amino-1,2-benzisoxazol-5-yl)-7-oxo-6-{4-[1-(1-pyrrolidinylmethyl)cyclopropyl]phenyl}-4,5,6,7-tetrahydro-1H-pyrazolo[3,4-c]pyridine-3-carboxamide;

1-(3-amino-1,2-benzisoxazol-5-yl)-6-{4-[1-(1-pyrrolidinylmethyl)cyclopropyl]phenyl}-3-(trifluoromethyl)-1,4,5,6-tetrahydro-7H-pyrazolo[3,4-c]pyridin-7-one;

1-(3-amino-1,2-benzisoxazol-5-yl)-7-oxo-6-{4-[1-(1-pyrrolidinylmethyl)cyclopropyl]phenyl}-4,5,6,7-tetrahydro-1H-pyrazolo[3,4-c]pyridine-3-carbonitrile;

1-[3-(aminomethyl)phenyl]-7-oxo-6-(4-{1-[(2-oxo-1-pyrrolidinyl)methyl]cyclopropyl}phenyl)-4,5,6,7-tetrahydro-1H-pyrazolo[3,4-c]pyridine-3-carboxamide;

6-[4-(1-{[acetyl(methyl)amino]methyl}cyclopropyl)phenyl]-1-[3-(aminomethyl)phenyl]-7-oxo-4,5,6,7-tetrahydro-1H-pyrazolo[3,4-c]pyridine-3-carboxamide;

1-[3-(aminocarbonyl)phenyl]-6-(4-{1-[(dimethylamino)methyl]cyclopropyl}phenyl)-7-oxo-4,5,6,7-tetrahydro-1H-pyrazolo[3,4-c]pyridine-3-carboxamide;

3-[3-cyano-6-(4-{1-[(dimethylamino)methyl]cyclopropyl}phenyl)-7-oxo-4,5,6,7-tetrahydro-1H-pyrazolo[3,4-c]pyridin-1-yl]benzamide;

1-(2,3-dihydro-1H-indol-6-yl)-6-(4-{1-[(dimethylamino)methyl]cyclopropyl}phenyl)-7-oxo-4,5,6,7-tetrahydro-1H-pyrazolo[3,4-c]pyridine-3-carboxamide;

1-(2,3-dihydro-1H-indol-6-yl)-7-oxo-6-{4-[1-(1-pyrrolidinylmethyl)cyclopropyl]phenyl}-4,5,6,7-tetrahydro-1H-pyrazolo[3,4-c]pyridine-3-carboxamide;

1-(2,3-dihydro-1H-indol-6-yl)-7-oxo-6-(4-{1-[(2-oxo-1-pyrrolidinyl)methyl]cyclopropyl}phenyl)-4,5,6,7-tetrahydro-1H-pyrazolo[3,4-c]pyridine-3-carboxamide;

6-(4-{1-[(dimethylamino)methyl]cyclobutyl}phenyl)-1-(4-methoxyphenyl)-7-oxo-4,5,6,7-tetrahydro-1H-pyrazolo[3,4-c]pyridine-3-carboxamide;

1-(4-methoxyphenyl)-6-{4-[1-(4-morpholinylmethyl)cyclobutyl]phenyl}-7-oxo-4,5,6,7-tetrahydro-1H-pyrazolo[3,4-c]pyridine-3-carboxamide;

1-(4-methoxyphenyl)-6-{4-[1-(4-morpholinylmethyl)cyclopentyl]phenyl}-7-oxo-4,5,6,7-tetrahydro-1H-pyrazolo[3,4-c]pyridine-3-carboxamide;

6-(4-{1-[(dimethylamino)methyl]cyclopentyl}phenyl)-1-(4-methoxyphenyl)-7-oxo-4,5,6,7-tetrahydro-1H-pyrazolo[3,4-c]pyridine-3-carboxamide;

1-(4-methoxyphenyl)-6-{4-[1-(2-oxo-pyrrolidin-1-yl)-cyclopropyl]phenyl}-3-trifluoromethyl-1,4,5,6-tetrahydro-pyrazolo[3,4-c]pyridin-7-one;

1-(4-methoxyphenyl)-6-{4-[1-(2-oxo-piperidin-1-yl)-cyclopropyl]phenyl}-3-trifluoromethyl-1,4,5,6-tetrahydro-pyrazolo[3,4-c]pyridin-7-one;

1-(4-methoxyphenyl)-6-[4-(1-methylaminocyclopropyl)-phenyl]-3-trifluoromethyl-1,4,5,6-tetrahydro-pyrazolo[3,4-c]pyridin-7-one;

6-[4-(1-dimethylaminocyclopropyl)phenyl]-1-(4-methoxyphenyl)-3-trifluoromethyl-1,4,5,6-tetrahydro-pyrazolo[3,4-c]pyridin-7-one;

N-(1-{4-[1-(4-methoxyphenyl)-7-oxo-3-trifluoromethyl-1,4,5,7-tetrahydro-pyrazolo[3,4-c]pyridin-6-yl]phenyl}-cyclopropyl)-N-methyl-acetamide;

N-(1-{4-[1-(4-methoxyphenyl)-7-oxo-3-trifluoromethyl-1,4,5,7-tetrahydro-pyrazolo[3,4-c]pyridin-6-yl]phenyl}-cyclopropyl)-N-methyl-methanesulfonamide;

N-(1-{4-[1-(4-methoxyphenyl)-7-oxo-3-trifluoromethyl-1,4,5,7-tetrahydro-pyrazolo[3,4-c]pyridin-6-yl]phenyl}-cyclopropyl)-N-methyl-2-methylaminoacetamide;

2-dimethylamino-N-(1-{4-[1-(4-methoxyphenyl)-7-oxo-3-trifluoromethyl-1,4,5,7-tetrahydro-pyrazolo[3,4-c]pyridin-6-yl]phenyl}cyclopropyl)-N-methylacetamide;

N-(1-{4-[1-(4-methoxyphenyl)-7-oxo-3-trifluoromethyl-1,4,5,7-tetrahydro-pyrazolo[3,4-c]pyridin-6-yl]phenyl}-cyclopropyl)-N-methyl-2-morpholin-4-yl-acetamide;

6-{4-[1-(1-hydroxyethyl)cyclopropyl]phenyl}-1-(4-methoxyphenyl)-3-trifluoromethyl-1,4,5,6-tetrahydro-pyrazolo[3,4-c]pyridin-7-one;

6-[4-(1-acetylcyclopropyl)phenyl]-1-(4-methoxyphenyl)-3-trifluoromethyl-1,4,5,6-tetrahydro-pyrazolo[3,4-c]pyridin-7-one;

6-{4-[1-(1-hydroxy-1-methyl-ethyl)cyclopropyl]phenyl}-1-(4-methoxyphenyl)-3-trifluoromethyl-1,4,5,6-tetrahydro-pyrazolo[3,4-c]pyridin-7-one;

6-[4-(1-methoxymethylcyclopropyl)phenyl]-1-(4-methoxyphenyl)-3-trifluoromethyl-1,4,5,6-tetrahydro-pyrazolo[3,4-c]pyridin-7-one;

6-{4-[1-(4,5-dihydro-oxazol-2-yl)cyclopropyl]phenyl}-1-(4-methoxyphenyl)-3-trifluoromethyl-1,4,5,6-tetrahydro-pyrazolo[3,4-c]pyridin-7-one;

1-{4-[1-(4-methoxy-phenyl)-7-oxo-3-trifluoromethyl-1,4,5,7-tetrahydro-pyrazolo[3,4-c]pyridin-6-yl]-phenyl}-cyclopropanecarboxylic acid 2-amino-ethyl ester;

6-{4-[1-(4,5-dihydro-oxazol-2-yl)-cyclopropyl]-phenyl}-1-(4-methoxy-phenyl)-7-oxo-4,5,6,7-tetrahydro-1H-pyrazolo[3,4-c]pyridine-3-carboxylic acid amide;

6-{4-[1-(4,5-dihydro-1H-imidazol-2-yl)cyclopropyl]phenyl}-1-(4-methoxyphenyl)-3-trifluoromethyl-1,4,5,6-tetrahydro-pyrazolo[3,4-c]pyridin-7-one;

1-(4-methoxyphenyl)-6-{4-[1-(1-methyl-4,5-dihydro-1H-imidazol-2-yl)cyclopropyl]phenyl}-3-trifluoromethyl-1,4,5,6-tetrahydro-pyrazolo[3,4-c]pyridin-7-one;

6-{4-[1-(1-methanesulfonyl-4,5-dihydro-1H-imidazol-2-yl)-cyclopropyl]phenyl}-1-(4-methoxyphenyl)-3-trifluoromethyl-1,4,5,6-tetrahydro-pyrazolo[3,4-c]pyridin-7-one;

6-{4-[1-(1H-imidazol-2-yl)cyclopropyl]phenyl}-1-(4-methoxy-phenyl)-3-trifluoromethyl-1,4,5,6-tetrahydro-pyrazolo[3,4-c]pyridin-7-one;

1-(4-methoxyphenyl)-6-{4-[1-(1-methyl-1H-imidazol-2-yl)-cyclopropyl]phenyl}-3-trifluoromethyl-1,4,5,6-tetrahydro-pyrazolo[3,4-c]pyridin-7-one;

2-[(1-{4-[1-(4-methoxyphenyl)-7-oxo-3-trifluoromethyl-1,4,5,7-tetrahydro-pyrazolo[3,4-c]pyridin-6-yl]phenyl}-cyclopropyl)-methyl-amino]-acetamide;

6-(4-{1-[(2-hydroxyethyl)-methylamino]cyclopropyl}phenyl)-1-(4-methoxyphenyl)-3-trifluoromethyl-1,4,5,6-tetrahydro-pyrazolo[3,4-c]pyridin-7-one;

1-{4-[1-(4-methoxy-phenyl)-7-oxo-3-trifluoromethyl-1,4,5,7-tetrahydro-pyrazolo[3,4-c]pyridin-6-yl]-phenyl}-cyclopropanecarboxylic acid methoxy-methyl-amide;

6-[4-(1-hydroxymethylcyclopropyl)phenyl]-1-(4-methoxyphenyl)-7-oxo-4,5,6,7-tetrahydro-1H-pyrazolo[3,4-c]pyridine-3-carboxylic acid amide;

6-[4-(1-acetyl-cyclopropyl)-phenyl]-1-(4-methoxy-phenyl)-7-oxo-4,5,6,7-tetrahydro-1H-pyrazolo[3,4-c]pyridine-3-carboxylic acid amide;

6-[4-(1-aminocyclopropyl)phenyl]-1-(4-methoxyphenyl)-7-oxo-4,5,6,7-tetrahydro-1H-pyrazolo[3,4-c]pyridine-3-carboxylic acid amide;

1-(4-methoxyphenyl)-6-[4-(1-methylaminocyclopropyl)phenyl]-7-oxo-4,5,6,7-tetrahydro-1H-pyrazolo[3,4-c]pyridine-3-carboxylic acid amid;

6-[4-(1-dimethylaminocyclopropyl)phenyl]-1-(4-methoxyphenyl)-7-oxo-4,5,6,7-tetrahydro-1H-pyrazolo[3,4-c]pyridine-3-carboxylic acid amide;

6-[4-(1-methylaminomethylcyclopentyl)phenyl]-1-(4-methoxy-phenyl)-7-oxo-4,5,6,7-tetrahydro-1H-pyrazolo[3,4-c]pyridine-3-carboxylic acid amide;

6-[4-(1-dimethylaminomethylcyclopentyl)phenyl]-1-(4-methoxyphenyl)-7-oxo-4,5,6,7-tetrahydro-1H-pyrazolo[3,4-c]pyridine-3-carboxylic acid amide;

6-[4-(1-dimethylaminomethylcyclopentyl)phenyl]-1-(4-methoxyphenyl)-7-oxo-4,5,6,7-tetrahydro-1H-pyrazolo[3,4-c]pyridine-3-carbonitrile;

6-[4-(1-[(2-hydroxyethyl)methylaminomethyl]-cyclopentyl)phenyl]-1-(4-methoxy-phenyl)-7-oxo-4,5,6,7-tetrahydro-1H-pyrazolo[3,4-c]pyridine-3-carboxylic acid amide;

6-[4-(1-hydroxymethyl-cyclopentyl)-phenyl]-1-(4-methoxy-phenyl)-7-oxo-4,5,6,7-tetrahydro-1H-pyrazolo[3,4-c]pyridine-3-carboxylic acid amide;

6-(4-{1-[(2-hydroxyethyl)methylamino]cyclopropyl}phenyl)-1-(4-methoxyphenyl)-7-oxo-4,5,6,7-tetrahydro-1H-pyrazolo[3,4-c]pyridine-3-carboxylic acid amide;

1-(4-methoxyphenyl)-6-{4-[1-(methyl-prop-2-ynylamino)-cyclopropyl]phenyl}-7-oxo-4,5,6,7-tetrahydro-1H-pyrazolo[3,4-c]pyridine-3-carboxylic acid amide;

3-(1-hydroxyethyl)-1-(4-methoxyphenyl)-6-[4-(1-methylamino-cyclopropyl)phenyl]-1,4,5,6-tetrahydro-pyrazolo[3,4-c]pyridin-7-one;

3-acetyl-1-(4-methoxyphenyl)-6-[4-(1-methylamino-cyclopropyl)phenyl]-1,4,5,6-tetrahydro-pyrazolo[3,4-c]pyridin-7-one;

1-(4-methoxyphenyl)-6-[4-(1-methylaminocyclopropyl)phenyl]-7-oxo-4,5,6,7-tetrahydro-1H-pyrazolo[3,4-c]pyridine-3-carboxylic acid methylamide;

1-(4-methoxyphenyl)-6-[4-(1-methylaminocyclopropyl)phenyl]-7-oxo-4,5,6,7-tetrahydro-1H-pyrazolo[3,4-c]pyridine-3-carboxylic acid dimethylamide;

6-[4-(1-aminocyclopropyl)phenyl]-1-(4-methoxyphenyl)-7-oxo-4,5,6,7-tetrahydro-1H-pyrazolo[3,4-c]pyridine-3-carbonitrile;

1-(4-methoxyphenyl)-6-[4-(1-methylaminocyclopropyl)phenyl]-7-oxo-4,5,6,7-tetrahydro-1H-pyrazolo[3,4-c]pyridine-3-carbonitrile;

6-[4-(1-dimethylaminocyclopropyl)phenyl]-1-(4-methoxyphenyl)-7-oxo-4,5,6,7-tetrahydro-1H-pyrazolo[3,4-c]pyridine-3-carbonitrile;

2-[(1-{4-[3-cyano-1-(4-methoxyphenyl)-7-oxo-1,4,5,7-tetrahydro-pyrazolo[3,4-c]pyridin-6-yl]phenyl}cyclopropyl)-methylamino]acetamide;

6-(4-{1-[(2-hydroxyethyl)methylamino]cyclopropyl}phenyl)-1-(4-methoxyphenyl)-7-oxo-4,5,6,7-tetrahydro-1H-pyrazolo[3,4-c]pyridine-3-carbonitrile;

1-(4-methoxyphenyl)-7-oxo-6-[4-(1-pyrrolidin-1-yl-cyclopropyl)phenyl]-4,5,6,7-tetrahydro-1H-pyrazolo[3,4-c]pyridine-3-carboxylic acid ethyl ester;

1-(4-methoxyphenyl)-7-oxo-6-[4-(1-pyrrolidin-1-yl-cyclopropyl)phenyl]-4,5,6,7-tetrahydro-1H-pyrazolo[3,4-c]pyridine-3-carboxylic acid amide;

1-(4-methoxyphenyl)-7-oxo-6-[4-(1-pyrrolidin-1-yl-cyclopropyl)phenyl]-4,5,6,7-tetrahydro-1H-pyrazolo[3,4-c]pyridine-3-carbonitrile;

1-(4-methoxyphenyl)-6-[4-(1-morpholin-4-yl-cyclopropyl)phenyl]-7-oxo-4,5,6,7-tetrahydro-1H-pyrazolo[3,4-c]pyridine-3-carboxylic acid amide;

1-(4-methoxyphenyl)-6-[4-(1-morpholin-4-yl-cyclopropyl)phenyl]-7-oxo-4,5,6,7-tetrahydro-1H-pyrazolo[3,4-c]pyridine-3-carbonitrile;

6-[4-(1-dimethylaminocyclopropyl)phenyl]-1-(4-methoxyphenyl)-7-oxo-4,5,6,7-tetrahydro-1H-pyrazolo[3,4-c]pyridine-3-carboxylic acid methylamide;

6-[4-(1-dimethylaminocyclopropyl)phenyl]-1-(4-methoxyphenyl)-7-oxo-4,5,6,7-tetrahydro-1H-pyrazolo[3,4-c]pyridine-3-carboxylic acid dimethylamide;
6-{4-[1-(1,1-dioxo-1$\lambda^6$-thiomorpholin-4-yl)cyclopropyl]phenyl}-1-(4-methoxyphenyl)-7-oxo-4,5,6,7-tetrahydro-1H-pyrazolo[3,4-c]pyridine-3-carboxylic acid amide;
6-[4-(1-aminocyclopropylmethyl)phenyl]-1-(4-methoxyphenyl)-7-oxo-4,5,6,7-tetrahydro-1H-pyrazolo[3,4-c]pyridine-3-carboxylic acid amide;
6-[4-(1-dimethylaminocyclopropylmethyl)phenyl]-1-(4-methoxyphenyl)-7-oxo-4,5,6,7-tetrahydro-1H-pyrazolo[3,4-c]pyridine-3-carboxylic acid amide;
1-(3-chloro-phenyl)-6-{4-[1,1-dimethyl-2-(2-oxo-pyrrolidin-1-yl)-ethyl]-phenyl}-7-oxo-4,5,6,7-tetrahydro-1H pyrazolo[3,4-c]pyridine-3-carboxylic acid amide;
6-{4-[1,1-dimethyl-2-(2-oxo-pyrrolidin-1-yl)-ethyl]-phenyl}-1-(4-methoxy-phenyl)-7-oxo-4,5,6,7-tetrahydro-1H-pyrazolo[3,4-c]pyridine-3-carbonitrile;
1-(4-methoxy-phenyl)-6-[4-(1-methyl-1-pyrrolidin-1-yl-ethyl)-phenyl]-7-oxo-4,5,6,7-tetrahydro-1H-pyrazolo[3,4-c]pyridine-3-carboxylic acid amide;
6-[4-(1-dimethylamino-1-methyl-ethyl)-phenyl]-1-(4-methoxy-phenyl)-7-oxo-4,5,6,7-tetrahydro-1H-pyrazolo[3,4-c]pyridine-3-carboxylic acid amide;
6-{4-[1-(4,4-dimethyl-4,5-dihydro-oxazol-2-yl)-cyclopropyl]-phenyl}-1-(4-methoxy-phenyl)-3-trifluoromethyl-1,4,5,6-tetrahydro-pyrazolo[3,4-c]pyridin-7-one;
6-[4-(1-methanesulfonyl-1-methyl-ethyl)-phenyl]-1-(4-methoxy-phenyl)-7-oxo-4,5,6,7-tetrahydro-1H-pyrazolo[3,4-c]pyridine-3-carboxylic acid amide;
6-[4-(1-hydroxy-1-methyl-ethyl)-phenyl]-1-(4-methoxy-phenyl)-7-oxo-4,5,6,7-tetrahydro-1H-pyrazolo[3,4-c]pyridine-3-carboxylic acid amide;
1-(4-methoxy-phenyl)-6-(4-{1-[2-(2-oxo-2H-pyridin-1-yl)-ethyl]-cyclopropyl}-phenyl)-3-trifluoromethyl-1,4,5,6-tetrahydro-pyrazolo[3,4-c]pyridin-7-one;
2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-acetamide;
2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-N-methyl-acetamide;
2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-N,N-dimethyl-acetamide;
1-(4-methoxy-phenyl)-6-{4-[1-(2-oxo-2-pyrrolidin-1-yl-ethyl)-cyclopropyl]-phenyl}-3-trifluoromethyl-1,4,5,6-tetrahydro-pyrazolo[3,4-c]pyridin-7-one;
6-{4-[1-(2-hydroxy-ethyl)-cyclopropyl]-phenyl}-1-(4-methoxy-phenyl)-3-trifluoromethyl-1,4,5,6-tetrahydro-pyrazolo[3,4-c]pyridin-7-one;
1-(4-methoxy-phenyl)-6-{4-[1-(2-methylamino-ethyl)-cyclopropyl]-phenyl}-3-trifluoromethyl-1,4,5,6-tetrahydro-pyrazolo[3,4-c]pyridin-7-one;
6-{4-[1-(2-dimethylamino-ethyl)-cyclopropyl]-phenyl}-1-(4-methoxy-phenyl)-3-trifluoromethyl-1,4,5,6-tetrahydro-pyrazolo[3,4-c]pyridin-7-one;
1-(4-methoxy-phenyl)-6-{4-[1-(2-pyrrolidin-1-yl-ethyl)-cyclopropyl]-phenyl}-3-trifluoromethyl-1,4,5,6-tetrahydro-pyrazolo[3,4-c]pyridin-7-one;
1-(4-methoxy-phenyl)-6-{4-[1-(2-morpholin-4-yl-ethyl)-cyclopropyl]-phenyl}-3-trifluoromethyl-1,4,5,6-tetrahydro-pyrazolo[3,4-c]pyridin-7-one;
1-(4-methoxy-phenyl)-6-{4-[1-(2-pyrrolidin-1-yl-acetyl)-cyclopropyl]-phenyl}-3-trifluoromethyl-1,4,5,6-tetrahydro-pyrazolo[3,4-c]pyridin-7-one;
6-[4-(1-carbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid ethyl ester;
6-[4-(1-carbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid amide;
1-(4-methoxy-phenyl)-6-[4-(1-methylcarbamoylmethyl-cyclopropyl)-phenyl]-7-oxo-4,5,6,7-tetrahydro-1H-pyrazolo[3,4-c]pyridine-3-carboxylic acid ethyl ester;
1-(4-methoxy-phenyl)-6-[4-(1-methylcarbamoylmethyl-cyclopropyl)-phenyl]-7-oxo-4,5,6,7-tetrahydro-1H-pyrazolo[3,4-c]pyridine-3-carboxylic acid amide;
6-[4-(1-dimethylcarbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid ethyl ester;
6-[4-(1-dimethylcarbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid amide;
6-{4-[1-(2-hydroxy-ethyl)-cyclopropyl]-phenyl}-1-(4-methoxy-phenyl)-7-oxo-4,5,6,7-tetrahydro-1H-pyrazolo[3,4-c]pyridine-3-carboxylic acid amide;
1-(4-methoxy-phenyl)-6-{4-[1-(2-morpholin-4-yl-ethyl)-cyclopropyl]-phenyl}-7-oxo-4,5,6,7-tetrahydro-1H-pyrazolo[3,4-c]pyridine-3-carboxylic acid amide;
1-(4-methoxy-phenyl)-7-oxo-6-(4-{1-[2-(2-oxo-pyrrolidin-1-yl)-ethyl]-cyclopropyl}-phenyl)-4,5,6,7-tetrahydro-1H-pyrazolo[3,4-c]pyridine-3-carboxylic acid amide;
1-(4-methoxy-phenyl)-6-{4-[1-(2-methylamino-ethyl)-cyclopropyl]-phenyl}-7-oxo-4,5,6,7-tetrahydro-1H-pyrazolo[3,4-c]pyridine-3-carboxylic acid amide;
6-{4-[1-(2-dimethylamino-ethyl)-cyclopropyl]-phenyl}-1-(4-methoxy-phenyl)-7-oxo-4,5,6,7-tetrahydro-1H-pyrazolo[3,4-c]pyridine-3-carboxylic acid amide;
6-{4-[1-(2-diethylamino-ethyl)-cyclopropyl]-phenyl}-(4-methoxy-phenyl)-7-oxo-4,5,6,7-tetrahydro-1H-pyrazolo[3,4-c]pyridine-3-carboxylic acid amide;
1-(4-methoxy-phenyl)-7-oxo-6-{4-[1-(2-pyrrolidin-1-yl-ethyl)-cyclopropyl]-phenyl}-4,5,6,7-tetrahydro-1H-pyrazolo[3,4-c]pyridine-3-carboxylic acid amide;
6-(4-{1-[2-(2,5-dimethyl-pyrrolidin-1-yl)-ethyl]-cyclopropyl}-phenyl)-1-(4-methoxy-phenyl)-7-oxo-4,5,6,7-tetrahydro-1H-pyrazolo[3,4-c]pyridine-3-carboxylic acid amide;
6-(4-{1-[2-(3-hydroxy-pyrrolidin-1-yl)-ethyl]-cyclopropyl}-phenyl)-1-(4-methoxy-phenyl)-7-oxo-4,5,6,7-tetrahydro-1H-pyrazolo[3,4-c]pyridine-3-carboxylic acid amide;
6-(4-{1-[2-(2,5-dimethyl-pyrrolidin-1-yl)-ethyl]-cyclopropyl}-phenyl)-1-(4-methoxy-phenyl)-7-oxo-4,5,6,7-tetrahydro-1H-pyrazolo[3,4-c]pyridine-3-carboxylic acid amide;
1-(4-methoxy-phenyl)-7-oxo-6-(4-{1-[2-(2-oxo-piperidin-1-yl)-ethyl]-cyclopropyl}-phenyl)-4,5,6,7-tetrahydro-1H-pyrazolo[3,4-c]pyridine-3-carboxylic acid amide;
1-(4-methoxy-phenyl)-7-oxo-6-(4-{1-[2-(2-oxo-2H-pyridin-1-yl)-ethyl]-cyclopropyl}-phenyl)-4,5,6,7-tetrahydro-1H-pyrazolo[3,4-c]pyridine-3-carboxylic acid amide;
1-(4-methoxy-phenyl)-6-(4-{1-[2-(methyl-thiazol-2-yl-amino)-ethyl]-cyclopropyl}-phenyl)-7-oxo-4,5,6,7-tetrahydro-1H-pyrazolo[3,4-c]pyridine-3-carboxylic acid amide;
6-[4-(1-{2-[(2-hydroxy-ethyl)-methyl-amino]-ethyl}-cyclopropyl)-phenyl]-1-(4-methoxy-phenyl)-7-oxo-4,5,6,7-tetrahydro-1H-pyrazolo[3,4-c]pyridine-3-carboxylic acid amide;

1-(4-methoxy-phenyl)-6-(4-{1-[2-(2-methyl-imidazol-1-yl)-ethyl]-cyclopropyl}-phenyl)-7-oxo-4,5,6,7-tetrahydro-1H-pyrazolo[3,4-c]pyridine-3-carboxylic acid amide;

6-(4-{1-[2-(2,6-dimethyl-piperidin-1-yl)-ethyl]-cyclopropyl}-phenyl)-1-(4-methoxy-phenyl)-7-oxo-4,5,6,7-tetrahydro-1H-pyrazolo[3,4-c]pyridine-3-carboxylic acid amide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopropyl)-N,N-dimethyl-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopropyl)-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopropyl)-N-methyl-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopropyl)-N,N-dimethyl-acetamide;

6-{4-[1-(2-hydroxy-ethyl)-cyclopropyl]-phenyl}-3-methanesulfonyl-1-(4-methoxy-phenyl)-1,4,5,6-tetrahydro-pyrazolo[3,4-c]pyridin-7-one;

3-methanesulfonyl-6-{4-[1-(2-methoxy-ethyl)-cyclopropyl]-phenyl}-1-(4-methoxy-phenyl)-1,4,5,6-tetrahydro-pyrazolo[3,4-c]pyridin-7-one;

3-methanesulfonyl-1-(4-methoxy-phenyl)-6-{4-[1-(2-methylamino-ethyl)-cyclopropyl]-phenyl}-1,4,5,6-tetrahydro-pyrazolo[3,4-c]pyridin-7-one;

6-{4-[1-(2-dimethylamino-ethyl)-cyclopropyl]-phenyl}-3-methanesulfonyl-1-(4-methoxy-phenyl)-1,4,5,6-tetrahydro-pyrazolo[3,4-c]pyridin-7-one;

6-{4-[1-(2-diethylamino-ethyl)-cyclopropyl]-phenyl}-3-methanesulfonyl-1-(4-methoxy-phenyl)-1,4,5,6-tetrahydro-pyrazolo[3,4-c]pyridin-7-one;

6-{4-[1-(2-isopropylamino-ethyl)-cyclopropyl]-phenyl}-3-methanesulfonyl-1-(4-methoxy-phenyl)-1,4,5,6-tetrahydro-pyrazolo[3,4-c]pyridin-7-one;

3-methanesulfonyl-1-(4-methoxy-phenyl)-6-{4-[1-(2-pyrrolidin-1-yl-ethyl)-cyclopropyl]-phenyl}-1,4,5,6-tetrahydro-pyrazolo[3,4-c]pyridin-7-one;

3-methanesulfonyl-1-(4-methoxy-phenyl)-6-(4-{1-[2-(2-oxo-pyrrolidin-1-yl)-ethyl]-cyclopropyl}-phenyl)-1,4,5,6-tetrahydro-pyrazolo[3,4-c]pyridin-7-one;

6-(4-{1-[2-(2,5-dimethyl-pyrrolidin-1-yl)-ethyl]-cyclopropyl}-phenyl)-3-methanesulfonyl-1-(4-methoxy-phenyl)-1,4,5,6-tetrahydro-pyrazolo[3,4-c]pyridin-7-one;

6-(4-{-[2-(3-hydroxy-pyrrolidin-1-yl)-ethyl]-cyclopropyl}-phenyl)-3-methanesulfonyl-1-(4-methoxy-phenyl)-1,4,5,6-tetrahydro-pyrazolo[3,4-c]pyridin-7-one;

3-methanesulfonyl-1-(4-methoxy-phenyl)-6-(4-{1-[2-(2-oxo-piperidin-1-yl)-ethyl]-cyclopropyl}-phenyl)-1,4,5,6-tetrahydro-pyrazolo[3,4-c]pyridin-7-one;

3-methanesulfonyl-1-(4-methoxy-phenyl)-6-{4-[1-(2-morpholin-4-yl-ethyl)-cyclopropyl]-phenyl}-1,4,5,6-tetrahydro-pyrazolo[3,4-c]pyridin-7-one;

6-[4-(1-{2-[(2-hydroxy-ethyl)-methyl-amino]-ethyl}-cyclopropyl)-phenyl]-3-methanesulfonyl-1-(4-methoxy-phenyl)-1,4,5,6-tetrahydro-pyrazolo[3,4-c]pyridin-7-one;

2-{[2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopropyl)-ethyl]-methyl-amino}-acetamide;

2-[2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopropyl)-ethylamino]-acetamide;

6-(4-{1-[2-(2-hydroxy-ethylamino)-ethyl]-cyclopropyl}-phenyl)-3-methanesulfonyl-1-(4-methoxy-phenyl)-1,4,5,6-tetrahydro-pyrazolo[3,4-c]pyridin-7-one;

3-methanesulfonyl-1-(4-methoxy-phenyl)-6-(4-{1-[2-(2-methyl-imidazol-1-yl)-ethyl]-cyclopropyl}-phenyl)-1,4,5,6-tetrahydro-pyrazolo[3,4-c]pyridin-7-one;

3-methanesulfonyl-1-(4-methoxy-phenyl)-6-(4-{1-[2-(thiazol-2-ylamino)-ethyl]-cyclopropyl}-phenyl)-1,4,5,6-tetrahydro-pyrazolo[3,4-c]pyridin-7-one;

3-methanesulfonyl-1-(4-methoxy-phenyl)-6-(4-{1-[2-(2-oxo-2H-pyridin-1-yl)-ethyl]-cyclopropyl}-phenyl)-1,4,5,6-tetrahydro-pyrazolo[3,4-c]pyridin-7-one;

2-(1-{4-[3-cyano-1-(4-methoxy-phenyl)-7-oxo-1,4,5,7-tetrahydro-pyrazolo[3,4-c]pyridin-6-yl]-phenyl}-cyclopropyl)-acetamide;

2-(1-{4-[3-cyano-1-(4-methoxy-phenyl)-7-oxo-1,4,5,7-tetrahydro-pyrazolo[3,4-c]pyridin-6-yl]-phenyl}-cyclopropyl)-N-methyl-acetamide;

2-(1-{4-[3-cyano-1-(4-methoxy-phenyl)-7-oxo-1,4,5,7-tetrahydro-pyrazolo[3,4-c]pyridin-6-yl]-phenyl}-cyclopropyl)-N,N-dimethyl-acetamide;

6-{4-[1-(2-hydroxy-ethyl)-cyclopropyl]-phenyl}-1-(4-methoxy-phenyl)-7-oxo-4,5,6,7-tetrahydro-1H-pyrazolo[3,4-c]pyridine-3-carbonitrile;

1-(4-methoxy-phenyl)-6-{4-[1-(2-methylamino-ethyl)-cyclopropyl]-phenyl}-7-oxo-4,5,6,7-tetrahydro-1H-pyrazolo[3,4-c]pyridine-3-carbonitrile;

6-{4-[1-(2-dimethylamino-ethyl)-cyclopropyl]-phenyl}-1-(4-methoxy-phenyl)-7-oxo-4,5,6,7-tetrahydro-1H-pyrazolo[3,4-c]pyridine-3-carbonitrile;

1-(4-methoxy-phenyl)-7-oxo-6-{4-[1-(2-pyrrolidin-1-yl-ethyl)-cyclopropyl]-phenyl}-4,5,6,7-tetrahydro-1H-pyrazolo[3,4-c]pyridine-3-carbonitrile;

1-(4-methoxy-phenyl)-6-{4-[1-(2-morpholin-4-yl-ethyl)-cyclopropyl]-phenyl}-7-oxo-4,5,6,7-tetrahydro-1H-pyrazolo[3,4-c]pyridine-3-carbonitrile;

6-(4-{1-[2-(1,1-dioxo-1l6-thiomorpholin-4-yl)-ethyl]-cyclopropyl}-phenyl)-1-(4-methoxy-phenyl)-7-oxo-4,5,6,7-tetrahydro-1H-pyrazolo[3,4-c]pyridine-3-carbonitrile;

6-(4-{1-[2-(2-hydroxy-ethylamino)-ethyl]-cyclopropyl}-phenyl)-1-(4-methoxy-phenyl)-7-oxo-4,5,6,7-tetrahydro-1H-pyrazolo[3,4-c]pyridine-3-carbonitrile;

2-[2-(1-{4-[3-cyano-1-(4-methoxy-phenyl)-7-oxo-1,4,5,7-tetrahydro-pyrazolo[3,4-c]pyridin-6-yl]-phenyl}-cyclopropyl)-ethylamino]-acetamide;

2-{[2-(1-{4-[3-cyano-1-(4-methoxy-phenyl)-7-oxo-1,4,5,7-tetrahydro-pyrazolo[3,4-c]pyridin-6-yl]-phenyl}-cyclopropyl)-ethyl]-methyl-amino}-acetamide;

6-[4-(1-{2-[(2-hydroxy-ethyl)-methyl-amino]-ethyl}-cyclopropyl)-phenyl]-1-(4-methoxy-phenyl)-7-oxo-4,5,6,7-tetrahydro-1H-pyrazolo[3,4-c]pyridine-3-carbonitrile;

N-[2-(1-{4-[3-cyano-1-(4-methoxy-phenyl)-7-oxo-1,4,5,7-tetrahydro-pyrazolo[3,4-c]pyridin-6-yl]-phenyl}-cyclopropyl)-ethyl]-N-methyl-methanesulfonamide;

N-[2-(1-{4-[3-cyano-1-(4-methoxy-phenyl)-7-oxo-1,4,5,7-tetrahydro-pyrazolo[3,4-c]pyridin-6-yl]-phenyl}-cyclopropyl)-ethyl]-N-methyl-acetamide;

1-(4-methoxy-phenyl)-7-oxo-6-(4-{1-[2-(2-oxo-pyrrolidin-1-yl)-ethyl]-cyclopropyl}-phenyl)-4,5,6,7-tetrahydro-1H-pyrazolo[3,4-c]pyridine-3-carbonitrile;

1-(4-methoxy-phenyl)-7-oxo-6-(4-{1-[2-(2-oxo-2H-pyridin-1-yl)-ethyl]-cyclopropyl}-phenyl)-4,5,6,7-tetrahydro-1H-pyrazolo[3,4-c]pyridine-3-carbonitrile;

6-{4-[1-(2-dimethylamino-ethyl)-cyclopropyl]-phenyl}-1-(4-methoxy-phenyl)-3-methyl-1,4,5,6-tetrahydro-pyrazolo[3,4-c]pyridin-7-one;

6-{4-[1-(2-dimethylamino-ethyl)-cyclopropyl]-phenyl}-1-(4-methoxy-phenyl)-1,4,5,6-tetrahydro-pyrazolo[3,4-c]pyridin-7-one;

5-{4-[1-(2-dimethylamino-ethyl)-cyclopropyl]-phenyl}-3-(4-methoxy-phenyl)-3,5,6,7-tetrahydro-[1,2,3]triazolo[4,5-c]pyridin-4-one;

5-{4-[1-(2-dimethylamino-ethyl)-cyclobutyl]-phenyl}-3-(4-methoxy-phenyl)-3,5,6,7-tetrahydro-[1,2,3]triazolo[4,5-c]pyridin-4-one;

6-{4-[1-(2-dimethylamino-ethyl)-cyclobutyl]-phenyl}-1-(4-methoxy-phenyl)-1,4,5,6-tetrahydro-pyrazolo[3,4-c]pyridin-7-one;

6-{4-[1-(2-dimethylamino-ethyl)-cyclobutyl]-phenyl}-1-(4-methoxy-phenyl)-3-methyl-1,4,5,6-tetrahydro-pyrazolo[3,4-c]pyridin-7-one;

6-{4-[1-(2-dimethylamino-ethyl)-cyclobutyl]-phenyl}-1-(4-methoxy-phenyl)-3-trifluoromethyl-1,4,5,6-tetrahydro-pyrazolo[3,4-c]pyridin-7-one;

6-{4-[1-(2-dimethylamino-ethyl)-cyclobutyl]-phenyl}-1-(4-methoxy-phenyl)-7-oxo-4,5,6,7-tetrahydro-1H-pyrazolo[3,4-c]pyridine-3-carbonitrile;

6-{4-[1-(2-dimethylamino-ethyl)-cyclobutyl]-phenyl}-1-(4-methoxy-phenyl)-7-oxo-4,5,6,7-tetrahydro-1H-pyrazolo[3,4-c]pyridine-3-carboxylic acid amide;

6-{4-[1-(2-dimethylamino-ethyl)-cyclobutyl]-phenyl}-3-methanesulfonyl-1-(4-methoxy-phenyl)-1,4,5,6-tetrahydro-pyrazolo[3,4-c]pyridin-7-one;

6-{4-[1-(2-dimethylamino-ethyl)-cyclopentyl]-phenyl}-3-methanesulfonyl-1-(4-methoxy-phenyl)-1,4,5,6-tetrahydro-pyrazolo[3,4-c]pyridin-7-one;

6-{4-[1-(2-dimethylamino-ethyl)-cyclopentyl]-phenyl}-1-(4-methoxy-phenyl)-7-oxo-4,5,6,7-tetrahydro-1H-pyrazolo[3,4-c]pyridine-3-carbonitrile;

6-{4-[1-(2-dimethylamino-ethyl)-cyclopentyl]-phenyl}-1-(4-methoxy-phenyl)-7-oxo-4,5,6,7-tetrahydro-1H-pyrazolo[3,4-c]pyridine-3-carboxylic acid amide;

6-{4-[1-(2-dimethylamino-ethyl)-cyclopentyl]-phenyl}-1-(4-methoxy-phenyl)-3-trifluoromethyl-1,4,5,6-tetrahydro-pyrazolo[3,4-c]pyridin-7-one;

6-{4-[1-(2-dimethylamino-ethyl)-cyclopentyl]-phenyl}-1-(4-methoxy-phenyl)-3-methyl-1,4,5,6-tetrahydro-pyrazolo[3,4-c]pyridin-7-one;

5-{4-[1-(2-dimethylamino-ethyl)-cyclopentyl]-phenyl}-3-(4-methoxy-phenyl)-3,5,6,7-tetrahydro-[1,2,3]triazolo[4,5-c]pyridin-4-one;

2-(1-{4-[3-(4-methoxy-phenyl)-4-oxo-3,4,6,7-tetrahydro-[1,2,3]triazolo[4,5-c]pyridin-5-yl]-phenyl}-cyclopentyl)-N-methyl-acetamide;

2-(1-{4-[3-(4-methoxy-phenyl)-4-oxo-3,4,6,7-tetrahydro-[1,2,3]triazolo[4,5-c]pyridin-5-yl]-phenyl}-cyclopentyl)-N,N-dimethyl-acetamide;

2-(1-{4-[3-(4-methoxy-phenyl)-4-oxo-3,4,6,7-tetrahydro-[1,2,3]triazolo[4,5-c]pyridin-5-yl]-phenyl}-cyclopentyl)-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopentyl)-acetamide;

6-[4-(1-carbamoylmethyl-cyclopentyl)-phenyl]-1-(4-methoxy-phenyl)-7-oxo-4,5,6,7-tetrahydro-1H-pyrazolo[3,4-c]pyridine-3-carboxylic acid amide;

1-(4-methoxy-phenyl)-6-[4-(1-methylcarbamoylmethyl-cyclopentyl)-phenyl]-7-oxo-4,5,6,7-tetrahydro-1H-pyrazolo[3,4-c]pyridine-3-carboxylic acid amide;

6-[4-(1-dimethylcarbamoylmethyl-cyclopentyl)-phenyl]-1-(4-methoxy-phenyl)-7-oxo-4,5,6,7-tetrahydro-1H-pyrazolo[3,4-c]pyridine-3-carboxylic acid amide;

2-(1-{4-[3-cyano-1-(4-methoxy-phenyl)-7-oxo-1,4,5,7-tetrahydro-pyrazolo[3,4-c]pyridin-6-yl]-phenyl}-cyclopentyl)-N,N-dimethyl-acetamide;

2-(1-{4-[3-cyano-1-(4-methoxy-phenyl)-7-oxo-1,4,5,7-tetrahydro-pyrazolo[3,4-c]pyridin-6-yl]-phenyl}-cyclopentyl)-N-methyl-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopentyl)-N-methyl-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopentyl)-N,N-dimethyl-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopentyl)-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclobutyl)-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclobutyl)-N-methyl-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclobutyl)-N,N-dimethyl-acetamide;

2-(1-{4-[3-cyano-1-(4-methoxy-phenyl)-7-oxo-1,4,5,7-tetrahydro-pyrazolo[3,4-c]pyridin-6-yl]-phenyl}-cyclobutyl)-N,N-dimethyl-acetamide;

2-(1-{4-[3-cyano-1-(4-methoxy-phenyl)-7-oxo-1,4,5,7-tetrahydro-pyrazolo[3,4-c]pyridin-6-yl]-phenyl}-cyclobutyl)-N-methyl-acetamide;

2-(1-{4-[3-cyano-1-(4-methoxy-phenyl)-7-oxo-1,4,5,7-tetrahydro-pyrazolo[3,4-c]pyridin-6-yl]-phenyl}-cyclobutyl)-acetamide;

2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclobutyl)-acetamide;

2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclobutyl)-N-methyl-acetamide;

2-(1-{4-[1-(4-methoxy-phenyl)-3-methyl-7-oxo-1,4,5,7-tetrahydro-pyrazolo[3,4-c]pyridin-6-yl]-phenyl}-cyclobutyl)-N-methyl-acetamide;

2-(1-{4-[1-(4-methoxy-phenyl)-3-methyl-7-oxo-1,4,5,7-tetrahydro-pyrazolo[3,4-c]pyridin-6-yl]-phenyl}-cyclobutyl)-acetamide;

2-(1-{4-[1-(4-methoxy-phenyl)-7-oxo-1,4,5,7-tetrahydro-pyrazolo[3,4-c]pyridin-6-yl]-phenyl}-cyclobutyl)-acetamide;

2-(1-{4-[1-(4-methoxy-phenyl)-7-oxo-1,4,5,7-tetrahydro-pyrazolo[3,4-c]pyridin-6-yl]-phenyl}-cyclobutyl)-N-methyl-acetamide;

2-(1-{4-[1-(4-methoxy-phenyl)-7-oxo-1,4,5,7-tetrahydro-pyrazolo[3,4-c]pyridin-6-yl]-phenyl}-cyclobutyl)-N,N-dimethyl-acetamide;

2-(1-{4-[3-(4-methoxy-phenyl)-4-oxo-3,4,6,7-tetrahydro-[1,2,3]triazolo[4,5-c]pyridin-5-yl]-phenyl}-cyclobutyl)-N,N-dimethyl-acetamide;

2-(1-{4-[3-(4-methoxy-phenyl)-4-oxo-3,4,6,7-tetrahydro-[1,2,3]triazolo[4,5-c]pyridin-5-yl]-phenyl}-cyclobutyl)-N-methyl-acetamide;

2-(1-{4-[3-(4-methoxy-phenyl)-4-oxo-3,4,6,7-tetrahydro-[1,2,3]triazolo[4,5-c]pyridin-5-yl]-phenyl}-cyclobutyl)-acetamide;

5-chloro-thiophene-2-carboxylic acid {2-[4-(1-dimethylaminomethyl-cyclopropyl)-benzyl]-1,3-dioxo-2,3-dihydro-1H-isoindol-4-yl}-amide;

5-chloro-thiophene-2-carboxylic acid {2-[4-(1-dimethylaminomethyl-cyclopropyl)-benzyl]-1-oxo-2,3-dihydro-1H-isoindol-4-yl}-amide;

5-chloro-thiophene-2-carboxylic acid {2-[4-(1-dimethylaminomethyl-cyclopropyl)-benzyl]-3-oxo-2,3-dihydro-1H-isoindol-4-yl}-amide;
5-chloro-thiophene-2-carboxylic acid [2-(2-{4-[1-(2-dimethylamino-ethyl)-cyclopropyl]-phenyl}-ethyl)-1,3-dioxo-2,3-dihydro-1H-isoindol-4-yl]-amide;
5-chloro-thiophene-2-carboxylic acid [2-(2-{4-[1-(2-dimethylamino-ethyl)-cyclopropyl]-phenyl}-ethyl)-1-oxo-2,3-dihydro-1H-isoindol-4-yl]-amide;
5-chloro-thiophene-2-carboxylic acid [2-(2-{4-[1-(2-dimethylamino-ethyl)-cyclopropyl]-phenyl}-ethyl)-3-oxo-2,3-dihydro-1H-isoindol-4-yl]-amide;
5-chloro-thiophene-2-carboxylic acid [2-(2-{3-[1-(2-dimethylamino-ethyl)-cyclopropyl]-phenyl}-ethyl)-1,3-dioxo-2,3-dihydro-1H-isoindol-4-yl]-amide;
5-chloro-thiophene-2-carboxylic acid [2-(2-{3-[1-(2-dimethylamino-ethyl)-cyclopropyl]-phenyl}-ethyl)-1-oxo-2,3-dihydro-1H-isoindol-4-yl]-amide;
5-chloro-thiophene-2-carboxylic acid [2-(2-{3-[1-(2-dimethylamino-ethyl)-cyclopropyl]-phenyl}-ethyl)-3-oxo-2,3-dihydro-1H-isoindol-4-yl]-amide;
5-chloro-thiophene-2-carboxylic acid (2-{2-[4-(1-dimethylaminomethyl-cyclopropyl)-phenyl]-ethyl}-1,3-dioxo-2,3-dihydro-1H-isoindol-4-yl)-amide;
5-chloro-thiophene-2-carboxylic acid (2-{2-[4-(1-dimethylaminomethyl-cyclopropyl)-phenyl]-ethyl}-1-oxo-2,3-dihydro-1H-isoindol-4-yl)-amide;
5-chloro-thiophene-2-carboxylic acid (2-{2-[4-(1-dimethylaminomethyl-cyclopropyl)-phenyl]-ethyl}-3-oxo-2,3-dihydro-1H-isoindol-4-yl)-amide;
5-chloro-thiophene-2-carboxylic acid (2-{2-[3-(1-dimethylaminomethyl-cyclopropyl)-phenyl]-ethyl}-1,3-dioxo-2,3-dihydro-1H-isoindol-4-yl)-amide;
5-chloro-thiophene-2-carboxylic acid (2-{2-[3-(1-dimethylaminomethyl-cyclopropyl)-phenyl]-ethyl}-1-oxo-2,3-dihydro-1H-isoindol-4-yl)-amide;
5-chloro-thiophene-2-carboxylic acid (2-{2-[3-(1-dimethylaminomethyl-cyclopropyl)-phenyl]-ethyl}-3-oxo-2,3-dihydro-1H-isoindol-4-yl)-amide;
5-chloro-thiophene-2-carboxylic acid {2-[3-(1-dimethylaminomethyl-cyclopropyl)-benzyl]-1,3-dioxo-2,3-dihydro-1H-isoindol-4-yl}-amide;
5-chloro-thiophene-2-carboxylic acid {2-[3-(1-dimethylaminomethyl-cyclopropyl)-benzyl]-1-oxo-2,3-dihydro-1H-isoindol-4-yl}-amide;
5-chloro-thiophene-2-carboxylic acid {2-[3-(1-dimethylaminomethyl-cyclopropyl)-benzyl]-3-oxo-2,3-dihydro-1H-isoindol-4-yl}-amide;
5-chloro-thiophene-2-carboxylic acid (2-{4-[1-(2-dimethylamino-ethyl)-cyclopropyl]-benzyl}-1,3-dioxo-2,3-dihydro-1H-isoindol-4-yl)-amide;
5-chloro-thiophene-2-carboxylic acid (2-{4-[1-(2-dimethylamino-ethyl)-cyclopropyl]-benzyl}-1-oxo-2,3-dihydro-1H-isoindol-4-yl)-amide;
5-chloro-thiophene-2-carboxylic acid (2-{4-[1-(2-dimethylamino-ethyl)-cyclopropyl]-benzyl}-3-oxo-2,3-dihydro-1H-isoindol-4-yl)-amide;
5-chloro-thiophene-2-carboxylic acid (2-{3-[1-(2-dimethylamino-ethyl)-cyclopropyl]-benzyl}-1,3-dioxo-2,3-dihydro-1H-isoindol-4-yl)-amide;
5-chloro-thiophene-2-carboxylic acid (2-{3-[1-(2-dimethylamino-ethyl)-cyclopropyl]-benzyl}-1-oxo-2,3-dihydro-1H-isoindol-4-yl)-amide;
5-chloro-thiophene-2-carboxylic acid (2-{3-[1-(2-dimethylamino-ethyl)-cyclopropyl]-benzyl}-3-oxo-2,3-dihydro-1H-isoindol-4-yl)-amide;
5-chloro-thiophene-2-carboxylic acid {6-chloro-2-[4-(1-dimethylaminomethyl-cyclopropyl)-benzyl]-1,3-dioxo-2,3-dihydro-1H-isoindol-4-yl}-amide;
5-chloro-thiophene-2-carboxylic acid {6-chloro-2-[4-(1-dimethylaminomethyl-cyclopropyl)-benzyl]-1-oxo-2,3-dihydro-1H-isoindol-4-yl}-amide;
5-chloro-thiophene-2-carboxylic acid {6-chloro-2-[4-(1-dimethylaminomethyl-cyclopropyl)-benzyl]-3-oxo-2,3-dihydro-1H-isoindol-4-yl}-amide;
5-chloro-thiophene-2-carboxylic acid [6-chloro-2-(2-{4-[1-(2-dimethylamino-ethyl)-cyclopropyl]-phenyl}-ethyl)-1,3-dioxo-2,3-dihydro-1H-isoindol-4-yl]-amide;
5-chloro-thiophene-2-carboxylic acid [6-chloro-2-(2-{4-[1-(2-dimethylamino-ethyl)-cyclopropyl]-phenyl}-ethyl)-1-oxo-2,3-dihydro-1H-isoindol-4-yl]-amide;
5-chloro-thiophene-2-carboxylic acid [6-chloro-2-(2-{4-[1-(2-dimethylamino-ethyl)-cyclopropyl]-phenyl}-ethyl)-3-oxo-2,3-dihydro-1H-isoindol-4-yl]-amide;
5-chloro-thiophene-2-carboxylic acid [6-chloro-2-(2-{3-[1-(2-dimethylamino-ethyl)-cyclopropyl]-phenyl}-ethyl)-1,3-dioxo-2,3-dihydro-1H-isoindol-4-yl]-amide;
5-chloro-thiophene-2-carboxylic acid [6-chloro-2-(2-{3-[1-(2-dimethylamino-ethyl)-cyclopropyl]-phenyl}-ethyl)-1-oxo-2,3-dihydro-1H-isoindol-4-yl]-amide;
5-chloro-thiophene-2-carboxylic acid [6-chloro-2-(2-{3-[1-(2-dimethylamino-ethyl)-cyclopropyl]-phenyl}-ethyl)-3-oxo-2,3-dihydro-1H-isoindol-4-yl]-amide;
5-chloro-thiophene-2-carboxylic acid (6-chloro-2-{2-[4-(1-dimethylaminomethyl-cyclopropyl)-phenyl]-ethyl}-1,3-dioxo-2,3-dihydro-1H-isoindol-4-yl)-amide;
5-chloro-thiophene-2-carboxylic acid (6-chloro-2-{2-[4-(1-dimethylaminomethyl-cyclopropyl)-phenyl]-ethyl}-1-oxo-2,3-dihydro-1H-isoindol-4-yl)-amide;
5-chloro-thiophene-2-carboxylic acid (6-chloro-2-{2-[4-(1-dimethylaminomethyl-cyclopropyl)-phenyl]-ethyl}-3-oxo-2,3-dihydro-1H-isoindol-4-yl)-amide;
5-chloro-thiophene-2-carboxylic acid (6-chloro-2-{2-[3-(1-dimethylaminomethyl-cyclopropyl)-phenyl]-ethyl}-1,3-dioxo-2,3-dihydro-1H-isoindol-4-yl)-amide;
5-chloro-thiophene-2-carboxylic acid (6-chloro-2-{2-[3-(1-dimethylaminomethyl-cyclopropyl)-phenyl]-ethyl}-1-oxo-2,3-dihydro-1H-isoindol-4-yl)-amide;
5-chloro-thiophene-2-carboxylic acid (6-chloro-2-{2-[3-(1-dimethylaminomethyl-cyclopropyl)-phenyl]-ethyl}-3-oxo-2,3-dihydro-1H-isoindol-4-yl)-amide;
5-chloro-thiophene-2-carboxylic acid {6-chloro-2-[3-(1-dimethylaminomethyl-cyclopropyl)-benzyl]-1,3-dioxo-2,3-dihydro-1H-isoindol-4-yl}-amide;
5-chloro-thiophene-2-carboxylic acid {6-chloro-2-[3-(1-dimethylaminomethyl-cyclopropyl)-benzyl]-1-oxo-2,3-dihydro-1H-isoindol-4-yl}-amide;
5-chloro-thiophene-2-carboxylic acid {6-chloro-2-[3-(1-dimethylaminomethyl-cyclopropyl)-benzyl]-3-oxo-2,3-dihydro-1H-isoindol-4-yl}-amide;
5-chloro-thiophene-2-carboxylic acid (6-chloro-2-{4-[1-(2-dimethylamino-ethyl)-cyclopropyl]-benzyl}-1,3-dioxo-2,3-dihydro-1H-isoindol-4-yl)-amide;
5-chloro-thiophene-2-carboxylic acid (6-chloro-2-{4-[1-(2-dimethylamino-ethyl)-cyclopropyl]-benzyl}-1-oxo-2,3-dihydro-1H-isoindol-4-yl)-amide;
5-chloro-thiophene-2-carboxylic acid (6-chloro-2-{4-[1-(2-dimethylamino-ethyl)-cyclopropyl]-benzyl}-3-oxo-2,3-dihydro-1H-isoindol-4-yl)-amide;
5-chloro-thiophene-2-carboxylic acid (6-chloro-2-{3-[1-(2-dimethylamino-ethyl)-cyclopropyl]-benzyl}-1,3-dioxo-2,3-dihydro-1H-isoindol-4-yl)-amide;

5-chloro-thiophene-2-carboxylic acid (6-chloro-2-{3-[1-(2-dimethylamino-ethyl)-cyclopropyl]-benzyl}-1-oxo-2,3-dihydro-1H-isoindol-4-yl)-amide;
5-chloro-thiophene-2-carboxylic acid (6-chloro-2-{3-[1-(2-dimethylamino-ethyl)-cyclopropyl]-benzyl}-3-oxo-2,3-dihydro-1H-isoindol-4-yl)-amide;
(1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-acetic acid;
2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-acetamide;
2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-N-methyl-acetamide;
2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-N,N-dimethyl-acetamide;
1-(4-methoxy-phenyl)-6-{4-[1-(2-oxo-2-pyrrolidin-1-yl-ethyl)-cyclopropyl]-phenyl}-3-trifluoromethyl-1,4,5,6-tetrahydro-pyrazolo[3,4-c]pyridin-7-one;
6-{4-[1-(2-hydroxy-ethyl)-cyclopropyl]-phenyl}-1-(4-methoxy-phenyl)-3-trifluoromethyl-1,4,5,6-tetrahydro-pyrazolo[3,4-c]pyridin-7-one;
1-(4-methoxy-phenyl)-6-{4-[1-(2-methylamino-ethyl)cyclopropyl]-phenyl}-3-trifluoromethyl-1,4,5,6-tetrahydro-pyrazolo[3,4-c]pyridin-7-one;
6-{4-[1-(2-dimethylamino-ethyl)-cyclopropyl]-phenyl}-1-(4-methoxy-phenyl)-3-trifluoromethyl-1,4,5,6-tetrahydro-pyrazolo[3,4-c]pyridin-7-one;
1-(4-methoxy-phenyl)-6-{4-[1-(2-pyrrolidin-1-yl-ethyl)-cyclopropyl]-phenyl}-3-trifluoromethyl-1,4,5,6-tetrahydro-pyrazolo[3,4-c]pyridin-7-one;
1-(4-methoxy-phenyl)-6-{4-[1-(2-morpholin-4-yl-ethyl)-cyclopropyl]-phenyl}-3-trifluoromethyl-1,4,5,6-tetrahydro-pyrazolo[3,4-c]pyridin-7-one
1-(4-methoxy-phenyl)-6-{4-[1-(2-pyrrolidin-1-yl-acetyl)-cyclopropyl]-phenyl}-3-trifluoromethyl-1,4,5,6-tetrahydro-pyrazolo[3,4-c]pyridin-7-one;
6-[4-(1-carbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid ethyl ester;
6-[4-(1-carbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid amide;
1-(4-methoxy-phenyl)-6-[4-(1-methylcarbamoylmethyl-cyclopropyl)-phenyl]-7-oxo-4,5,6,7-tetrahydro-1H-pyrazolo[3,4-c]pyridine-3-carboxylic acid ethyl ester;
1-(4-Methoxy-phenyl)-6-[4-(1-methylcarbamoylmethyl-cyclopropyl)-phenyl]-7-oxo-4,5,6,7-tetrahydro-1H-pyrazolo[3,4-c]pyridine-3-carboxylic acid amide;
6-[4-(1-dimethylcarbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid ethyl ester;
6-[4-(1-dimethylcarbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid amide;
6-{4-[1-(2-hydroxy-ethyl)-cyclopropyl]-phenyl}-1-(4-methoxy-phenyl)-7-oxo-4,5,6,7-tetrahydro-1H-pyrazolo[3,4-c]pyridine-3-carboxylic acid amide;
1-(4-methoxy-phenyl)-6-{4-[1-(2-morpholin-4-yl-ethyl)-cyclopropyl]-phenyl}-7-oxo-4,5,6,7-tetrahydro-1H-pyrazolo[3,4-c]pyridine-3-carboxylic acid amide; and,
1-(4-methoxy-phenyl)-6-{4-[1-(2-morpholin-4-yl-ethyl)-cyclopropyl]-phenyl}-7-oxo-4,5,6,7-tetrahydro-1H-pyrazolo[3,4-c]pyridine-3-carbonitrile;
or a pharmaceutically acceptable salt form thereof.

[9] In another preferred embodiment, the present invention provides a novel compound, wherein the compound is of Formula IIIa, IIIb, or IIIc:

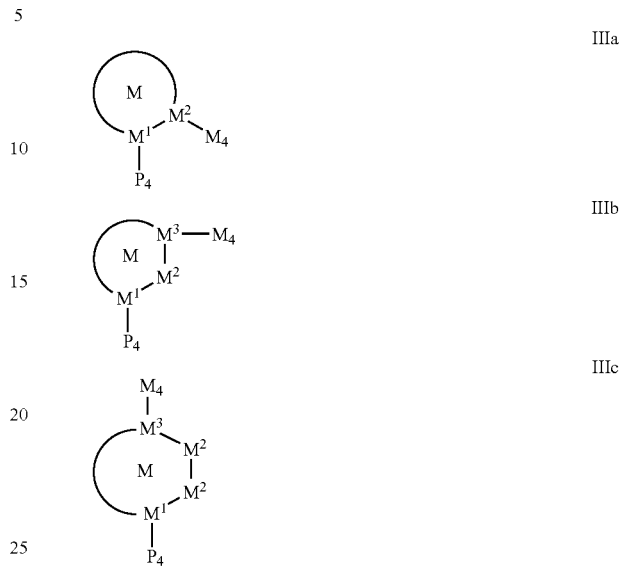

or a stereoisomer or pharmaceutically acceptable salt thereof, wherein;
ring M, including $M_1$, $M_2$, and, if present, $M_3$, is phenyl or a 3–10 membered carbocyclic or 4–10 membered heterocyclic ring consisting of: carbon atoms and 1–4 heteroatoms selected from O, $S(O)_p$, N, and $NZ^2$;
ring M is substituted with 0–3 $R^{1a}$ and 0–2 carbonyl groups, and there are 0–3 ring double bonds;
one of $P_4$ and $M_4$ is -Z-A-B and the other -$G_1$-G;
G is a group of formula IIa or IIb:

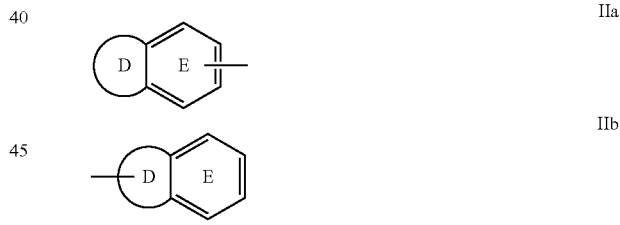

ring D, including the two atoms of Ring E to which it is attached, is a 5–6 membered ring consisting of carbon atoms and 0–2 heteroatoms selected from the group consisting of N, O, and $S(O)_p$;
ring D is substituted with 0–2 R and there are 0–3 ring double bonds;
E is selected from phenyl, pyridyl, pyrimidyl, pyrazinyl, and pyridazinyl, and is substituted with 1–3 R;
alternatively, ring D is absent, and ring E is selected from phenyl, pyridyl, pyrimidyl, and thienyl, and ring E is substituted with 1–3 R;
alternatively, ring D is absent, ring E is selected from phenyl, pyridyl, and thienyl, and ring E is substituted with 1 R and substituted with a 5–6 membered heterocycle consisting of: carbon atoms and 1–4 heteroatoms selected from the group consisting of N, O, and $S(O)_p$, wherein the 5–6 membered heterocycle is substituted with 0–2 carbonyls and 1–3 R and there are 0–3 ring double bonds;

R is selected from H, $C_{1-4}$ alkyl, F, Cl, OH, $OCH_3$, $OCH_2CH_3$, $OCH(CH_3)_2$, CN, C(=NH)$NH_2$, C(=NH)NHOH, C(=NH)$NHOCH_3$, $NH_2$, NH($C_{1-3}$ alkyl), N($C_{1-3}$ alkyl)$_2$, C(=NH)$NH_2$, $CH_2NH_2$, $CH_2NH(C_{1-3}$ alkyl), $CH_2N(C_{1-3}$ alkyl)$_2$, $(CR^8R^9)_rNR^7R^8$, $C(O)NR^7R^8$, $CH_2C(O)NR^7R^8$, $S(O)_pNR^7R^8$, $CH_2S(O)_pNR^7R^8$, $SO_2R^3$, and $OCF_3$;

alternatively, when 2 R groups are attached to adjacent atoms, they combine to form methylenedioxy or ethylenedioxy;

A is selected from:
$C_{5-10}$ carbocycle substituted with 0–2 $R^4$, and
5–10 membered heterocycle substituted with 0–2 $R^4$ and consisting of: carbon atoms and 1–4 heteroatoms selected from the group consisting of N, O, and $S(O)_p$;

X is selected from —$(CR^2R^{2a})_{1-4}$—, —C(O)—, —C(O)$CR^2R^{2a}$—, —$CR^2R^{2a}$C(O), —$S(O)_2$—, —$S(O)_2CR^2R^{2a}$—, —$CR^2R^{2a}S(O)_2$—, —$NR^2S(O)_2$—, —$S(O)_2NR^2$—, —$NR^2C(O)$—, —$C(O)NR^2$—, $NR^2$, —$NR^2CR^2R^{2a}$—, —$CR^2R^{2a}NR^2$—, O, —$OCR^2R^{2a}$—, and —$CR^2R^{2a}O$—;

Y is a $C_{3-7}$ monocyclic carbocycle or 3–7 membered monocyclic heterocycle, wherein the carobocycle or heterocycle consists of: carbon atoms and 0–2 heteroatoms selected from N, O, and $S(O)_p$, the carbocycle or heterocycle further comprises 0–2 double bonds and 0–2 carbonyl groups, and the carbocycle or heterocycle is substituted with 0–2 $R^4$;

alternatively, Y is $CY^1Y^2$, and $Y^1$ and $Y^2$ are independently $C_{1-3}$ alkyl substituted with 0–1 $R^4$;

Z is selected from a bond, $CH_2$, $CH_2CH_2$, $CH_2O$, $OCH_2$, C(O), NH, $CH_2NH$, $NHCH_2$, $CH_2C(O)$, $C(O)CH_2$, C(O)NH, NHC(O), NHC(O)NH, NHC(O)$CH_2C(O)$NH, NHC(O)C(O)NH, $C(O)NHS(O)_2$, $S(O)_2$, $CH_2S(O)_2$, $S(O)_2(CH_2)$, $SO_2NH$, and $NHSO_2$, provided that Z does not form a N—S, $NCH_2N$, $NCH_2O$, or $NCH_2S$ bond with either group to which it is attached;

$Z^2$ is selected from H, $C_{1-4}$ alkyl, phenyl, benzyl, $C(O)R^{3b}$, $S(O)R^{3f}$, and $S(O)_2R^{3f}$;

$R^{1a}$, at each occurrence, is selected from H, —$(CH_2)_r$—$R^{1b}$, —$(CH(CH_3))_r$—$R^{1b}$, —$(C(CH_3)_2)_r$—$R^{1b}$, —O—$(CR^3R^{3a})_r$—$R^{1b}$, —$NR^2$—$(CR^3R^{3a})_r$—$R^{1b}$, and —S—$(CR^3R^{3a})_r$—$R^{1b}$, provided that $R^{1a}$ forms other than an N-halo, N—S, O—O, or N—CN bond;

alternatively, when two $R^{1a}$ groups are attached to adjacent atoms or to the same carbon atom, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH^2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C_{3-6}$ carbocycle substituted with 0–2 $R^{4b}$, and 5–6 membered heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, a $C_{5-6}$ carbocycle-$CH_2$-substituted with 0–2 $R^{4b}$, and 5–6 membered heterocycle substituted with 0–2 $R^{4b}$ and consisting of: carbon atoms and 1–4 heteroatoms selected from the group consisting of N, O, and $S(O)_p$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{3-6}$ carbocycle substituted with 0–2 $R^{4b}$, and 5–6 membered heterocycle substituted with 0–2 $R^{4b}$ and consisting of: carbon atoms and 1–4 heteroatoms selected from the group consisting of N, O, and $S(O)_p$;

alternatively, $R^2$ and $R^{2a}$, together with the nitrogen atom to which they are attached, combine to form a 3–6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $C_{1-6}$ alkyl substituted with 0–3 $R^{4b}$, benzyl, $C_{3-6}$ carbocycle substituted with 0–2 $R^{4b}$, and 4–6 membered heterocycle substituted with 0–2 $R^{4b}$ and consisting of: carbon atoms and 1–4 heteroatoms selected from the group consisting of N, O, and $S(O)_p$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle substituted with 0–2 $R^{4b}$ and consisting of carbon atoms and from 1–4 heteroatoms selected from the group consisting of N, O, and $S(O)_p$;

$R^{2d}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, when two $R^{2d}$'s are attached to the same nitrogen atom, then $R^{2d}$ and $R^{2d}$, together with the nitrogen atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and C(=O)$R^{3c}$;

R$^{3g}$, at each occurrence, is selected from H, CH$_3$, CH$_2$CH$_3$, CH$_2$CH$_2$CH$_3$, CH(CH$_3$)$_2$, cyclopropyl, cyclopropyl-methyl, benzyl, and phenyl;

alternatively, when R$^3$ and R$^{3g}$ are attached to the same carbon atom, they combine with the attached carbon atom to form a cyclopropyl group;

R$^4$, at each occurrence, is selected from H, =O, OR$^2$, CH$_2$OR$^2$, (CH$_2$)$_2$OR$^2$, F, Cl, Br, I, C$_{1-4}$ alkyl, —CN, NO$_2$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, SO$_2$NR$^2$R$^{2a}$, S(O)$_p$R$^{5a}$, CF$_3$, CF$_2$CF$_3$, 5–6 membered carbocycle substituted with 0–1 R$^5$, and a 5–6 membered heterocycle substituted with 0–1 R$^5$ and consisting of: carbon atoms and 1–4 heteroatoms selected from the group consisting of N, O, and S(O)$_p$;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^3$R$^{3a}$, CH$_2$NR$^3$R$^{3a}$, C(O)R$^3$, CH$_2$—C(O)R$^3$, C(O)OR$^{3c}$, CH$_2$C(O)OR$^{3c}$, NR$^3$C(O)R$^{3a}$, CH$_2$NR$^3$C(O)R$^{3a}$, C(O)NR$^3$R$^{3a}$, CH$_2$C(O)NR$^3$R$^{3a}$, NR$^3$C(O)NR$^3$R$^{3a}$, CH$_2$NR$^3$C(O)NR$^3$R$^{3a}$, C(=NR$^3$)NR$^3$R$^{3a}$, CH$_2$C(=NR$^3$)NR$^3$R$^{3a}$, NR$^3$C(=NR$^3$)NR$^3$R$^{3a}$, CH$_2$NR$^3$C(=NR$^3$)NR$^3$R$^{3a}$, SO$_2$NR$^3$R$^{3a}$, CH$_2$SO$_2$NR$^3$R$^{3a}$, NR$^3$SO$_2$NR$^3$R$^{3a}$, CH$_2$NR$^3$SO$_2$NR$^3$R$^{3a}$, NR$^3$SO$_2$—C$_{1-4}$ alkyl, CH$_2$NR$^3$SO$_2$—C$_{1-4}$ alkyl, NR$^3$SO$_2$CF$_3$, CH$_2$NR$^3$SO$_2$CF$_3$, NR$^3$SO$_2$-phenyl, CH$_2$NR$^3$SO$_2$-phenyl, S(O)$_p$CF$_3$, CH$_2$S(O)$_p$CF$_3$, S(O)—C$_{1-4}$ alkyl, CH$_2$S(O)—C$_{1-4}$ alkyl, S(O)$_p$-phenyl, CH$_2$S(O)$_p$-phenyl, CF$_3$, and CH$_2$—CF$_3$;

R$^{4c}$, at each occurrence, is selected from =O, (CR$^3$R$^{3a}$)$_r$OR$^2$, (CR$^3$R$^{3a}$)$_r$F, (CR$^3$R$^{3a}$)$_r$Br, (CR$^3$R$^{3a}$)$_r$Cl, (CR$^3$R$^{3a}$)$_r$CF$_3$, C$_{1-4}$ alkyl, C$_{2-4}$ alkenyl, C$_{2-4}$ alkynyl, (CR$^3$R$^{3a}$)$_r$CN, (CR$^3$R$^{3a}$)$_r$NO$_2$, (CR$^3$R$^{3a}$)$_r$NR$^2$R$^{2a}$, (CR$^3$R$^{3a}$)$_r$N(→O)R$^2$R$^{2a}$, (CR$^3$R$^{3a}$)$_r$C(O)R$^{2c}$, (CR$^3$R$^{3a}$)$_r$NR$^2$C(O)R$^{2b}$, (CR$^3$R$^{3a}$)$_r$C(O)NR$^2$R$^{2a}$, (CR$^3$R$^{3a}$)$_r$NR$^2$C(O)NR$^2$R$^{2a}$, (CR$^3$R$^{3a}$)$_r$SO$_2$NR$^2$R$^{2a}$, (CR$^3$R$^{3a}$)$_r$NR$^2$SO$_2$NR$^2$R$^{2a}$, (CR$^3$R$^{3a}$)$_r$NR$^2$SO$_2$R$^{5a}$, (CR$^3$R$^{3a}$)$_r$S(O)$_p$R$^{5a}$, (CF$_2$)$_r$CF$_3$, (CR$^3$R$^{3a}$)$_r$C$_{3-10}$ carbocycle substituted with 0–2 R$^{4b}$, and (CR$^3$R$^{3a}$)$_r$5–10 membered heterocycle substituted with 0–2 R$^{4b}$ and consisting of carbon atoms and from 1–4 heteroatoms selected from the group consisting of N, O, and S(O)$_p$;

R$^5$, at each occurrence, is selected from H, =O, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, OR$^3$, CH$_2$OR$^3$, F, Cl, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, C(O)NR$^3$R$^{3a}$, NR$^3$C(O)NR$^3$R$^{3a}$, CH(=NOR$^{3d}$), C(=NR$^3$)NR$^3$R$^{3a}$, NR$^3$C(=NR$^3$)NR$^3$R$^{3a}$, SO$_2$NR$^3$R$^{3a}$, NR$^3$SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$;

R$^6$, at each occurrence, is selected from H, OH, OR$^2$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl; and, r, at each occurrence, is selected from 0, 1, 2, and 3.

[10] In another preferred embodiment, the present invention provides a novel compound, wherein:

ring M, including M$_1$, M$_2$, and, if present, M$_3$, is selected from phenyl, pyrrole, furan, thiophene, pyrazole, imidazole, isoxazole, oxazole, isothiazole, thiazole, 1,2,3-triazole, 1,2,4-triazole, 1,3,4-triazole, 1,2,3-oxadiazole, 1,2,4-oxadiazole, 1,3,4-oxadiazole, 1,2,3-thiadiazole, 1,2,4-thiadiazole, 1,3,4-thiadiazole, 1,2,3,4-tetrazole, 1,2,3,5-tetrazole, pyran, thiopyran, thiopyran-1,1-dioxide, pyridine, pyrimidine, pyridazine, pyrazine, 1,2,3-triazine, 1,2,4-triazine, 1,2,3,4-tetrazine, dihydro-pyrrole, dihydro-furan, dihydro-thiophene, dihydro-pyrazole, dihydro-imidazole, dihydro-isoxazole, dihydro-oxazole, dihydro-isothiazole, dihydro-thiazole, dihydro-1,2,3-triazole, dihydro-1,2,4-triazole, dihydro-1,3,4-triazole, dihydro-1,2,3-oxadiazole, dihydro-1,2,4-oxadiazole, dihydro-1,3,4-oxadiazole, dihydro-1,2,3-thiadiazole, dihydro-1,2,4-thiadiazole, dihydro-1,3,4-thiadiazole, dihydro-1,2,3,4-tetrazole, dihydro-1,2,3,5-tetrazole, dihydro-pyran, dihydro-thiopyran, dihydro-thiopyran-1,1-dioxide, dihydro-pyridine, dihydro-pyrimidine, dihydro-pyridazine, dihydro-pyrazine, dihydro-1,2,3-triazine, dihydro-1,2,4-triazine, dihydro-1,2,3,4-tetrazine, cyclopropane, cyclobutane, cyclopentene, cyclopentane, cyclohexene, cyclohexane, cycloheptane, tetrahydro-pyrrole, tetrahydro-furan, tetrahydro-thiophene, tetrahydro-thiophene-1,1-dioxide, tetrahydro-pyrazole, tetrahydro-imidazole, tetrahydro-isoxazole, tetrahydro-oxazole, tetrahydro-isothiazole, tetrahydro-thiazole, tetrahydro-1,2,3-triazole, tetrahydro-1,2,4-triazole, tetrahydro-1,3,4-triazole, tetrahydro-1,2,3-oxadiazole, tetrahydro-1,2,4-oxadiazole, tetrahydro-1,3,4-oxadiazole, tetrahydro-1,2,3-thiadiazole, tetrahydro-1,2,4-thiadiazole, tetrahydro-1,3,4-thiadiazole, tetrahydro-1,2,3,4-tetrazole, tetrahydro-1,2,3,5-tetrazole, tetrahydro-pyran, tetrahydro-thiopyran, tetrahydro-thiopyran-1,1-dioxide, tetrahydro-pyridine, tetrahydro-pyrimidine, tetrahydro-pyridazine, tetrahydro-pyrazine, tetrahydro-1,2,3-triazine, tetrahydro-1,2,4-triazine, tetrahydro-1,2,3,4-tetrazine, piperidine, indan, isothiazolidine 1,1-dioxide, [1,2]thiazinane 1,1-dioxide, 1,2,3,4-tetrahydro-naphthalene, 7,8-dimethyl-1-oxa-spiro[4.4]nonane, 6,7-dihydro-5H-[1]pyrindine, 6,7-dihydro-5H-[2]pyrindine, 5,6,7,8-tetrahydro-quinoline, 5,6,7,8-tetrahydro-isoquinoline, 5,6,7,8-tetrahydro-quinoxaline, 6,7-dihydro-5H-cyclopentapyrazine, 4,5,6,7-tetrahydro-1H-benzoimidazole, 4,5,6,7-tetrahydro-benzothiazole, 4,5,6,7-tetrahydro-benzooxazole, 4,5,6,7-tetrahydro-benzo[c]isothiazole, 4,5,6,7-tetrahydro-benzo[c]isoxazole, 4,5,6,7-tetrahydro-2H-indazole, 4,5,6,7-tetrahydro-2H-isoindole, 4,5,6,7-tetrahydro-1H-indole, 5,6,7,8-tetrahydro-tetrazolo[1,5-a]pyridine, 5,6,7,8-tetrahydro-imidazo[1,2-a]pyridine, 4,5,6,7-tetrahydro-pyrazolo[1,5-a]pyridine, 5,6,7,8-tetrahydro-[1,2,4]triazolo[1,5-a]pyridine, 6,7-dihydro-5H-pyrrolo[1,2-c]imidazole, 6,7-dihydro-5H-pyrrolo[1,2-a]imidazole, 6,7-dihydro-5H-pyrrolo[1,2-b][1,2,4]triazole, 6,7-dihydro-5H-pyrrolotetrazole, 5,6-dihydro-4H-pyrrolo[1,2-b]pyrazole, 5,6-dihydro-4H-cyclopenta[d]isoxazole, 5,6-dihydro-4H-cyclopentaoxazole, 5,6-dihydro-4H-cyclopenta[c]isoxazole, 5,6-dihydro-4H-cyclopenta[d]isothiazole, 5,6-dihydro-4H-cyclopentathiazole, 5,6-dihydro-4H-cyclopenta[c]isothiazole, 1,4,5,6-tetrahydro-cyclopentapyrazole, 1,4,5,6-tetrahydro-cyclopentaimidazole, 2,4,5,6-tetrahydro-cyclopentapyrazole, 5,6-dihydro-4H-cyclopenta[1,2,5]thiadiazole, 5,6-dihydro-4H-cyclopenta[1,2,5]oxadiazole, 5,6-dihydro-4H-cyclopenta[c]furan, 2,4,5,6-tetrahydro-cyclopenta[c]pyrrole, 5,6-dihydro-4H-cyclopenta[b]furan, 5,6-dihydro-4H-cyclopenta[c]thiophene, 5,6-dihydro-4H-cyclopenta[b]furan, 5,6-dihydro-4H-cyclopenta[b]thiophene, 1,4,5,6-tetrahydro-cyclopenta[b]pyrrole, 2,3-dihydro-1H-indolizin-5-one, 6,7,8,9-tetrahydroquinolizin-4-one, 1-oxa-spiro[4.4]nonane, 1-aza-spiro[4.4]nonane, 2-oxa-spiro[4.4]nonane, 2-aza-spiro[4.4]nonane, 1-aza-spiro[4.5]decane, 1-oxa-spiro[4.5]decane, 2-oxa-spiro[4.5]decane, 2-aza-spiro[4.5]decane, 1-thia-spiro[4.4]nonane, 1-thia-spiro[4.5]decane, 2-thia-spiro[4.4]nonane, 2-thia-spiro[4.5]decane, 7-oxa-bicyclo[2.2.1]heptane, 2-oxa-bicyclo[2.2.1]heptane, 7-thia-bicyclo[2.2.1]heptane, 2-thia-bicyclo[2.2.1]heptane, 2-aza-bicyclo[2.2.1]heptane, 7-aza-bicyclo[2.2.1]heptane, 4,5,6,7-tetrahydro-benzo[d]isoxazole, 4,5,6,7-tetrahydro-benzooxazole, 4,5,6,7-tetrahydro-benzo[d]isothiazole, 4,5,6,7-tetrahydro-benzothiazole, 4,5,6,7-tetrahydro-1H-indazole, 4,5,6,7-tetrahydro-benzo[c]thiophene, 4,5,6,7-tetrahydro-benzo[b]thiophene, 4,5,6,7-tetrahydro-isobenzofuran, 4,5,6,7-tetrahydro-benzofuran, 5,6,7,8-tetrahydro-quinoxaline, 6,7-dihydro-5H-cyclopentapyrazine, 5,6,7,8-tetrahydro-imidazo[1,5-a]pyridine, 5,6,7,8-tetrahydro-imidazo[1,2-a]pyridine, 5,6,7,8-tetrahydro-[1,2,4]triazolo[1,5-a]pyridine, 5,6,7,8-tetrahydro-tetrazolo[1,5-a]pyridine, 4,5,6,7-tetrahydro-pyrazolo[1,5-a]pyridine, 6,7-dihydro-5H-pyrrolo[1,2-a]imidazole, 6,7-dihydro-5H-pyrrolo[1,2-b][1,2,4]triazole, 5,6-dihydro-4H-pyrrolo[1,2-b]pyrazole, and 6,7-dihydro-5H-pyrrolotetrazole;

ring M is substituted with 0–3 $R^{1a}$ and 0–1 carbonyl group;

G is selected from the group:

phenyl; 4-ethyl-phenyl; 2,5-bis-aminomethyl-phenyl; 2-amido-4-methoxy-phenyl; 2-amido-5-chloro-phenyl; 2-amido-phenyl; 2-aminomethyl-3-fluoro-phenyl; 2-aminomethyl-3-methoxy-phenyl; 2-aminomethyl-4-fluoro-phenyl; 2-aminomethyl-4-methoxy-phenyl; 2-aminomethyl-5-fluoro-phenyl; 2-aminomethyl-5-methoxy-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 2-hydroxy-4-methoxy-phenyl; 2-methylsulfonyl-phenyl; 3-(N,N-dimethylamino)-4-chloro-phenyl; 3-(N,N-dimethylamino)-phenyl; 3-(N-hydroxy-amidino)-phenyl; 3-(N-methoxy-amidino)-phenyl; 3-(N-methylamino)-4-chloro-phenyl; 3-(N-methylamino)-phenyl; 3-amidino-phenyl; 3-amido-6-hydroxy-phenyl; 3-amido-phenyl; 3-amino-4-chloro-phenyl; 3-aminomethyl-phenyl; 3-amino-phenyl; 3-chloro-4-fluoro-phenyl; 3-chloro-phenyl; 3-hydroxy-4-methoxy-phenyl; 3,5-dichloro-thien-2-yl; 4-(N,N-dimethylamino)-5-chloro-thien-2-yl; 4-(N-methylamino)-5-chloro-thien-2-yl; 4-amino-5-chloro-thien-2-yl; 4-amino-pyrid-2-yl; 4-chloro-3-fluoro-phenyl; 4-chloro-phenyl; 4-chloro-pyrid-2-yl; 4-methoxy-2-methylsulfonyl-phenyl; 4-methoxy-phenyl; 2-methoxy-pyrid-5-yl; 5-(N,N-dimethylamino)-4-chloro-thien-2-yl; 5-(N-methylamino)-4-chloro-thien-2-yl; 5-amino-4-chloro-thien-2-yl; 5-chloro-2-aminosulfonyl-phenyl; 5-chloro-2-methylsulfonyl-phenyl; 5-chloro-pyrid-2-yl; 5-chloro-thien-2-yl; 5-methoxy-thien-2-yl; 6-amino-5-chloro-pyrid-2-yl; 6-amino-pyrid-2-yl; 5-chloro-pyrimidin-3-yl; 6-chloro-pyridazin-3-yl; 2-aminomethyl-4-chloro-phenyl; 2-aminosulfonyl-4-chloro-phenyl; 2-amido-4-chloro-phenyl; 4-chloro-2-methylsulfonyl-phenyl; 2-aminosulfonyl-4-fluoro-phenyl; 2-amido-4-fluoro-phenyl; 4-fluoro-2-methylsulfonyl-phenyl; 2-aminomethyl-4-bromo-phenyl; 2-aminosulfonyl-4-bromo-phenyl; 2-amido-4-bromo-phenyl; 4-bromo-2-methylsulfonyl-phenyl; 2-aminomethyl-4-methyl-phenyl; 2-aminosulfonyl-4-methyl-phenyl; 2-amido-4-methyl-phenyl; 2-methylsulfonyl-4-methyl-phenyl; 4-fluoro-pyrid-2-yl; 4-bromo-pyrid-2-yl; 4-methyl-pyrid-2-yl; 5-fluoro-thien-2-yl; 5-bromo-thien-2-yl; 5-methyl-thien-2-yl; 2-amido-4-methoxy-phenyl;

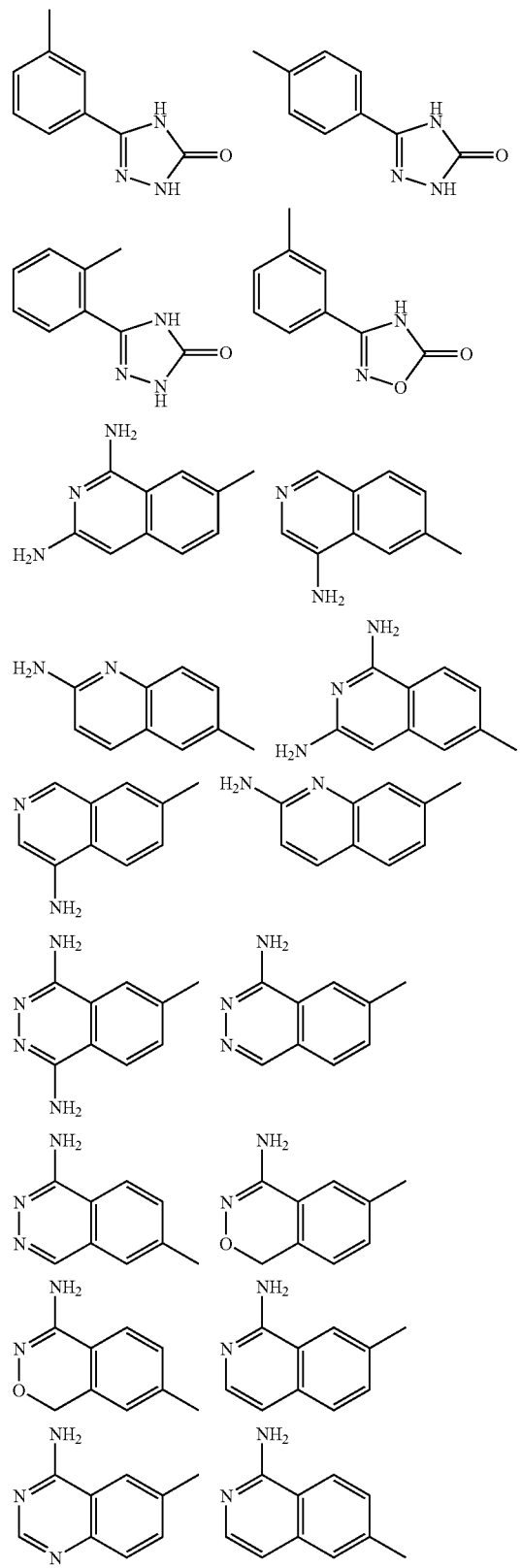

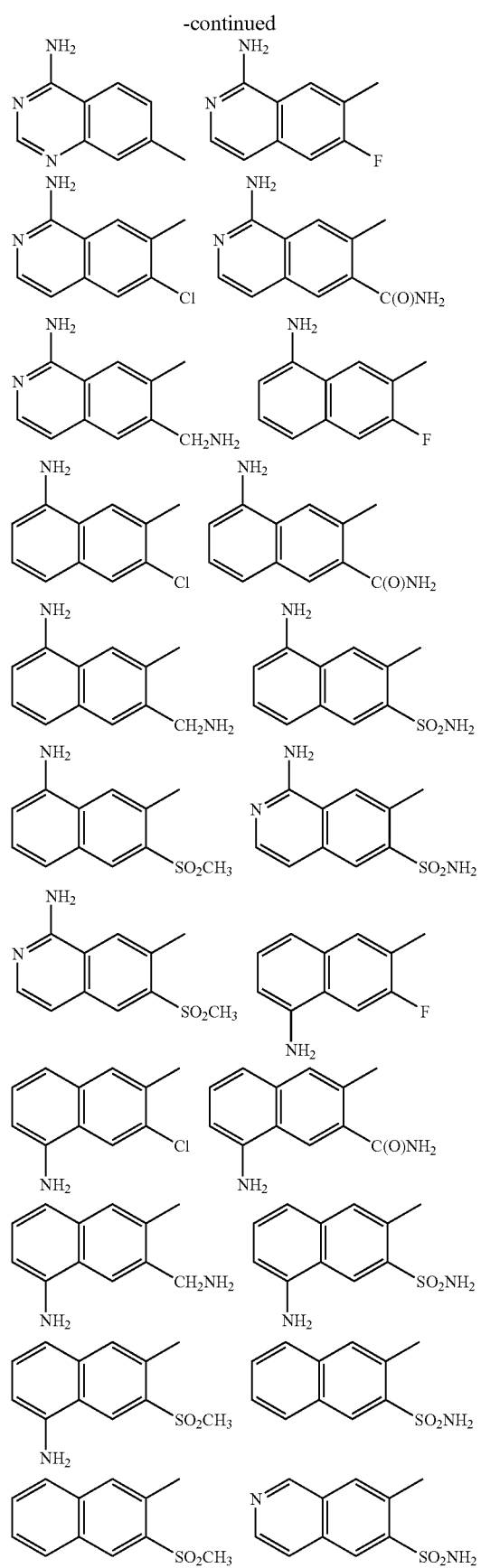
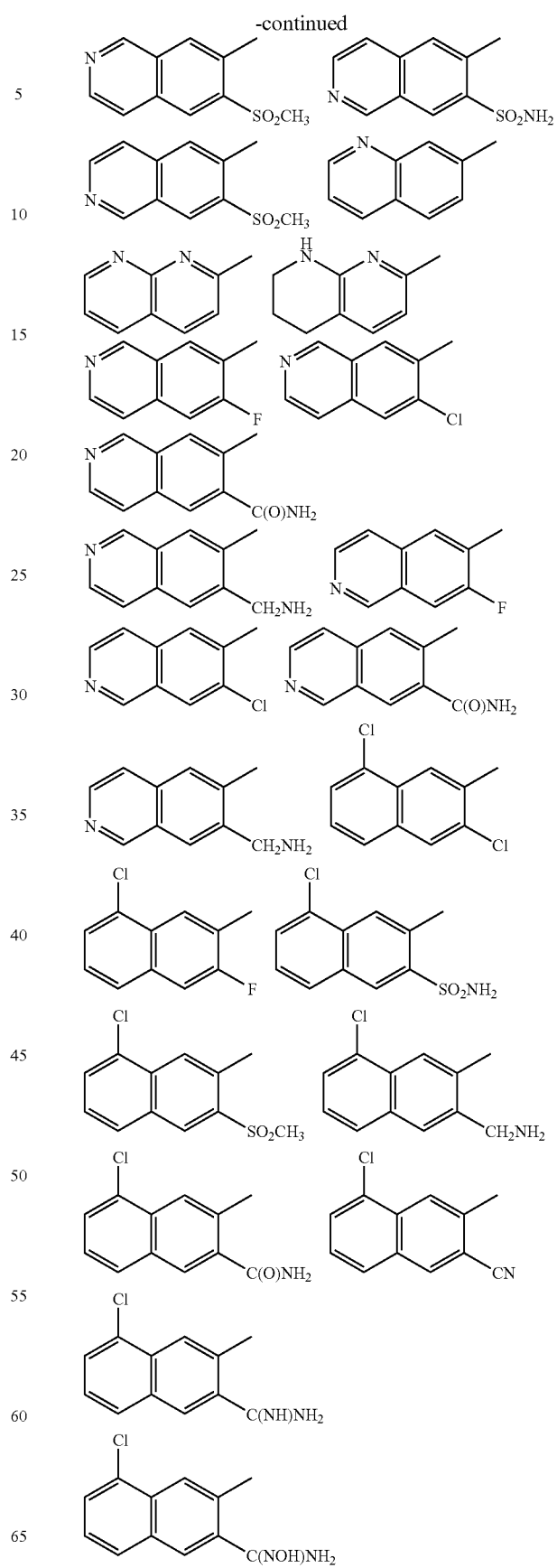

-continued
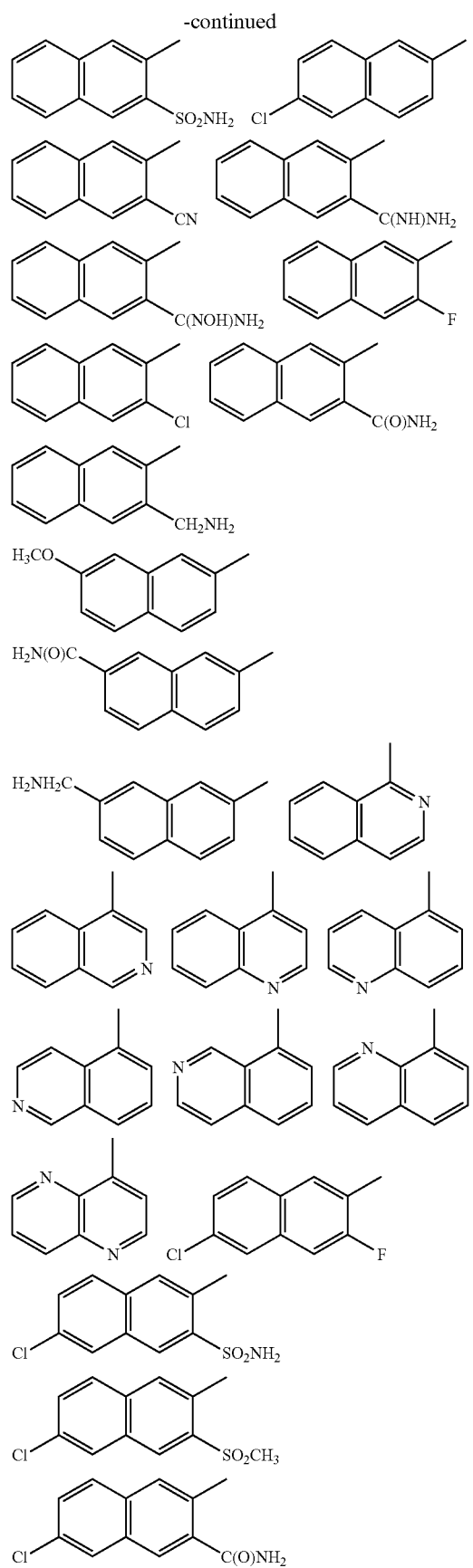
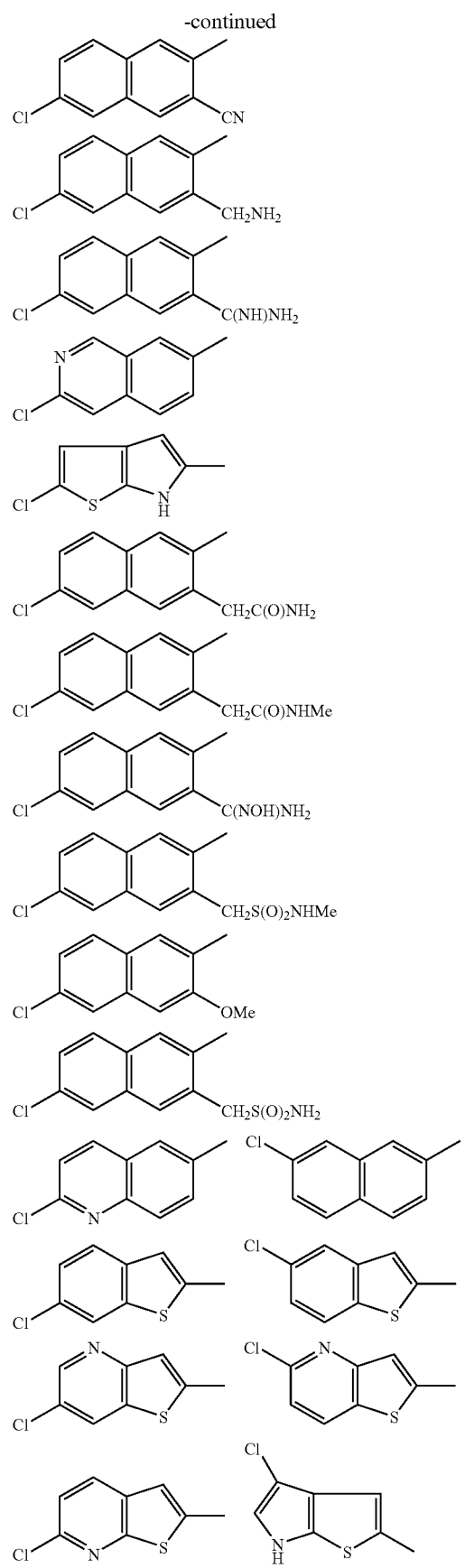

-continued
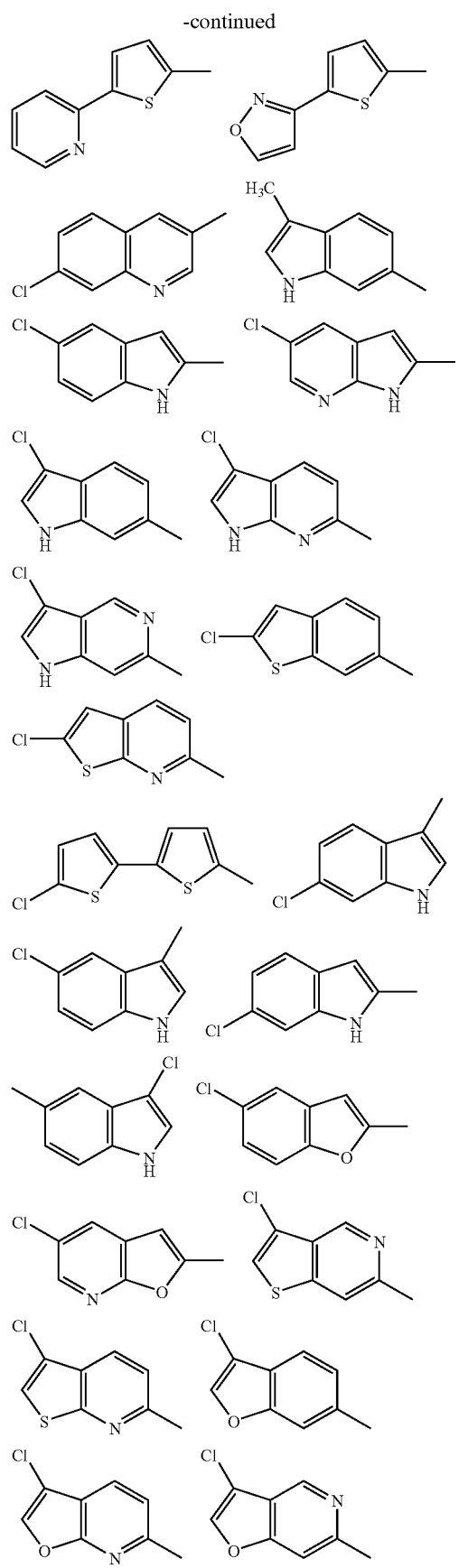
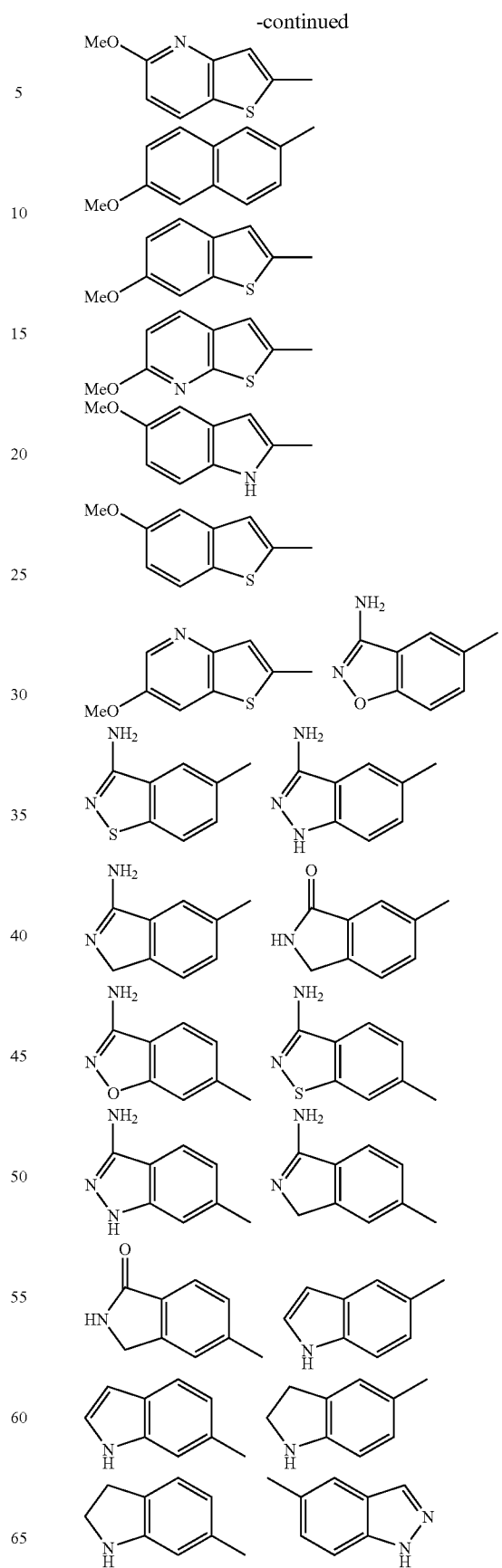

-continued

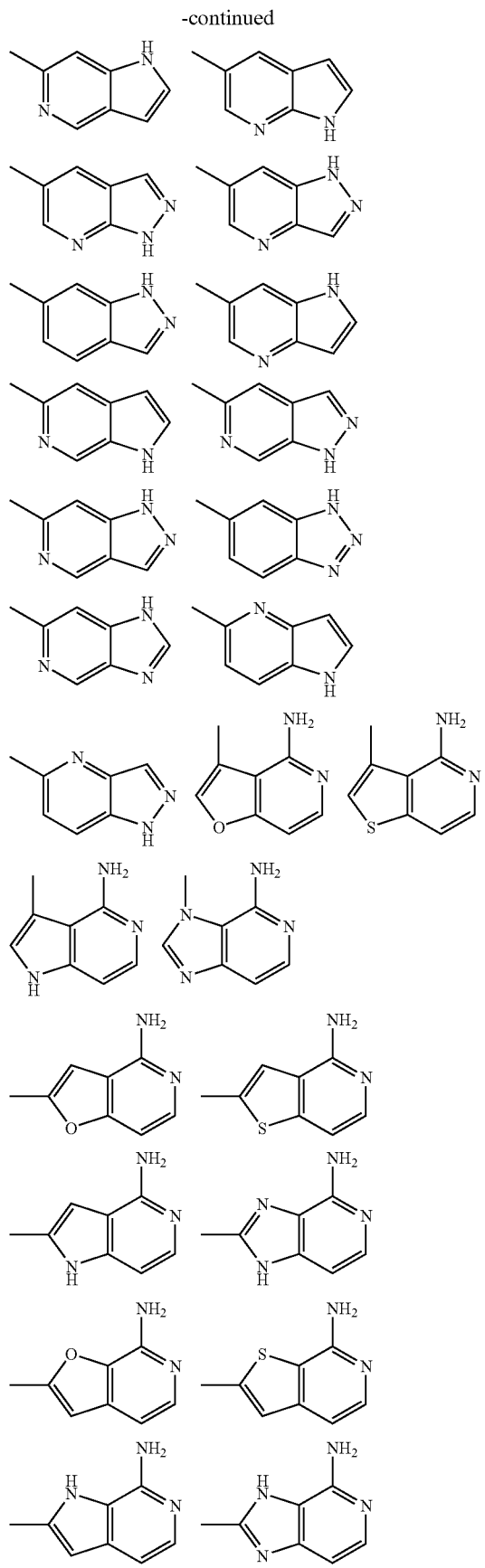

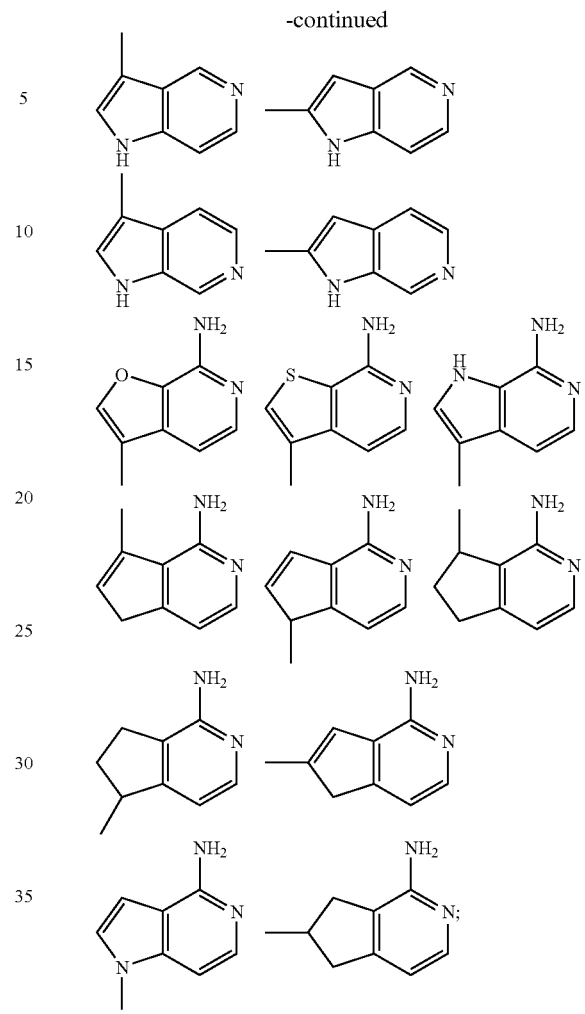

$G_1$ is absent or is selected from $(CR^3R^{3a})_{1-3}$, $CR^3$=$CR^3$, $(CR^3R^{3a})_uC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, $(CR^3R^{3a})_uC(O)NR^{3b}S(O)_2(CR^3R^{3a})_w$, $(CR^3R^{3a})_uNR^{3b}C(S)(CR^3R^{3a})_uC(O)NR^{3b}(CR^3R^{3a})_w$, and $(CR^3R^{3a})_uNR^{3b}C(O)(CR^3R^{3a})_uC(S)NR^{3b}(CR^3R^{3a})_w$, wherein u+w total 0, 1, or 2, provided that $G_1$ does not form a N—S, NCH$_2$N, NCH$_2$O, or NCH$_2$S bond with either group to which it is attached;

A is selected from one of the following carbocycles and heterocycles which are substituted with 0–2 $R^4$;

cyclohexyl, phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

X is selected from $-(CR^2R^{2a})_{1-2}-$, $-C(O)-$, $-S(O)_2-$, $-NR^2S(O)_2-$, $-NR^2S(O)_2NR^2-$, $-NR^2C(O)-$, $-C(O)NR^2-$, $NR^2$, $-NR^2CR^2R^{2a}-$, $-CR^2R^{2a}NR^2-$, O, $-OCR^2R^{2a}-$, and $-CR^2R^{2a}O-$;

Y is a $C_{3-6}$ monocyclic carbocycle or 5–6 membered monocyclic heterocycle, wherein the carobocycle or heterocycle consists of carbon atoms and 0–2 heteroatoms selected from N, O, and $S(O)_p$, the carbocycle or heterocycle further comprises 0–1 double bonds and 0–1 carbonyl groups, and the carbocycle or heterocycle is substituted with 0–2 $R^4$;

alternatively, Y is $CY^1Y^2$, and $Y^1$ and $Y^2$ are independently $C_{1-2}$ alkyl substituted with 0–1 $R^4$;

$R^{1a}$, at each occurrence, is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

alternatively, when two $R^{1a}$ groups are attached to adjacent atoms or to the same carbon atom, together with the atoms to which they are attached, they form a 5–6 membered ring consisting of: carbon atoms and 0–2 heteroatoms selected from the group consisting of N, O, and $S(O)_p$, this ring being substituted with 0–2 $R^{4b}$ and comprising: 0–3 double bonds;

$R^{1b}$ is selected from H, $CH_3$, $CH_2CH_3$, F, Cl, Br, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $C(O)NR^2R^{2a}$, $SO_2NR^2R^{2a}$, $NR^2SO_2R^2$, $C_{3-6}$ carbocycle substituted with 0–2 $R^{4b}$, and 5–6 membered aromatic heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, phenyl substituted with 0–2 $R^{4b}$, benzyl substituted with 0–2 $R^{4b}$, and 5–6 membered aromatic heterocycle substituted with 0–2 $R^{4b}$ and consisting of: carbon atoms and 1–4 heteroatoms selected from the group consisting of N, O, and $S(O)_p$;

$R^{2a}$, at each occurrence, is selected from H, $CF_3$, $CH_3$, $CH_2CH_3$, $CH_2CH_2CH_3$, $CH(CH_3)_2$, benzyl, $C_{3-6}$ carbocycle substituted with 0–2 $R^{4b}$, and 5–6 membered aromatic heterocycle substituted with 0–2 $R^{4b}$ and consisting of: carbon atoms and 1–4 heteroatoms selected from the group consisting of N, O, and $S(O)_p$;

$R^{2b}$, at each occurrence, is selected from $CF_3$, $C_{1-4}$ alkoxy, $C_{1-5}$ alkyl substituted with 0–3 $R^{4b}$, benzyl, $C_{3-6}$ carbocycle substituted with 0–2 $R^{4b}$, and 4–6 membered substituted with 0–2 $R^{4b}$ and consisting of: carbon atoms and 1–4 heteroatoms selected from the group consisting of N, O, and $S(O)_p$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle substituted with 0–2 $R^{4b}$ and consisting of carbon atoms and from 1–4 heteroatoms selected from the group consisting of N, O, and $S(O)_p$;

alternatively, $R^2$ and $R^{2a}$, together with the nitrogen atom to which they are attached, combine to form a 3–6 membered saturated, partially saturated or unsaturated ring substituted with 0–2 $R^{4b}$ and consisting of: 0–1 additional heteroatoms selected from the group consisting of N, O, and $S(O)_p$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, $-(CR^3R^{3a})-C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and $-(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—S $(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, $-(CR^3R^{3a})-C_{3-6}$ carbocycle substituted with 0–2 $R^{4c}$, 5–6 membered heterocycle substituted with 0–2 $R^{4c}$ consisting of: carbon atoms and 1–4 heteroatoms selected from the group consisting of N, O, and $S(O)_p$, and $-(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^4$, at each occurrence, is selected from H, $(CH_2)_2OR^2$, $CH_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$ is selected from $-(CR^3R^{3g})_r$-5–6 membered carbocycle substituted with 0–3 $R^{4c}$, $-(CR^3R^{3g})_r$-5-6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r$—$NR^{2d}C(O)R^{2e}$, $(CR^3R^{3g})_r$—$C(O)R^{2e}$, $(CR^3R^{3g})_r$—$OC(O)R^{2e}$, $(CR^3R^{3g})_r$—$C(O)NR^{2d}R^{2d}$, $(CR^3R^{3g})_r$—$C(O)OR^{2d}$, $(CR^3R^{3g})_r$—$NR^{2d}C(O)NR^{2d}R^{2d}$, $(CR^3R^{3g})_r$—$NR^{2d}C(O)OR^{2d}$, $(CR^3R^{3g})_r$—$SO_2NR^{2d}R^{2d}$, $(CR^3R^{3g})_r$—$NR^{2d}SO_2R^{2d}$, and $(CR^3R^{3g})_r$—$S(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, CH, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2$—$C(O)R^3$, $C(O)OR^{3c}$, $CH_2$—$C(O)OR^{3c}$, $NR^3C(O)R^{3a}$, $CH_2NR^3C(O)R^{3a}$, $C(O)NR^3R^{3a}$, $CH_2$—$C(O)NR^3R^{3a}$, $SO_2NR^3R^{3a}$, $CH_2SO_2NR^3R^{3a}$, $NR^3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})F$, Br, $(CR^3R^{3a})Br$, Cl, $(CR^3R^{3a})Cl$, $CF_3$, $(CR^3R^{3a})CF_3$, $C_{1-4}$ alkyl, $C_{2-3}$ alkenyl, $C_{2-3}$ alkynyl, —CN, $(CR^3R^{3a})CN$, $NO_2$, $(CR^3R^{3a})NO_2$, $NR^2R^{2a}$, $(CR^3R^{3a})NR^2R^{2a}$, $N(\rightarrow O)R^2R^{2a}$, $(CR^3R^{3a})N(\rightarrow O)R^2R^{2a}$, $C(O)R^{2c}$, $(CR^3R^{3a})C(O)R^{2c}$, $NR^2C(O)R^{2b}$, $(CR^3R^{3a})NR^2C(O)R^{2b}$, $C(O)NR^2R^{2a}$, $(CR^3R^{3a})C(O)NR^2R^{2a}$, $NR^2C(O)NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})NR^2SO_2NR^2R^{2a}$, $NR^2SO_2R^{5a}$, $(CR^3R^{3a})NR^2SO_2R^{5a}$, $S(O)_pR^{5a}$, $(CR^3R^{3a})S(O)_pR^{5a}$, $CF_3$, $CF_2CF_3$, $C_{3-10}$ carbocycle substituted with 0–2 $R^{4b}$, $(CR^3R^{3a})C_{3-10}$ carbocycle substituted with 0–2 $R^{4b}$, 5–10 membered heterocycle substituted with 0–2 $R^{4b}$ and consisting of carbon atoms and from 1–4 heteroatoms selected from the group consisting of N, O, and $S(O)_p$, and $(CR^3R^{3a})$ 5–10 membered heterocycle substituted with 0–2 $R^{4b}$ and consisting of carbon atoms and from 1–4 heteroatoms selected from the group consisting of N, O, and $S(O)_p$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl; and, r, at each occurrence, is selected from 0, 1, and 2.

[11] In another preferred embodiment, the present invention provides a novel compound, wherein the compound is selected from:

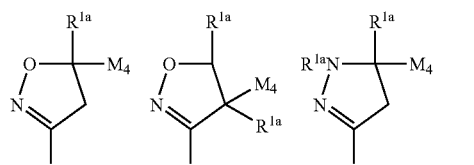
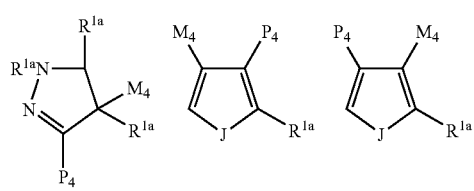
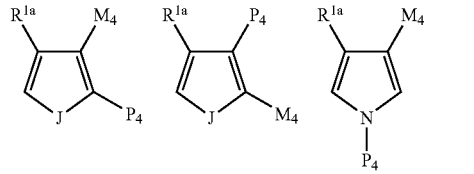
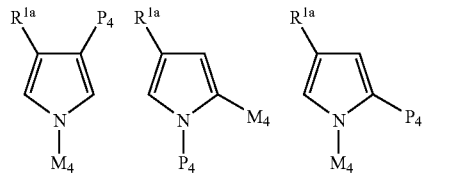
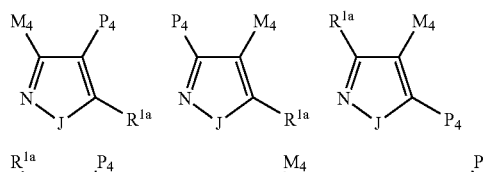
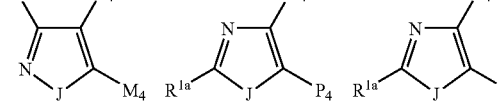

-continued

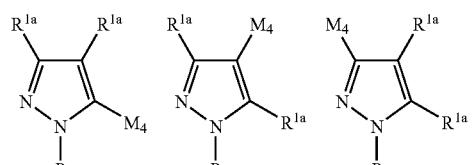
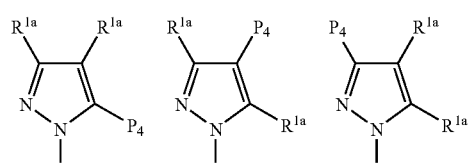
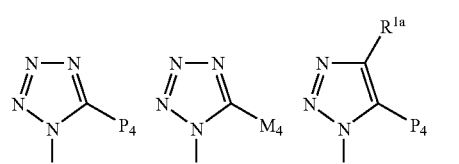
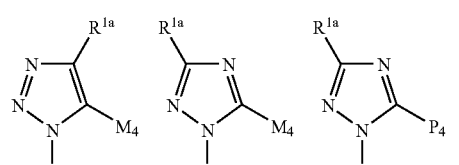
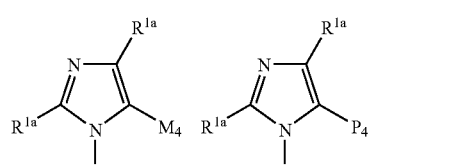
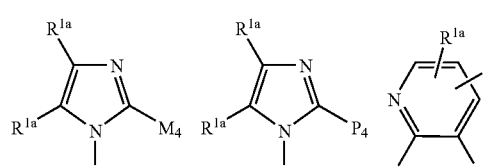
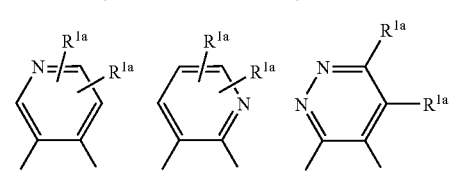
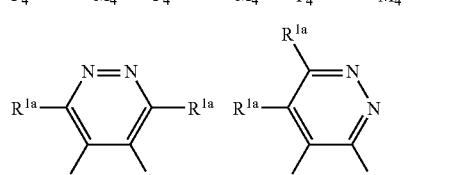
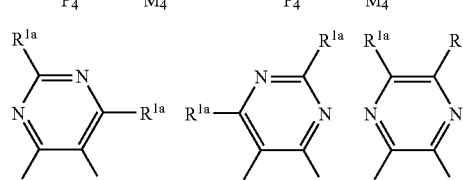

-continued
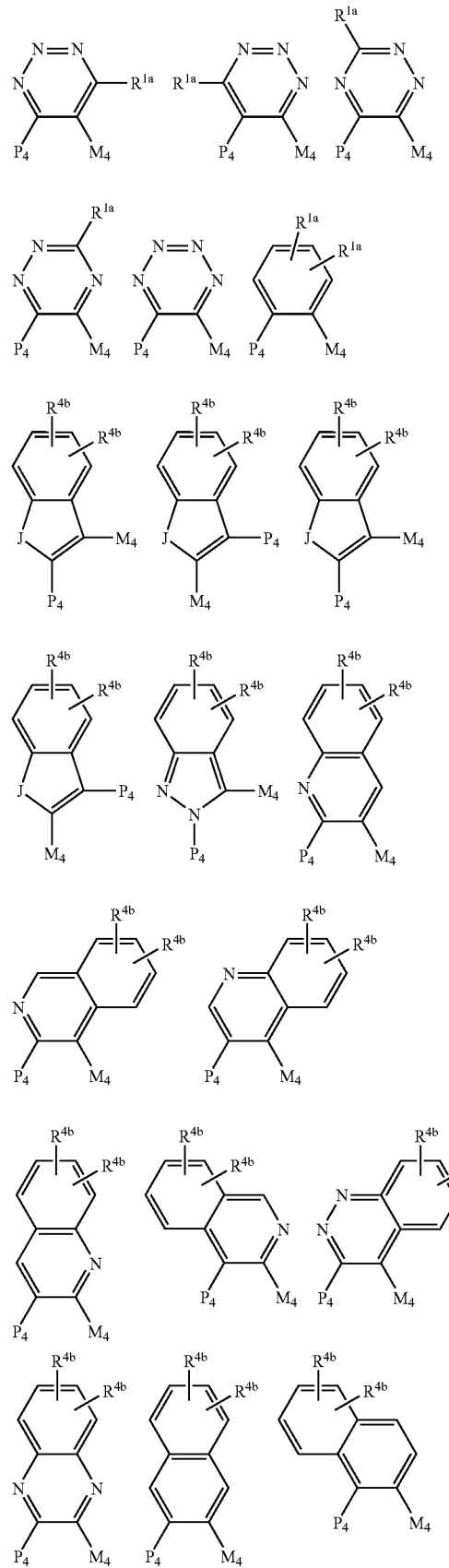
-continued
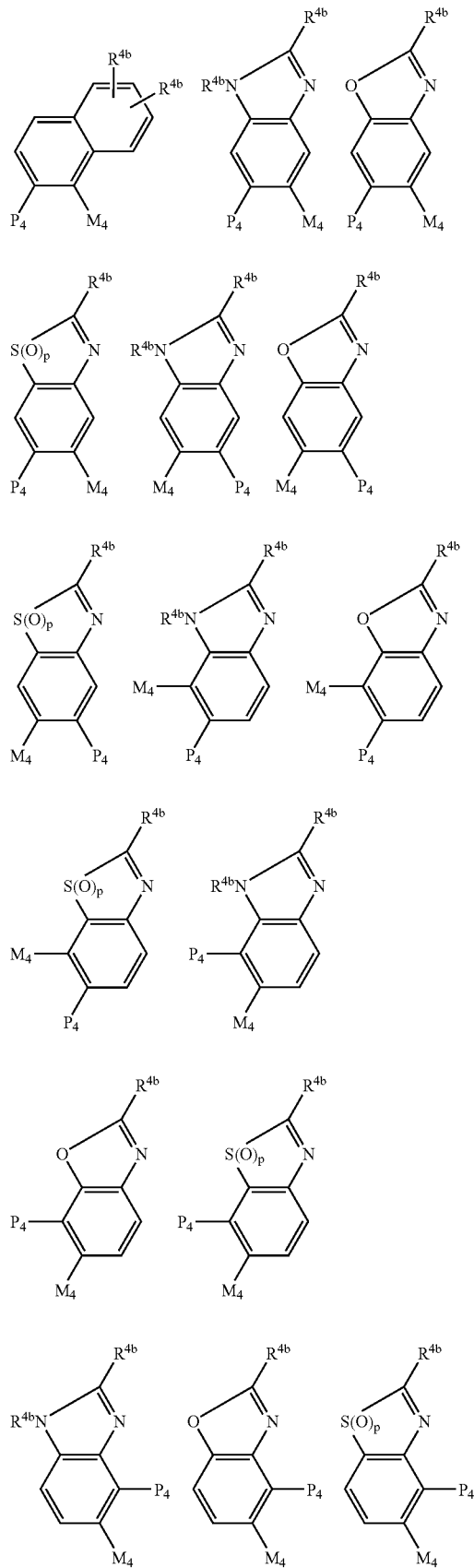

-continued
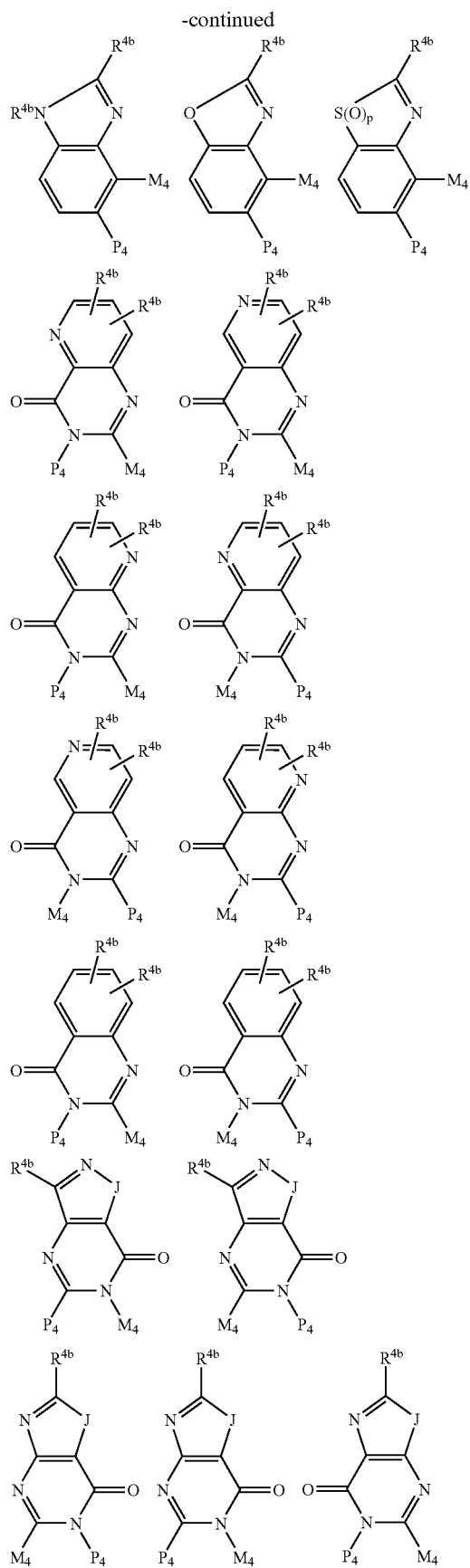
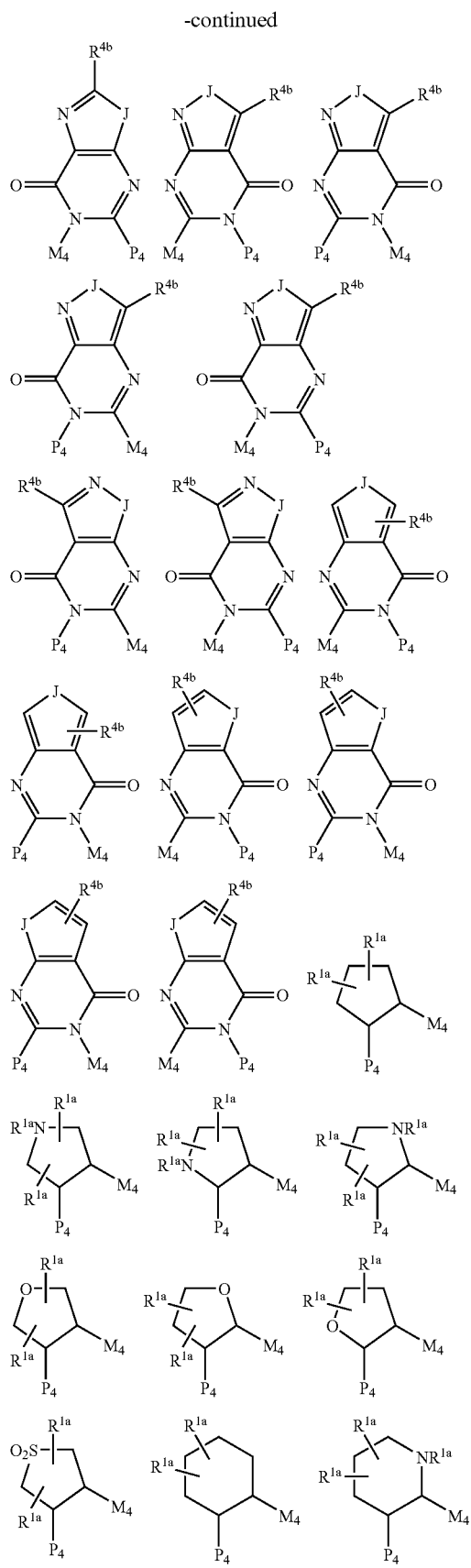

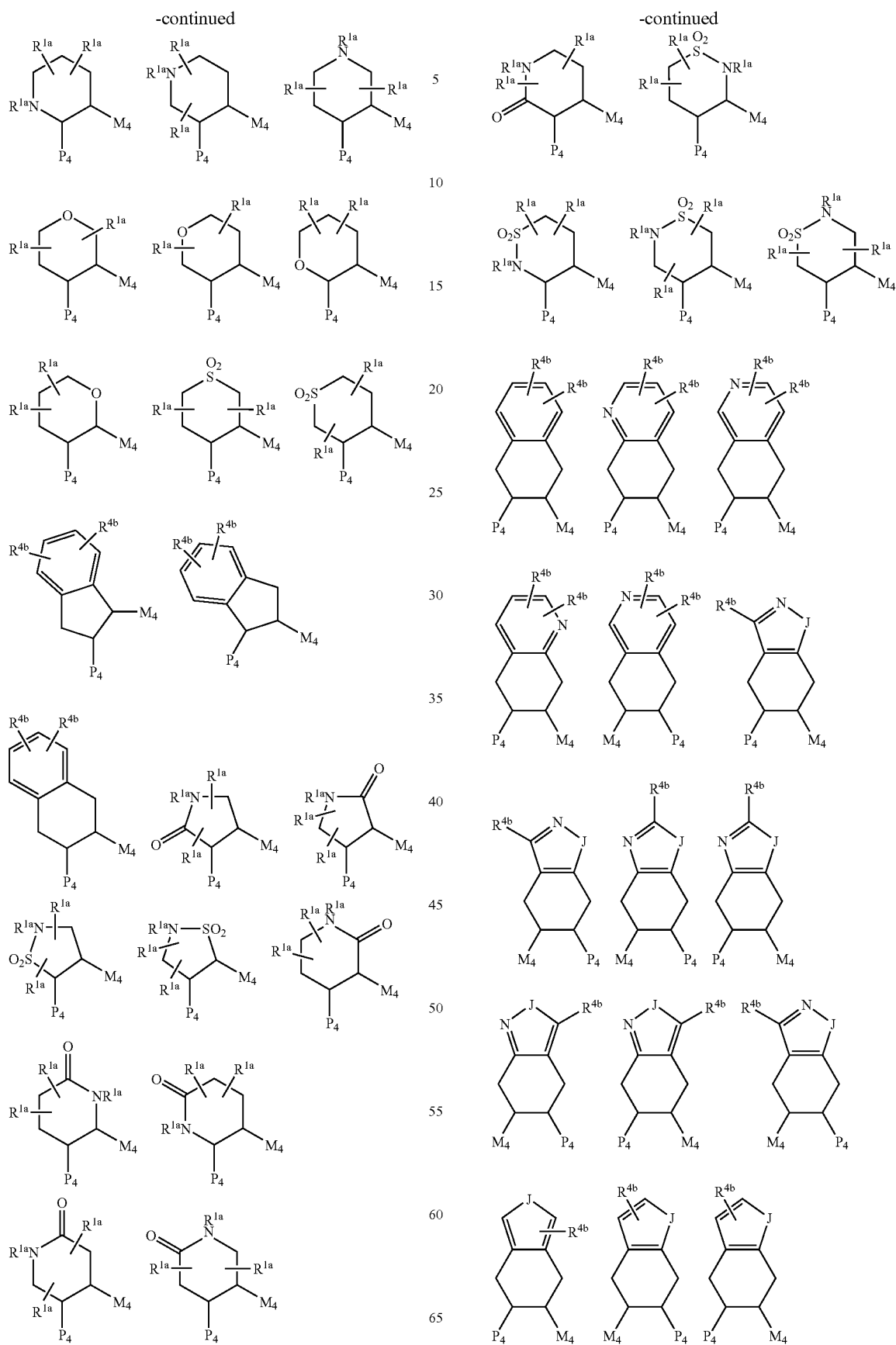

-continued
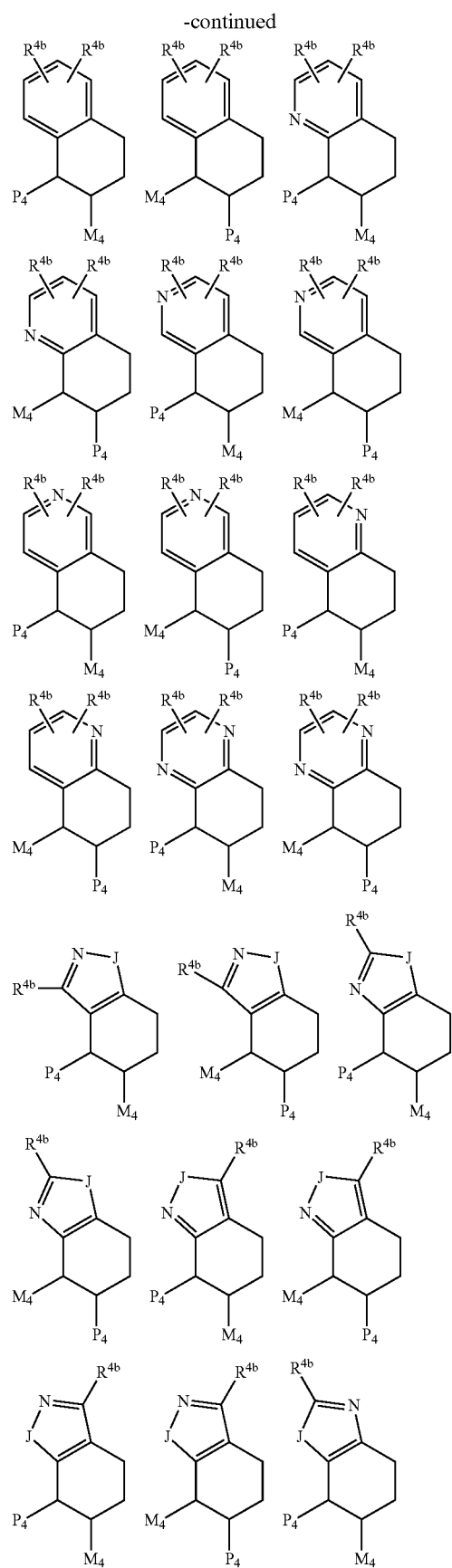
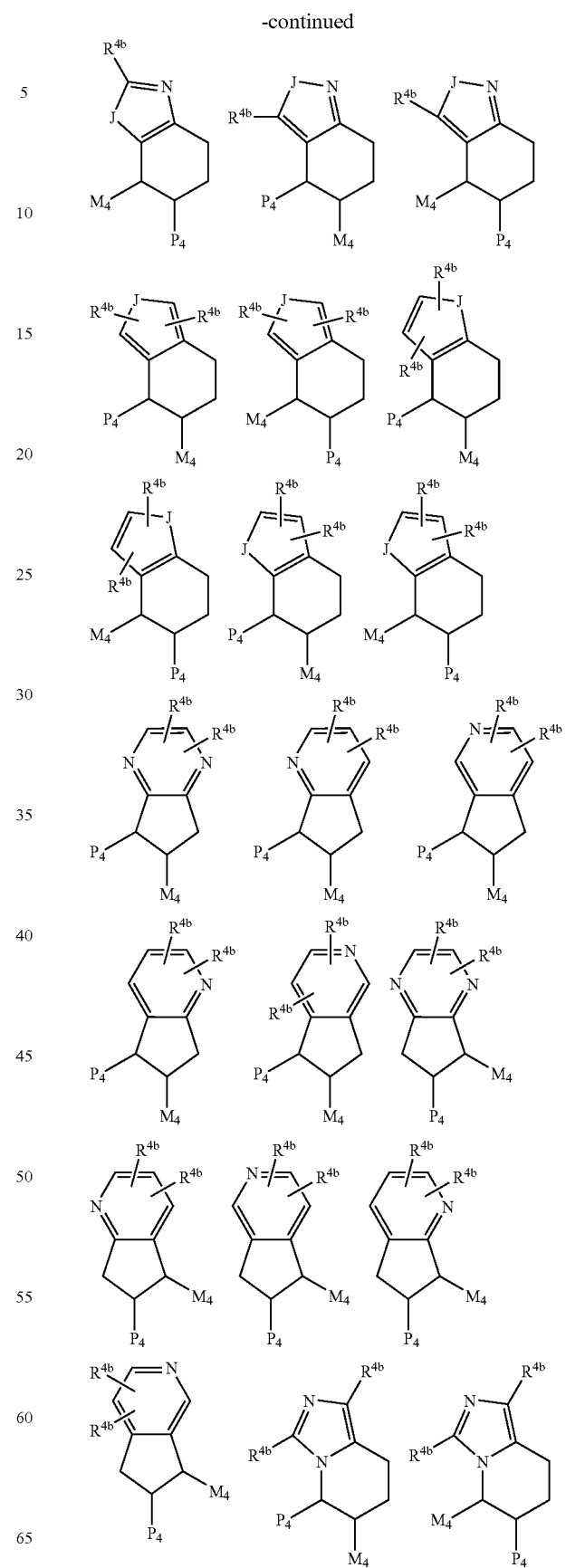

-continued
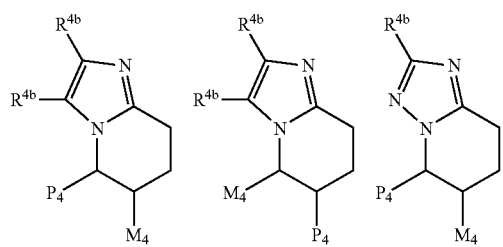
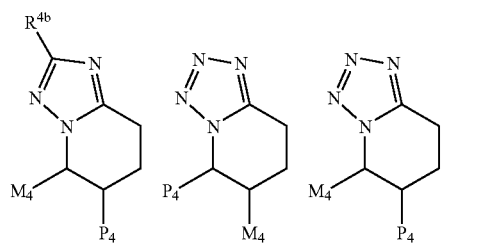
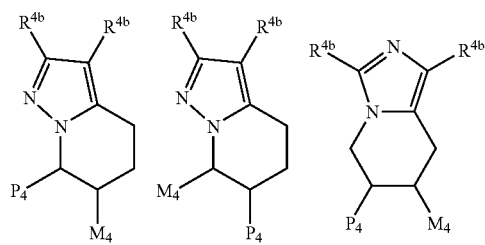
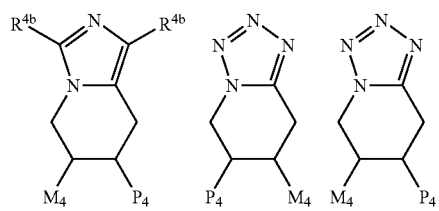
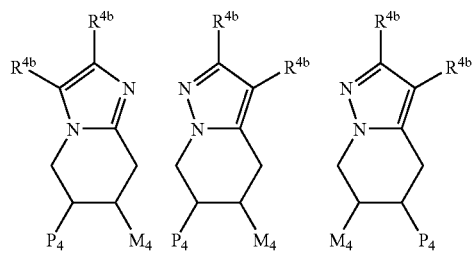
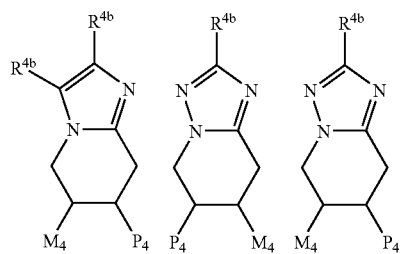
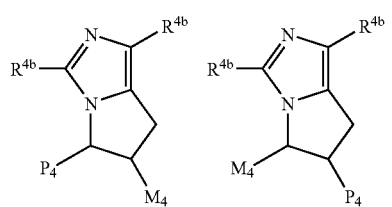
-continued
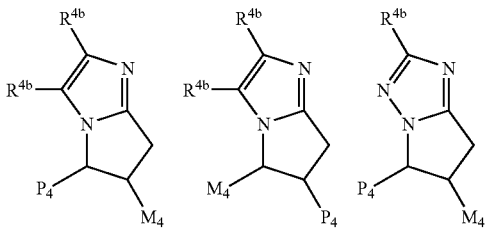
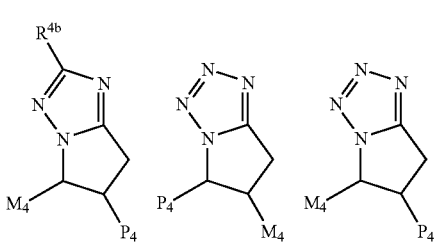
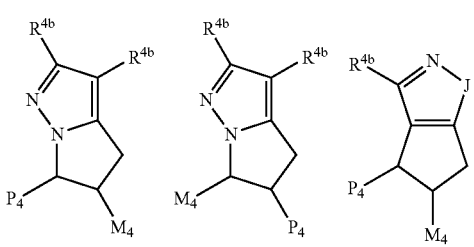
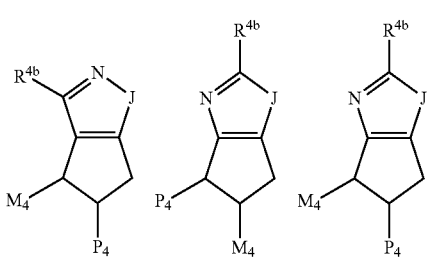
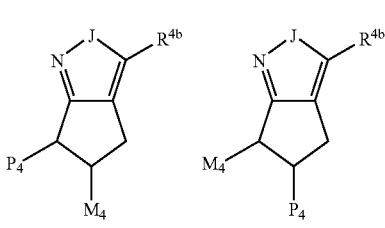
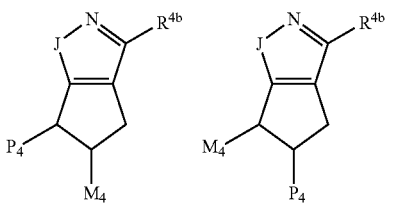
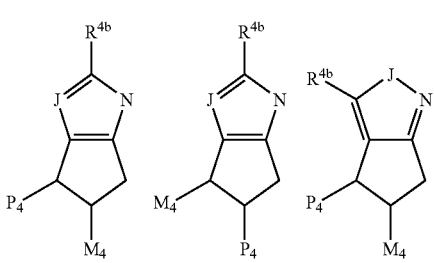

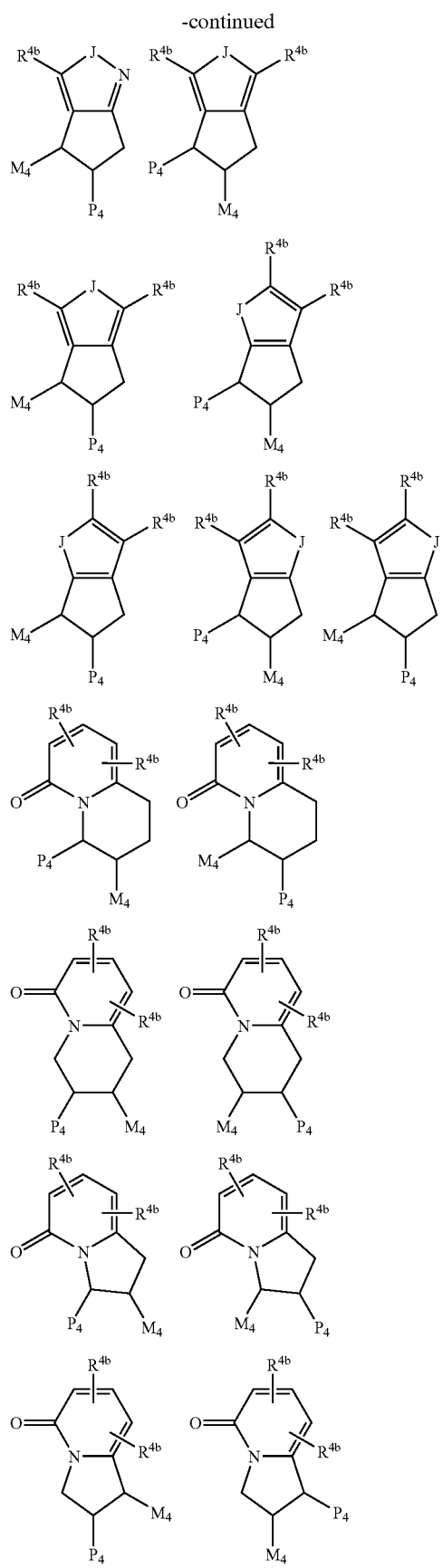
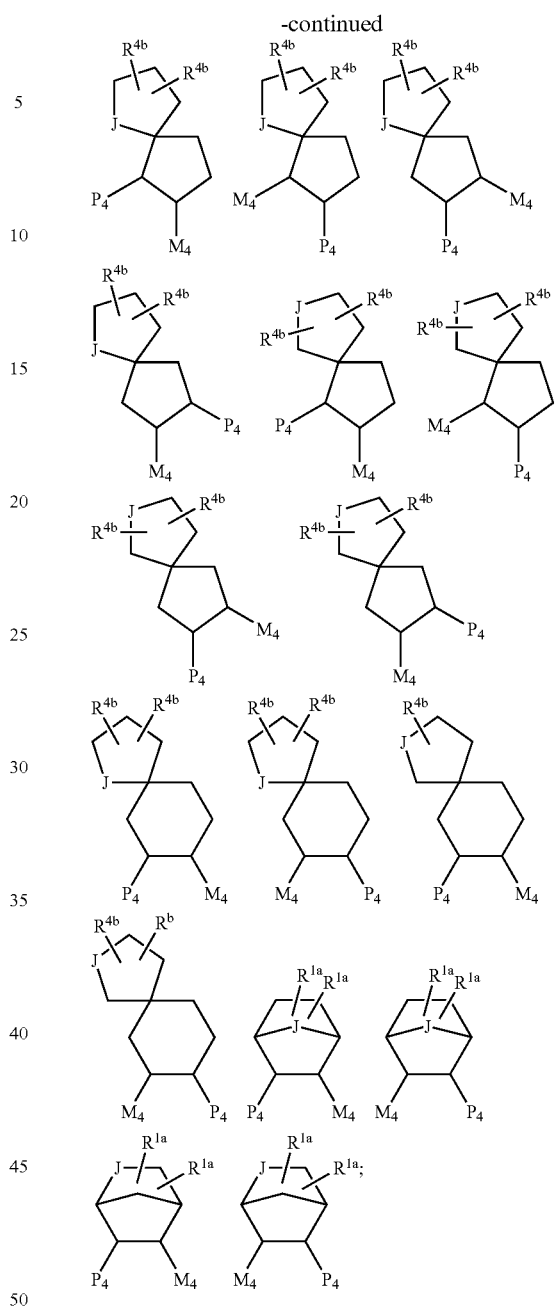

J is selected from O, S, NH, and $NR^{1a}$;
G is selected from the group:
2-amido-4-methoxy-phenyl; 2-amido-phenyl; 2-aminomethyl-3-fluoro-phenyl; 2-aminomethyl-4-fluoro-phenyl; 2-aminomethyl-4-methoxy-phenyl; 2-aminomethyl-5-fluoro-phenyl; 2-aminomethyl-5-methoxy-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 2-methylsulfonyl-phenyl; 3-(N,N-dimethylamino)-4-chloro-phenyl; 3-(N,N-dimethylamino)-phenyl; 3-(N-methylamino)-4-chloro-phenyl; 3-(N-methylamino)-phenyl; 3-amido-phenyl; 3-amino-4-chloro-phenyl; 3-aminomethyl-phenyl; 3-amino-phenyl; 3-chloro-phenyl; 3,5-dichloro-thien-2-yl; 4-(N,N-dimethylamino)-5-chloro-thien-2-yl; 4-(N-methylamino)-5- chloro-thien-2-yl; 4-amino-5-chloro-thien-2-yl; 4-chloro-phenyl; 4-methoxy-2-methylsulfonyl-phenyl; 4-methoxy-phenyl; 5-(N,N-dimethylamino)-4-chloro-thien-2-yl; 5-(N-methylamino)-4-chloro-thien-2-yl; 5-amino-4-chloro-thien-2-yl; 5-chloro-pyrid-2-yl; 5-chloro-thien-2-yl; 5-methoxy-thien-2-yl; 6-amino-5-chloro-pyrid-2-yl; 6-amino-pyrid-2-yl; 5-chloro-pyrimidin-3-yl; 6-chloro-pyridazin-3-yl; 2-aminomethyl-4-chloro-phenyl; 2-aminosulfonyl-4-chloro-phenyl; 2-amido-4-chloro-phenyl; 4-chloro-2-methylsulfonyl-phenyl; 2-aminosulfonyl-4-fluoro-phenyl; 2-amido-4-fluoro-phenyl; 4-fluoro-2-methylsulfonyl-phenyl; 2-aminomethyl-4-bromo-phenyl; 2-aminosulfonyl-4-bromo-phenyl; 2-amido-4-bromo-phenyl; 4-bromo-2-methylsulfonyl-phenyl; 2-aminomethyl-4-methyl-phenyl; 2-aminosulfonyl-4-methyl-phenyl; 2-amido-4-methyl-phenyl; 2-methylsulfonyl-4-methyl-phenyl; 4-fluoro-pyrid-2-yl; 4-bromo-pyrid-2-yl; 4-methyl-pyrid-2-yl; 5-fluoro-thien-2-yl; 5-bromo-thien-2-yl; 5-methyl-thien-2-yl; 2-amido-4-methoxy-phenyl;

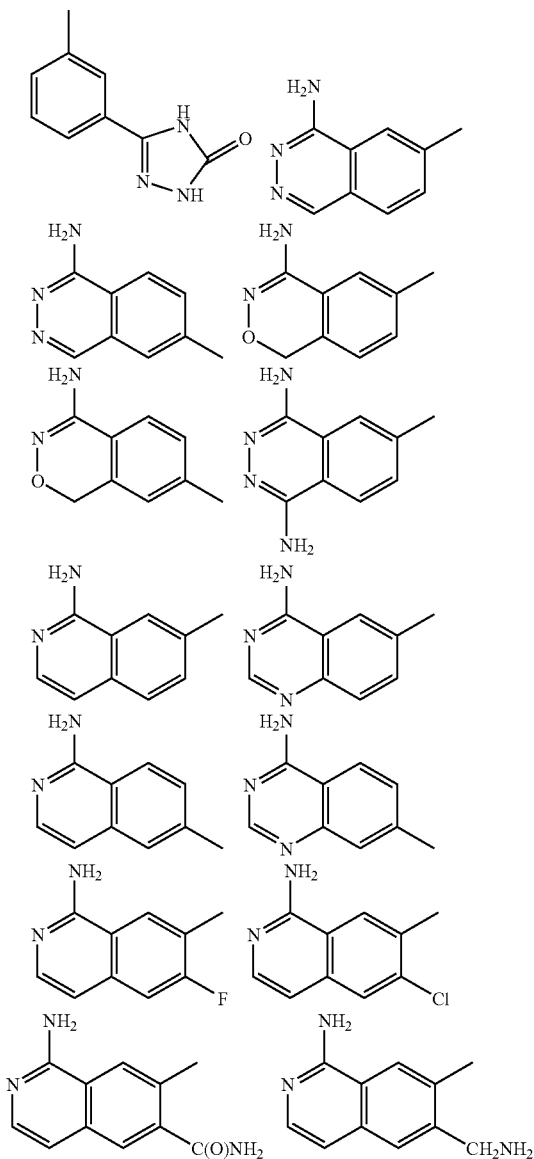

-continued

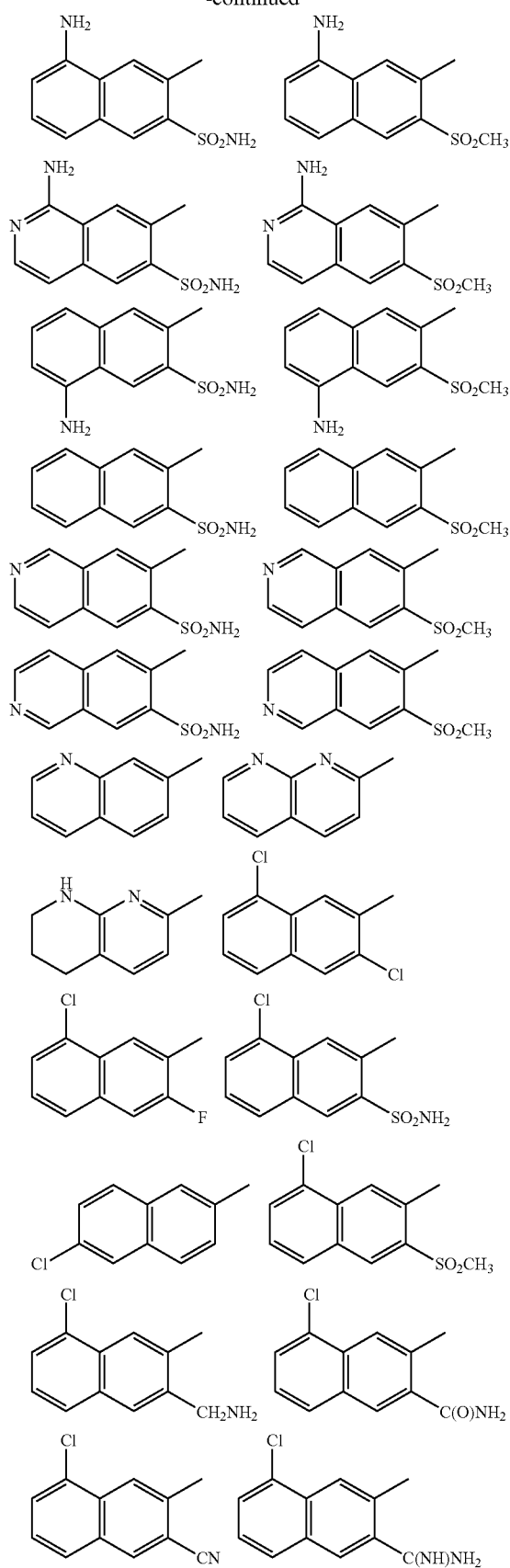

-continued
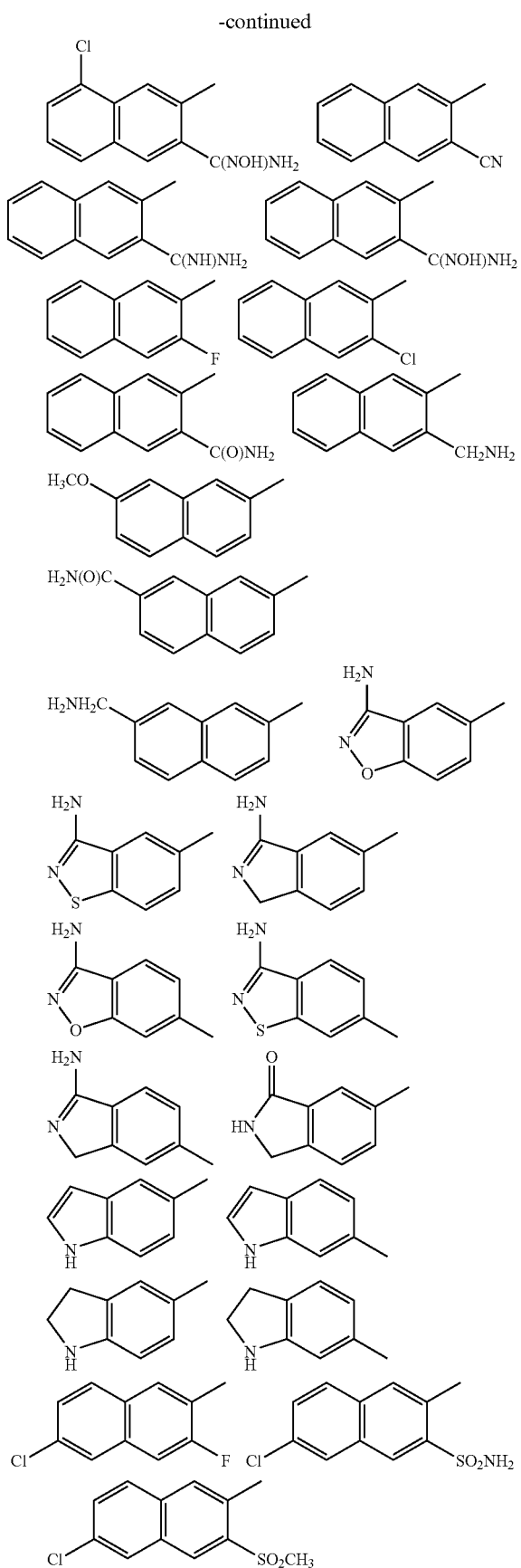
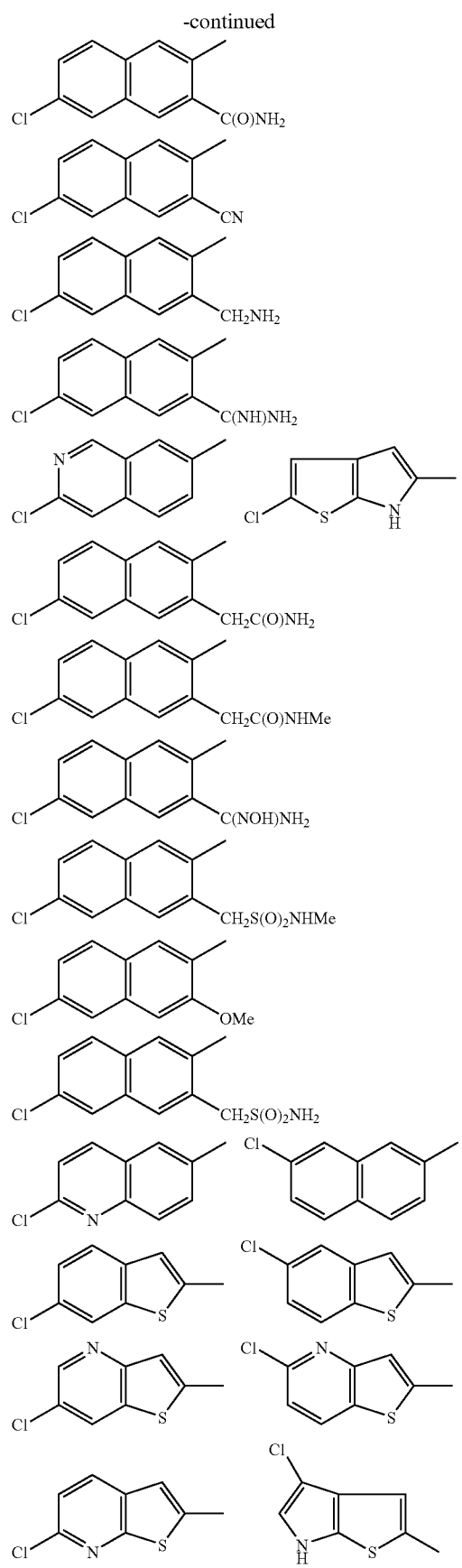

-continued

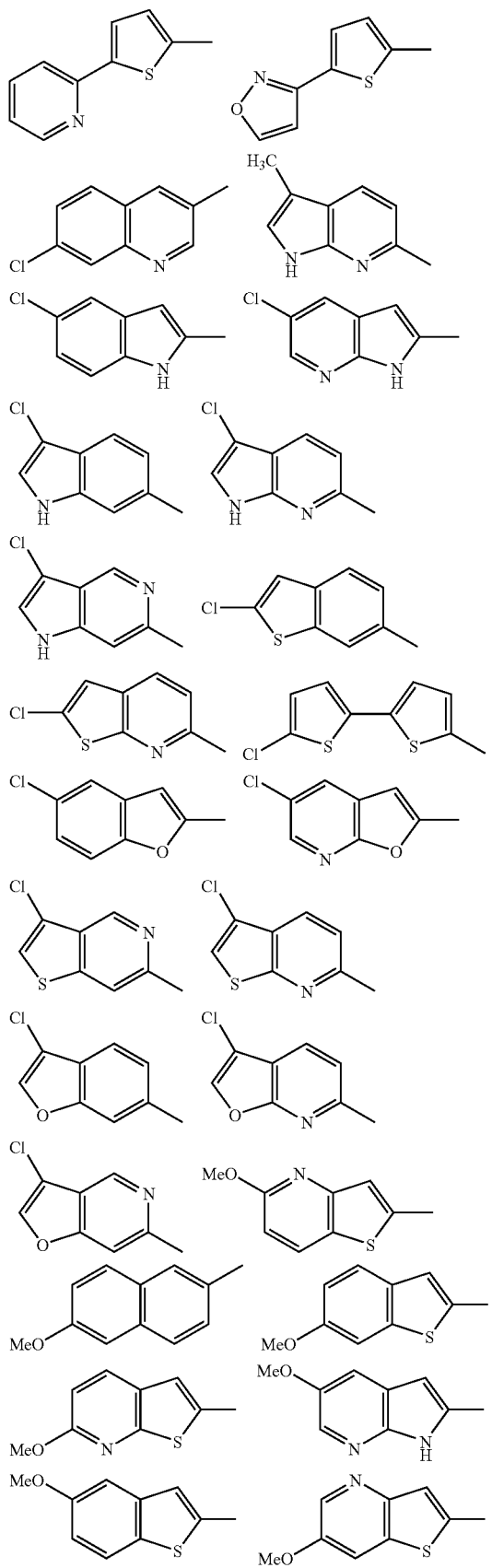
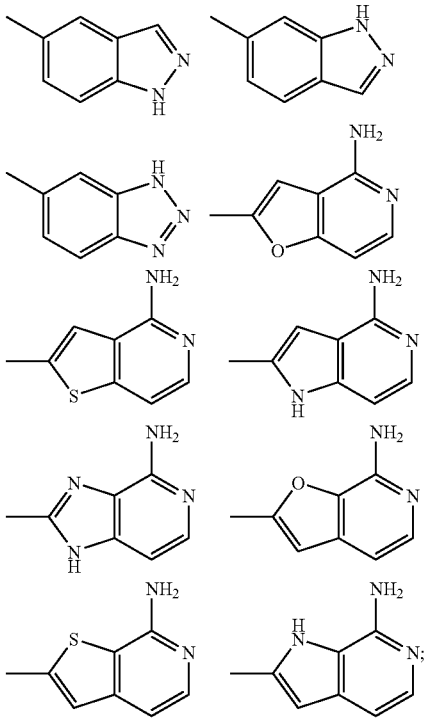

G₁ is absent or is selected from $CH_2$, $CH_2CH_2$, CH=CH, $CH_2O$, $OCH_2$, NH, $CH_2NH$, $NHCH_2$, $CH_2C(O)$, $C(O)CH_2$, $C(O)NH$, NHC(O), NHC(O)NH, $C(O)NHS(O)_2$, NHCOCONH, NHCOC(S)NH, NHC(S)CONH, $CH_2S(O)_2$, $S(O)_2(CH_2)$, $SO_2NH$, and $NHSO_2$, provided that $G_1$ does not form a N—S, $NCH_2N$, $NCH_2O$, or $NCH_2S$ bond with either group to which it is attached;

A is selected from cyclohexyl, indolinyl, piperidinyl, phenyl, pyridyl, and pyrimidyl, and is substituted with 0–2 $R^4$;

X is selected from $CH_2$, C(O), $—S(O)_2—$, —NHC(O)—, —C(O)NH—, —$CH_2NH$—, O, and —$CH_2O$—;

Y is selected from $C(CH_3)_2$, $C(CH_2CH_3)_2$, cyclopropyl, cyclobutyl, cyclopentyl, cyclopentanonyl, cyclohexyl, cyclohexanonyl, pyrrolidinyl, pyrrolidinonyl, piperidinyl, piperidinonyl, tetrahydrofuranyl, and tetrahydropyranyl, and, when Y is a ring, Y is substituted with 0–1 $R^4$;

$R^{1a}$, at each occurrence, is selected from H, $R^{1b}$, $CH(CH_3)R^{1b}$, $C(CH_3)_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^2$, $C(O)NR^2R^{2a}$, $SO_2NR^2R^{2a}$, $NR^2SO_2R^2$, $C_{3-6}$ carbocycle substituted with 0–2 $R^{4b}$, and 5–6 membered aromatic heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5–6 membered aromatic heterocycle substituted with 0–1 $R^{4b}$ and consisting of: carbon atoms and 1–4 heteroatoms selected from the group consisting of N, O, and $S(O)_p$;

$R^{2a}$, at each occurrence, is selected from H, $CH_3$, $CH_2CH_3$, $CH_2CH_2CH_3$, $CH(CH_3)_2$, cyclopropyl, benzyl, phenyl substituted with 0–1 $R^{4b}$, and 5–6 membered aromatic heterocycle substituted with 0–1 $R^{4b}$ and consisting of: carbon atoms and 1–4 heteroatoms selected from the group consisting of N, O, and $S(O)_p$;

alternatively, $R^2$ and $R^{2a}$, together with the nitrogen atom to which they are attached, combine to form a 3–6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from OH, $OCH_3$, $OCH_2CH_3$, $OCH_2CH_2CH_3$, $OCH(CH_3)_2$, $C_{1-5}$ alkyl substituted with 0–3 $R^{4b}$, benzyl, $C_{3-6}$ carbocycle substituted with 0–2 $R^{4b}$, and 4–6 membered aromatic heterocycle substituted with 0–1 $R^{4b}$ and consisting of: carbon atoms and 1–4 heteroatoms selected from the group consisting of N, O, and $S(O)_p$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle substituted with 0–1 $R^{4b}$ and consisting of carbon atoms and from 1–4 heteroatoms selected from the group consisting of N, O, and $S(O)_p$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —($CH_2$)—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —($CH_2$)-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—S(O)$_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —($CH_2$)—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —($CH_2$)-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—S(O)$_p$ moiety;

$R^4$, at each occurrence, is selected from OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $CF_3$, and $CF_2CF_3$;

$R^{4a}$ is selected from —$(CR^3R^{3g})_r$-5–6 membered carbocycle substituted with 0–3 $R^{4c}$, —$(CR^3R^{3g})_r$-5–6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r$—C(O)NR$^{2d}$R$^{2d}$, $(CR^3R^{3g})_r$—NR$^{2d}$C(O)R$^{2e}$, $(CR^3R^{3g})_r$—C(O)R$^{2e}$, $(CR^3R^{3g})_r$—NR$^{2d}$C(O)NR$^{2d}$R$^{2d}$, $(CR^3R^{3g})_r$—NR$^{2d}$C(O)OR$^{2d}$, $(CR^3R^{3g})_r$—NR$^{2d}$SO$_2$R$^{2d}$, and $(CR^3R^{3g})_r$—S(O)$_p$R$^{2d}$, provided that S(O)$_p$R$^{2d}$ forms other than S(O)$_2$H or S(O)H;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, and $CF_3$;

$R^{4c}$, at each occurrence, is selected from =O, $OR^2$, $CH_2OR^2$, F, Br, Cl, $CF_3$, $CH_3$, $CH_2CH_3$, $CH_2CH_2CH_3$, $CH(CH_3)_2$, $C_{2-3}$ alkenyl, $C_{2-3}$ alkynyl, —CN, $NO_2$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, $CF_2CF_3$, $C_{3-6}$ carbocycle substituted with 0–2 $R^{4b}$, $(CH_2)C_{3-6}$ carbocycle substituted with 0–2 $R^{4b}$, 5–6 membered heterocycle substituted with 0–2 $R^{4b}$ and consisting of carbon atoms and from 1–4 heteroatoms selected from the group consisting of N, O, and $S(O)_p$, and $(CH_2)$ 5–6 membered heterocycle substituted with 0–2 $R^{4b}$ and consisting of carbon atoms and from 1–4 heteroatoms selected from the group consisting of N, O, and $S(O)_p$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

[12] In another preferred embodiment, the present invention provides a novel compound, wherein the compound is selected from:

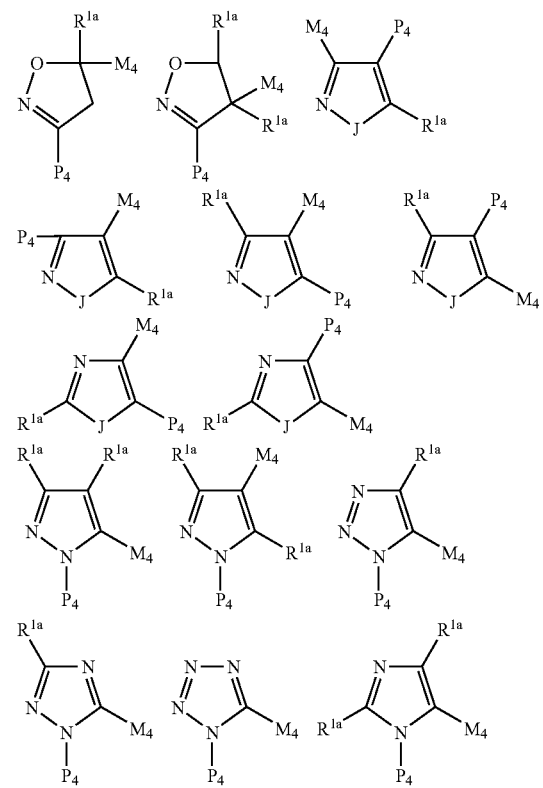

-continued
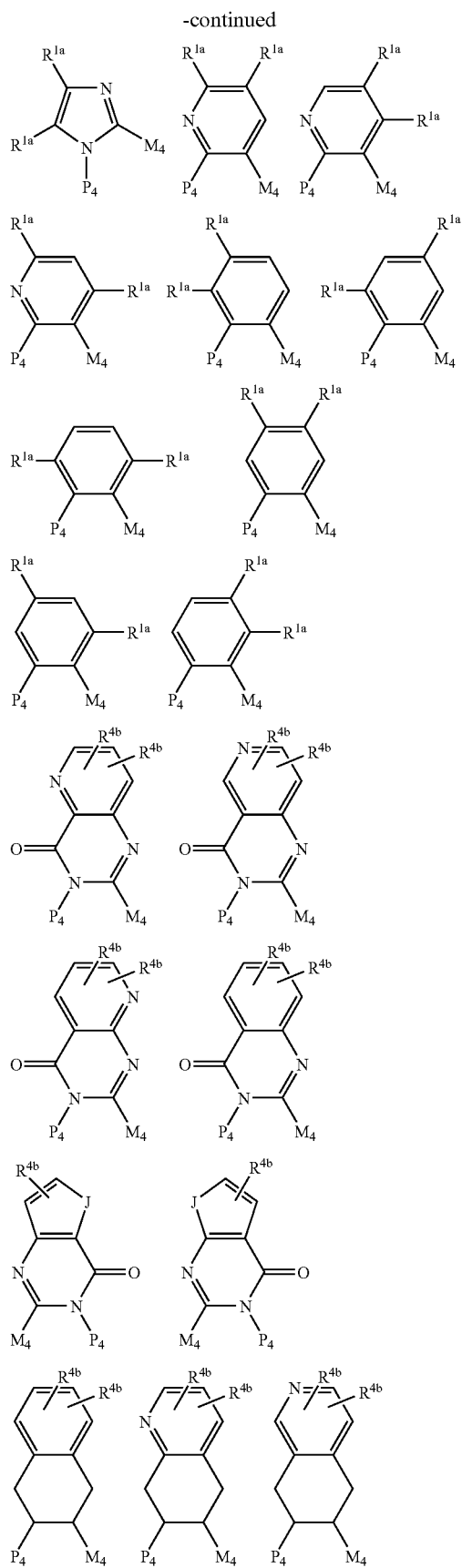
-continued
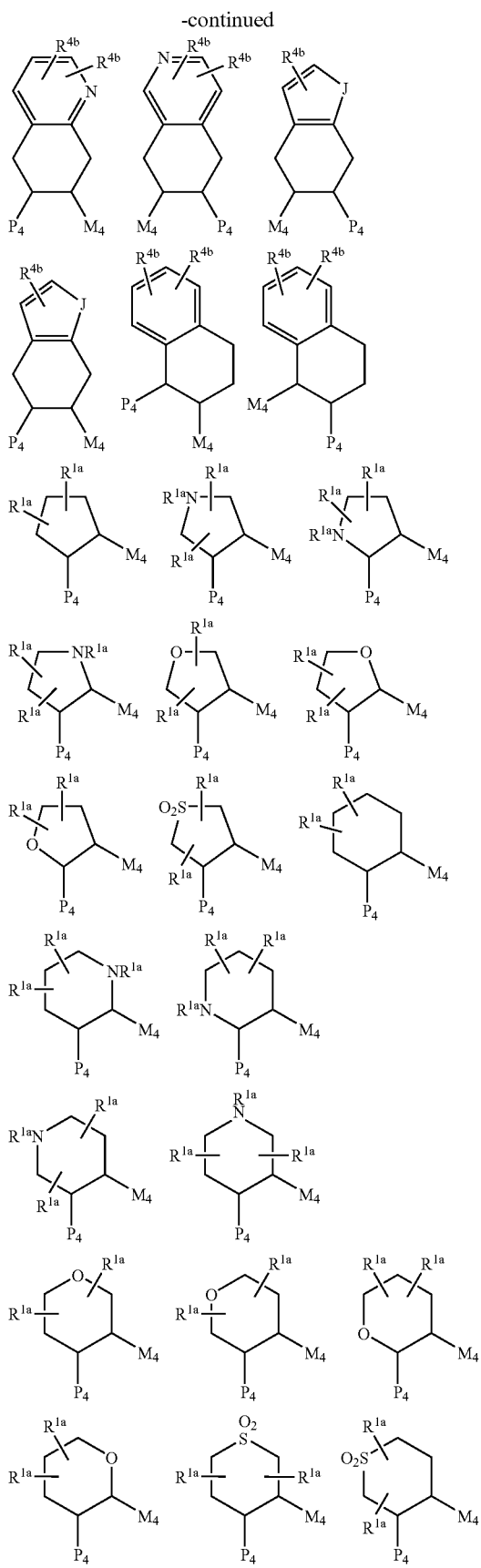

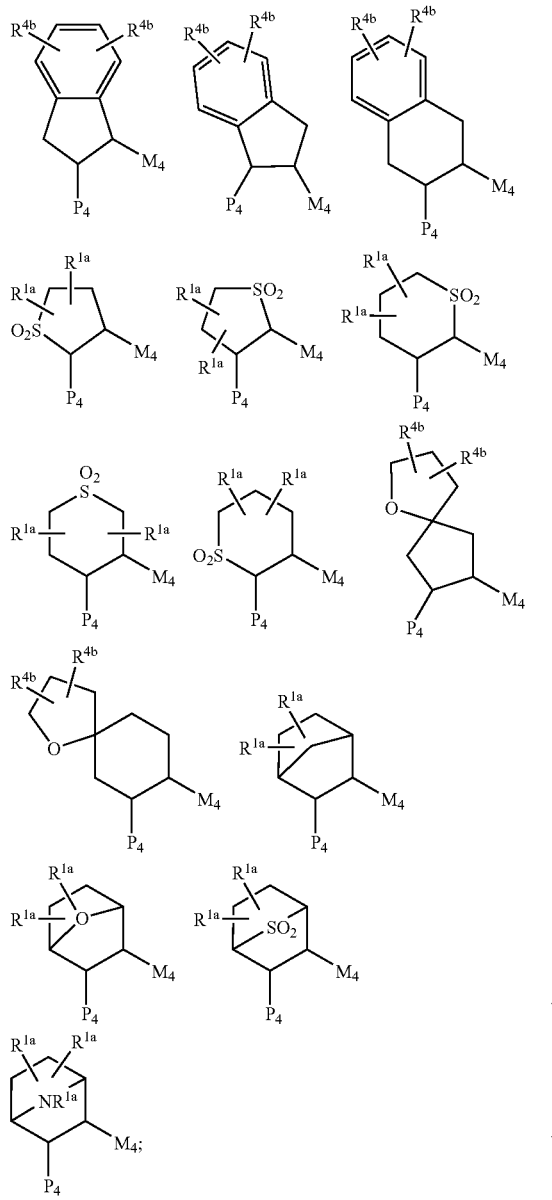

J is selected from O, S, NH, and $NR^{1a}$;

$P_4$ is -$G_1$-G;

$M_4$ is -Z-A-B;

G is selected from:

2-amido-4-methoxy-phenyl; 2-amido-phenyl; 2-aminomethyl-3-fluoro-phenyl; 2-aminomethyl-4-fluoro-phenyl; 2-aminomethyl-5-fluoro-phenyl; 2-aminomethyl-6-fluoro-phenyl; 2-aminomethyl-phenyl; 2-aminopyrid-4-yl; 2-aminosulfonyl-4-methoxy-phenyl; 2-aminosulfonyl-phenyl; 3-amido-phenyl; 3-amino-4-chloro-phenyl; 3-aminomethyl-phenyl; 3-chloro-phenyl; 4-chloro-phenyl; 4-methoxy-phenyl; 5-chloro-pyrid-2-yl; 5-chloro-thien-2-yl; 6-amino-5-chloro-pyrid-2-yl; 6-amino-pyrid-2-yl; 5-chloro-pyrimidin-3-yl; 6-chloro-pyridazin-3-yl; 2-aminomethyl-4-chloro-phenyl; 2-aminosulfonyl-4-chloro-phenyl; 2-amido-4-chloro-phenyl; 4-chloro-2-methylsulfonyl-phenyl;

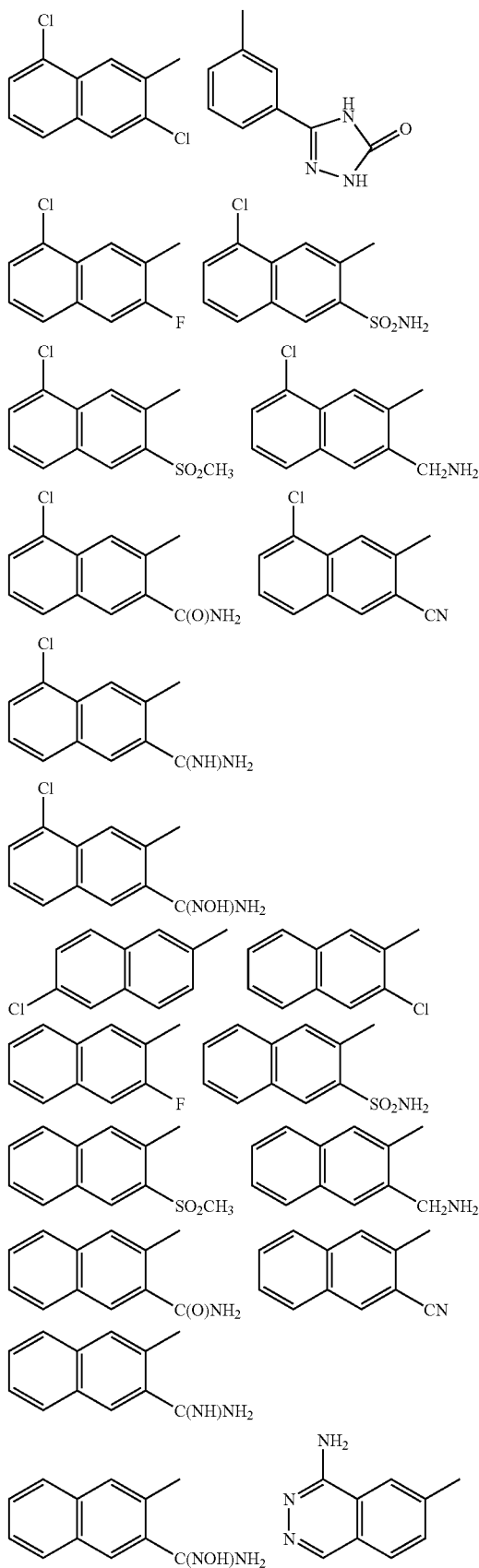

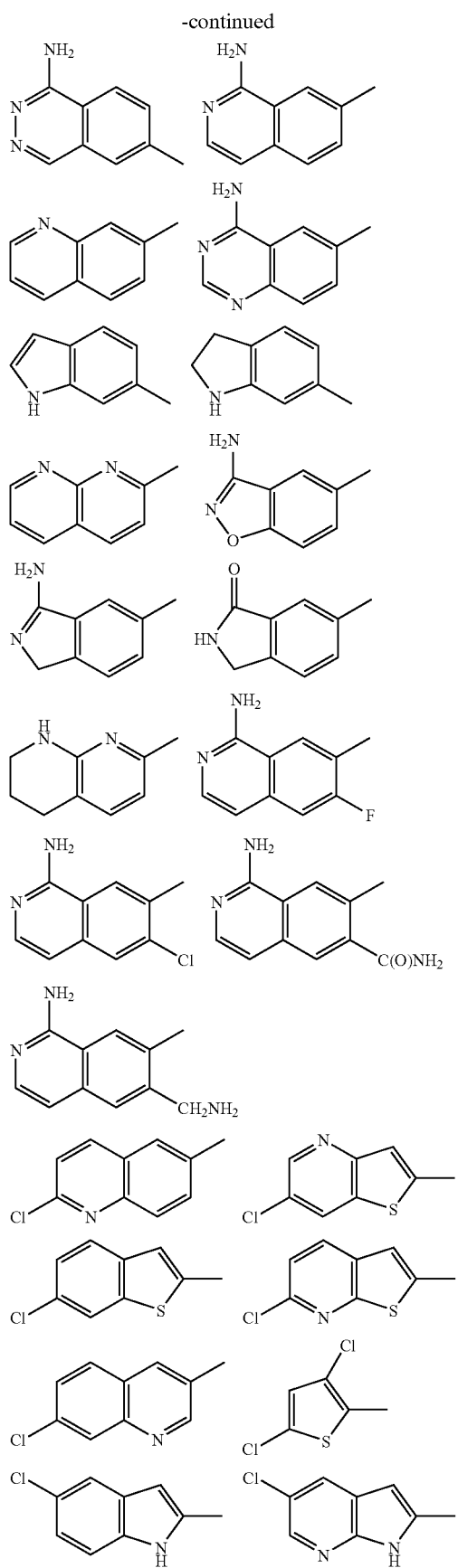
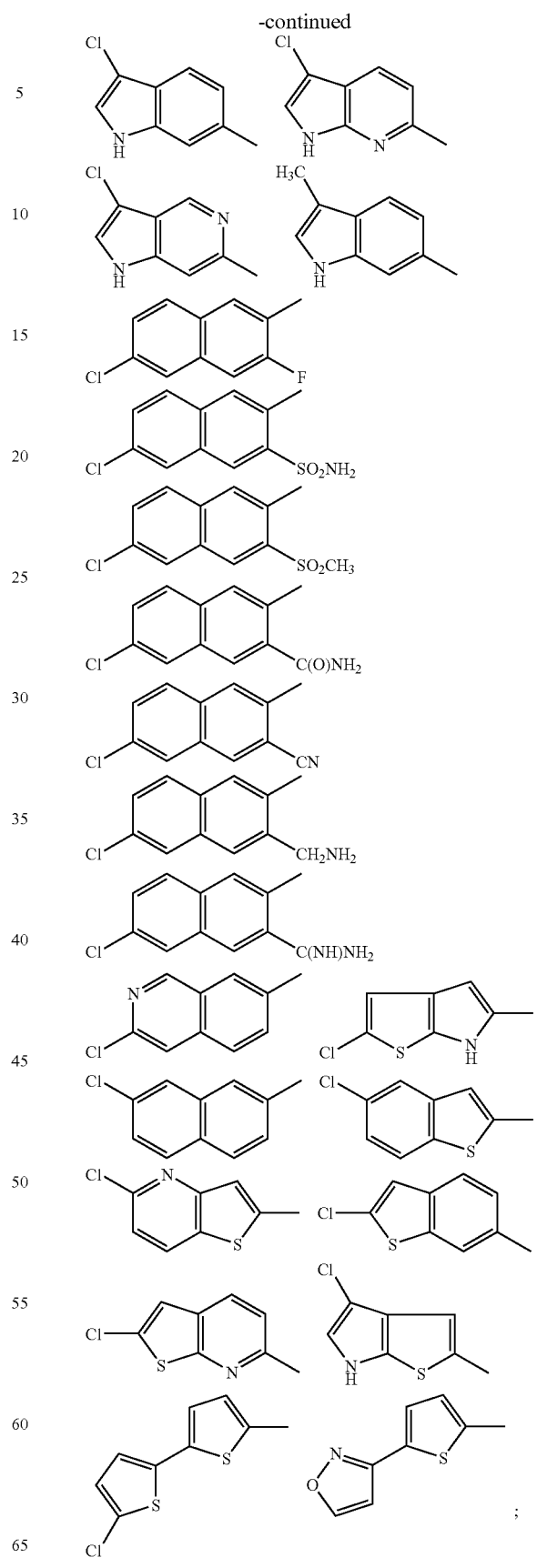

G₁ is absent or is selected from CH=CH, CH₂NH, NHCH₂, CH₂C(O), C(O)CH₂, C(O)NH, NHC(O), NHC(O)NH, CH₂S(O)₂, S(O)₂(CH₂), SO₂NH, and NHSO₂, provided that G₁ does not form a N—S, NCH₂N, NCH₂O, or NCH₂S bond with either group to which it is attached;

A is selected from the group: cyclohexyl, indolinyl, piperidinyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

Y is selected from C(CH₃)₂, C(CH₂CH₃)₂, cyclopropyl, cyclobutyl, cyclopentyl, 2-cyclopentanonyl, cyclohexyl, 2-cyclohexanonyl, pyrrolidinyl (attached to A and R$^{4a}$ at the 2-position), pyrrolidinyl (attached to A and R$^{4a}$ at the 3-position), 2-pyrrolidinonyl (attached to A and R$^{4a}$ at the 3-position), piperidinyl (attached to A and R$^{4a}$ at the 4-position), 4-piperdinonyl (attached to A and R$^{4a}$ at the 3-position), tetrahydrofuranyl, and tetrahydropyranyl (attached to A and R$^{4a}$ at the 4-position);

R$^{1a}$, at each occurrence, is selected from H, CH₃, CH₂CH₃, CH₂CH₂CH₃, CH₂F, CH₂Cl, Br, CH₂Br, —CN, CH₂CN, CF₃, CH₂CF₃, OCH₃, CH₂OH, C(CH₃)₂OH, CH₂OCH₃, CH₂CH₂OCH₃, NH₂, CH₂NH₂, NHCH₃, CH₂NHCH₃, N(CH₃)₂, CH₂N(CH₃)₂, CO₂H, CH₂CO₂H, CH₂CH₂CO₂H, COCH₃, CO₂CH₃, CH₂CO₂CH₃, SCH₃, CH₂SCH₃, S(O)CH₃, CH₂S(O)CH₃, S(O)₂CH₃, CH₂S(O)₂CH₃, C(O)NH₂, CH₂C(O)NH₂, SO₂NH₂, CH₂SO₂NH₂, NHSO₂CH₃, CH₂NHSO₂CH₃, COCH₂C(CH₃)₃, COCH₂OH, COCH₂OCH₃, COC(CH₃)₂OH, COC(CH₃)₂CH₂OH, COC(CH₃)₂CH₂OCH₃, C(O)OCH₂CH₂OCH₃, COCF₃, CO₂CH₂CH₃, CO₂CH(CH₃)₂, CO₂C(CH₃)₃, CH₂CH₂CO₂CH₂CH₃, CONH(CH₃), CONH(CH₂CH₃), CONHC(CH₃)₃, CON(CH₃)₂, CON(CH₃)(CH₂CH₃), CON(CH₃)CH(CH₃)₂, CH₂CON(CH₃)₂, C(O)-phenyl, C(O)-cyclopropyl, C(O)-cyclobutyl, C(O)-cyclopentyl, pyridin-2-yl, pyridin-3-yl, pyridin-4-yl, pyridin-2-yl-N-oxide, pyridin-3-yl-N-oxide, pyridin-4-yl-N-oxide, imidazol-1-yl, CH₂-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, CH₂-1,2,3,4-tetrazol-1-yl, and CH₂-1,2,3,4-tetrazol-5-yl, provided that R$^{1a}$ forms other than an N-halo, N—S, or N—CN bond;

alternatively, R$^{1a}$ is selected from:

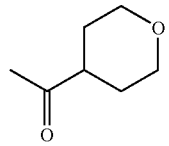 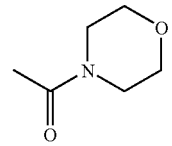
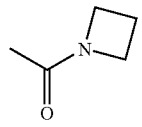 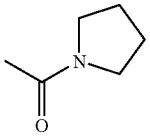
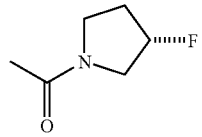 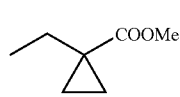

-continued

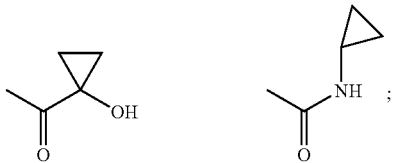

R², at each occurrence, is selected from H, CH₃, CH₂CH₃, CH₂CH₂CH₃, CH(CH₃)₂, phenyl substituted with 0–1 R$^{4b}$, benzyl substituted with 0–1 R$^{4b}$, and 5 membered aromatic heterocycle substituted with 0–1 R$^{4b}$ and consisting of: carbon atoms and 1–4 heteroatoms selected from the group consisting of N, O, and S(O)$_p$;

R$^{2a}$, at each occurrence, is selected from H, CH₃, and CH₂CH₃;

alternatively, R² and R$^{2a}$, together with the nitrogen atom to which they are attached, combine to form a 3–6 membered saturated, partially saturated or unsaturated ring substituted with 0–1 R$^{4b}$ and consisting of: 0–1 additional heteroatoms selected from the group consisting of N, O, and S(O)$_p$;

R$^{2b}$, at each occurrence, is selected from OH, OCH₃, OCH₂CH₃, CH₃, and CH₂CH₃;

R$^{2c}$, at each occurrence, is selected from OH, OCH₃, OCH₂CH₃, CH₃, and CH₂CH₃;

R$^{2d}$, at each occurrence, is selected from H, R$^{4c}$, C$_{1-4}$ alkyl substituted with 0–2 R$^{4c}$, C$_{3-6}$ cycloalkyl substituted with 0–2 R$^{4c}$, phenyl substituted with 0–2 R$^{4c}$, and 5–6 membered aromatic heterocycle substituted with 0–2 R$^{4c}$ consisting of: carbon atoms and 1–4 heteroatoms selected from the group consisting of N, O, and S(O)$_p$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

R$^{2e}$, at each occurrence, is selected from H, R$^{4c}$, C$_{1-4}$ alkyl substituted with 0–2 R$^{4c}$, C$_{3-6}$ cycloalkyl substituted with 0–2 R$^{4c}$, phenyl substituted with 0–2 R$^{4c}$, and 5–6 membered aromatic heterocycle substituted with 0–2 R$^{4c}$ and consisting of: carbon atoms and 1–4 heteroatoms selected from the group consisting of N, O, and S(O)$_p$, provided that R$^{2e}$ forms other than a C(O)-halo or C(O)—S(O)$_p$ moiety;

R$^{4a}$ is selected from —(CH₂)$_r$-5–6 membered carbocycle substituted with 0–3 R$^{4c}$, —(CH₂)$_r$-5–6 membered heterocycle substituted with 0–3 R$^{4c}$ and consisting of: carbon atoms and 1–4 heteroatoms selected from the group consisting of N, O, and S(O)$_p$, (CH₂)$_r$NR$^{2d}$R$^{2d}$, (CH₂)$_r$N(→O)R$^{2d}$R$^{2d}$, (CH₂)$_r$OR$^{2d}$, (CH₂)$_r$—C(O)NR$^{2d}$R$^{2d}$, (CH₂)$_r$—NR$^{2d}$C(O)R$^{2e}$, (CH₂)$_r$—C(O)R$^{2e}$, (CH₂)$_r$—NR$^{2d}$C(O)NR$^{2d}$R$^{2d}$, (CH₂)$_r$—NR$^{2d}$C(O)OR$^{2d}$, (CH₂)$_r$—NR$^{2d}$SO₂R$^{2d}$, and (CH₂)$_r$—S(O)$_p$R$^{2d}$, provided that S(O)$_p$R$^{2d}$ forms other than S(O)₂H or S(O)H;

R$^{4b}$, at each occurrence, is selected from H, =O, OR³, CH₂OR³, F, Cl, CH₃, CH₂CH₃, NR³R$^{3a}$, CH₂NR³R$^{3a}$, C(O)R³, C(O)OR$^{3c}$, NR³C(O)R$^{3a}$, C(O)NR³R$^{3a}$, SO₂NR³R$^{3a}$, NR³SO₂-phenyl, S(O)₂CH₃, S(O)₂-phenyl, and CF₃;

R$^{4c}$, at each occurrence, is selected from =O, OH, OCH₃, OCH₂CH₃, OCH₂CH₂CH₃, OCH(CH₃)₂, CH₃, CH₂CH₃, CH₂CH₂CH₃, CH(CH₃)₂, C$_{2-3}$ alkenyl, C$_{2-3}$ alkynyl, CH₂OH, CH₂OCH₃, CH₂OCH₂CH₃, CH₂OCH₂CH₂CH₃, CH₂OCH(CH₃)₂, F, Br, Cl, CF₃, NR²R$^{2a}$, CH₂NR²R$^{2a}$, N(→O)R²R$^{2a}$, CH₂N(→O)R²R$^{2a}$, C(O)R$^{2c}$, CH₂C(O)R$^{2c}$, NR²C(O)R$^{2b}$, CH₂NR²C(O)R$^{2b}$, C(O)NR²R$^{2a}$, CH₂C(O)NR²R²ᵃ, SO₂NR²R²ᵃ, CH₂SO₂NR²R²ᵃ, NR²SO₂R⁵ᵃ, CH₂NR²SO₂R⁵ᵃ, S(O)ₚR⁵ᵃ, CH₂S(O)ₚR⁵ᵃ, CF₃, cyclopropyl substituted with 0–1 R⁴ᵇ, cyclobutyl substituted with 0–1 R⁴ᵇ, cyclopentyl substituted with 0–1 R⁴ᵇ, phenyl substituted with 0–1 R⁴ᵇ, —CH₂-cyclopropyl substituted with 0–1 R⁴ᵇ, —CH₂-cyclobutyl substituted with 0–1 R⁴ᵇ, —CH₂-cyclopentyl substituted with 0–1 R⁴ᵇ, benzyl substituted with 0–2 R⁴ᵇ, 5–6 membered aromatic heterocycle substituted with 0–2 R⁴ᵇ and consisting of carbon atoms and from 1–4 heteroatoms selected from the group consisting of N, O, and S(O)ₚ, and (CH₂)5–6 membered aromatic heterocycle substituted with 0–2 R⁴ᵇ and consisting of carbon atoms and from 1–4 heteroatoms selected from the group consisting of N, O, and S(O)ₚ;

R⁵, at each occurrence, is selected from H, =O, CH₃, CH₂CH₃, OR³, CH₂OR³, F, Cl, NR³R³ᵃ, CH₂NR³R³ᵃ, C(O)R³, C(O)OR³ᶜ, NR³C(O)R³ᵃ, C(O)NR³R³ᵃ, SO₂NR³R³ᵃ, NR³SO₂—C₁₋₄ alkyl, NR³SO₂-phenyl, S(O)₂—CH₃, S(O)₂-phenyl, CF₃, phenyl substituted with 0–2 R⁶, naphthyl substituted with 0–2 R⁶, and benzyl substituted with 0–2 R⁶; and, R⁶, at each occurrence, is selected from H, OH, OR², F, Cl, CH₃, CH₂CH₃, NR²R²ᵃ, CH₂NR²R²ᵃ, C(O)R²ᵇ, CH₂C(O)R²ᵇ, NR²C(O)R²ᵇ, and SO₂NR²R²ᵃ.

[13] In another preferred embodiment, the present invention provides a novel compound, wherein the compound is selected from:

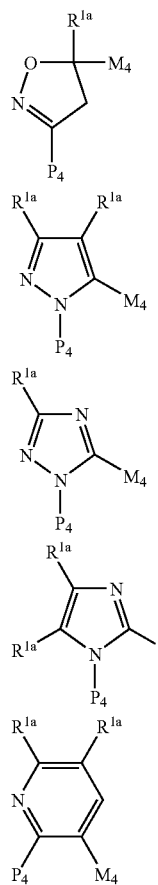
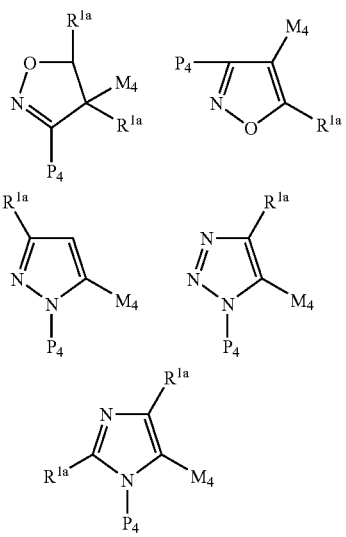

-G₁-G is selected from:

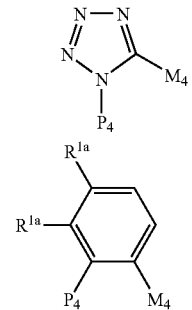

-continued
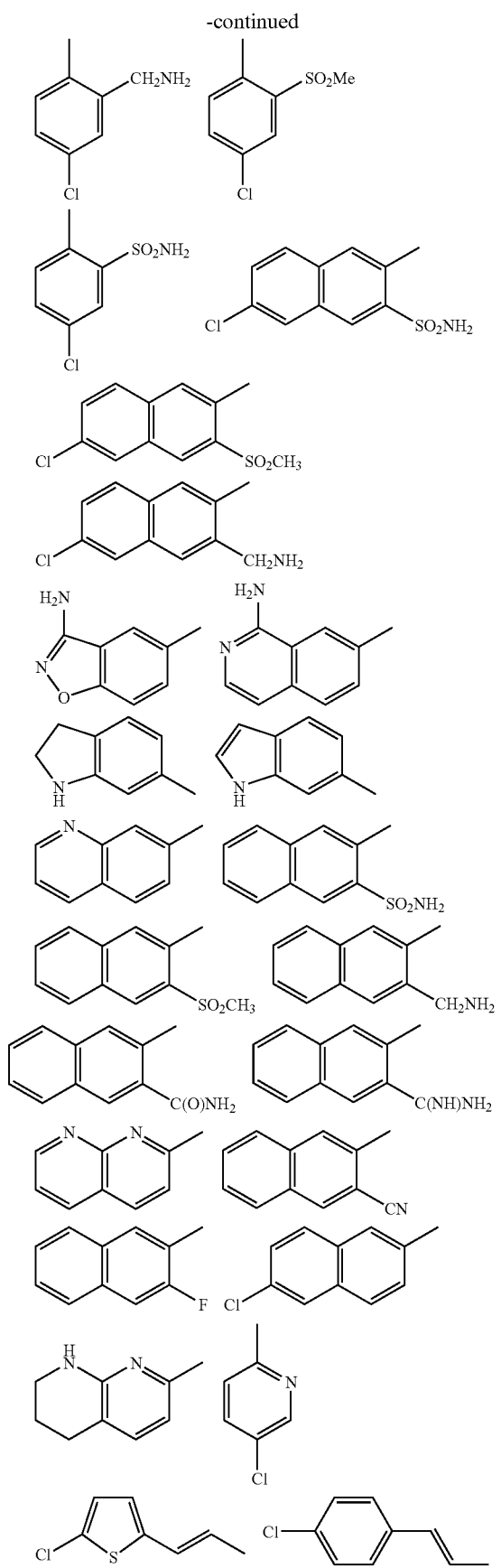
-continued
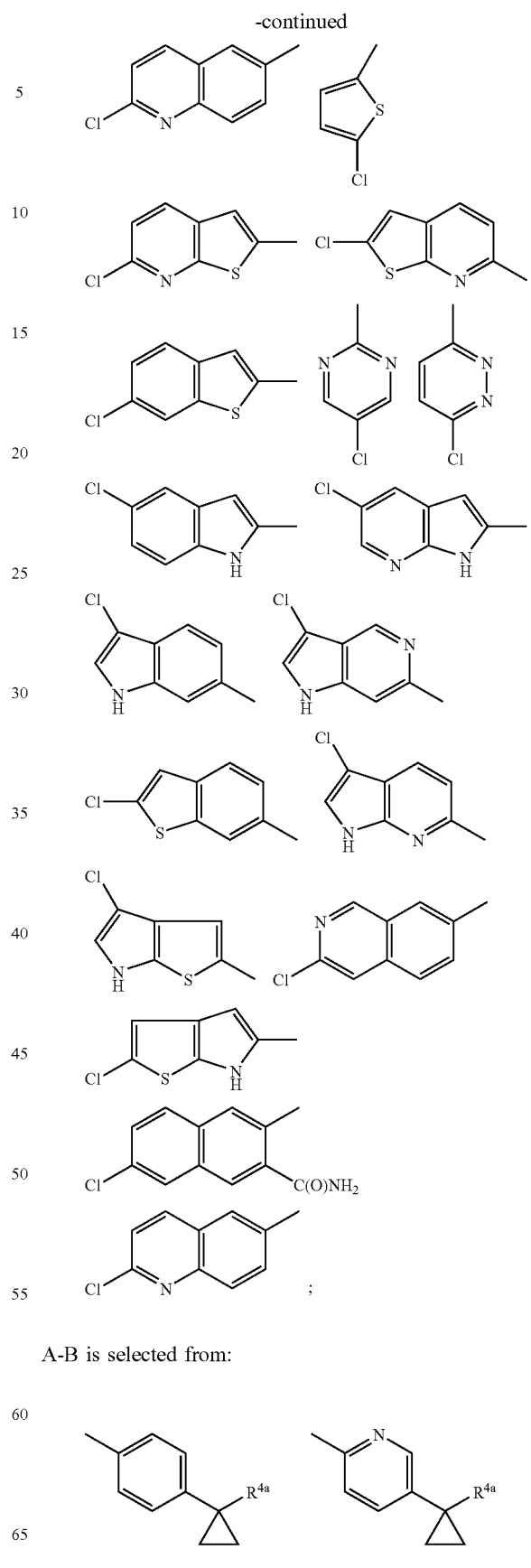
A-B is selected from:

-continued

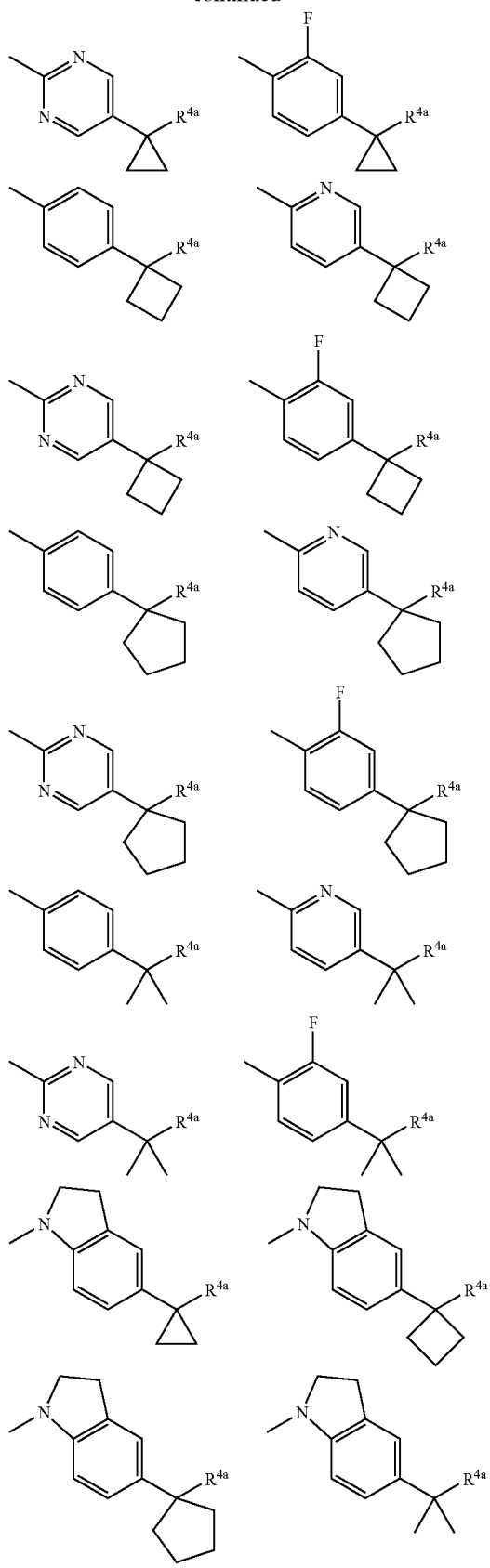

$R^{2d}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $C_{1-4}$ alkyl substituted with 0–1 $R^{4c}$, $C_{3-6}$ cycloalkyl substituted with 0–2 $R^{4c}$, phenyl, substituted with 0–2 $R^{4c}$, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from $NR^{2d}R^{2d}$, $CH_2NR^{2d}R^{2d}$, $CH_2CH_2NR^{2d}R^{2d}$, $N(\rightarrow O)R^{2d}R^{2d}$, $CH_2N(\rightarrow O)R^{2d}R^{2d}$, $CH_2OR^{2d}$, $C(O)R^{2e}$, $C(O)NR^{2d}R^{2d}$, $CH_2C(O)NR^{2d}R^{2d}$, $NR^{2d}C(O)R^{2e}$, $CH_2NR^{2d}C(O)R^{2e}$, $NR^{2d}C(O)NR^{2d}R^{2d}$, $CH_2NR^{2d}C(O)NR^{2d}R^{2d}$, $NR^{2d}C(O)OR^{2d}$, $CH_2NR^{2d}C(O)OR^{2d}$, $NR^{2d}SO_2R^{2d}$, $CH_2NR^{2d}SO_2R^{2d}$, $S(O)_pR^{2d}$, $CH_2S(O)_pR^{2d}$, 5–6 membered carbocycle substituted with 0–2 $R^{4c}$, —(CH_2)-5–6 membered carbocycle substituted with 0–2 $R^{4c}$, —(CH_2)_2-5–6 membered carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, —(CH_2)-5–6 membered heterocycle substituted with 0–2 $R^{4c}$ and consisting of: carbon atoms and 1–4 heteroatoms selected from the group consisting of N, O, and $S(O)_p$, and —(CH_2)_2-5–6 membered heterocycle substituted with 0–2 $R^{4c}$ and consisting of: carbon atoms and 1–4 heteroatoms selected from the group consisting of N, O, and $S(O)_p$ provided that $S(O)_pR^{2d}$ forms other than $S(O)_2H$ or $S(O)H$; and, $R^{4c}$ is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH=CH_2$, $CH\equiv CH$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, and $CH_2S(O)_pR^{5a}$.

[14] In another preferred embodiment, the present invention provides a novel compound, wherein the compound is selected from:

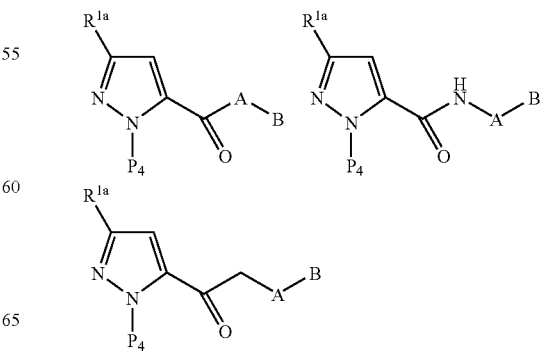

-continued
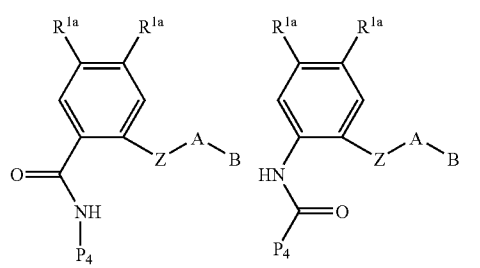
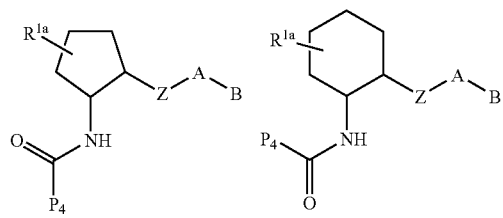
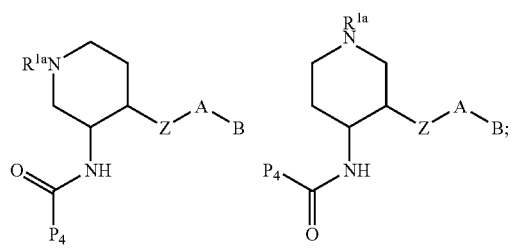
Z is selected from a NHCH$_2$, C(O)NH, NHC(O), and NHSO$_2$; and,
A-B is selected from:
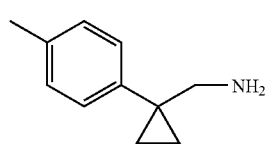
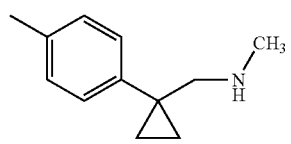
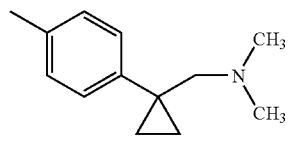
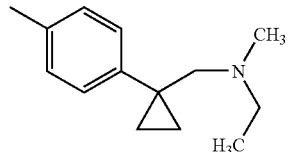
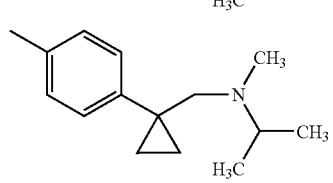
-continued
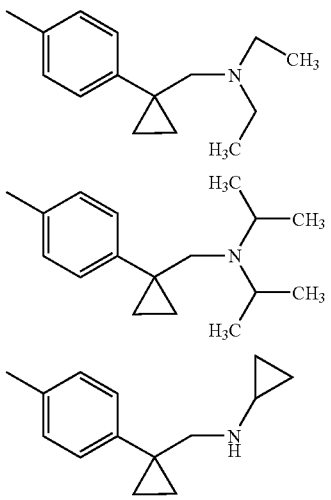
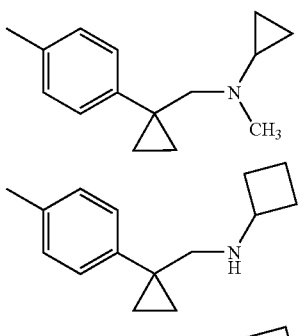
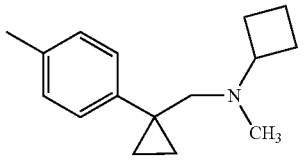
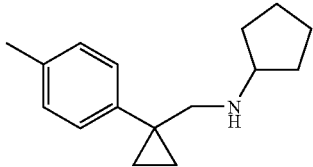
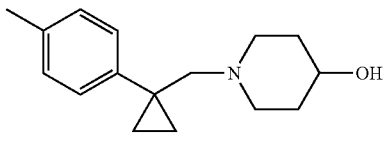
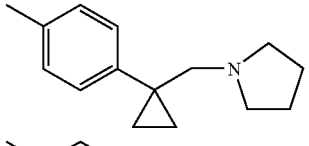
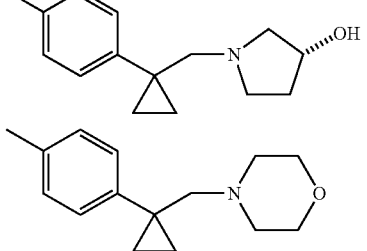

-continued
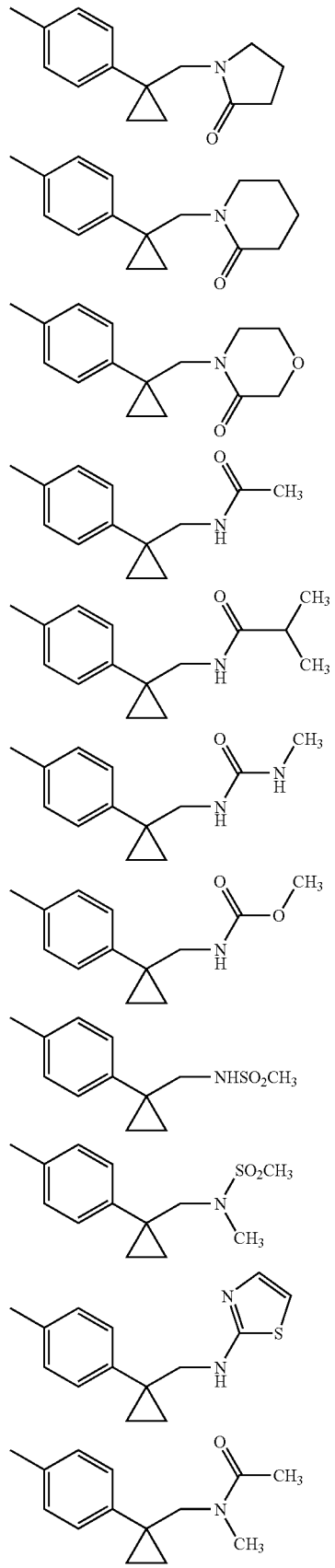
-continued
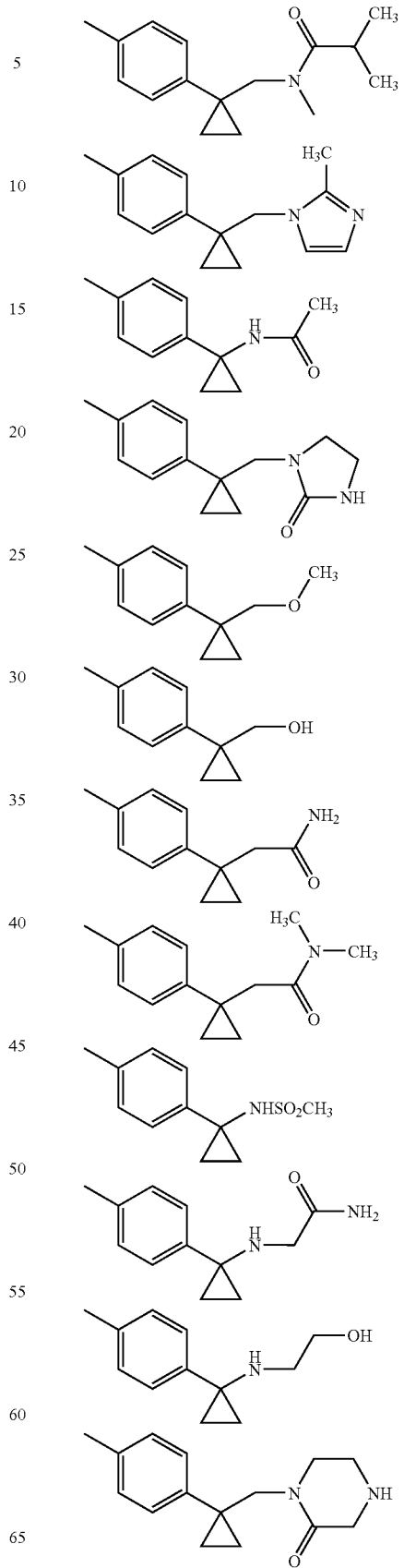

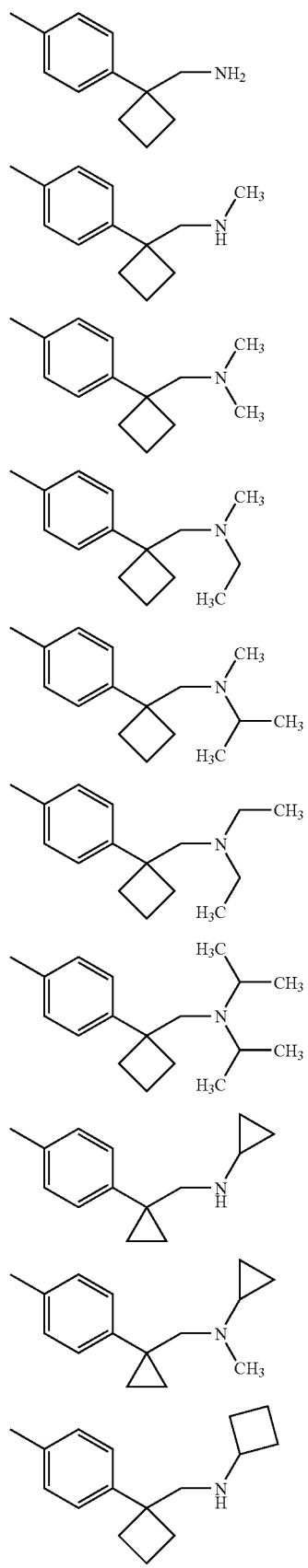
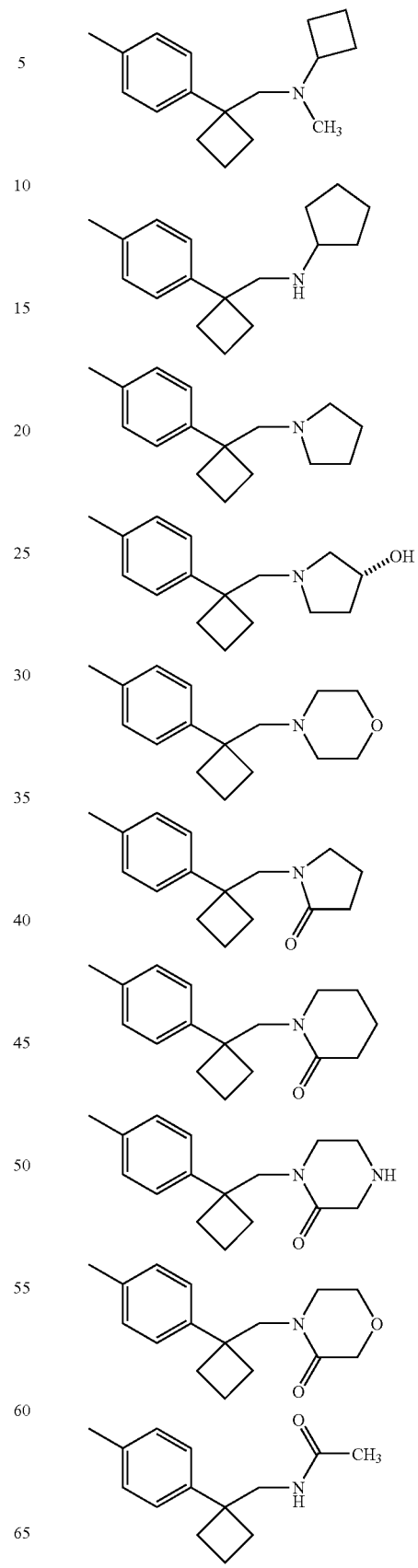

-continued
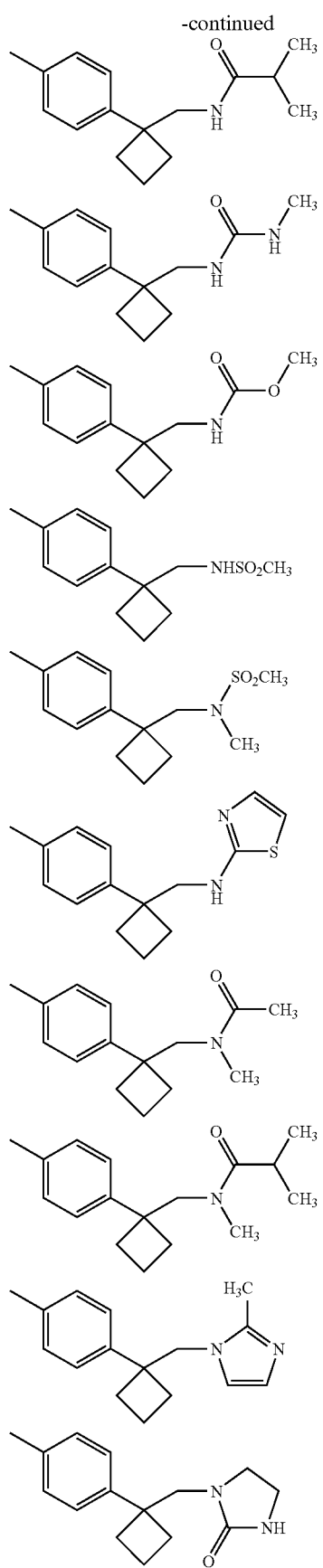
-continued
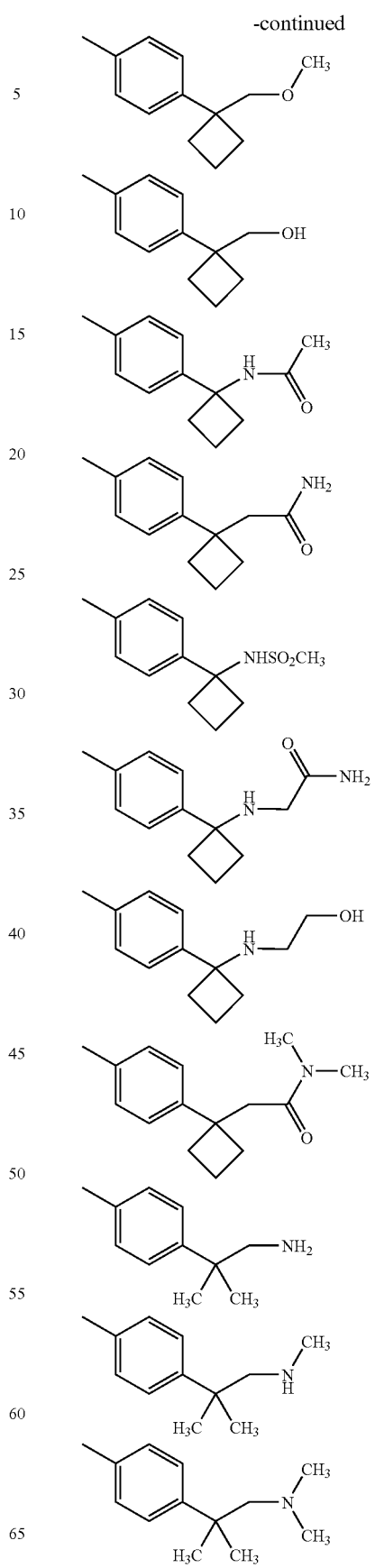

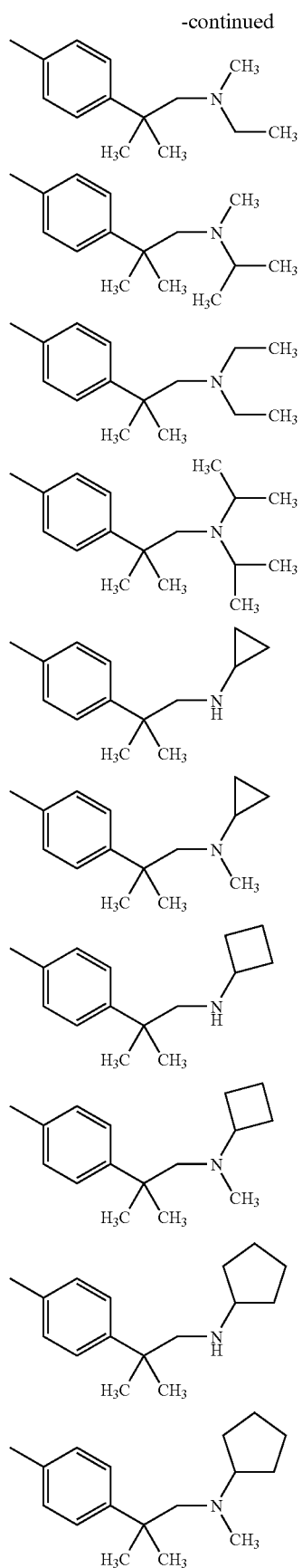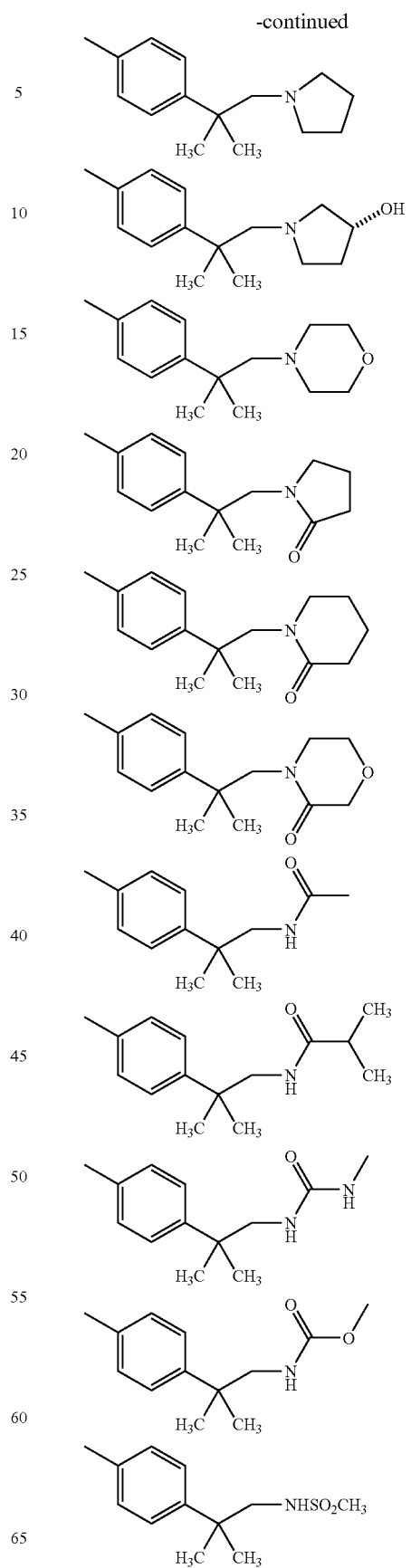

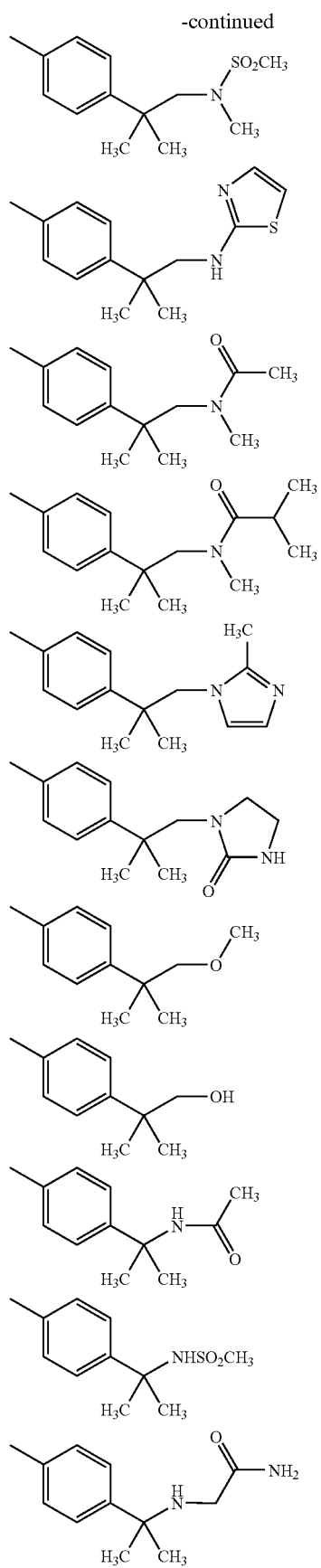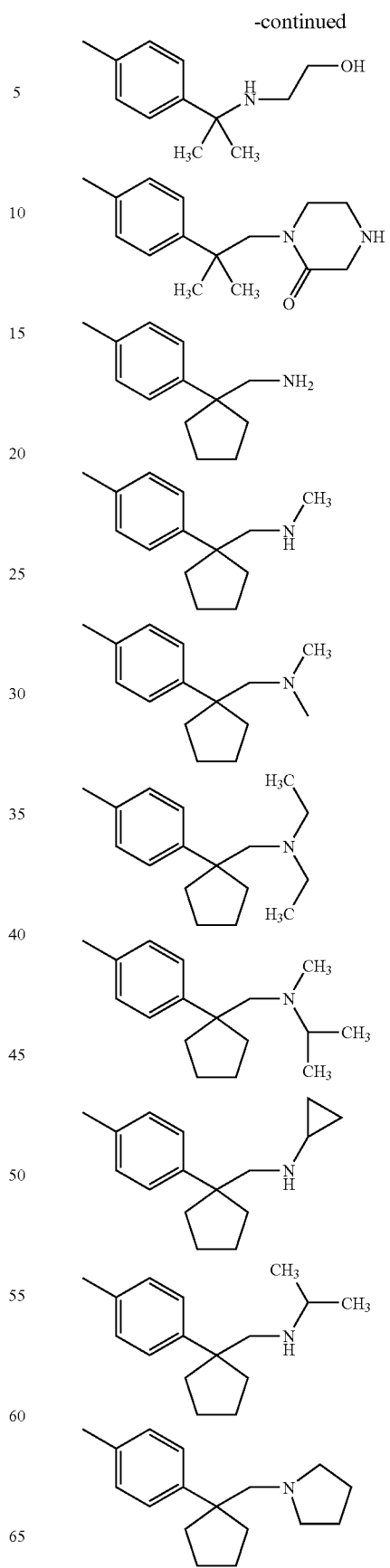

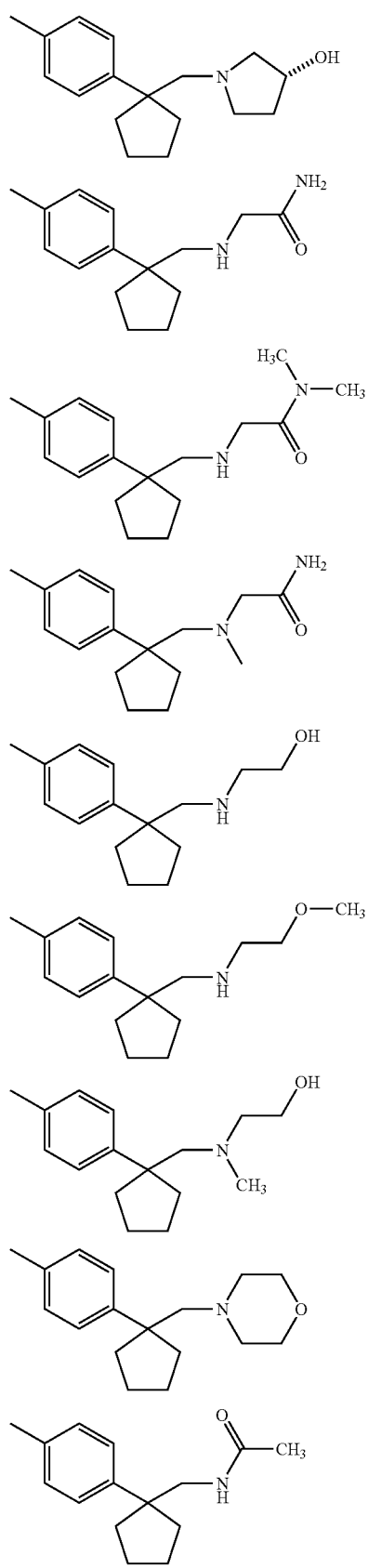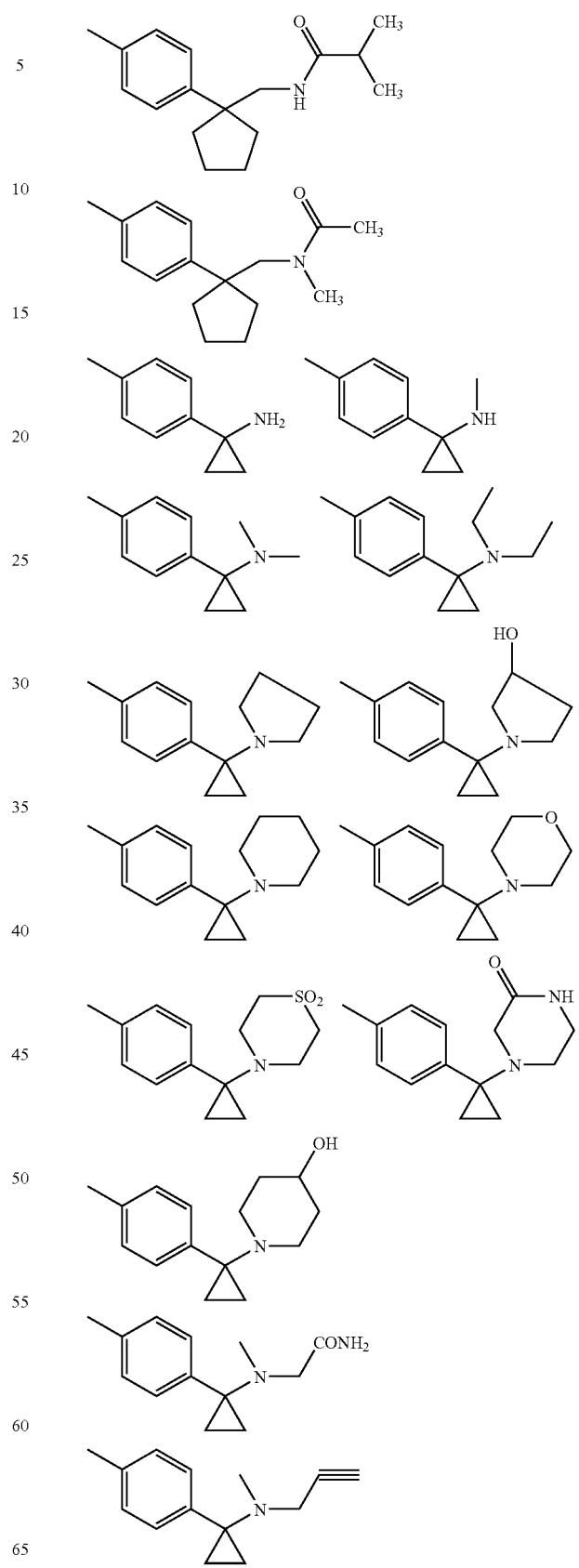

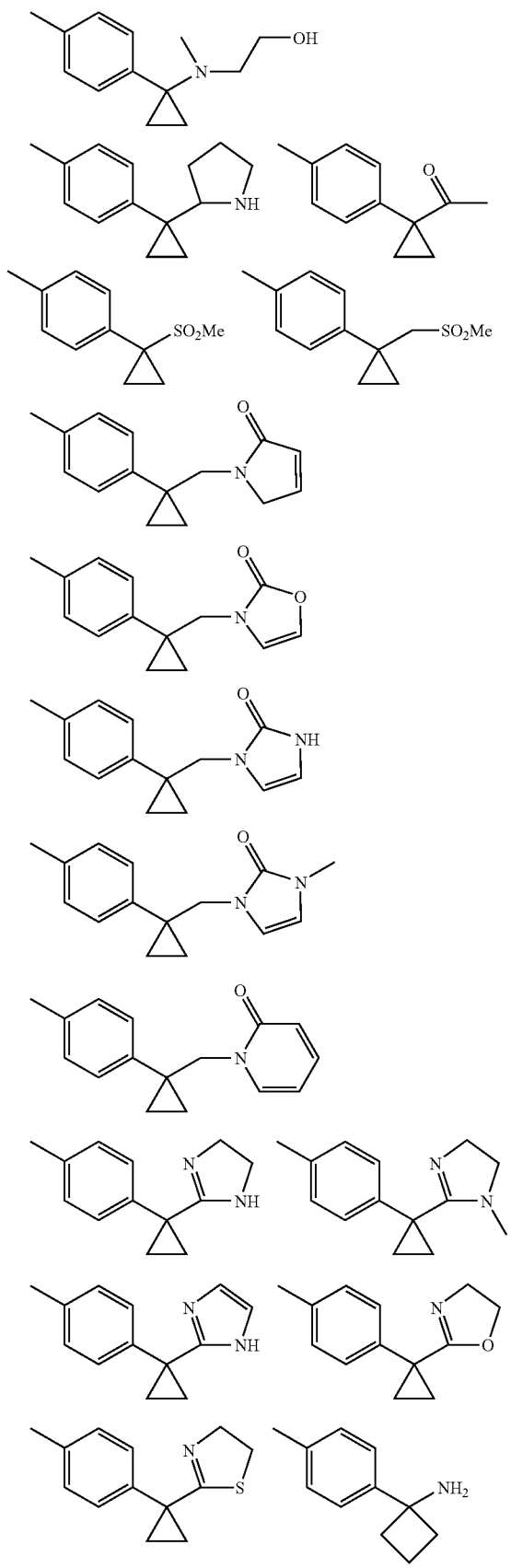
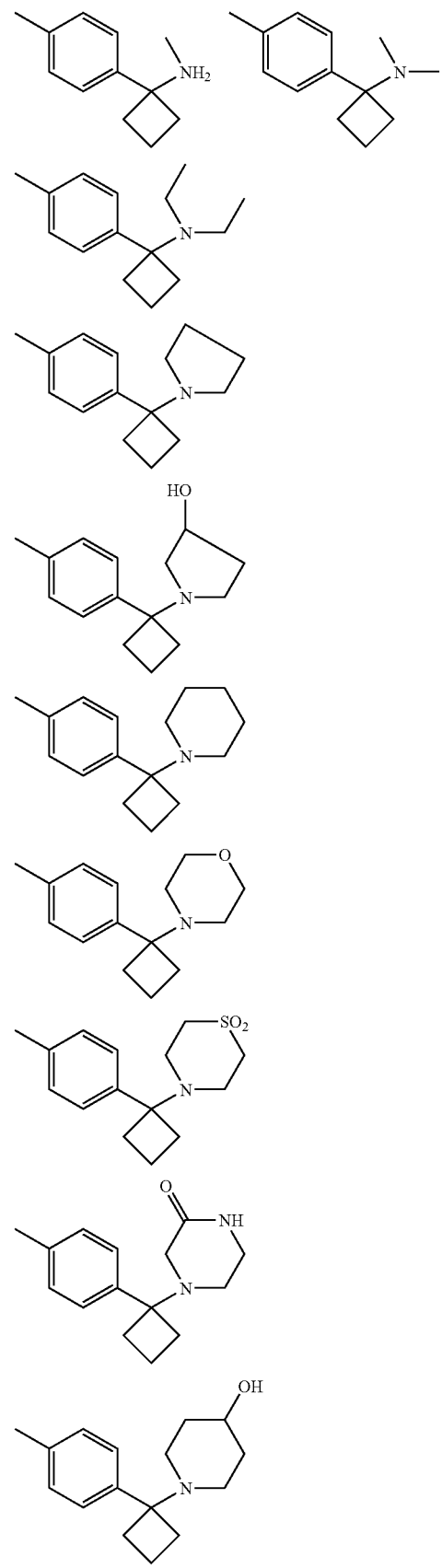

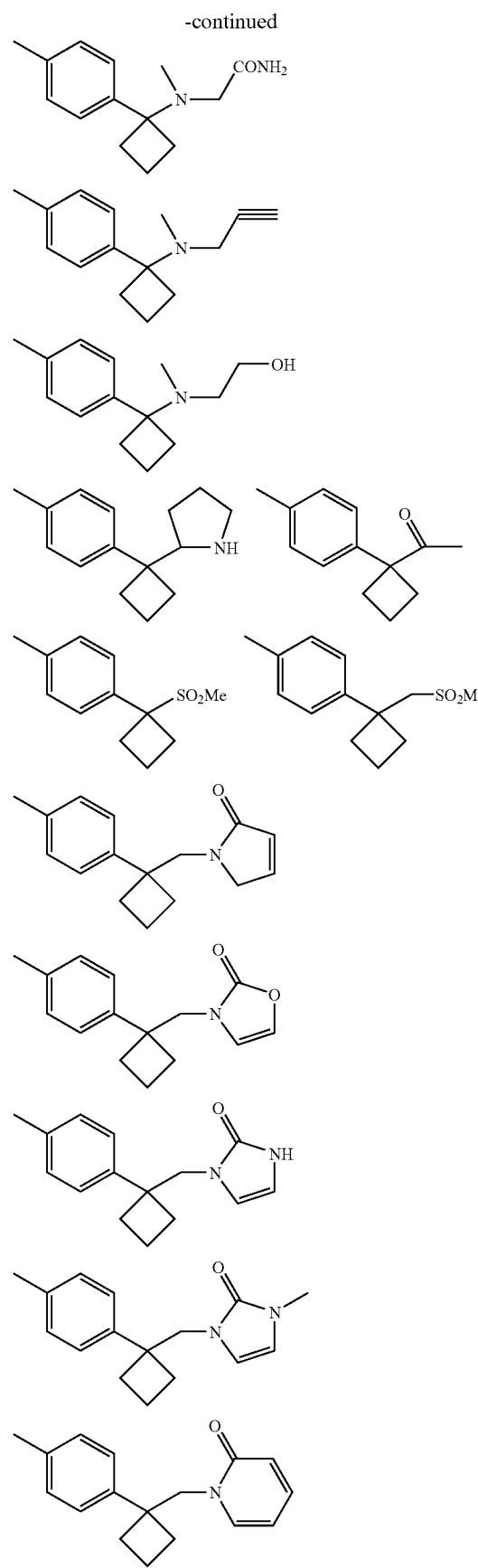
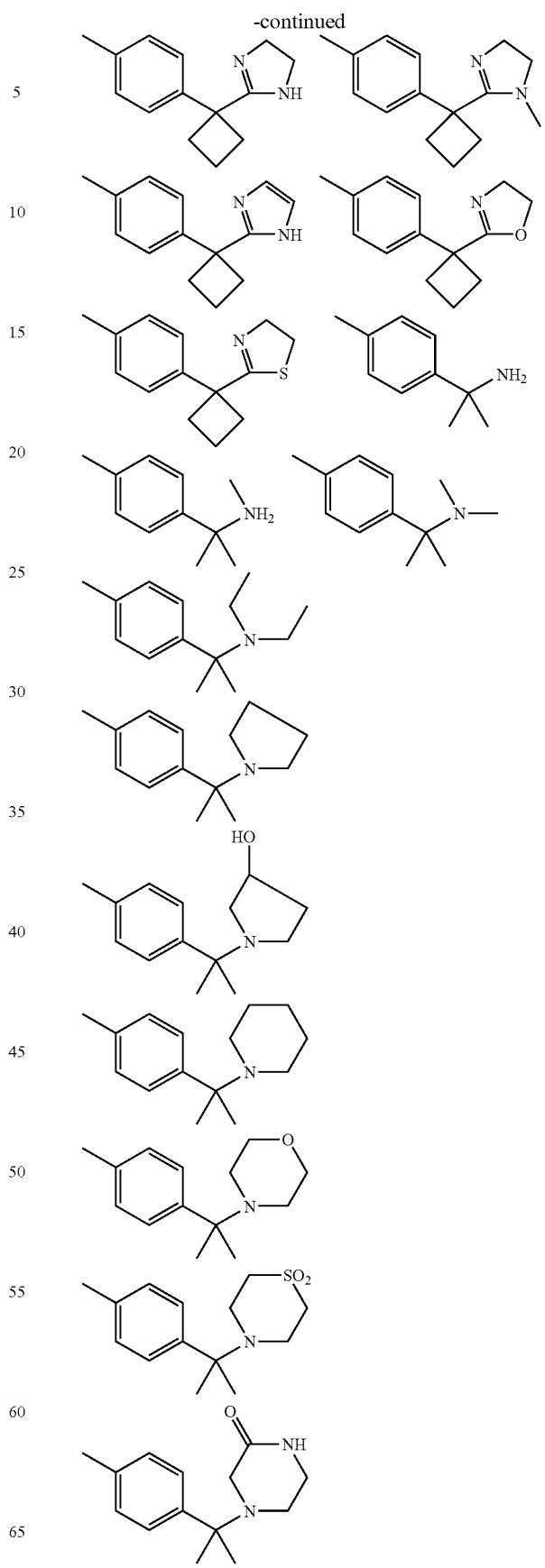

-continued
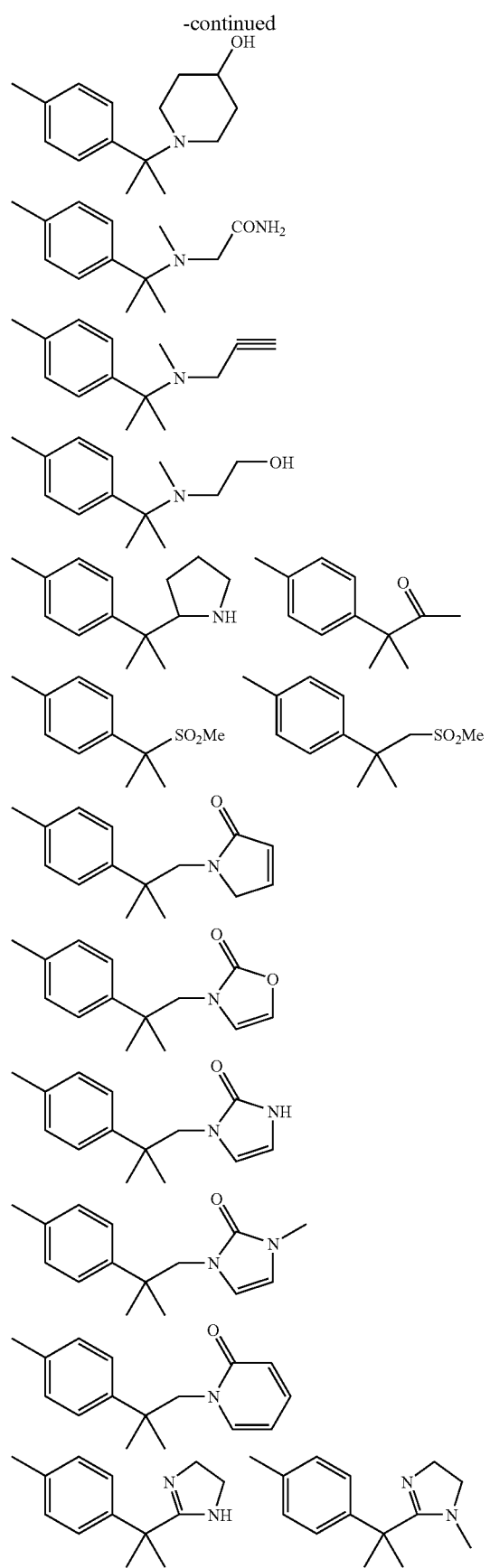
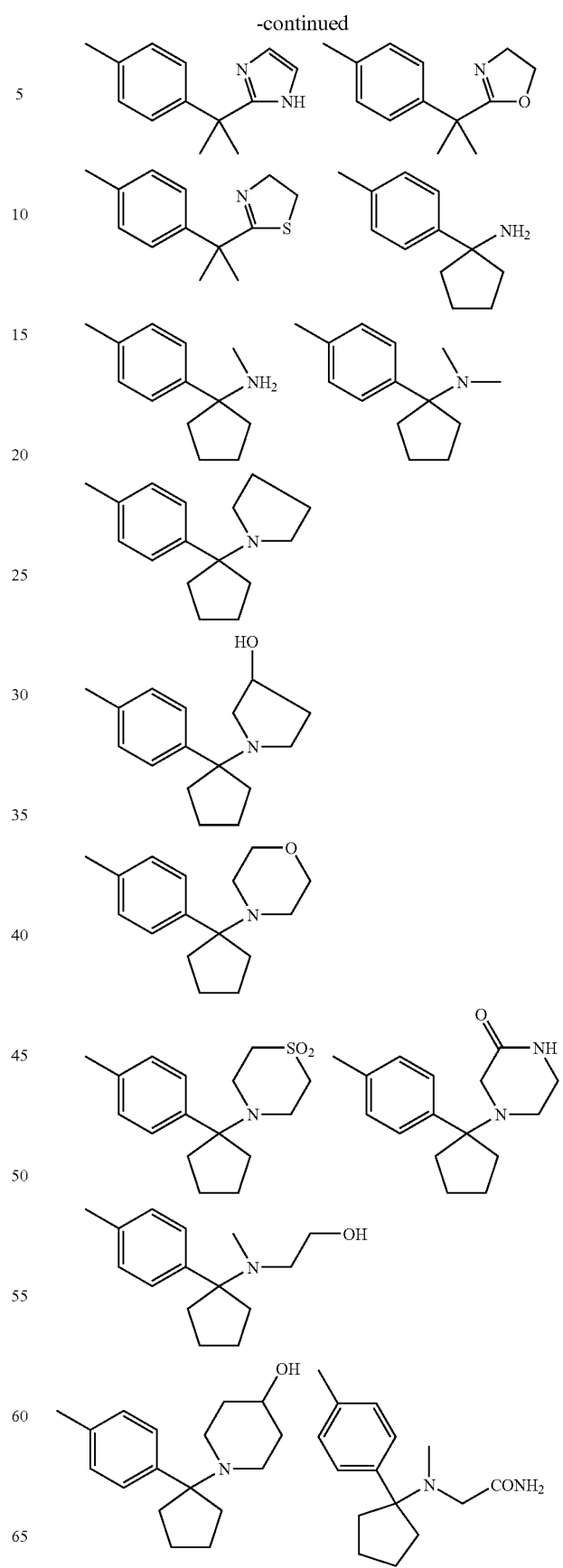

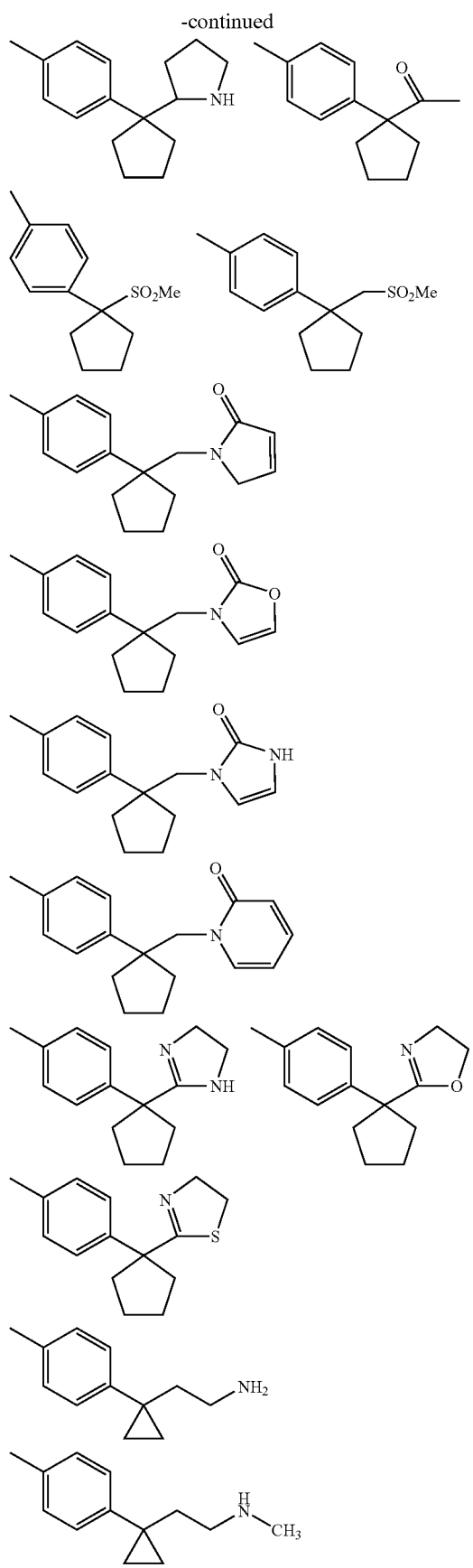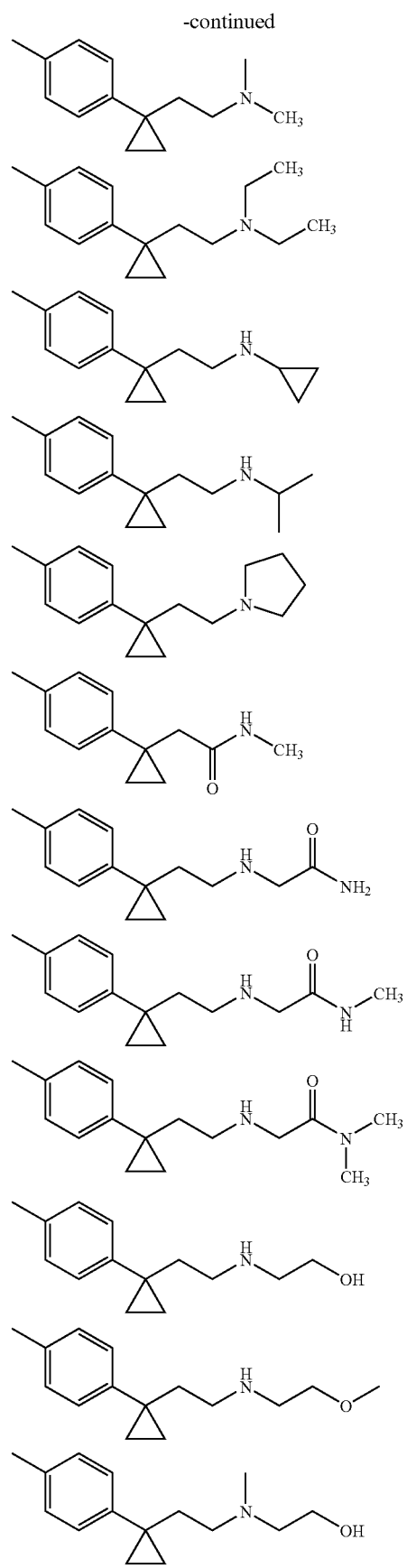

-continued
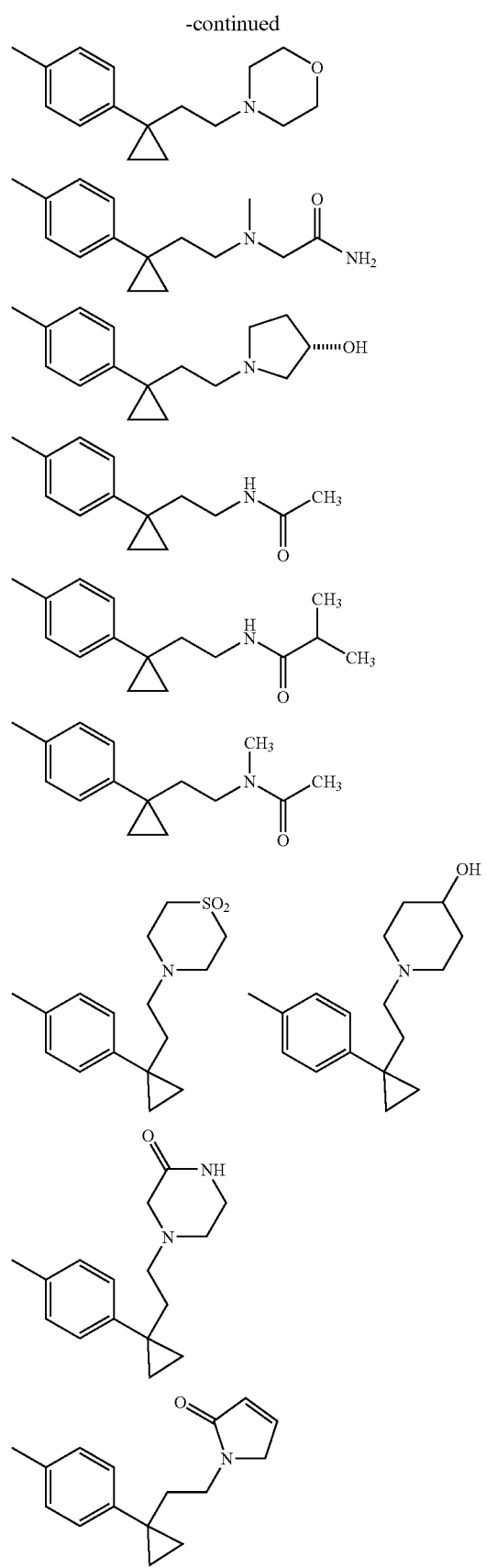
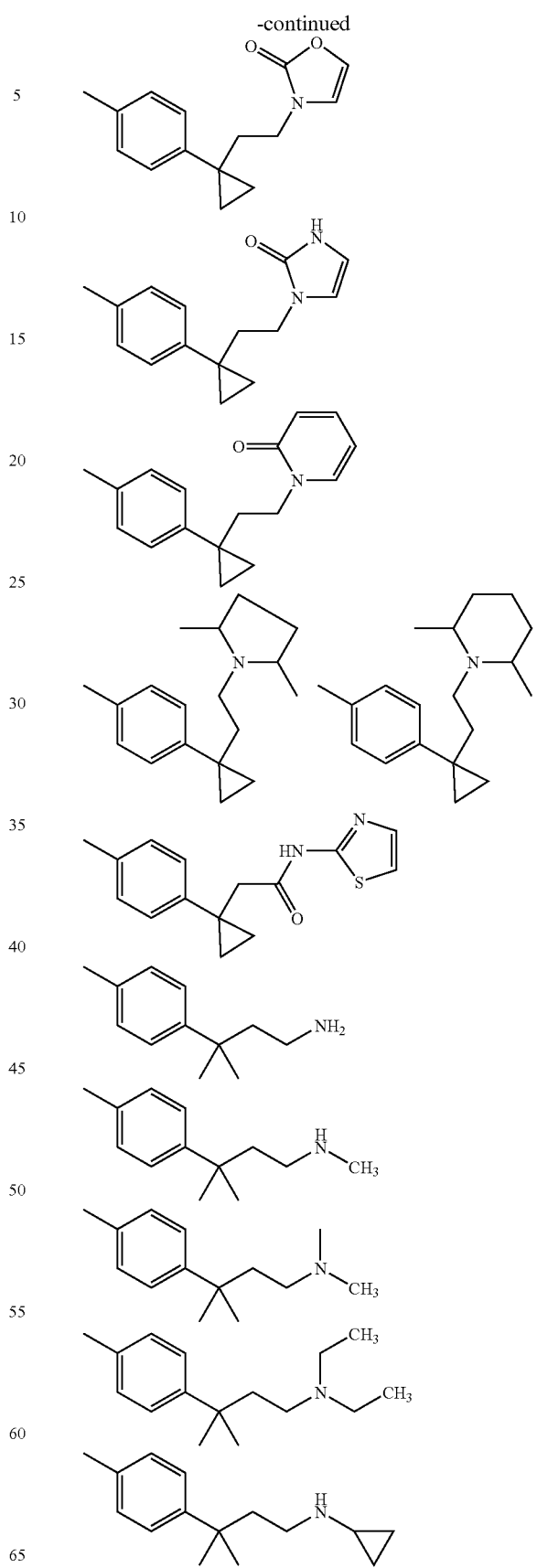

-continued
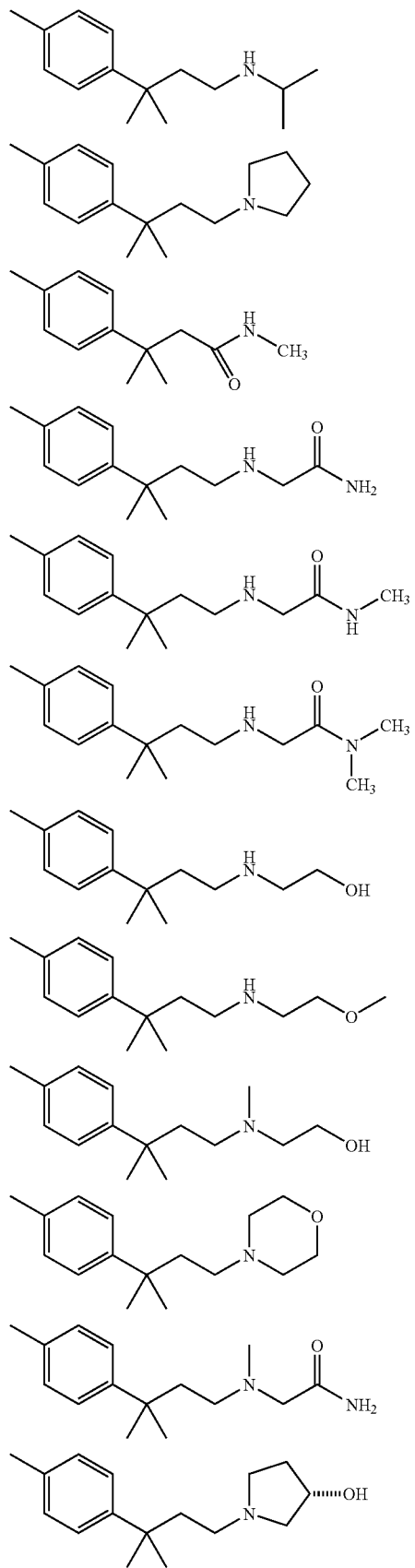
-continued
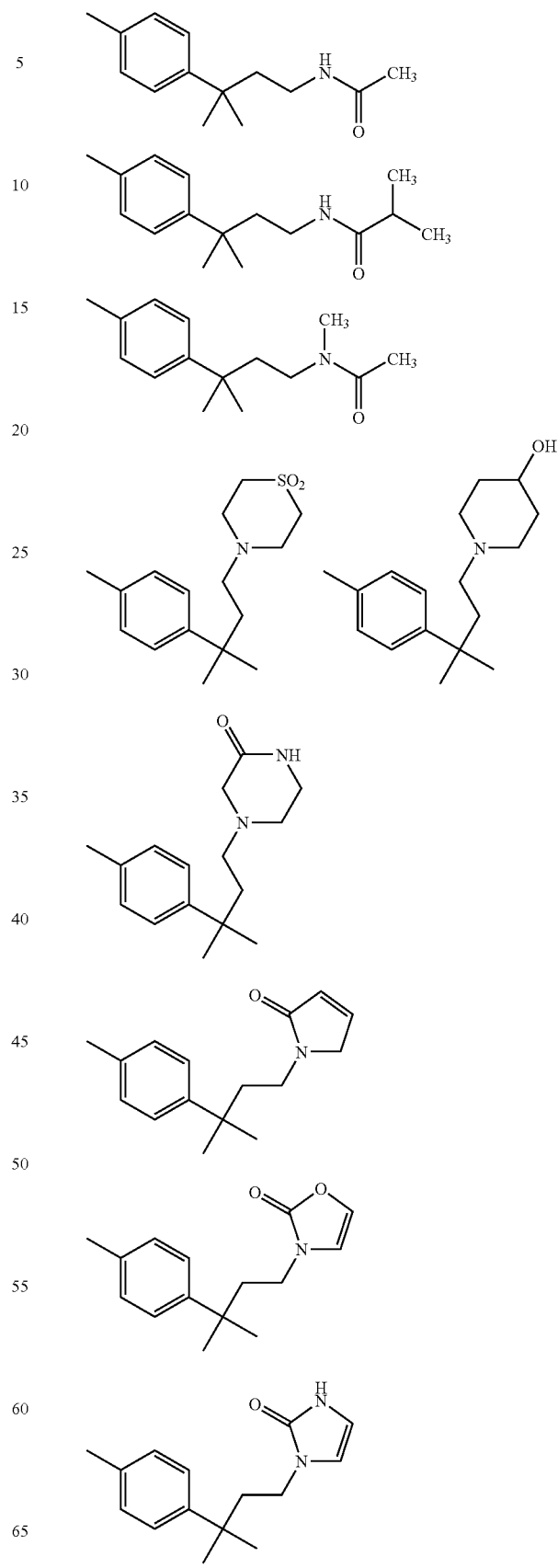

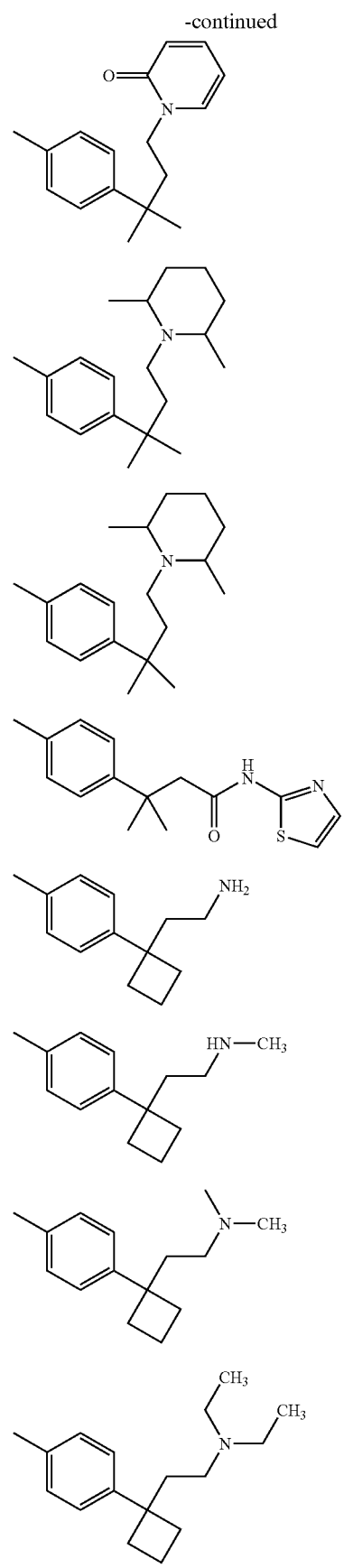
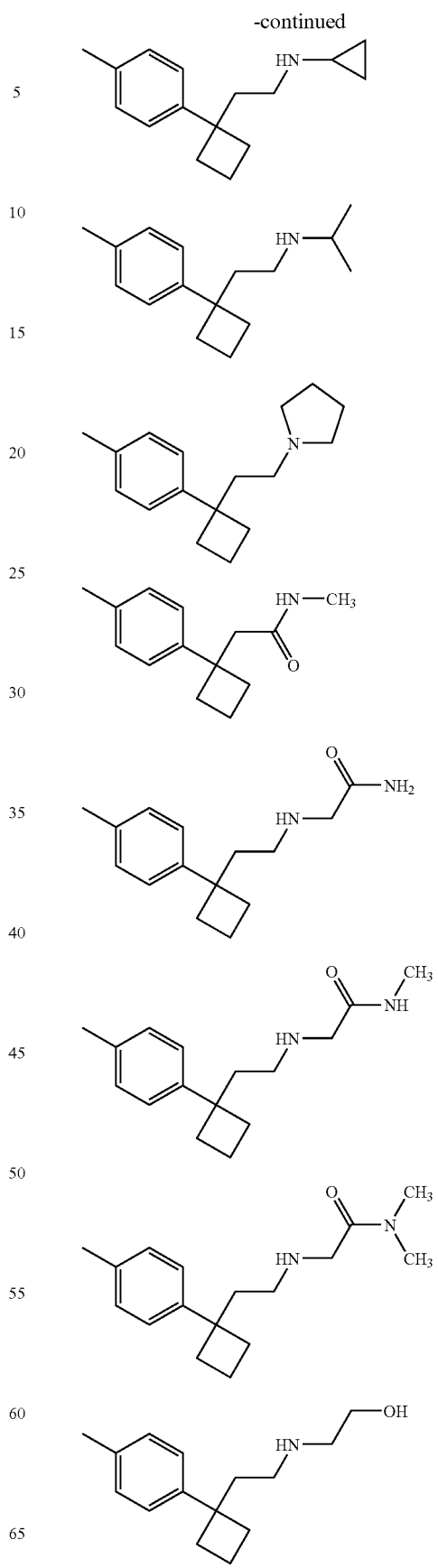

-continued
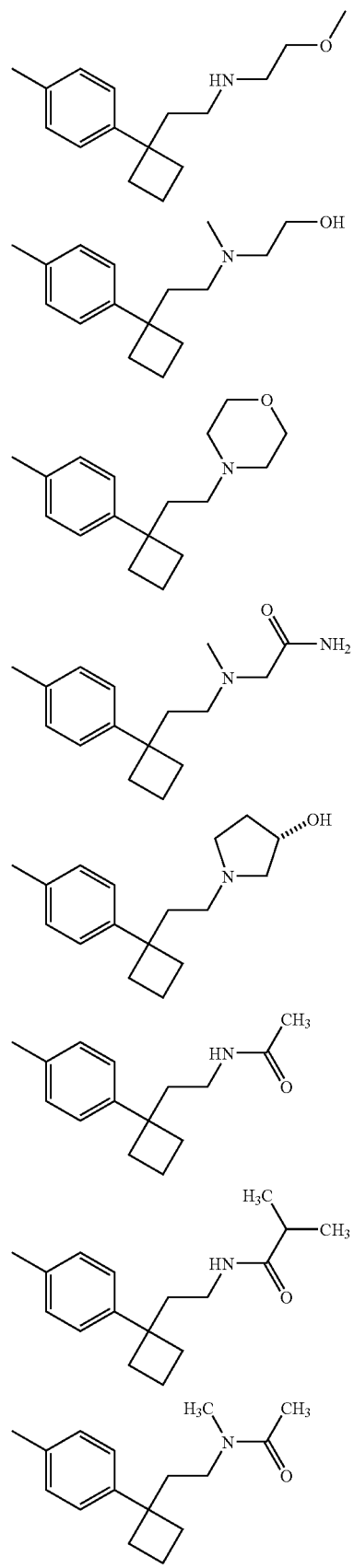
-continued
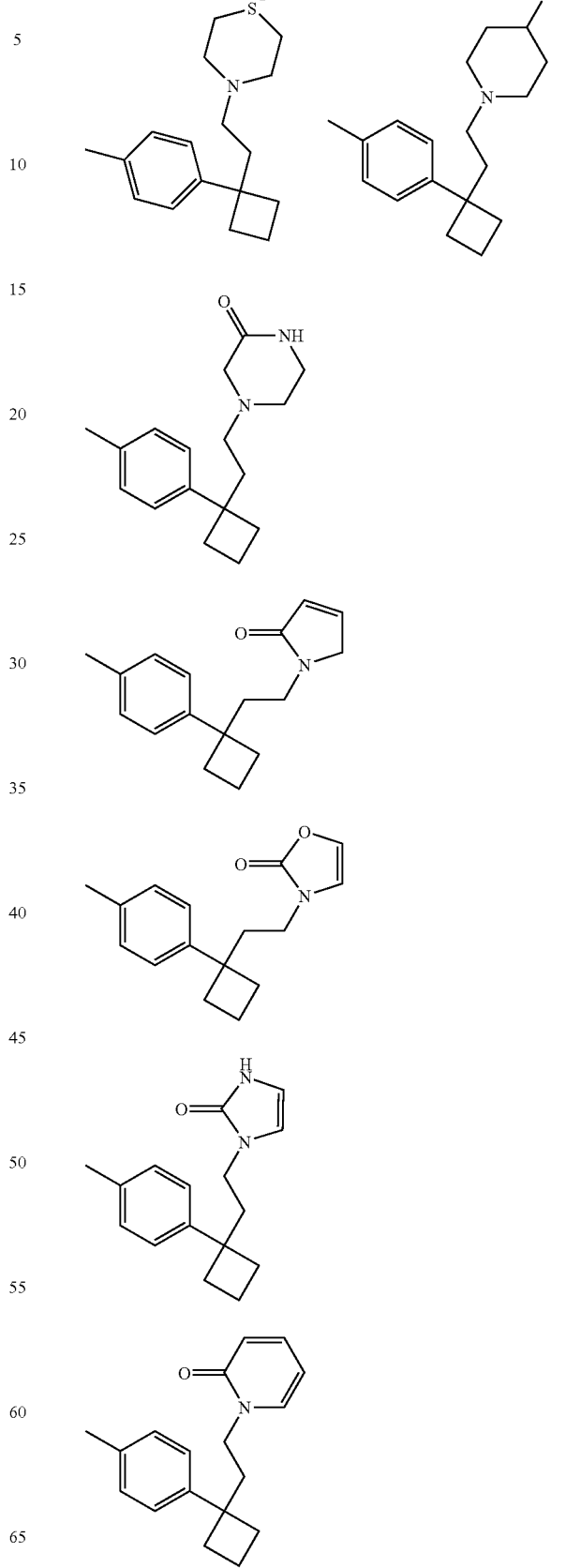

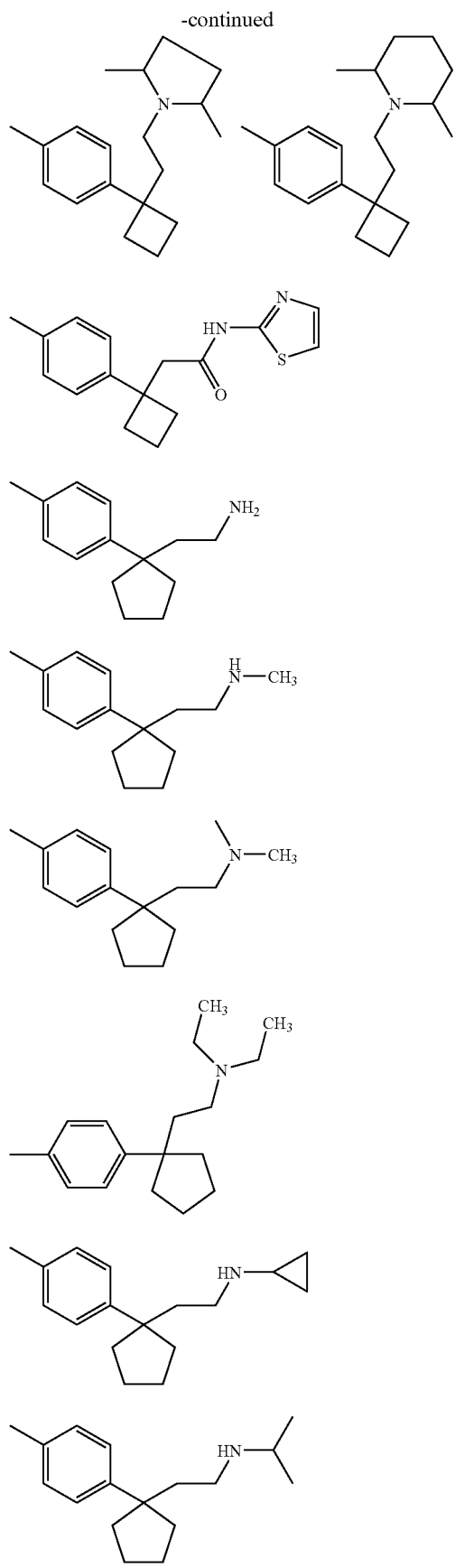
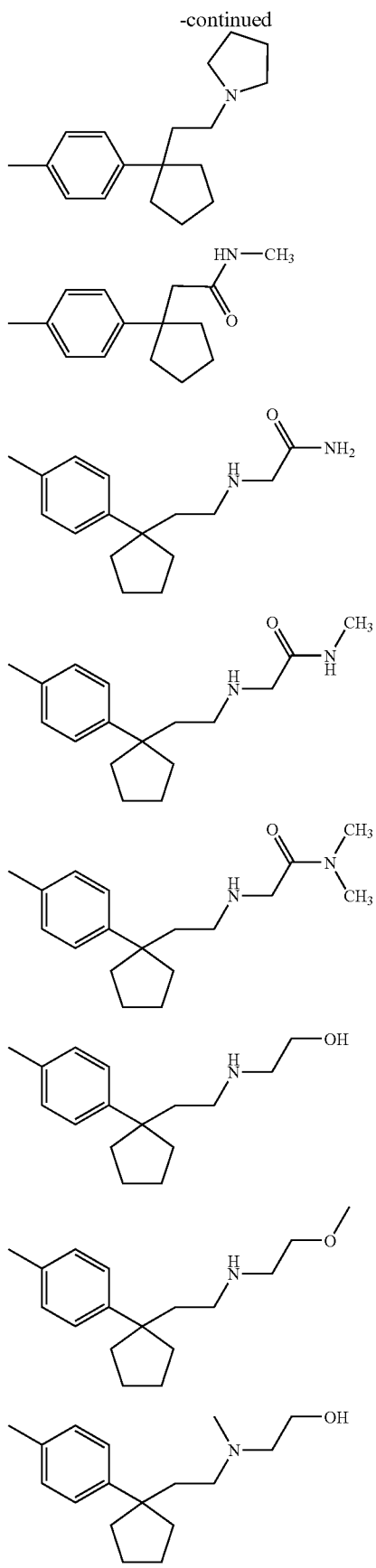

207
-continued
208
-continued
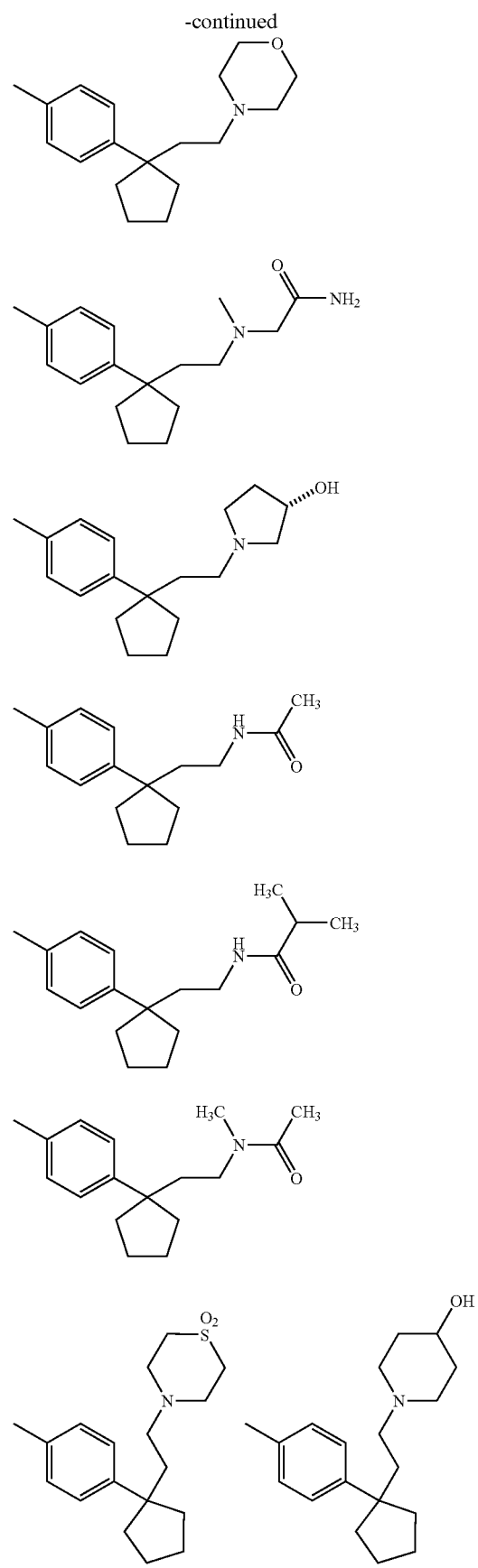
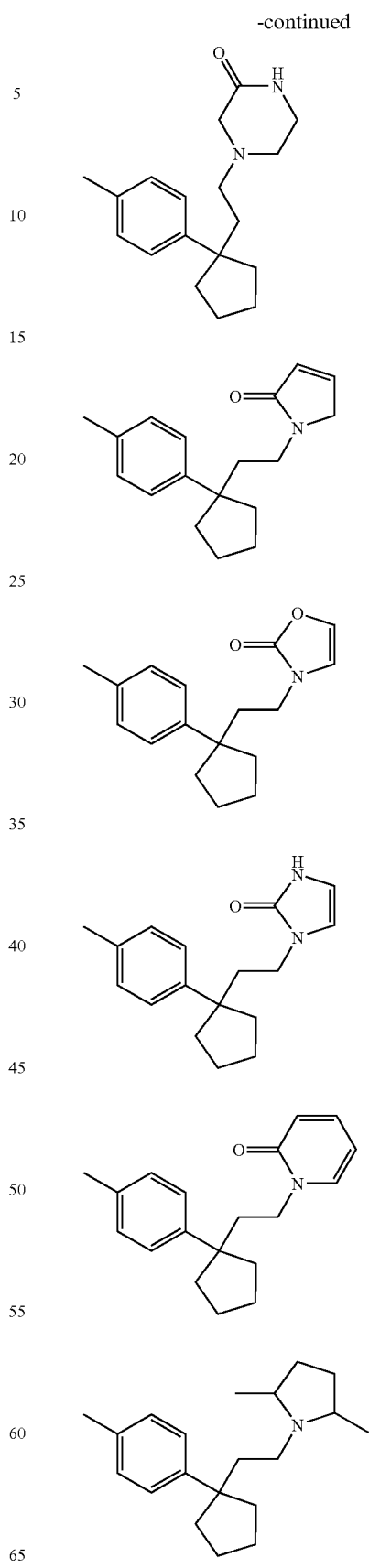

209
-continued
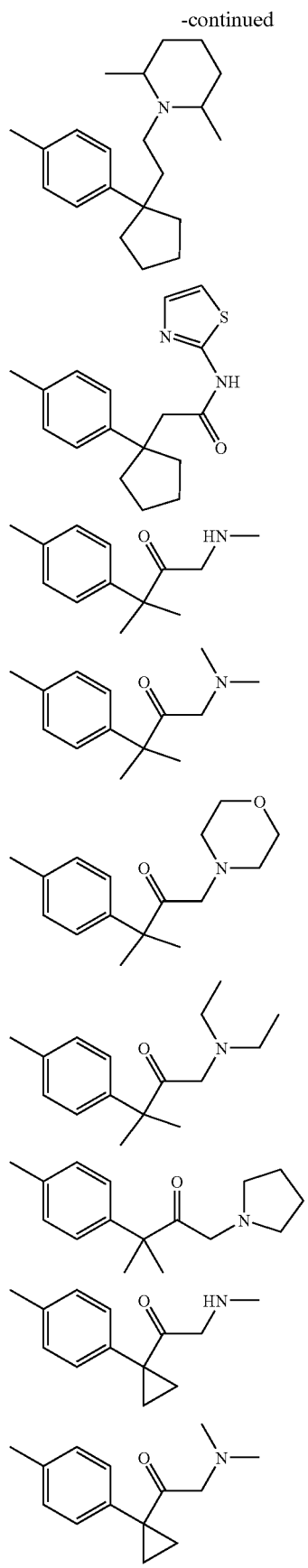
210
-continued
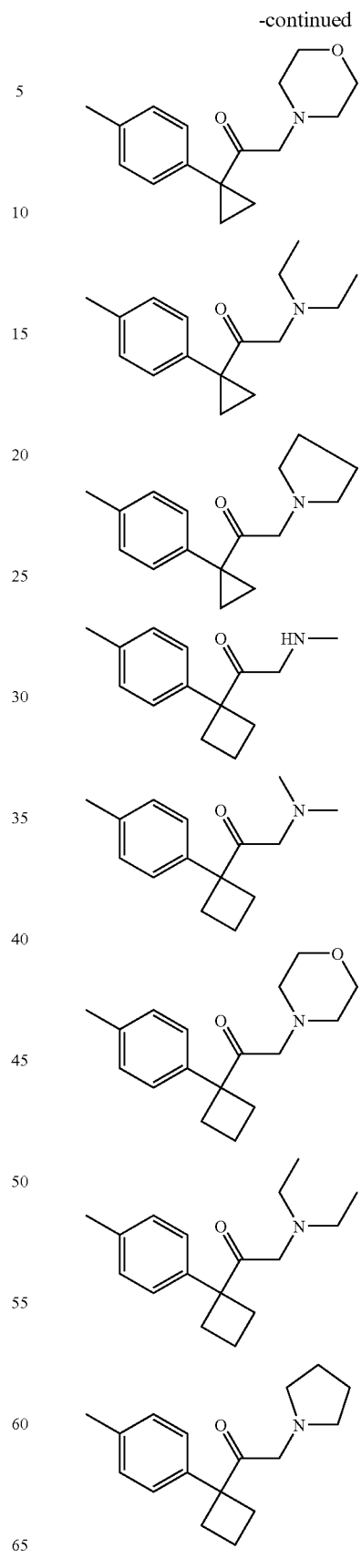

-continued

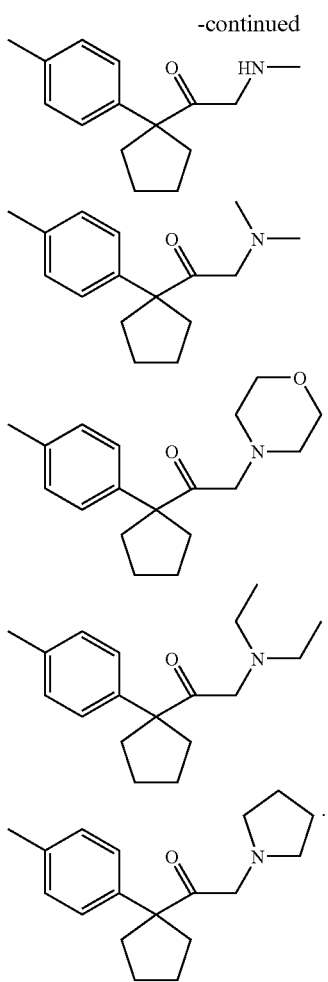

[15] In another preferred embodiment, the present invention provides a novel compound, wherein the compound is selected from the group:

1-[(6-chloro-2-naphthyl)sulfonyl]-4-{4-[1-(1-pyrrolidinylmethyl)cyclopropyl]benzoyl}piperazine;
5-chloro-N-(5-chloro-2-pyridinyl)-2-({4-[1-(1-pyrrolidinylmethyl)cyclopropyl]benzoyl}amino)benzamide
N-{4-[1,1-dimethyl-2-(1-pyrrolidinyl)ethyl]phenyl}-1-(4-methoxyphenyl)-1H-1,2,3-triazole-5-carboxamide;
N-{4-[2-(dimethylamino)-1,1-dimethylethyl]phenyl}-1-(4-methoxyphenyl)-1H-1,2,3-triazole-5-carboxamide;
$N^5$-{4-[2-(dimethylamino)-1,1-dimethylethyl]phenyl}-1-(4-methoxyphenyl)-1H-pyrazole-3,5-dicarboxamide;
3-cyano-N-{4-[2-(dimethylamino)-1,1-dimethylethyl]phenyl}-1-(4-methoxyphenyl)-1H-pyrazole-5-carboxamide;
N-{4-[2-(dimethylamino)-1,1-dimethylethyl]phenyl}-1-(4-methoxyphenyl)-3-(trifluoromethyl)-1H-pyrazole-5-carboxamide;
N-{4-[2-(dimethylamino)-1,1-dimethylethyl]phenyl}-1-(4-methoxyphenyl)-1H-1,2,3-triazole-5-carboxamide;
N-(4-{1-[(dimethylamino)methyl]cyclopentyl}phenyl)-1-(4-methoxyphenyl)-1H-1,2,3-triazole-5-carboxamide;
N-(4-{1-[(dimethylamino)methyl]cyclobutyl}phenyl)-1-(4-methoxyphenyl)-1H-1,2,3-triazole-5-carboxamide;
N-(4-{1-[(dimethylamino)methyl]cyclopropyl}phenyl)-1-(4-methoxyphenyl)-1H-1,2,3-triazole-5-carboxamide;
1-(2,3-dihydro-1H-indol-6-yl)-$N^5$-(4-{1-[(2-oxo-1-pyrrolidinyl)methyl]cyclopropyl}phenyl)-1H-pyrazole-3,5-dicarboxamide;
1-(2,3-dihydro-1H-indol-6-yl)-$N^5$-(4-{1-[(dimethylamino)methyl]cyclopropyl}phenyl)-1H-pyrazole-3,5-dicarboxamide;
5-chloro-N-(5-chloro-2-pyridinyl)-2-({4-[2-(dimethylamino)-1,1-dimethylethyl]benzoyl}amino)benzamide;
5-chloro-N-(5-chloro-2-pyridinyl)-2-[(4-{1-[(methylamino)methyl]cyclopropyl}benzoyl)amino]benzamide;
5-chloro-N-(5-chloro-2-pyridinyl)-2-({4-[1-(methoxymethyl)cyclopropyl]benzoyl}amino)benzamide;
5-chloro-N-(5-chloro-2-pyridinyl)-2-[(4-{1-[(dimethylamino)methyl]cyclopropyl}benzoyl)amino]benzamide;
5-chloro-N-(5-chloro-2-pyridinyl)-2-[(4-{1-[(2-methyl-1-pyrrolidinyl)methyl]cyclopropyl}benzoyl)amino]benzamide;
5-chloro-N-(5-chloro-2-pyridinyl)-2-[(4-{1-[(2-oxo-1-pyrrolidinyl)methyl]cyclopropyl}benzoyl)amino]benzamide;
5-chloro-N-(5-chloro-2-pyridinyl)-2-[(4-{1-[(isopropylamino)methyl]cyclopropyl}benzoyl)amino]benzamide;
5-chloro-N-(5-chloro-2-pyridinyl)-2-[(4-{1-[(cyclopropylamino)methyl]cyclopropyl}benzoyl)amino]benzamide;
5-chloro-N-(5-chloro-2-pyridinyl)-2-[(4-{1-[(cyclobutylamino)methyl]cyclopropyl}benzoyl)amino]benzamide;
5-chloro-N-(5-chloro-2-pyridinyl)-2-{[4-(1-{[(2-hydroxyethyl)amino]methyl}cyclopropyl)benzoyl]amino}benzamide;
5-chloro-N-(5-chloro-2-pyridinyl)-2-{[4-(1-{[(2-hydroxyethyl)(methyl)amino]methyl}cyclopropyl)benzoyl]amino}benzamide;
5-chloro-N-(5-chloro-2-pyridinyl)-2-[(4-{1-[(3-hydroxy-1-pyrrolidinyl)methyl]cyclopropyl}benzoyl)amino]benzamide;
5-chloro-N-(5-chloro-2-pyridinyl)-2-[(4-{1-[(4-hydroxy-1-piperidinyl)methyl]cyclopropyl}benzoyl)amino]benzamide;
5-chloro-N-(5-chloro-2-pyridinyl)-2-({4-[1-(1-piperidinylmethyl)cyclopropyl]benzoyl}amino)benzamide;
5-chloro-N-(5-chloro-2-pyridinyl)-2-[(4-{1-[(2-oxo-1-piperidinyl)methyl]cyclopropyl}benzoyl)amino]benzamide
5-chloro-N-(5-chloro-2-pyridinyl)-2-[(4-{1-[(2-oxo-1-imidazolidinyl)methyl]cyclopropyl}benzoyl)amino]benzamide;
5-chloro-N-(5-chloro-2-pyridinyl)-2-[(4-{1-[(2-oxo-1-pyrrolidinyl)methyl]cyclopropyl}benzyl)amino]benzamide;
2-{[4-(1-{[acetyl(methyl)amino]methyl}cyclopropyl)benzyl]amino}-5-chloro-N-(5-chloro-2-pyridinyl)benzamide;
5-chloro-N-(5-chloro-2-pyridinyl)-2-({4-[1-({methyl[(methylamino)carbonyl]amino}methyl)cyclopropyl]benzyl}amino)benzamide;
5-chloro-N-(5-chloro-2-pyridinyl)-2-{[4-(1-{[methyl(methylsulfonyl)amino]methyl}cyclopropyl)benzyl]amino}benzamide;
5-chloro-N-(5-chloro-2-pyridinyl)-2-[(4-{1-[(methylsulfonyl)amino]cyclopropyl}benzyl)amino]benzamide;
2-({4-[1-(acetylamino)cyclopropyl]benzyl}amino)-5-chloro-N-(5-chloro-2-pyridinyl)benzamide;
5-chloro-N-(5-chloro-2-pyridinyl)-2-{[4-(1-{[(2-hydroxyethyl)amino]methyl}cyclopropyl)benzyl]amino}benzamide;
5-chloro-N-(5-chloro-2-pyridinyl)-2-{[4-(1-{[(2-hydroxyethyl)(methyl)amino]methyl}cyclopropyl)benzyl]amino}benzamide;

5-chloro-N-(5-chloro-2-pyridinyl)-2-[(4-{1-[(1,3-thiazol-2-ylamino)methyl]cyclopropyl}benzoyl)amino]benzamide;
5-chloro-N-(5-chloro-2-pyridinyl)-2-[(4-{1-[(2-methyl-1H-imidazol-1-yl)methyl]cyclopropyl}benzoyl)amino]benzamide;
5-chloro-N-(5-chloro-2-pyridinyl)-2-({4-[1-({[(methylamino)carbonyl]amino}methyl)cyclopropyl]benzoyl}amino)benzamide;
methyl [1-(4-{[(4-chloro-2-{[(5-chloro-2-pyridinyl)amino]carbonyl}phenyl)amino]carbonyl}phenyl)cyclopropyl]methylcarbamate;
5-chloro-N-(5-chloro-2-pyridinyl)-2-{[4-(1-{[(methylsulfonyl)amino]methyl}cyclopropyl)benzoyl]amino}benzamide;
2-({4-[1-(2-amino-2-oxoethyl)cyclopropyl]benzoyl}amino)-5-chloro-N-(5-chloro-2-pyridinyl)benzamide;
5-chloro-N-(5-chloro-2-pyridinyl)-2-[(4-{1-[2-(dimethylamino)-2-oxoethyl]cyclopropyl}benzyl)amino]benzamide;
2-({4-[1-(2-amino-2-oxoethyl)cyclopropyl]benzyl}amino)-5-chloro-N-(5-chloro-2-pyridinyl)benzamide;
N-{4-[1-(2-amino-2-oxoethyl)cyclopropyl]phenyl}-1-(4-methoxyphenyl)-1H-1,2,3-triazole-5-carboxamide;
N-{4-[1-(aminomethyl)cyclopropyl]phenyl}-1-(4-methoxyphenyl)-1H-1,2,3-triazole-5-carboxamide;
1-(4-methoxyphenyl)-N-(4-{1-[(methylamino)methyl]cyclopropyl}phenyl)-1H-1,2,3-triazole-5-carboxamide;
1-(4-methoxyphenyl)-N-{4-[1-(1-pyrrolidinylmethyl)cyclopropyl]phenyl}-1H-1,2,3-triazole-5-carboxamide;
1-(4-methoxyphenyl)-N$^5$-{4-[1-(1-pyrrolidinylmethyl)cyclopropyl]phenyl}-1H-pyrazole-3,5-dicarboxamide;
1-(4-methoxyphenyl)-N$^5$-(4-{1-[(2-oxo-1-pyrrolidinyl)methyl]cyclopropyl}phenyl)-1H-pyrazole-3,5-dicarboxamide;
1-(4-methoxyphenyl)-N$^5$-(4-{1-[(methylamino)methyl]cyclopropyl}phenyl)-1H-pyrazole-3,5-dicarboxamide;
3-cyano-1-(4-methoxyphenyl)-N-(4-{1-[(methylamino)methyl]cyclopropyl}phenyl)-1H-pyrazole-5-carboxamide;
3-cyano-1-(4-methoxyphenyl)-N-{4-[1-(1-pyrrolidinylmethyl)cyclopropyl]phenyl}-1H-pyrazole-5-carboxamide;
3-cyano-1-(4-methoxyphenyl)-N-(4-{1-[(2-oxo-1-pyrrolidinyl)methyl]cyclopropyl}phenyl)-1H-pyrazole-5-carboxamide;
1-(4-methoxyphenyl)-3-(methylsulfonyl)-N-(4-{1-[(2-oxo-1-pyrrolidinyl)methyl]cyclopropyl}phenyl)-1H-pyrazole-5-carboxamide;
N-(4-{1-[(3-hydroxy-1-pyrrolidinyl)methyl]cyclopropyl}phenyl)-1-(4-methoxyphenyl)-3-(methylsulfonyl)-1H-pyrazole-5-carboxamide;
5-chloro-thiophene-2-carboxylic acid {1-[4-(1-pyrrolidin-1-ylmethyl-cyclopropyl)-benzoyl]-pyrrolidin-3-yl}-amide;
5-chloro-thiophene-2-carboxylic acid {1-[4-(1-dimethylaminomethyl-cyclopropyl)-benzoyl]-pyrrolidin-3-yl}-amide;
3-chloro-1H-indole-6-carboxylic acid {1-[4-(1-pyrrolidin-1-ylmethyl-cyclopropyl)-benzoyl]-pyrrolidin-3-yl}-amide;
3-chloro-1H-indole-6-carboxylic acid {1-[4-(1-dimethylaminomethyl-cyclopropyl)-benzoyl]-pyrrolidin-3-yl}-amide;
3-chloro-1H-indole-6-carboxylic acid {2-[4-(1-pyrrolidin-1-ylmethyl-cyclopropyl)-benzoylamino]-cyclohexyl}-amide;
5-chloro-thiophene-2-carboxylic acid {2-[4-(1-pyrrolidin-1-ylmethyl-cyclopropyl)-benzoylamino]-cyclohexyl}-amide;
2-{4-[4-chloro-2-(5-chloro-pyridin-2-ylcarbamoyl)-phenylcarbamoyl]-phenyl}-2-methyl-propionic acid methyl ester;
2-{4-[4-chloro-2-(5-chloro-pyridin-2-ylcarbamoyl)-phenylcarbamoyl]-phenyl}-2-methyl-propyl alcohol;
5-chloro-N-(5-chloropyridin-2-yl)-2-({4-[2-(ethylamino)-1,1-dimethylethyl]benzoyl}amino)benzamide;
5-chloro-N-(5-chloropyridin-2-yl)-2-{[4-(1,1-dimethyl-2-pyrrolidin-1-ylethyl)benzoyl]amino}benzamide;
5-chloro-N-(5-chloropyridin-2-yl)-2-{[4-(1,1-dimethyl-2-morpholin-4-ylethyl)benzoyl]amino}benzamide;
2-{4-[2-(5-chloro-pyridin-2-ylcarbamoyl)-phenylcarbamoyl]-phenyl}-2-methyl-propionic acid methyl ester;
2-{4-[2-(5-chloro-pyridin-2-ylcarbamoyl)-4-methoxy-phenylcarbamoyl]-phenyl}-2-methyl-propionic acid methyl ester;
N-(5-chloropyridin-2-yl)-2-{[4-(2-hydroxy-1,1-dimethylethyl)benzoyl]amino}benzamide;
N-(5-chloropyridin-2-yl)-2-{[4-(2-hydroxy-1,1-dimethylethyl)benzoyl]amino}-5-methoxybenzamide;
N-(5-chloropyridin-2-yl)-2-{[4-(1,1-dimethyl-2-pyrrolidin-1-ylethyl)benzoyl]amino}benzamide;
N-(5-chloropyridin-2-yl)-2-{[4-(1,1-dimethyl-2-morpholin-4-ylethyl)benzoyl]amino}benzamide;
N-(5-chloropyridin-2-yl)-2-{[4-(1,1-dimethyl-2-pyrrolidin-1-ylethyl)benzoyl]amino}-5-methoxybenzamide;
2-[(4-{2-[acetyl(methyl)amino]-1,1-dimethylethyl}benzoyl)amino]-N-(5-chloropyridin-2-yl)benzamide;
2-(4-{[2-(5-chloro-pyridin-2-ylcarbamoyl)-phenylamino]methyl}-phenyl)-2-methyl-propionic acid methyl ester;
5-chloro-N-(5-chloropyridin-2-yl)-2-{[4-(2-hydroxy-1,1-dimethylethyl)benzyl]amino}benzamide;
5-chloro-N-(5-chloro-pyridin-2-yl)-2-[4-(2-dimethylamino-1,1-dimethyl-ethyl)-benzylamino]-benzamide;
N-(5-chloropyridin-2-yl)-2-({4-[1-(hydroxymethyl)cyclopropyl]benzoyl}amino)-5-methoxybenzamide;
N-(5-chloropyridin-2-yl)-5-methoxy-2-({4-[1-(pyrrolidin-1-ylmethyl)cyclopropyl]benzoyl}amino)benzamide;
N-(5-chloropyridin-2-yl)-2-({4-[1-(pyrrolidin-1-ylmethyl)cyclopropyl]benzoyl}amino)benzamide;
1-{4-[2-(5-chloro-pyridin-2-ylcarbamoyl)-phenylcarbamoyl]-phenyl}-cyclopropanecarboxylic acid methyl ester;
N-(5-chloropyridin-2-yl)-2-({4-[1-(hydroxymethyl)cyclopropyl]benzoyl}amino)benzamide;
6-chloro-3-(5-chloropyridin-2-yl)-2-[4-(1,1-dimethyl-2-morpholin-4-ylethyl)phenyl]quinazolin-4(3H)-one;
3-(5-chloropyridin-2-yl)-2-{4-[1-(pyrrolidin-1-ylmethyl)cyclopropyl]phenyl}quinazolin-4(3H)-one;
2-(4-methoxy-phenyl)-5-trifluoromethyl-2H-pyrazole-3-carboxylic acid {4-[1-(2-methylamino-ethyl)-cyclopropyl]-phenyl}-amide;
2-(4-methoxy-phenyl)-5-trifluoromethyl-2H-pyrazole-3-carboxylic acid {4-[1-(2-dimethylamino-ethyl)-cyclopropyl]-phenyl}-amide;
2-(4-methoxy-phenyl)-5-trifluoromethyl-2H-pyrazole-3-carboxylic acid {4-[1-(2-pyrrolidin-1-yl-ethyl)-cyclopropyl]-phenyl}-amide;
2-(4-methoxy-phenyl)-5-trifluoromethyl-2H-pyrazole-3-carboxylic acid [4-(1-{2-[(2-hydroxy-ethyl)-methyl-amino]-ethyl}-cyclopropyl)-phenyl]-amide;
2-(4-methoxy-phenyl)-5-trifluoromethyl-2H-pyrazole-3-carboxylic acid (4-{1-[2-(carbamoylmethyl-methyl-amino)-ethyl]-cyclopropyl}-phenyl)-amide;
2-(4-methoxy-phenyl)-5-trifluoromethyl-2H-pyrazole-3-carboxylic acid {4-[1-(2-morpholin-4-yl-ethyl)-cyclopropyl]-phenyl}-amide;

2-(4-methoxy-phenyl)-5-trifluoromethyl-2H-pyrazole-3-carboxylic acid [4-(1-carbamoylmethyl-cyclopropyl)-phenyl]-amide;

2-(4-methoxy-phenyl)-5-trifluoromethyl-2H-pyrazole-3-carboxylic acid [4-(1-methylcarbamoylmethyl-cyclopropyl)-phenyl]-amide;

2-(4-methoxy-phenyl)-5-trifluoromethyl-2H-pyrazole-3-carboxylic acid [4-(1-methylcarbamoylmethyl-cyclobutyl)-phenyl]-amide;

2-(4-methoxy-phenyl)-5-trifluoromethyl-2H-pyrazole-3-carboxylic acid [4-(1-carbamoylmethyl-cyclobutyl)-phenyl]-amide;

2-(4-methoxy-phenyl)-5-trifluoromethyl-2H-pyrazole-3-carboxylic acid {4-[1-(2-methylamino-ethyl)-cyclobutyl]-phenyl}-amide;

2-(4-methoxy-phenyl)-5-trifluoromethyl-2H-pyrazole-3-carboxylic acid {4-[1-(2-dimethylamino-ethyl)-cyclobutyl]-phenyl}-amide;

2-(4-methoxy-phenyl)-5-trifluoromethyl-2H-pyrazole-3-carboxylic acid {4-[1-(2-pyrrolidin-1-yl-ethyl)-cyclobutyl]-phenyl}-amide;

2-(4-methoxy-phenyl)-5-trifluoromethyl-2H-pyrazole-3-carboxylic acid {4-[1-(2-morpholin-4-yl-ethyl)-cyclobutyl]-phenyl}-amide;

2-(4-methoxy-phenyl)-5-trifluoromethyl-2H-pyrazole-3-carboxylic acid {4-[1-(2-dimethylamino-ethyl)-cyclopentyl]-phenyl}-amide;

5-cyano-2-(4-methoxy-phenyl)-2H-pyrazole-3-carboxylic acid {4-[1-(2-dimethylamino-ethyl)-cyclopropyl]-phenyl}-amide;

2-(4-methoxy-phenyl)-5-methyl-2H-pyrazole-3-carboxylic acid {4-[1-(2-dimethylamino-ethyl)-cyclopropyl]-phenyl}-amide;

1-(4-methoxy-phenyl)-1H-pyrazole-3,5-dicarboxylic acid 3-amide 5-({4-[1-(2-dimethylamino-ethyl)-cyclopropyl]-phenyl}-amide);

5-methanesulfonyl-2-(4-methoxy-phenyl)-2H-pyrazole-3-carboxylic acid {4-[1-(2-dimethylamino-ethyl)-cyclopropyl]-phenyl}-amide;

3-(4-methoxy-phenyl)-3H-[1,2,3]triazole-4-carboxylic acid {4-[1-(2-dimethylamino-ethyl)-cyclopropyl]-phenyl}-amide;

3-(4-methoxy-phenyl)-3H-[1,2,3]triazole-4-carboxylic acid [4-(1-carbamoylmethyl-cyclopropyl)-phenyl]-amide;

3-(4-methoxy-phenyl)-3H-[1,2,3]triazole-4-carboxylic acid [4-(1-methylcarbamoylmethyl-cyclopropyl)-phenyl]-amide;

2-[1-(4-{2-[3-(4-methoxy-phenyl)-3H-[1,2,3]triazol-4-yl]-2-oxo-ethyl}-phenyl)-cyclopropyl]-N-methyl-acetamide;

2-[1-(4-{2-[3-(4-methoxy-phenyl)-3H-[1,2,3]triazol-4-yl]-2-oxo-ethyl}-phenyl)-cyclopropyl]-acetamide;

2-[1-(4-{2-[2-(4-methoxy-phenyl)-5-trifluoromethyl-2H-pyrazol-3-yl]-2-oxo-ethyl}-phenyl)-cyclopropyl]-acetamide;

2-[1-(4-{2-[5-cyano-2-(4-methoxy-phenyl)-2H-pyrazol-3-yl]-2-oxo-ethyl}-phenyl)-cyclopropyl]-acetamide;

2-[1-(4-{2-[5-methanesulfonyl-2-(4-methoxy-phenyl)-2H-pyrazol-3-yl]-2-oxo-ethyl}-phenyl)-cyclopropyl]-acetamide;

2-[1-(4-{2-[5-methanesulfonyl-2-(4-methoxy-phenyl)-2H-pyrazol-3-yl]-2-oxo-ethyl}-phenyl)-cyclopropyl]-N-methyl-acetamide;

5-chloro-N-(5-chloro-2-pyridinyl)-2-({4-[1-(2-dimethylamino-ethyl)cyclopropyl]benzoyl}amino)benzamide;

N-(5-chloro-2-pyridinyl)-5-methoxy-2-({4-[1-(2-dimethylamino-ethyl)cyclopropyl]benzoyl}amino)benzamide;

N-(5-chloro-2-pyridinyl)-5-fluoro-2-({4-[1-(2-dimethylamino-ethyl)cyclopropyl]benzoyl}amino)benzamide;

N-(5-chloro-2-pyridinyl)-5-methyl-2-({4-[1-(2-dimethylamino-ethyl)cyclopropyl]benzoyl}amino)benzamide;

N-(5-chloro-2-pyridinyl)-5-methylsulfonyl-2-({4-[1-(2-dimethylamino-ethyl)cyclopropyl]benzoyl}amino)benzamide;

N-(5-chloro-2-pyridinyl)-5-cyano-2-({4-[1-(2-dimethylamino-ethyl)cyclopropyl]benzoyl}amino)benzamide;

N-(5-chloro-2-pyridinyl)-2-({4-[1-(2-dimethylamino-ethyl)cyclopropyl]benzoyl}amino)benzamide;

3-{4-[1-(2-dimethylamino-ethyl)-cyclopropyl]-benzoylamino}-pyridine-2-carboxylic acid (5-chloro-pyridin-2-yl)-amide;

N-(5-chloro-pyridin-2-yl)-4-{4-[1-(2-dimethylamino-ethyl)-cyclopropyl]-benzoylamino}-nicotinamide;

N-(5-chloro-pyridin-2-yl)-3-{4-[1-(2-dimethylamino-ethyl)-cyclopropyl]-benzoylamino}-isonicotinamide;

N-(5-chloro-pyridin-2-yl)-2-{4-[1-(2-dimethylamino-ethyl)-cyclopropyl]-benzoylamino}-nicotinamide;

5-chloro-N-(5-chloro-2-pyridinyl)-2-(4-{1-[2-(2-oxo-pyrrolidin-1-yl)-ethyl]-cyclopropyl}-benzoylamino)benzamide;

N-(5-chloro-2-pyridinyl)-5-methoxy-2-(4-{1-[2-(2-oxo-pyrrolidin-1-yl)-ethyl]-cyclopropyl}-benzoylamino)benzamide;

N-(5-chloro-2-pyridinyl)-5-fluoro-2-(4-{1-[2-(2-oxo-pyrrolidin-1-yl)-ethyl]-cyclopropyl}-benzoylamino)benzamide;

N-(5-chloro-2-pyridinyl)-5-methyl-2-(4-{1-[2-(2-oxo-pyrrolidin-1-yl)-ethyl]-cyclopropyl}-benzoylamino)benzamide;

N-(5-chloro-2-pyridinyl)-5-methylsulfonyl-2-(4-{1-[2-(2-oxo-pyrrolidin-1-yl)-ethyl]-cyclopropyl}benzoylamino)benzamide;

N-(5-chloro-2-pyridinyl)-5-cyano-2-(4-{1-[2-(2-oxo-pyrrolidin-1-yl)-ethyl]-cyclopropyl}-benzoylamino)benzamide;

N-(5-chloro-2-pyridinyl)-2-(4-{1-[2-(2-oxo-pyrrolidin-1-yl)-ethyl]-cyclopropyl}-benzoylamino)benzamide;

3-(4-{1-[2-(2-oxo-pyrrolidin-1-yl)-ethyl]-cyclopropyl}-benzoylamino)-pyridine-2-carboxylic acid (5-chloro-pyridin-2-yl)-amide;

N-(5-chloro-pyridin-2-yl)-4-(4-{1-[2-(2-oxo-pyrrolidin-1-yl)-ethyl]-cyclopropyl}-benzoylamino)-nicotinamide;

N-(5-chloro-pyridin-2-yl)-3-(4-{1-[2-(2-oxo-pyrrolidin-1-yl)-ethyl]-cyclopropyl}-benzoylamino)-isonicotinamide;

N-(5-chloro-pyridin-2-yl)-2-(4-{1-[2-(2-oxo-pyrrolidin-1-yl)-ethyl]-cyclopropyl}-benzoylamino)-nicotinamide;

3-chloro-1H-indole-6-carboxylic acid {4-dimethylcarbamoyl-2-[4-(1-pyrrolidin-1-ylmethyl-cyclopropyl)-benzoylamino]-cyclohexyl}-amide;

3-chloro-1H-indole-6-carboxylic acid {5-dimethylcarbamoyl-2-[4-(1-pyrrolidin-1-ylmethyl-cyclopropyl)-benzoylamino]-cyclohexyl}-amide;

3-chloro-1H-indole-6-carboxylic acid {4-[4-(1-pyrrolidin-1-ylmethyl-cyclopropyl)-benzoylamino]-tetrahydro-pyran-3-yl}-amide;

3-chloro-1H-indole-6-carboxylic acid {3-[4-(1-pyrrolidin-1-ylmethyl-cyclopropyl)-benzoylamino]-tetrahydro-pyran-4-yl}-amide;

3-chloro-1H-indole-6-carboxylic acid {1,1-dioxo-3-[4-(1-pyrrolidin-1-ylmethyl-cyclopropyl)-benzoylamino]-hexahydro-1$\lambda^6$-thiopyran-4-yl}-amide;

3-chloro-1H-indole-6-carboxylic acid {1,1-dioxo-4-[4-(1-pyrrolidin-1-ylmethyl-cyclopropyl)-benzoylamino]-hexahydro-1$\lambda^6$-thiopyran-3-yl}-amide;

3-chloro-1H-indole-6-carboxylic acid {1-acetyl-3-[4-(1-pyrrolidin-1-ylmethyl-cyclopropyl)-benzoylamino]-piperidin-4-yl}-amide;

3-chloro-1H-indole-6-carboxylic acid {1-acetyl-3-[4-(1-pyrrolidin-1-ylmethyl-cyclopropyl)-benzoylamino]-piperidin-4-yl}-amide;

4-[(3-chloro-1H-indole-6-carbonyl)-amino]-3-[4-(1-pyrrolidin-1-ylmethyl-cyclopropyl)-benzoylamino]-piperidine-1-carboxylic acid methyl ester;

3-chloro-1H-indole-6-carboxylic acid {1-(2-methoxy-acetyl)-3-[4-(1-pyrrolidin-1-ylmethyl-cyclopropyl)-benzoylamino]-piperidin-4-yl}-amide;

5-chloro-thiophene-2-carboxylic acid {2-[4-(1-dimethyl-aminomethyl-cyclopropyl)-benzoylamino]-cyclopentyl}-amide;

5-chloro-thiophene-2-carboxylic acid {4-[4-(1-dimethyl-aminomethyl-cyclopropyl)-benzoylamino]-tetrahydro-furan-3-yl}-amide;

5-chloro-thiophene-2-carboxylic acid {1-acetyl-4-[4-(1-dimethylaminomethyl-cyclopropyl)-benzoylamino]-pyrrolidin-3-yl}-amide;

5-chloro-thiophene-2-carboxylic acid {1-cyclopropanecarbonyl-4-[4-(1-dimethylaminomethyl-cyclopropyl)-benzoylamino]-pyrrolidin-3-yl}-amide;

3-[(5-chloro-thiophene-2-carbonyl)-amino]-4-[4-(1-dimethylaminomethyl-cyclopropyl)-benzoylamino]-pyrrolidine-1-carboxylic acid methyl ester;

5-chloro-thiophene-2-carboxylic acid {4-[4-(1-dimethyl-aminomethyl-cyclopropyl)-benzoylamino]-1-(2-methoxy-acetyl)-pyrrolidin-3-yl}-amide;

5-chloro-thiophene-2-carboxylic acid {2-[4-(1-dimethyl-aminomethyl-cyclopropyl)-benzoylamino]-4-dimethylcarbamoyl-cyclopentyl}-amide;

5-chloro-thiophene-2-carboxylic acid {1-[4-(1-dimethyl-aminomethyl-cyclopropyl)-benzoylamino]-indan-2-yl}-amide;

3-chloro-1H-indole-6-carboxylic acid {3-[4-(1-dimethyl-aminomethyl-cyclopropyl)-benzoylamino]-1,2,3,4-tetrahydro-naphthalen-2-yl}-amide;

3-chloro-1H-indole-6-carboxylic acid {3-[4-(1-dimethyl-aminomethyl-cyclopropyl)-benzoylamino]-7-oxa-bicyclo[2.2.1]hept-2-yl}-amide;

5-chloro-thiophene-2-carboxylic acid {2-[4-(1-dimethyl-aminomethyl-cyclopropyl)-benzoylamino]-4-dimethylcarbamoyl-cyclopentyl}-amide;

5-chloro-thiophene-2-carboxylic acid {8-[4-(1-dimethyl-aminomethyl-cyclopropyl)-benzoylamino]-1-oxa-spiro[4.4]non-7-yl}-amide;

5-chloro-thiophene-2-carboxylic acid (8-{4-[1-(2-dimethy-lamino-ethyl)-cyclopropyl]-benzoylamino}-1-oxa-spiro[4.4]non-7-yl)-amide;

5-chloro-thiophene-2-carboxylic acid (2-{4-[1-(2-dimethy-lamino-ethyl)-cyclopropyl]-benzoylamino}-cyclopentyl)-amide;

5-chloro-thiophene-2-carboxylic acid (2-{4-[1-(2-dimethy-lamino-ethyl)-cyclopropyl]-benzoylamino}-4-dimethylcarbamoyl-cyclopentyl)-amide;

3-[(5-chloro-thiophene-2-carbonyl)-amino]-4-{4-[1-(2-dimethylamino-ethyl)-cyclopropyl]-benzoylamino}-pyrrolidine-1-carboxylic acid methyl ester;

5-chloro-thiophene-2-carboxylic acid (4-{4-[1-(2-dimethy-lamino-ethyl)-cyclopropyl]-benzoylamino}-tetrahydro-furan-3-yl)-amide;

3-chloro-1H-indole-6-carboxylic acid (2-{4-[1-(2-dimethy-lamino-ethyl)-cyclopropyl]-benzoylamino}-cyclohexyl)-amide;

3-chloro-1H-indole-6-carboxylic acid (2-{4-[1-(2-dimethy-lamino-ethyl)-cyclopropyl]-benzoylamino}-4-dimethyl-carbamoyl-cyclohexyl)-amide;

4-[(3-Chloro-1H-indole-6-carbonyl)-amino]-3-{4-[1-(2-dimethylamino-ethyl)-cyclopropyl]-benzoylamino}-piperidine-1-carboxylic acid methyl ester;

3-chloro-1H-indole-6-carboxylic acid (3-{4-[1-(2-dimethy-lamino-ethyl)-cyclopropyl]-benzoylamino}-1,1-dioxo-hexahydro-1$\lambda^6$-thiopyran-4-yl)-amide;

3-chloro-1H-indole-6-carboxylic acid (4-{4-[1-(2-dimethy-lamino-ethyl)-cyclopropyl]-benzoylamino}-1,1-dioxo-hexahydro-1$\lambda^6$-thiopyran-3-yl)-amide;

3-chloro-1H-indole-6-carboxylic acid (4-{4-[1-(2-dimethy-lamino-ethyl)-cyclopropyl]-benzoylamino}-tetrahydro-pyran-3-yl)-amide;

3-chloro-1H-indole-6-carboxylic acid (3-{4-[1-(2-dimethy-lamino-ethyl)-cyclopropyl]-benzoylamino}-tetrahydro-pyran-4-yl)-amide;

(1R,2S)-5-chloro-thiophene-2-carboxylic acid {2-[4-(1-pyrrolidin-1-ylmethyl-cyclopropyl)-benzoylamino]-cyclopentyl}-amide;

(1R,2S)-3-chloro-1H-indole-6-carboxylic acid {2-[4-(1-pyrrolidin-1-ylmethyl-cyclopropyl)-benzoylamino]-cyclopentyl}-amide;

(1R,2S)-5-chloro-thiophene-2-carboxylic acid {2-[4-(1-pyrrolidin-1-ylmethyl-cyclopropyl)-benzoylamino]-cyclohexyl}-amide; and, Cis-3-chloro-1H-indole-6-carboxylic acid {2-[4-(1-pyrrolidin-1-ylmethyl-cyclopropyl)-phenylcarbamoyl]-cyclohexyl}-amide;

or a pharmaceutically acceptable salt form thereof.

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides a novel method for treating a thromboembolic disorder, comprising: administering to a patient in need thereof a therapeutically effective amount of a compound of the present invention or a pharmaceutically acceptable salt form thereof.

In another preferred embodiment, the present invention provides a novel method, wherein the thromboembolic disorder is selected from the group consisting of arterial cardiovascular thromboembolic disorders, venous cardiovascular thromboembolic disorders, and thromboembolic disorders in the chambers of the heart.

In another preferred embodiment, the present invention provides a novel method, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder In another embodiment, the present invention provides a novel method, comprising: administering a compound of the present invention or a pharmaceutically acceptable salt form thereof in an amount effective to treat a thromboembolic disorder.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used in combination with a second therapeutic agent to treat a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides a compound of the present invention for use in therapy.

In another embodiment, the present invention provides the use of a compound of the present invention as described above for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). The present invention, in general, does not cover groups such as N-halo, S(O)H, and SO$_2$H.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

As used herein, "alkyl" is intended to include both branched and straight-chain saturated aliphatic hydrocarbon groups having the specified number of carbon atoms. $C_{1-6}$ alkyl, is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. "Alkenyl" is intended to include hydrocarbon chains of either straight or branched configuration and one or more unsaturated carbon-carbon bonds that may occur in any stable point along the chain, such as ethenyl and propenyl. $C_{2-6}$ alkenyl is intended to include $C_2$, $C_3$, $C_4$, $C_5$, and $C_6$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-6}$ Alkynyl is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, or unsaturated (aromatic). Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a trycyclic ring. When a ring is bridged, the substituents recited for the ring may also be present on the bridge.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 ring heteroatoms independently selected from the group consisting of N, O and S and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O and S. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a trycyclic ring. When a ring is bridged, the substituents recited for the ring may also be present on the bridge.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p 1445, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor Xa. "Therapeutically effective amount" is also intended to include an amount of the combination of compounds claimed that is effective to inhibit factor Xa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

The compounds of the present invention of formula I (Scheme 1) where P is not fused onto ring M can be prepared as outlined in Scheme 2 to Scheme 10 and via standard methods known to those skilled in the art.

Scheme 1

Formula I

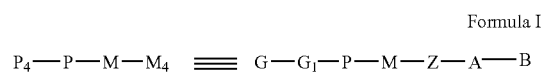

The compounds of the present invention of formula I where Y is $C_3$–$C_7$ cycloalkyl can be prepared as shown in Scheme 2. Commercially available 4-nitrophenylacetonitrile (or properly protected 4-aminophenylacetonitrile) can be used as the starting material. Alkylation with NaH, KtOBu, NaNH$_2$, n-BuLi, s-BuLi, NaOEt, or aq NaOH, etc. as the base, and X—(CH$_2$)$_n$—Y (X, Y can be Cl, Br, I, OMs or OTs, $^+$S(CH$_3$)$_2$, n=2–6) as the alkylating reagent can afford the cycloalkyl intermediate 1. Hydrolysis of the nitrile group, followed by reduction of the ester group can provide the alcohol 2. Oxidation of 2, then reductive amination with NHR$^{2d}$R$^{2d}$ will provide 3. Reduction of the nitro group or deprotection of the amino group can produce the A-B precursor 4, which can be coupled with 5 using standard coupling conditions to provide 6. When one of the R$^{2d}$ groups is H, 6 can react with acid chlorides, carbamoyl chlorides, sulfonyl chlorides, and isocyanates to provide compounds of the invention with structures 7, 8, 9, and 10. Alternatively, alcohol 2 can react with alkyl halides and amines to form compounds of the invention with structures 11 and 12. Alcohol 2 can also be transferred into a halide or its equivalents (X=Cl, Br, I, OMs, or OTs), followed by alkylation with a variety of alkylating reagents to afford compounds of the invention with structures 13, 14, and 15.

Scheme 2

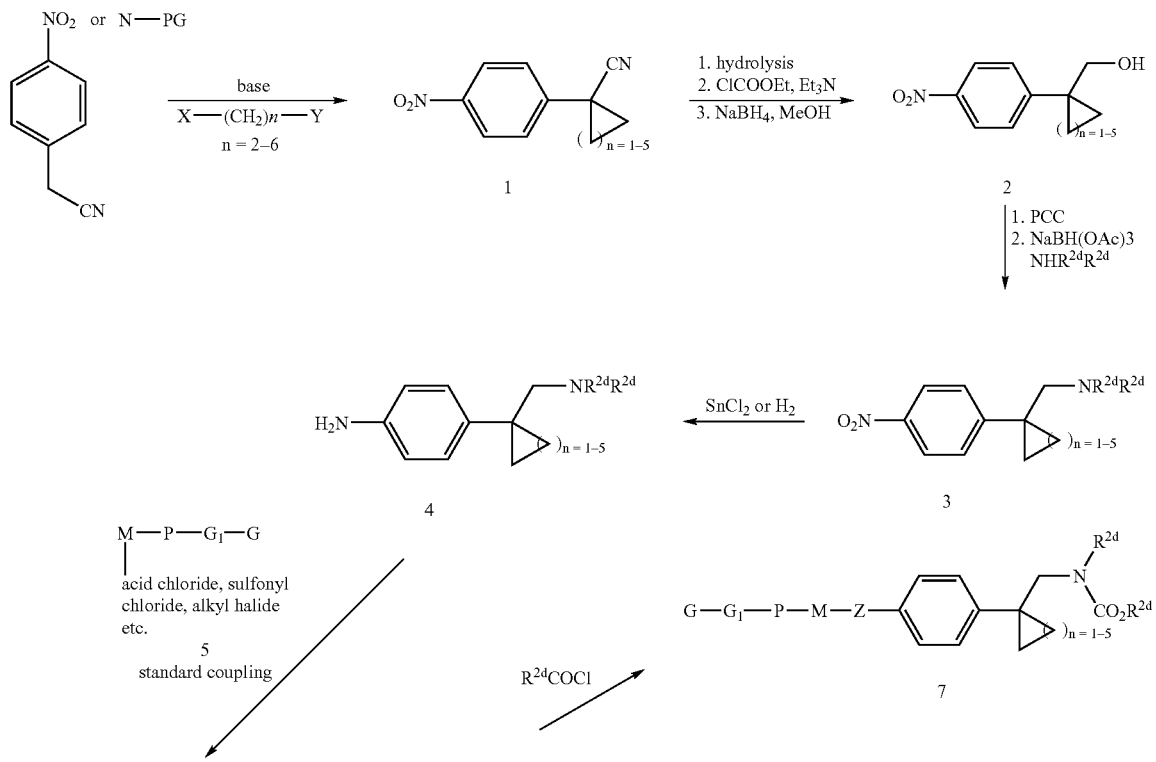

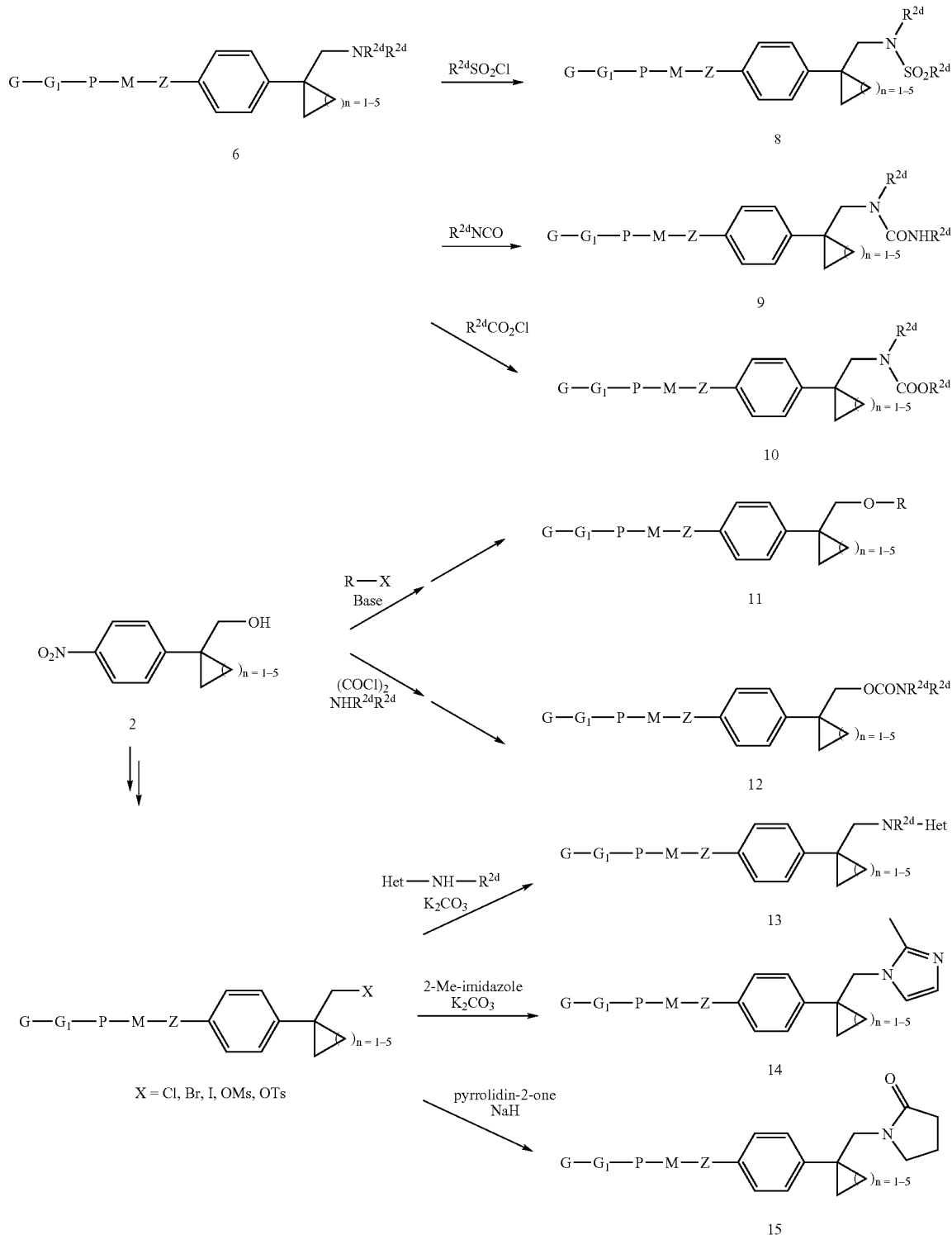

Other compounds of the present invention where Y is a cycloalkyl derivative can be prepared using commercial available 1-phenylcycloalkylcarboxylic acids (or 1-phenylcycloalkylcarbonitriles) as the starting material as illustrated in Scheme 3. Thus, nitration, followed by reduction of the $NO_2$ group and protection of the acid group can provide the A-B precursor 16, which can be coupled with 5 using standard coupling conditions to provide 17. Alternatively, iodination will provide the desired para-substituted compound 18, which can in turn be transformed to the amine 16 via Buchwald palladium-catalyzed amination (*Tetrahedron Lett.* 1997, 38, 6367–6370) and the acid 19 via paladiumcatalyzed carboxylation (CO, Pd(OAc)2, dppf). Additional Z-linkers to the A-B intermediates can be synthesized by chemical manipulation of the amino and carboxylic acid functionality in 16 and 19, respectively. Compound 19 can be homologated via the Arndt-Eistert methodology to afford other A-B intermediates in 20. Alternatively, the acid functionality in 19 can be reduced to the alcohol that in turn can be converted to a variety of A-B intermediates 20 by procedures known to those skilled in the art. Further elaboration of these intermediates using the methods described above and by those skilled in the art should provide compounds of the present invention.

Other compounds of the present invention where Y is a cycloalkyl derivative can be prepared using organometalic reagents (Zn, Mg, etc) 21 as starting materials as shown in Scheme 4. Reaction of 21 with properly substituted cycloalkyl halides 22 (X=Cl, Br, I, OMs, OTs, etc.) using $Pd(dba)_2$/1,2-bis(diphenylphosphino)ethane (dppe) or $NiCl_2(PPh_3)_2$ as catalyst system will provide intermediate 23. Alternatively, Grignard reaction of 21 with cycloalkyl ketones will provide intermediate 24. Further elaboration of 23 and 24 using the methods described above and by those known in the art should provide compounds of the present invention.

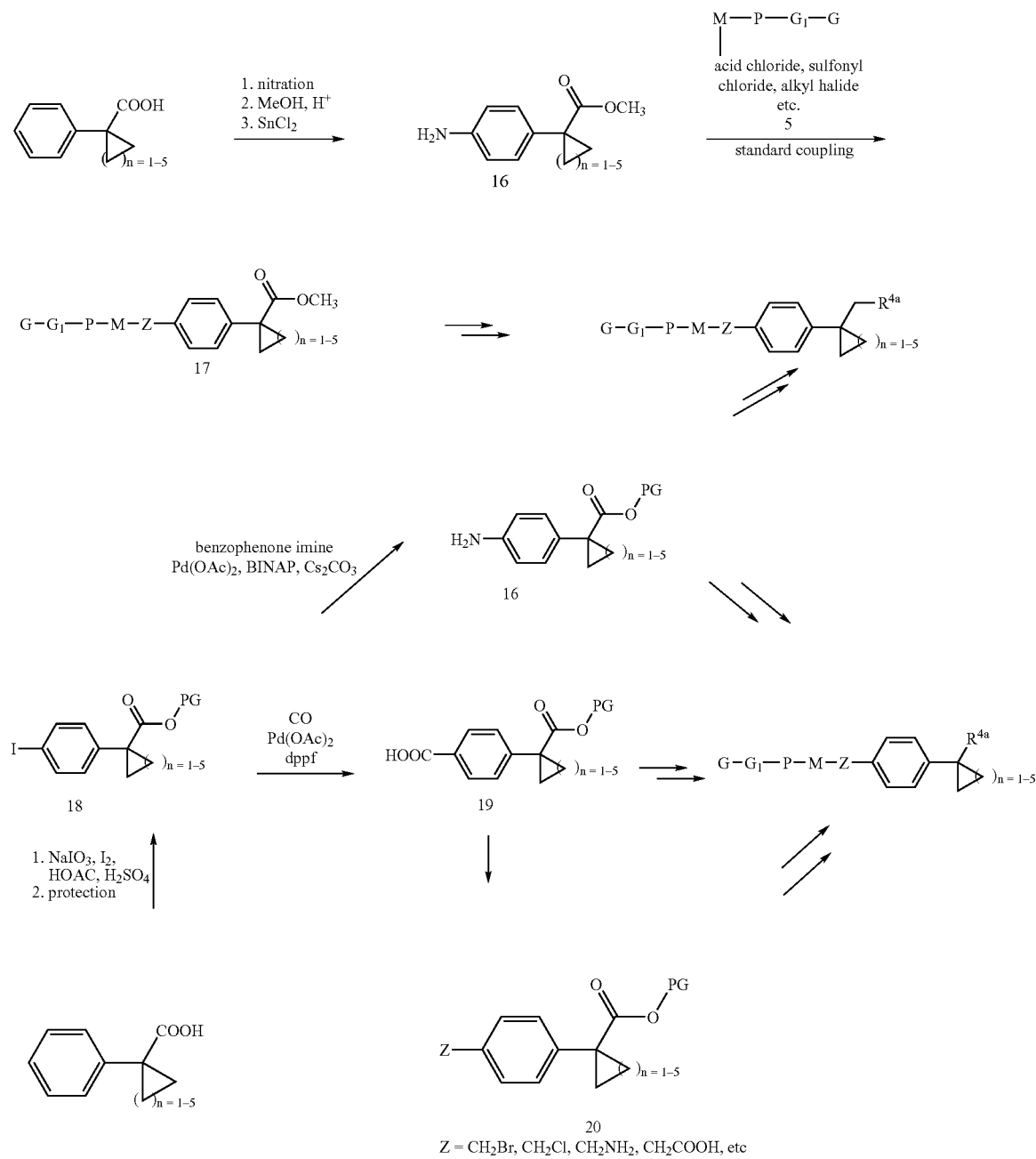

Scheme 4

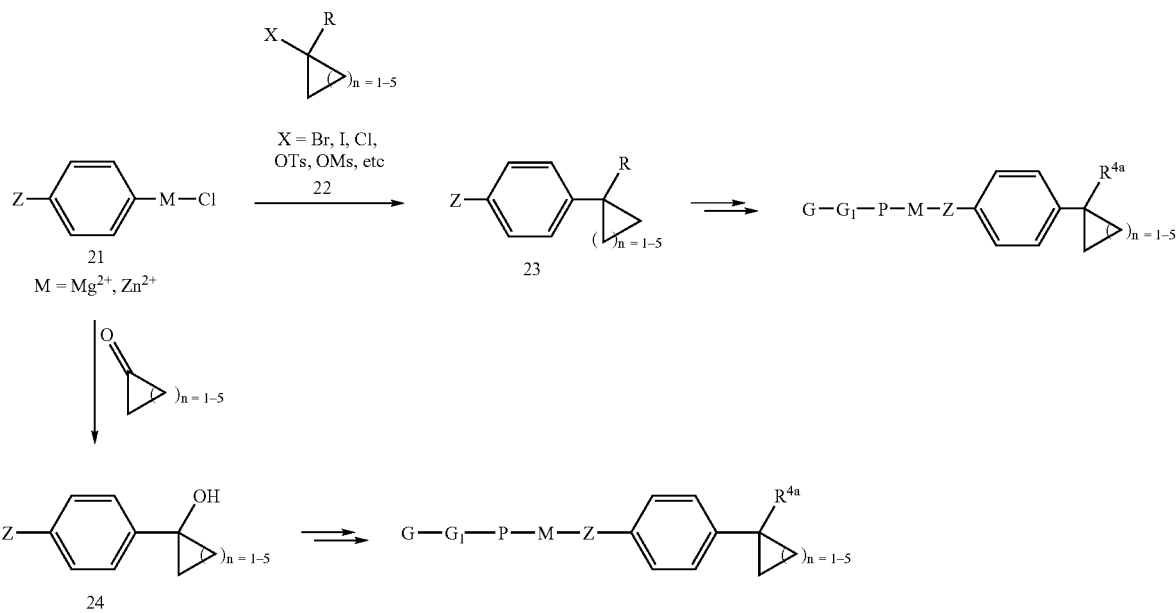

Compounds of formula I where Y is a pyrrolidine or piperidine derivative can be prepared as shown in Scheme 5. Thus, phenylcyanoacetate can be alkylated with X—(CH$_2$)$_n$—Cl (X, Y=Br, I, OMs, OTs, etc, n=2,3) to provide the chloronitrile 25, which can be reduced to the corresponding primary amine, followed by cyclization in refluxing EtOH to form 3-pyrrolidine or 3-piperdine derivatives 26. Alkylation or reductive amination can provide the N-substituted intermediate 27. Further elaboration using the methods described above and by those skilled in the art should provide compounds of the present invention.

Scheme 5

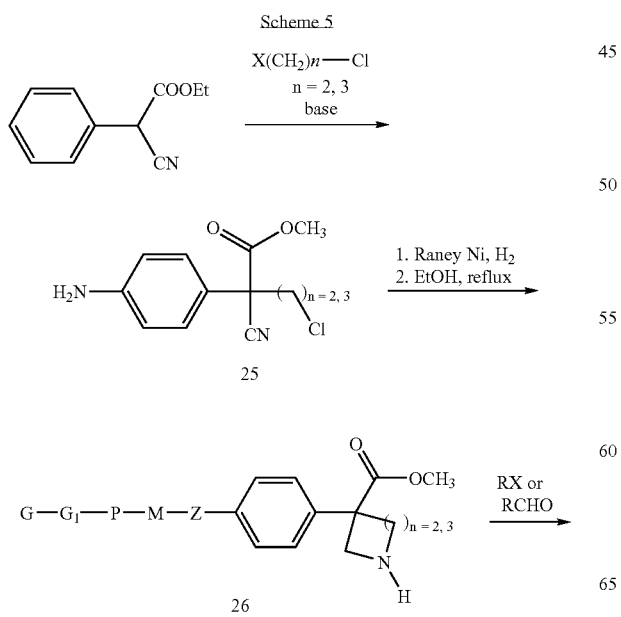

-continued

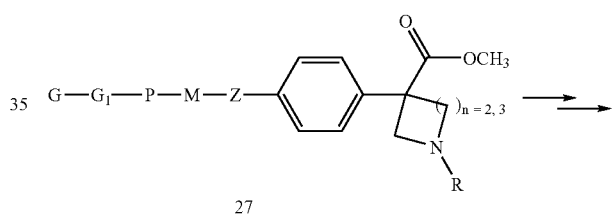

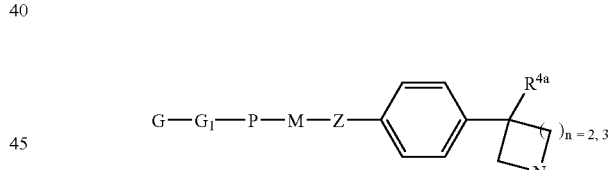

Compounds of formula I where Y is a pyrrolidine derivative can also be prepared as illustrated in Scheme 6. The Grignard reaction of 1-substituted 4-piperidone 28 with the appropriate arylmagnesium halide followed by dehydration will give tetrahydropyridine derivative 29. Epoxidation, followed by rearrangement with heating in boron trifluroride etherate (Chem. Pharm. Bull. 28(5), 1387–1393 (1980)) will provide pyrrolidine aldehyde 30. Alternatively, radical cyclization of alkyl azide 31 (*Tetrahedron Lett.* 1997, 38, 3915–1918) can provide the pyrrolidine intermediate 32. Further elaboration of these intermediates using the methods described above and by those skilled in the art should provide compounds of the present invention.

Scheme 6

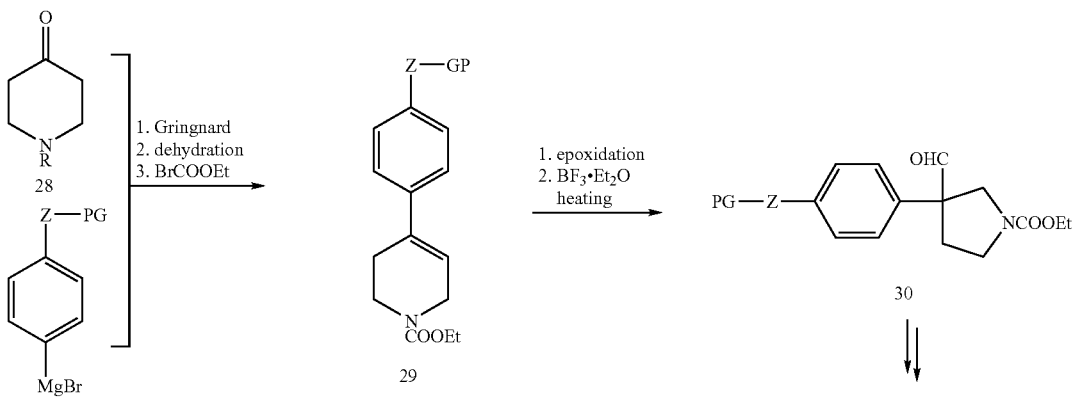

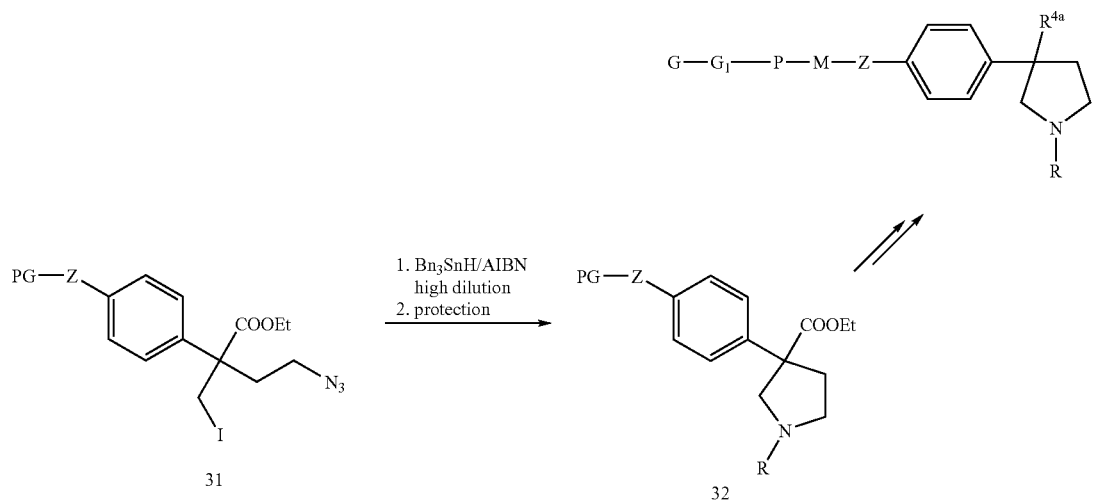

Compounds of formula I where Y is a 4-piperidine derivative can be prepared using 2-aryl acetonitriles 33 as starting materials as shown in Scheme 7. Dialkylation of 33 with bromoacetaldehyde dimethyl acetal, followed by hydrolysis of the acetals and reductive amination will give the 4-aryl-4-cyanopiperidine 34. Further elaboration of these intermediates using the methods described above and by those skilled in the art should provide compounds of the present invention.

Scheme 7

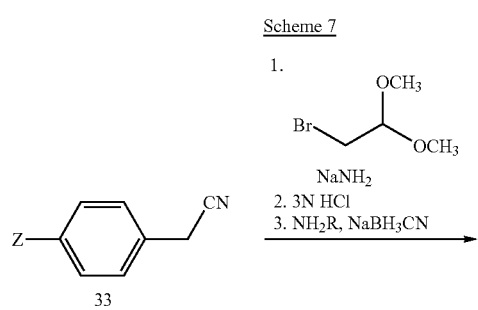

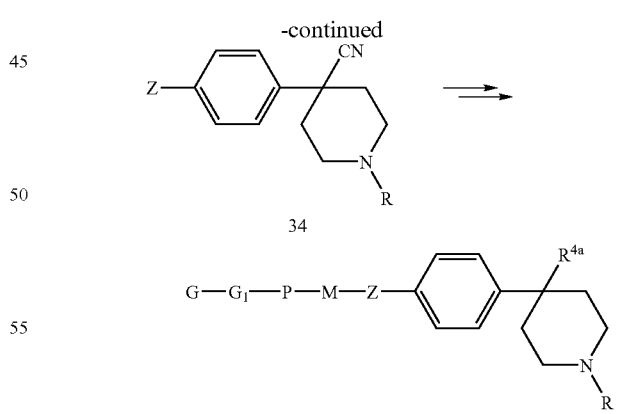

Compounds of formula I where Y is a 4-tetrahydrfuran derivative can be prepared using diol 35 as the starting material as illustrated in Scheme 8. Cyclization of 35 with HBr will give the 4-aryl-4-substituted trahydrofuran 36. Further elaboration using the methods described above and by those skilled in the art should provide compounds of the present invention.

Scheme 8

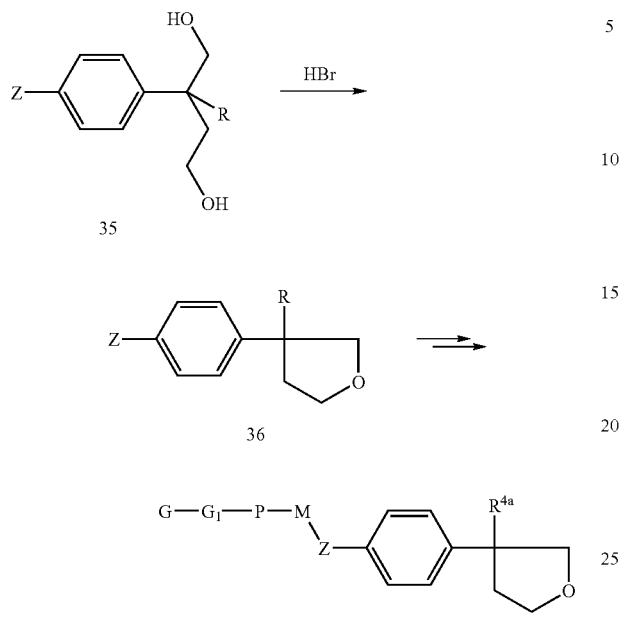

Compounds of formula I where Y is a 4-tetrahydropyran derivative can be prepared using 2-aryl acetonitriles 33 as starting materials as shown in Scheme 9. Alkylation of 33 with di-2-chloroethyl ether will give the 4-aryl-4-cyanotetrahydropyran 37. Further elaboration using the methods described above and by those skilled in the art should provide compounds of the present invention.

Scheme 9

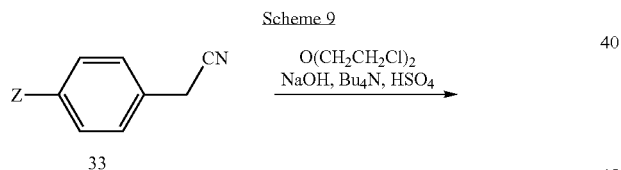

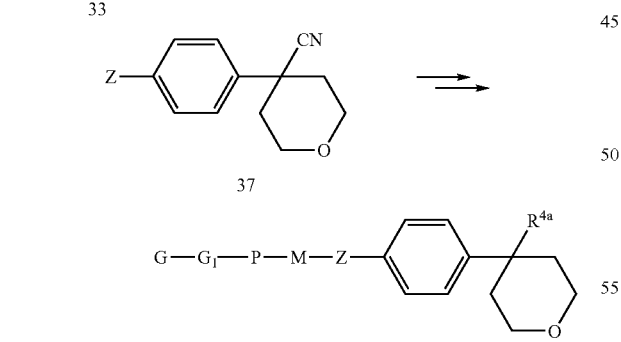

Compounds of formula I where Y is a lactam derivative can be prepared using intermediate 38 as the starting material as shown in Scheme 10. Reduction of $NO_2$ group or nitrile group will provide the primary amine 39, which can be coupled intramolecularly with the acid or ester to form the lactam 40. Further elaboration using the methods described above and by those skilled in the art should provide compounds of the present invention.

Scheme 10

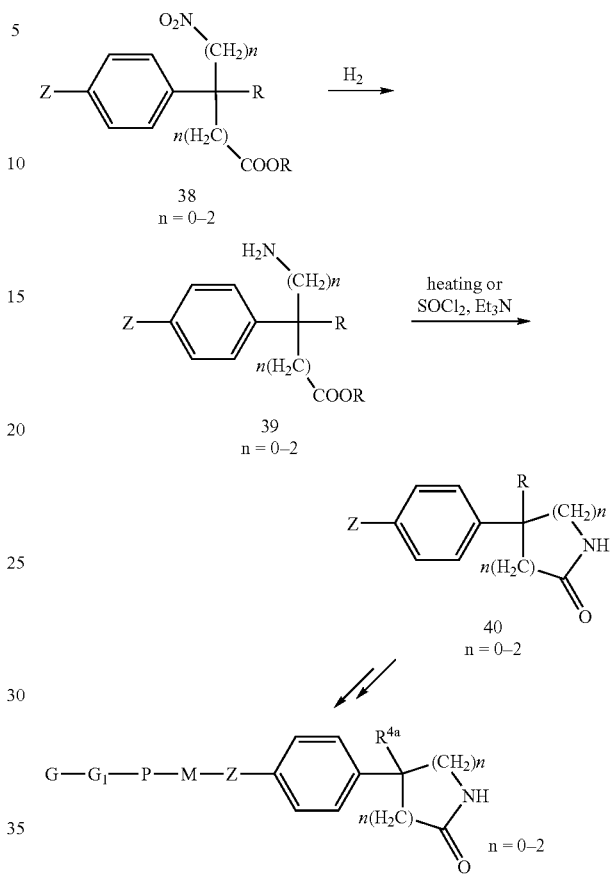

Aminopyridyl and aminopyrimidyl A-B analogs (see structures in Scheme 11) can be prepared using routes similar to those of Schemes 2–10 and by those skilled in the art. These intermediates can then be further manipulated to compounds of this invention with formula I via procedures previously described.

Scheme 11

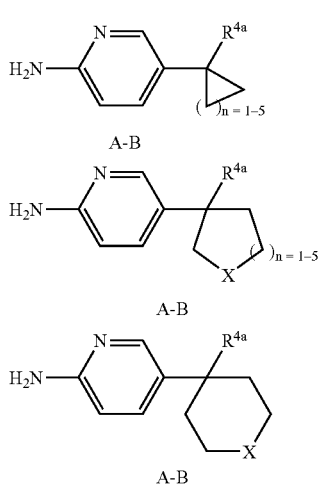

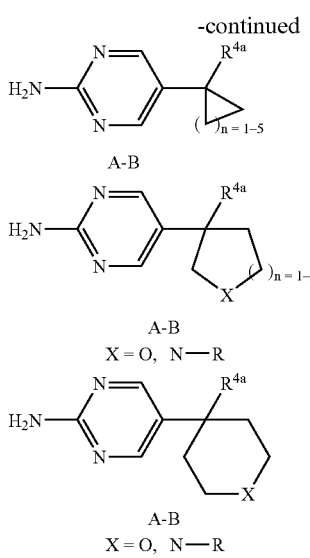

Compounds of formula I (Scheme 1) where P is fused onto ring M can be prepared as outlined in Schemes 12 and 13, and via standard methods known to those skilled in the art. The ester or nitrile intermediates 41 illustrated in these Scheme 12 can be subjected to alkylation conditions, followed by other manipulations as described in Schemes 2–10. Further elaboration of intermediates 42 to incorporate the appropriate $R^{4a}$ groups using the methods described above and by those skilled in the art should provide compounds of the present invention.

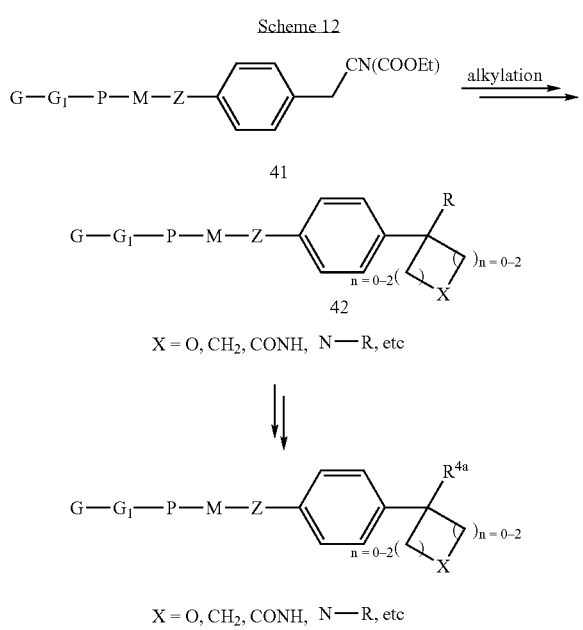

Scheme 13 illustrates the synthesis of compounds of formula I (Scheme 1) when P-M moiety 43 is a bicyclic lactam moiety. Thus, the iodo A-B intermediate 44 will react with 43 under Buchwald modified Ullman reaction (*J. Am. Chem. Soc.* 2001, 123, 7727) using CuI and 1,2-cyclohexyldiamine or 1,10-phenanthroline as the catalyst system to provide 45 in high yields. Further elaboration of 45 to incorporate the appropriate $R^{4a}$ groups art should provide compounds of the present invention by using the methods described above and by those skilled in the art.

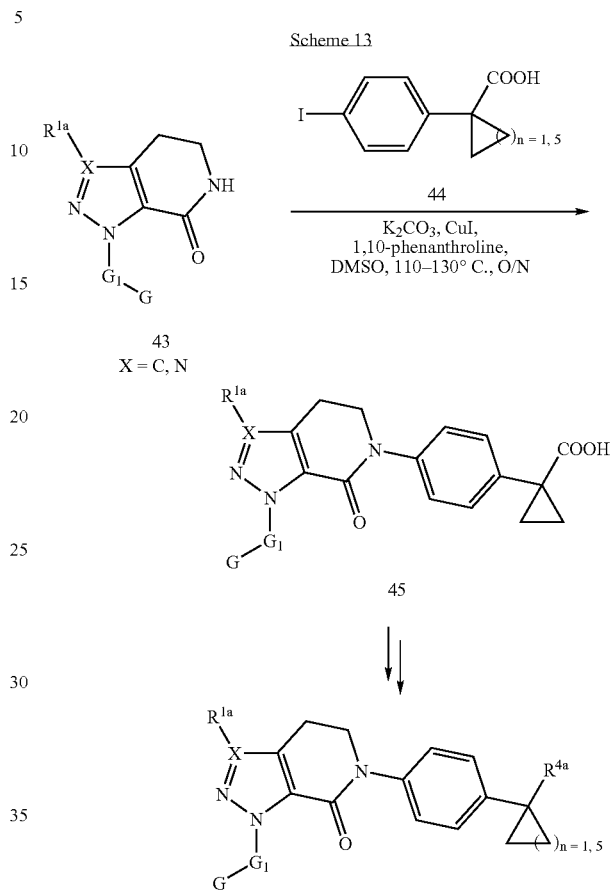

Schemes 2–13 describe how to make the A-B moieties of the present invention and how to couple them to prepare compounds of the present invention. Schemes 2–13 describe A-B wherein B is Y—$R^{4a}$ and Y is a cycloalkyl or heterocyclyl. Compounds of the present invention wherein Y is $CY^1Y^2$ can be made analogously to the cycloalkyl/heterocyclyl compounds of Schemes 2–13. For example, in Scheme 2, instead of intermediate 1 being a cycloalkyl intermediate, it can be $Y^1Y^2$ disubstituted intermediate. This intermediate could be made by a number of methods including di-substituting the starting 4-nitrophenylacetonitrile by reaction with a base and a $Y^1$-leaving group and a $Y^2$-leaving group. One of ordinary skill in the art would recognize that other routes to the $Y^1Y^2$ disubstituted intermediate are available. The remainder of the chemistry shown in Scheme 3 will then follow.

In Scheme 3, instead of use the starting 1-phenylcycloalkylcarboxylic acids or 1-phenylcycloalkylcarbonitriles of Scheme 3, one could use the corresponding $Y^1Y^2$ disubstituted intermediates. Just like in Scheme 2, these intermediates could be prepared by di-substituting a phenylcarboxylic acid or phenylcarbonitrile. One of ordinary skill in the art would recognize that other routes to these types of $Y^1Y^2$ disubstituted intermediate are also available. The remainder of the chemistry shown in Scheme 3 will then follow.

The compounds of this invention and the intermediates described above wherein the B group contains an oxidizable group can be oxidized, e.g., N to N-oxide.

In the above Schemes, the Z group may or may not be present depending on how the A-B group is coupled. The coupling portion of the A-B group could (a) be displaced by the incoming Z or M group, (b) become the Z group, or (c) be incorporated into ring M.

The remaining portions of the compounds of the present invention, G-G$_1$-P-M-Z, G-G$_1$-M-P-Z, G-G$_1$-P-M, G-G$_1$-M-P, G-G$_1$-M-Z, and G-G$_1$-M, can be prepared using methods known to those of ordinary skill in the art. All of the following patents and publications are incorporated herein by reference. For compounds wherein ring P is absent and ring M is a 5-, 6-, or 7-membered ring, one of ordinary skill in the art can look to U.S. Pat. No. 5,939,418, U.S. Pat. No. 5,925,635, U.S. Pat. No. 6,057,342, U.S. Pat. No. 6,187,797, U.S. Pat. No. 6,020,357, U.S. Pat. No. 6,060,491, U.S. Pat. No. 5,998,424, U.S. Pat. No. 6,191,159, WO98/57951, WO99/32454, WO00/039108, WO00/059902, WO01/32628, WO01/005785, WO02/00651, WO02/102380, and WO02/00647 for starting materials and intermediates to which the present B and/or A-B groups can be coupled. For compounds wherein ring P is fused to ring M (i.e., a bicyclic moiety is present), one of ordinary skill in the art can look to WO00/39131, WO02/094197, U.S. Ser. No. 10/104,467, U.S. Ser. No. 10/105,477, and WO02/00655 for starting materials and intermediates to which the present B and/or A-B groups can be coupled.

For compounds wherein G is a ring substituted with a basic moiety, one of ordinary skill in the art can look to U.S. Pat. No. 5,939,418, U.S. Pat. No. 5,925,635, U.S. Pat. No. 6,057,342, U.S. Pat. No. 6,187,797, U.S. Pat. No. 6,020,357, U.S. Pat. No. 6,060,491, U.S. Pat. No. 6,191,159, WO98/57951, WO99/32454 WO00/059902, WO01/32628, WO00/39131, WO02/00651, WO02/102380, WO02/094197, U.S. Ser. No. 10/104,467, and U.S. Ser. No. 10/105,477 for starting materials and intermediates to form the present G-G$_1$-P-M-Z, G-G$_1$-M-P-Z, G-G$_1$-P-M-Z-A, and/or G-G$_1$-M-P-Z-A groups to which the present B and/or A-B groups can be coupled. For compounds wherein G is a ring substituted with a non-basic group, one of ordinary skill in the art can look to U.S. Pat. No. 5,998,424, WO00/39131, WO00/059902, WO01/32628, WO02/00651, WO02/102380, WO02/094197, U.S. Ser. No. 10/104,467, and U.S. Ser. No. 10/105,477 for starting materials and intermediates to form the present G-G$_1$-P-M-Z, G-G$_1$-M-P-Z, G-G$_1$-P-M-Z-A, and/or G-G$_1$-M-P-Z-A groups to which the present B and/or A-B groups can be coupled. For compounds wherein G is a bicyclic moiety, one of ordinary skill in the art can look to WO98/57951 WO00/039108, WO00/39131, WO02/00651, WO02/102380, WO02/094197, U.S. Ser. No. 10/104,467, and U.S. Ser. No. 10/105,477 for starting materials and intermediates to form the present G-G$_1$-P-M-Z, G-G$_1$-M-P-Z, G-G$_1$-P-M-Z-A, and/or G-G$_1$-M-P-Z-A groups to which the present B and/or A-B groups can be coupled. For compounds wherein A is an indoline or similar bicycle, one of ordinary skill in the art can look to WO01/005785 for starting materials and intermediates to which the present B group can be coupled or from which the present A-B groups can be formed. Scheme 14 illustrates some of the numerous pyrrole intermediates that can be used to prepare compounds of the present invention (R$^z$ is the point of attachment for Z-A-B and can be H, a protecting group, a group modifiable to Z or Z-A, Z, Z-A, or A). These intermediates are described in the above-noted patents and publications.

Scheme 14

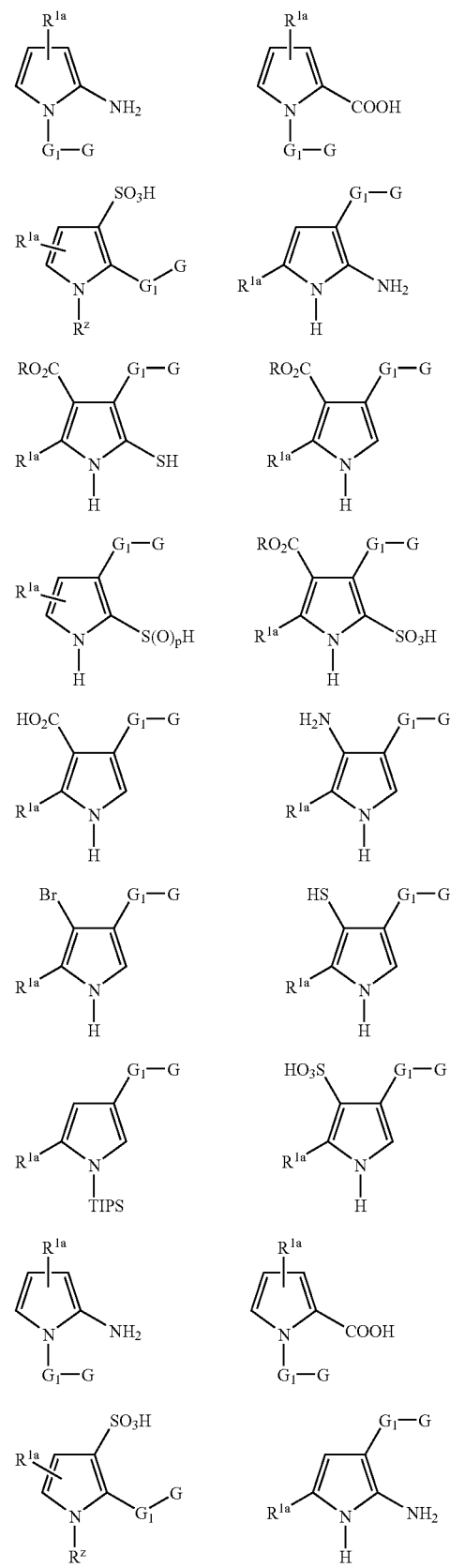

-continued

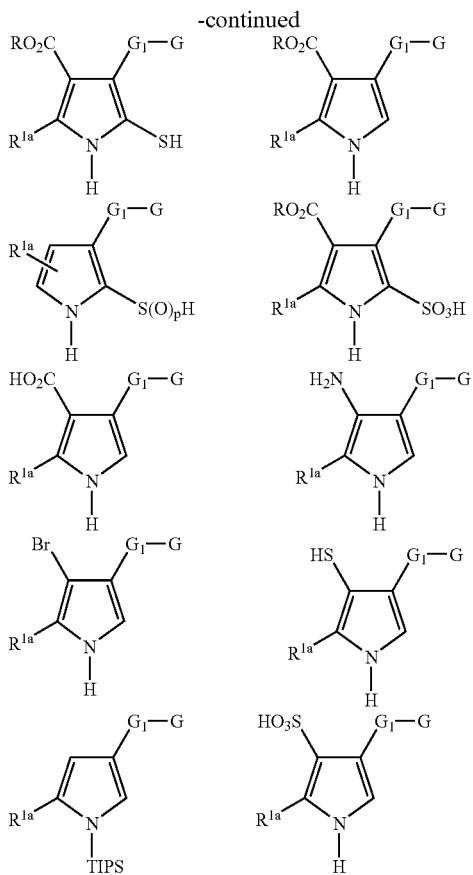

Scheme 15 illustrates some of the numerous imidazole, triazole, and tetrazole intermediates that can be used to prepare compounds of the present invention. These intermediates are described in the above-noted patents and publications. In Scheme 15, V is nitro, amino, thio, hydroxy, sulfonic acid, sulfonic ester, sulfonyl chloride, ester, acid, or halide. In Scheme 15, U is aldehyde, ester, acid, amide, amino, thiol, hydroxy, sulfonic acid, sulfonic ester, sulfonyl chloride, or methylene halide.

Scheme 15

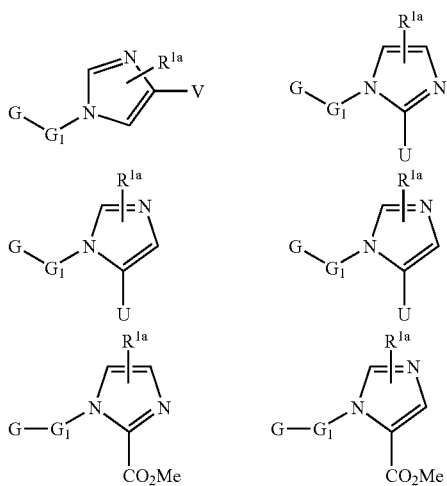

-continued

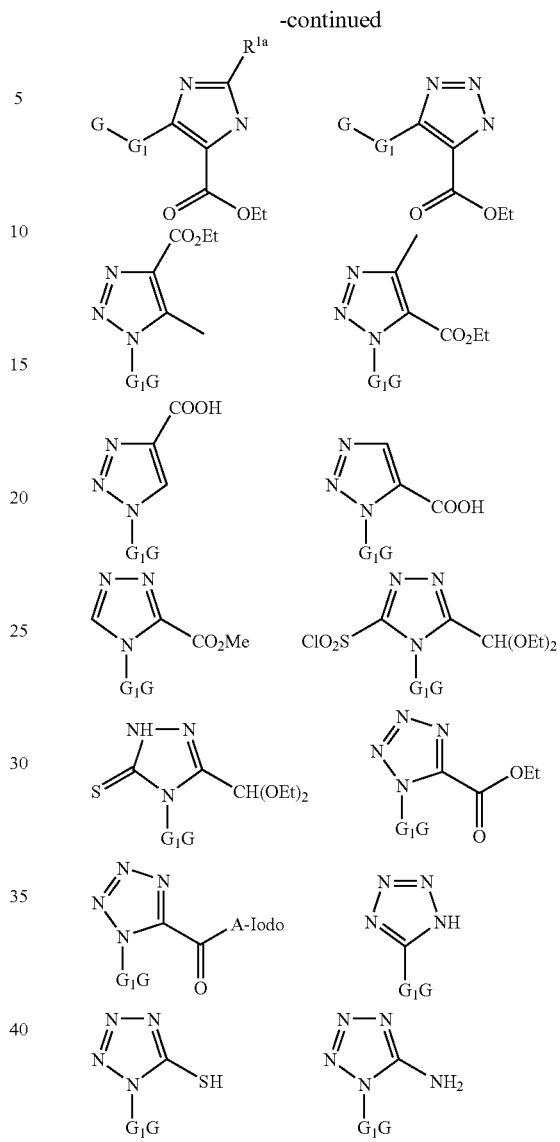

Scheme 16 shows some of the numerous pyrazole intermediates that can be used to prepare compounds of the present invention. These intermediates are described in the above-noted patents and publications.

Scheme 16

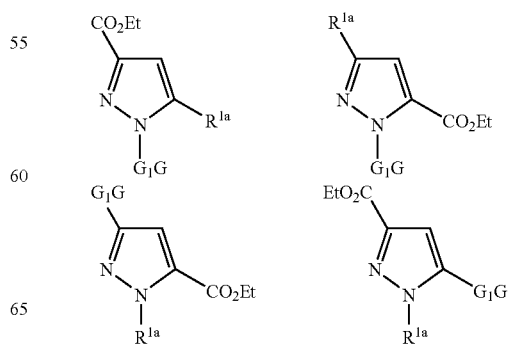

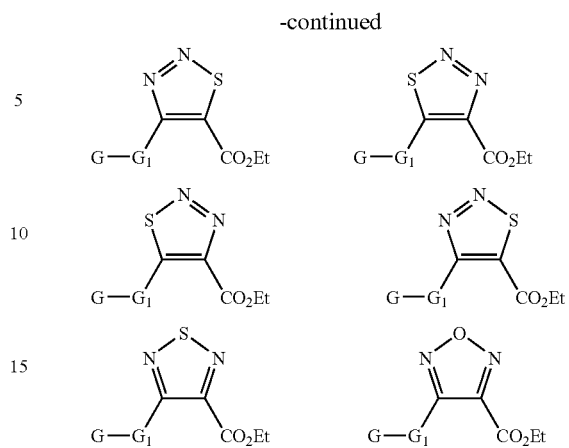

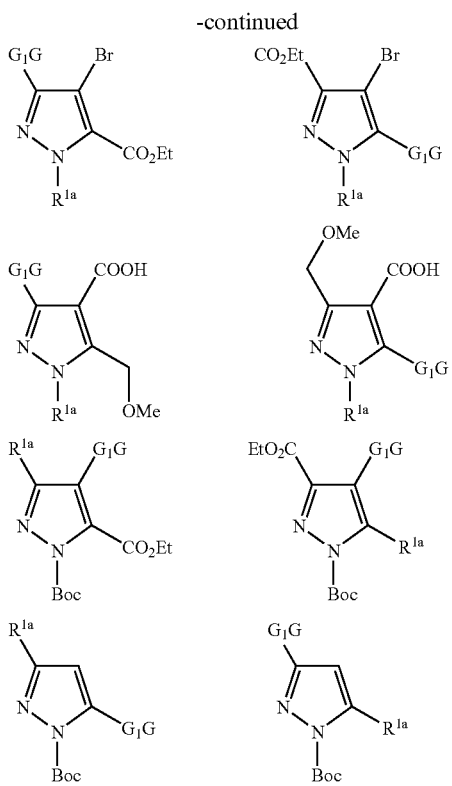

Scheme 17 depicts some of the numerous oxazole, thiazole, isoxazole, oxadiazole, and thiadiazole intermediates that can be used to prepare compounds of the present invention. These intermediates are described in the above-noted patents and publications. In Scheme 17, V is nitro, amino, ester, or acid.

Scheme 18 illustrates two intermediates useful for making a compound of the present invention wherein ring P is fused to ring M. Scheme 18 also illustrates a number of bicyclic compounds that can be made from these intermediates or derivatives thereof. These intermediates and their modification are described in the above-noted patents and publications.

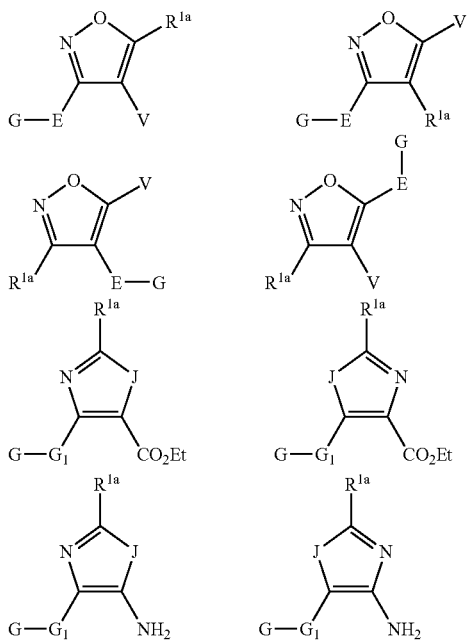

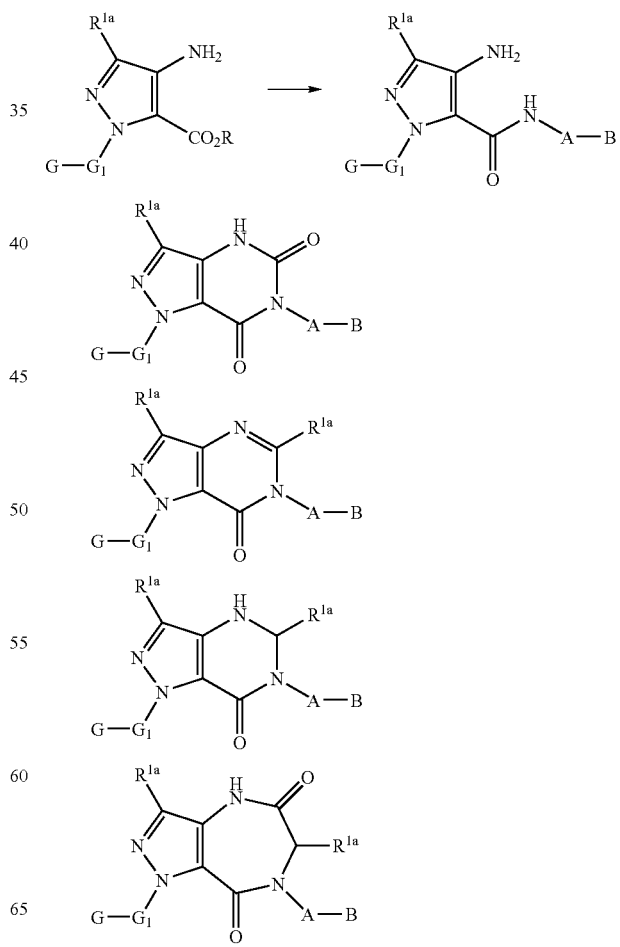

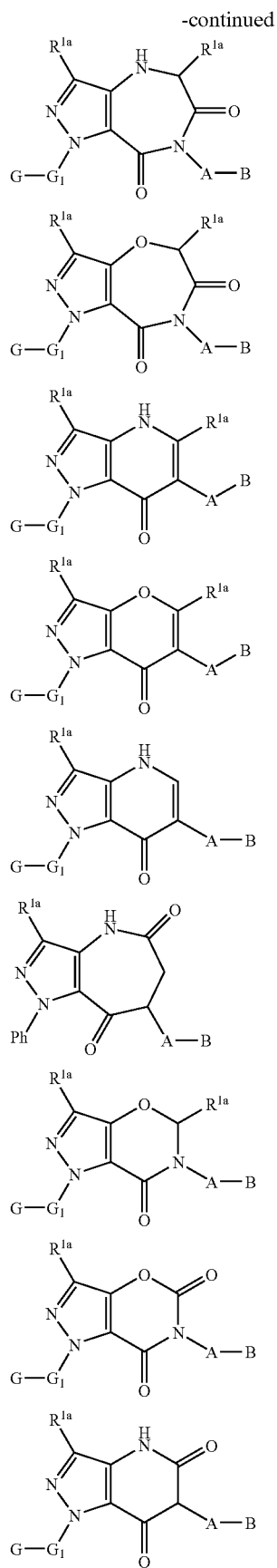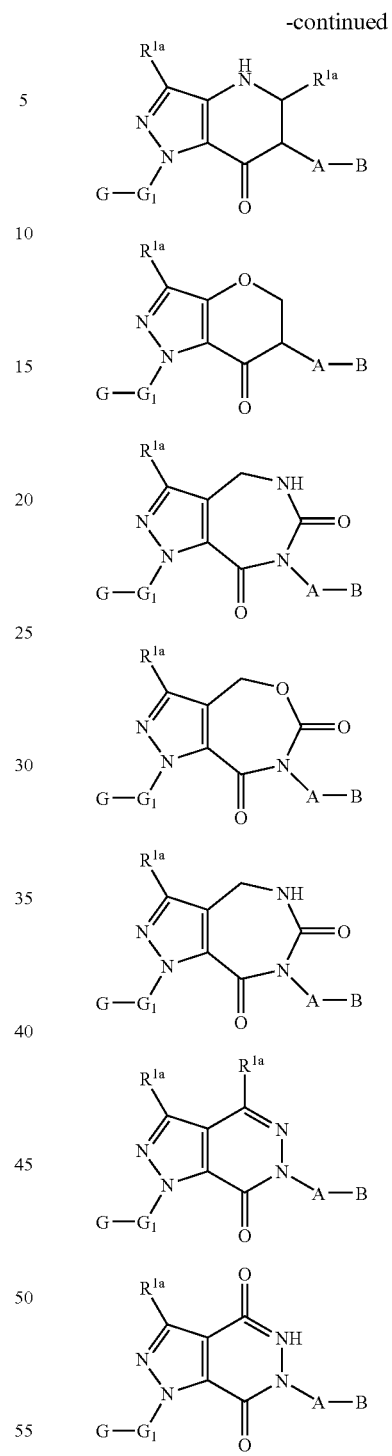

Scheme 19 depicts another intermediate useful for making a compound of the present invention wherein ring P is fused to ring M. Scheme 19 also illustrates a number of bicyclic compounds that can be made from this intermediate or derivatives thereof (e.g., the corresponding cyclohexenone). In Scheme 19, U is OH or morpholine and V is H or $C(O)R^{1a}$. This intermediate, derivatives thereof, and their modification are described in the above-noted patents and publications.

Scheme 19

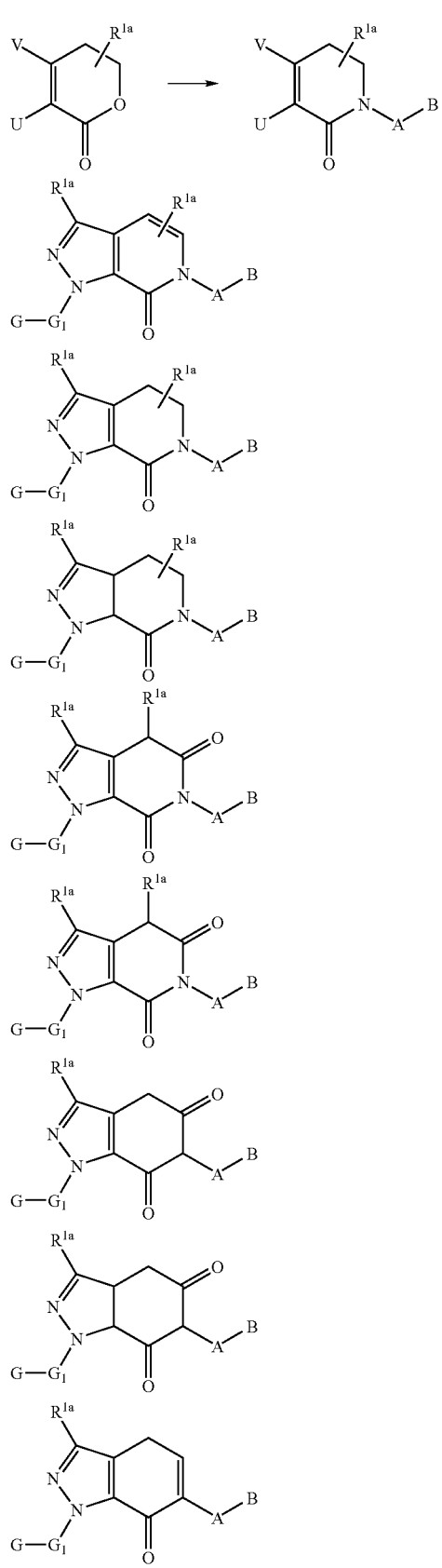

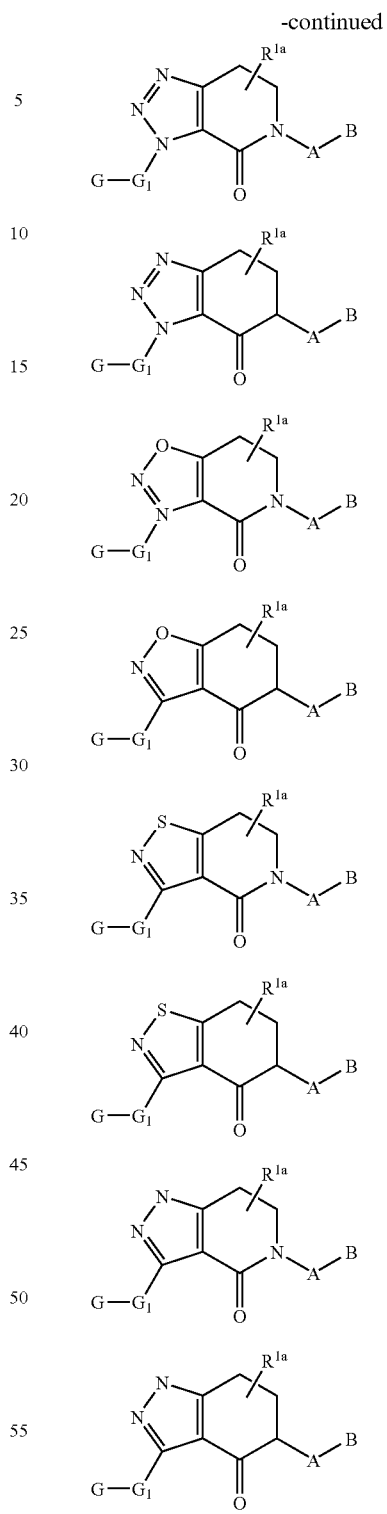

Scheme 20 shows another intermediate useful for making a compound of the present invention wherein ring P is fused to ring M. Scheme 20 also illustrates a number of bicyclic compounds that can be made from this intermediate or derivatives thereof. This intermediate, derivatives thereof, and their modification are described in the above-noted patents and publications.

Scheme 20

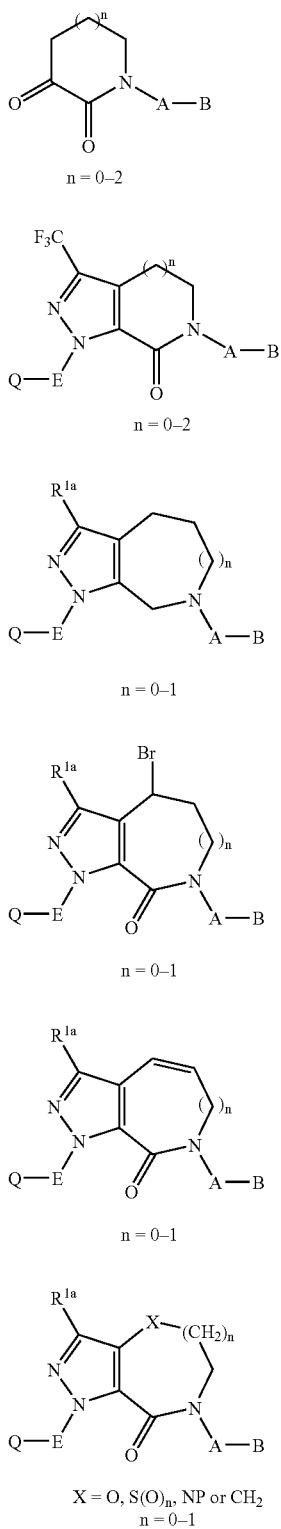

n = 0–2 n = 0–2 n = 0–1 n = 0–1 n = 0–1

X = O, S(O)$_n$, NP or CH$_2$
n = 0–1

Scheme 21 illustrates a number of other bicyclic rings that are considered to be part of the present bicyclic group, rings P-M. Scheme 21 also describes a method of converting the shown rings to compounds of the present invention. As one of ordinary skill in the art would recognize, this method would be applicable to other heterobicyclics not shown.

Scheme 21

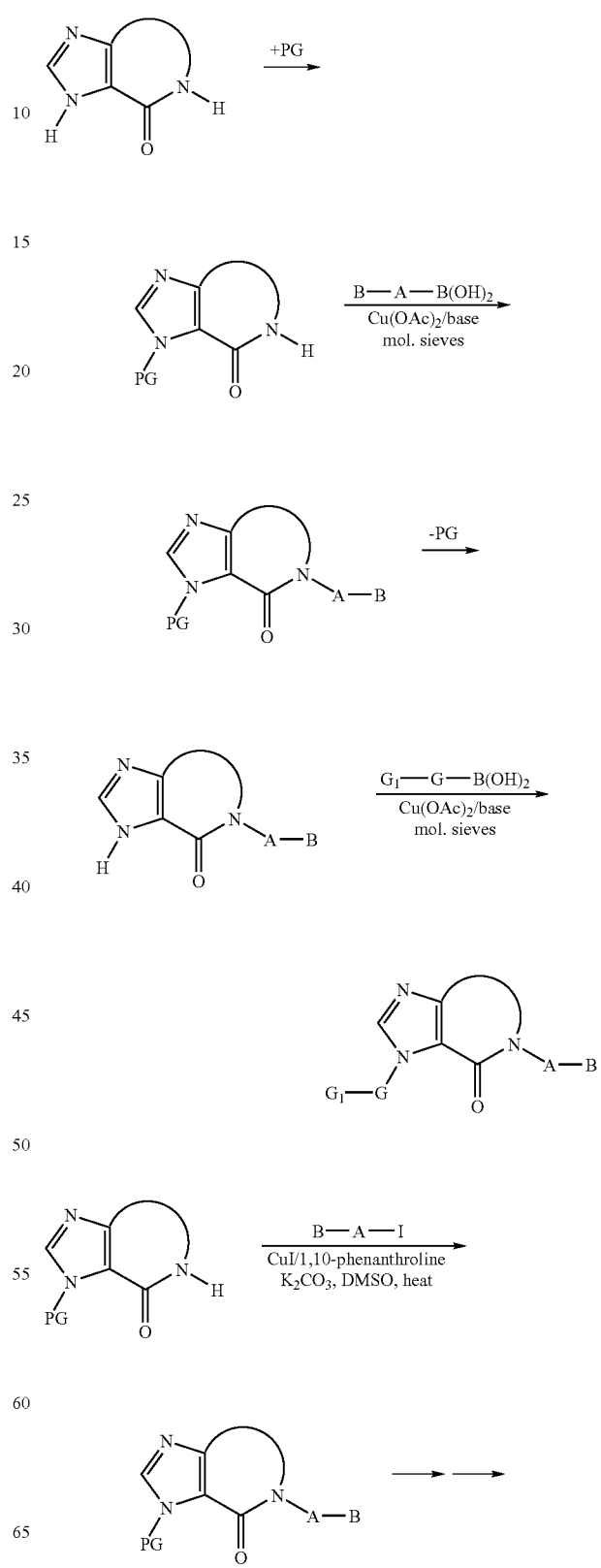

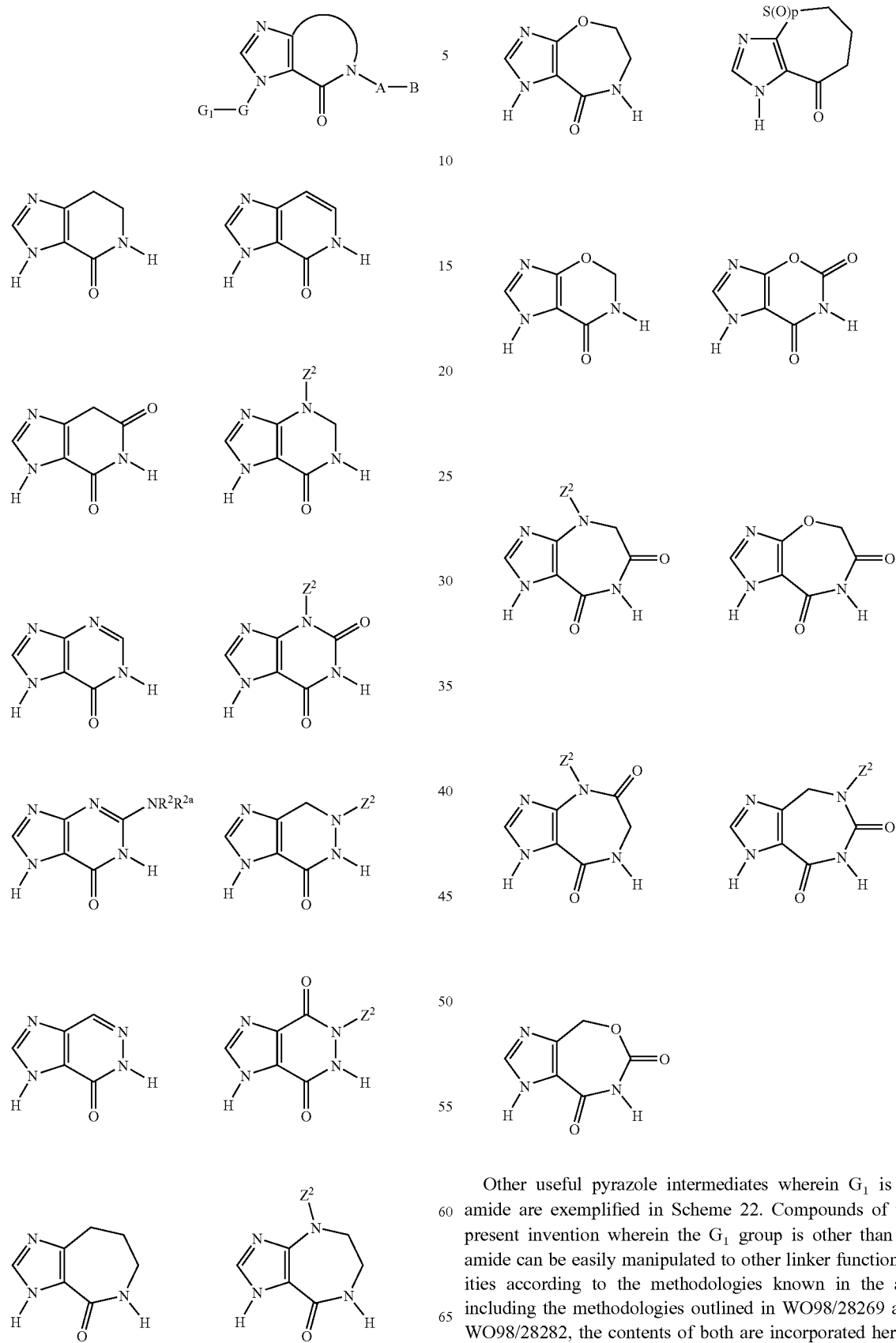

Other useful pyrazole intermediates wherein $G_1$ is an amide are exemplified in Scheme 22. Compounds of the present invention wherein the $G_1$ group is other than an amide can be easily manipulated to other linker functionalities according to the methodologies known in the art, including the methodologies outlined in WO98/28269 and WO98/28282, the contents of both are incorporated herein by reference.

Scheme 22
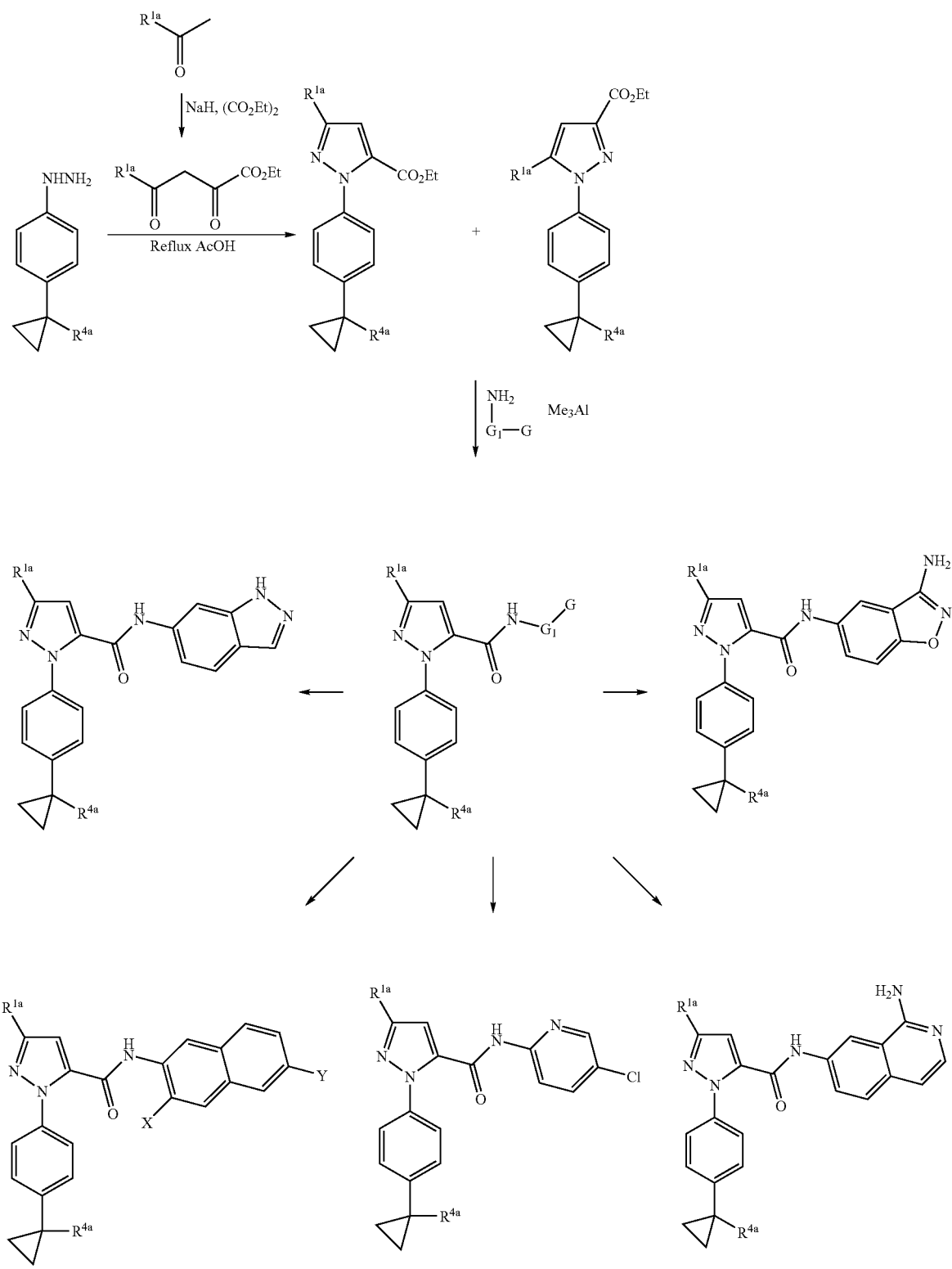
X = H, Cl, F, SO$_2$CH$_3$, SO$_2$NH$_2$, CONH$_2$
Y = H, F, or Cl Scheme 23 depicts some of the numerous 6-membered aromatic ring intermediates that can be used to prepare compounds of the present invention. These intermediates are described in the above-noted patents and publications. In Scheme 23, V is nitro, protected sulfonamide, or ester group and is a precursor of group Z of the present invention.

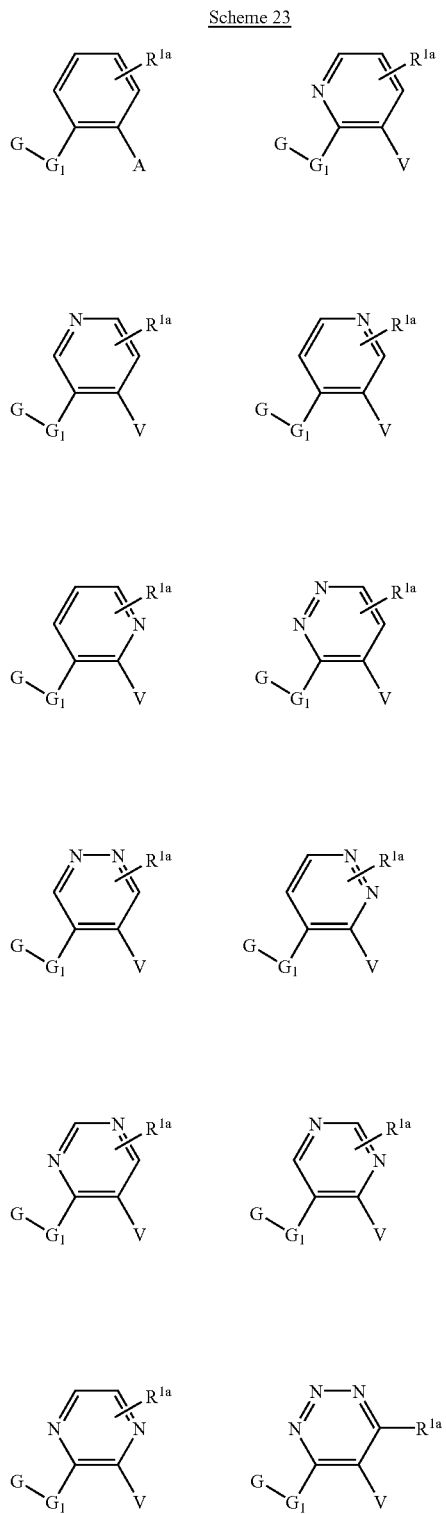

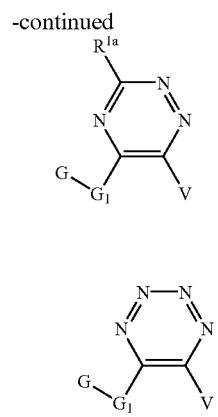

Benzo fused dihydro-pyridone intermediates of the present invention can be prepared from readily available starting materials as shown in Scheme 24.

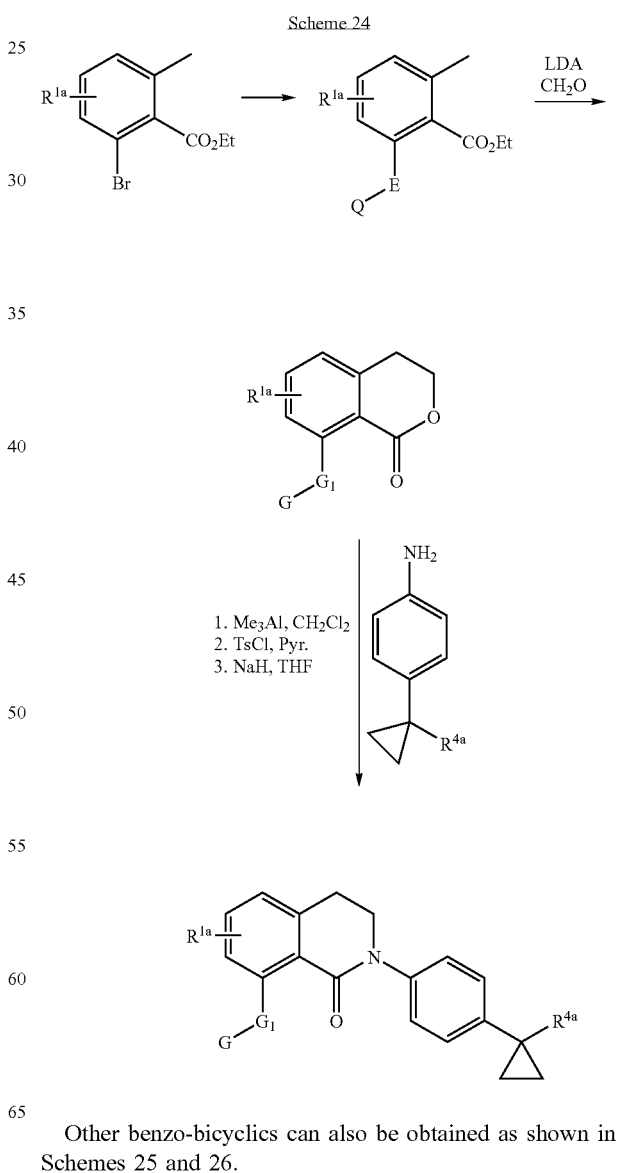

Other benzo-bicyclics can also be obtained as shown in Schemes 25 and 26.

Scheme 25
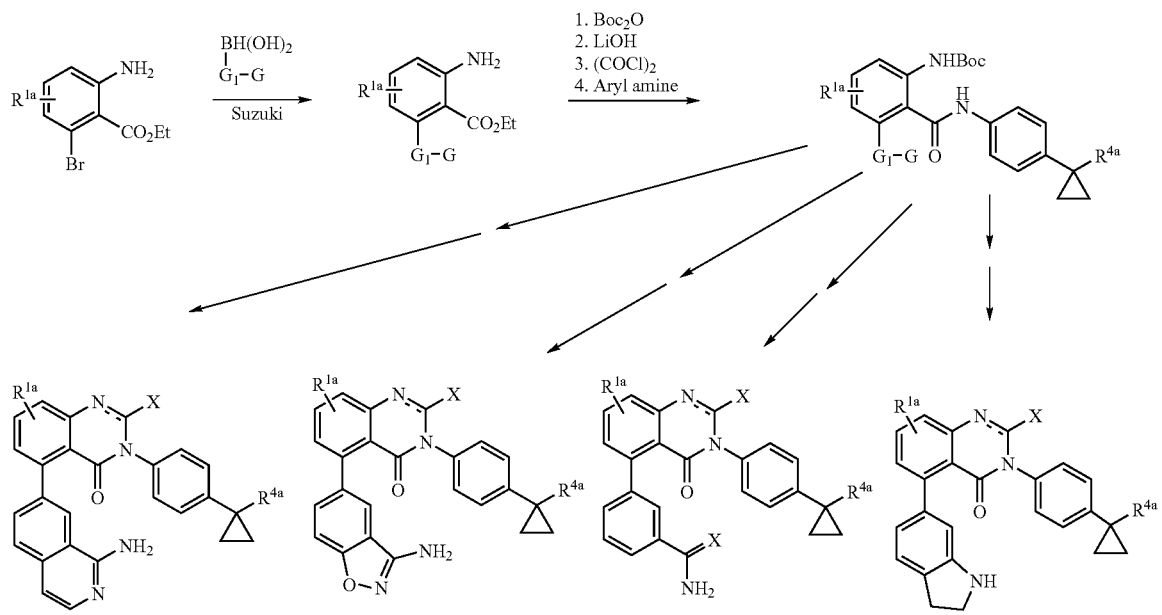
X = H, NH, O, S, NHCORR
Scheme 26
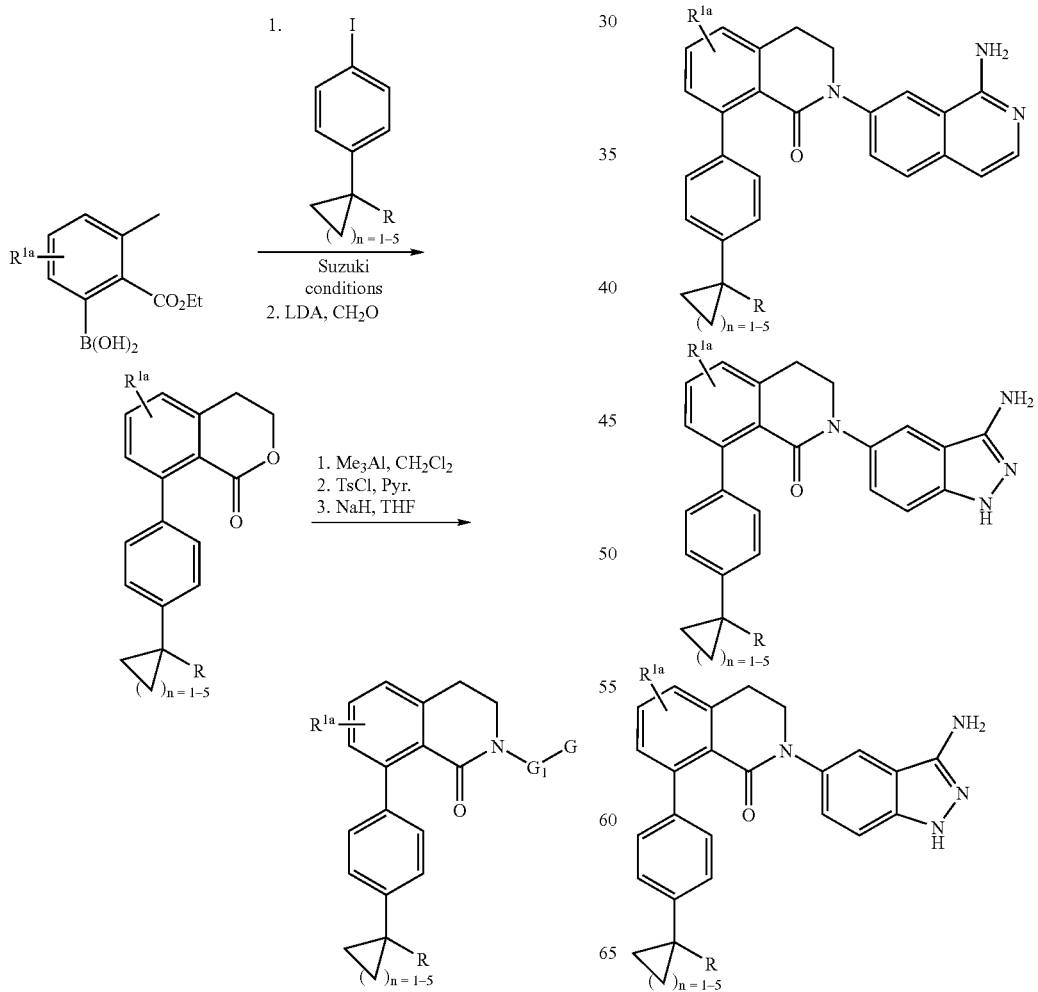

Intermediates A-B of the present invention wherein A is indoline can be prepared as shown in scheme 27. This type of intermediate can then be attached to the remainder of the desired compound as described previously. Alternatively, the indoline can be attached to the other half of the desired compound prior to formation of the carbocyclic or heterocyclic ring.

In an analogous fashion the anthranilates can be coupled with a suitable amine, aniline, or aminopyrimidyl to afford the corresponding benzamide. The benzamides can then be coupled with an appropriate B-A-V (wherein V is a acid chloride derivative, an alkyl halide, or a sulfonyl chloride) to afford additional compounds of the present invention (see scheme 29).

Scheme 27

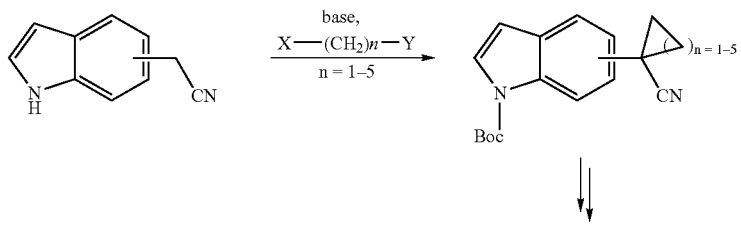

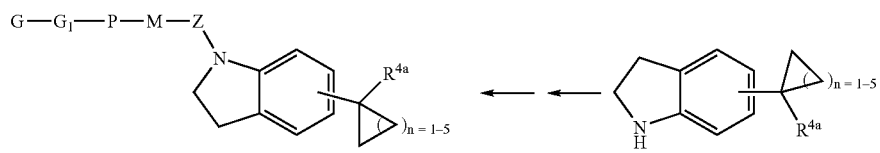

Compounds of the present invention wherein ring P is absent and ring M is a six-membered ring can be obtained as shown in scheme 28. These types of compounds can be obtained from commercially available anthranilic acids or their anthranilates. Anthranilic acids or their nitro precursors can be coupled with a suitable B-A-$NH_2$ in presence of a base such as triethyl amine, pyridine, or DMAP. Subsequent coupling with an appropriate acid chloride or aniline or aminopyridyl should afford compounds of the present invention.

Scheme 28

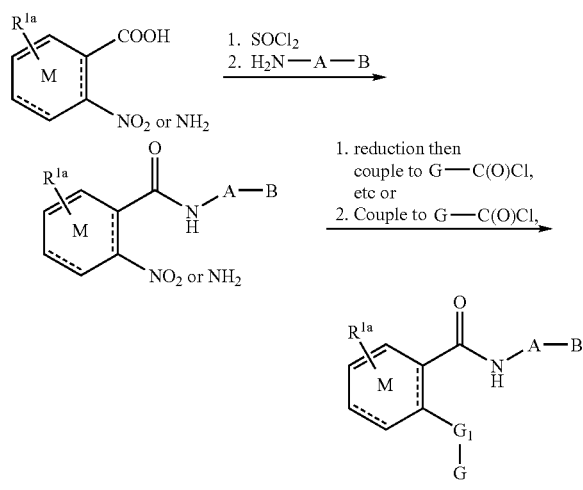

Scheme 29

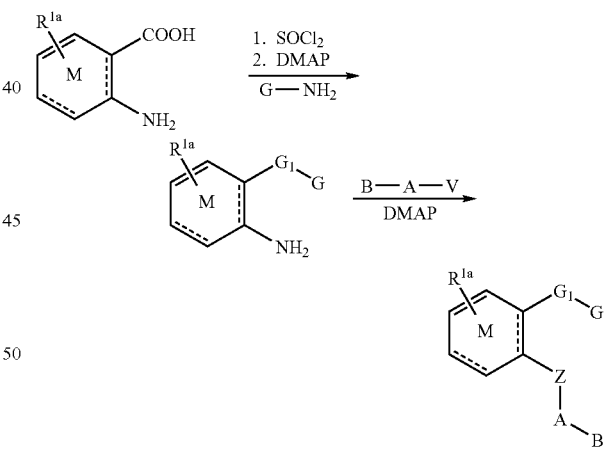

Commercially available ring M derivatives bearing a nitro and amino functionality can also be derivatized as shown above to afford bisamide analogs. In this case, coupling of the aniline with B-A-V (wherein V is an acid chloride, a sulfonyl chloride, or an alkylhalide) affords an intermediate that can be subjected to treatment with an appropriate G-U (wherein U is either an acid chloride or an alkyl halide) in presence of a suitable base such as DMAP. It should be noted that the order of addition of B-A-V and G-U can be reversed to obtain other compounds of the present invention (see scheme 30).

Scheme 30

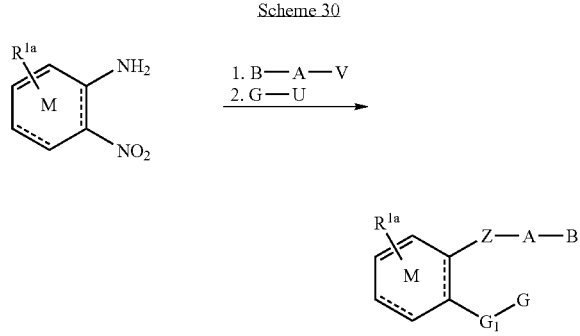

It should be noted that the syntheses shown above could be modified to use coupling intermediates such as Iodo-A-V, wherein V is an acid chloride, amino, alkylhalide, or sulfonyl chloride. These in turn could be coupled to a G-U group. The iodo intermediate could then be subjected to Ullman or Buchwald coupling as described previously to afford compounds of the present invention. The iodo intermediate could also be converted to an amine via standard Buchwald conditions to afford the corresponding anilino intermediate. This in turn could be coupled as previously described to afford compounds of the present invention.

The syntheses of bisamide compounds shown in Schemes 28–30 can also be applied to the syntheses of compounds with ring M as a 5-membered heterocycle. The bisamides can also be further converted into bicyclic pyrimidin-4-ones under acidic conditions as shown in Scheme 31.

Scheme 31

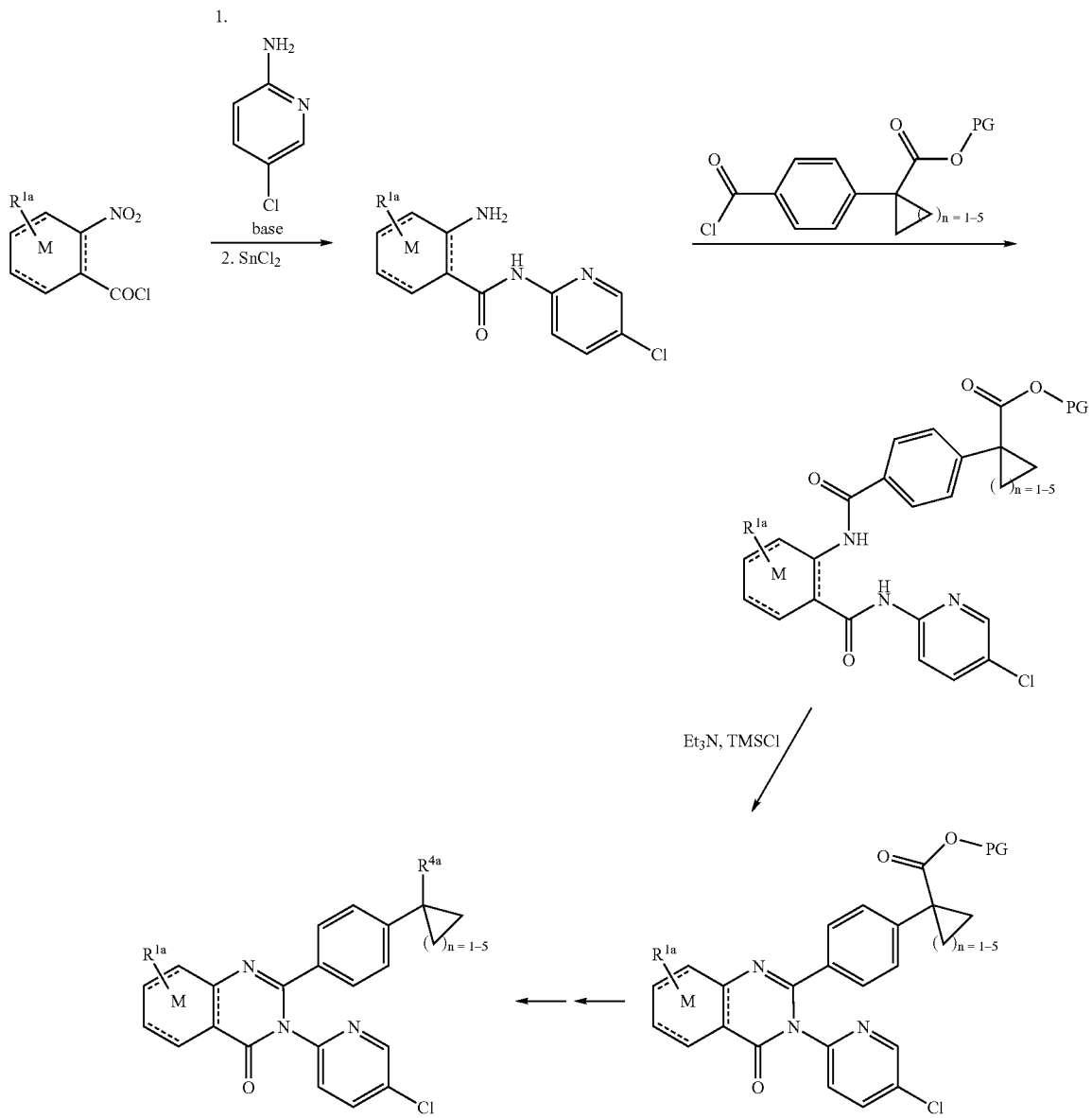

-continued
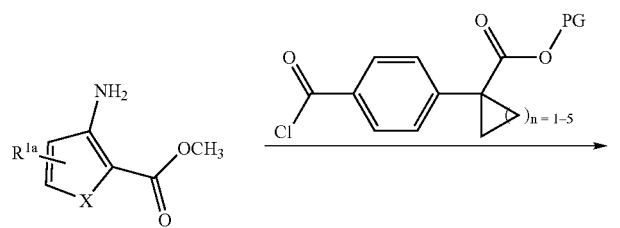
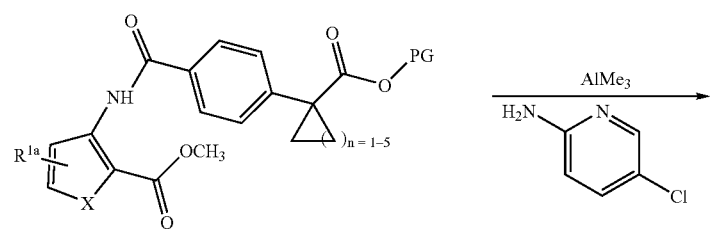
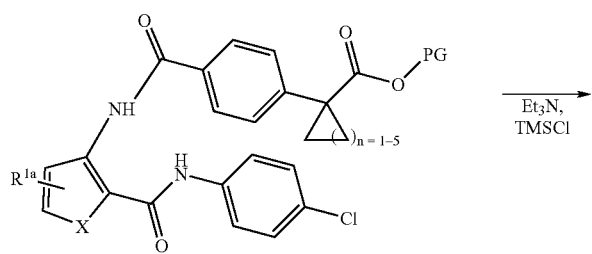
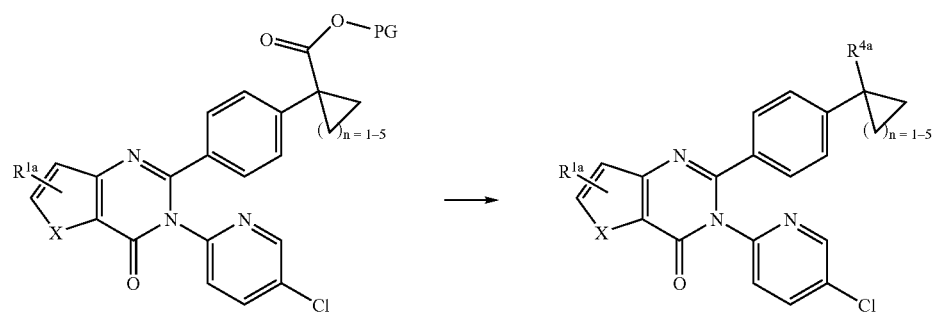
X = O or S

Scheme 32 depicts the synthesis of aminobenzines by using the methods described above and by those skilled in the art.
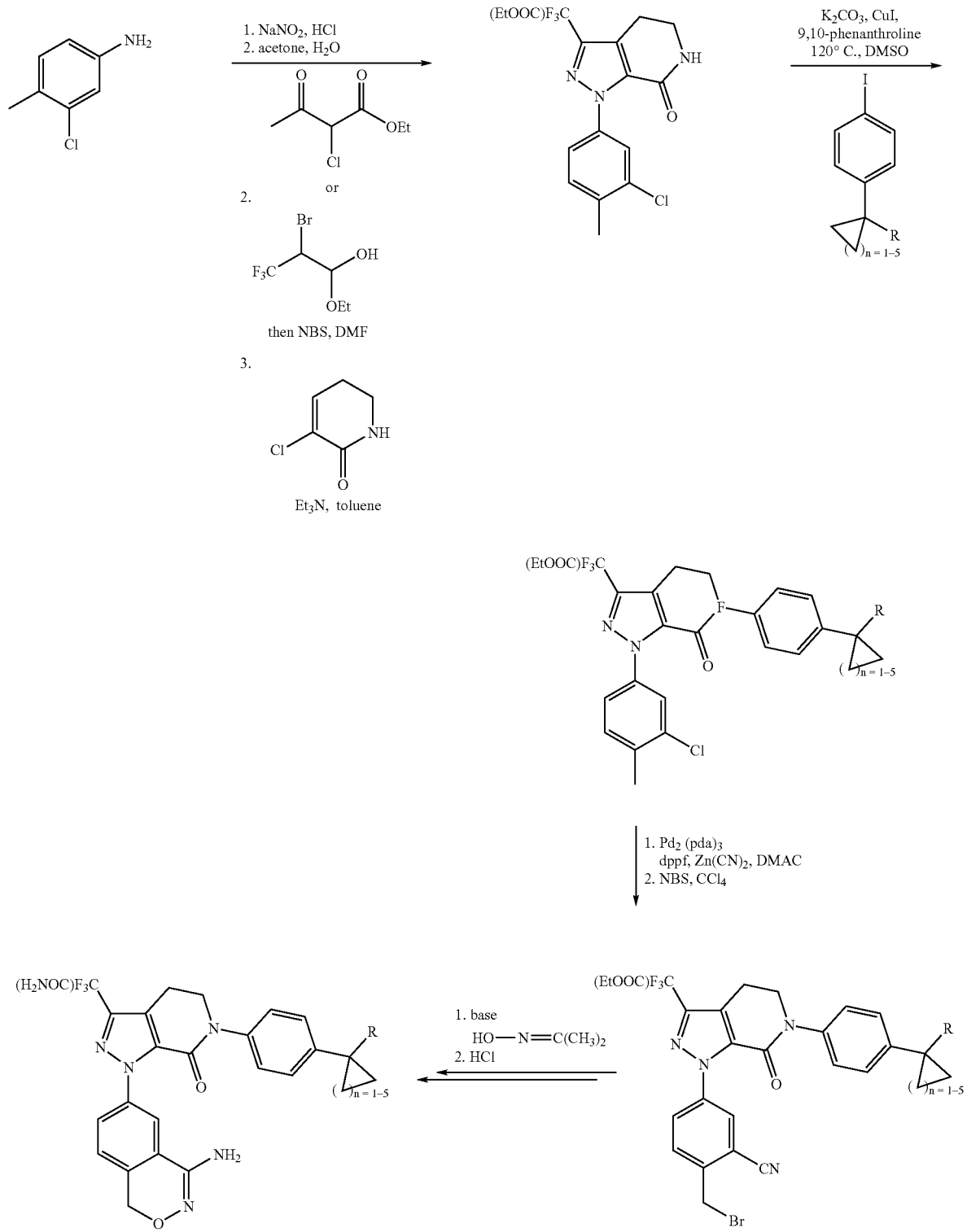

Scheme 33 illustrates the synthesis of piperidine derivatives by using the methods described above and known by those skilled in the art.
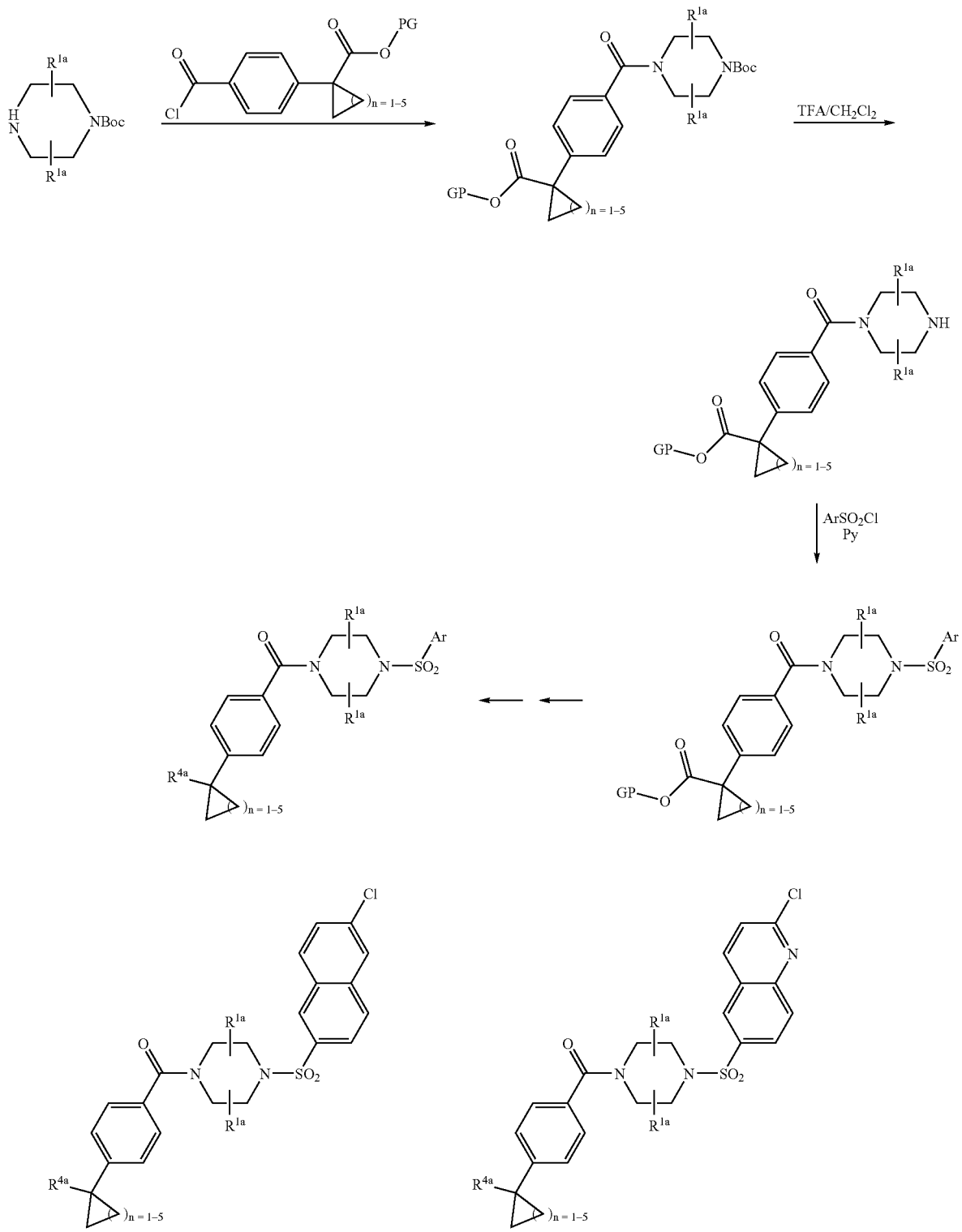

-continued

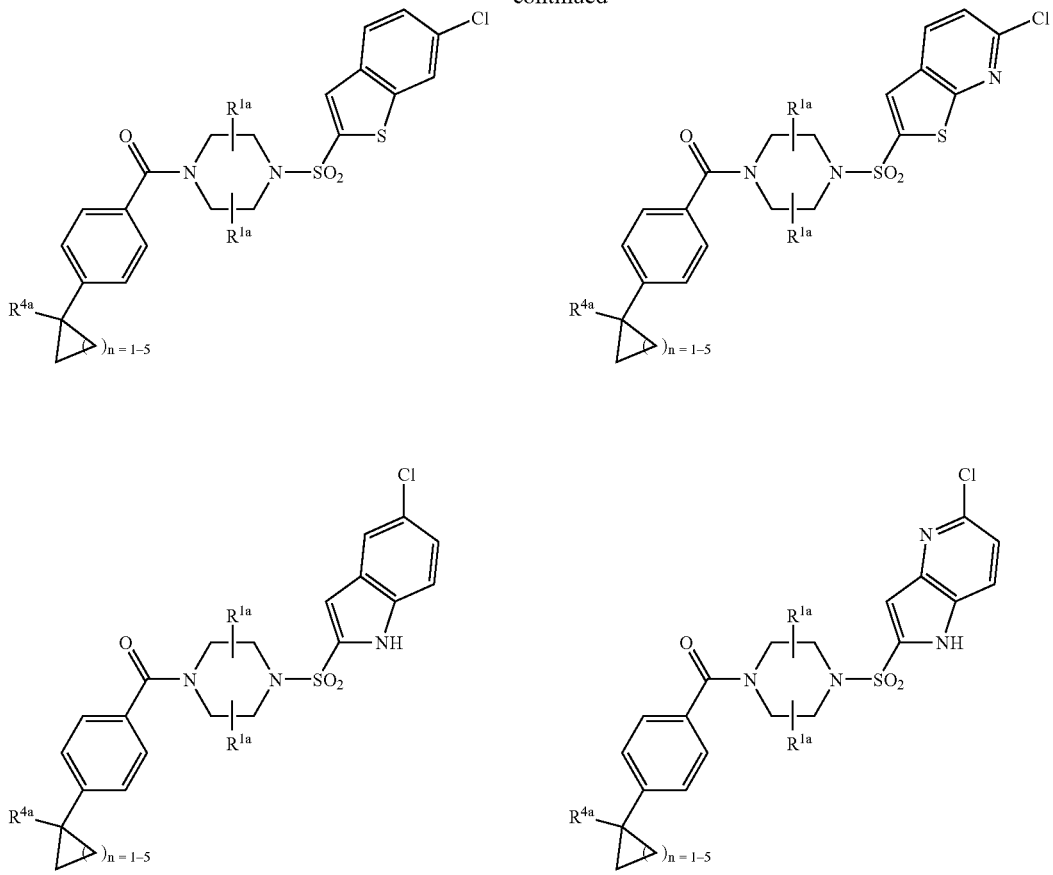

Scheme 34 depicts the syntheses of phenylcyclopropyl amine derivatives. Starting from 4-iodophenylcyclopropyl carboxylic acid, Curtius rearrangement with DPPA in $CH_2Cl_2$ at RT followed by heating in t-BUOH afforded Boc-protected cyclopropylamine intermediate. This intermediate underwent a sequence of methylation (MeI, NaH, THF), Buchwald Ullman coupling (CuI, $K_2CO_3$, 9,10-phenanthroline, DMSO), and then amination of the ethyl ester ($NH_3$ in ethylene glycol) to yield the desire product. Reductive amination with aqueous formaldehyde and $NaBH_3CN$ in $CH_3CN$ afforded the dimethyl compound. On the other hand, alkylation with bromoethanol dibromobutane, or dibromoethylether using $K_2CO_3$ as the base yielded tertiary or cyclic amines, respectively. The C3-methylketone analogue was synthesized through a sequence involving a nucleophilic reaction of $ZnMe_2$ with the aldehyde in the presence of $TiCl_4$.

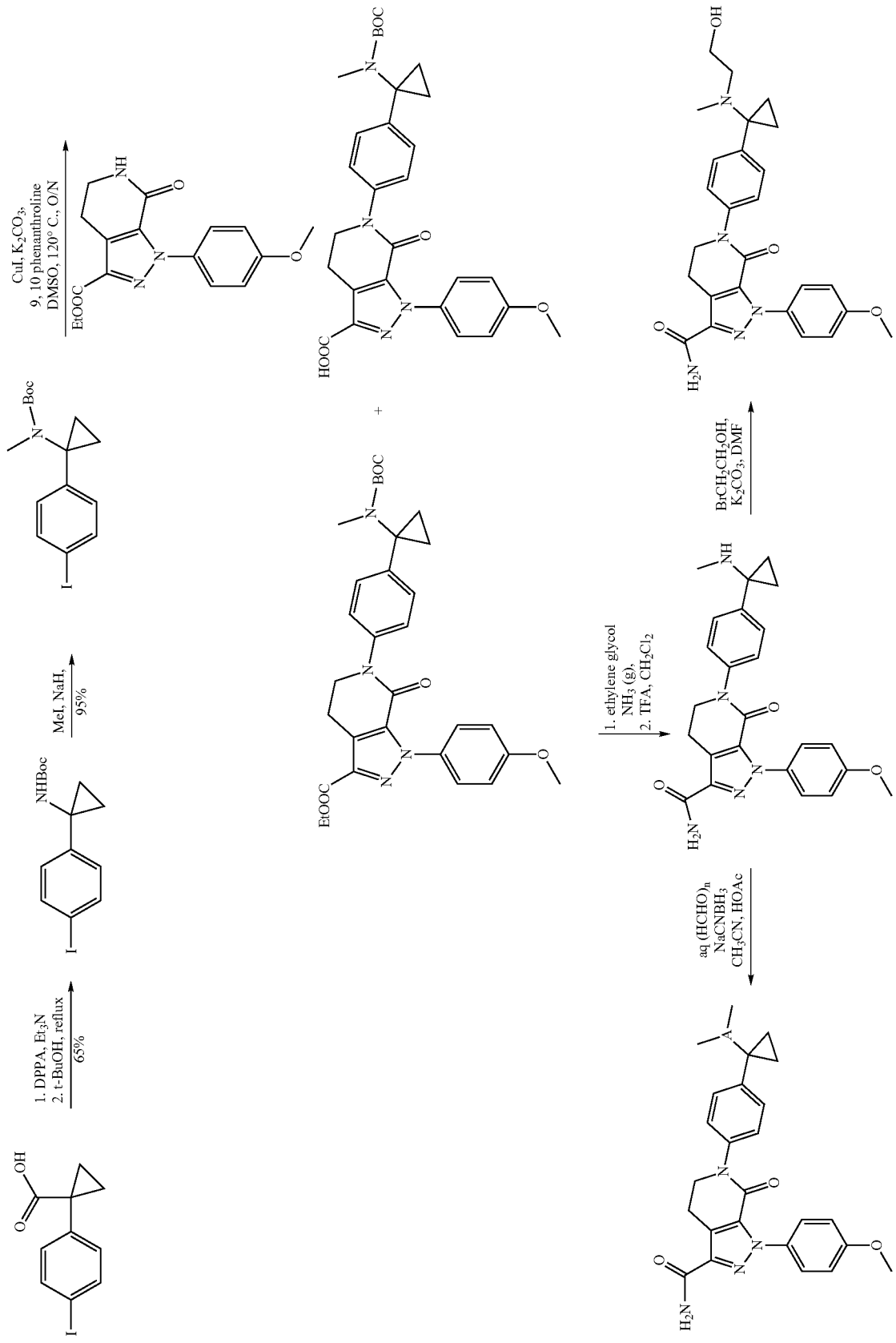

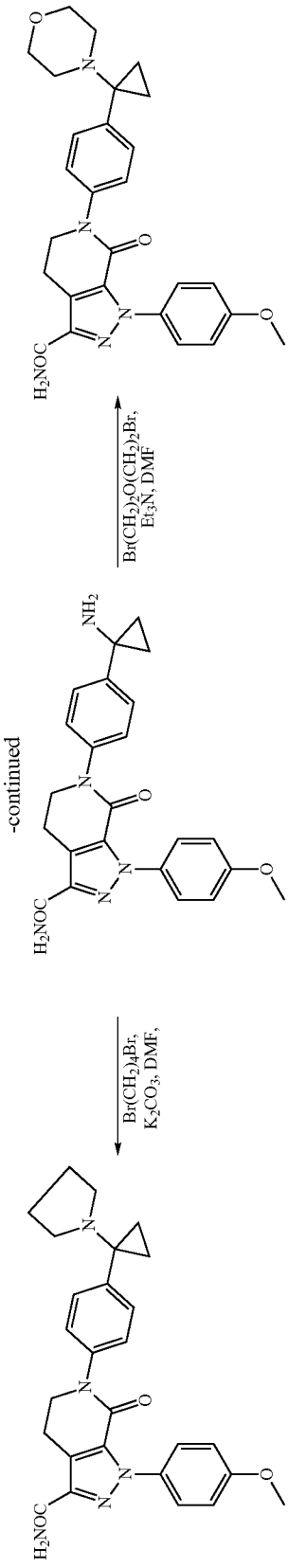
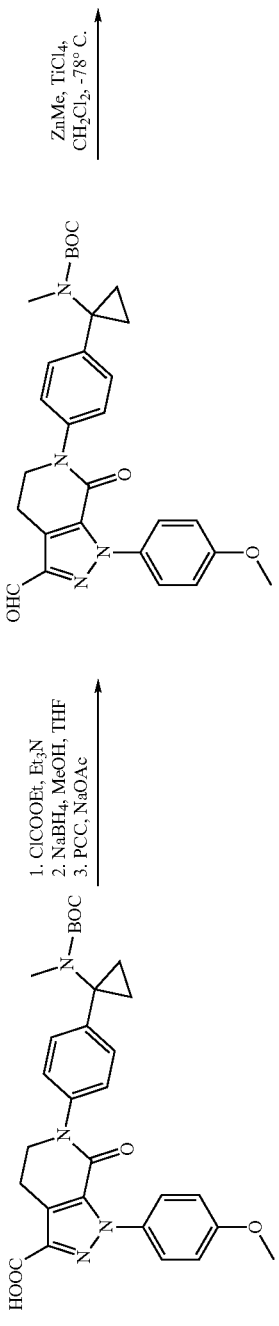

Compounds of the present invention wherein ring P is absent and ring M is a 3–10 membered non-aromatic carbocycle or heterocycle can also be prepared by using the methods described previously and known to those skilled in the art. Scheme 34 illustrates a number of nonaromatic M rings that are considered to be part of the present invention. Scheme 34 also describes general methods of converting the shown rings to compounds of the present invention. As one of ordinary skill in the art would recognize, this method would be applicable to other non-aromatic rings not shown.

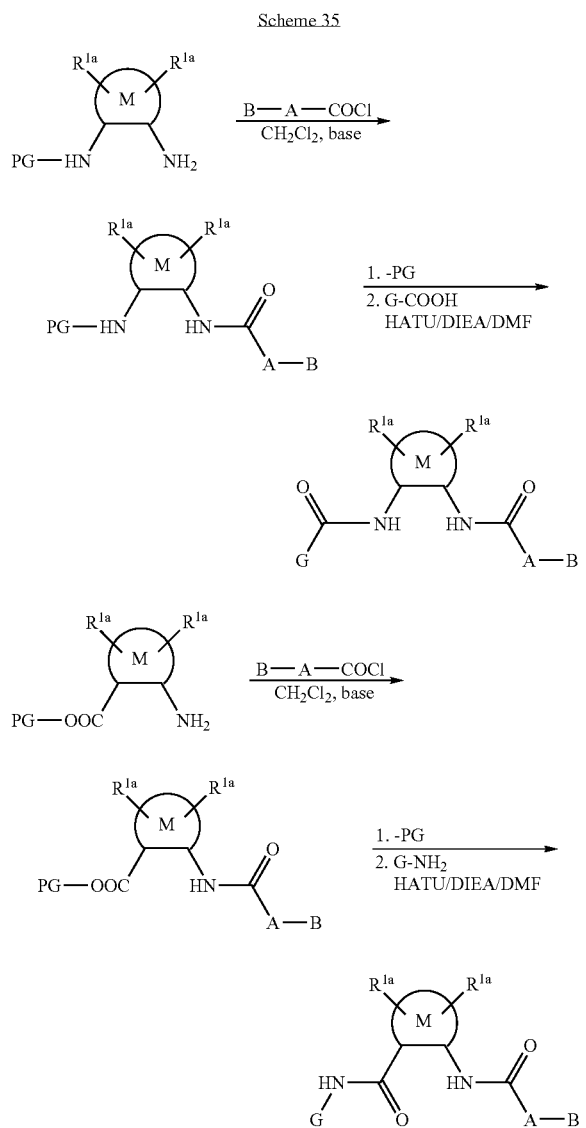

M rings can be:

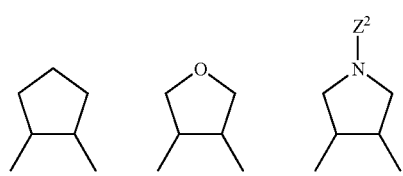

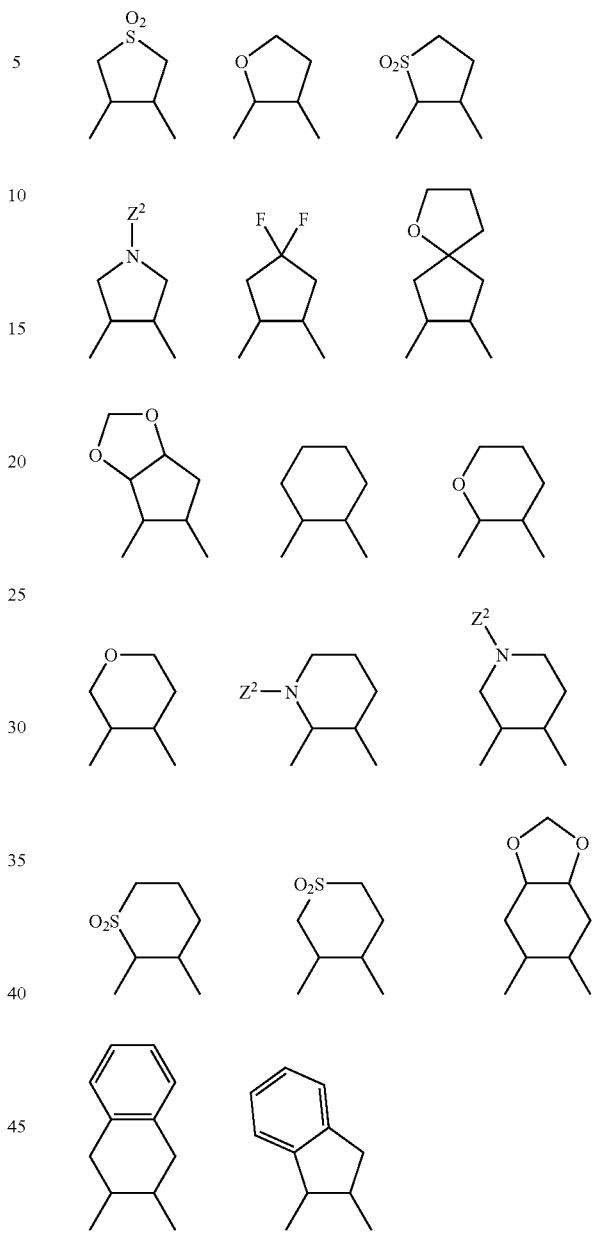

The properly protected, enantiomerically pure cyclic amino acid cores can be obtained via Davies' protocol (*J. Chem. Soc. Perkin Trans I,* 1994, 1411) or via the reduction of enamines described by Cimarelli, C. et al (*J. Org. Chem.* 1996, 61, 5557). The corresponding diamino compounds can be obtained via saponification of the ester of the cyclic amino acids followed by Curtius rearrangement. On the other hand, the cyclic diamines can be prepared via literature methods. (See, for example, Skarzewski, J. and Gupta, A. *Tetrahedron: Assymmetry,* 1997, 8, 1861 and Kim, B. M.; Bae, S. J.; and Seomoon, G., *Tetrahedron Lett.* 1998, 39, 6921).

A series of compounds of formula I wherein $G_1$ is 1,1-dioxo-sulfonylmethyl group are prepared following the sequence outlined in Scheme 36.

Scheme 36
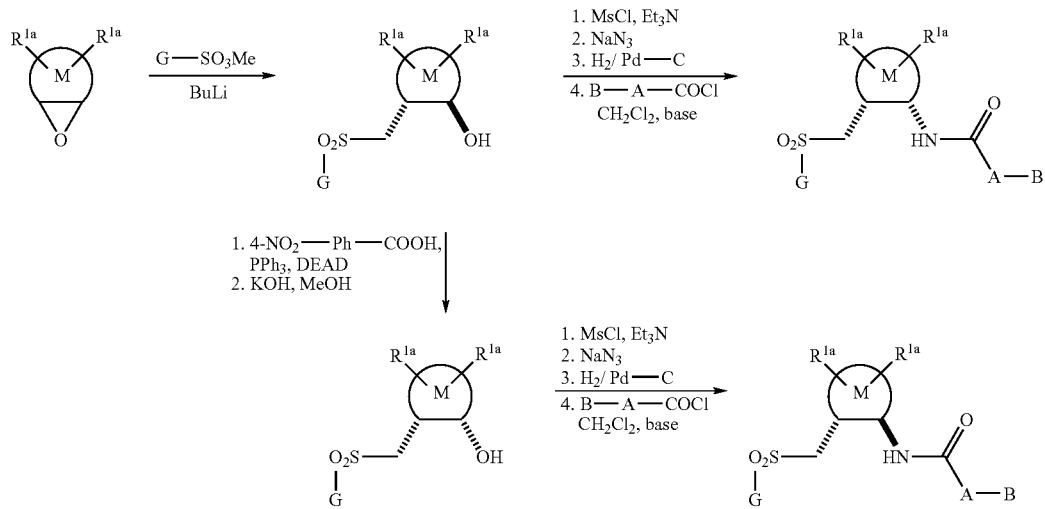
Scheme 37 illustrates numerous bicyclic M intermediates that can be used to prepare compounds of the present invention. These intermediates can be prepared using methods known to those of ordinary skill in the art and using similar methods described previously.
Scheme 37
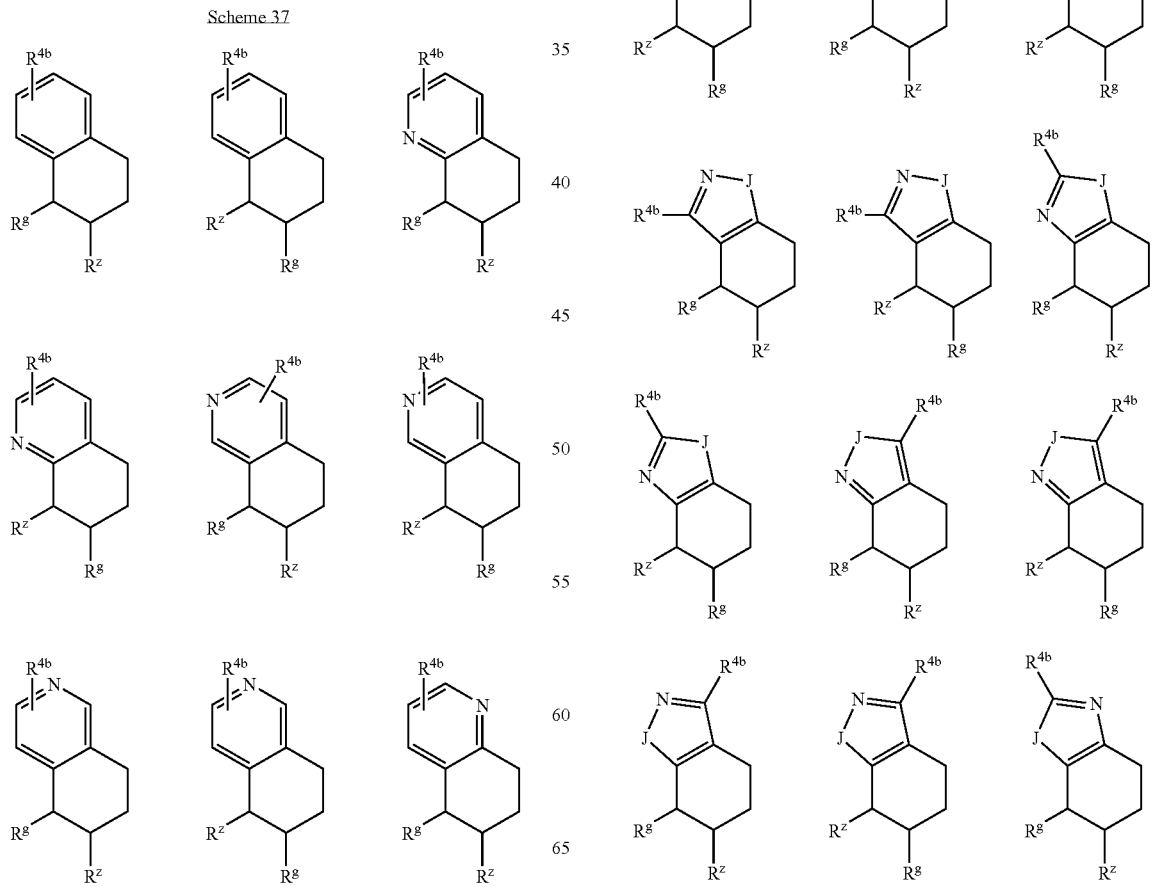

-continued
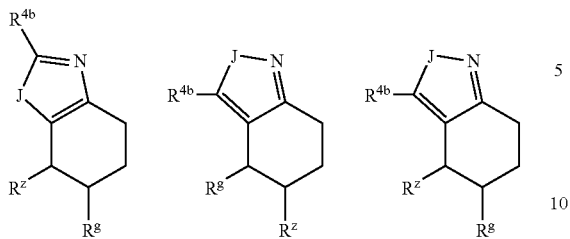
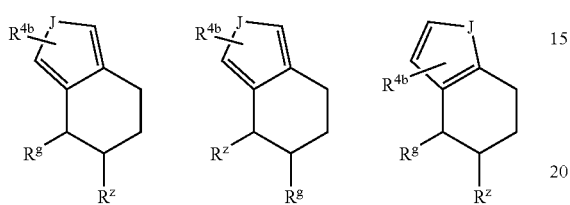
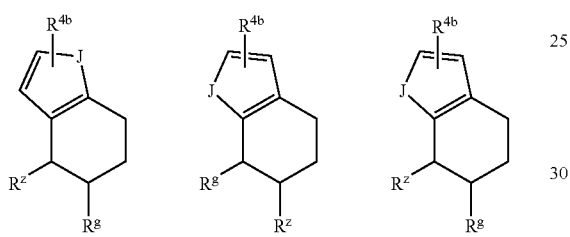
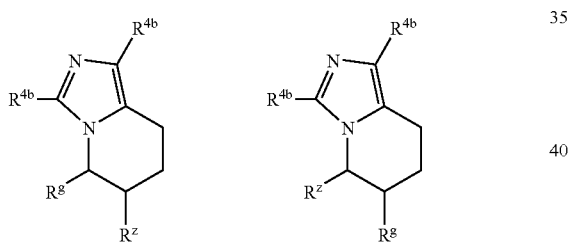
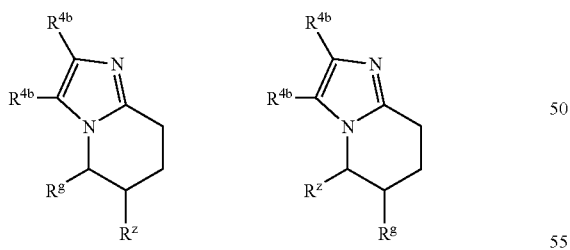
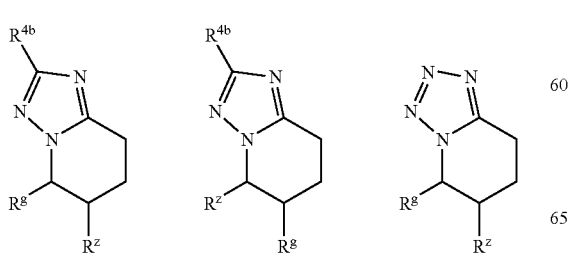
-continued
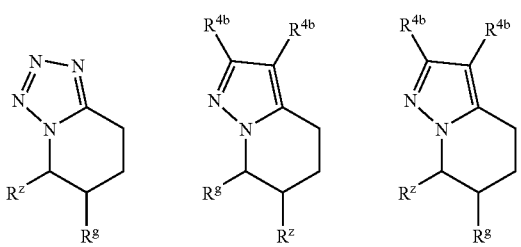
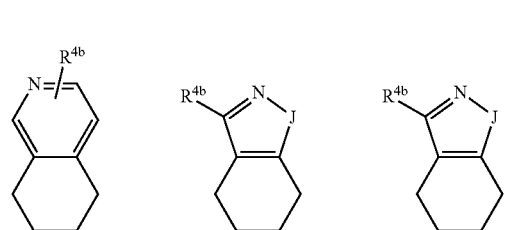
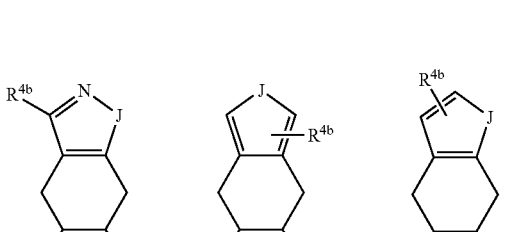
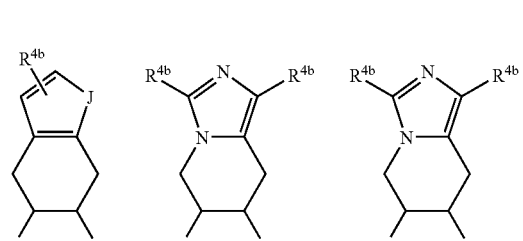
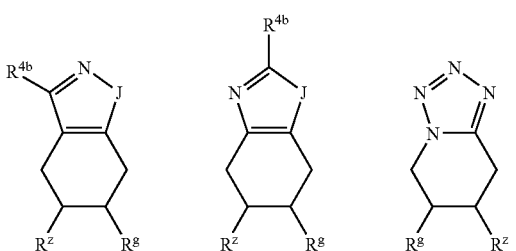

-continued

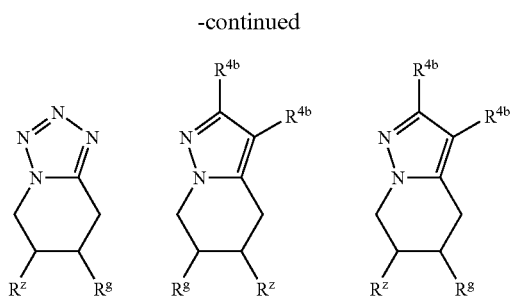

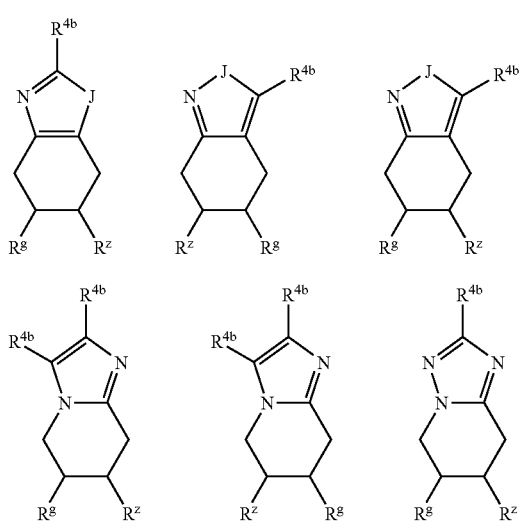

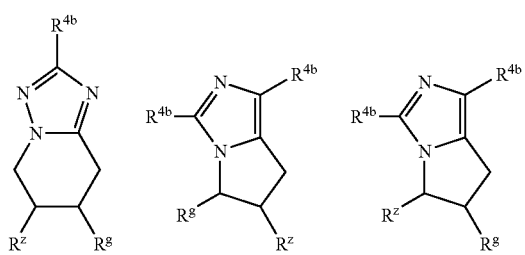

-continued

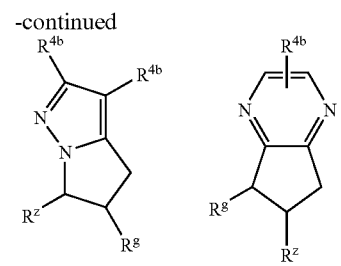

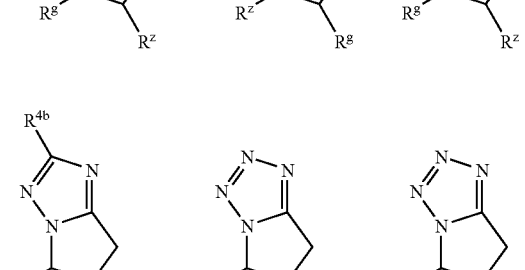

Scheme 38 illustrates the synthesis of benzofused M intermediates of the present invention. The α- or β-amino acid derivatives can undergo Friedel-Crafts reaction followed by reduction to afford the fused ring intermediates. Replacement of the OH group with $NH_2$ group as described previously, followed by standard coupling reactions will provide the compounds of the present invention. On the other hand, oxime formation of the ketone intermediate followed by reduction with $NaBH_4$ can provide the amino alcohol intermediate, which can also be obtained via epoxidation of the olefin and then nucleophilic displacement. Protection of the amino group followed by azide displacement of the mesylate and then reduction of the azide group will give the Boc protected diamines. Functional groups U and V can be acid chloride, carboxylic acid, sulfonyl chloride, etc. in formula U-$G_1$-G and V-A-B. The compounds of the present invention can be obtained from the mono-Boc protected diamines using methods known to those of ordinary skill in the art and using similar methods described previously.

Scheme 38
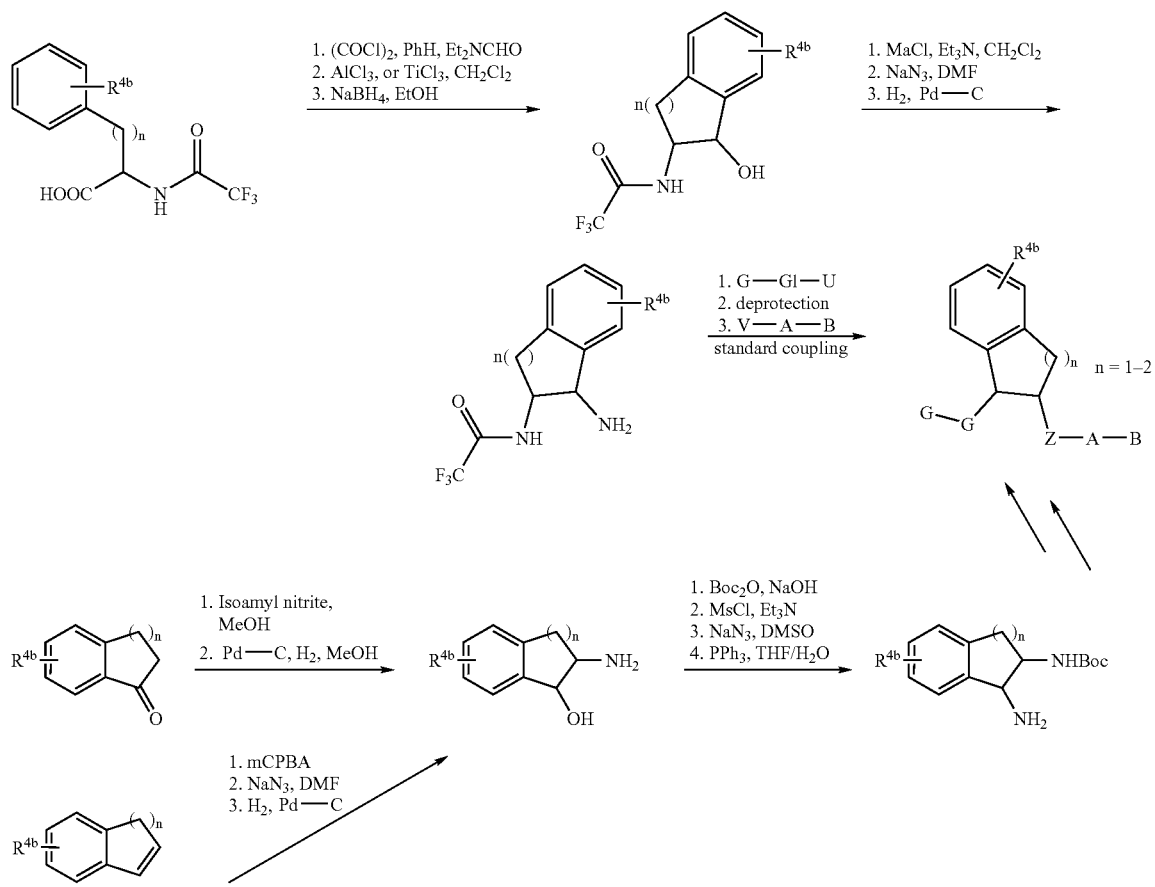
Scheme 39 depicts numerous spiro and bridged M intermediates that can be used to prepare compounds of the present invention. These intermediates can be prepared using methods known to those of ordinary skill in the art and using the methods described previously.
Scheme 39
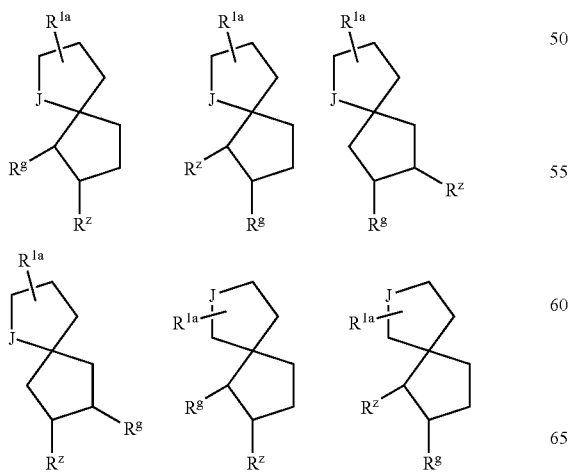
-continued
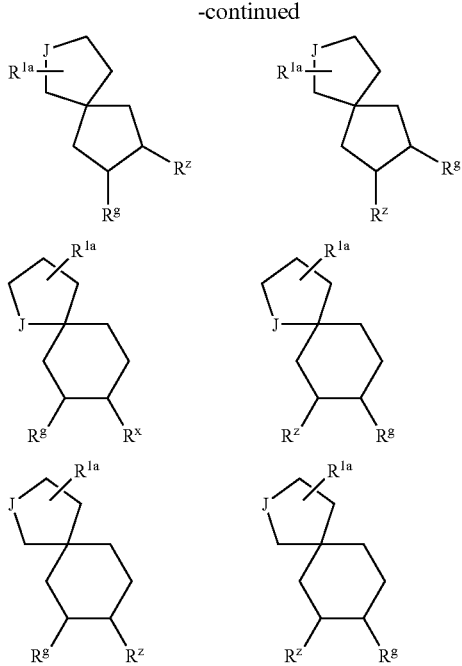

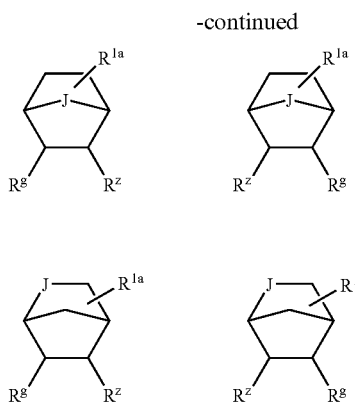

Scheme 40 depicts the synthesis of spiro intermediates of the present invention. Epoxidation of the olefin followed by displacement with TMSN$_3$ and reduction with 10-CSA can provide the amino alcohol intermediate. Protection of the amino and alcohol groups followed by nucleophilic addition to the carbonyl group and spiro ring formation can afford the spiro tetrahydrafuran intermediate. This intermediate can undergo a similar sequence of reactions described previously to give compounds of the present invention.

Scheme 40

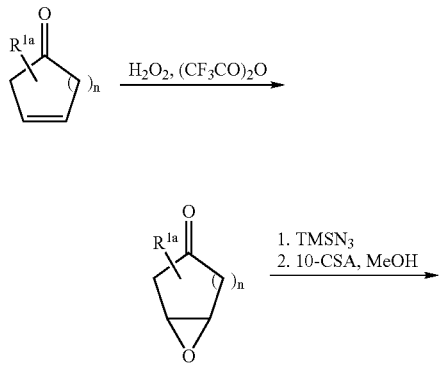

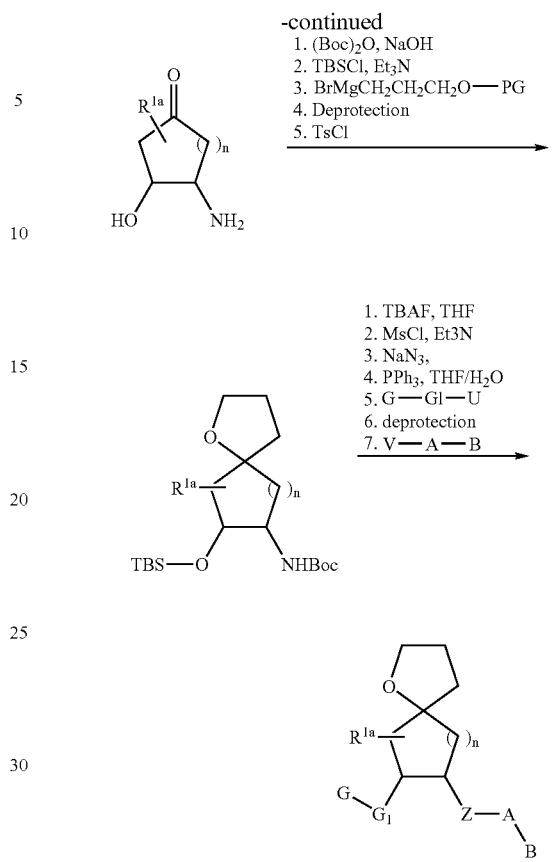

Different diastereomers of compounds of the present invention can be prepared as exemplified in Scheme 41 with cyclopentyl as the central ring. Starting from enantiomerically-pure commercially-available (1S,2S)-2-benzyloxy-cyclopentyl amine, Boc protection followed by debenzylation gave the alcohol. SN$_2$ displacement with NaN$_3$ of the mesylate, followed by reduction of the azide afforded the key mono-boc protected diamine intermediate. Amide formation as described previously provided one pair of enantiomers. On the other hand, inversion of the stereo center of the alcohol (p-NO$_2$-Ph-COOH, DEAD, PPh$_3$, THF; then NaOMe, MeOH) followed by the same amide formation sequence should afford the other pair of enantiomers.

Scheme 41

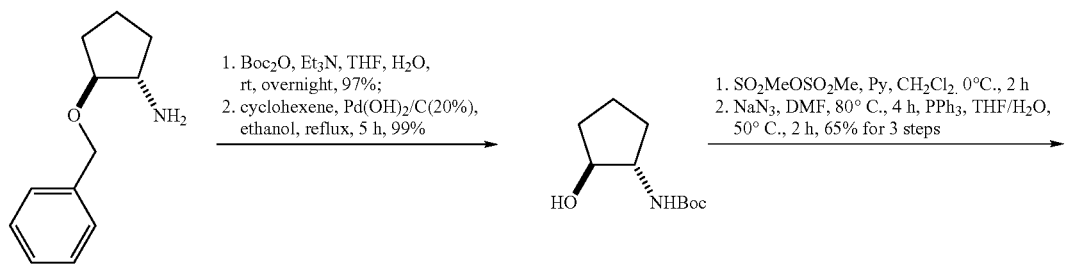

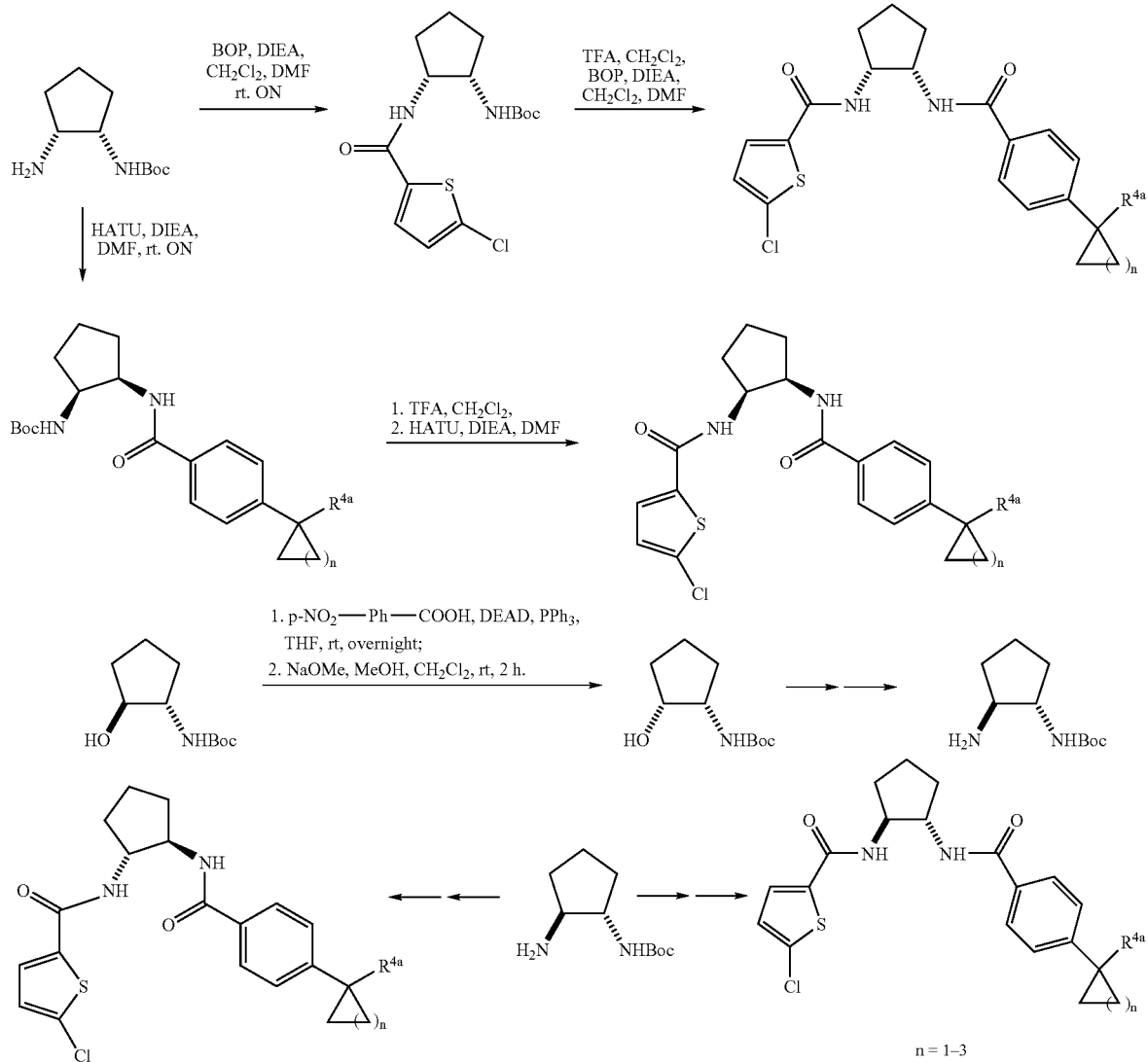
Compounds of present invention wherein M-P is an isoindole derivative can be prepared as exemplified in Scheme 42. These compounds can be obtained via standard organic transformations such as Mitsunomo reactions.
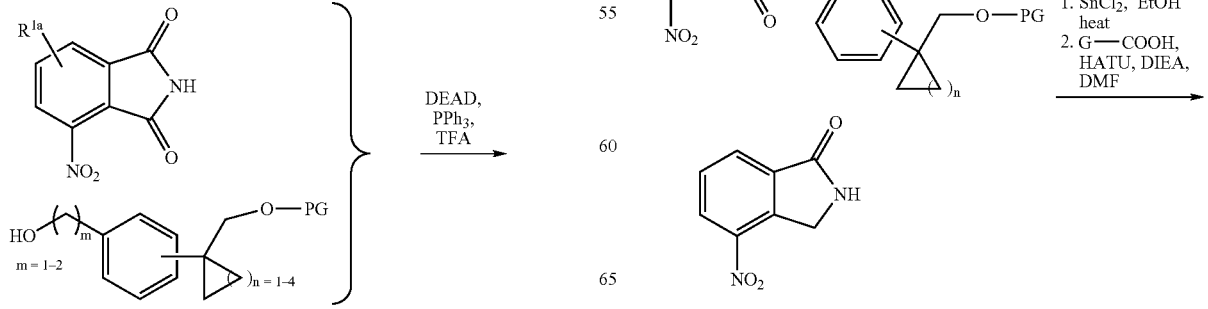

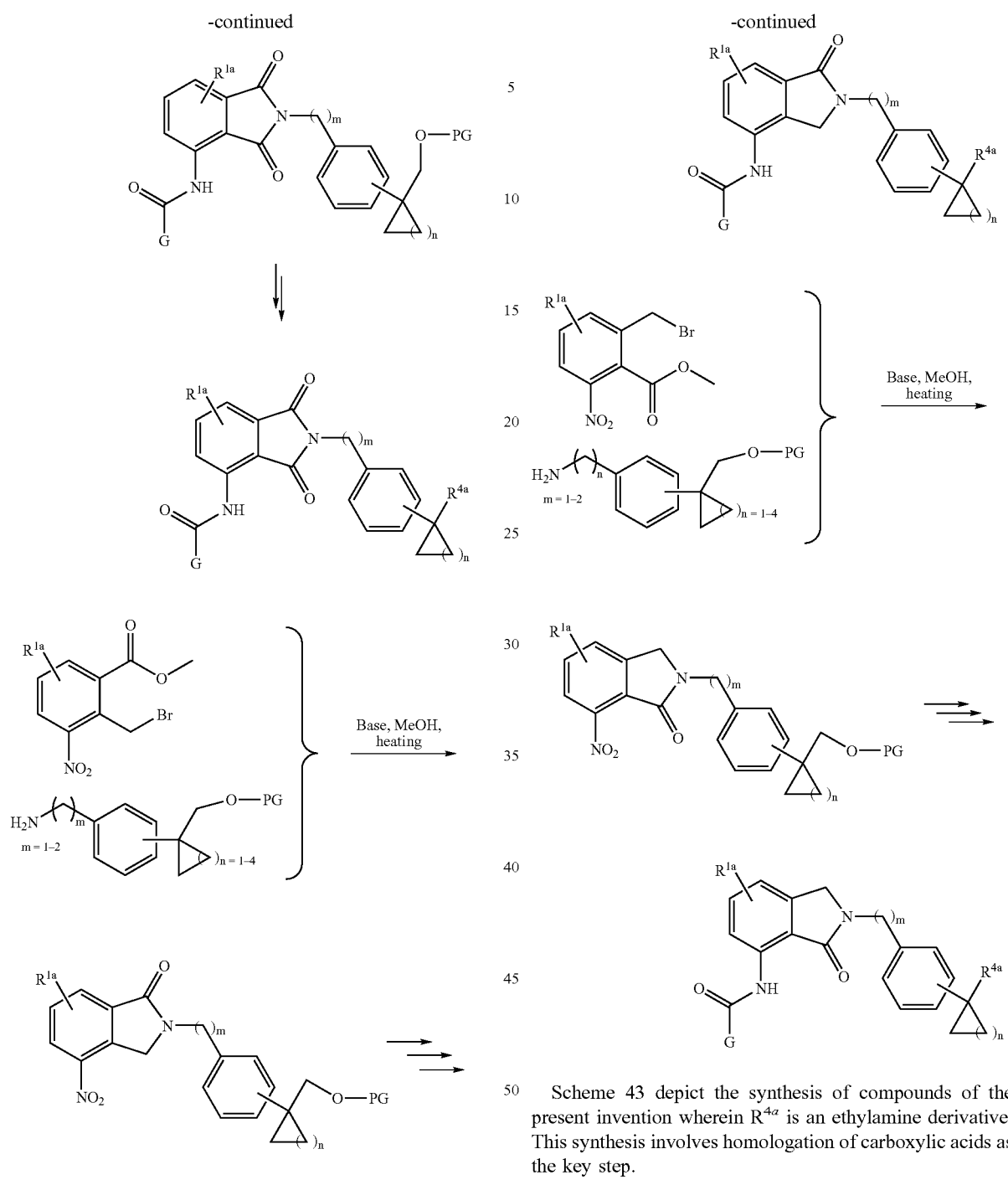
Scheme 43 depict the synthesis of compounds of the present invention wherein $R^{4a}$ is an ethylamine derivative. This synthesis involves homologation of carboxylic acids as the key step.
Scheme 43
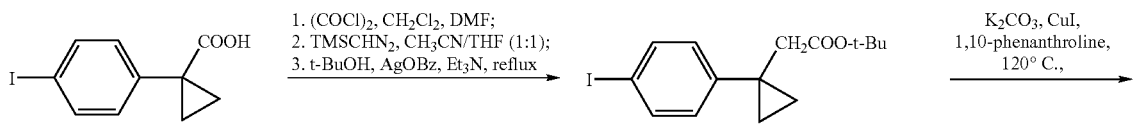

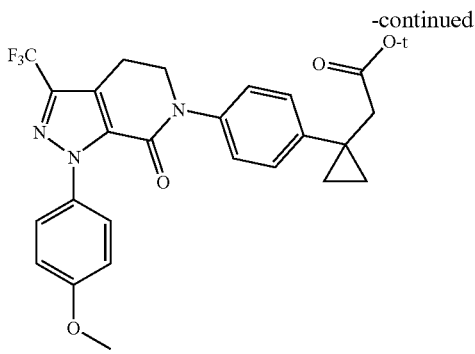

-continued

1. TFA, CH$_2$Cl$_2$;
2. ClCOOEt, Et$_3$N, THF, 0° C.;
   then NaBH4, THF/MeOH, 0° C.;
3. PCC, NaOAc, 4Å MS, CH$_2$Cl$_2$;
4. Pyrrolidine, NaBH(OAc)$_3$,
   HOAc, ClCH$_2$CH$_2$Cl, rt

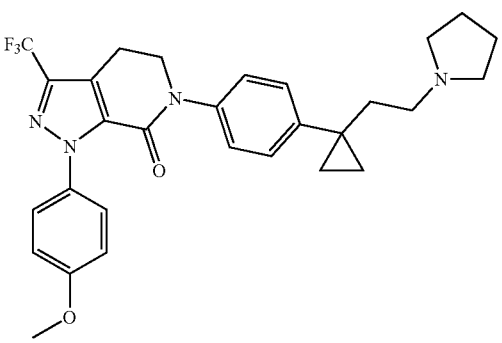

One diastereomer of a compound of Formula I may be more potent against fXa than the others. Thus, the following stereochemistries are considered to be a part of the present invention.

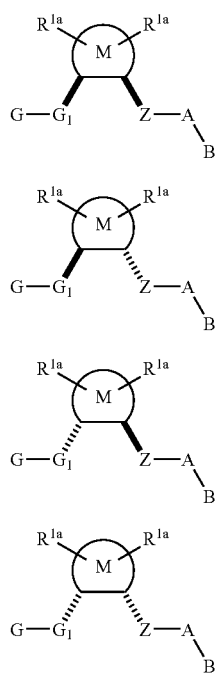

Ia

Ib

Ic

Id

When required, separation of the racemic material can be achieved by HPLC using a chiral column or by a resolution using a resolving agent such as camphonic chloride (Steven D. Young, et al, *Antimicrobial Agents and Chemotheraphy,* 1995, 2602–2605). A chiral compound of Formula I may also be directly synthesized using a chiral catalyst or a chiral ligand (for example, Andrew S. Thompson, et al, *Tetrahedron Lett.* 1995, 36, 8937–8940).

Other features of the invention will become apparent in the course of the following descriptions of exemplary embodiments that are given for illustration of the invention and are not intended to be limiting thereof.

UTILITY

The compounds of this invention are inhibitors of factor Xa and are useful as anticoagulants for the treatment or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to-atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o-v_s)/v_s=I/(K_i(1+S/K_m))$$

where:
  $v_o$ is the velocity of the control in the absence of inhibitor;
  $v_s$ is the velocity in the presence of inhibitor;
  I is the concentration of inhibitor;
  $K_i$ is the dissociation constant of the enzyme:inhibitor complex;
  S is the concentration of substrate;
  $K_m$ is the Michaelis constant.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM. Using the methodology described above, a number of compounds of the present invention were found to exhibit $K_i$'s of $\leq 10$ μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, Factor XIa, urokinase, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to prevent or ameliorate the thromboembolic disease condition or the progression of the disease.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatrobanas well as other factor Xa inhibitors such as those described in the publications identified above under Background of the Invention.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates).

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable phospodiesterase inhibitors for use in combination with the compounds of the present invention include: PDE III inhibitors (such as cilostazol); and PDE V inhibitors (such as sildenafil).

Examples of suitable cholesterol/lipid lowering agents and lipid profile therapies for use in combination with the compounds of the present invention include: HMG-COA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indometacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P, and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are administered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Other features of the invention will become apparent in the course of the following descriptions of exemplary embodiments that are afforded for illustration of the invention and are not intended to be limiting thereof.

EXAMPLE 1

1-(4-methoxyphenyl)-6-(4-{1-[(methylamino)methyl]cyclopropyl}phenyl)-3-(trifluoromethyl)-1,4,5,6-tetrahydro-7H-pyrazolo[3,4-c]pyridin-7-one, trifluoroacetic acid salt

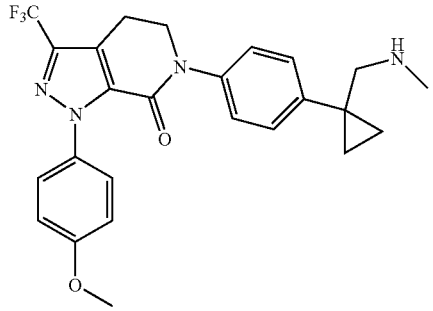

303

Part A. δ-Valerolactam (22.22 g, 222.89 mmol) was stirred in CHCl₃ (500 mL) at 0° C. PCl₅ (140.0 g, 68.29 mmol) was added portionwise. The resulting slurry was stirred at reflux for 3 h until the solution became clear. The mixture was cooled in an ice bath and H₂O was added carefully until the PCl₅ was quenched completely. The two layers were separated. The organic layer was washed with H₂O (3×) and brine (2×), dried over MgSO₄, filtered, and concentrated to dryness to give 3,3-dichloro-2-piperidinone (31.63 g, yield: 85%). This solid (16.50 g, 98.80 mmol) was dissolved in DMF (20 mL), and Li₂CO₃ (21.93 g, 296.40 mmol, 3.0 eq) was added. The mixture was stirred at 120° C. for 1 day. The solvent was further concentrated, and 1N HCl was added to acidify the mixture. It was then extracted with CHCl₃ (6×). The organic layers were washed with H₂O, brine, dried over MgSO₄, and concentrated to dryness to give almost pure 3-chloro-5,6-dihydro-2(1H)-pyridinone (11.13 g, 87%).

Part B. The product from Part A (5.50 g, 41.98 mmol) and 2,2,2-trifluoro-N-(4-methoxyphenyl)-ethanehydrazonoyl bromide (12.90 g, 43.58 mmol) were stirred in toluene (100 mL) at room temperature under N₂. Et₃N (28.0 mL, 200.1 mmol) was then added. The mixture was stirred at 85° C. for 15 h. It was cooled to room temperature and extracted with EtOAc (3×). The organic layers were washed with H₂O (2×) and brine (2×), dried over MgSO₄, filtered, and concentrated to dryness. The residue was purified by flash column chromatography (silica gel, CH₂Cl₂, then CH₂Cl₂:EtOAc=4:1, then EtOAc) to produce 1-(4-methoxyphenyl)-3-(trifluoromethyl)-1,4,5,6-tetrahydro-7H-pyrazolo[3,4-c]pyridin-7-one as a light-tan solid (5.09 g, yield: 39%). LC/MS (ESI⁺) 312.4 (M+H)⁺.

Part C. 1-Phenyl-cyclopropylcarboxylic acid (16.50 g, 101.0 mmol) was stirred in HOAC (70 mL) at RT under N₂. I₂ (27.94 g, 101.0 mmol) was added, followed by the addition of NaIO₃ (4.98 g, 25.25 mmol) and conc. H₂SO₄ (1 mL). The resulting mixture was stirred at 70° C. for 3 days. LC-MS showed completion of the reaction. The cooled mixture was concentrated, poured into H₂O, and extracted with EtOAc (2×). The organic layer was washed with sodium thiosulfate (2×) and brine, dried over MgSO₄, filtered, and concentrated to dryness to give almost pure 4-iodophenylcyclopropyl carboxylic acid (23.56 g, yield: 81%). LC/MS (ESI⁺) 472.4 (M+H)⁺.

Part D. The product of part C (0.22 g, 0.76 mmol) and the product from part B (0.11 g, 0.35 mmol) were stirred in DMSO (0.5 mL) under N₂. K₂CO₃ (0.15 g, 1.09 mmol, 3.0 eq) was added, followed by the addition of 1,10-phenanthroline (28 mg, 20 mol %) and CuI (30 mg, 20% mol). The resulting mixture was stirred at 130° C. overnight. LC-MS showed completion of the reaction. EtOAc was added to the cooled solution. It was washed with 1N HCl, H₂O, and brine; dried over MgSO₄; filtered; and concentrated in vacuo to give almost pure 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropanecarboxylic acid (460 mg, 94%). LC/MS (ESI⁺) 472.6 (M+H)⁺, t_R=2.39 min (35–98% CH₃CN in H₂O in a 6-min run).

Part E. The product from Part D (0.28 g, 0.59 mmol) was stirred in THF (5 mL) at 0° C. under N₂. Et₃N (0.15 mL, 1.06 mmol) was added, followed by dropwise addition of ClCO₂Et (0.098 mL, 1.03 mmol). The reaction mixture was then stirred at 0° C. for 1 h. TLC showed the completion of the reaction. The mixture was filtered through a filter funnel and rinsed with anhydrous THF. The THF filtrate (ca. 10 mL) was stirred at 0° C. under N₂. MeOH (2.5 mL) was added followed by addition of NaBH₄ (0.31 g, 8.16 mmol,

304

13.8 eq) portionwise. The resulting mixture was stirred at 0° C. for 15 min. Analytical LC-MS showed completion of the reaction. Sat'd Na₂SO₄ was then added. The mixture was extracted with EtOAc (2×). The organic layer was washed with H₂O (2×) and brine (2×), dried over Na₂SO₄, filtered, and concentrated to dryness to give 6-{4-[1-(hydroxymethyl)cyclopropyl]phenyl}-1-(4-methoxyphenyl)-3-(trifluoromethyl)-1,4,5,6-tetrahydro-7H-pyrazolo[3,4-c]pyridin-7-one (0.23 g, 84.7%). LC/MS(ESI⁺) 458.6 (M+H)⁺, t_R=6.06 min (5–98% CH₃CN in H₂O in a 10-min run). ¹H NMR (CHCl₃) δ 7.38 (d, J=9.1 Hz, 2H), 7.29 (d, J=8.4 Hz, 2H), 7.16 (m, 2H), 6.83 (d, J=9.1 Hz, 2H), 4.03 (t, J=6.6 Hz, 2H), 3.72 (s, 3H), 3.54 (s, 2H), 3.07 (t, J=6.6 Hz, 2H), 0.75 (s, br, 2H) ppm.

The above aldehyde (0.22 g, 0.49 mmol) was stirred in anhydrous CH₂Cl₂ (5 mL) at RT under N₂. NaOAc (88 mg, 1.07 mmol, 2.2 eq) and 4 Å molecular sieves (200 mg) were added, followed by the addition of PCC (0.19 g, 0.88 mmol, 1.8 eq). The resulting slurry was stirred at RT for 1.5 h. Analytical LC-MS showed completion of the reaction. The mixture was filtered through Celite® and rinsed with CH₂Cl₂. The filtrate was washed with H₂O (2×) and brine (2×), dried over Na₂SO₄, filtered, and concentrated to dryness to give almost pure 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropanecarbaldehyde (0.20 g, yield: 87.4%). LC/MS (ESI⁺) 455.4 (M+H)⁺.

Part F. The product from Part E (20 mg, 0.95 mmol), methylamine hydrochloride (20 mg, excess) were stirred in dichloroethane (0.7 mL) in a capped vial. NaBH(OAc)₃ (50 mg, excess) was added, followed by addition of one drop of HOAc. The reaction mixture was stirred at RT for 1.5 h. Analytical LC-MS showed completion of the reaction. The mixture was evaporated, and dissolved in aqueous MeOH. It was then purified by prep LC-MS (5–98% CH₃CN/H₂O in a 10-min run, t_R=4.65 min) to obtain the product 1-(4-methoxy-phenyl)-6-(4-{1-[(methylamino)methyl]cyclopropyl}phenyl)-3-(trifluoromethyl)-1,4,5,6-tetrahydro-7H-pyrazolo[3,4-c]pyridin-7-one (18 mg, 86%). LC/MS (ESI⁺) 471.4 (M+H)⁺. HRMS C₂₅H₂₆O₂F₃N₄ (M+H)⁺ 471.2011 calcd for 471.2008. ¹H NMR (acetone-d₆) δ 7.51 (m, 4H), 7.32 (d, J=8.5 Hz, 2H), 6.99 (d, J=9.1 Hz, 2H), 4.16 (t, J=6.6 Hz, 2H), 3.83 (s, 3H), 3.37 (m, 2H), 3.16 (t, J=6.3 Hz, 2H), 2.70 (s, 3H), 1.27 (d, J=6.2 Hz, 6H), 1.12 (m, 2H), 0.96 (m, 2H) ppm.

EXAMPLE 2

6-(4-{1-[(dimethylamino)methyl]cyclopropyl}phenyl)-1-(4-methoxyphenyl)-3-(trifluoromethyl)-1,4,5,6-tetrahydro-7H-pyrazolo[3,4-c]pyridin-7-one, trifluoroacetic acid salt

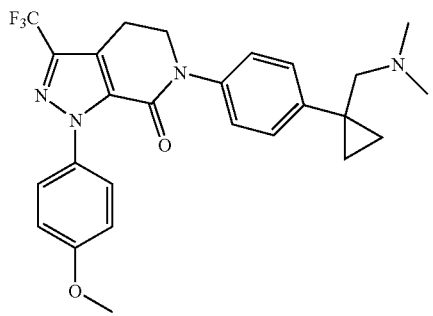

Following a procedure analogous to that used for step F in Example 1, but using dimethylamine hydrochloride, the title compound was prepared. The product was purified by RP-prep LC-MS (5–98% CH$_3$CN/H$_2$O in a 10-min run). LC/MS (ESI$^+$) 485.4 (M+H)$^+$, $t_R$=4.66 min. HRMS C$_{26}$H$_{28}$O$_2$F$_3$N$_4$ (M+H)$^+$ 485.2158 calcd for 485.2164. $^1$H NMR (acetone-d$_6$) δ 7.51 (m, 4H), 7.35 (d, J=8.4 Hz, 2H), 6.98 (d, J=9.0 Hz, 2H), 4.17 (t, J=6.6 Hz, 2H), 3.83 (s, 3H), 3.60 (m, 2H), 3.16 (t, J=6.3 Hz, 2H), 2.82 (s, 6H), 1.15 (m, 2H), 1.08 (m, 2H) ppm.

EXAMPLE 3

6-(4-{1-[(diethylamino)methyl]cyclopropyl}phenyl)-1-(4-methoxyphenyl)-3-(trifluoromethyl)-1,4,5,6-tetrahydro-7H-pyrazolo[3,4-c]pyridin-7-one, trifluoroacetic acid salt

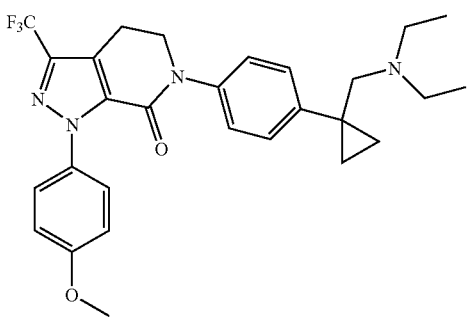

Following a procedure analogous to that used for step F in Example 1, but using diethylamine, the title compound was prepared. The product was purified by RP-prep LC-MS (5–98% CH$_3$CN/H$_2$O in a 10-min run). LC/MS (ESI$^+$) 513.4 (M+H)$^+$, $t_R$=4.79 min.

EXAMPLE 4

6-(4-{1-[(isopropylamino)methyl]cyclopropyl}phenyl)-1-(4-methoxyphenyl)-3-(trifluoromethyl)-1,4,5,6-tetrahydro-7H-pyrazolo[3,4-c]pyridin-7-one, trifluoroacetic acid salt

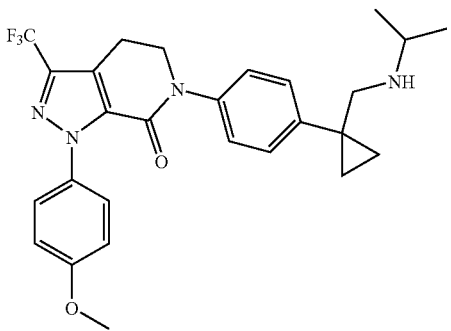

Following a procedure analogous to that used for step F in Example 1, but using isopropylamine, the title compound was prepared. The product was purified by RP-prep LC-MS (5–98% CH$_3$CN/H$_2$O in a 10-min run). LC/MS (ESI$^+$) 499.4 (M+H)$^+$, $t_R$=4.79 min. $^1$H NMR (acetone-d$_6$) δ 7.51 (d, J=8.4 Hz, 4H), 7.31 (d, J=8.1 Hz, 2H), 6.99 (d, J=8.4 Hz, 2H), 4.16 (t, J=6.5 Hz, 2H), 3.83 (s, 3H), 3.45 (m, 1H), 3.37 (m, 2H), 3.16 (t, J=6.3 Hz, 2H), 1.27 (d, J=6.2 Hz, 6H), 1.13 (m, 2H), 0.93 (m, 2H) ppm.

EXAMPLE 5

6-(4-{1-[(cyclopentylamino)methyl]cyclopropyl}phenyl)-1-(4-methoxyphenyl)-3-(trifluoromethyl)-1,4,5,6-tetrahydro-7H-pyrazolo[3,4-c]pyridin-7-one, trifluoroacetic acid salt

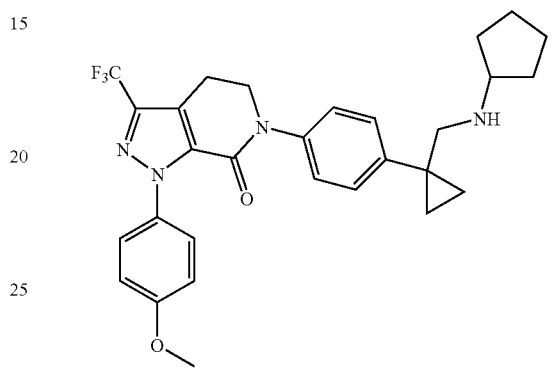

Following a procedure analogous to that used for step F in Example 1, but using cyclopentylamine, the title compound was prepared. The product was purified by RP-prep LC-MS (5–98% CH$_3$CN/H$_2$O in a 10-min run). LC/MS (ESI$^+$) 525.4 (M+H)$^+$, $t_R$=5.03 min. HRMS C$_{29}$H$_{32}$O$_2$F$_3$N$_4$ (M+H)$^+$ 525.2486 calcd for 525.2477. $^1$H NMR (acetone-d$_6$) δ 7.50 (m, 4H), 7.31 (d, J=8.0 Hz, 2H), 6.99 (d, J=8.8 Hz, 2H), 4.16 (t, J=6.6 Hz, 2H), 3.83 (s, 3H), 3.62 (m, 1H), 3.31 (m, 2H), 3.16 (t, J=6.5 Hz, 2H), 1.99 (m, 2H), 1.68 (m, 4H), 1.50 (m, 2H), 1.14 (m, 2H), 0.96 (m, 2H) ppm.

EXAMPLE 6

1-(4-methoxyphenyl)-6-{4-[1-(1-pyrrolidinylmethyl)cyclopropyl]phenyl}-3-(trifluoromethyl)-1,4,5,6-tetrahydro-7H-pyrazolo[3,4-c]pyridin-7-one, trifluoroacetic acid salt

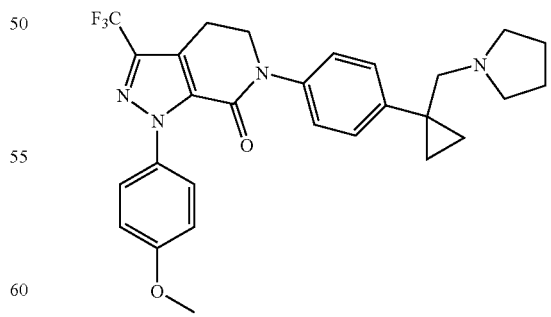

Following a procedure analogous to that used for step F in Example 1, but using pyrrolidine, the title compound was prepared. The product was purified by RP-prep LC-MS (5–98% CH$_3$CN/H$_2$O in a 10-min run). LC/MS(ESI$^+$) 511.4 (M+H)$^+$, $t_R$=4.86 min. HRMS C$_{28}$H$_{30}$O$_2$F$_3$N$_4$ (M+H)$^+$ 511.2320 calcd for 511.2321. $^1$H NMR (acetone-$d_6$) δ 7.52 (m, 4H), 7.36 (d, J=8.4 Hz, 2H), 6.98 (d, J=8.8 Hz, 2H), 4.17 (t, J=6.6 Hz, 2H), 3.83 (s, 3H), 3.60 (m, 2H), 3.49 (m, 2H), 3.16 (t, J=6.3 Hz, 2H), 2.93 (m, 2H), 1.93 (m, 4H), 1.14 (m, 2H), 1.01 (m, 2H) ppm.

EXAMPLE 7

6-[4-(1-{[(3R)-3-hydroxy-1-pyrrolidinyl]methyl}cyclopropyl)phenyl]-1-(4-methoxyphenyl)-3-(trifluoromethyl)-1,4,5,6-tetrahydro-7H-pyrazolo[3,4-c]pyridin-7-one, trifluoroacetic acid salt

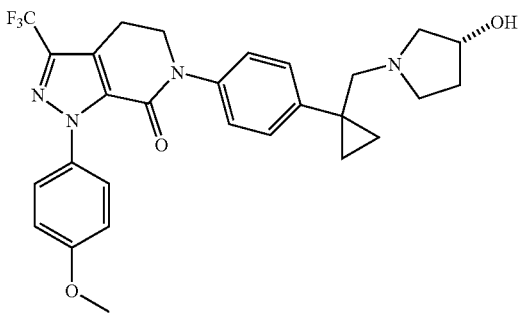

Following a procedure analogous to that used for step F in Example 1, but using (R)-(+)-pyrrolidinol, the title compound was prepared. The product was purified by RP-prep LC-MS (5–98% CH$_3$CN/H$_2$O in a 10-min run). LC/MS (ESI$^+$) 527.4 (M+H)$^+$, $t_R$=4.49 min. $^1$H NMR (acetone-$d_6$) δ 7.55 (d, J=8.4 Hz, 2H), 7.50 (d, J=9.2 Hz, 2H), 7.36 (d, J=8.1 Hz, 2H), 6.98 (d, J=9.1 Hz, 2H), 4.17 (t, J=6.6 Hz, 2H), 3.83 (s, 3H), 3.72 (m, 1H), 3.40–3.27 (m, 4H), 3.16 (t, J=6.3 Hz, 2H), 1.92 (m, 2H), 1.15 (m, 2H), 1.02 (m, 2H) ppm.

EXAMPLE 8

6-(4-{1-[(4-hydroxy-1-piperidinyl)methyl]cyclopropyl}phenyl)-1-(4-methoxyphenyl)-3-(trifluoromethyl)-1,4,5,6-tetrahydro-7H-pyrazolo[3,4-c]pyridin-7-one, trifluoroacetic acid salt

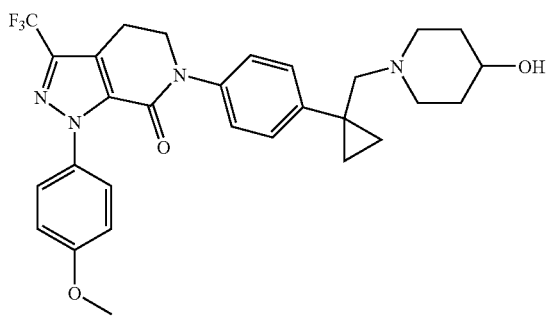

Following a procedure analogous to that used for step F in Example 1, but using 4-hydroxypiperidine, the title compound was prepared. The product was purified by RP-prep LC-MS (5–98% CH$_3$CN/H$_2$O in a 10-min run). LC/MS (ESI$^+$) 541.4 (M+H)$^+$, $t_R$=4.63 min. $^1$H NMR (acetone-$d_6$) δ 7.51 (m, 4H), 7.33 (d, J=8.4 Hz, 2H), 6.98 (d, J=9.1 Hz, 2H), 4.17 (t, J=6.5 Hz, 2H), 3.83 (s, 3H), 3.58 (m, 2H), 3.38 (m, 5H), 3.16 (t, J=6.3 Hz, 2H), 1.92 (m, 2H), 1.78 (m, 2H), 1.19 (m, 2H), 1.05 (m, 2H) ppm.

EXAMPLE 9

1-(4-methoxyphenyl)-6-{4-[1-(4-morpholinylmethyl)cyclopropyl]phenyl}-3-(trifluoromethyl)-1,4,5,6-tetrahydro-7H-pyrazolo[3,4-c]pyridin-7-one, trifluoroacetic acid salt

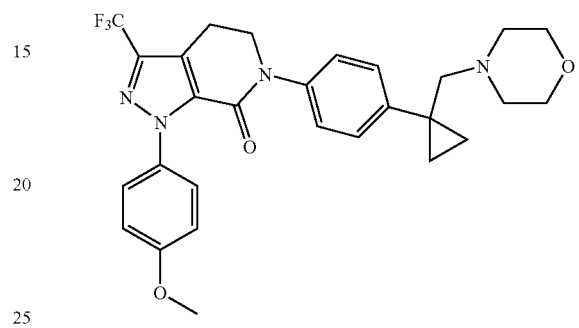

Following a procedure analogous to that used for step F in Example 1, but using morpholine, the title compound was prepared. The product was purified by RP-prep LC-MS (5–98% CH$_3$CN/H$_2$O in a 10-min run). LC/MS(ESI$^+$) 527.4 (M+H)$^+$, $t_R$=6.08 min. HRMS C$_{28}$H$_{30}$O$_3$F$_3$N$_4$ (M+H)$^+$ 527.2280 calcd for 527.2270. $^1$H NMR (acetone-$d_6$) δ 7.52 (m, 4H), 7.33 (d, J=8.4 Hz, 2H), 6.98 (d, J=9.1 Hz, 2H), 4.17 (t, J=6.6 Hz, 2H), 3.83 (s, 3H), 3.64 (m, 1H), 3.17 (t, J=6.6 Hz, 2H), 1.92 (m, 2H), 1.18 (t, J=4.4 Hz, 2H), 1.06 (t, J=4.4 Hz, 2H) ppm.

EXAMPLE 10

1-(4-methoxyphenyl)-6-{4-[1-(1-pyrrolidinylcarbonyl)cyclopropyl]phenyl}-3-(trifluoromethyl)-1,4,5,6-tetrahydro-7H-pyrazolo[3,4-c]pyridin-7-one

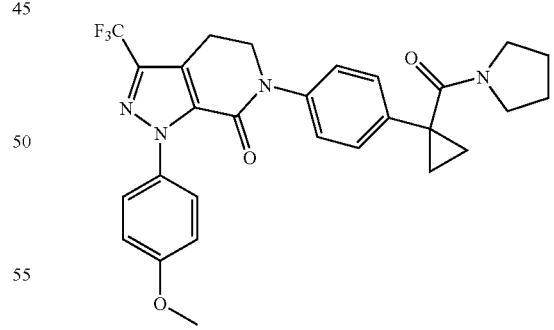

Part A. The product from part D of Example 1 (0.21 g, 0.45 mmol) was stirred in CH$_2$Cl$_2$ (10 mL) at RT under N$_2$. SOCl$_2$ (0.1 mL) was added. The mixture was stirred at RT for 1 h. It was then concentrated to dryness in vacuo. The product (20 mg) was stirred in CH$_2$Cl$_2$ (0.6 mL). Pyrrolidine (0.02 mL) was added, followed by the addition of DIEA (0.05 mL) and one piece of DMAP. The mixture was stirred at RT for 0.5 h. LC-MS showed completion of the reaction. It was purified by RP-prep LC-MS (5–98% CH$_3$CN/H$_2$O in a 10-min run) to afford 1-(4-methoxyphenyl)-6-{4-[1-(1-pyrrolidinyl carbonyl)cyclopropyl]phenyl}-3-(trifluoromethyl)-1,4,5,6-tetrahydro-7H-pyrazolo[3,4-c]pyridin-7-one (15 mg, yield, 67%). LC/MS(ESI$^+$) 525.4 (M+H)$^+$, t$_R$=6.17 min. $^1$H NMR (acetone-d$_6$) δ 7.49 (d, J=9.2 Hz, 2H), 7.31 (d, J=8.8 Hz, 2H), 7.20 (d, J=8.5 Hz, 2H), 6.97 (d, J=9.1 Hz, 2H), 4.16 (t, J=6.6 Hz, 2H), 3.83 (s, 3H), 3.35 (m, 2H), 3.20 (m, 2H), 3.16 (t, J=6.6 Hz, 2H), 1.74 (m, 4H), 1.31 (m, 2H), 1.08 (m, 2H) ppm.

EXAMPLE 11

1-{4-[1-(4-methoxyphenyl)-7-oxo-3-(trifluoromethyl)-1,4,5,7-tetrahydro-6H-pyrazolo[3,4-c]pyridin-6-yl]phenyl}-N,N-dimethylcyclopropanecarboxamide

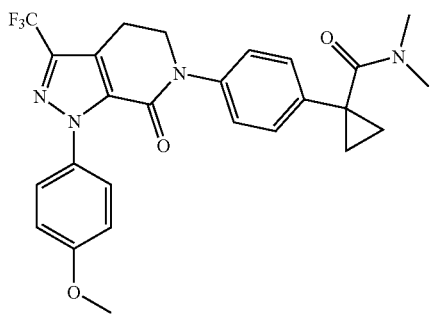

Following a procedure analogous to that used for the preparation of Example 10, but using dimethylamine hydrochloride, the title compound was prepared. The product was purified by RP-prep LC-MS (5–98% CH$_3$CN/H$_2$O in a 10-min run). LC/MS(ESI$^+$) 499.4 (M+H)$^+$, t$^R$=6.01 min. HRMS C$_{26}$H$_{26}$O$_3$F$_3$N$_4$ (M+H)$^+$ 499.1948 calcd for 499.1957. $^1$H NMR (acetone-d$_6$) δ 7.49 (d, J=9.1 Hz, 2H), 7.32 (d, J=8.8 Hz, 2H), 7.17 (d, J=8.8 Hz, 2H), 6.97 (d, J=8.8 Hz, 2H), 4.16 (t, J=6.6 Hz, 2H), 3.83 (s, 3H), 3.16 (t, J=6.2 Hz, 2H), 2.87 (s, 6H), 1.30 (m, 2H), 1.14 (m, 2H) ppm.

EXAMPLE 12

1-(4-methoxyphenyl)-6-(4-{1-[(4-methyl-1-piperazinyl)carbonyl]cyclopropyl}phenyl)-3-(trifluoromethyl)-1,4,5,6-tetrahydro-7H-pyrazolo[3,4-c]pyridin-7-one, trifluoroacetic acid salt

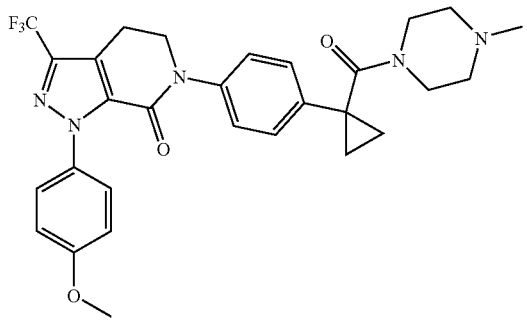

Following a procedure analogous to that used for the preparation of Example 10, but using 4-methylpiperazine, the title compound was prepared. The product was purified by RP-prep LC-MS (5–98% CH$_3$CN/H$_2$O in a 10-min run). LC/MS(ESI$^+$) 554.6 (M+H)$^+$, t$_R$=4.49 min. HRMS C$_{29}$H$_{31}$O$_3$F$_3$N$_5$ (M+H)$^+$ 554.2384 calcd for 554.2379. $^1$H NMR (acetone-d$_6$) δ 7.50 (d, J=8.8 Hz, 2H), 7.30 (AA'BB', J=8.4 Hz, 4H), 6.97 (d, J=9.1 Hz, 2H), 4.17 (t, J=6.6 Hz, 2H), 3.83 (s, 3H), 3.16 (t, J=6.4 Hz, 2H), 2.85 (s, 3H), 1.39 (m, 2H), 1.20 (m, 2H) ppm.

EXAMPLE 13

6-{4-[1-(4-hydroxypiperidine-1-carbonyl)cyclopropyl]phenyl}-1-(4-methoxyphenyl)-3-(trifluoromethyl)-1,4,5,6-tetrahydro-7H-pyrazolo[3,4-c]pyridin-7-one

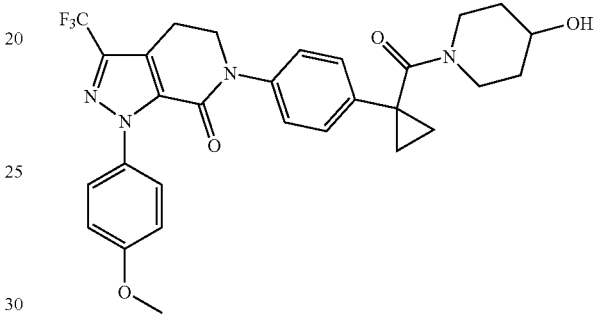

Following a procedure analogous to that used for the preparation of Example 10, but using morpholine, the title compound was prepared. The product was purified by RP-prep LC-MS (5–98% CH$_3$CN/H$_2$O in a 10-min run). LC/MS (ESI$^+$) 555.4 (M+H)$^+$, t$_R$=5.50 min. HRMS C$_{29}$H$_{30}$O$_4$F$_3$N$_4$ (M+H)$^+$ 555.2241 calcd for 555.2219.

EXAMPLE 14

1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropanecarboxamide

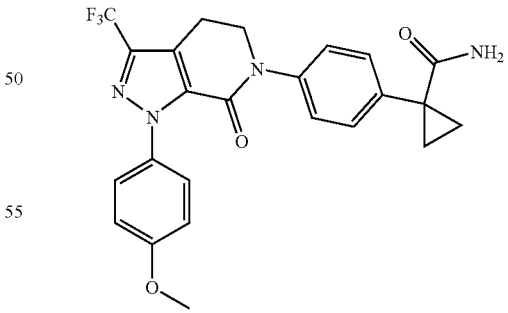

Following a procedure analogous to that used for the preparation of Example 10, but using concentrated NH$_4$OH as the amine source and THF as solvent, the title compound was prepared. The product was purified by prep LC-MS (5–98% CH$_3$CN/H$_2$O in a 10-min run). LC/MS(ESI$^+$) 471.6 (M+H)$^+$, t$_R$=2.56 min (10–90% CH$_3$CN/H$_2$O in a 10-min run). $^1$H NMR (acetone-d$_6$) δ 7.50 (d, J=8.8 Hz, 2H), 7.43

(d, J=8.8 Hz, 2H), 7.26 (d, J=8.8 Hz, 2H), 6.98 (d, J=8.8 Hz, 2H), 4.18 (t, J=6.6 Hz, 2H), 3.83 (s, 3H), 3.17 (t, J=6.6 Hz, 2H), 1.40 (m, 2H), 0.96 (m, 2H) ppm. $^{19}$F NMR (acetone-d$_6$) δ −77.14 ppm.

EXAMPLE 15

1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropanecarboxylic acid cyclopentylamide

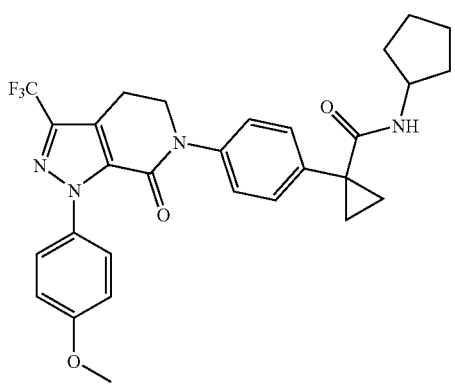

Following a procedure analogous to that used for the preparation of Example 10, but using cyclopentylamine, the title compound was prepared. The product was purified by RP-prep LC-MS (5–98% CH$_3$CN/H$_2$O in a 10-min run). LC/MS(ESI$^+$) 539.4 (M+H)$^+$, t$_R$=6.65 min. $^1$H NMR (acetone-d$_6$) δ 7.51 (d, J=8.8 Hz, 2H), 7.37 (m, 4H), 6.99 (d, J=8.8 Hz, 2H), 4.16 (t, J=6.6 Hz, 2H), 3.83 (s, 3H), 4.05 (m, 1H), 3.16 (t, J=6.2 Hz, 2H), 1.79 (m, 2H), 1.45 (m, 4H), 1.22 (m, 2H), 1.39 (m, 2H), 0.92 (m, 2H) ppm.

EXAMPLE 16

1-{4-[1-(4-methoxyphenyl)-7-oxo-3-(trifluoromethyl)-1,4,5,7-tetrahydro-6H-pyrazolo[3,4-c]pyridin-6-yl]phenyl}-N-(1,3,4-thiadiazol-2-yl)cyclopropanecarboxamide

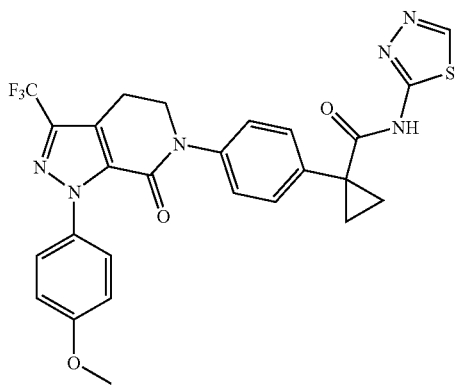

Following a procedure analogous to that used for the preparation of Example 10, but using 2-aminothiadiazole, the title compound was prepared. The product was purified by RP-prep LC-MS (5–98% CH$_3$CN/H$_2$O in a 10-min run). LC/MS(ESI$^+$) 555.4 (M+H)$^+$, t$_R$=6.17 min. $^1$H NMR (acetone-d$_6$) δ 8.96 (s, 1H), 7.54 (m, 4H), 7.43 (d, J=8.4 Hz, 2H), 6.98 (d, J=8.9 Hz, 2H), 4.22 (t, J=6.6 Hz, 2H), 3.84 (s, 3H), 3.16 (t, J=6.2 Hz, 2H), 1.67 (m, 2H), 1.31 (m, 2H) ppm.

EXAMPLE 17

1-{4-[1-(4-methoxyphenyl)-7-oxo-3-(trifluoromethyl)-1,4,5,7-tetrahydro-6H-pyrazolo[3,4-c]pyridin-6-yl]phenyl}-N-(1H-tetraazol-5-yl)cyclopropanecarboxamide

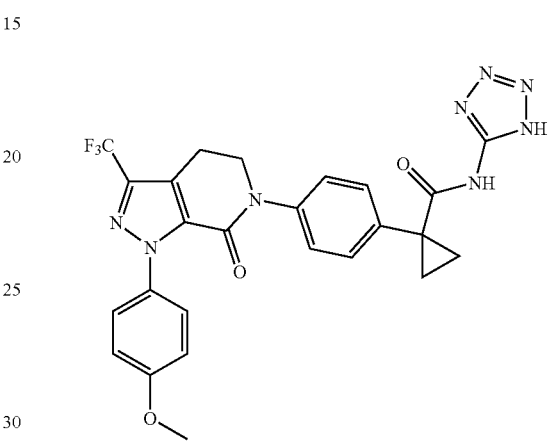

Following a procedure analogous to that used for the preparation of Example 10, but using 5-amino-1H-tetrazole, the title compound was prepared. The product was purified by RP-prep LC-MS (5–98% CH$_3$CN/H$_2$O in a 10-min run). LC/MS(ESI$^+$) 539.6 (M+H), t$_R$=5.86 min. $^1$H NMR (acetone-d$_6$) δ 7.53 (m, 4H), 7.39 (d, J=8.4 Hz, 2H), 6.99 (d, J=9.1 Hz, 2H), 4.20 (t, J=6.6 Hz, 2H), 3.84 (s, 3H), 3.18 (t, J=6.6 Hz, 2H), 1.68 (m, 2H), 1.29 (m, 2H) ppm.

EXAMPLE 18 methyl 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropanecarboxylate

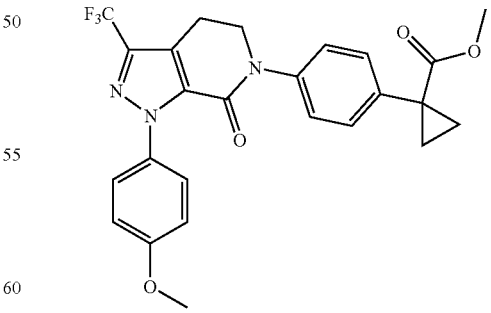

The product from part D in Example 1 (mg, mmol) was stirred in anhydrous MeOH (5 mL) at RT. Catalytic amount of conc. HCl was added. The resulting solution was stirred at RT overnight. The product was purified by RP-prep LC-MS (5–98% CH$_3$CN/H$_2$O in a 10-min run). LC/MS (ESI⁺) 486.6 (M+H)⁺, $t_R$=2.98 min (10–90% $CH_3CN/H_2O$ in a 4-min run). ¹H NMR (acetone-$d_6$) δ 7.50 (d, J=8.8 Hz, 2H), 7.35 (AA'BB', J=8.8 Hz, 4H), 6.97 (d, J=9.1 Hz, 2H), 4.18 (t, J=6.6 Hz, 2H), 3.82 (s, 3H), 3.55 (s, 3H), 3.17 (t, J=6.4 Hz, 2H), 1.49 (m, 2H), 1.16 (m, 2H) ppm.

EXAMPLE 19

1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropanecarbonitrile

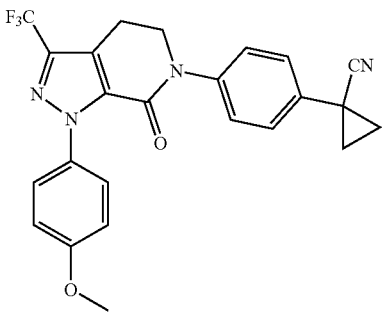

The product from Example 14 (22 mg, 0.047 mmol) was stirred in DMF (0.3 mL) at RT in a capped vial. $SOCl_2$ (0.05 mL) was added. The mixture was stirred at RT for 1.5 h. LC-MS showed completion of the reaction. Prep LC-MS purification (35–98% $CH_3CN$ in $H_2O$) provided the title compound (15 mg, yield, 71%). LC/MS(ESI⁺) 453.4 (M+H)⁺, $t_R$=5.24 min. ¹H NMR (acetone-$d_6$) δ 7.50 (d, J=9.2 Hz, 2H), 7.39 (m, 4H), 6.97 (d, J=8.8 Hz, 2H), 4.18 (t, J=6.6 Hz, 2H), 3.84 (s, 3H), 3.17 (t, J=6.6 Hz, 2H), 1.71 (m, 2H), 1.48 (m, 2H) ppm. ¹⁹F NMR (acetone-$d_6$) δ −77.16 ppm.

EXAMPLE 20

6-{4-[1-(aminomethyl)cyclopropyl]phenyl}-1-(4-methoxyphenyl)-3-(trifluoromethyl)-1,4,5,6-tetrahydro-7H-pyrazolo[3,4-c]pyridin-7-one, trifluoroacetic acid salt

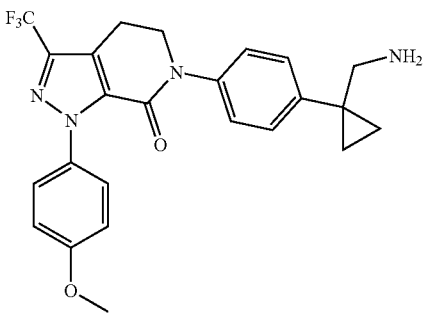

Part A. The product from part E in Example 1 (24 mg, 0.052 mmol) was stirred in $CH_2Cl_2$ (1 mL) at 0° C. under $N_2$. $Et_3N$ (11 μL, 1.5 eq) was added followed by the dropwise addition of MsCl (4.5 μL, 1.1 eq). The mixture was stirred at 0° C. for 1 h. TLC showed completion of the reaction. Sat'd $NH_4Cl$ was added. The mixture was extracted with EtOAc. The organic layer was washed with $H_2O$ and brine, dried over $Na_2SO_4$, filtered, and concentrated to dryness. The residue was dissolved in DMF (1 mL). $NaN_3$ (50 mg, mmol) was added. The mixture was stirred at RT under $N_2$ overnight. LC-MS showed the azide as the major component in the mixture. Sat'd $NH_4Cl$ was then added. The mixture was extracted with EtOAc. And the organic layer was washed with $H_2O$ and brine, dried over $Na_2SO_4$, filtered, and concentrated to dryness to give crude 6-{4-[1-azidomethyl-cyclopropyl]phenyl}-1-(4-methoxyphenyl)-3-(trifluoromethyl)-1,4,5,6-tetrahydro-7H-pyrazolo[3,4-c]pyridin-7-one. LC/MS(ESI⁺) 483.4 (M+H)⁺, $t_R$=3.06 min (10–90% $CH_3CN$ in $H_2O$ in a 4-min run).

Part B. The product from part A (18 mg) and $PPh_3$ (38 mg) were stirred in THF (1.5 mL) at RT for 20 min. $H_2O$ (0.3 mL) was added, and the mixture was stirred at 30° C. for 2 h. The solvents were evaporated. The residue was purified by prep LC-MS (5–98% $CH_3CN$ in $H_2O$) to give pure 6-{4-[1-(aminomethyl)cyclopropyl]phenyl}-1-(4-methoxyphenyl)-3-(trifluoromethyl)-1,4,5,6-tetrahydro-7H-pyrazolo[3,4-c]pyridin-7-one (7 mg, yield: 29%). LC/MS(ESI⁺) 457.4 (M+H)⁺.

EXAMPLE 21

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropyl)methyl]-N-methylacetamide

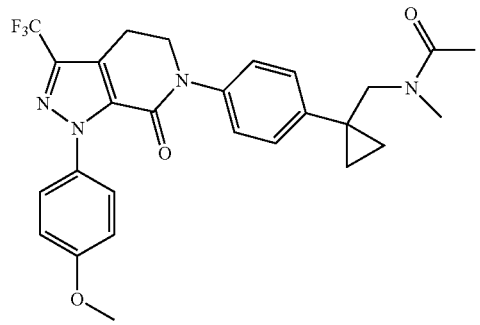

The product of Example 1 (40 mg, 0.084 mmol) was stirred in $CH_2Cl_2$ (1 mL) in a capped vial at RT. $Et_3N$ (4 drops) was added followed by addition of acetyl chloride (2 drops). The resulting mixture was stirred at RT for 10 min. LC-MS showed completion of the reaction. After evaporation of the solvents, the residue was dissolved in MeOH (1 mL) and purified by prep LC-MS (5–98% $CH_3CN/H_2O$ in a 10-min run) to afford pure N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropyl)methyl]-N-methylacetamide (35 mg, yield: 80.3%). LC/MS(ESI⁺) 513.4 (M+H)⁺, $t_R$=6.08 min. HRMS $C_{27}H_{28}O_3F_3N_4$ (M+H)⁺ 513.2120 calcd for 513.2113. ¹H NMR (acetone-$d_6$) δ 7.49 (d, J=9.1 Hz, 2H), 7.33 (m, 4H), 6.97 (d, J=9.0 Hz, 2H), 4.15 (t, J=6.6 Hz, 2H), 3.83 (s, 3H), 3.58 (s, 1H), 3.49 (s, 1H), 3.16 (t, J=6.6 Hz, 2H), 2.91, 2.80 (2×s, 3H), 1.89, 1.50 (2×s, 3H), 0.87 (m, 2H), 0.78 (m, 2H) ppm.

EXAMPLE 22

N'-ethyl-N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropyl)methyl]-N-methylurea

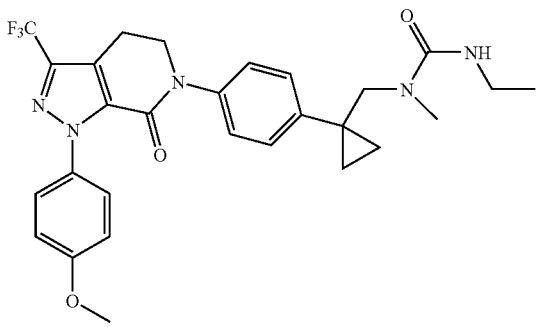

The product of Example 1 (20 mg, 0.042 mmol) was stirred in CH$_2$Cl$_2$ (1 mL) in a capped vial at RT. Et$_3$N (4 drops) was added followed by addition of ethyl isocyanide (2 drops). The resulting mixture was stirred at RT for 2 h. LC-MS showed completion of the reaction. After evaporation of the solvents, the residue was dissolved in MeOH (1 mL), and purified by prep LC-MS (5–98% CH$_3$CN/H$_2$O in a 10-min run) to afford pure N'-ethyl-N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropyl)methyl]-N-methylurea (16 mg, yield: 70%). HRMS C$_{28}$H$_{31}$O$_3$F$_3$N$_5$ 542.2370 (M+H), calcd for 542.2380. $^1$H NMR (acetone-d$_6$) δ 7.49 (d, J=9.2 Hz, 2H), 7.30 (AA'BB', J=8.4 Hz, 4H), 6.97 (d, J=8.8 Hz, 2H), 4.14 (t, J=6.3 Hz, 2H), 3.82 (s, 3H), 3.51 (s, 2H), 3.16 (t, J=6.4 Hz, 2H), 3.02 (q, J=7.0 Hz, 2H), 2.70 (s, 3H), 0.92 (t, J=7.0 Hz, 3H), 0.86 (m, 2H), 0.76 (m, 2H) ppm.

EXAMPLE 23

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropyl)methyl]-N-methylmethanesulfonamide

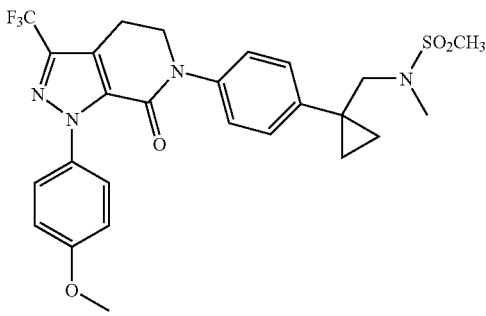

The product of Example 1 (20 mg, 0.042 mmol) was stirred in CH$_2$Cl$_2$ (1 mL) in a capped vial at RT. Pyridine (4 drops) was added followed by two drops of methanesulfonyl chloride. The resulting mixture was stirred for 20 min. LC-MS showed completion of the reaction. After evaporation of the solvents, the residue was dissolved in MeOH (1 mL), and purified by prep LC-MS (5–98% CH$_3$CN/H$_2$O in a 10-min run) to afford pure N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropyl)methyl]-N-methylmethanesulfonamide (16 mg, yield: 69%). LC/MS (ESI$^+$) 549.4 (M+H)$^+$, t$_R$=6.40 min.

EXAMPLE 24

1-(4-methoxyphenyl)-6-{4-[1-(2-methylimidazol-1-ylmethyl)cyclopropyl]phenyl}-3-trifluoromethyl-1,4,5,6-tetrahydro-pyrazolo[3,4-c]pyridin-7-one

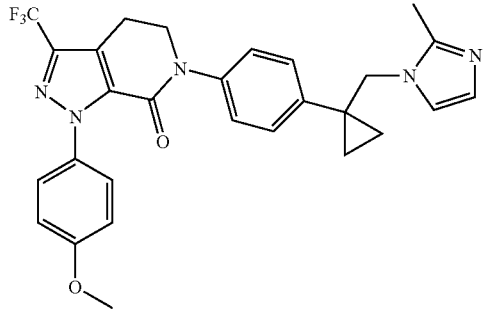

Part A. The product of part E in Example 1 (0.45 g, 0.98 mmol) was stirred in CH$_2$Cl$_2$ (10 mL) at 0° C. under N$_2$. PPh$_3$ (0.52 g, 2.0 eq) was added, followed by the addition of CBr$_4$ (0.33 g, 1.0 eq). The resulting mixture was stirred at 0° C. for 30 min. LC-MS showed completion of the reaction. The mixture was extracted with EtOAc. The organic layer was washed with H$_2$O and brine, dried over MgSO$_4$, filtered, and concentrated to dryness. It was used directly in the next step without purification. LC/MS(ESI$^+$) 520.4, 522.4 (M+H)$^+$.

Part B. The product of Part A (0.20 g, 0.38 mmol), 2-methylimidazole (0.10 g, 1.22 mmol), and K$_2$CO$_3$ (0.25 g, 3.62 mmol) were stirred in DMF (0.4 mL) at RT under N$_2$. The mixture was heated at 85–90° C. for 30 min. LC-MS showed completion of the reaction. After cooling to RT, H$_2$O was added. The mixture was purified by prep LC-MS (35–98% CH$_3$CN in H$_2$O) to give pure 1-(4-methoxyphenyl)-6-{4-[1-(2-methylimidazol-1-ylmethyl)cyclopropyl]phenyl}-3-trifluoromethyl-1,4,5,6-tetrahydro-pyrazolo[3,4-c]pyridin-7-one (53 mg, yield: 27%). LC/MS(ESI$^+$) 522.4 (M+H)$^+$. $^1$H NMR (acetone-d$_6$) δ 7.53 (m, 1H), 7.49 (d, J=8.8 Hz, 2H), 7.39 (m, 1H), 7.25 (AA'BB', J=8.4 Hz, 4H), 6.98 (d, J=8.8 Hz, 2H), 4.38 (s, 2H), 4.15 (t, J=6.6 Hz, 2H), 3.83 (s, 3H), 3.14 (t, J=6.6 Hz, 2H), 2.10 (s, 3H), 1.26 (t, J=5.5 Hz, 2H), 1.02 (t, J=5.5 Hz, 2H) ppm.

EXAMPLE 25

1-(4-methoxyphenyl)-6-{4-[1-(thiazol-2-ylaminomethyl)-cyclopropyl]phenyl}-3-trifluoromethyl-1,4,5,6-tetrahydro-pyrazolo[3,4-c]pyridin-7-one

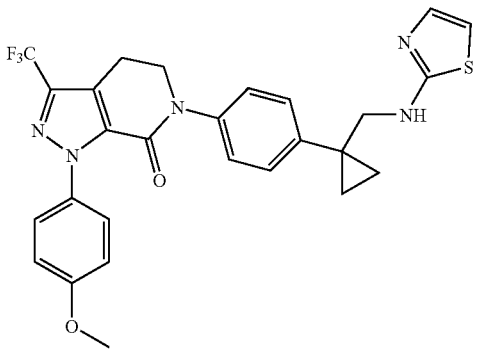

Following a procedure analogous to that of Example 24, the title compound was prepared by using 2-aminothiazole. The product was purified by RP-prep LC-MS (35–98% $CH_3CN/H_2O$ in a 10-min run). LC/MS (ESI$^+$) 540.6 (M+H)$^+$, $t_R$=3.37 min.

EXAMPLE 26 methyl 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopentanecarboxylate

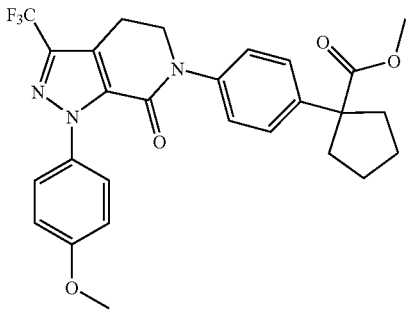

Part A. 1-Phenyl-cyclopentylcarboxylic acid (3.0 g, 15.8 mmol) was stirred in HOAc (10 mL) at RT under $N_2$. $I_2$ (4.01 g, 15.8 mmol) was added followed by the addition of $NaIO_3$ (0.78 g, 3.94 mmol) and conc. $H_2SO_4$ (0.3 mL). The resulting mixture was stirred at 70° C. for 3 days. The cooled mixture was poured into $H_2O$, and extracted with EtOAc. The organic layer was washed with sodium thiosulfate and brine, dried over $MgSO_4$, filtered, and concentrated to dryness to yield 4-iodophenylcylcopentylcarboxylic acid (4.45 g, yield: 89%). LC/MS(ESI$^+$) 317.6 (M+H)$^+$.

Part B. The product from part A (1.08 g, 3.43 mmol) and 1-(4-methoxyphenyl)-3-(trifluoromethyl)-1,4,5,6-tetrahydro-7H-pyrazolo[3,4-c]pyridin-7-one (0.82 g, 2.64 mmol) were stirred in DMSO (3 mL) under $N_2$. $K_2CO_3$ (1.09 g, 7.90 mmol, 3.0 eq) was added followed by the addition of 1,10-phenanthroline (96 mg, 20 mol %) and CuI (100 mg, 20 mol %). The resulting mixture was stirred at 130° C. for 5 h. LC-MS showed completion of the reaction. It was acidified with 1N HCl, and extracted with EtOAc (2×). The organic layer was washed with $H_2O$, brine, dried over $MgSO_4$, filtered, and concentrated to afford 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopentanecarboxylic acid (1.30 g, yield: 99%). LC/MS(ESI$^+$) 500.6 (M+H)$^+$.

Part C. The product of part B (40 mg, 0.080 mmol) was dissolved in MeOH (5 mL), and conc. HCl (0.5 mL) was added. The resulting mixture was stirred at 60° C. overnight. After cooling, the mixture was purified by prep LC-MS (35–98% $CH_3CN$ in $H_2O$ in a 10-min run) to afford methyl 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopentane carboxylate (32 mg, yield: 78%). LC/MS(ESI$^+$) 514.6 (M+H)$^+$, $t_R$=6.09 min. $^1$H NMR (CDCl$_3$) δ 7.45 (d, J=8.8 Hz, 2H), 7.30 (AA'BB', J=8.6 Hz, 4H), 6.92 (d, J=9.0 Hz, 2H), 4.13 (t, J=6.8 Hz, 2H), 3.81 (s, 3H), 3.39 (s, 3H), 3.15 (t, J=6.6 Hz, 2H), 2.65–2.58 (m, 2H), 1.89–1.82 (m, 2H), 1.73–1.69 (m, 4H), 1.58 (m, 2H) ppm.

EXAMPLE 27

1-(4-methoxyphenyl)-6-(4-{1-[(methylamino)methyl]cyclopentyl}phenyl)-3-(trifluoromethyl)-1,4,5,6-tetrahydro-7H-pyrazolo[3,4-c]pyridin-7-one, trifluoroacetic acid salt

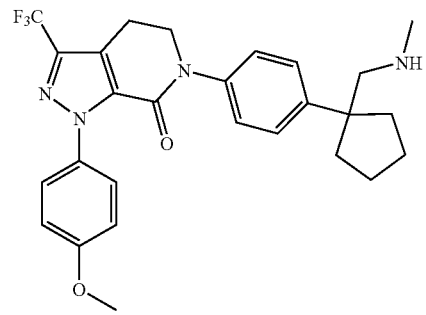

Part A. The product from part B of Example 26 (1.46 g, 2.93 mmol) was stirred in THF (10 mL) at 0° C. under $N_2$. $Et_3N$ (0.62 mL, 4.40 mmol, 1.5 eq) was added followed by dropwise addition of $ClCO_2Et$ (0.31 mL, 3.24 mmol, 1.1 eq). The reaction mixture was then stirred at 0° C. for 1 h. TLC showed completion of the reaction. The mixture was filtered, and rinsed with anhydrous THF. The THF filtrate (ca. 20 mL) was stirred at 0° C. under $N_2$. MeOH (5 mL) was added followed by the addition of $NaBH_4$ (1.03 g, 27.10 mmol, 9.3 eq). The resulting mixture was stirred at 0° C. for 40 min. Analytical LC-MS showed completion of the reaction. Sat'd $Na_2SO_4$ was then added. The mixture was extracted with EtOAc (2×). The organic layer was washed with $H_2O$ (2×) and brine (2×), dried over $Na_2SO_4$, filtered, and concentrated to dryness to give 6-{4-[1-(hydroxymethyl)cyclopentyl]phenyl}-1-(4-methoxyphenyl)-3-(trifluoromethyl)-1,4,5,6-tetrahydro-7H-pyrazolo[3,4-c]pyridin-7-one (1.38 g, 97%). LC/MS (ESI$^+$) 486.4 (M+H)$^+$.

Part B. The product from part A (0.80 g, 1.65 mmol) was stirred in anhydrous $CH_2Cl_2$ (10 mL) at RT under $N_2$. NaOAc (0.5 g, 6.10 mmol) and molecular sieves (4 Å, 1.2 g) were added followed by the addition of PCC (0.89 g, 4.12 mmol). The resulting slurry was stirred at RT for 4 h.

Analytical LC-MS showed completion of the reaction. The mixture was filtered, and rinsed with CH$_2$Cl$_2$. The filtrate was washed with H$_2$O (2×) and brine (2×), dried over Na$_2$SO$_4$, filtered, and concentrated to dryness to afford 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopentanecarbaldehyde (0.78 g, yield: 99%). LC/MS (ESI$^+$) 484.6 (M+H)$^+$.

Part C. The product from part B (100 mg, 0.21 mmol) and methylamine hydrochloride (100 mg, excess) were stirred in dichloroethane (1.0 mL) in a capped vial. NaBH(OAc)$_3$ (200 mg, 0.94 mmol) was added followed by addition of three drops of HOAc. The reaction mixture was stirred at RT for 2 h. Analytical LC-MS showed completion of the reaction. The mixture was evaporated and dissolved in aqueous MeOH. It was then purified by prep LC-MS (5–98% CH$_3$CN/H$_2$O in a 10-min run) to obtain 1-(4-methoxyphenyl)-6-(4-{1-[(methylamino)methyl]cyclopentyl}phenyl)-3-(trifluoromethyl)-1,4,5,6-tetrahydro-7H-pyrazolo[3,4-c]pyridin-7-one (35 mg, yield: 34%). LC/MS (ESI$^+$) 499.4 (M+H)$^+$, t$_R$=4.85 min. $^1$H NMR (acetone-d$_6$) δ 7.50 (m, 4H), 7.35 (d, J=8.4 Hz, 2H), 6.99 (d, J=9.1 Hz, 2H), 4.17 (t, J=6.6 Hz, 2H), 3.83 (s, 3H), 3.39 (s, 2H), 3.16 (t, J=6.3 Hz, 2H), 2.64 (s, 3H), 2.14–1.66 (m, 8H) ppm.

EXAMPLE 28

6-(4-{1-[(dimethylamino)methyl]cyclopentyl}phenyl)-1-(4-methoxyphenyl)-3-(trifluoromethyl)-1,4,5,6-tetrahydro-7H-pyrazolo[3,4-c]pyridin-7-one, trifluoroacetic acid salt

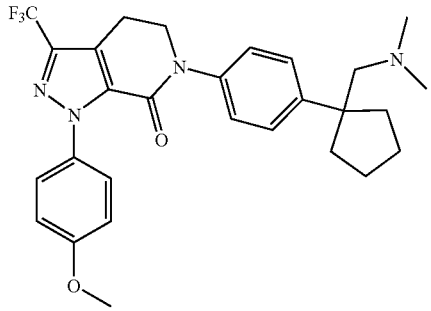

Following a procedure analogous to that used for Example 27, the title compound was prepared. The product was purified by RP-prep LC-MS (5–98% CH$_3$CN/H$_2$O in a 10-min run). LC/MS(ESI$^+$) 513.6 (M+H)$^+$, t$_R$=4.96 min. $^1$H NMR (acetone-d$_6$) δ 7.52 (m, 4H), 7.38 (d, J=8.5 Hz, 2H), 6.98 (d, J=8.8 Hz, 2H), 4.19 (t, J=6.6 Hz, 2H), 3.83 (s, 3H), 3.60 (s, 2H), 3.17 (t, J=6.3 Hz, 2H), 2.62 (s, 6H), 2.16–1.64 (m, 8H) ppm.

EXAMPLE 29

1-(4-methoxyphenyl)-6-{4-[1-(1-pyrrolidinylmethyl)cyclopentyl]phenyl}-3-(trifluoromethyl)-1,4,5,6-tetrahydro-7H-pyrazolo[3,4-c]pyridin-7-one, trifluoroacetic acid salt

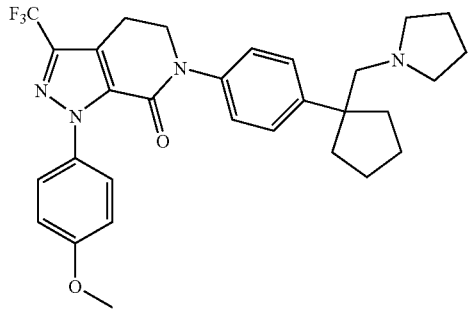

Following a procedure analogous to that used for Example 27, the title compound was prepared. The product was purified by RP-prep LC-MS (5–98% CH$_3$CN/H$_2$O in a 10-min run). LC/MS (ESI$^+$) 539.6 (M+H)$^+$, t$_R$=5.13 min. $^1$H NMR (acetone-d$_6$) δ 7.52 (m, 4H), 7.40 (d, J=8.1 Hz, 2H), 6.99 (d, J=8.8 Hz, 2H), 4.19 (t, J=6.3 Hz, 2H), 3.83 (s, 3H), 3.75 (s, 2H), 3.52 (m, 2H), 3.17 (t, J=6.3 Hz, 2H), 2.92 (m, 2H), 2.18 (m, 2H), 2.04–1.62 (m, 10H) ppm. $^{19}$F NMR (acetone-d$_6$) δ −62.17 (TFA salt), −79.82 (CF$_3$) ppm.

EXAMPLE 30

6-[4-(1-{[(3R)-3-hydroxy-1-pyrrolidinyl]methyl}cyclopentyl)phenyl]-1-(4-methoxyphenyl)-3-(trifluoromethyl)-1,4,5,6-tetrahydro-7H-pyrazolo[3,4-c]pyridin-7-one, trifluoroacetic acid salt

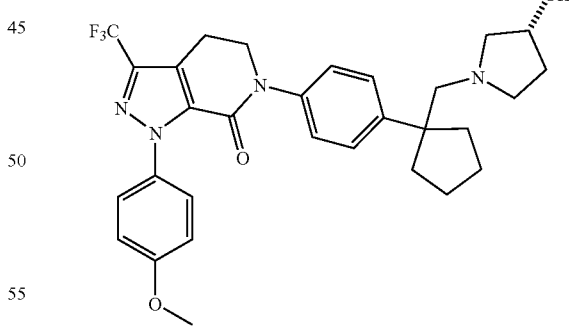

Following a procedure analogous to that used for Example 27, the title compound was prepared. The product was purified by RP-prep LC-MS (5–98% CH$_3$CN/H$_2$O in a 10-min run). LC/MS (ESI$^+$) 555.6 (M+H)$^+$, t$_R$=4.77 min. $^1$H NMR (acetone-d$_6$) δ 7.52 (m, 4H), 7.40 (d, J=8.4 Hz, 2H), 6.99 (d, J=8.8 Hz, 2H), 4.36 (s, br, 1H), 4.19 (t, J=6.3 Hz, 2H), 3.83 (s, 3H), 3.72 (m, 2H), 3.59 (m, 2H), 3.17 (t, J=6.3 Hz, 2H), 2.92 (m, 2H), 2.16–1.63 (m, 10H) ppm. $^{19}$F NMR (acetone-d$_6$) δ −62.16 (TFA salt), −76.70 (CF$_3$) ppm.

EXAMPLE 31

1-(4-methoxyphenyl)-6-{4-[1-(4-morpholinylmethyl)cyclopentyl]phenyl}-3-(trifluoromethyl)-1,4,5,6-tetrahydro-7H-pyrazolo[3,4-c]pyridin-7-one, trifluoroacetic acid salt

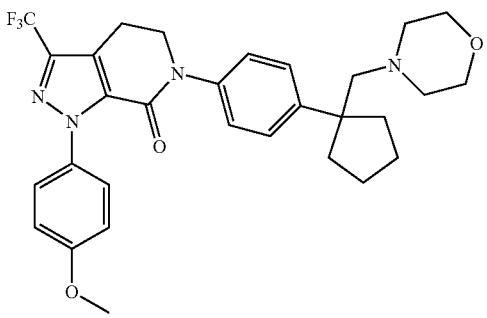

Following a procedure analogous to that used for Example 27, the title compound was prepared. The product was purified by RP-prep LC-MS (5–98% CH$_3$CN/H$_2$O in a 10-min run). LC/MS (ESI$^+$) 555.6 (M+H)$^+$, t$_R$=4.49 min. $^1$H NMR (acetone-d$_6$) δ 7.43 (m, 4H), 7.28 (d, J=8.0 Hz, 2H), 6.89 (d, J=8.4 Hz, 2H), 4.09 (t, J=6.6 Hz, 2H), 3.74 (s, 3H), 3.65 (m, 4H), 3.50 (s, 2H), 3.33 (m, 2H), 3.07 (t, J=6.3 Hz, 2H), 2.89 (m, 2H), 2.02–1.52 (m, 8H) ppm.

EXAMPLE 32

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopentyl)methyl]-N-methylacetamide

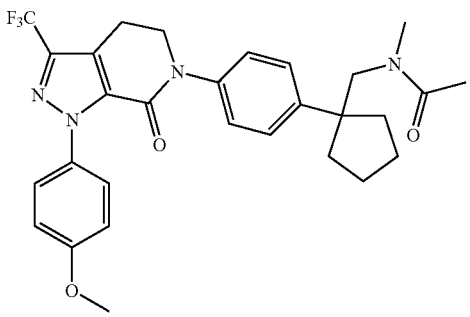

Following a procedure analogous to that used for Example 21, the title compound was prepared. The product was purified by RP-prep LC-MS (5–98% CH$_3$CN/H$_2$O in a 10-min run). LC/MS (ESI$^+$) 541.6 (M+H)$^+$, t$_R$=6.50 min. $^1$H NMR (acetone-d$_6$) δ 7.49 (dd, J=8.8, 1.8 Hz, 2H), 7.34 (m, 4H), 6.97 (dd, J=8.8, 1.8 Hz, 2H), 4.17 (t, J=6 Hz, 2H), 3.82 (s, 3H), 3.52 (s, 2H), 3.17 (t, J=6 Hz, 2H), 2.34 (s, 3H), 2.03–1.59 (m, 11H) ppm.

EXAMPLE 33

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopentyl)methyl]-N-methylmethanesulfonamide

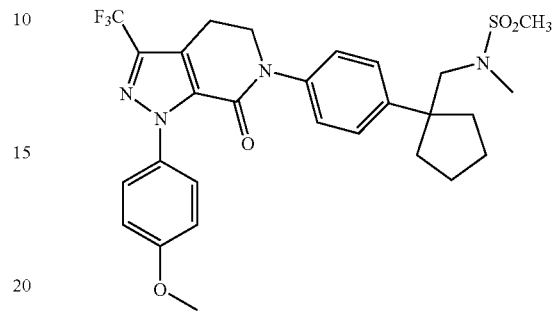

Following a procedure analogous to that used for Example 23, the title compound was prepared. The product was purified by RP-prep LC-MS (5–98% CH$_3$CN/H$_2$O in a 10-min run). LC/MS (ESI$^+$) 577.4 (M+H)$^+$, t$_R$=6.74 min. $^1$H NMR (acetone-d$_6$) δ 7.50 (d, J=9 Hz, 2H), 7.35 (m, 4H), 6.98 (d, J=9 Hz, 2H), 4.18 (t, J=6.5 Hz, 2H), 3.83 (s, 3H), 3.22 (s, 2H), 3.17 (t, J=6.5 Hz, 2H), 2.70 (s, 3H), 2.17 (s, 3H), 2.13 (m, 2H), 1.80 (m, 4H), 1.64 (m, 2H) ppm.

EXAMPLE 34 methyl 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclobutanecarboxylate

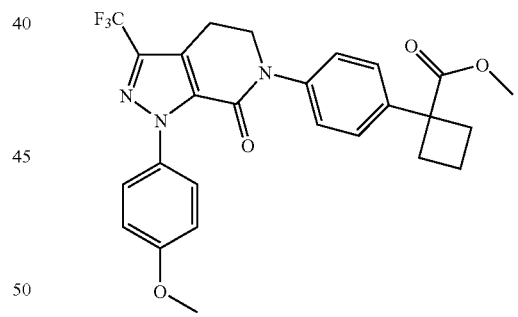

Part A. 1-Phenyl-1-cyclobutylcarbonitrile (5.0 g, 31.83 mmol) and KOH (85%, 6.29 g, 95.49 mmol, 3 eq) were heated in ethylene glycol (10 mL) at 185–190° C. for 6 h under N$_2$. LC-MS showed completion of the reaction. H$_2$O was added to the cooled mixture. It was extracted with Et$_2$O (3×). The aqueous layer was acidified with conc. HCl, and then extracted with CHCl$_3$ (2×). The chloroform layer was washed with H$_2$O, brine, dried over MgSO$_4$, filtered, and concentrated to dryness to give 1-phenyl-1-cyclobutyl carboxylic acid (4.43 g, yield: 79.2%). LC/MS (ESI$^+$) 177.4 (M+H)$^+$, t$_R$=2.56 min (10–90% CH$_3$CN/H$_2$O in a 6-min run).

Part B. The product from part A (4.43 g, 25.2 mmol) was stirred in HOAc (20 mL) at RT under N$_2$. I$_2$ (6.40 g, 25.2 mmol) was added, followed by the addition of NaIO$_3$ (1.25 g, 6.3 mmol) and conc. H$_2$SO$_4$ (0.5 mL). The resulting mixture was stirred at 70° C. for 2 days. LC-MS showed completion of the reaction. The cooled mixture was poured into H$_2$O, and extracted with EtOAc. The organic layer was washed with sodium thiosulfate, brine, dried over MgSO$_4$, filtered, and concentrated to dryness to give 4-iodophenyl-cylcobutyl carboxylic acid (6.49 g, 85%). LC/MS (ESI$^+$) 303.2 (M+H)$^+$, $t_R$=2.55 min (10–90% CH$_3$CN/H$_2$O in a 4-min run).

Part C. The product from part B (1.20 g, 3.97 mmol) and 1-(4-methoxyphenyl)-3-(trifluoromethyl)-1,4,5,6-tetrahydro-7H-pyrazolo[3,4-c]pyridin-7-one (0.87 g, 2.8 mmol) were stirred in DMSO (3 mL) under N$_2$. K$_2$CO$_3$ (1.16 g, mmol, 3.0 eq) was added followed by the addition of 1,10-phenanthroline (100 mg, 20 mol %) and CuI (106 mg, 20 mol %). The resulting mixture was stirred at 130° C. overnight. LC-MS showed completion of the reaction. EtOAc was added to the cooled solution. The solution was acidified with 1N HCl, and the organic layer was washed with H$_2$O and and brine, dried over MgSO$_4$, filtered, and concentrated to afford 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclobutane carboxylic acid (1.34 g, yield 97%). LC/MS (ESI$^+$) 486.6 (M+H)$^+$, $t_R$=2.81 min (10–90% CH$_3$CN/H$_2$O in a 4-min run).

Part D. The product from part C (50 mg, 0.103 mmol) was dissolved in MeOH (5 mL), and conc. HCl (0.5 mL) was added. The resulting mixture was stirred at reflux for 2 h. After cooling, the mixture was purified by prep LC-MS (35–98% CH$_3$CN in H$_2$O) to afford the title compound (35 mg, yield: 68%). LC/MS (ESI$^+$) 499.4 (M+H)$^+$, $t_R$=5.70 min. $^1$H NMR (CDCl$_3$) δ 7.45 (d, J=8.8 Hz, 2H), 7.28 (AA'BB', J=8 Hz, 4H), 6.91 (d, J=8.8 Hz, 2H), 4.13 (t, J=6.9 Hz, 2H), 3.80 (s, 3H), 3.63 (s, 3H), 3.15 (t, J=6.6 Hz, 2H), 2.81 (m, 2H), 2.48 (m, 2H), 2.03 (m, 1H), 1.86 (m, 1H) ppm.

EXAMPLE 35

1-(4-methoxyphenyl)-6-(4-{1-[(methylamino)methyl]cyclobutyl}phenyl)-3-(trifluoromethyl)-1,4,5,6-tetrahydro-7H-pyrazolo[3,4-c]pyridin-7-one, trifluoroacetic acid salt

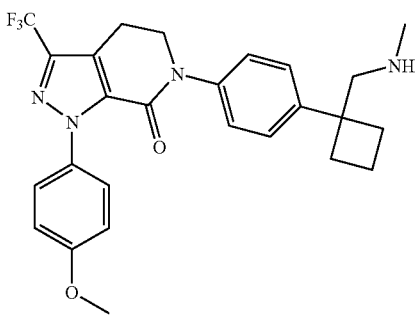

Part A. The product from part C of Example 34 (1.32 g, 2.72 mmol) was stirred in THF (10 mL) at 0° C. under N$_2$. Et$_3$N (0.59 mL, 4.08 mmol, 1.5 eq) was added followed by dropwise addition of ClCO$_2$Et (0.38 mL, 3.54 mmol, 1.3 eq). The reaction mixture was then stirred at 0° C. for 30 min. TLC showed completion of the reaction. The mixture was filtered and rinsed with anhydrous THF. The THF filtrate (ca. 20 mL) was stirred at 0° C. under N$_2$. MeOH (4 mL) was added followed by the addition of NaBH$_4$ (1.03 g, 27.10 mmol, 10 eq). The resulting mixture was stirred at 0° C. for 40 min. Analytical LC-MS showed completion of the reaction. Sat'd Na$_2$SO$_4$ was then added. The mixture was extracted with EtOAc (2×). The organic layer was washed with H$_2$O (2×) and brine (2×), dried over Na$_2$SO$_4$, filtered, and concentrated to dryness to give 6-{4-[1-(hydroxymethyl)cyclobutyl]phenyl}-1-(4-methoxyphenyl)-3-(trifluoromethyl)-1,4,5,6-tetrahydro-7H-pyrazolo[3,4-c]pyridin-7-one (1.30 g, 99%). LC/MS (ESI$^+$) 472.6 (M+H)$^+$, $t_R$=2.84 min (10–90% CH$_3$CN/H$_2$O in a 4-min run).

Part B. The product from part A (0.90 g, 1.91 mmol) was stirred in anhydrous CH$_2$Cl$_2$ (10 mL) at RT under N$_2$. NaOAc (0.32 g, 3.82 mmol, 2.0 eq) and molecular sieves (4 A, 0.90 g) were added followed by the addition of PCC (0.69 g, 2.87 mmol, 1.5 eq). The resulting slurry was stirred at RT for 4 h. Analytical LC-MS showed completion of the reaction. The mixture was filtered and rinsed with CH$_2$Cl$_2$. The filtrate was washed with H$_2$O (2×) and brine (2×), dried over Na$_2$SO$_4$, filtered, and concentrated to dryness to afford 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclobutanecarbaldehyde (0.88 g, yield: 99%). LC/MS (ESI$^+$) 470.6 (M+H)$^+$, $t_R$=3.01 min (10–90% CH$_3$CN/H$_2$O in a 4-min run).

Part C. The product from part B (500 mg, 1.04 mmol), methylamine hydrochloride (200 mg, excess) were stirred in dichloroethane (15 mL) at RT under N$_2$. NaBH(OAc)$_3$ (1.03 g, 4.86 mmol) was added followed by addition of three drops of HOAc. The reaction mixture was stirred at RT for 2.5 h. Analytical LC-MS showed completion of the reaction. The mixture was evaporated, and dissolved in aqueous MeOH. It was then purified by prep LC-MS (5–98% CH$_3$CN/H$_2$O in a 10-min run) to obtain 1-(4-methoxyphenyl)-6-(4-{1-[(methylamino)methyl]cyclobutyl}phenyl)-3-(trifluoromethyl)-1,4,5,6-tetrahydro-7H-pyrazolo[3,4-c]pyridin-7-one (230 mg, 46%). LC/MS (ESI$^+$) 485.4 (M+H)$^+$, $t_R$=4.93 min. $^1$H NMR (acetone-d$_6$) δ 7.51 (d, 2H), 7.33 (m, 4H), 6.99 (d, 2H), 4.17 (m, 2H), 3.83 (s, 3H), 3.62 (m, 2H), 3.17 (m, 2H), 2.73 (s, 3H), 2.46 (m, 4H), 2.15–1.86 (m, 2H) ppm. $^{19}$F NMR (acetone-d$_6$) δ −62.18 (TFA), −76.65 (CF$_3$) ppm.

EXAMPLE 36

6-(4-{1-[(dimethylamino)methyl]cyclobutyl}phenyl)-1-(4-methoxyphenyl)-3-(trifluoromethyl)-1,4,5,6-tetrahydro-7H-pyrazolo[3,4-c]pyridin-7-one, trifluoroacetic acid salt

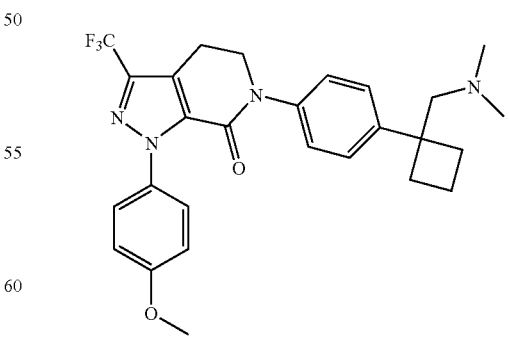

Following a procedure analogous to that used for Example 35, the title compound was prepared. The product was purified by RP-prep LC-MS (5–98% CH$_3$CN/H$_2$O in a 10-min run). LC/MS (ESI$^+$) 499.6 (M+H)$^+$, $t_R$=4.75 min. $^1$H NMR (acetone-d$_6$) δ 7.49 (m, 4H), 7.39 (d, J=8.0 Hz, 2H), 6.98 (d, J=9.1 Hz, 2H), 4.19 (t, J=6.4 Hz, 2H), 3.83 (s, 3H), 3.77 (m, 2H), 3.17 (t, J=6.3 Hz, 2H), 2.68 (s, 6H), 2.48 (t, J=7.5 Hz, 4H), 2.09 (m, 1H), 1.89 (m, 1H) ppm.

EXAMPLE 37

6-(4-{1-[(diethylamino)methyl]cyclobutyl}phenyl)-1-(4-methoxyphenyl)-3-(trifluoromethyl)-1,4,5,6-tetrahydro-7H-pyrazolo[3,4-c]pyridin-7-one, trifluoroacetic acid salt

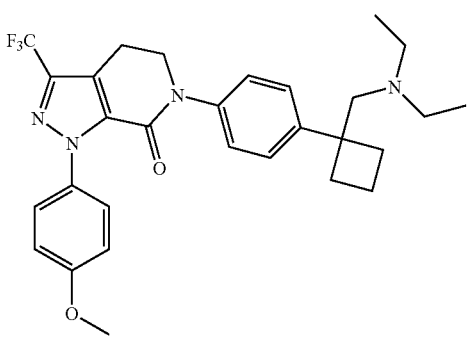

Following a procedure analogous to that used for Example 35, the title compound was prepared. The product was purified by RP-prep LC-MS (5–98% CH$_3$CN/H$_2$O in a 10-min run). LC/MS (ESI$^+$) 527.6 (M+H)$^+$, t$_R$=5.04 min. $^1$H NMR (acetone-d$_6$) δ 7.53 (m, 4H), 7.39 (d, J=8.5 Hz, 4H), 6.98 (d, J=9.1 Hz, 2H), 4.19 (t, J=6.3 Hz, 2H), 3.83 (s, 3H), 3.68 (s, 2H), 3.17 (t, J=6.3 Hz, 2H), 2.95 (m, 4H), 2.48 (t, J=7.8 Hz, 4H), 2.10–1.85 (m, 2H), 1.16 (m, 6H) ppm.

EXAMPLE 38

1-(4-methoxyphenyl)-6-{4-[1-(1-pyrrolidinylmethyl)cyclobutyl]phenyl}-3-(trifluoromethyl)-1,4,5,6-tetrahydro-7H-pyrazolo[3,4-c]pyridin-7-one, trifluoroacetic acid salt

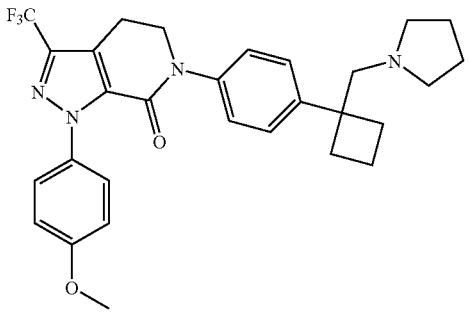

Following a procedure analogous to that used for Example 35, the title compound was prepared. The product was purified by RP-prep LC-MS (5–98% CH$_3$CN/H$_2$O in a 10-min run). LC/MS (ESI$^+$) 525.6 (M+H)$^+$, t$_R$=4.97 min. $^1$H NMR (acetone-d$_6$) δ 7.51 (d, J=8.4 Hz, 2H), 7.39 (m, 4H), 6.98 (d, J=8.8 Hz, 2H), 4.19 (t, J=6.4 Hz, 2H), 3.87 (m, 2H), 3.83 (s, 3H), 3.51 (m, 2H), 3.17 (t, J=6.3 Hz, 2H), 2.93 (m, 2H), 2.47 (m, 4H), 2.09–1.85 (m, 6H) ppm. $^{19}$F NMR (acetone-d$_6$) δ −62.16 (TFA), −76.74 (CF$_3$) ppm.

EXAMPLE 39

6-[4-(1-{[(3R)-3-hydroxy-1-pyrrolidinyl]methyl}cyclobutyl)phenyl]-1-(4-methoxyphenyl)-3-(trifluoromethyl)-1,4,5,6-tetrahydro-7H-pyrazolo[3,4-c]pyridin-7-one, trifluoroacetic acid salt

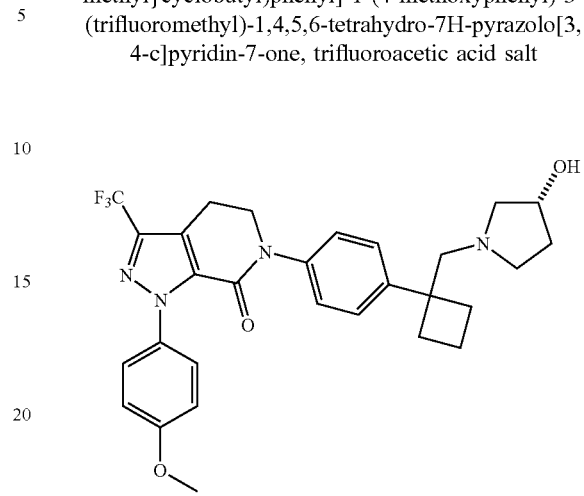

Following a procedure analogous to that used for Example 35, the title compound was prepared. The product was purified by RP-prep LC-MS (5–98% CH$_3$CN/H$_2$O in a 10-min run). LC/MS (ESI$^+$) 541.6 (M+H)$^+$, t$_R$=4.77 min. $^1$H NMR (acetone-d$_6$) δ 7.51 (d, J=8.9 Hz, 2H), 7.39 (m, 4H), 6.98 (d, J=9.1 Hz, 2H), 4.33 (m, 1H), 4.20 (t, J=6.5 Hz, 2H), 3.83 (m, 7H), 3.52 (m, 2H), 3.17 (t, J=6.5 Hz, 2H), 2.47 (m, 4H), 2.14–1.84 (m, 4H). $^{19}$F NMR (acetone-d$_6$) δ −62.16 (TFA), −76.34 (CF$_3$) ppm.

EXAMPLE 40

1-(4-methoxyphenyl)-6-{4-[1-(4-morpholinylmethyl)cyclobutyl]phenyl}-3-(trifluoromethyl)-1,4,5,6-tetrahydro-7H-pyrazolo[3,4-c]pyridin-7-one, trifluoroacetic acid salt

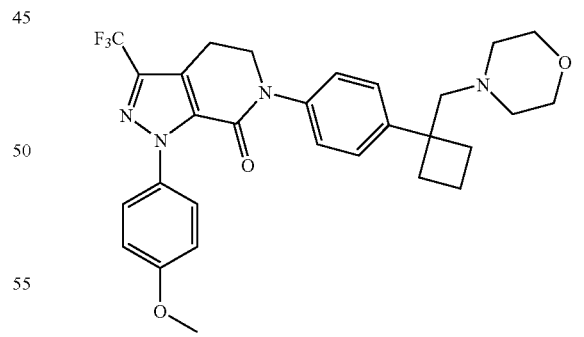

Following a procedure analogous to that used for Example 35, the title compound was prepared. The product was purified by RP-prep LC-MS (5–98% CH$_3$CN/H$_2$O in a 10-min run). LC/MS (ESI$^+$) 541.6 (M+H)$^+$, t$_R$=4.86 min. $^1$H NMR (acetone-d$_6$) δ 7.49 (m, 4H), 7.37 (m, 2H), 6.98 (d, J=8.8 Hz, 2H), 4.18 (m, 2H), 3.83 (s, 3H), 3.74 (m, 8H), 3.17 (t, J=6.5 Hz, 2H), 3.00 (m, 2H), 2.46 (m, 4H), 1.86 (m, 2H) ppm.

EXAMPLE 41

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclobutyl)methyl]-N-methylacetamide

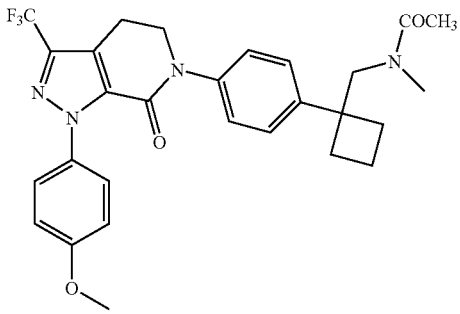

Following a procedure analogous to that used for Example 21, the title compound was prepared by using the product from Example 37 and acetyl chloride as the starting material. The mixture was purified by RP-prep LC-MS (5–98% $CH_3CN/H_2O$ in a 10-min run). LC/MS (ESI+) 527.2 (M+H)+, $t_R$=6.36 min. $^1$H NMR (acetone-$d_6$) δ 7.50 (d, J=9.2 Hz, 2H), 7.33 (d, J=8.7 Hz, 2H), 7.24 (m, 2H), 6.98 (d, J=9.2 Hz, 2H), 4.17 (d, J=6.6 Hz, 2H), 3.83 (s, 3H), 3.71, 3.67 (s, 2H), 3.17 (t, J=6.5 Hz, 2H), 2.76, 2.45 (s, 3H), 2.35 (m, 2H), 2.18 (m, 1H), 2.08 (m, 1H), 1.76 (m, 2H), 1.33 (m, 1H) ppm.

EXAMPLE 42

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclobutyl)methyl]-N-methylmethanesulfonamide

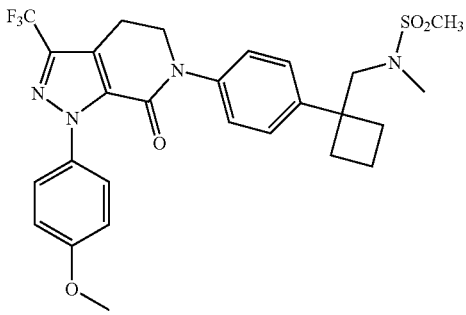

Following a procedure analogous to that used for Example 23, the title compound was prepared. The mixture was purified by RP-prep LC-MS (5–98% $CH_3CN/H_2O$ in a 10-min run). LC/MS (ESI+) 563.2 (M+H)+, $t_R$=6.62 min. $^1$H NMR (acetone-$d_6$) δ 7.50 (d, J=8.8 Hz, 4H), 7.34 (d, J=8.5 Hz, 2H), 7.23 (d, J=8.4 Hz, 2H), 6.98 (d, J=8.8 Hz, 2H), 4.18 (d, J=6.6 Hz, 2H), 3.83 (s, 3H), 3.45 (s, 2H), 3.17 (t, J=6.5 Hz, 2H), 2.70 (s, 3H), 2.38 (m, 2H), 2.28 (s, 3H), 2.26 (m, 2H), 2.03 (m, 1H), 1.81 (m, 1H) ppm.

EXAMPLE 43

1-{4-[1-(4-Methoxyphenyl)-7-oxo-3-trifluoromethyl-1,4,5,7-tetrahydro-pyrazolo[3,4-c]pyridin-6-yl]-phenyl}cyclohexanecarboxylic acid methyl ester

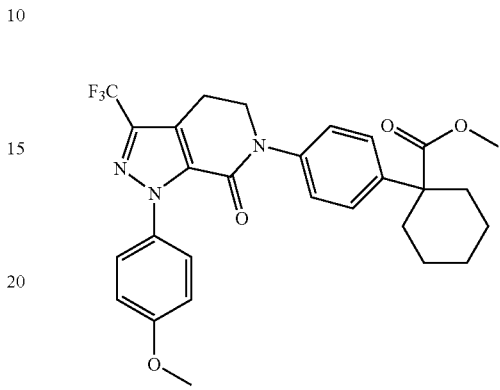

Part A. 1-Phenyl-cyclohexylcarboxylic acid (3.0 g, 14.70 mmol) was stirred in HOAc (10 mL) at RT under $N_2$. $I_2$ (3.73 g, 14.70 mmol) was added, followed by the addition of $NaIO_3$ (0.72 g, 3.64 mmol) and conc. $H_2SO_4$ (0.2 mL). The resulting mixture was stirred at 70° C. for 2 days. LC-MS showed the majority was the desired product. After partial evaporation, the cooled mixture was poured into $H_2O$ and extracted with EtOAc. The organic layer was washed with sodium thiosulfate and brine, dried over $MgSO_4$, filtered, and concentrated to dryness to give almost pure 4-iodophenylcyclohexylcaroxylic acid (4.56 g, yield: 93.7%). LC/MS (ESI+) 331.4 (M+H)+, $t_R$=3.96 min (10–90% $CH_3CN/H_2O$ in a 6-min run).

Part B. The product of part A (0.70 g, 2.25 mmol) and 1-(4-methoxyphenyl)-3-(trifluoromethyl)-1,4,5,6-tetrahydro-7H-pyrazolo[3,4-c]pyridin-7-one (0.70 g, 2.25 mmol) were stirred in DMSO (3 mL) under $N_2$. $K_2CO_3$ (0.93 g, mmol, 3.0 eq) was added, followed by the addition of 1,10-phenanthroline (80 mg, 20 mmol %) and CuI (85 mg, 20 mmol %). The resulting mixture was stirred at 130° C. for 2 days. LC-MS showed completion of the reaction. EtOAc was added to the cooled solution. It was acidified with 1N HCl; and the organic layer was washed with $H_2O$ and brine, dried over $MgSO_4$, filtered, and concentrated. LC/MS (ESI+) 514.4 (M+H)+. The residue (50 mg) was dissolved in MeOH (5 mL), and conc. HCl (0.5 mL) was added. The resulting mixture was stirred at 60° C. for 4 h. After cooling, the mixture was purified by prep LC-MS (35–98% $CH_3CN$ in $H_2O$) to give pure 1-{4-[1-(4-Methoxyphenyl)-7-oxo-3-trifluoromethyl-1,4,5,7-tetrahydro-pyrazolo[3,4-c]pyridin-6-yl]-phenyl}cyclohexanecarboxylic acid methyl ester (43 mg, yield: 83.7%). LC/MS (ESI+) 528.4 (M+H)+, $t_R$=6.38 min. $^1$H NMR (CDCl$_3$) δ 7.45 (d, J=9.1 Hz, 2H), 7.32 (AA'BB', J=8.6 Hz, 4H), 6.92 (d, J=8.8 Hz, 2H), 4.13 (t, J=6.6 Hz, 2H), 3.81 (s, 3H), 3.63 (s, 3H), 3.15 (t, J=6.6 Hz, 2H), 2.45 (m, 2H), 1.72–1.24 (m, 8H) ppm.

EXAMPLE 44

1-(4-methoxyphenyl)-6-(4-{1-[(methylamino)methyl]cyclohexyl}phenyl)-3-(trifluoromethyl)-1,4,5,6-tetrahydro-7H-pyrazolo[3,4-c]pyridin-7-one, trifluoroacetic acid salt

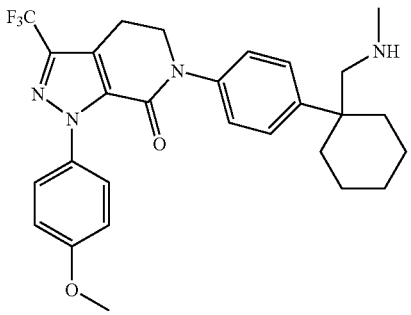

Part A. The product from part B of Example 43 (1.34 g, 2.61 mmol) was stirred in THF (10 mL) at 0° C. under $N_2$. $Et_3N$ (0.55 mL, 3.92 mmol, 1.5 eq) was added followed by dropwise addition of $ClCO_2Et$ (0.33 mL, 3.34 mmol, 1.3 eq). The reaction mixture was then stirred at 0° C. for 20 min. TLC showed completion of the reaction. The mixture was filtered, and rinsed with anhydrous THF. The THF filtrate (ca. 20 mL) was stirred at 0° C. under $N_2$. MeOH (3.5 mL) was added followed by the addition of $NaBH_4$ (1.00 g, 26.3 mmol, 10 eq). The resulting mixture was stirred at 0° C. for 40 min. Analytical LC-MS showed completion of the reaction. Sat'd $Na_2SO_4$ was then added. The mixture was extracted with EtOAc (2×). The organic layer was washed with $H_2O$ (2×) and brine (2×), dried over $Na_2SO_4$, filtered, and concentrated to dryness to give 6-{4-[1-(hydroxymethyl)cyclohexyl]phenyl}-1-(4-methoxyphenyl)-3-(trifluoromethyl)-1,4,5,6-tetrahydro-7H-pyrazolo[3,4-c]pyridin-7-one (1.21 g, yield 92.8%). LC/MS (ESI$^+$) 500.6 (M+H)$^+$, $t_R$=3.06 min (10–90% $CH_3CN/H_2O$ in a 4-min run). $^1$H NMR (CDCl$_3$) δ 7.46 (d, J=8.8 Hz, 2H), 7.34 (AA'BB', J=8.4 Hz, 4H), 6.92 (d, J=8.8 Hz, 2H), 4.15 (t, J=6.7 Hz, 2H), 3.81 (s, 3H), 3.49 (s, 2H), 3.16 (t, J=6.6 Hz, 2H), 2.24 (m, 2H), 2.13 (m, 2H), 1.56 (m, 4H), 1.34 (m, 2H) ppm.

Part B. The product from part A (0.56 g, 1.12 mmol) was stirred in anhydrous $CH_2Cl_2$ (10 mL) at RT under $N_2$. NaOAc (0.37 g, 4.48 mmol, 4 eq) and molecular sieves (4 Å, 1.0 g) were added followed by the addition of PCC (0.73 g, 3.36 mmol, 3 eq). The resulting slurry was stirred at RT for 1.5 h. Analytical LC-MS showed completion of the reaction. The mixture was filtered, and rinsed with $CH_2Cl_2$. The filtrate was washed with $H_2O$ (2×) and brine (2×), dried over $Na_2SO_4$, filtered, and concentrated to dryness to afford 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclohexanecarbaldehyde (0.54 g, yield: 100%). LC/MS (ESI$^+$) 498.6 (M+H)$^+$, $t_R$=3.20 min (10–90% $CH_3CN$ in $H_2O$ in a 4-min run).

Part C. The product from part B (0.4 g, 0.85 mmol) and methylamine hydrochloride (0.2 mg, 2.99 mmol, excess) were stirred in dichloroethane (8 mL) at RT under $N_2$. NaBH(OAc)$_3$ (0.85 mg, 4.01 mmol) was added followed by addition of HOAc (0.1 mL). The reaction mixture was stirred at RT for 2 h. Analytical LC-MS showed completion of the reaction. The mixture was evaporated, and dissolved in aqueous MeOH. The mixture was purified by RP-prep LC-MS (5–98% $CH_3CN/H_2O$ in a 10-min run) to afford 1-(4-methoxyphenyl)-6-(4-{1-[(methylamino)methyl]cyclohexyl}phenyl)-3-(trifluoromethyl)-1,4,5,6-tetrahydro-7H-pyrazolo[3,4-c]pyridin-7-one (120 mg. Yield: 29%). LC/MS (ESI$^+$) 513.4 (M+H)$^+$, $t_R$=4.97 min. $^1$H NMR (acetone-d$_6$) δ 7.52 (m, 4H), 7.38 (d, J=8.5 Hz, 2H), 6.97 (d, J=8.8 Hz, 2H), 4.19 (t, J=6.3 Hz, 2H), 3.81 (s, 3H), 3.60 (s, 2H), 3.17 (t, J=6.3 Hz, 2H), 2.62 (s, 6H), 2.16–1.64 (m, 8H) ppm.

EXAMPLE 45

6-(4-{1-[(dimethylamino)methyl]cyclohexyl}phenyl)-1-(4-methoxyphenyl)-3-(trifluoromethyl)-1,4,5,6-tetrahydro-7H-pyrazolo[3,4-c]pyridin-7-one, trifluoroacetic acid salt

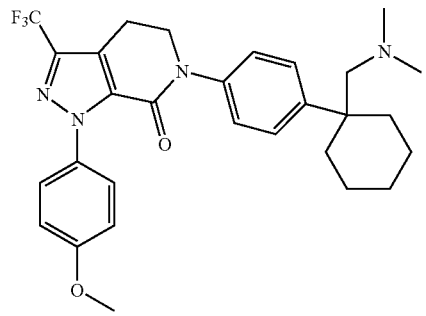

Following a procedure analogous to that used for Example 44, the title compound was prepared. The product was purified by RP-prep LC-MS (5–98% $CH_3CN/H_2O$ in a 10-min run). LC/MS (ESI$^+$) 526.4 (M+H)$^+$. $^1$H NMR (acetone-d$_6$) δ 7.52 (m, 4H), 7.38 (d, J=8.5 Hz, 2H), 6.97 (d, J=8.8 Hz, 2H), 4.19 (t, J=6.3 Hz, 2H), 3.81 (s, 3H), 3.60 (s, 2H), 3.17 (t, J=6.3 Hz, 2H), 2.62 (s, 6H), 2.16–1.64 (m, 8H) ppm.

EXAMPLE 46

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclohexyl)methyl]-N-methylacetamide

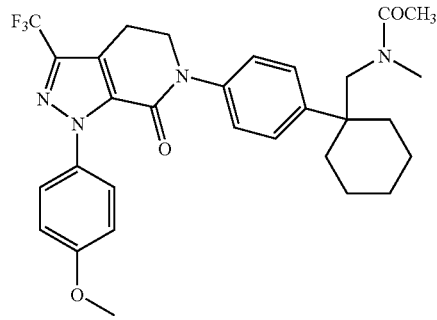

Following a procedure analogous to that used for Example 21, the title compound was prepared. The product was purified by RP-prep LC-MS (5–98% CH$_3$CN/H$_2$O in a 10-min run). LC/MS (ESI$^+$) 555.2 (M+H)$^+$, t$_R$=6.76 min. $^1$H NMR (acetone-d$_6$) δ 7.50 (d, J=8.8 Hz, 2H), 7.38 (m, 4H), 6.98 (d, J=9.2 Hz, 2H), 4.19 (t, J=6.4 Hz, 2H), 3.83 (s, 3H), 3.39 (m, 2H), 3.17 (t, J=6.4 Hz, 2H), 2.70, 2.42 (s, 3H), 2.02, 1.93 (m, 3H), 1.56 (m, 6H), 1.40 (m, 4H) ppm.

EXAMPLE 47

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclohexyl)methyl]-N-methylmethanesulfonamide

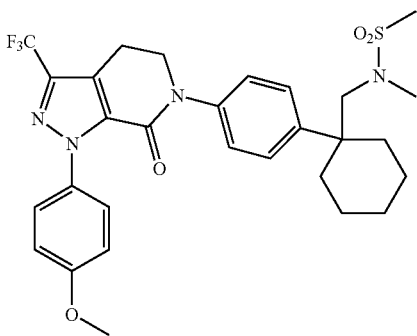

Following a procedure analogous to that used for Example 23, the title compound was prepared. The product was purified by RP-prep LC-MS (5–98% CH$_3$CN/H$_2$O in a 10-min run). LC/MS (ESI$^+$) 591.2 (M+H)$^+$, t$_R$=6.90 min. $^1$H NMR (acetone-d$_6$) δ 7.50 (d, J=8.8 Hz, 2H), 7.42 (AA'BB', J=8.8 Hz, 4H), 6.98 (d, J=8.7 Hz, 2H), 4.19 (t, J=6.6 Hz, 2H), 3.83 (s, 3H), 3.17 (t, J=6.6 Hz, 2H), 3.10 (s, 2H), 2.69 (m, 3H), 2.21 (m, 3H), 1.57 (m, 6H), 1.29 (m, 4H) ppm.

EXAMPLE 48

1-(4-methoxyphenyl)-6-(4-{1-[(methylamino)methyl]cyclopropyl}phenyl)-3-(methylsulfonyl)-1,4,5,6-tetrahydro 7H-pyrazolo[3,4-c]pyridin-7-one, trifluoroacetic acid salt

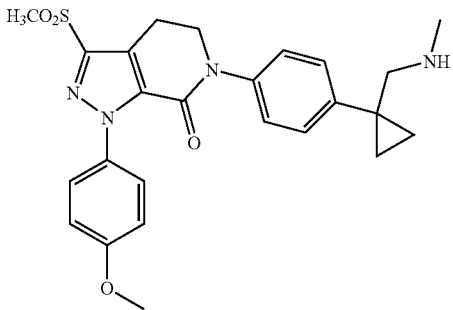

Part A. 3-Chloro-5,6-dihydro-2(1H)-pyridinone (10.0 g, 38.17 mmol) and (1Z)-1-[chloro(methylsulfonyl)methylene]-2-(4-methoxyphenyl)hydrazine (5.0 g, 38.17 mmol) were stirred in toluene (200 mL) at RT under N$_2$. Et$_3$N (30 mL, 215.24 mmol) in toluene (150 mL) was added dropwise to the solution. After addition, the mixture was heated at 85° C. overnight. After cooling, H$_2$O was added. It was extracted with EtOAc (2×). The organic layers were washed with H$_2$O (2×) and brine, dried over MgSO$_4$, filtered, and concentrated to dryness. The residue was purified by flash column chromatography (silica gel, CH$_2$Cl$_2$, then CH$_2$Cl$_2$:EtOAc=1:1, then EtOAc) to give 1-(4-methoxyphenyl)-3-(methylsulfonyl)-1,4,5,6-tetrahydro-7H-pyrazolo[3,4-c]pyridin-7-one (3.85 g, yield: 31%). LC/MS (ESI$^+$) 322.4 (M+H)$^+$, t$_R$=1.79 min (10–90% CH$_3$CN/H$_2$O in a 4-min run).

Part B. The product from part A (2.07 g, 6.23 mmol) and 4-iodophenylcyclopropylcarboxylic acid (2.75 g, 9.54 mmol, 1.5 eq) were stirred in DMSO (6 mL) under N$_2$. K$_2$CO$_3$ (2.57 g, 18.62 mmol, 3.0 eq) was added, followed by the addition of CuI (0.24 g, 20 mol %) and 1,10-phenanthroline (0.23 g, 20 mol %). The resulting mixture was heated at 130° C. overnight. After cooling, 1N HCl was added to acidify the solution. It was extracted with EtOAc (2×), washed with H$_2$O and brine, dried over MgSO$_4$, filtered, and concentrated to dryness to give 1-{4-[1-(4-methoxyphenyl)-3-(methylsulfonyl)-7-oxo-1,4,5,7-tetrahydro-6H-pyrazolo[3,4-c]pyridin-6-yl]phenyl}cyclopropanecarboxylic acid (2.95 g, yield: 95%). LC/MS (ESI$^+$) 482.4 (M+H)$^+$, t$_R$=2.25 min (10–90% CH$_3$CN/H$_2$O in a 4-min run).

Part C. The product from part B (2.21 g, 4.59 mmol) was stirred in THF (15 mL) at 0° C. under N$_2$. Et$_3$N (0.96 mL, 6.89 mmol, 1.5 eq) was added, followed by dropwise addition of ClCO$_2$Et (0.57 mL, 5.48 mmol, 1.2 eq). The reaction mixture was then stirred at 0° C. for 40 min. TLC showed completion of the reaction. The mixture was filtered, and rinsed with anhydrous THF. The THF filtrate (ca. 20 mL) was stirred at 0° C. under N$_2$. MeOH (4 mL) was added, followed by portionwise addition of NaBH$_4$ (1.62 g, 42.63 mmol, 9 eq). The resulting mixture was stirred at 0° C. for 35 min. Analytical LC-MS showed completion of the reaction. Sat'd Na$_2$SO$_4$ was then added. The mixture was extracted with EtOAc (2×). The organic layer was washed with H$_2$O (2×) and brine (2×), dried over Na$_2$SO$_4$, filtered, and concentrated to dryness to give 6-{4-[1-(hydroxymethyl)cyclopropyl]phenyl}-1-(4-methoxyphenyl)-3-(methylsulfonyl)-1,4,5,6-tetrahydro-7H-pyrazolo[3,4-c]pyridin-7-one (0.23 g, 84.7%). LC/MS (ESI$^+$) 468.4 (M+H)$^+$, t$_R$=2.24 min (10–90% CH$_3$CN/H$_2$O in a 4-min run).

Part D. The product from part C (1.52 g, 3.27 mmol) was stirred in anhydrous CH$_2$Cl$_2$ (15 mL) at RT under N$_2$. NaOAc (0.54 g, 6.54 mmol, 2.0 eq) and molecular sieves (4 Å, 1.5 g) were added, followed by the addition of PCC (1.06 g, 4.90 mmol, 1.5 eq). The resulting slurry was stirred at RT for 2 h. Analytical LC-MS showed completion of the reaction. The mixture was filtered through Celite®, and rinsed with CH$_2$Cl$_2$. The filtrate was washed with H$_2$O (2×) and brine (2×), dried over Na$_2$SO$_4$, filtered, and concentrated to dryness to give 1-{4-[1-(4-methoxyphenyl)-3-(methylsulfonyl)-7-oxo-1,4,5,7-tetrahydro-6H-pyrazolo[3,4-c]pyridin-6-yl]phenyl}cyclopropanecarbaldehyde (1.35 g, yield: 89%). LC/MS (ESI$^+$) 466.4 (M+H)$^+$, t$_R$=2.38 min (10–90% CH$_3$CN/H$_2$O in a 4-min run).

Part E. The product from Part E (100 mg, 0.22 mmol) and methylamine hydrochloride (50 mg, excess) were stirred in dichloroethane (1 mL) in a capped vial. NaBH(OAc)$_3$ (250 mg, 1.16 mmol) was added followed by addition of one drop of HOAc. The reaction mixture was stirred at RT for 1.5 h. Analytical LC-MS showed completion of the reaction. The mixture was evaporated, and dissolved in aqueous MeOH. It was then purified by prep LC-MS (5–98% CH$_3$CN/H$_2$O in a 10-min run) to obtain the product 1-(4-methoxyphenyl)-6-(4-{1-[(methylamino)methyl]cyclopropyl}phenyl)-3-

(methylsulfonyl)-1,4,5,6-tetrahydro 7H-pyrazolo[3,4-c]pyridin-7-one (33 mg, 31.3%). LC/MS (ESI$^+$) 481.4 (M+H)$^+$, $t_R$=3.99 min. $^1$H NMR (acetone-d$_6$) δ 7.53 (m, 4H), 7.32 (d, J=7.7 Hz, 2H), 7.00 (d, J=8.8 Hz, 2H), 4.13 (t, J=6.4 Hz, 2H), 3.83 (s, 3H), 3.46 (m, 2H), 3.26 (m, 5H), 2.80 (m, 3H), 1.11 (m, 2H), 1.00 (m, 2H) ppm.

EXAMPLE 49

6-(4-{1-[(dimethylamino)methyl]cyclopropyl}phenyl)-1-(4-methoxyphenyl)-3-(methylsulfonyl)-1,4,5,6-tetrahydro-7H-pyrazolo[3,4-c]pyridin-7-one, trifluoroacetic acid salt

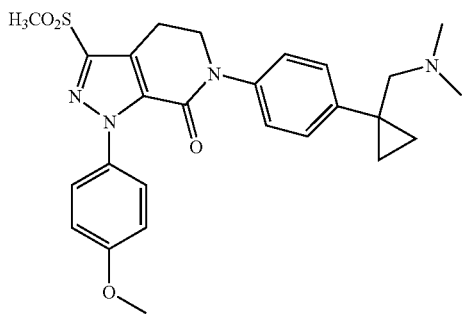

Following a procedure analogous to that used for the preparation of Example 48, the title compound was prepared. The product was purified by RP-prep LC-MS (5–98% CH$_3$CN/H$_2$O in a 10-min run). LC/MS (ESI$^+$) 495.6 (M+H)$^+$, $t_R$=4.06 min. $^1$H NMR (acetone-d$_6$) δ 7.55 (m, 4H), 7.38(d, J=7.5 Hz, 2H), 7.02 (d, J=8.4 Hz, 2H), 4.16 (d, J=6.6 Hz, 2H), 3.86 (m, 3H), 3.71 (m, 2H), 3.64 (m, 2H), 3.29, 3.25 (m, 6H), 3.09 (t, J=6.6 Hz, 2H), 2.99 (m, 3H), 1.17 (m, 2H), 1.13 (m, 2H) ppm.

EXAMPLE 50

6-(4-{1-[(isopropylamino)methyl]cyclopropyl}phenyl)-1-(4-methoxyphenyl)-3-(methylsulfonyl)-1,4,5,6-tetrahydro-7H-pyrazolo[3,4-c]pyridin-7-one, trifluoroacetic acid salt

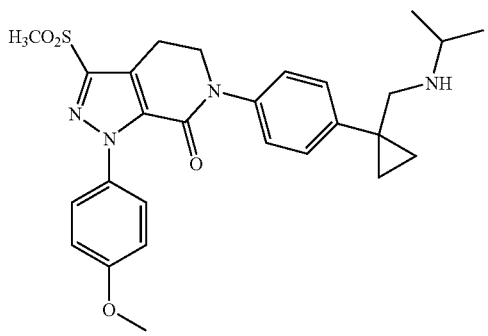

Following a procedure analogous to that used for the preparation of Example 48, the title compound was prepared. The product was purified by RP-prep LC-MS (5–98% CH$_3$CN/H$_2$O in a 10-min run). LC/MS (ESI$^+$) 509.6 (M+H)$^+$, $t_R$=4.34 min. $^1$H NMR (acetone-d$_6$) δ 7.58 (m, 4H), 7.33 (d, J=8.4 Hz, 2H), 7.02 (d, J=9.1 Hz, 2H), 4.52 (m, 1H), 4.16 (d, J=6.6 Hz, 2H), 3.86 (s, 3H), 3.79 (m, 2H), 3.61 (m, 1H), 3.48 (m, 2H), 3.29 (m, 5H), 1.33 (d, J=6.2 Hz, 2H), 1.17 (m, 2H), 1.07 (m, 2H) ppm.

EXAMPLE 51

6-(4-{1-[(cyclopentylamino)methyl]cyclopropyl}phenyl)-1-(4-methoxyphenyl)-3-(methylsulfonyl)-1,4,5,6-tetrahydro-7H-pyrazolo[3,4-c]pyridin-7-one, trifluoroacetic acid salt

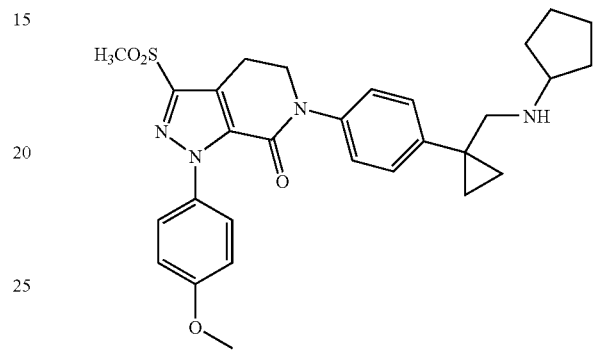

Following a procedure analogous to that used for the preparation of Example 48, the title compound was prepared. The product was purified by RP-prep LC-MS (5–98% CH$_3$CN/H$_2$O in a 10-min run). LC/MS (ESI$^+$) 535.4 (M+H)$^+$, $t_R$=4.30 min. $^1$H NMR (acetone-d$_6$) δ 7.55 (m, 4H), 7.33 (d, J=7.4 Hz, 2H), 7.02 (d, J=8.8 Hz, 2H), 4.16 (t, J=6.6 Hz, 2H), 3.85 (s, 3H), 3.64 (m, 1H), 3.44 (m, 2H), 3.09 (m, 2H), 2.05 (m, 2H), 1.70 (m, 4H), 1.53 (m, 2H), 1.16 (m, 2H), 0.98 (m, 2H) ppm.

EXAMPLE 52

1-(4-methoxyphenyl)-3-(methylsulfonyl)-6-{4-[1-(1-pyrrolidinylmethyl)cyclopropyl]phenyl}-1,4,5,6-tetrahydro-7H-pyrazolo[3,4-c]pyridin-7-one, trifluoroacetic acid salt

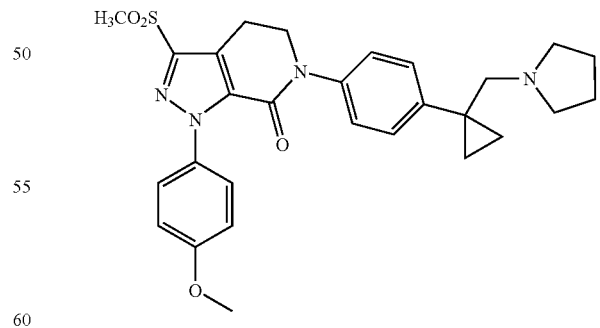

Following a procedure analogous to that used for the preparation of Example 48, the title compound was prepared. The product was purified by RP-prep LC-MS (5–98% CH$_3$CN/H$_2$O in a 10-min run). LC/MS (ESI$^+$) 521.4 (M+H)$^+$, $t_R$=4.07 min. $^1$H NMR (acetone-d$_6$) δ 7.58 (m, 4H), 7.37 (d, J=7.7 Hz, 2H), 7.02 (d, J=7.7 Hz, 2H), 4.19 (t, J=6.6

Hz, 2H), 3.85 (s, 3H), 3.70 (m, 4H), 3.28 (m, 5H), 3.09 (t, J=6.6 Hz, 2H), 2.08–2.03 (m, 2H), 1.16 (m, 2H), 1.06 (m, 2H) ppm.

EXAMPLE 53

6-[4-(1-{[(3R)-3-hydroxy-1-pyrrolidinyl]methyl}cyclopropyl)phenyl]-1-(4-methoxyphenyl)-3-(methylsulfonyl)-1,4,5,6-tetrahydro-7H-pyrazolo[3,4-c]pyridin-7-one, trifluoroacetic acid salt

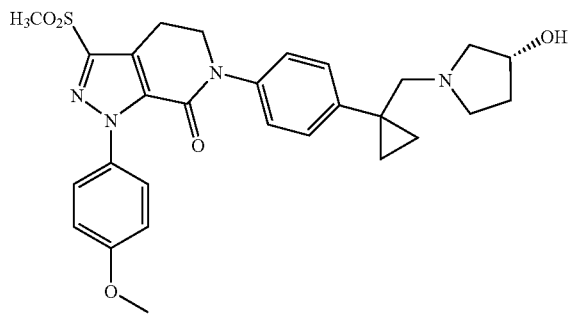

Following a procedure analogous to that used for the preparation of Example 48, the title compound was prepared. The product was purified by RP-prep LC-MS (5–98% $CH_3CN/H_2O$ in a 10-min run). LC/MS (ESI$^+$) 537.6 (M+H)$^+$, $t_R$=3.90 min. $^1$H NMR (acetone-$d_6$) δ 7.55 (m, 4H), 7.38 (m, 2H), 7.01 (d, J=8.5 Hz, 2H), 4.52 (m, 1H), 4.17 (m, 2H), 3.85 (s, 3H), 3.79 (m, 2H), 3.63 (m, 2H), 3.29 (m, 5H), 3.09 (m, 2H), 2.17 (m, 2H), 1.17 (m, 2H), 1.07 (m, 2H) ppm.

EXAMPLE 54

6-(4-{1-[(diethylamino)methyl]cyclopropyl}phenyl)-1-(4-methoxyphenyl)-3-(methylsulfonyl)-1,4,5,6-tetrahydro-7H-pyrazolo[3,4-c]pyridin-7-one, trifluoroacetic acid salt

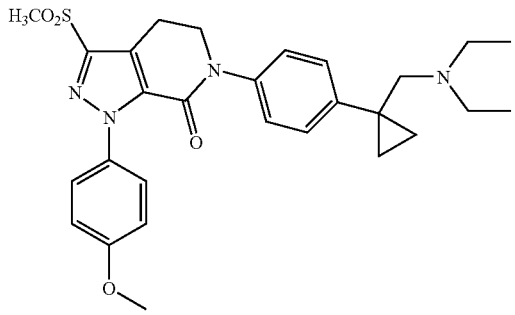

Following a procedure analogous to that used for the preparation of Example 48, the title compound was prepared. The product was purified by RP-prep LC-MS (5–98% $CH_3CN/H_2O$ in a 10-min run). LC/MS (ESI$^+$) 523.4 (M+H)$^+$, $t_R$=4.54 min. $^1$H NMR (acetone-$d_6$) δ 7.55 (m, 4H), 7.35 (d, J=7.5 Hz, 2H), 7.00 (d, J=8.8 Hz, 2H), 4.16 (d, J=6.6 Hz, 2H), 3.84 (s, 3H), 3.56 (m, 4H), 3.28 (m, 3H), 3.10 (m, 2H), 1.17 (m, 5H), 1.17 (m, 2H), 1.05 (m, 2H) ppm.

EXAMPLE 55

1-(4-methoxyphenyl)-3-(methylsulfonyl)-6-{4-[1-(4-morpholinylmethyl)cyclopropyl]phenyl}-1,4,5,6-tetrahydro-7H-pyrazolo[3,4-c]pyridin-7-one

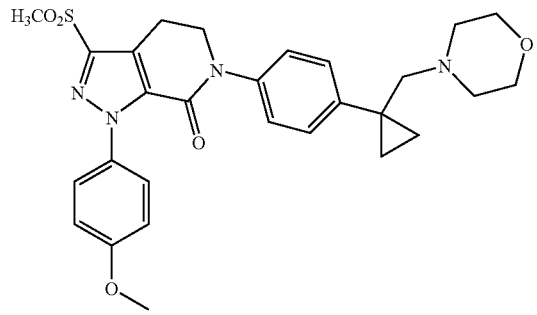

Following a procedure analogous to that used for the preparation of Example 48, the title compound was prepared. The product was purified by RP-prep LC-MS (5–98% $CH_3CN/H_2O$ in a 10-min run). LC/MS (ESI$^+$) 537.6 (M+H)$^+$, $t_R$=4.18 min. $^1$H NMR (acetone-$d_6$) δ 7.54 (m, 4H), 7.36 (d, J=7.7 Hz, 2H), 7.00 (d, J=8.8 Hz, 2H), 4.17 (t, J=6.6 Hz, 2H), 3.83 (m, 7H), 3.68 (m, 2H), 3.61 (m, 2H), 3.25 (m, 5H), 3.15 (m, 2H), 2.08–2.03 (m, 2H), 1.18 (m, 2H), 1.07 (m, 2H), ppm.

EXAMPLE 56

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}cyclopropyl)methyl]-N-methylacetamide

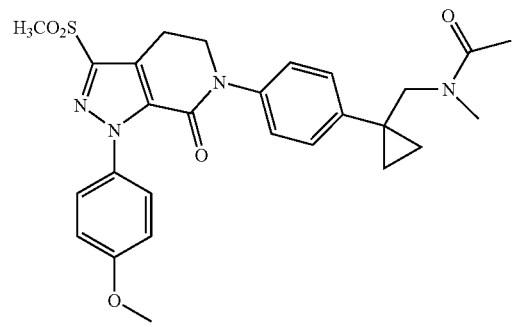

Following a procedure analogous to that used for the preparation of Example 21, the title compound was prepared. The product was purified by RP-prep LC-MS (5–98% $CH_3CN/H_2O$ in a 10-min run). LC/MS (ESI$^+$) 523.6 (M+H)$^+$, $t_R$=5.07 min.

EXAMPLE 57

3-methanesulfonyl-1-(4-methoxyphenyl)-6-{4-[1-(2-methylimidazol-1-ylmethyl)cyclopropyl]phenyl}-1,4,5,6-tetrahydro-pyrazolo[3,4-c]pyridin-7-one

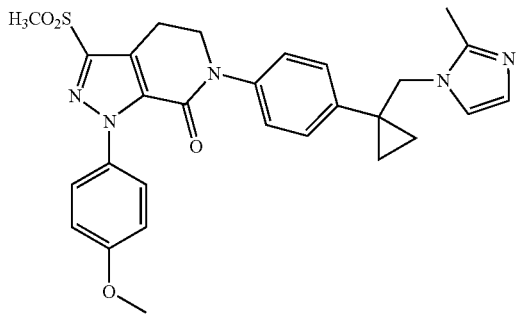

Part A. The product of part C in example 48 (0.69 g, 1.48 mmol) was stirred in CH$_2$Cl$_2$ (6 mL) at 0° C. under N$_2$. PPh$_3$ (0.50 g, 1.91 mmol, 1.3 eq) was added, followed by the addition of CBr$_4$ (0.49 g, 1.48 mmol, 1.0 eq). The resulting mixture was stirred at 0° C. for 30 min. LC-MS showed completion of the reaction (10–90% CH$_3$CN in H$_2$O in a 4-min run, t$_R$=2.73 min). Sat'd NH$_4$Cl was then added. The mixture was extracted with EtOAc. The organic layer was washed with H$_2$O and brine, dried over MgSO$_4$, filtered, and concentrated to dryness (0.39 g, yield: 50%). The product was used directly in the next step. LC/MS (ESI$^+$) 530.2, 532.2 (M+H)$^+$.

Part B. The product of Part A (0.13 g, 0.25 mmol), 2-methylimidazole (50 mg, 0.64 mmol), and K$_2$CO$_3$ (0.13 g, 1.0 mmol) were stirred in DMF (0.4 mL) under N$_2$. The mixture was heated at 85–90° C. for 30 min. LC-MS showed completion of the reaction. After cooling to RT, H$_2$O was added. The mixture was purified by prep LC-MS (15–70% CH$_3$CN in H$_2$O) to give pure 3-methanesulfonyl-1-(4-methoxyphenyl)-6-{4-[1-(2-methylimidazol-1-ylmethyl)cyclopropyl]phenyl}-1,4,5,6-tetrahydro-pyrazolo[3,4-c]pyridin-7-one (36 mg, yield %). LC/MS (ESI$^+$) 532.4 (M+H)$^+$, t$_R$=4.43 min. $^1$H NMR (acetone-d$_6$) δ 7.57 (m, 1H), 7.52 (d, J=8.8 Hz, 2H), 7.45 (m, 1H), 7.26 (AA'BB', J=8.4 Hz, 4H), 6.99 (d, J=9.1 Hz, 2H), 4.41 (s, 2H), 4.13 (t, J=6.6 Hz, 2H), 3.83 (s, 3H), 3.25 (m, 5H), 2.11 (s, 3H), 1.27 (t, J=5.8 Hz, 2H), 1.03 (t, J=5.8 Hz, 2H) ppm.

EXAMPLE 58

3-methanesulfonyl-1-(4-methoxyphenyl)-6-{4-[1-(thiazol-2-ylaminomethyl)cyclopropyl]phenyl}-1,4,5,6-tetrahydro-pyrazolo[3,4-c]pyridin-7-one

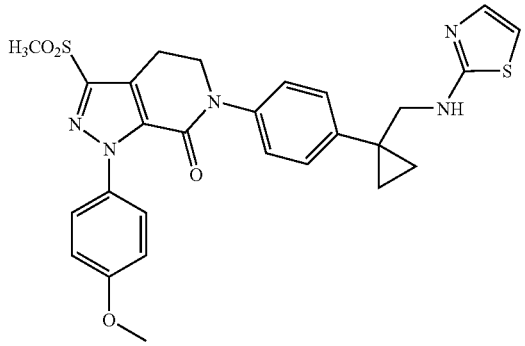

Following a procedure analogous to that of Example 25, the title compound was prepared. The product was purified by RP-prep LC-MS (35–98% CH$_3$CN/H$_2$O in a 10-min run). LC/MS (ESI$^+$) 550.4 (M+H)$^+$, t$_R$=2.36 min.

EXAMPLE 59

1-(4-methoxyphenyl)-6-(4-{1-[(methylamino)methyl]cyclobutyl}phenyl)-3-(methylsulfonyl)-1,4,5,6-tetrahydro 7H-pyrazolo[3,4-c]pyridin-7-one, trifluoroacetic acid salt

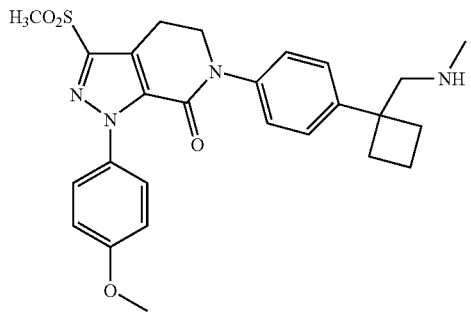

Following a procedure analogous to that used for Example 48, the title compound was prepared. It was then purified by prep LC-MS (5–98% CH$_3$CN/H$_2$O in a 10-min run, t$_R$=4.04 min). LC/MS (ESI$^+$) 495.4 (M+H)$^+$. $^1$H NMR (acetone-d$_6$) δ 7.53 (d, J=8.8 Hz, 4H), 7.32 (m, 4H), 7.00 (d, J=9.1 Hz, 2H), 4.14 (t, J=6.6 Hz, 2H), 3.83 (s, 3H), 3.47 (br, s, 2H), 3.27 (m, 5H), 2.61 (br, s, 3H), 2.48–1.85 (m, 6H) ppm.

EXAMPLE 60

6-(4-{1-[(dimethylamino)methyl]cyclobutyl}phenyl)-1-(4-methoxyphenyl)-3-(methylsulfonyl)-1,4,5,6-tetrahydro-7H-pyrazolo[3,4-c]pyridin-7-one, trifluoroacetic acid salt

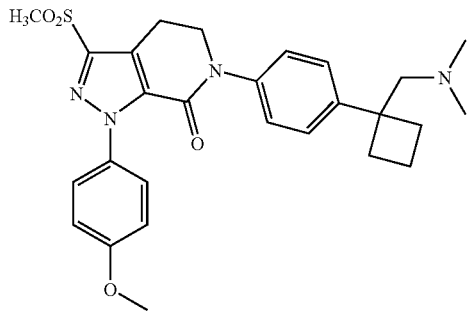

Following a procedure analogous to that used in Example 48, the title compound was prepared. The product was purified by RP-prep LC-MS (5–98% CH$_3$CN/H$_2$O in a 10-min run). LC/MS (ESI$^+$) 509.4 (M+H)$^+$, t$_R$=4.15 min.

EXAMPLE 61

6-(4-{1-[(isopropylamino)methyl]cyclobutyl}phenyl)-1-(4-methoxyphenyl)-3-(methylsulfonyl)-1,4,5,6-tetrahydro-7H-pyrazolo[3,4-c]pyridin-7-one, trifluoroacetic acid salt

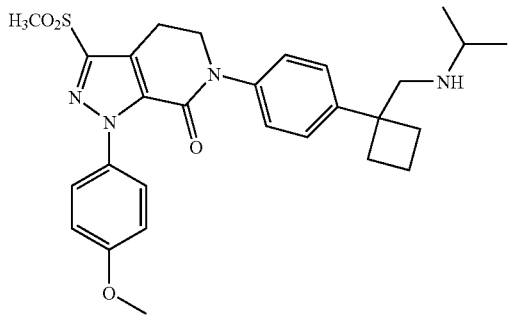

Following a procedure analogous to that used in Example 48, the title compound was prepared. The product was purified by RP-prep LC-MS (5–98% $CH_3CN/H_2O$ in a 10-min run). LC/MS (ESI$^+$) 523.4 (M+H)$^+$, $t_R$=4.27 min. $^1$H NMR (acetone-$d_6$) δ 7.53 (d, J=9.1 Hz, 4H), 7.36 (AA'BB', J=8.4 Hz, 4H), 7.00 (d, J=8.8 Hz, 2H), 4.16 (t, J=6.6 Hz, 2H), 3.84 (s, 3H), 3.52 (br, s, 2H), 3.27 (m, 5H), 2.81 (m, 1H), 2.42 (m, 4H), 2.04–1.94 (m, 2H), 1.17 (d, J=7.3 Hz, 6H) ppm.

EXAMPLE 62

1-(4-methoxyphenyl)-3-(methylsulfonyl)-6-{4-[1-(1-pyrrolidinylmethyl)cyclobutyl]phenyl}-1,4,5,6-tetrahydro-7H-pyrazolo[3,4-c]pyridin-7-one, trifluoroacetic acid salt

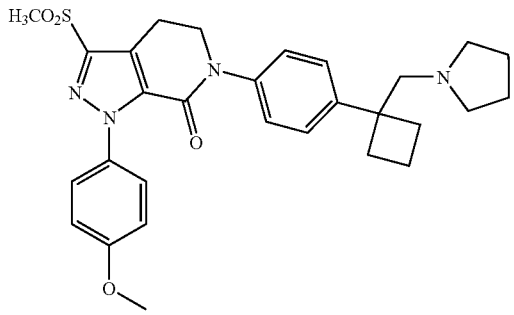

Following a procedure analogous to that used in Example 48, the title compound was prepared. The product was purified by RP-prep LC-MS (15–70% $CH_3CN/H_2O$ in a 10-min run). LC/MS (ESI$^+$) 535.4 (M+H)$^+$, $t_R$=4.74 min. $^1$H NMR (acetone-$d_6$) δ 7.53 (d, J=8.8 Hz, 2H), 7.41 (AA'BB', J=8.8 Hz, 2H), 6.99 (d, J=8.4 Hz, 2H), 4.18 (t, J=6.6 Hz, 2H), 4.14 (m, 4H), 3.83 (m, 5H), 3.27 (m, 5H), 2.46 (m, 4H), 2.09–1.85 (m, 6H) ppm.

EXAMPLE 63

6-[4-(1-{[(3R)-3-hydroxy-1-pyrrolidinyl]methyl}cyclobutyl)phenyl]-1-(4-methoxyphenyl)-3-(methylsulfonyl)-1,4,5,6-tetrahydro-7H-pyrazolo[3,4-c]pyridin-7-one, trifluoroacetic acid salt

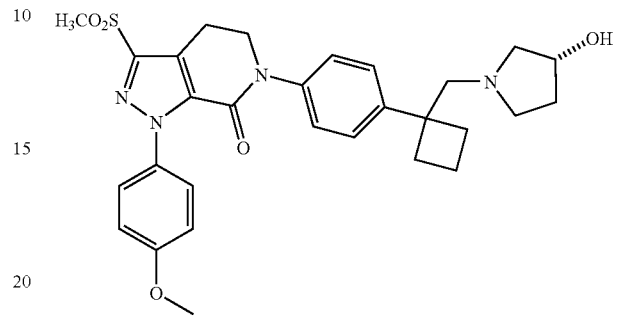

Following a procedure analogous to that used in Example 48, the title compound was prepared. The product was purified by RP-prep LC-MS (5–98% $CH_3CN/H_2O$ in a 10-min run). LC/MS (ESI$^+$) 551.4 (M+H)$^+$, $t_R$=4.06 min. $^1$H NMR (acetone-$d_6$) δ 7.53 (d, J=9.1 Hz, 2H), 7.40 (m, 4H), 6.99 (d, J=9.1 Hz, 2H), 4.30 (m, 1H), 4.18 (t, J=6.6 Hz, 2H), 3.83 (s, 3H), 3.78 (m, 2H), 3.49 (m, 2H), 3.27 (m, 5H), 2.82 (m, 2H), 2.46 (m, 6H), 2.10–1.81 (m, 2H) ppm.

EXAMPLE 64

6-(4-{1-[(diethylamino)methyl]cyclobutyl}phenyl)-1-(4-methoxyphenyl)-3-(methylsulfonyl)-1,4,5,6-tetrahydro-7H-pyrazolo[3,4-c]pyridin-7-one, trifluoroacetic acid salt

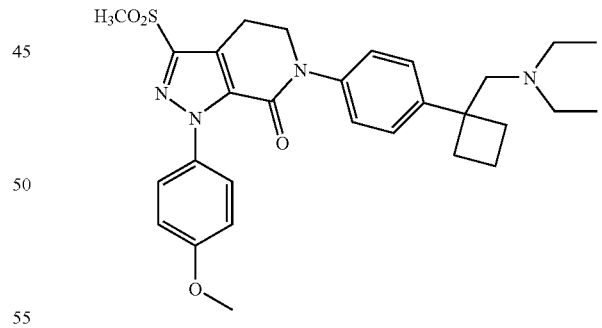

Following a procedure analogous to that used in Example 48, the title compound was prepared. The product was purified by RP-prep LC-MS (5–98% $CH_3CN/H_2O$ in a 10-min run). LC/MS (ESI$^+$) 537.4 (M+H)$^+$, $t_R$=4.62 min. $^1$H NMR (acetone-$d_6$) δ 7.53 (d, J=8.8 Hz, 4H), 7.41 (d, J=8.4 Hz, 2H), 7.00 (d, J=9.2 Hz, 2H), 4.18 (t, J=6.6 Hz, 2H), 3.83 (s, 3H), 3.74 (m, 2H), 3.27 (s+t, 5H), 3.03 (m, 4H), 2.49 (t, J=7.5 Hz, 4H), 2.09–1.89 (m, 2H), 1.19 (t, J=7.4 Hz, 6H) ppm.

EXAMPLE 65

1-(4-methoxyphenyl)-3-(methylsulfonyl)-6-{4-[1-(4-morpholinylmethyl)cyclobutyl]phenyl}-1,4,5,6-tetrahydro-7H-pyrazolo[3,4-c]pyridin-7-one, trifluoroacetic acid salt

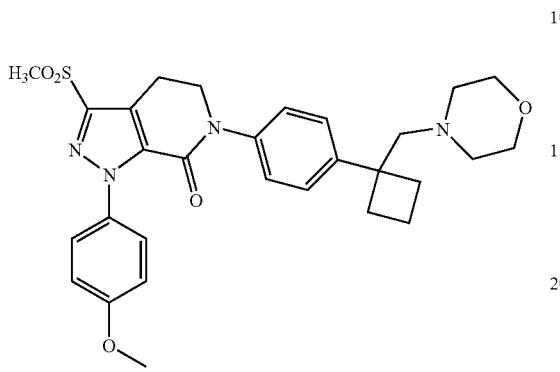

Following a procedure analogous to that used in Example 48, the title compound was prepared. The product was purified by RP-prep LC-MS (5–98% $CH_3CN/H_2O$ in a 10-min run). LC/MS (ESI$^+$) 551.4 (M+H)$^+$, $t_R$=4.12 min. $^1$H NMR (acetone-$d_6$) δ 7.53 (d, J=8.8 Hz, 2H), 7.48 (d, J=8.4 Hz, 2H), 7.37 (d, J=8.8 Hz, 2H), 7.00 (d, J=9.1 Hz, 2H), 4.17 (t, J=6.6 Hz, 2H), 3.83 (s, 3H), 3.74 (m, 10H), 3.27 (m, 5H), 2.46 (m, 4H), 2.10–1.84 (m, 2H) ppm.

EXAMPLE 66

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}cyclopropyl)methyl]-N-methylacetamide

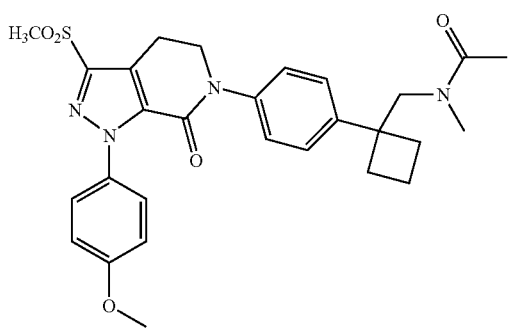

Following a procedure analogous to that of Example 21, the title compound was prepared. The product was purified by RP-prep LC-MS (5–98% $CH_3CN/H_2O$ in a 10-min run). ESI, LC/MS (ESI$^+$) 551.4 (M+H)$^+$, $t_R$=4.12 min.

EXAMPLE 67

1-(4-methoxyphenyl)-6-(4-{1-[(methylamino)methyl]cyclopropyl}phenyl)-7-oxo-4,5,6,7-tetrahydro-1H-pyrazolo[3,4-c]pyridine-3-carboxamide, trifluoroacetic acid salt

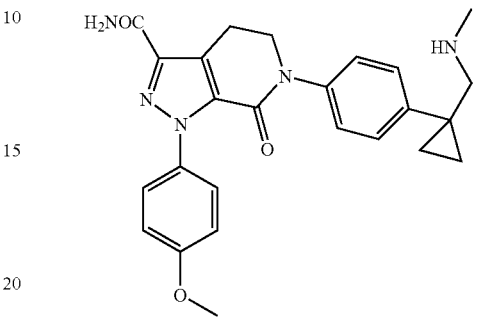

Part A. 4-Iodophenylcyclopropyl acetic acid (1.93 g, 6.70 mmol) and 1-(4-methoxyphenyl)-3-(ethoxycarbonyl)-1,4,5,6-tetrahydro-7H-pyrazolo[3,4-c]pyridin-7-one (1.41 g, 4.46 mmol) were stirred in DMSO (4 mL) under $N_2$. $K_2CO_3$ (1.84 g, 13.33 mmol, 3.0 eq) was added followed by the addition of 1,10-phenanthroline (0.15 g, 20 mol %) and CuI (0.16 g, 20 mol %). The resulting mixture was stirred at 110° C. overnight. LC-MS showed completion of the reaction. EtOAc was added to the cooled solution. It was acidified with 1N HCl, and the organic layer was washed with $H_2O$, and brine, dried over $MgSO_4$, filtered, and concentrated to afford 1-{4-[3-(ethoxycarbonyl)-1-(4-methoxyphenyl)-7-oxo-1,4,5,7-tetrahydro-6H-pyrazolo[3,4-c]pyridin-6-yl]phenyl}cyclopropanecarboxylic acid (1.54 g, yield: 72.6%). LC/MS (ESI$^+$) 476.4 (M+H)$^+$, $t_R$=2.58 min (10–90% $CH_3CN/H_2O$ in a 4-min run).

Part B. The product from part B (1.43 g, 3.01 mmol) was stirred in THF (13 mL) at 0° C. under $N_2$. $Et_3N$ (0.63 mL, 4.32 mmol, 1.5 eq) was added followed by dropwise addition of ClCOOEt (0.37 mL, 4.16 mmol, 1.3 eq). The reaction mixture was then stirred at 0° C. for 20 min. TLC showed completion of the reaction. The mixture was filtered, and rinsed with anhydrous THF. The THF filtrate (ca. 20 mL) was stirred at 0° C. under $N_2$. MeOH (3 mL) was added followed by the addition of $NaBH_4$ (1.03 g, 27.10 mmol, 10 eq). The resulting mixture was stirred at 0° C. for 15 min. Analytical LC-MS showed completion of the reaction. Sat'd $Na_2SO_4$ was then added. The mixture was extracted with EtOAc (2×). The organic layer was washed with $H_2O$ (2×) and brine (2×), dried over $Na_2SO_4$, filtered, and concentrated to dryness to give 6-{4-[1-(hydroxymethyl)cyclopropyl]phenyl}-1-(4-methoxyphenyl)-3-(ethoxycarbonyl)-1,4,5,6-tetrahydro-7H-pyrazolo[3,4-c]pyridin-7-one (1.30 g, 99%). LC/MS (ESI$^+$) 462.6 (M+H)$^+$, $t_R$=2.57 min (10–90% $CH_3CN/H_2O$ in a 4-min run).

Part C. The product from part B (1.90 g, 4.12 mmol) was stirred in anhydrous $CH_2Cl_2$ (13 mL) at RT under $N_2$. NaOAc (1.01 g, 12.20 mmol, 3 eq) and molecular sieves (2.0 g) were added followed by the addition of PCC (1.78 g, 8.24 mmol, 2 eq). The resulting slurry was stirred at RT for 1.5 h. Analytical LC-MS showed completion of the reaction. The mixture was filtered, and rinsed with $CH_2Cl_2$. The filtrate was washed with $H_2O$ (2×) and brine (2×), dried over $Na_2SO_4$, filtered, and concentrated to dryness to afford ethyl 6-[4-(1-formylcyclopropyl)phenyl]-1-(4-methoxyphenyl)-7-oxo-4,5,6,7-tetrahydro-1H-pyrazolo[3,4-c]pyridine-3-carboxylate (1.90 g, yield: 100%). LC/MS (ESI⁺) 460.6 (M+H)⁺, $t_R$=2.69 min (10–90% CH₃CN/H₂O in a 4-min run).

Part D. The product from part C (250 mg, 0.55 mmol), methylamine hydrochloride (0.5 g, excess) were stirred in dichloroethane (15 mL) at RT under N₂. NaBH(OAc)₃ (1.03 g, 4.86 mmol) was added followed by addition of three drops of HOAc. The reaction mixture was stirred at RT for 1.5 h. Analytical LC-MS showed completion of the reaction. The mixture was quenched with H₂O, and extracted with EtOAc (2×). The organic layer was washed with brine, dried over MgSO₄, filtered, and concentrated to dryness to obtain crude ethyl 1-(4-methoxyphenyl)-6-(4-{1-[(methylamino)methyl]cyclopropyl}phenyl)-7-oxo-4,5,6,7-tetrahydro-1H-pyrazolo[3,4-c]pyridine-3-carboxylate (109 mg, yield: 42%). LC/MS (ESI⁺) 475.4 (M+H)⁺, $t_R$=2.08 min.

Part E. The product from part D (50 mg, 0.105 mmol) was stirred in ethylene glycol (saturated with NH₃) in a capped Pyrex tube at 80° C. for 4 h. After cooling, the mixture was diluted with MeOH, and purified by prep LC-MS (5–98% CH₃CN in H₂O in a 10-min run) to afford 1-(4-methoxyphenyl)-6-(4-{1-[(methylamino)methyl]cyclopropyl}phenyl)-7-oxo-4,5,6,7-tetrahydro-1H-pyrazolo[3,4-c]pyridine-3-carboxamide (29 mg, yield: 60%). LC/MS (ESI⁺) 445.4 (M+H)⁺, $t_R$=3.53 min. ¹H NMR (acetone-d₆) δ 7.49 (m, 4H), 7.29 (d, J=8.1 Hz, 2H), 6.97 (d, J=9.1 Hz, 2H), 4.06 (t, J=6.6 Hz, 2H), 3.82 (s, 3H), 3.32 (s, 2H), 3.24 (t, J=6.6 Hz, 2H), 2.66 (s, 3H), 1.10 (m, 2H), 0.94 (m, 2H) ppm.

EXAMPLE 68

6-(4-{1-[(dimethylamino)methyl]cyclopropyl}phenyl)-1-(4-methoxyphenyl)-7-oxo-4,5,6,7-tetrahydro-1H-pyrazolo[3,4-c]pyridine-3-carboxamide, trifluoroacetic acid salt

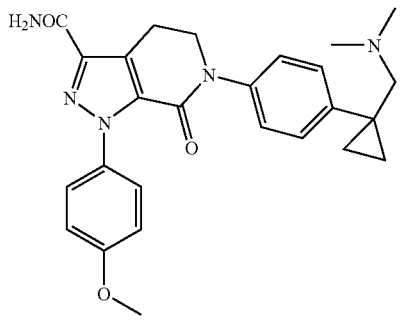

Following a procedure analogous to that used in Example 67, the title compound was prepared. The product was purified by RP-prep LC-MS (5–98% CH₃CN/H₂O in a 10-min run). LC/MS (ESI⁺) 460.6 (M+H)⁺, $t_R$=3.93 min. ¹H NMR (acetone-d₆) δ 7.52 (m, 4H), 7.33 (m, 2H), 6.97 (d, J=9.2 Hz, 2H), 4.10 (t, J=6.3 Hz, 2H), 3.82 (s, 3H), 3.52 (m, 2H), 3.26 (t, J=6.3 Hz, 2H), 2.69 (m, 6H), 1.18 (m, 2H), 1.04 (m, 2H) ppm.

EXAMPLE 69

6-(4-{1-[(diethylamino)methyl]cyclopropyl}phenyl)-1-(4-methoxyphenyl)-7-oxo-4,5,6,7-tetrahydro-1H-pyrazolo[3,4-c]pyridine-3-carboxamide, trifluoroacetic acid salt

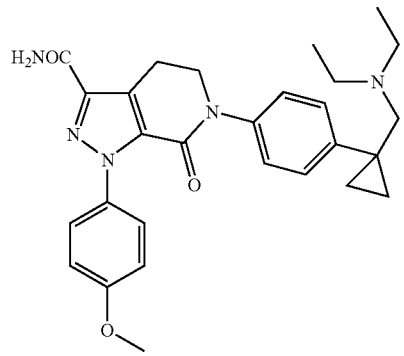

Following a procedure analogous to that used in Example 67, the title compound was prepared. The product was purified by RP-prep LC-MS (5–98% CH₃CN/H₂O in a 10-min run). LC/MS (ESI⁺) 488.6 (M+H)⁺, $t_R$=3.90 min. ¹H NMR (acetone-d₆) δ 7.57 (d, J=8.8 Hz, 2H), 7.51 (d, J=8.8 Hz, 2H), 7.34 (d, J=8.8 Hz, 2H), 6.97 (d, J=9.1 Hz, 2H), 4.08 (t, J=6.6 Hz, 2H), 3.83 (s, 3H), 3.62 (m, 2H), 3.24 (m, 6H), 1.16 (m, 8H), 1.05 (m, 2H) ppm.

EXAMPLE 70

1-(4-methoxyphenyl)-7-oxo-6-{4-[1-(1-pyrrolidinylmethyl)cyclopropyl]phenyl}-4,5,6,7-tetrahydro-1H-pyrazolo[3,4-c]pyridine-3-carboxamide, trifluoroacetic acid salt

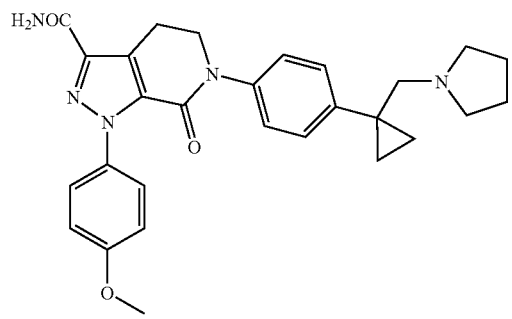

Following a procedure analogous to that used in Example 67, the title compound was prepared. The product was purified by RP-prep LC-MS (5–98% CH₃CN/H₂O in a 10-min run). LC/MS (ESI⁺) 486.4 (M+H)⁺, $t_R$=3.88 min. ¹H NMR (acetone-d₆) δ 7.52 (m, 2H), 7.32 (m, 4H), 6.99 (m, 2H), 4.09 (m, 2H), 3.82 (s, 3H), 3.56 (m, 6H), 3.26 (m, 2H), 1.91 (m, 4H), 1.13 (m, 2H), 0.98 (m, 2H) ppm.

EXAMPLE 71

1-(4-methoxyphenyl)-6-{4-[1-(4-morpholinylmethyl)cyclopropyl]phenyl}-7-oxo-4,5,6,7-tetrahydro-1H-pyrazolo[3,4-c]pyridine-3-carboxamide, trifluoroacetic acid salt

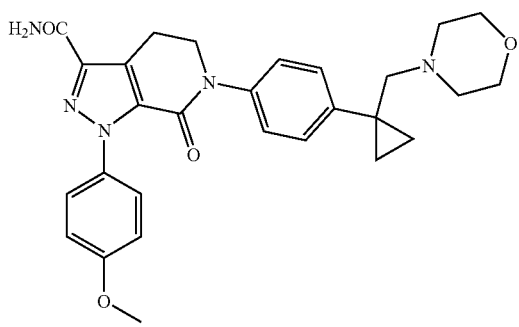

Following a procedure analogous to that used in Example 67, the title compound was prepared. It was then purified by prep LC-MS (5–98% CH$_3$CN/H$_2$O in a 10-min run, t$_R$=3.67 min). LC/MS (ESI$^+$) 502.6 (M+H)$^+$. $^1$H NMR (acetone-d$_6$) δ 7.51 (d, J=8.6 Hz, 4H), 7.34 (d, J=8.4 Hz, 2H), 7.25 (d, J=8.4 Hz, 4H), 6.95 (d, J=9.2 Hz, 2H), 4.09 (t, J=6.6 Hz, 2H), 3.82 (s, 3H), 3.48 (m, 6H), 3.26 (t, J=6.6 Hz, 2H), 2.82 (m, 2H), 2.40 (m, 2H), 0.81 (m, 2H), 0.73 (m, 2H) ppm.

EXAMPLE 72

6-(4-{1-[(isopropylamino)methyl]cyclopropyl}phenyl)-1-(4-methoxyphenyl)-7-oxo-4,5,6,7-tetrahydro-1H-pyrazolo[3,4-c]pyridine-3-carboxamide, trifluoroacetic acid salt

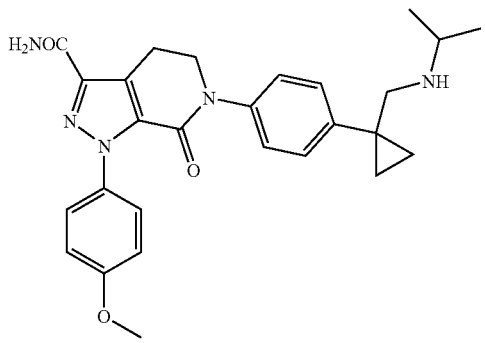

Following a procedure analogous to that used in Example 67, the title compound was prepared. It was then purified by prep LC-MS (5–98% CH$_3$CN/H$_2$O in a 10-min run, t$_R$=4.18 min). LC/MS (ESI$^+$) 474.4 (M+H)$^+$. $^1$H NMR (acetone-d$_6$) δ 7.53 (m, 4H), 7.28 (d, J=8.1 Hz, 2H), 6.97 (d, J=7.7 Hz, 2H), 4.08 (m, 2H), 3.82 (s, 3H), 3.35 (m, 3H), 3.25 (m, 2H), 1.27 (d, J=6.2 Hz, 6H), 1.11 (m, 2H), 0.92 (m, 2H) ppm.

EXAMPLE 73

6-[4-(1-{[(3R)-3-hydroxy-1-pyrrolidinyl]methyl}cyclopropyl)phenyl]-1-(4-methoxyphenyl)-7-oxo-4,5,6,7-tetrahydro-1H-pyrazolo[3,4-c]pyridine-3-carboxamide, trifluoroacetic acid salt

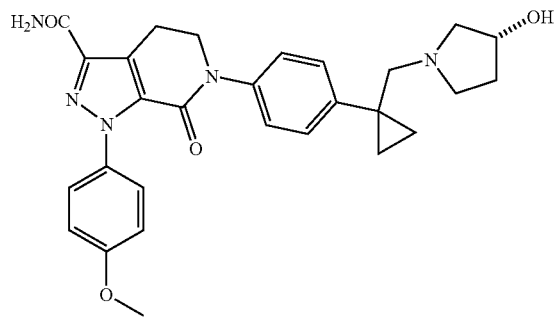

Following a procedure analogous to that used in Example 67, the title compound was prepared. The product was purified by RP-prep LC-MS (5–98% CH$_3$CN/H$_2$O in a 10-min run). LC/MS (ESI$^+$) 502.4 (M+H)$^+$, t$_R$=3.81 min.

EXAMPLE 74

1-(4-methoxyphenyl)-6-(4-{1-[(methylamino)methyl]cyclopropyl}phenyl)-7-oxo-4,5,6,7-tetrahydro-1H-pyrazolo[3,4-c]pyridine-3-carbonitrile, trifluoroacetic acid salt

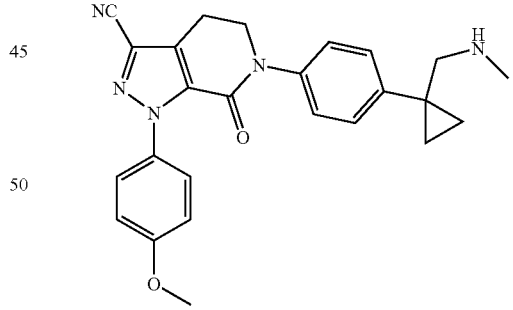

The product of Example 67 (15 mg) was stirred in DMF (0.5 mL) at RT in a capped vial. Two drops of thionyl chloride was added. The reaction was completed in 10 min. The mixture was purified by RP-prep LC-MS (5–98% CH$_3$CN/H$_2$O in a 10-min run) to give pure 1-(4-methoxyphenyl)-6-(4-{1-[(methylamino)methyl]cyclopropyl}phenyl)-7-oxo-4,5,6,7-tetrahydro-1H-pyrazolo[3,4-c]pyridine-3-carbonitrile (11 mg, yield: 76.2%). LC/MS (ESI$^+$) 428.4 (M+H)$^+$, t$_R$=4.49 min.

EXAMPLE 75

6-(4-{1-[(dimethylamino)methyl]cyclopropyl}phenyl)-1-(4-methoxyphenyl)-7-oxo-4,5,6,7-tetrahydro-1H-pyrazolo[3,4-c]pyridine-3-carbonitrile, trifluoroacetic acid salt

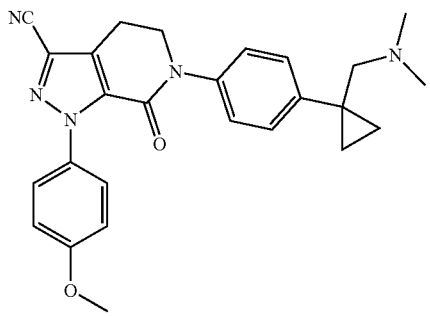

Following a procedure analogous to that used in Example 74, the title compound was prepared. It was then purified by prep LC-MS (5–98% CH$_3$CN/H$_2$O in a 10-min run, t$_R$=4.44 min) LC/MS (ESI$^+$) 442.6 (M+H)$^+$. $^1$H NMR (acetone-d$_6$) δ 7.53 (m, 4H), 7.33 (d, J=8.4 Hz, 2H), 6.99 (d, J=9.2 Hz, 2H), 4.18 (t, J=6.6 Hz, 2H), 3.83 (s, 3H), 3.57 (s, 2H), 3.18 (t, J=6.6 Hz, 2H), 2.78 (s, 6H), 1.16 (m, 2H), 1.06 (m, 2H) ppm.

EXAMPLE 76

6-(4-{1-[(diethylamino)methyl]cyclopropyl}phenyl)-1-(4-methoxyphenyl)-7-oxo-4,5,6,7-tetrahydro-1H-pyrazolo[3,4-c]pyridine-3-carbonitrile, trifluoroacetic acid salt

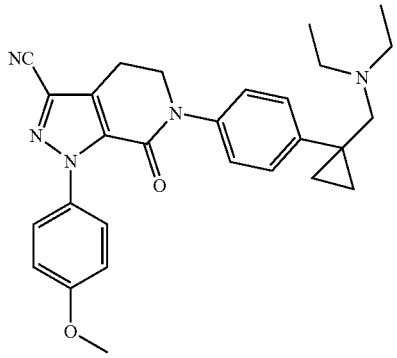

Following a procedure analogous to that used in Example 74, the title compound was prepared. It was then purified by prep LC-MS (5–98% CH$_3$CN/H$_2$O in a 10-min run, t$_R$=4.60 min). LC/MS (ESI$^+$) 470.6 (M+H)$^+$. $^1$H NMR (acetone-d$_6$) δ 7.58 (d, J=8.4 Hz, 2H), 7.54 (d, J=8.4 Hz, 2H), 7.35 (d, J=8.4 Hz, 2H), 6.99 (d, J=9.1 Hz, 2H), 4.19 (t, J=6.6 Hz, 2H), 3.83 (s, 3H), 3.58–3.18 (m, 6H), 3.19 (t, J=6.6 Hz, 2H), 1.18 (m, 8H), 1.06 (m, 2H) ppm.

EXAMPLE 77

1-(4-methoxyphenyl)-7-oxo-6-{4-[1-(1-pyrrolidinylmethyl)cyclopropyl]phenyl}-4,5,6,7-tetrahydro-1H-pyrazolo[3,4-c]pyridine-3-carbonitrile, trifluoroacetic acid salt

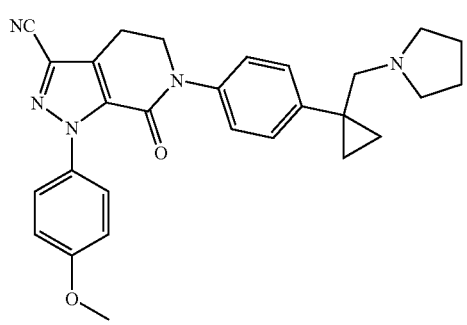

Following a procedure analogous to that used in step F of Example 74, the title compound was prepared. LC/MS (ESI$^+$) 468.4 (M+H)$^+$, t$_R$=4.49 min. $^1$H NMR (acetone-d$_6$) δ 7.52 (d, J=9.0 Hz, 2H), 7.44 (AA'BB', J=8.6 Hz, 4H), 6.99 (d, J=8.8 Hz, 2H), 4.18 (t, J=6.6 Hz, 2H), 3.83 (s, 3H), 3.59 (m, 2H), 3.19 (t, J=6.6 Hz, 2H), 2.75 (m, 4H), 2.01 (m, 4H), 1.14 (m, 2H), 1.00 (m, 2H).

EXAMPLE 78

6-(4-{1-[(isopropylamino)methyl]cyclopropyl}phenyl)-1-(4-methoxyphenyl)-7-oxo-4,5,6,7-tetrahydro-1H-pyrazolo[3,4-c]pyridine-3-carbonitrile, trifluoroacetic acid salt

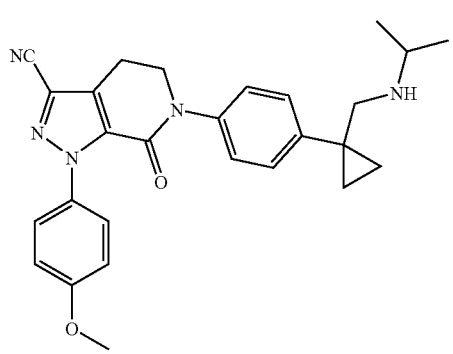

Following a procedure analogous to that used in Example 74, the title compound was prepared. It was then purified by prep LC-MS (5–98% CH$_3$CN/H$_2$O in a 10-min run, t$_R$=4.57 min). LC/MS (ESI$^+$) 456.6 (M+H)$^+$. $^1$H NMR (acetone-d$_6$) δ 7.53 (m, 4H), 7.31 (d, J=8.4 Hz, 2H), 7.00 (d, J=9.1 Hz, 2H), 4.17 (t, J=6.6 Hz, 2H), 3.83 (s, 3H), 3.19 (t, J=6.6 Hz, 2H), 3.17 (m, 3H), 1.28 (d, J6.6 Hz, 6H), 1.13 (m, 2H), 0.93 (m, 2H) ppm.

EXAMPLE 79

6-[4-(1-{[(3R)-3-hydroxy-1-pyrrolidinyl]methyl}cyclopropyl)phenyl]-1-(4-methoxyphenyl)-7-oxo-4,5,6,7-tetrahydro-1H-pyrazolo[3,4-c]pyridine-3-carbonitrile, trifluoroacetic acid salt

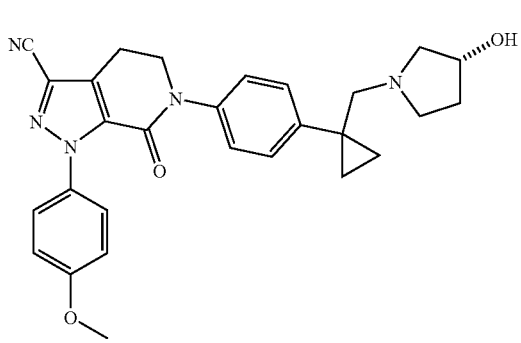

Following a procedure analogous to that used in Example 74, the title compound was prepared. It was then purified by prep LC-MS (5–98% CH$_3$CN/H$_2$O in a 10-min run, t$_R$=4.34 min) LC/MS (ESI$^+$) 484.4 (M+H)$^+$. $^1$H NMR (acetone-d$_6$) δ 7.53 (m, 4H), 7.35 (d, J=8.4 Hz, 2H), 6.99 (d, J=9.2 Hz, 2H), 4.19 (t, J=6.6 Hz, 2H), 3.83 (s, 3H), 3.62 (m, 5H), 3.19 (t, J=6.6 Hz, 2H), 2.91 (m, 2H), 1.85 (m, 2H), 1.18 (m, 2H), 1.01 (m, 2H) ppm.

EXAMPLE 80

1-(4-methoxyphenyl)-6-{4-[1-(4-morpholinylmethyl)cyclopropyl]phenyl}-7-oxo-4,5,6,7-tetrahydro-1H-pyrazolo[3,4-c]pyridine-3-carbonitrile, trifluoroacetic acid salt

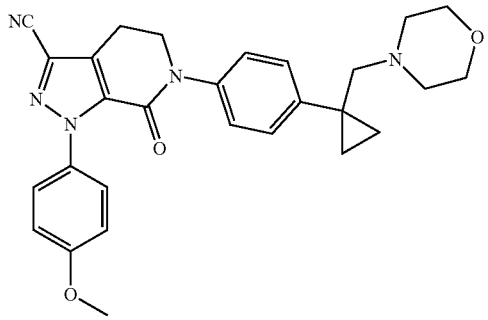

Following a procedure analogous to that used in Example 67, the title compound was prepared. It was then purified by prep LC-MS (5–98% CH$_3$CN/H$_2$O in a 10-min run, t$_R$=4.46 min). LC/MS (ESI$^+$) 484.6 (M+H)$^+$. $^1$H NMR (acetone-d$_6$) δ 7.52 (m, 4H), 7.32 (d, J=8.4 Hz, 2H), 6.99 (d, J=9.2 Hz, 2H), 4.17 (t, J=6.6 Hz, 2H), 3.83 (s, 3H), 3.47 (m, 7H), 3.62 (s, 2H), 3.49 (m, 2H), 3.17 (t, J=6.6 Hz, 2H), 3.07 (m, 2H), 1.17 (m, 2H), 1.06 (m, 2H) ppm.

EXAMPLE 81

1-(3-chlorophenyl)-6-{4-[1-(isopropylamino)methyl)cyclopropyl]phenyl}-7-oxo-4,5,6,7-tetrahydro-1H-pyrazolo[3,4-c]pyridine-3-carboxamide

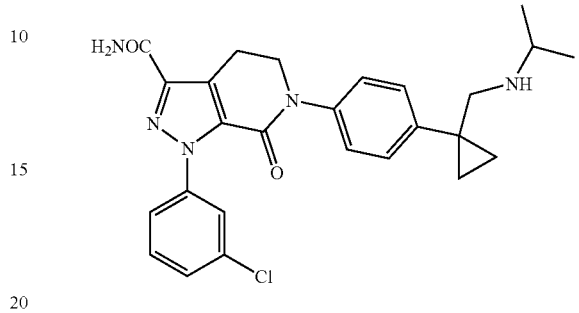

Part A. 1-(3-Chlorophenyl)-3-(ethoxycarbonyl)-1,4,5,6-tetrahydro-7H-pyrazolo[3,4-c]pyridin-7-one (1.14 g, 3.57 mmol) and 4-iodophenylcyclopropyl acetic acid (1.13 g, 1.1 eq) were stirred in DMSO (4 mL) under N$_2$. K$_2$CO$_3$ (1.48 g, mmol, 3 eq) was added, followed by the addition of 1,10-phenanthroline (0.13 g, 20 mol %) and CuI (0.14 g, 20 mol %). The resulting mixture was stirred at 130° C. overnight. LC-MS showed completion of the reaction. EtOAc was added to the cooled solution. It was washed with 1N HCl, H$_2$O, and brine; dried over MgSO$_4$; filtered; and concentrated in vacuo to give almost pure 1-{4-[1-(3-chlorophenyl)-7-oxo-3-(trifluoromethyl)-1,4,5,7-tetrahydro-6H-pyrazolo[3,4-c]pyridin-6-yl]phenyl}cyclopropanecarboxylic acid (0.87 g, yield: 51%). LC/MS (ESI$^+$) 480.4 (M+H)$^+$.

Part B. The product from Part A (0.54 g, 1.13 mmol) was stirred in THF (6 mL) at 0° C. under N$_2$. Et$_3$N (0.24 mL, 1.5 eq) was added, followed by dropwise addition of ClCOOEt (0.14 mL, 1.3 eq). The reaction mixture was then stirred at 0° C. for 1 h. TLC showed the completion of the reaction. The mixture was filtered through a filter funnel and rinsed with anhydrous THF. The THF filtrate (ca. 10 mL) was stirred at 0° C. under N$_2$. NaBH$_4$ (0.52 g, 10 eq) was added, followed by the addition of MeOH (2.5 mL). The resulting mixture was stirred at 0° C. Analytical LC-MS showed completion of the reaction. Sat'd Na$_2$SO$_4$ was then added. The mixture was extracted with EtOAc (2×). The organic layer was washed with H$_2$O (2×) and brine (2×), dried over Na$_2$SO$_4$, filtered, and concentrated to dryness to give 1-(3-chlorophenyl)-6-{4-[1-(hydroxymethyl)cyclopropyl]phenyl}-3-(ethoxycarbonyl)-1,4,5,6-tetrahydro-7H-pyrazolo[3,4-c]pyridin-7-one (0.31 g, yield: 52.4%). LC/MS (ESI$^+$) 466.4 (M+H)$^+$.

Part C. The product from Part B (0.31 g, 0.22 mmol) was stirred in anhydrous CH$_2$Cl$_2$ (5 mL) at RT under N$_2$. NaOAc (0.16 g, 1.95 mmol) and molecular sieves (0.5 g) were added, followed by the addition of PCC (0.29 g, 1.34 mmol). The resulting slurry was stirred at RT for 1.5 h. Analytical LC-MS showed completion of the reaction. The mixture was filtered through Celite, and rinsed with CH$_2$Cl$_2$. The filtrate was washed with H$_2$O (2×), brine (2×), dried over Na$_2$SO$_4$, filtered, and concentrated to dryness to give 1-(3-chlorophenyl)-6-[4-(1-(formylcyclopropyl)phenyl]-7-oxo-4,5,6,7-tetrahydro-1H-pyrazolo[3,4-c]pyridine-3-carboxylic acid ethyl ester (0.20 g, yield: 87.4%). LC/MS (ESI$^+$) 464.4 (M+H)$^+$.

Part D. The product from Part C (100 mg) and isopropyl amine (0.1 mL, excess) were stirred in dichloroethane (1 mL) in a capped vial. NaBH(OAc)$_3$ (200 mg) was added, followed by addition of one drop of HOAC. The reaction mixture was stirred at RT for 1.5 h. Analytical LC-MS showed completion of the reaction. The mixture was evaporated, and dissolved in aqueous MeOH. It was then purified by prep LC-MS (5–98% CH$_3$CN/H$_2$O in a 10-min run) to obtain pure 1-(3-chlorophenyl)-6-{4-[1-(isopropylamino) methyl)cyclopropyl]phenyl}-7-oxo-4,5,6,7-tetrahydro-1H-pyrazolo[3,4-c]pyridine-3-carboxamide (60 mg, yield: 55%). LC/MS (ESI$^+$) 507.4 (M+H)$^+$, $t_R$=4.68 min.

Part E. The product from part D (60 mg) was stirred in ethylene glycol (saturated with NH$_3$) in a capped Pyrex tube at 80° C. for 4 h. After cooling, the mixture was diluted with MeOH and purified by prep LC-MS (5–98% CH$_3$CN in H$_2$O in a 10-min run) to afford the title compound (35 mg, yield: 62%). LC/MS (ESI$^+$) 478.4 (M+H)$^+$, $t_R$=4.34 min. $^1$H NMR (acetone-d$_6$) δ 7.74 (s, 1H), 7.63 (m, 1H), 7.45 (m, 4H), 7.30 (d, J=8.4 Hz, 2H), 4.11 (t, J=6.6 Hz, 2H), 3.44 (m, 1H), 3.38 (m, 2H), 3.26 (t, J=6.6 Hz, 2H), 1.29 (d, J=6.6 Hz, 6H), 1.12 (m, 2H), 0.94 (m, 2H) ppm.

EXAMPLE 82

1-(3-chlorophenyl)-6-{4-[1-(4-morpholinylmethyl) cyclopropyl]phenyl}-7-oxo-4,5,6,7-tetrahydro-1H-pyrazolo[3,4-c]pyridine-3-carboxamide, trifluoroacetic acid salt

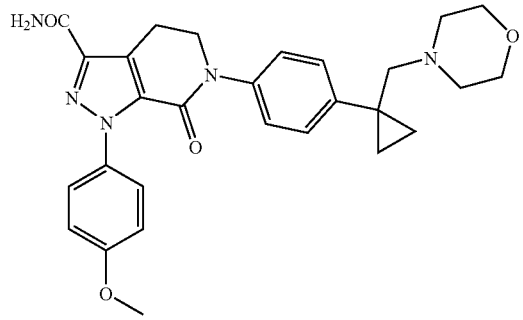

Following a procedure analogous to that used in Example 81, the title compound was prepared. The product was purified by prep LC-MS (5–98% CH$_3$CN in H$_2$O in a 10-min run). LC/MS (ESI$^+$) 506.6 (M+H)$^+$, $t_R$=4.57 min. $^1$H NMR (acetone-d$_6$) δ 7.73 (s, 1H), 7.63 (m, 1H), 7.47 (m, 4H), 7.29 (m, 2H), 4.09 (t, J=6.6 Hz, 2H), 3.74 (m, 4H), 3.53 (m, 2H), 3.27 (m, 2H), 3.07 (m, 4H), 1.07 (m, 2H), 1.00 (m, 2H) ppm.

EXAMPLE 83

6-(4-{1-[(isopropylamino)methyl] cyclopropyl}phenyl)-1-(4-methoxyphenyl)-7-oxo-4, 5,6,7-tetrahydro-1H-pyrazolo[3,4-c]pyridine-3-carbonitrile, trifluoroacetic acid salt

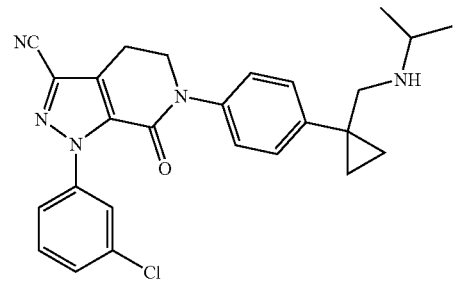

Following a procedure analogous to that used in step F of Example 74, the title compound was prepared. It was then purified by prep LC-MS (35–98% CH$_3$CN/H$_2$O in a 10-min run, $t_R$=2.78 min). LC/MS (ESI$^+$) 460.6 (M+H)$^+$. $^1$H NMR (acetone-d$_6$) δ 7.75 (s, 1H), 7.63 (m, 1H), 7.53 (m, 4H), 7.31 (d, J=8.8 Hz, 2H), 4.19 (t, J=6.6 Hz, 2H), 3.48 (m, 1H), 3.41 (m, 2H), 3.21 (t, J=6.6 Hz, 2H), 1.29 (d, J=6.3 Hz, 6H), 1.14 (m, 2H), 0.95 (m, 2H) ppm.

EXAMPLE 84

1-(4-methoxyphenyl)-6-{4-[1-(4-morpholinylmethyl)cyclopropyl]phenyl}-7-oxo-4,5,6,7-tetrahydro-1H-pyrazolo[3,4-c]pyridine-3-carbonitrile, trifluoroacetic acid salt

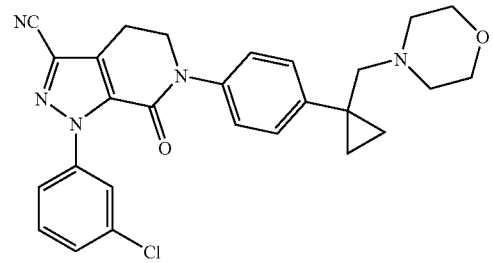

Following a procedure analogous to that used in Example 74, the title compound was prepared. It was then purified by prep LC-MS (35–98% CH$_3$CN/H$_2$O in a 10-min run, $t_R$=2.80 min). LC/MS (ESI$^+$) 488.6 (M+H)$^+$. $^1$H NMR (acetone-d$_6$) δ 7.73 (s, 1H), 7.62 (m, 1H), 7.54 (m, 4H), 7.34 (m, 2H), 4.19 (m, 2H), 3.83 (m, 8H), 3.61 (m, 2H), 3.19 (m, 2H), 1.17 (m, 2H), 1.05 (m, 2H) ppm.

EXAMPLE 85

1-[(6-chloro-2-naphthyl)sulfonyl]-4-{4-[1-(1-pyrrolidinylmethyl)cyclopropyl]benzoyl}piperazine

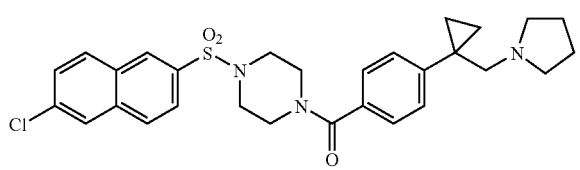

Part A. 1-(4-Iodophenyl)cyclopropane carboxylic acid (0.64 g, 2.25 mmol) was stirred in THF (10 mL) at 0° C. under $N_2$. $Et_3N$ (0.47 mL, 3.37 mmol) was added, followed by dropwise addition of $ClCO_2Et$ (0.28 mL, 2.93 mmol). The reaction mixture was then stirred at 0° C. for 30 min. TLC showed the completion of the reaction. The mixture was filtered through a filter funnel and rinsed with anhydrous THF. The THF filtrate (ca.15 mL) was stirred at 0° C. under $N_2$. $NaBH_4$ (0.41 g, 10.8 mmol) was added, followed by addition of MeOH (3 mL). The resulting mixture was stirred at 0° C. for 30 min. Analytical LC-MS showed completion of the reaction. Sat'd $Na_2SO_4$ was then added. The mixture was extracted with EtOAc (2×). The organic layer was washed with $H_2O$ (2×) and brine (2×), dried over $Na_2SO_4$, filtered, and concentrated to dryness. The resulting alcohol was stirred in anhydrous $CH_2Cl_2$ (10 mL) at RT under $N_2$. NaOAc (0.42 g, 5.12 mmol) and molecular sieves (4 Å, 0.75 g) were added, followed by the addition of PCC (0.83 g, 3.84 mmol). The resulting slurry was stirred at RT for 1.5 h. Analytical LC-MS showed completion of the reaction. The mixture was filtered through Celite, and rinsed with $CH_2Cl_2$. The filtrate was washed with $H_2O$ (2×) and brine (2×), dried over $Na_2SO_4$, filtered, and concentrated in vacuo to give almost pure 4-iodophenylcyclopropanecarbaldehyde. This aldehyde and pyrrolidine (0.37 mmol) were stirred in dichloroethane (6 mL) at RT under $N_2$. NaBH$(OAc)_3$ (1.37 mg, mmol) was added, followed by addition of several drops of HOAc. The reaction mixture was stirred at RT for 20 min. Analytical LC-MS showed completion of the reaction. $H_2O$ was added. The mixture was extracted with EtOAc; and the organic extracts were washed with $H_2O$ (2×) and brine (2×), dried over $Na_2SO_4$, filtered, and concentrated to dryness to give almost pure 1-{[1-(4-iodophenyl)cyclopropyl]methyl}pyrrolidine (0.41 g, yield % for 3 steps). LC/MS (ESI$^+$) 328.2 (M+H)$^+$. (10–90% $CH_3CN/H_2O$ in a 4-min run, $t_R$=1.77 min).

Part B. The product from part A (0.40 g, 1.24 mmol), KOAc (0.61 g, 5.0 eq), Pd(OAc)$_2$ (0.03 g, 0.1 eq), and dppf (0.14 g, 0.2 eq) were stirred in DMF (3 mL) at RT. The mixture was degassed twice and purged with CO. The mixture was heated at 60° C. under CO atmosphere with a balloon for 2.5 h. LS-MS showed completion of the reaction. After cooling, $H_2O$ was added. The mixture was extracted with EtOAc (2×). The aqueous layer was then acidified, and concentrated to dryness. MeOH was added, and filtered off inorganic salts. The filtrate was concentrated and vacuum dried to give almost pure 4-[1-(1-pyrrolidinylmethyl)cyclopropyl]benzoic acid (0.32 g, yield: 96%). LC/MS (ESI$^+$) 246.4 (M+H)$^+$. (10–90% $CH_3CN/H_2O$ in a 4-min run, $t_R$=1.32 min).

Part C. The product of part B (0.41 g, 1.68 mmol) was stirred in $CH_2Cl_2$ (10 mL) at RT under $N_2$. (COCl)$_2$ (0.5 mL) was added, followed by the addition of one drop of DMF. The mixture was stirred at RT for 1 h. The solvent was evaporated and dried in vacuo. The resulting acid chloride (0.16 g, 0.61 mmol) was dissolved in $CH_2Cl_2$ (10 mL), 1-[(6-chloro-2-naphthyl)sulfonyl]piperazine (0.21 g, 0.61 mmol) was added, followed by the addition of DIEA (0.21 mL, 1.21 mmol). The resulting mixture was stirred at RT for 20 min. Analytical LC-MS showed completion of the reaction. The solvent was evaporated. The residue was dissolve in MeOH, and purified by RP Prep LC-MS (5–98% $CH_3CN$ in $H_2O$ in a 10-min run) to give pure title compound (210 mg, yield: 64.1%). It was then purified by prep LC-MS (5–98% $CH_3CN/H_2O$ in a 10-min run, $t_R$=4.71 min). LC/MS (ESI$^+$) 538.4 (M+H)$^+$.

EXAMPLE 86

5-chloro-N-(5-chloro-2-pyridinyl)-2-({4-[1-(1-pyrrolidinylmethyl)cyclopropyl]benzoyl}amino)benzamide, trifluoroacetic acid salt

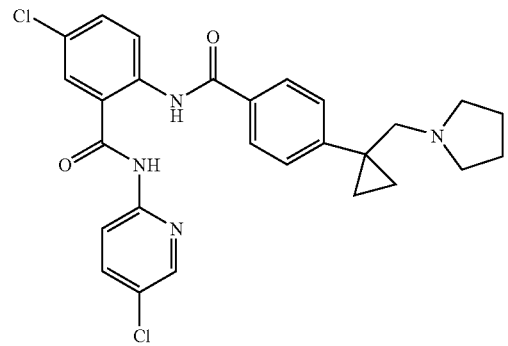

Part A. The product from Part B of Example 85 (0.16 g, 0.65 mmol) was stirred in $CH_2Cl_2$ (5 mL) at RT under $N_2$. (COCl)$_2$ (0.2 mL) was added. The mixture was stirred at RT for 1 h. The solvent was evaporated and dried in vacuo. The resulting acid chloride was dissolved in $CH_2Cl_2$ (6 mL), 2-amino-5-chlorobenzoic acid methyl ester (0.16 g, 0.86 mmol) was added, followed by the addition of DIEA (0.30 mL). The resulting mixture was stirred at RT for 2 h. Analytical LC-MS showed completion of the reaction. The solvent was evaporated. The residue was dissolve in EtOAc, washed with $H_2O$, brine, dried over $MgSO_4$, and concentrated to give methyl 5-chloro-2-({4-[1-(1-pyrrolidinylmethyl)cyclopropyl]benzoyl}amino)benzoate (55 mg, yield: 21%). LC/MS (ESI$^+$) 413.4 (M+H)$^+$, $t_R$=2.19 min (10–90% $CH_3CN/H_2O$ in a 4-min run).

Part B. The product from Part A (30 mg) and 5-chloro-2-aminopyridine (14 mg) were stirred in $CH_2Cl_2$ (1 mL) at RT under $N_2$. Me$_3$Al in toluene (0.45 mL, 0.23 mmol) was added dropwise. The resulting solution was stirred at RT for 1 h and at reflux for 2 h. The solvent was evaporated after cooling. The residue was dissolved in MeOH, and purified by LC-MS (5–98% $CH_3CN$ in $H_2O$ in a 10-min run) to give pure 5-chloro-N-(5-chloro-2-pyridinyl)-2-({4-[1-(1-pyrrolidinylmethyl)cyclopropyl]benzoyl}amino)benzamide (6 mg, yield: 16%). LC/MS (ESI$^+$) 509.2 (M+H)$^+$, $t_R$=2.21 min (10–90% $CH_3CN/H_2O$ in a 4-min run).

EXAMPLE 87

1-(4-Methoxyphenyl)-3-methanesulfonyl-6-{4-[1-(2-oxo-pyrrolidin-1-ylmethyl)cyclopropyl]phenyl}-1,4,5,6-tetrahydro-pyrazolo[3,4-c]pyridin-7-one

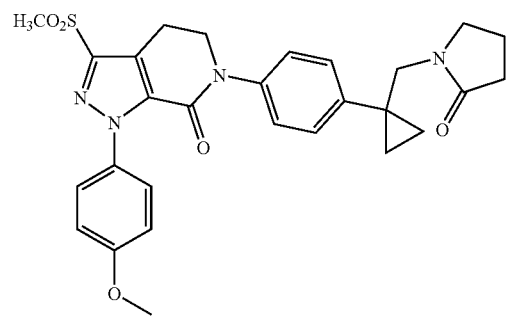

Part A. 1-(1-Bromomethylcyclopropyl)-4-iodobenzene (2.0 g, 5.97 mmol) and NaN₃ (1.0 g, 15.38 mmol, 2.6 eq) were stirred in DMF (10 mL) overnight. Analytical LC-MS showed completion of the reaction. EtOAc was added to the solution. The mixture was washed with H₂O and brine, dried over MgSO₄, and concentrated to give 1-(1-azidomethyl-cyclopropyl)-4-iodobenzene (1.43 g, yield: 80%). The azide (1.40 g, 4.68 mmol) and PPh₃ (1.84 g, 7.02 mmol, 1.5 eq) were stirred in THF (10 mL) at RT for 40 min. H₂O (2 mL) was added, and the solution was stirred at 50° C. for 6 h. LC-MS showed completion of the reaction. The mixture was extracted with Et₂O (2×). The aqueous layer was basified with 50% NaOH, extracted with CH₂Cl₂ (2×), washed with H₂O, brine, dried over MgSO₄, and concentrated to give 1-(4-iodophenyl)cyclopropyl methylamine (0.98 g, yield: 75%).

Part B. The product from Part A (0.36 g, 1.31 mmol) was stirred in dry CH₂Cl₂ (10 mL) at RT. NaOH (0.16 g, 3.93 mmol, 3 eq) was added, followed by the addition of 4-chlorobutyryl chloride (0.16 mL, 1.42 mmol). The reaction mixture was stirred at RT for 1 h. It was washed with H₂O and brine, dried over MgSO₄, and concentrated to dryness. The residue was dissolved in THF (10 mL). K-O-tBu (0.29 g, 2.62 mmol) was added as one single portion. The mixture was stirred at 0° C. under N₂ for 1 h. LC-MS showed completion of the reaction. EtOAc was added. It was washed with H₂O and brine, dried over MgSO₄, and concentrated to produce 1-[1-(4-iodophenyl)cyclopropylmethyl]-pyrrolidin-2-one (0.36 g, yield: 86%). LC/MS (ESI⁺) 342.0 (M+H)⁺, $t_R$=2.86 min (10–90% CH₃CN/H₂O in a 4-min run).

Part C. The product from Part B (0.18 g, 0.56 mmol) and 1-(4-methoxyphenyl)-3-(methylsulfonyl)-1,4,5,6-tetrahydro-7H-pyrazolo[3,4-c]pyridin-7-one (0.16 g, 0.47 mmol) were stirred in DMSO (1 mL) under N₂. K₂CO₃ (0.20 g, 1.44 mmol) was added, followed by the addition of CuI (0.030 g, 20 mol %) and 1,10-phenanthroline (0.028 g, 20 mol %). The resulting mixture was heated at 120° C. overnight. After cooling, it was extracted with EtOAc (2×), washed with H₂O and brine, dried over MgSO₄, filtered, and concentrated to dryness. The residue was purified by flash column chromatography (silica gel, CH₂Cl₂:EtOAc 1:1, then EtOAc) to give the desired compound (83 mg, yield: 25%). LC/MS (ESI⁺) 535.2 (M+H)⁺, $t_R$=3.45 min (10–90% CH₃CN/H₂O in a 6-min run). ¹H NMR (CDCl₃) δ 7.45 (d, J=8.8 Hz, 2H), 7.25 (AA'BB', J=8.6 Hz, 4H), 6.91 (d, J=9.2 Hz, 2H), 4.10 (t, J=6.6 Hz, 2H), 3.80 (s, 3H), 3.68 (s, 2H), 3.46 (m, 2H), 3.29 (m, 3H), 3.23 (t, J=6.6 Hz, 2H), 2.25 (m, 2H), 1.86 (m, 2H), 0.86 (m, 4H) ppm.

EXAMPLE 88

1-(4-Methoxyphenyl)-7-oxo-6-{4-[1-(2-oxo-pyrrolidin-1-ylmethyl)cyclopropyl]phenyl}-4,5,6,7-tetrahydro-1H-pyrazolo[3,4-c]pyridine-3-carboxylic acid ethyl ester

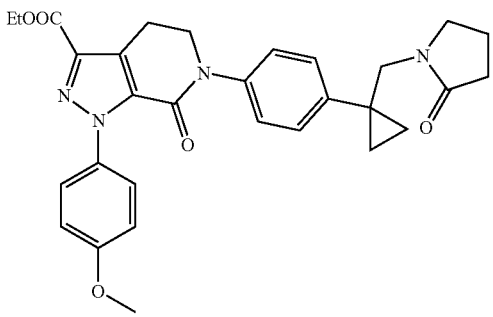

Following a procedure analogous to that used for the preparation of Example 87, the title compound was prepared. The product was purified by silica gel column chromatography. LC/MS (ESI⁺) 529.4 (M+H)⁺, $t_R$=3.14 min (25–90% CH₃CN/H₂O in a 6-min run).

EXAMPLE 89

1-(4-Methoxyphenyl)-7-oxo-6-{4-[1-(2-oxo-pyrrolidin-1-ylmethyl)cyclopropyl]phenyl}-4,5,6,7-tetrahydro-1H-pyrazolo[3,4-c]pyridine-3-carboxylic acid amide

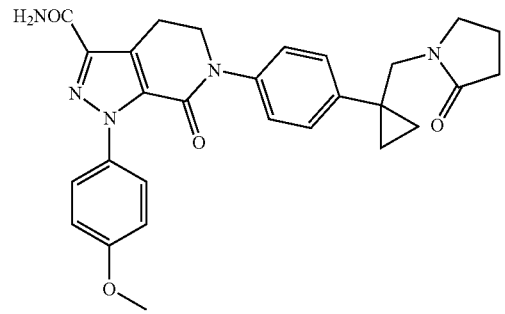

Following a procedure analogous to that used for the preparation of Example 67, the title compound was prepared. The product was purified by RP-prep LC-MS (5–98% CH₃CN/H₂O in a 10-min run). LC/MS (ESI⁺) 500.2 (M+H)⁺, $t_R$=3.28 min (10–90% CH₃CN/H₂O in a 6-min run).

EXAMPLE 90

1-(4-Methoxyphenyl)-7-oxo-6-{4-[1-(2-oxo-pyrrolidin-1-ylmethyl)cyclopropyl]phenyl}-4,5,6,7-tetrahydro-1H-pyrazolo[3,4-c]pyridine-3-carbonitrile

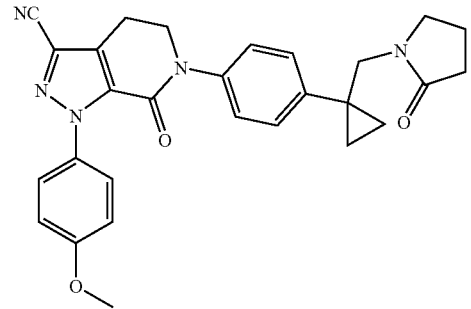

Following a procedure analogous to that used for the preparation of Example 74, the title compound was prepared. The product was purified by RP-prep LC-MS (5–98% CH₃CN/H₂O in a 10-min run). Analytical LC/MS (ESI⁺) 482.4 (M+H)⁺, $t_R$=2.63 min (35–95% CH₃CN/H₂O in a 6-min run).

EXAMPLE 91

6-[4-(1-Aminocyclopropyl)phenyl]-1-(4-methoxyphenyl)-3-trifluoromethyl-1,4,5,6-tetrahydro-pyrazolo[3,4-c]pyridin-7-one, trifluoroacetic acid salt

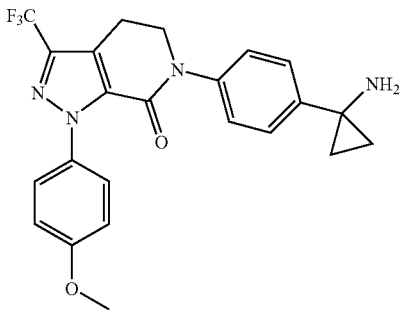

The product of Part D in Example 1 (ca. 0.50 g) was stirred in dry toluene at RT. DPPA (0.25 mL) was added, followed by the addition of Et$_3$N (0.35 mL). The resulting mixture was stirred at 100° C. for 3 h. After cooling to RT, 8N HCl (10 mL) was added. The resulting mixture was heated at 100° C. overnight. The cooled mixture was extracted with Et$_2$O (2×). The aqueous layer was basified with 50% NaOH. The mixture was extract with chloroform (2×). The organics were washed with H$_2$O and brine, dried over MgSO$_4$, and concentrated to dryness. The residue was dissolved in MeOH, and purified by prep LC/MC (5–98% CH$_3$CN/H$_2$O in a 10-min run) to give the desired product. Analytical LC/MS (ESI$^+$) 443.2 (M+H)$^+$, t$_R$=2.69 min (35–95% CH$_3$CN/H$_2$O in a 6-min run).

EXAMPLE 92

(1-{4-[1-(4-Methoxyphenyl)-7-oxo-3-trifluoromethyl-1,4,5,7-tetrahydro-pyrazolo[3,4-c]pyridin-6-yl]phenyl}cyclopropyl)-carbamic acid methyl ester

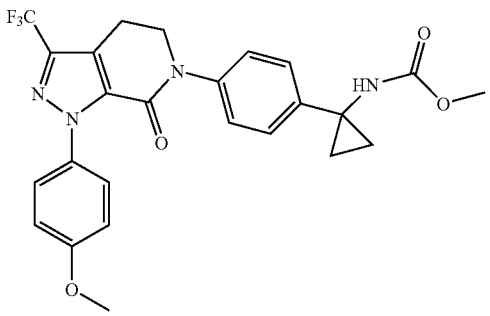

Following a procedure analogous to that used for the preparation of Example 91, the title compound was prepared by using MeOH instead of conc. HCl as the solvent. Silica gel purification yielded the pure desired product. LC/MS (ESI$^+$) 501.6 (M+H)$^+$, t$_R$=3.19 min (35–95% CH$_3$CN/H$_2$O in a 6-min run). $^1$H NMR (CDCl$_3$) δ 7.46 (d, J=8.8 Hz, 2H), 7.24 (m, 4H), 6.91 (d, J=9.2 Hz, 2H), 4.12 (t, J=6.6 Hz, 2H), 3.81 (s, 3H), 3.64 (s, 2H), 3.14 (t, J=6.6 Hz, 2H), 1.22 (m, 4H) ppm.

EXAMPLE 93

N-(1-{4-[1-(4-Methoxyphenyl)-7-oxo-3-trifluoromethyl-1,4,5,7-tetrahydro-pyrazolo[3,4-c]pyridin-6-yl]phenyl}-cyclopropyl)-acetamide

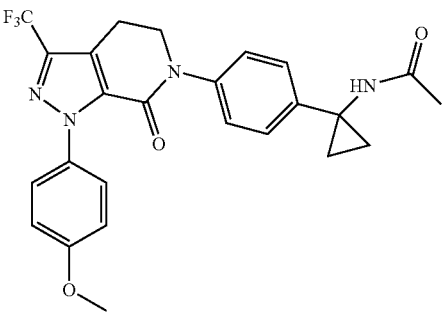

Following a procedure analogous to that used for the preparation of Example 21, the title compound was prepared. Silica gel purification yielded the pure desired product. LC/MS (ESI$^+$) 485.2 (M+H)$^+$, t$_R$=3.06 min (35–95% CH$_3$CN/H$_2$O in a 6-min run). $^1$H NMR (CDCl$_3$) δ 7.46 (d, J=8.8 Hz, 2H), 7.24 (d, J=8.8 Hz, 2H), 6.94 (AA'BB', J=9.1 Hz, 4H), 4.09 (m, 2H), 3.81 (m, 2H), 3.14 (t, J=6.6 Hz, 2H), 2.38 (s, 3H), 1.57 (m, 2H), 1.40 (m, 2H) ppm.

EXAMPLE 94

N-(1-{4-[1-(4-Methoxyphenyl)-7-oxo-3-trifluoromethyl-1,4,5,7-tetrahydro-pyrazolo[3,4-c]pyridin-6-yl]phenyl}-cyclopropyl)-methanesulfonamide

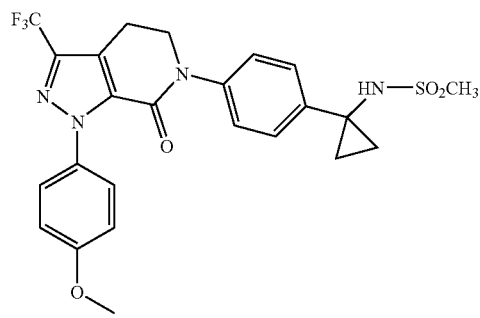

Silica gel purification yielded the pure desired product. LC/MS (ESI$^+$) 521.2 (M+H)$^+$, t$_R$=3.14 min (35–95% CH$_3$CN/H$_2$O in a 6-min run). $^1$H NMR (CDCl$_3$) δ 7.46 (d, J=9.2 Hz, 2H), 7.35 (AA'BB', J=8.8 Hz, 4H), 6.92 (d, J=8.8 Hz, 2H), 5.19 (s, 1H), 4.13 (t, J=6.6 Hz, 2H), 3.81 (s, 3H), 3.16 (t, J=6.6 Hz, 2H), 1.26 (m, 2H), 1.18 (m, 2H) ppm.

EXAMPLE 95

6-[4-(1-Hydroxymethylcyclopropyl)phenyl]-3-(methanesulfonyl)-1-(4-methoxyphenyl)-1,4,5,6-tetrahydro-pyrazolo[3,4-c]pyridin-7-one

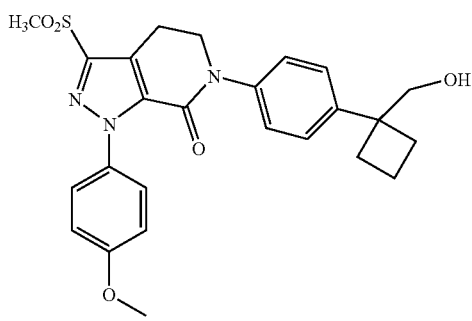

Following a procedure analogous to that used for the preparation of product of Part C in Example 48, the title compound was prepared. The product was purified by RP-prep LC-MS (5–98% CH$_3$CN/H$_2$O in a 10-min run). LC/MS (ESI$^+$) 481.4 (M+H)$^+$, t$_R$=5.51 min. $^1$H NMR (acetone-d$_6$) δ 7.53 (d, J=8.8 Hz, 2H), 7.27 (d, J=8.8 Hz, 2H), 7.14 (d, J=8.8 Hz, 2H), 6.98 (d, J=8.8 Hz, 2H), 4.14 (t, J=6.6 Hz, 2H), 3.83 (m, 4H), 3.63 (s, 2H), 3.27 (t, J=6.6 Hz, 2H), 3.26 (s, 3H), 2.02 (m, 4H), 1.81 (m, 2H) ppm.

EXAMPLE 96

Ethyl 6-[4-(cyano-dimethyl-methyl)phenyl]-1-(4-methoxy-phenyl)-7-oxo-4,5,6,7-tetrahydro-1H-pyrazolo[3,4-c]pyridine-3-carboylate

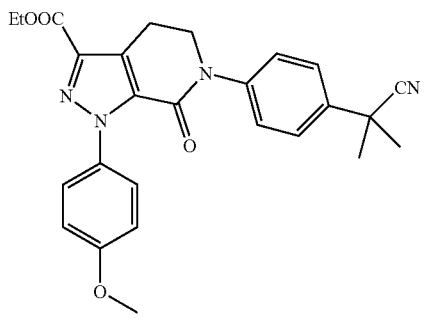

Part A. To 4-iodobenzylbromide (25 g, 84 mmol) in boiling EtOH (100 mL) was added potassium cyanide (8.2 g, 126 mmol) through the condenser. The reaction was heated 24 h, then cooled and EtOH removed. The aqueous layer was extracted with EtOAc and dried (Na$_2$SO$_4$) to afford crude 4-iodobenzylnitrile. The 4-iodobenzylnitrile was first treated with HCl gas in MeOH to afford conversion to the ester. The mixture was concentrated in vacuo and treated with MeOH (4.7 mL) and chlorotrimethylsilane (10.7 mL) at 50° C. for 4 h. The reaction was cooled and quenched with H$_2$O (3.5 mL). Dichloromethane (150 mL) was added followed by Na$_2$CO$_3$ (8.9 g) and the mixture was stirred at room temperature for 1 h. The organics were separated and dried (Na$_2$SO$_4$), filtered, and concentrated to afford 21 g crude (4-iodo-phenyl)-acetic acid methyl ester. $^1$H NMR (CDCl$_3$) δ 7.66 (d, J=8.4 Hz, 2H), 7.04 (d, J=8.4 Hz, 2H), 3.69 (s, 3H), 3.56 (s, 2H) ppm.

Part B. To a THF (100 mL) solution containing sodium hydride (9.5 g, 0.23 mol) at 0° C. was added dropwise crude methyl-(4-iodo-phenyl)-acetic acid methyl ester (21 g, 79 mmol, from Part A in THF (50 mL). After the addition was complete, methyl iodide (11.4 mL, 0.18 mol) in THF (20 mL) was added and the reaction was stirred 72 h at rt. The reaction mixture was quenched with ice water followed by extraction with EtOAc. Drying with Na$_2$SO$_4$ afforded 27 g of a crude mixture of two products. Purification by chromatography on silica gel (10:1 hexanes/ethyl acetate) afforded 5 g pure methyl 2-(4-iodophenyl)-2-methyl propronate and 10 g mixture of the desired ester and 2-(4-iodophenyl)-2-methylproprionitrile. $^1$H NMR for methyl 2-(4-iodophenyl)-2-methyl propronate (CDCl$_3$) δ 7.65 (d, J=8.5, 2H), 7.09 (d, J=8.8 Hz, 2H), 3.64 (s, 3H), 1.54 (s, 6H) ppm.

Part C. To 8 g of the crude mixture from Part B in THF (75 mL) and H$_2$O (25 mL) was added LiOH (3 g), and the reaction was stirred overnight. Acid/base extraction afforded 3.6 g of 2-(4-iodophenyl)2-methylproprionic acid, Mass Spec (M+H)$^+$ 290.8 and 5.3 g of 2-(4-iodophenyl)2-methylproprionitrile. IR(KBr) CN at 2236.66.

Part D. To a DMSO (4 mL, degassed) solution of ethyl 1-(4-methoxyphenyl)-7-oxo-4,5,6,7-tetrahydro-1H-pyrazolo[3,4-c]pyridine-3-carboxylate (0.6 g, 1.9 mmol), and 2-(4-iodophenyl) 2-methylproprionitrile (0.6 g, 2.2 mmol), and K$_2$CO$_3$ (0.66 g, 4.8 mmol) and was added CuI (73 mg, 0.3 mmol). The reaction was heated to 130° C. for 18 h. The reaction was cooled, extracted with EtOAc, washed with H$_2$O, and dried (MgSO$_4$). Purification by chromatography on silica gel (1:1 hexanes/ethyl acetate) afforded the title compound 0.4 g (45.9%) of a pale yellow solid; Mass Spec (M+H)$^+$ 459.3.

EXAMPLE 97

6-[4-(1-cyano-1-methylethyl)phenyl]-1-(4-methoxyphenyl)-7-oxo-4,5,6,7-tetrahydro-1H-pyrazolo[3,4-c]pyridine-3-carboxamide

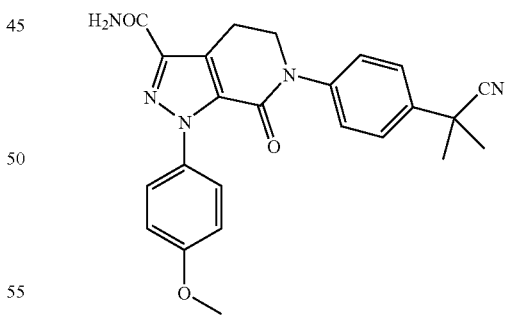

Ethyl 6-[4-(cyano-dimethyl-methyl)phenyl]-1-(4-methoxy-phenyl)-7-oxo-4,5,6,7-tetrahydro-1H-pyrazolo[3,4-c]pyridine-3-carboylate (0.38 g, 0.83 mmol) obtained in Example 96 was placed in a sealed tube containing 10% ammonia in ethylene glycol (3 mL) and heated 80° C. for 2 h. The reaction was cooled, quenched with H$_2$O, extracted with EtOAc, and dried (MgSO$_4$). Recrystallization from CH$_2$Cl$_2$/Hexanes afforded 0.31 g (88%) of the title amide. High Resolution Mass Spec (M+H)$^+$. for C$_{24}$H$_{24}$N$_5$O$_3$ 430.1898.

EXAMPLE 98

6-[4-(2-Amino-1,1-dimethylethyl)phenyl]-1-(4-methoxyphenyl)-7-oxo-4,5,6,7-tetrahydro-1H-pyrazolo[3,4-c]pyridine-3-carboxamide

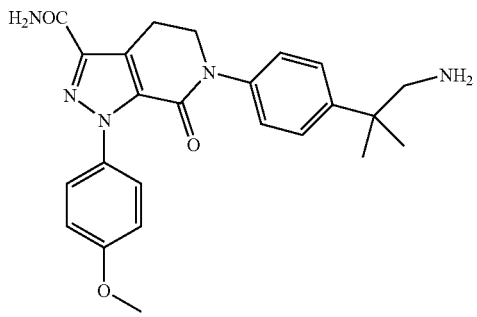

6-[4-(1-Cyano-1-methylethyl)phenyl]-1-(4-methoxyphenyl)-7-oxo-4,5,6,7-tetrahydro-1H-pyrazolo[3,4-c]pyridine-3-carboxamide (0.1 g) was hydrogenated at 40 psi in EtOH/HCl with 20 mg 10% Pd/C and purified by HPLC to afford 70 mg (56%) of title amine. High Resolution Mass Spec (M+H)$^+$ for $C_{24}H_{28}N_5O_3$ 434.2176.

EXAMPLE 99

1-{4-[(1-methoxyphenyl)-3-(methylsulfonyl)-7-oxo-1,4,5,7-tetrahydro-6H-pyrazolo[3,4-c]pyridinyl-6-yl]phenyl}-2-methylpropanenitrile

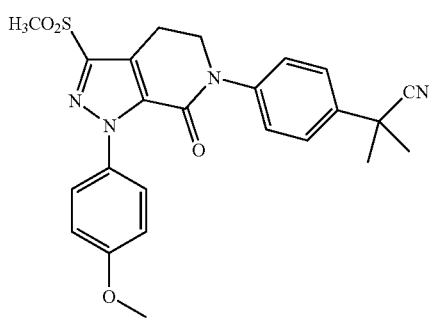

To a degassed DMSO (4 mL) solution containing 1-(4-methoxyphenyl)-3-methylsulfonyl-1,4,5,6-tetrahydro-7H-pyrazolo[3,4-c]pyridin-7-one (0.6 g, 1.8 mmol) and 2-(4-iodophenyl)2-methylproprionitrile (0.6 g, 2.2 mmol) was added $K_2CO_3$ (0.64 g, 4.6 mmol) and CuI (71 mg, 0.3 mmol). The reaction was heated to 130° C. for 18 h. The reaction was cooled, extracted with EtOAc, washed with $H_2O$, and dried ($MgSO_4$). Purification by chromatography on silica gel (1:1 hexanes/ethyl acetate) afforded 0.52 g (61%) of a pale yellow foam; High Resolution Mass Spec (M+H)$^+$ for $C_{24}H_{25}N_4O_4S$ 456.1624.

EXAMPLE 100

6-[4-(2-amino-1,1-dimethyl)phenyl]-1-(4-methoxyphenyl)-3-(methylsulfonyl)-1,4,5,6-tetrahydro-7H-pyrazolo[3,4-c]pyridin-7-one

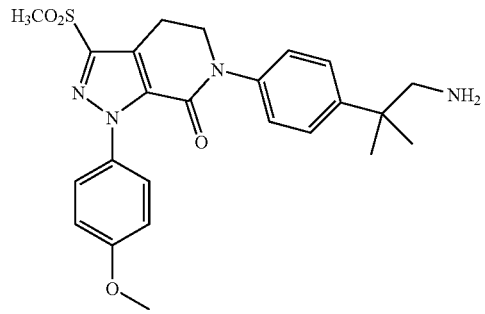

1-{1-[(4-Methoxyphenyl)-3-(methylsulfonyl)-7-oxo-1,4,5,7-tetrahydro-6H-pyrazolo[3,4-c]pyridinyl-6-yl]phenyl}-2-methylpropanenitrile (0.1 g) was hydrogenated at 40 psi in EtOH/HCl with 20 mg 10% Pd/C and purified by HPLC to afford 85 mg (68%) of the title amine. High Resolution Mass Spec (M+H)$^+$ for $C_{24}H_{28}N_4O_4S$ 469.1907.

EXAMPLE 101

Preparation of 2-{4-[3-methanesulfonyl-1-(4-methoxyphenyl)-7-oxo-1,4,5,7-tetrahydropyrazolo[3,4-c]pyridin-6-yl]phenyl}-2-methylprionic acid methyl ester

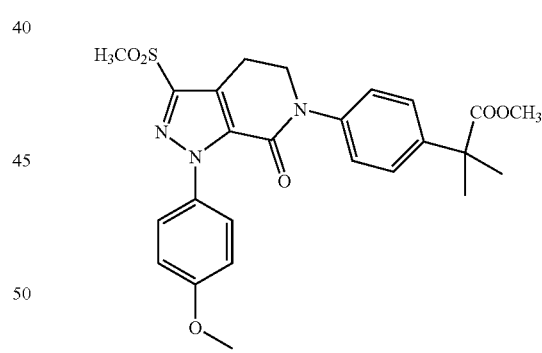

To a degassed DMSO (4 mL) solution was added ethyl 1-(4-methoxyphenyl)-7-oxo-4,5,6,7-tetrahydro-1H-pyrazolo[3,4-c]pyridine-3-carboxylate (0.4 g, 1.2 mmol) and methyl 2-(4-iodophenyl)2-methyl propronate (0.53 g, 1.7 mmol) was added $K_2CO_3$ (0.43 g, 3.1 mmol) and CuI (47 mg, 0.25 mmol). The reaction was heated to 130° C. for 18 h, cooled, extracted with EtOAc, washed with $H_2O$, and dried ($MgSO_4$). Purification by chromatography on silica gel (1:1 hexanes/ethyl acetate) afforded the titled compound 0.43 g (45.9%) of a pale yellow foam. High Resolution Mass Spec (M+H)$^+$ for $C_{25}H_{28}N_3O_6S$ 498.1691.

EXAMPLE 102

2-{4-[1-(4-methoxypheny)-3-(methylsulfonyl)-7-oxo-1,4,5,7-tetrahydro-6H-pyrazolo[3,4-c]pyridin-6-yl]phenyl}-2-methylpropnamide

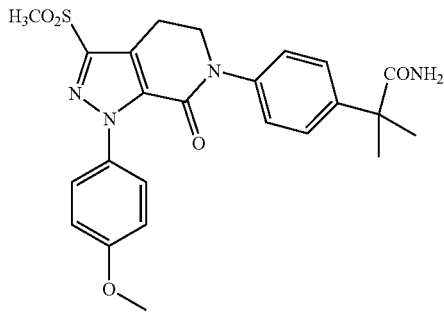

2-{4-[3-Methanesulfonyl-1-(4-methoxyphenyl)-7-oxo-1,4,5,7-tetrahydropyrazolo[3,4-c]pyridin-6-yl]phenyl}-2-methylproprionic acid methyl ester (0.095 g, 0.19 mmol) was placed in a sealed tube containing 10% ammonia in ethylene glycol (3 mL) and heated 80° C. for 18 h. The reaction was cooled, quenched with $H_2O$, extracted with EtOAc, and dried ($MgSO_4$). Purification by HPLC afforded 35 mg (36%) title compound; High Resolution Mass Spec $(M+H)^+$ for $C_{24}H_{27}N_4O_5S$ 483.1725.

EXAMPLE 103

2-Hydroxyethyl-2-{4-[1-(4-methoxypheny)-3-(methlysulfonyl)-7-oxo-1,4,5,7-tetrahydro-6H-pyrazolo[3,4-c]pyridin-6-yl]phenyl}-2-methylpropanoate

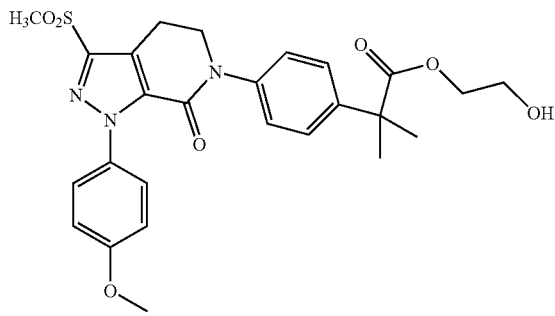

2-{4-[3-Methanesulfonyl-1-(4-methoxyphenyl)-7-oxo-1,4,5,7-tetrahydropyrazolo[3,4-c]pyridin-6-yl]phenyl}-2-methylproprionic acid methyl ester (0.077 g, 0.15 mmol) was placed in a sealed tube containing 10% ammonia in ethylene glycol (3 mL) and heated 80° C. for 2 h. The reaction was cooled, quenched with $H_2O$, extracted with EtOAc, and dried ($MgSO_4$). Purification by chromatography on silica (1:1 hexanes/ethyl acetate) and then HPLC purification afforded 27 mg (33%) title compound. High Resolution Mass Spec $(M+H)^+$ for $C_{26}H_{30}N_3O_7S$ 528.1776.

EXAMPLE 104

6-{4-[1,1-dimethyl-2-(methylamino)ethyl]phenyl}-1-(4-methoxyphenyl)-7-oxo-4,5,6,7-tetrahydro-1H-pyrazolo[3,4-c]pyridine-3-carboxamide

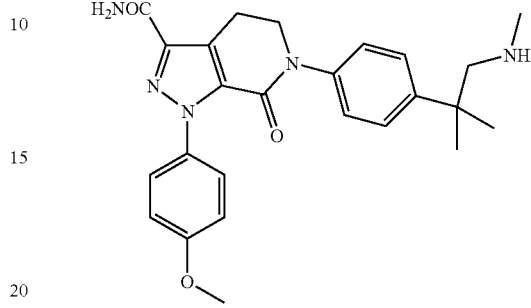

Part A. To ethyl 1-(4-methoxyphenyl)-7-oxo-4,5,6,7-tetrahydro-1H-pyrazolo[3,4-c]pyridine-3-carboxylate (2.35 g, 7.5 mmol) and 2-(4-iodophenyl)2-methylproprionic acid (2.6 g, 8.9 mmol) was added $K_2CO_3$ (3.1 g, 0.022 mol), DMSO (4 mL), and CuI (0.28 mg, 1.4 mmol). The reaction was heated to 130° C. for 18 h cooled, extracted with EtOAc, washed with $H_2O$, and dried ($MgSO_4$). Purification by chromatography on silica gel (5% $MeOH/CH_2Cl_2$) afforded 1.1 g product.

Part B. To the acid from Part A (1 g, 2 mmol) in THF (30 mL) at 0° C. was added 1M Borane in THF (2.5 mL, 2.5 mmol) and the reaction was allowed to stir 18 h. The reaction was extracted with EtOAc, washed with brine, and dried ($Na_2SO_4$) to afford crude alcohol. To the alcohol was added $CH_2Cl_2$ (100 mL), molecular sieves, sodium acetate (0.17 g, 2 mmol), and pyridinium chlorochromate (0.72 g, 3.3 mmol) and the reaction was stirred 24 h. After dilution with $Et_2O$, filtration through paper, and concentration, the crude residue was purified by chromatography on silica gel (2:1 hexanes/EtOAc) to afford 0.527 g of the desired aldehyde. $^1H$ NMR ($CDCl_3$) δ 9.46 (s, 1H), 7.48 (d, J=9.2 Hz, 2H), 7.35 (d, J=8.7 Hz, 2H), 7.28 (d, J=9.1 Hz, 2H), 6.92 (d, J=9.2 Hz, 2H), 4.49 (q, J=7 Hz, 2H), 4.13 (t, J=6.6 Hz, 2H), 3.80 (s, 3H), 3.35 (t, J=6.6 Hz, 2H), 1.45 (t, J=7.3 Hz, 3H) ppm.

Part C. To the aldehyde from Part B (95 mg, 0.2 mmol) in 1:1 THF/MeOH (5 mL) was added excess 33% methylamine in EtOH (0.1 mL). After 15 min 0.5M $ZnCl_2$ in THF (0.2 mL, 0.1 mmol) followed by sodium cyanoborohydride (13 mg, 0.2 mmol) were added. The reaction was stirred 24 h. The solvents were removed and the residue was partitioned between EtOAc and $H_2O$. Extraction with EtOAc and drying ($MgSO_4$) afforded crude ester/amine.

Part D. The ester/amine from Part C was heated in a sealed tube containing 2 mL of 10% $NH_3$/ethylene glycol at 80° C. for 2 h. After cooling the product was extracted by EtOAc, washed with water and dried ($MgSO_4$). Purification by HPLC and freeze-drying afforded the titled compound 78 mg (69%) as a white solid. High Resolution Mass Spec $(M+H)^+$ for $C_{25}H_{30}N_5O_3$ 448.2337.

EXAMPLE 105

6-{4-[2-dimethylamino)-1,1-dimethylethyl]phenyl}-1-(4-methoxyphenyl)-7-oxo-4,5,6,7-tetrahydro-1H-pyrazolo[3,4-c]pyridine-3-carboxamide

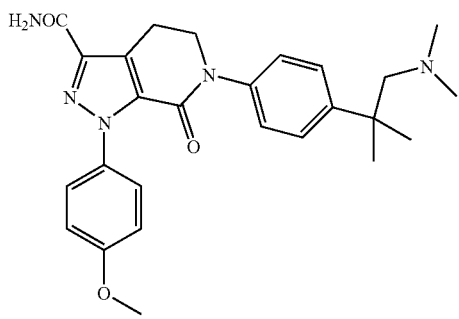

Following a procedure analogous to that used in Example 104, the title compound was prepared. High Resolution Mass Spec (M+H)+ for $C_{26}H_{32}N_5O_3$ 462.2529.

EXAMPLE 106

6-{4-[1,1-dimethyl-2-(1-morpholinyl)ethyl]phenyl}-1-(4-methoxyphenyl)-7-oxo-4,5,6,7-tetrahydro-1H-pyrazolo[3,4-c]pyridine-3-carboxamide

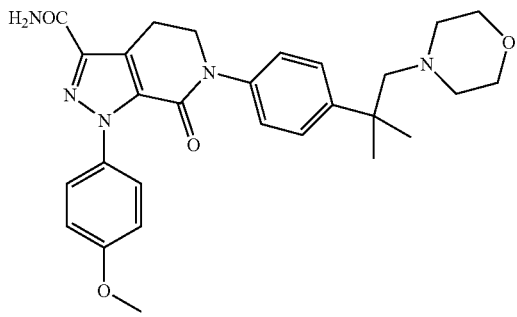

Following a procedure analogous to that used in Example 104, the title compound was prepared. High Resolution Mass Spec (M+H)+ for $C_{28}H_{34}N_5O_4$ 504.2637.

EXAMPLE 107

6-{4-[1,1-dimethyl-2-(1-pyrrolidinyl)ethyl]phenyl}-1-(4-methoxyphenyl)-7-oxo-4,5,6,7-tetrahydro-1H-pyrazolo[3,4-c]pyridine-3-carboxamide

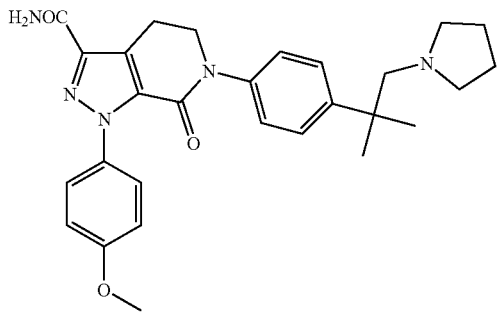

Following a procedure analogous to that used in Example 104, the title compound was prepared. High Resolution Mass Spec (M+H)+ for $C_{28}H_{34}N_5O_3$ 488.2667.

EXAMPLE 108

6-{4-[2-(isopropylamino)1,1-dimethylethyl]phenyl}-1-(4-methoxyphenyl)-7-oxo-4,5,6,7-tetrahydro-1H-pyrazolo[3,4-c]pyridine-3-carboxamide

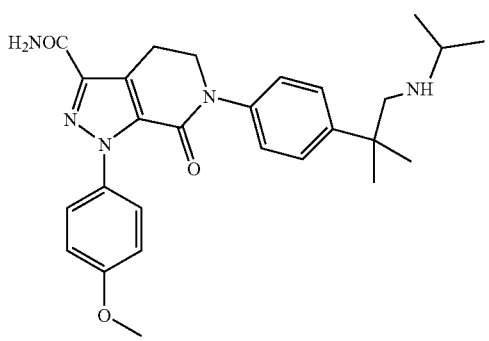

Following a procedure analogous to that used in Example 104, the title compound was prepared. High Resolution Mass Spec (M+H)+ for $C_{27}H_{34}N_5O_3$ 476.2666.

EXAMPLE 109

6-(4-{2-[(cyclopropylmethyl)amino]-1,1-dimethylethyl}phenyl)-1-(4-methoxyphenyl)-7-oxo-4,5,6,7-tetrahydro-1H-pyrazolo[3,4-c]pyridine-3-carboxamide

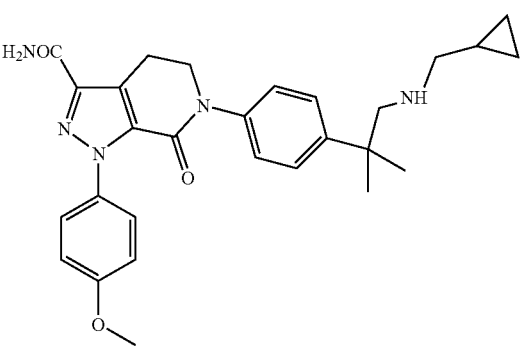

Following a procedure analogous to that used in Example 104, the title compound was prepared. High Resolution Mass Spec (M+H)+ for $C_{28}H_{33}N_5O_3$ 488.2670.

EXAMPLE 110

6-{4-[2-(cyclobutylamino)1,1-dimethylethyl]phenyl}-1-(4-methoxyphenyl)-7-oxo-4,5,6,7-tetrahydro-1H-pyrazolo[3,4-c]pyridine-3-carboxamide

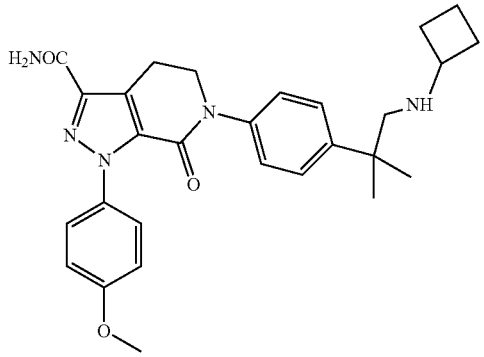

Following a procedure analogous to that used in Example 104, the title compound was prepared. High Resolution Mass Spec (M+H)+ for $C_{28}H_{34}N_5O_3$ 488.2668.

EXAMPLE 111

6-{4-[2-(cyclopropylamino)1,1-dimethylethyl]phenyl}-1-(4-methoxyphenyl)-7-oxo-4,5,6,7-tetrahydro-1H-pyrazolo[3,4-c]pyridine-3-carboxamide

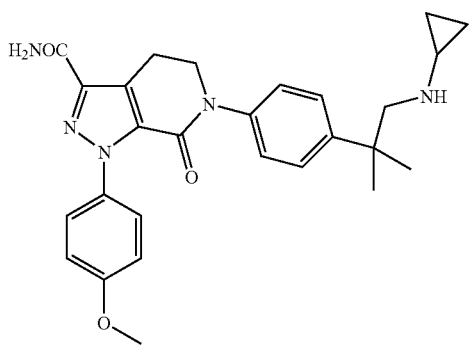

Following a procedure analogous to that used in Example 104, the title compound was prepared. High Resolution Mass Spec (M+H)+ for $C_{27}H_{32}N_5O_3$ 474.2513

EXAMPLE 112

6-{4-[2-(cyclopentylamino)1,1-dimethylethyl]phenyl}-1-(4-methoxyphenyl)-7-oxo-4,5,6,7-tetrahydro-1H-pyrazolo[3,4-c]pyridine-3-carboxamide

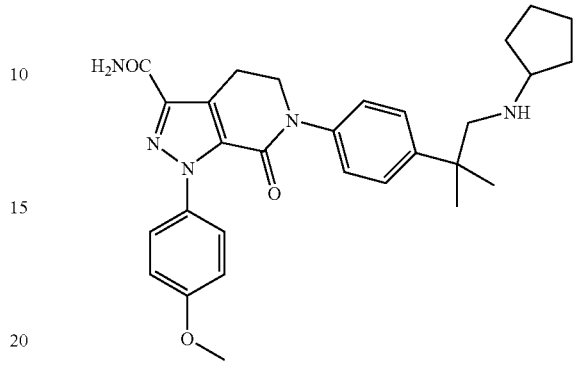

Following a procedure analogous to that used in Example 104, the title compound was prepared. High Resolution Mass Spec (M+H)+ for $C_{29}H_{36}N_5O_3$ 502.2814.

EXAMPLE 113

6-[4-(2-hydroxy-1,1-dimethylethyl)phenyl]-1-(4-methoxyphenyl)-3-(methylsulfonyl)-1,4,5,7-tetrahydro-7H-pyrazolo[3,4-c]pyridin-7-one

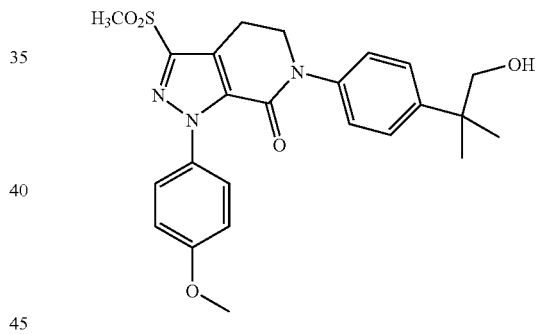

Part A. To crude 2-{4-[3-methanesulfonyl-1-(4-methoxyphenyl)-7-oxo-1,4,5,7-tetrahydropyrazolo[3,4-c]pyridin-6-yl]phenyl}-2-methylproprionic acid methyl ester (2 g, 0.4 mmol) was added LiOH (0.5 g, 12 mmol) in THF/MeOH/H$_2$O for 24 h. The reaction was acidified with 1N HCl and extracted with EtOAc and concentrated to afford crude acid as a semi solid mass.

Part B. The crude acid from Part A was then reduced with 1M borane in THF (7.3 mL, 7.3 mmol) in THF (25 mL) over 24 h. The reaction was quenched with water and extracted with EtOAc and dried (MgSO$_4$) to afford the corresponding alcohol.

Part C. The crude alcohol from Part B (2.3 g, 4.9 mmol) was oxidized with pyridinium chlorochromate (1.7 g, 7.8 mmol), sodium acetate (0.4 g, 4.9 mmol), and molecular sieves in CH$_2$Cl$_2$ for 24 h. Dilution with diethyl ether and filtration followed by chromatography on silica gel (1:1 hexanes/EtOAc) afforded 0.6 g (27%) of aldehyde; $^1$H NMR CDCl$_3$ δ 9.46 (s, 1H), 7.48 (d, J=8.8 Hz, 2H), 7.31 (m, 4H), 6.94 (d, J=8.8 Hz, 2H), 4.15 (t, J=6.6 Hz, 2H), 3.81 (s, 3H), 3.36 (t, J=6.6 Hz, 2H), 3.31 (s, 3H), 1.44 (s, 6H) ppm.

Part D. To the aldehyde from Part C (34 mg, 0.072 mmol) was added 2-aminoimidazole sulfate (19 mg, 0.144 mmol) in 1:1 THF/MeOH (5 mL) followed by 0.5M $ZnCl_2$ (0.05 mL, 0.027 mmol) and 1M sodium cyanoborohydride in THF (0.07 mL, 0.07 mmol) and the reaction was stirred 24 h. The reaction was quenched with water, extracted with EtOAc, and dried ($MgSO_4$). Purification by HPLC and freeze-drying afforded 12 mg (35%) of the desired alcohol: $^1$H NMR ($CDCl_3$) δ 7.48 (d, J=9.2 Hz, 2H), 7.41 (d, J=8.4 Hz, 2H), 7.28 (d, J=8.8 Hz, 2H), 6.94 (d, J=9.1 Hz, 2H), 4.15 (t, J=6.6 Hz, 2H), 3.81 (s, 3H), 3.61 (s, 2H), 3.34 (t, J=6.6 Hz, 2H), 3.31 (s, 3H), 1.31 (s, 6H) ppm.

EXAMPLE 114

6-{4-[1,1-dimethyl-2-(methylamino)ethyl]phenyl}-1-(4-methoxyphenyl)-3-(methylsulfonyl)-1,4,5,7-tetrahydro-7H-pyrazolo[3,4-c]pyridin-7-one

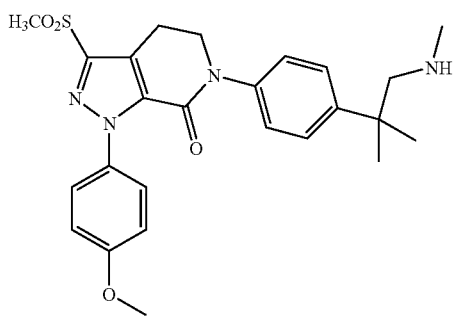

Following a procedure analogous to that used in Example 104, the title compound was prepared. High Resolution Mass Spec (M+H)$^+$ for $C_{25}H_{31}N_4O_4S$ 483.2049.

EXAMPLE 115

6-{4-[2-(dimethylamino) 1,1-dimethylethyl]phenyl}-1-(4-methoxyphenyl)-3-(methylsulfonyl)-1,4,5,7-tetrahydro-7H-pyrazolo[3,4-c]pyridin-7-one

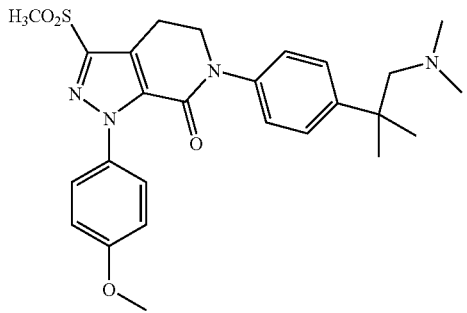

Following a procedure analogous to that used in Example 104, the title compound was prepared. High Resolution Mass Spec (M+H)$^+$ for $C_{26}H_{33}N_4O_4S$ 497.2201.

EXAMPLE 116

6-(4-{2-[(cyclopropylmethyl)amino]-1,1-dimethylethyl}phenyl)-1-(4-methoxyphenyl)-3-(methylsulfonyl)-1,4,5,7-tetrahydro-7H-pyrazolo[3,4-c]pyridin-7-one

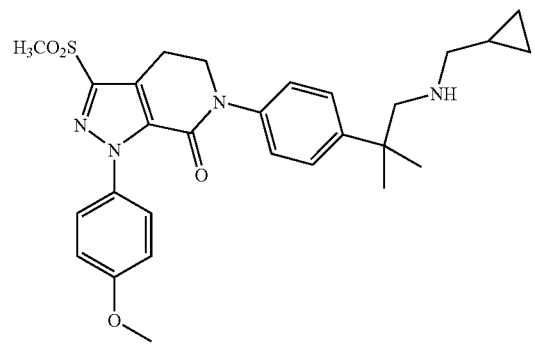

Following a procedure analogous to that used in Example 104, the title compound was prepared. High Resolution Mass Spec (M+H)$^+$ for $C_{28}H_{35}N_4O_4S$ 523.2362.

EXAMPLE 117

6-{4-[1,1-dimethyl-2-(isopropylamino)ethyl]phenyl}-1-(4-methoxyphenyl)-3-(methylsulfonyl)-1,4,5,7-tetrahydro-7H-pyrazolo[3,4-c]pyridin-7-one

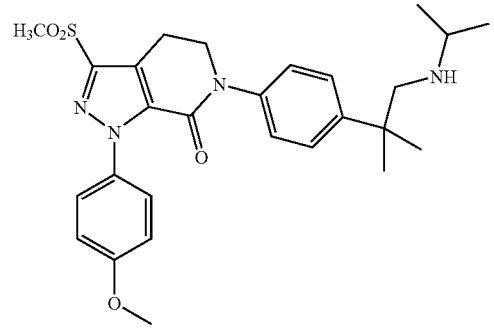

Following a procedure analogous to that used in Example 104, the title compound was prepared. High Resolution Mass Spec (M+H)$^+$ for $C_{27}H_{35}N_4O_4S$ 511.2379.

EXAMPLE 118

6-{4-[1,1-dimethyl-2-(1-pyrrolidinyl)ethyl]phenyl}-1-(4-methoxyphenyl)-3-(methylsulfonyl)-1,4,5,7-tetrahydro-7H-pyrazolo[3,4-c]pyridin-7-one

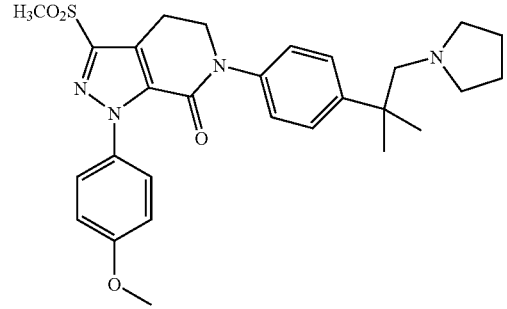

Following a procedure analogous to that used in Example 104, the title compound was prepared. High Resolution Mass Spec (M+H)$^+$ for $C_{28}H_{35}N_4O_4S$ 523.2388.

EXAMPLE 119

6-{4-[1,1-dimethyl-2-(1-morpholinyl)ethyl]phenyl}-1-(4-methoxyphenyl)-3-(methylsulfonyl)-1,4,5,7-tetrahydro-7H-pyrazolo[3,4-c]pyridin-7-one

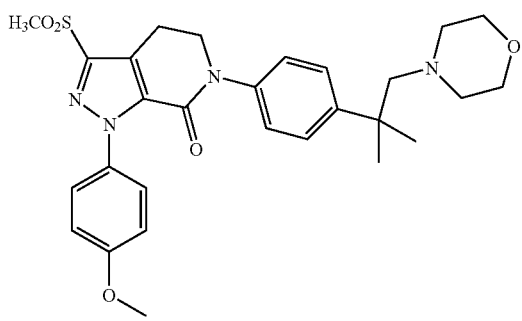

Following a procedure analogous to that used in Example 104, the title compound was prepared. High Resolution Mass Spec (M+H)$^+$ for $C_{28}H_{35}N_4O_5S$ 539.2342.

EXAMPLE 120

6-{4-[2-(cyclopentylamino) 1,1-dimethylethyl]phenyl}-1-(4-methoxyphenyl)-3-(methylsulfonyl)-1,4,5,7-tetrahydro-7H-pyrazolo[3,4-c]pyridin-7-one

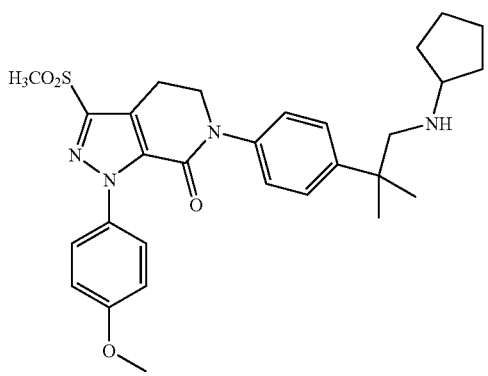

Following a procedure analogous to that used in Example 104, the title compound was prepared. High Resolution Mass Spec (M+H)$^+$ for $C_{29}H_{37}N_4O_4S$ 537.2539.

EXAMPLE 121

6-(4-{2-[(cyclopropylamino) 1,1-dimethylethyl]phenyl}-1-(4-methoxyphenyl)-3-(methylsulfonyl)-1,4,5,7-tetrahydro-7H-pyrazolo[3,4-c]pyridin-7-one

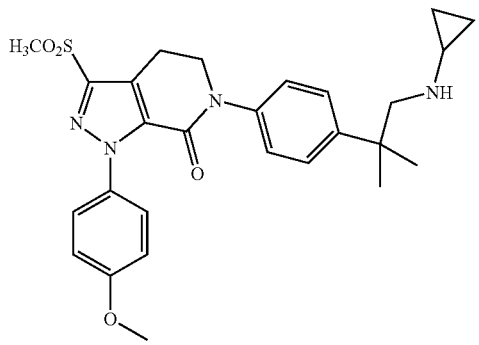

Following a procedure analogous to that used in Example 104, the title compound was prepared. High Resolution Mass Spec (M+H)$^+$ for $C_{27}H_{33}N_4O_4S$ 509.2227.

EXAMPLE 122

6-{4-[2-(cyclobutylamino) 1,1-dimethylethyl]phenyl}-1-(4-methoxyphenyl)-3-(methylsulfonyl)-1,4,5,7-tetrahydro-7H-pyrazolo[3,4-c]pyridin-7-one

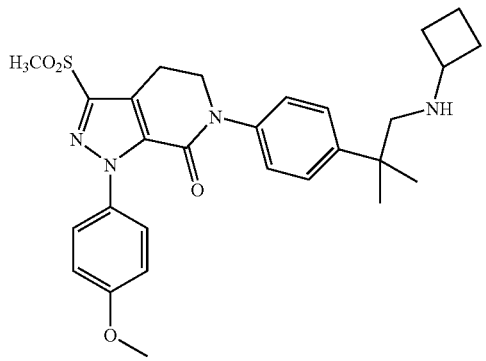

Following a procedure analogous to that used in Example 104, the title compound was prepared. High Resolution Mass Spec (M+H)$^+$ for $C_{28}H_{35}N_4O_4S$ 523.238.

EXAMPLE 123

6-{4-[1,1-dimethyl-2-(1,3-thiazol-2yl amino)ethyl]phenyl}-1-(4-methoxyphenyl)-3-(methylsulfonyl)-1,4,5,7-tetrahydro-7H-pyrazolo[3,4-c]pyridin-7-one

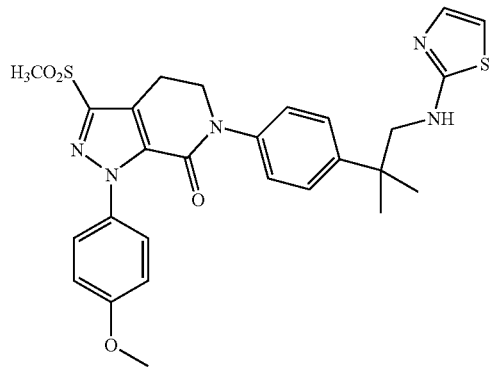

Prepared as previously described above. High Resolution Mass Spec (M+H)$^+$ for $C_{27}H_{30}N_5O_4S_2$ 552.1727.

EXAMPLE 124

6-[4-(2-hydroxy-1,1-dimethylethyl)phenyl]-1-(4-methoxyphenyl)-7-oxo-4,5,6,7-tetrahydro-1H-pyrazolo[3,4-c]pyridine-3-carboxamide

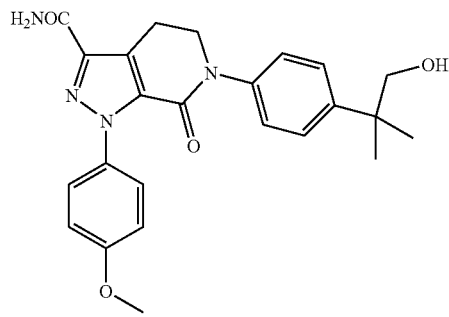

Following a procedure analogous to that used in Example 113, the title compound was prepared. High Resolution Mass Spec (M+H)$^+$ for $C_{24}H_{27}N_4O_4$ 435.2016.

EXAMPLE 125

6-{4-[1,1-dimethyl-2-(2-oxo-1-piperidinyl)ethyl]phenyl}-1-(4-methoxyphenyl)-7-oxo-4,5,6,7-tetrahydro-1H-pyrazolo[3,4-c]pyridine-3-carboxamide

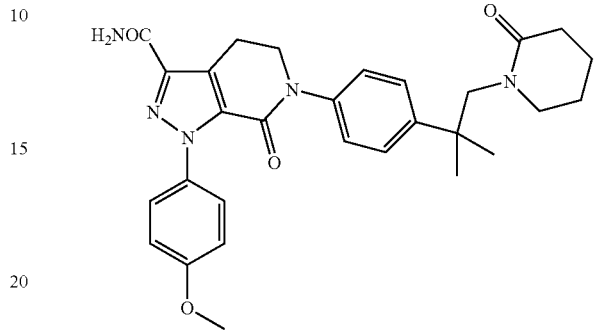

To 6-[4-(1-cyano-1-methylethyl)phenyl]-1-(4-methoxyphenyl)-7-oxo-4,5,6,7-tetrahydro-1H-pyrazolo[3,4-c]pyridine-3-carboxamide (0.17 g, 0.39 mmol) was hydrogenated at 40 psi in ethanol with 0.5 mL conc. HCl and 10% palladium on carbon (25 mg) for 72 h. The reaction was filtered and concentrated. To the amine in THF (5 mL) at 0° C. was added 5-bromovaleryl chloride (99 mg, 0.5 mmol) and TEA (1 mL) and the reaction was stirred 1 h. To the reaction was added potassium t-butoxide (0.24 g, 1.9 mmol) and the reaction was stirred 24 h. The reaction was quenched with water and extracted with ethyl acetate and dried (MgSO$_4$). Purification by HPLC and freeze-drying afforded 15 mg (7.5%). Mass Spec (M+H)$^+$ 516.3.

EXAMPLE 126

6-{4-[1,1-dimethyl-2-(2-oxo-1-piperidinyl)ethyl]phenyl}-1-(4-methoxyphenyl)-3-(methylsulfonyl)-1,4,5,6-tetrahydro-7H-pyrazolo[3,4-c]pyridin-7-one

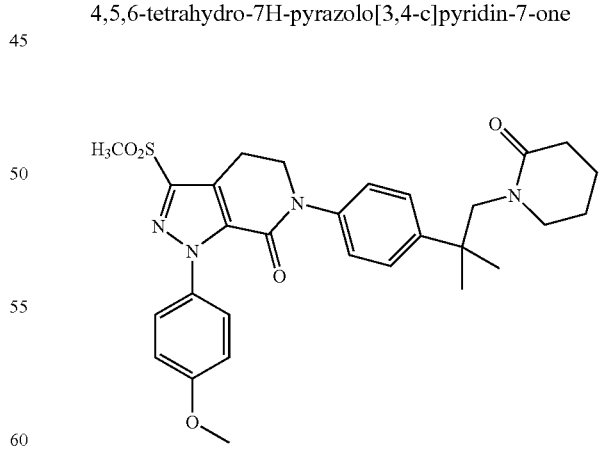

1-{4-[(1-Methoxyphenyl)-3-(methylsulfonyl)-7-oxo-1,4,5,7-tetrahydro-6H-pyrazolo[3,4-c]pyridinyl-6-yl]phenyl}-2-methylpropanenitrile was converted into the target compound by the same procedure as that of Example 125. Mass Spec (M+H)$^+$ 551.3.

EXAMPLE 127

6-[4-(1-Hydroxymethylcyclopropyl)phenyl]-1-(4-methoxy-phenyl)-7-oxo-4,5,6,7-tetrahydro-1H-pyrazolo[3,4-c]pyridine-3-carboxylic acid amide

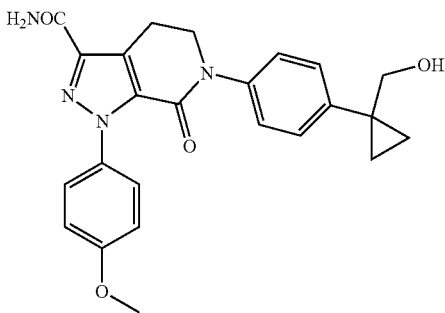

Following a procedure analogous to that used in Example 95, the title compound was prepared. LC/MS (ESI+) 433.4 (M+H)+.

EXAMPLE 128

1-(4-Methoxyphenyl)-6-{4-[1-(2-oxo-pyrrolidin-1-yl)-cyclopropyl]phenyl}-3-trifluoromethyl-1,4,5,6-tetrahydro-pyrazolo[3,4-c]pyridin-7-one

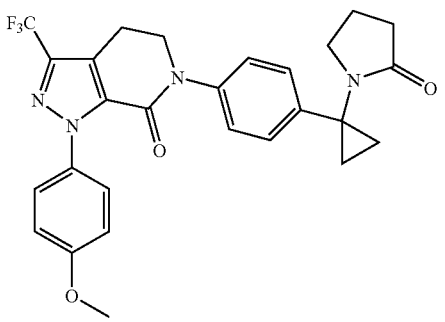

Part A. 4-Iodophenylcyclopropyl carboxylic acid (7.42 g, 25.76 mmol) was stirred in CH$_2$Cl$_2$ (60 mL) at rt under N$_2$. Et$_3$N (5.4 mL, 38.64 mmol, 1.5 eq) was added followed by the addition of DPPA (8.27 mL, 38.64 mmol, 1.5 eq). The resulting mixture was stirred at rt overnight. It was poured into ice H$_2$O (100 mL), acidified with 6N HCl, and then extracted with CH$_2$Cl$_2$. The organic layer was washed with H$_2$O and brine, dried over MgSO$_4$, filtered, and concentrated under vacuum. The oil residue obtained was dissolved in t-BuOH (40 mL) and refluxed for 2–3 h. After cooling, the solvent was evaporated. The residue was purified by FCC (silica gel, hexane:CH$_2$Cl$_2$=1:1, then CH$_2$Cl$_2$, then CH$_2$Cl$_2$:MeOH=100:1 to 25:1) to give pure [1-(4-iodophenyl)-cyclopropyl]-carbamic acid tert-butyl ester (6.01 g, yield: 65%). This compound (2.12 g, 5.89 mmol) was stirred in CH$_2$Cl$_2$ (10 mL) and TFA (10 mL) at rt for 2 h. After evaluation, the residue was taken up in CHCl$_3$ (100 mL) and H$_2$O (100 mL). The aqueous layer was basified with K$_2$CO$_3$, extracted with CHCl$_3$ (2 ×), dried over MgSO$_4$, filtered, and concentrated to dryness to give pure 1-(4-iodophenyl)cyclopropylamine (1.50 g, yield: 98%). $^1$H NMR (CDCl$_3$) δ 7.62 (m, 2H), 7.06 (m, 2H), 1.88 (m, 2H), 1.07 (m, 2H), 0.95 (m, 2H) ppm. HRMS C$_9$H$_{11}$IN (M+H)+ 259.9930 calcd for 259.9936.

Part B. The mixture of the product from Part A (0.32 g, 1.24 mmol), NaOH (0.15 g, 3.72 mmol, 3.0 eq), and 4-chlorobutyryl chloride (0.18 mL, 1.61 mmol, 1.3 eq) was stirred in CH$_2$Cl$_2$ (7 mL) at rt for 1 h under N$_2$. H$_2$O was added. It was extracted with EtOAc (2×), washed with H$_2$O and brine, dried over MgSO$_4$, and concentrated to dryness. The residue was dissolved in THF (10 mL). KOLBu (0.40 g, 4.16 mmol) was added as one portion. The mixture was stirred at 0° C. under N$_2$ for 30 min. EtOAc was added. It was washed with H$_2$O and brine, dried over MgSO$_4$, and concentrated to produce 1-[1-(4-iodophenyl)cyclopropyl]-pyrrolidin-2-one (0.27 g, yield: 100%). $^1$H NMR (CDCl$_3$) δ 7.68 (d, J=8.5 Hz, 2H), 6.87 (d, J=8.5 Hz, 2H), 3.26 (t, J=7.3 Hz, 2H), 2.26 (t, J=7.6 Hz, 2H) 1.88 (t, J=7.0 Hz, 2H), 1.22 (m, 2H), 1.10 (m, 2H) ppm.

Part C. The product from Part B (64 mg, 0.196 mmol) and 1-(4-methoxyphenyl)-3-(trifluoromethyl)-1,4,5,6-tetrahydro-7H-pyrazolo[3,4-c]pyridin-7-one (0.061 g, 0.196 mmol) were stirred in DMSO (0.3 mL) under N$_2$. K$_2$CO$_3$ (0.067 g, 0.49 mmol, 2.5 eq) was added, followed by the addition of CuI (0.037 g, 0.194 mmol) and 1,10-phenanthroline (0.020 g, 0.108 mmol). The resulting mixture was heated at 120° C. for 3 h. After cooling, it was extracted with EtOAc (2×), washed with H$_2$O and brine, dried over MgSO$_4$, filtered, and concentrated to dryness. The residue was purified by FCC (silica gel, CH$_2$Cl$_2$:EtOAc=1:1, then EtOAc) to give 1-(4-methoxyphenyl)-6-{4-[1-(2-oxo-pyrrolidin-1-yl)-cyclopropyl]phenyl}-3-trifluoromethyl-1,4,5,6-tetrahydro-pyrazolo[3,4-c]pyridin-7-one (45 mg, yield: 45%). $^1$H NMR (CDCl$_3$) δ 7.46 (d, J=8.8 Hz, 2H), 7.25 (AA'BB', J=8.6 Hz, 4H), 6.91 (d, J=9.2 Hz, 2H), 4.10 (t, J=6.6 Hz, 2H), 3.81 (s, 3H), 3.38 (t, J=7.2 Hz, 2H), 3.14 (t, J=6.6 Hz, 2H), 2.37 (t, J=7.7 Hz, 2H), 1.98 (q, J=7.7 Hz, 2H), 1.32 (m, 2H), 1.21 (m, 2H) ppm. HRMS C$_{27}$H$_{26}$F$_3$N$_3$O$_4$ (M+H)+ 511.1931 calcd for 511.1958.

EXAMPLE 129

1-(4-Methoxyphenyl)-6-{4-[1-(2-oxo-piperidin-1-yl)-cyclopropyl]phenyl}-3-trifluoromethyl-1,4,5,6-tetrahydro-pyrazolo[3,4-c]pyridin-7-one

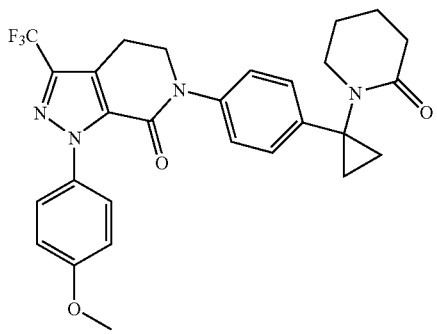

Following the procedures analogous to those used in Example 128, the title compound was prepared. The product was purified by RP-prep LC-MS (35–98% CH$_3$CN/H$_2$O in a 10-min run). HRMS C$_{29}$H$_{32}$O$_2$F$_3$N$_4$ (M+H)+ 525.2486 calcd for 525.2477. $^1$H NMR (CDCl$_3$) δ 7.46 (d, J=8.8 Hz, 2H), 7.25 (d, J=8.4 Hz, 2H), 6.91 (d, J=9.2 Hz, 2H), 4.10 (t, J=6.6 Hz, 2H), 3.82 (s, 3H), 3.37 (t, J=6 Hz, 2H), 3.15 (t, J=6.6 Hz, 2H), 2.51 (t, J=6 Hz, 2H), 1.79 (m, 4H), 1.33 (m, 2H), 1.29 (m, 2H) ppm.

EXAMPLE 130

1-(4-Methoxyphenyl)-6-[4-(1-methylaminocyclopropyl)-phenyl]-3-trifluoromethyl-1,4,5,6-tetrahydro-pyrazolo[3,4-c]pyridin-7-one

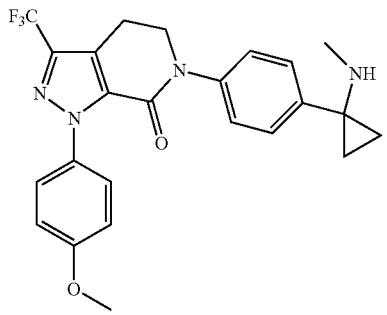

Part A. 1-(4-Iodophenyl)cyclopropyl-carbamic acid tert-butyl ester (2.14 g, 5.85 mmol) was stirred in THF (20 mL) at 0° C. under $N_2$. MeI (3 mL) was added followed by portionwise addition of NaH (2.34 g, 5 eq). The reaction was stirred at rt overnight. Several drops of $H_2O$ and EtOAc (20 mL) were added to quench the reaction. The organic solvent was evaporated, and $H_2O$ was added. It was extracted with $Et_2O$ (2×), washed with brine, dried over $MgSO_4$, and concentrated to dryness. The residue was purified by FCC (silica gel, $CH_2Cl_2$:hexanes=0:1 to 1:1 to 1:0) to give pure [1-(4-iodophenyl)cyclopropyl]-methyl-carbamic acid tert-butyl ester as a white solid (2.07 g, yield 95%). LC/MS (ESI$^+$) 373.8 (M+H), $t_R$=2.95 min (10–90% $CH_3CN$ in $H_2O$ in a 4-min run).

Part B. The product from Part A (205 mg, 0.55 mmol) and 1-(4-methoxyphenyl)-3-(trifluoromethyl)-1,4,5,6-tetrahydro-7H-pyrazolo[3,4-c]pyridin-7-one (170 mg, 0.55 mmol) were stirred in DMSO (0.4 mL) under $N_2$. $K_2CO_3$ (250 mg, 1.81 mmol, 3.3 eq) was added, followed by the addition of CuI (52 mg, 0.27 mmol, 0.5 eq) and 1,10-phenanthroline (50 mg, 0.27 mmol, 0.5 eq). The resulting mixture was heated at 120° C. for 2 h. After cooling, it was extracted with EtOAc (2×), washed with $H_2O$ and brine, dried over $MgSO_4$, filtered, and concentrated to dryness. The residue was purified by flash column chromatography (silica gel, $CH_2Cl_2$: EtOAc=1:1, then EtOAc) to give (1-{4-[1-(4-methoxyphenyl)-7-oxo-3-trifluoromethyl-1,4,5,7-tetrahydro-pyrazolo[3,4-c]pyridin-6-yl]phenyl}cyclopropyl)-methyl-carbamic acid tert-butyl ester (250 mg, yield: 82%). $^1$H NMR (CDCl$_3$) δ 7.46 (d, J=9.2 Hz, 2H), 7.23 (d, J=8.4 Hz, 2H), 7.09 (m, 2H), 6.91 (d, J=9.1 Hz, 2H), 4.12 (t, J=6.6 Hz, 2H), 3.81 (s, 3H), 3.15 (t, J=6.6 Hz, 2H), 2.90 (s, br, 3H), 1.42 (s, br, 9H), 1.33 (m, 2H), 1.20 (m, 2H) ppm. LC/MS (ESI$^+$) 557.4.

Part C. The product from Part B (250 mg, 0.45 mmol) was stirred in $CH_2Cl_2$ (2 mL) and TFA (2 mL) at rt for 20 min. The solvents were evaporated. The residue was purified by FCC (silica gel, EtOAc, then EtOAc:MeOH=10:1) to yield the title compound (188 mg, 92%). $^1$H NMR (CDCl$_3$) δ 7.55 (d, J=8.4 Hz, 2H), 7.45 (d, J=9.2 Hz, 4H), 7.36 (d, J=8.4 Hz, 2H), 6.91 (d, J=8.8 Hz, 2H), 4.15 (t, J=6.6 Hz, 2H), 3.80 (s, 3H), 3.17 (t, J=6.6 Hz, 2H), 2.50 (s, 3H), 1.56 (m, 2H), 1.12 (m, 2H) ppm. LC/MS (ESI$^+$) 457.4.

EXAMPLE 131

6-[4-(1-Dimethylaminocyclopropyl)phenyl]-1-(4-methoxyphenyl)-3-trifluoromethyl-1,4,5,6-tetrahydro-pyrazolo[3,4-c]pyridin-7-one

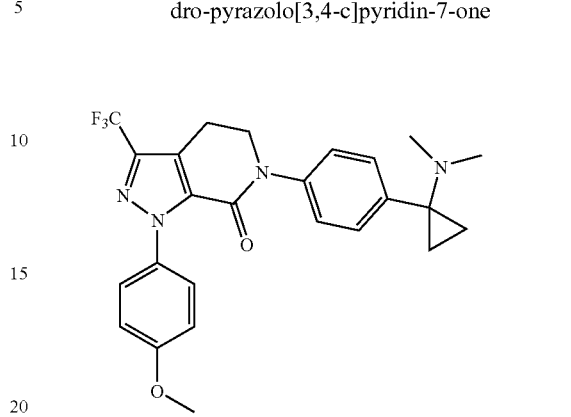

The product from Example 130 (30 mg, 0.066 mmol) was stirred in $CH_3CN$ (0.2 mL) at rt under $N_2$. Aqueous formaldehyde (0.07 mL, 7 mmol, 10 eq) was added followed by the addition of HOAc (0.012 mL, 0.21 mmol, 3.2 eq). The mixture was stirred for 15 min, and then NaBH$_3$CN (12 mg, 0.198 mmol) was added. The mixture was stirred at rt for 2 h. Several drops of acetone were added followed by 1N NaOH. The mixture was extracted with $CH_2Cl_2$, washed with $H_2O$ and brine, dried over $MgSO_4$, and concentrated to dryness. The residue was purified by FCC (silica gel, EtOAc, than EtOAc:MeOH=10:1) to yield the title compound (15.7 mg, 51%). $^1$H NMR (CDCl$_3$) δ 7.46 (d, J=8.8 Hz, 2H), 7.29 (m, 4H), 6.92 (d, J=9.2 Hz, 2H), 4.15 (t, J=6.6 Hz, 2H), 3.81 (s, 3H), 3.16 (t, J=6.6 Hz, 2H), 2.28 (s, 6H), 1.02 (m, 2H), 0.81 (m, 2H) ppm. LC/MS (ESI$^+$) 471.4.

EXAMPLE 132

N-(1-{4-[1-(4-Methoxyphenyl)-7-oxo-3-trifluoromethyl-1,4,5,7-tetrahydro-pyrazolo[3,4-c]pyridin-6-yl]phenyl}-cyclopropyl)-N-methyl-acetamide

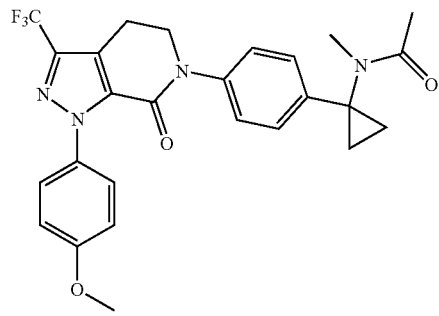

Following a procedure analogous to that used for the preparation of Example 93, the title compound was prepared. Silica gel purification yielded the title compound. LC/MS (ESI$^+$) 499.4 (M+H). $^1$H NMR (CDCl$_3$) δ 7.46 (d, J=9.2 Hz, 2H), 7.26 (m, 2H), 6.93 (AA'BB', J=8.8, 7.0 Hz, 4H), 4.12 (t, J=6.6 Hz, 2H), 3.81 (s, 3H), 3.16 (t, J=6.6 Hz, 2H), 3.01 (s, 3H), 2.05 (s, 3H), 1.50 (m, 4H) ppm.

EXAMPLE 133

N-(1-{4-[1-(4-Methoxyphenyl)-7-oxo-3-trifluoromethyl-1,4,5,7-tetrahydro-pyrazolo[3,4-c]pyridin-6-yl]phenyl}-cyclopropyl)-N-methyl-methanesulfonamide

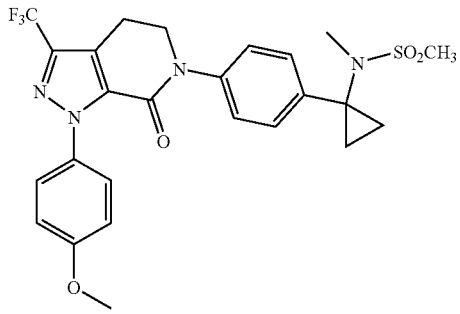

Following a procedure analogous to that used for the preparation of Example 94, the title compound was prepared. Silica gel purification yielded the pure desired product. LC/MS (ESI+) 535.6 (M+H)+.

EXAMPLE 134

N-(1-{4-[1-(4-Methoxyphenyl)-7-oxo-3-trifluoromethyl-1,4,5,7-tetrahydro-pyrazolo[3,4-c]pyridin-6-yl]phenyl}-cyclopropyl)-N-methyl-2-methylaminoacetamide

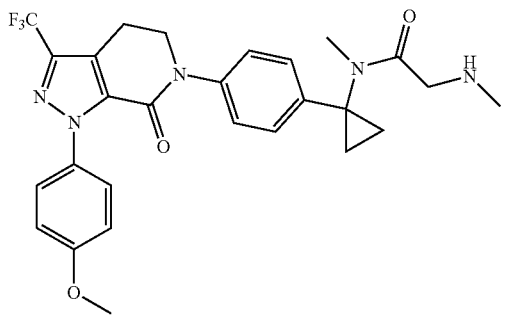

Part A. The product of Example 130 (45 mg, 0.1 mmol) was stirred in $CH_2Cl_2$ (1 mL) at rt. NaOH (12 mg, 3.0 eq) was added followed by the addition of chloroacetyl chloride (0.015 mL, 2.0 eq). The mixture was stirred at rt for 3 h. Additional NaOH (20 mg) and chloroacetyl chloride (0.020 mL) were added. The mixture was stirred at rt overnight. The mixture was extracted with $CH_2Cl_2$ (2×), washed with $H_2O$ and brine, dried over $MgSO_4$, filtered, and concentrated to dryness. The residue was used directly in the next step without further purification. LC/MS (ESI+) 533.6 (M+H), $t_R$=2.63 min (10–90% $CH_3CN$ in $H_2O$ in a 4-min run).

Part B. The product from part A (15 mg, 0.028 mmol) was stirred in DMF (0.1 mL) in a Pyrex tube under $N_2$. $K_2CO_3$ (20 mg) was added, followed by the addition of a solution of $NHMe_2$ in THF (2M, 0.1 mL). The reaction mixture was stirred at 80° C. overnight. $H_2O$ was added, and the mixture was extracted with EtOAc, washed with brine, dried over $MgSO_4$, filtered, and concentrated. The residue was purified by FCC (silica gel, $CH_2Cl_2$, then $CH_2Cl_2$:EtOAc, then EtOAc:MeOH=10:1) to give the title compound (5.0 mg, yield: 33%). $^1$H NMR (CDCl$_3$) δ 7.46 (d, J=8.8 Hz, 2H), 7.29 (m, 4H), 6.92 (d, J=9.2 Hz, 2H), 4.15 (t, J=6.6 Hz, 2H), 3.81 (s, 3H), 3.16 (t, J=6.6 Hz, 2H), 2.28 (s, 6H), 1.02 (m, 2H), 0.81 (m, 2H) ppm. LC/MS (ESI+) 528.6 (M+H), $t_R$=2.07 min (10–90% $CH_3CN$ in $H_2O$ in a 4-min run).

EXAMPLE 135

2-Dimethylamino-N-(1-{4-[1-(4-methoxyphenyl)-7-oxo-3-trifluoromethyl-1,4,5,7-tetrahydro-pyrazolo[3,4-c]pyridin-6-yl]phenyl}cyclopropyl)-N-methylacetamide

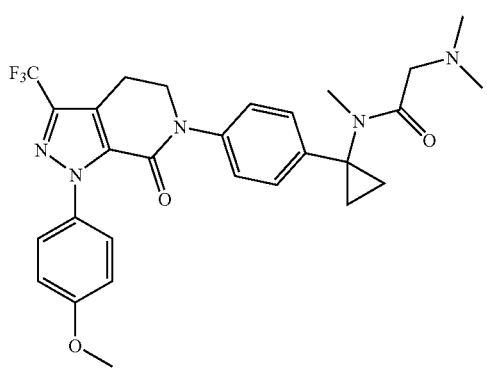

Following a procedure analogous to that used for the preparation of Example 134, the title compound was prepared. Silica gel purification yielded the pure desired product. LC/MS (ESI+) 542.6 (M+H), $t_R$=2.10 min (10–90% $CH_3CN$ in $H_2O$ in a 4-min run).

EXAMPLE 136

N-(1-{4-[1-(4-Methoxyphenyl)-7-oxo-3-trifluoromethyl-1,4,5,7-tetrahydro-pyrazolo[3,4-c]pyridin-6-yl]phenyl}-cyclopropyl)-N-methyl-2-morpholin-4-yl-acetamide

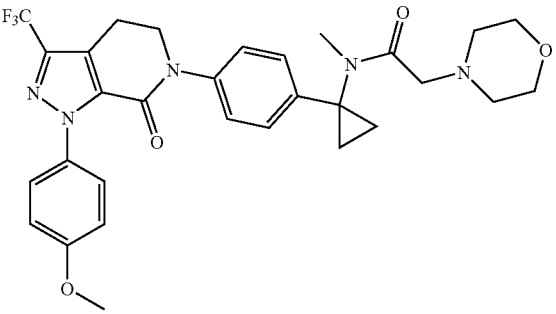

Following a procedure analogous to that used for the preparation of Example 134, the title compound was prepared. Silica gel purification yielded the pure desired product. LC/MS (ESI+) 584.2 (M+H)+, $t_R$=2.05 min (10–90% $CH_3CN/H_2O$ in a 4-min run).

EXAMPLE 137

6-{4-[1-(1-Hydroxyethyl)cyclopropyl]phenyl}-1-(4-methoxyphenyl)-3-trifluoromethyl-1,4,5,6-tetrahydro-pyrazolo[3,4-c]pyridin-7-one

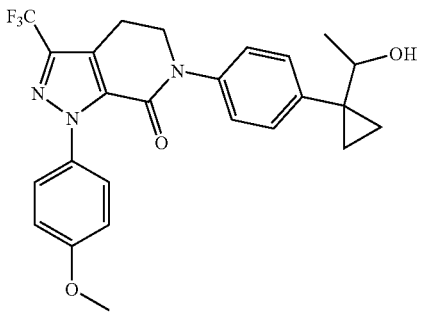

1-{4-[1-(4-Methoxy-phenyl)-7-oxo-3-trifluoromethyl-1,4,5,7-tetrahydro-pyrazolo[3,4-c]pyridin-6-yl]-phenyl}-cyclopropanecarbaldehyde (93 mg, 0.21 mmol) was stirred in Et$_2$O (2 mL) at −78° C. ZnMe$_2$ (2M in toluene, 0.16 mL, 1.5 eq) was added followed by the addition of TiCl$_4$ (1 M in CH$_2$Cl$_2$, 0.3 mL). The resulting mixture was stirred for 1 h. The reaction was quenched by addition of NH$_4$Cl, extracted with EtOAc, washed with H$_2$O and brine, dried over MgSO$_4$, filter, and concentrated. The residue was purified by silica gel column to yield the pure desired product (62 mg, yield: 64.5%). LC/MS (ESI$^+$) 472.6 (M+H)$^+$, $t_R$=2.44 min (35–95% CH$_3$CN/H$_2$O in a 6-min run).

EXAMPLE 138

6-[4-(1-Acetylcyclopropyl)phenyl]-1-(4-methoxyphenyl)-3-trifluoromethyl-1,4,5,6-tetrahydro-pyrazolo[3,4-c]pyridin-7-one

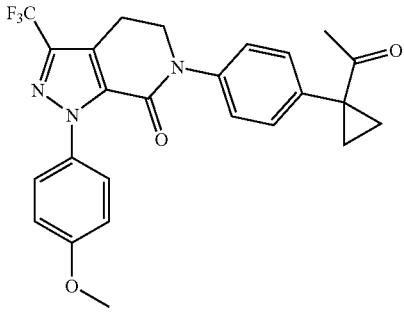

The product from Example 137 (30 mg, 0.063 mmol) was stirred in CH$_2$Cl$_2$ (1 mL) at rt under N$_2$. 4 Å molecular sieves (30 mg) and NaOAc (15.4 mg, 0.187 mmol) were added followed by the addition of PCC (27.5 mg, 0.126 mmol). The reaction mixture was stirred at rt for 1.5 h. The mixture was filtered through Celite®, rinsed with CH$_2$Cl$_2$, washed with H$_2$O, brine, concentrated to dryness. Silica gel purification afforded the title compound. LC/MS(ESI$^+$) 470.6 (M+H)$^+$, $t_R$=2.77 min (10–90% CH$_3$CN/H$_2$O in a 4-min run). $^1$H NMR (CDCl$_3$) δ 7.47 (d, J=8.4 Hz, 2H), 7.33 (AA'BB', J=8.8 Hz, 4H), 6.93 (dd, J=8.8, 2.3 Hz, 2H), 4.16 (t, J=6.6 Hz, 2H), 3.83 (s, 3H), 3.29 (t, J=6.6 Hz, 2H), 2.77 (s, 6H), 1.67 (m, 2H), 1.15 (m, 2H) ppm.

EXAMPLE 139

6-{4-[1-(1-Hydroxy-1-methyl-ethyl)cyclopropyl]phenyl}-1-(4-methoxyphenyl)-3-trifluoromethyl-1,4,5,6-tetrahydro-pyrazolo[3,4-c]pyridin-7-one

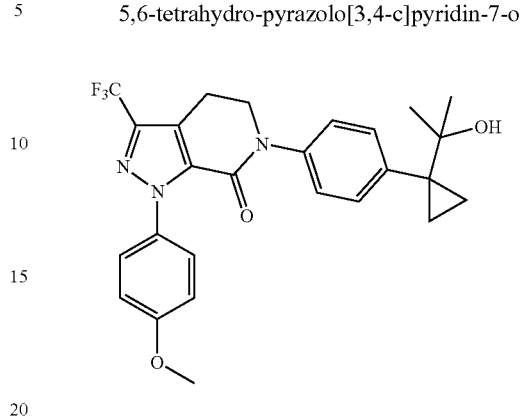

Part A. 1-(4-Iodo-phenyl)-cyclopropanecarboxylic acid methyl ester (0.96 g, 3.17 mmol) was stirred in THF (15 mL) at −78° C. under N$_2$. MeMgCl (3.0 M in THF, 4.2 mL, 4.0 eq) was added dropwise, and the reaction was stirred for 1 h during which period the temperature was raised from −78° C. to 0° C. It was quenched by the addition of sat'd NH$_4$Cl, and extracted with EtOAc (2×). The organics were washed with H$_2$O and brine, dried over MgSO$_4$, filtered, and concentrated to dryness. The residue was purified by FCC (silica gel, hexanes, then hexanes:CH$_2$Cl$_2$=1:1 to 0:1) to give 2-[1-(4-iodo-phenyl)-cyclopropyl]-propan-2-ol (0.71 g, yield: 73.9%). LC/MS(ESI$^+$) 303.4 (M+H)$^+$, $t_R$=2.57 min (10–90% CH$_3$CN/H$_2$O in a 4-min run).

Part B. The product from Part A (102 mg, 0.33 mmol) and (105 mg, 0.34 mmol) were stirred in dry DMSO (0.5 mL). K$_2$CO$_3$ (90.5 mg, 2.0 eq) was added followed by the addition of CuI (32 mg, 0.17 mmol) and 1,10-phenanthroline (31 mg, 0.17 mmol). The resulting mixture was heated at 120° C. for 3 h. After cooling, it was extracted with EtOAc (2×), washed with H$_2$O and brine, dried over MgSO$_4$, filtered, and concentrated to dryness. The residue was purified by FCC (silica gel, CH$_2$Cl$_2$:EtOAc=1:1, then EtOAc) to give the title compound (95 mg, yield: 59.4%). LC/MS(ESI$^+$) 486.8 (M+H)$^+$, $t_R$=3.03 min (10–90% CH$_3$CN/H$_2$O in a 4-min run).

EXAMPLE 140

6-[4-(1-Methoxymethylcyclopropyl)phenyl]-1-(4-methoxyphenyl)-3-trifluoromethyl-1,4,5,6-tetrahydro-pyrazolo[3,4-c]pyridin-7-one

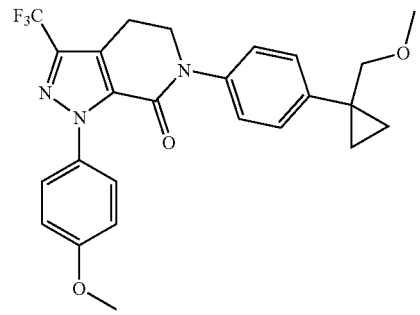

Part A. [1-(4-Iodo-phenyl)-cyclopropyl]-methanol (0.25 g, 0.94 mmol) was dissolved in $CH_2Cl_2$ (1.5 mL). Proton sponge (0.21 g, 0.97 mmol) was added followed by trimethoxyloxonium tetrafluoroborate (0.15 g, 1.0 mmol). The reaction was allowed to stir for 3 h and was then quenched with $H_2O$, concentrated, and purified via flash chromatography (silica, 100% EtOAc) to afford the title compound (0.13 g, yield: 47%). $^1$H NMR ($CDCl_3$) δ 7.64 (d, J=8.4 Hz, 2H), 7.11 (d, J=8.2 Hz, 2H), 3.65 (d, J=6.2 Hz, 2H), 1.57 (s, 3H), 0.86 (s, 4H) ppm.

Part B. The product from Part A and 1-(4-methoxyphenyl)-3-(trifluoromethyl)-1,4,5,6-tetrahydro-7H-pyrazolo[3,4-c]pyridin-7-one were coupled using the usual Buchwald Ullman procedure. LC/MS (ESI$^+$) 472.6 (M+H)$^+$, $t_R$=2.98 min (10–90% $CH_3CN/H_2O$ in a 4-min run). $^1$H NMR (($CD_3$)$_2$CO, 300 MHz) δ 7.49 (d, J=9.1 Hz, 2H), 7.29 (AA'BB', J=8.8 Hz, 4H), 6.96 (dd, J=9.2 Hz, 2H), 4.15 (t, J=6.6 Hz, 2H), 3.82 (s, 3H), 3.44 (s, 2H), 3.23 (s, 3H), 3.16 (t, J=6.3 Hz, 2H), 0.84 (d, J=2.2 Hz, 2H), 0.81 (d, J=2.5 Hz, 2H) ppm.

EXAMPLE 141

6-{4-[1-(4,5-Dihydro-oxazol-2-yl)cyclopropyl]phenyl}-1-(4-methoxyphenyl)-3-trifluoromethyl-1,4,5,6-tetrahydro-pyrazolo[3,4-c]pyridin-7-one

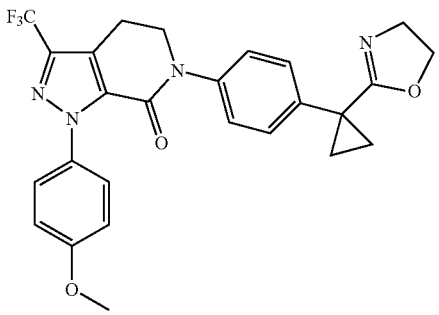

Part A. To a slurry of 1-(4-iodo-phenyl)-cyclopropanecarboxylic acid (0.693 g, 2.41 mmol) in $CH_2Cl_2$ (3.0 mL) at 0° C. was added (COCl)$_2$ (0.40 mL, 4.6 mmol) dropwise. The reaction was warmed to rt and stirred under $N_2$ for 1 h. The reaction was monitored by LC/MS. Upon completion the reaction was concentrated on the rotary evaporator and diluted with $CH_2Cl_2$ (3 mL). Ethanolamine (0.30 mL, 4.54 mmol) was added drop-wise and the reaction stirred for 1.5 h. The reaction was then quenched with $H_2O$ and extracted with EtOAc (2×). The organic layers were washed with brine, dried over $Na_2SO_4$, filtered, and concentrated to dryness. The crude 1-(4-iodo-phenyl)-cyclopropanecarboxylic acid (2-hydroxy-ethyl)-amide was taken directly to the next reaction without further purification. LC/MS (ESI$^+$) 332.2 (M+H)$^+$, $t_R$=2.16 min (10–90% $CH_3CN/H_2O$ in a 4-min run). It was dissolved in THF (10.0 mL) and methoxycarbonylsulfamoyl triethylammonium hydroxide inner salt (0.61 g, 2.56 mmol) was added. The reaction was heated to 70° C. for 2 h and then cooled. The reaction mixture was diluted with EtOAc and washed with $H_2O$ (2×), brine, dried over $Na_2SO_4$, filtered, and concentrated to dryness. The residue was purified by flash chromatography (silica, EtOAc:Hexanes 3:1) to 2-[1-(4-iodo-phenyl)-cyclopropyl]-4,5-dihydro-oxazole (0.41 g, yield: 55%). LC/MS (ESI$^+$) 314.0 (M+H), $t_R$=1.62 min (10–90% $CH_3CN/H_2O$ in a 4-min run). $^1$H NMR ($CDCl_3$) δ 7.65 (d, J=8 Hz, 2H), 7.13 (d, J=8.4 Hz, 2H), 4.32 (t, J=9.5 Hz, 2H), 3.87 (t, J=9.1, 9.6, 2H), 1.67 (m, 2H), 1.23 (m, 2H) ppm.

Part B. The product from Part A (75.2 mg, 0.240 mmol) and 1-(4-methoxyphenyl)-3-(trifluoromethyl)-1,4,5,6-tetrahydro-7H-pyrazolo[3,4-c]pyridin-7-one (76.8 mg, 0.247 mmol) were dissolved in DMSO (0.5 mL). Potassium carbonate (0.109 g, 0.788 mmol), copper iodide (spatula tip), and 1,10-phenanthroline (spatula tip) were added and the reaction was heated to 120° C. for 12 h under an environment of $N_2$. The reaction was cooled, diluted with EtOAc, washed with $H_2O$ (2×), brine, dried over $Na_2SO_4$, filtered, and concentrated in vacuo. Flash chromatography (silica, 100% EtOAc) afforded the title compound. LC/MS (ESI$^+$) 497.6 (M+H), $t_R$=2.44 min (10–90% $CH_3CN/H_2O$ in a 4-min run). $^1$H NMR (($CD_3$)$_2$CO, 300 MHz) δ 7.51 (d, J=9.0 Hz, 2H), 7.32 (AA'BB', J=8.4 Hz, 4H), 6.97 (d, J=9.0 Hz, 2H), 4.16 (m, 4H), 3.82 (s, 3H), 3.67 (t, J=9.2 Hz, 2H), 3.17 (t, J=6.6 Hz, 2H), 2.02 (m, 2H), 1.42 (m, 2H), 1.17 (m, 2H) ppm.

EXAMPLE 142

1-{4-[1-(4-Methoxy-phenyl)-7-oxo-3-trifluoromethyl-1,4,5,7-tetrahydro-pyrazolo[3,4-c]pyridin-6-yl]-phenyl}-cyclopropanecarboxylic acid 2-aminoethyl ester

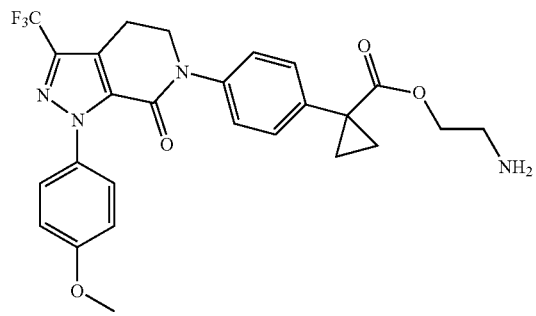

A side product resulting from a minor impurity in the starting material of Part C of Example 141 was isolated and characterized to be the title compound. LC/MS (ESI$^+$) 515.6 (M+H)$^+$, $t_R$=2.22 min (10–90% $CH_3CN/H_2O$ in a 4-min run). $^1$H NMR ($CD_3$)$_2$CO, δ 7.50 (d, J=8.8 Hz, 2H), 7.38 (AA'BB', J=8.6 Hz, 4H), 7.00 (d, J=8.8 Hz, 2H), 4.20, (t, 2H), 3.83 (s, 3H), 3.45 (t, 2H), 3.20 (m, 4H), 1.40 (m, 2H), 0.95 (m, 2H) ppm.

EXAMPLE 143

6-{4-[1-(4,5-Dihydro-oxazol-2-yl)-cyclopropyl]-phenyl}-1-(4-methoxy-phenyl)-7-oxo-4,5,6,7-tetrahydro-1H-pyrazolo[3,4-c]pyridine-3-carboxylic acid amide

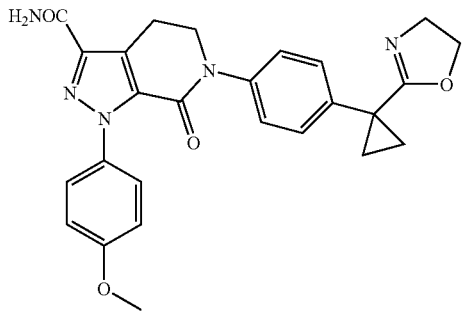

Part A. The product of Part A from Example 141 (0.10 g, 0.32 mmol) and 1-(4-methoxy-phenyl)-7-oxo-4,5,6,7-tetrahydro-1H-pyrazolo[3,4-c]pyridine-3-carboxylic acid ethyl ester (0.10 g, 0.32 mmol) were dissolved in DMSO (1.5 mL). Potassium carbonate (1.3 g, 0.94 mmol), copper iodide (0.02 g, 0.10 mmol), and 1,10-phenanthroline (0.02 g, 0.11 mmol) were then added and the reaction was heated to 120° C. for 12 h under an environment of $N_2$. The reaction was cooled, diluted with EtOAc, washed with $H_2O$ (2×), brine, dried over $Na_2SO_4$, filtered, and concentrated to dryness to give 6-{4-[1-(4,5-dihydro-oxazol-2-yl)-cyclopropyl]-phenyl}-1-(4-methoxy-phenyl)-7-oxo-4,5,6,7-tetrahydro-1H-pyrazolo[3,4-c]pyridine-3-carboxylic acid ethyl ester. LC/MS (ESI$^+$) 501.8 (M+H)$^+$, $t_R$=2.64 min (10–90% $CH_3CN/H_2O$ in a 4-min run).

Part B. The product from Part A (0.10 g, 0.20 mmol) was dissolved in ethylene glycol saturated with ammonia (2.0 mL) and heated to 85° C. for 4 h. Reaction was cooled, diluted with $H_2O$, and washed with EtOAc (3×). Organic portions were combined and washed with brine (2×), dried over $Na_2SO_4$, filtered, and concentrated to dryness. The title compound was recrystalized from EtOAc/Hexanes (0.03 g, yield: 32%). LC/MS (ESI$^+$) 472.6 (M+H)$^+$, $t_R$=1.49 min (10–90% $CH_3CN/H_2O$ in a 4-min run). $^1$H NMR (CD$_3$O D) δ 7.47 (d, J=9.2 Hz, 2H), 7.38 (AA'BB', J=8.5 Hz, 4H), 4.86 (t, 2H), 4.25 (t, 2H), 3.81 (s, 3H), 3.72 (t, 2H), 1.49 (m, 2H), 1.16 (m, 2H) ppm.

EXAMPLE 144

6-{4-[1-(4,5-Dihydro-1H-imidazol-2-yl)cyclopropyl]phenyl}-1-(4-methoxyphenyl)-3-trifluoromethyl-1,4,5,6-tetrahydro-pyrazolo[3,4-c]pyridin-7-one

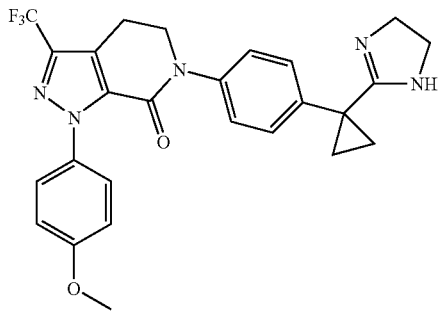

Part A. 1-(4-Iodo-phenyl)-cyclopropanecarboxylic acid (0.99 g, 3.4 mmol), DCC (0.71 g, 3.4 mmol), and pentafluorophenol (0.91 g, 4.9 mmol) were added into $CH_2Cl_2$ (6 mL) and allowed to stir for 2 h. Piperidine (0.7 mL, 7.1 mmol) was then added dropwise to the slurry. Reaction was allowed to stir for an additional 12 h. The reaction was then diluted with EtOAc; filtered; washed with 1N HCl, 1N NaOH (2×), and brine; dried over MgSO$_4$; filtered; and concentrated to dryness. The crude mixture was purified by flash chromatography (silica, EtOAc:hexanes (3:1) to give [1-(4-iodo-phenyl)-cyclopropyl]-piperidin-1-yl-methanone (1.09, yield: 88%). $^1$H NMR (CDCl$_3$, 300 MHz) δ 7.60 (d, J=8.8 Hz, 2H), 6.92 (d, J=8.4 Hz, 2H), 3.55 (bs, 2H), 3.67 (bs, 2H), 1.60, (bs, 2H), 1.54 (bs, 2H), 1.41 (m, 2H), 1.25 (bs, 2H), 1.13 (m, 2H) ppm.

Part B. The product from part A (1.09 g, 3.03 mmol) was dissolved in toluene (10.0 mL) and [2,4-bis(4-methoxyphenyl)-1,3-dithia-2,4-diphosphetane-2,4-disulfide] (0.9 g, 2.2 mmol) was added. The reaction was heated to 90° C. for 1.5 h and cooled. An additional 0.5 g (1.23 mmol) of [2,4-bis(4-methoxyphenyl)-1,3-dithia-2,4-diphosphetane-2,4-disulfide] was added and heated for 12 h. The reaction mixture was concentrated and purified via flash chromatography (silica, EtOAc:Hexanes=3:1) to yield [1-(4-Iodo-phenyl)-cyclopropyl]-piperidin-1-yl-methanethione (0.92 g, yield: 88%). LC/MS (ESI$^+$) 372.0 (M+H)$^+$, $t_R$=6.56 min (5–98% $CH_3CN/H_2O$ in a 10-min run).

Part C. The product from Part B (0.92 g, 2.4 mmol) was treated with neat methyl iodide (2.00 mL, 32.1 mmol) at rt and allowed to stir under $N_2$ for 48 h. The reaction was concentrated and stripped (3×) with methanol to provide a yellow solid of 1-{[1-(4-iodo-phenyl)-cyclopropyl]-methylsulfanyl-methylene}-piperidinium; iodide (0.51 g, yield: 41%).

Part D. The product from Part C (0.51 g, 0.99 mmol) was dissolved in methanol (3.0 mL) and ethylenediamine (0.1 mL, 1.49 mmol) was added dropwise at rt. After 2 h, reaction mixture was concentrated to dryness and purified via flash chromatography (silica, 100% EtOAc, then 0.5% Et$_3$N:10% MeOH:CH$_2$Cl$_2$) to yield 2-[1-(4-iodo-phenyl)-cyclopropyl]-4,5-dihydro-1H-imidazole (0.20 g, yield: 66%). $^1$H NMR (CD$_3$OD, 300 MHz) δ 7.68 (d, J=8.4 Hz, 2H), 7.14 (d, J=8.5 Hz, 2H), 3.61 (s, 4H), 1.48 m, 2H), 1.25 (s, 2H) ppm.

Part E. The product from Part D (0.093 g, 0.298 mmol) and 1-(4-methoxyphenyl)-3-(trifluoromethyl)-1,4,5,6-tetrahydro-7H-pyrazolo[3,4-c]pyridin-7-one (0.096 g, 0.309 mmol) and 2-[1-(4-iodo-phenyl)-cyclopropyl]-4,5-dihydro-1H-imidazole (0.093 g, 0.298 mmol) were coupled by the usual procedure. Purification was accomplished using flash chromatography (silica, 100% EtOAc then 0.5% Et$_3$N:10% MeOH:CH$_2$Cl$_2$) to give product (35 mg, yield: 38%). LC/MS (ESI$^+$) 496.6 (M+H)$^+$, $t_R$=2.16 min (10–90% $CH_3CN/H_2O$ in a 4-min run). $^1$H NMR (CD$_3$OD, 300 MHz) δ 7.47 (AA'BB', J=8.6 Hz, 4H), 7.30 (d, J=8.4 Hz, 2H), 6.98 (d, J=9.1 Hz, 2H), 4.11 (t, J=6.6 Hz, 2H) 3.82 (s, 3H), 3.52 (s, 4H), 3.15 (t, J=6.6 Hz, 2H), 1.44 (m, 2H), 1.16 (m, 2H) ppm.

EXAMPLE 145

1-(4-Methoxyphenyl)-6-{4-[1-(1-methyl-4,5-dihydro-1H-imidazol-2-yl)cyclopropyl]phenyl}-3-trifluoromethyl-1,4,5,6-tetrahydro-pyrazolo[3,4-c]pyridin-7-one

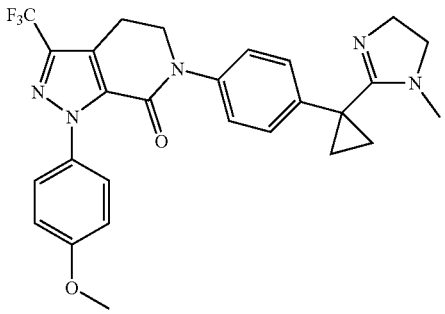

The title compound was obtained following the same sequence as those in Example 145 but using N-methylethylenediamine instead of ethylene diamine. LC/MS (ESI⁺) 510.6 (M+H)⁺, $t_R$=2.75 min (10–90% $CH_3CN/H_2O$ in a 4-min run). ¹H NMR ($CD_3Cl_3$, 300 MHz) δ 7.45 (d, J=8.8 Hz, 2H), 7.27 (m, 4H), 6.92 (d, J=9.2 Hz, 4H), 4.12 (m, 2H), 3.85 (m, 2H), 3.81 (s, 3H), 3.16 (t, J=6.6 Hz, 2H), 2.89 (s, br, 3H), 1.59 (m, 2H), 1.28 (m, 2H) ppm.

EXAMPLE 146

6-{4-[1-(1-Methanesulfonyl-4,5-dihydro-1H-imidazol-2-yl)-cyclopropyl]phenyl}-1-(4-methoxyphenyl)-3-trifluoromethyl-1,4,5,6-tetrahydro-pyrazolo[3,4-c]pyridin-7-one

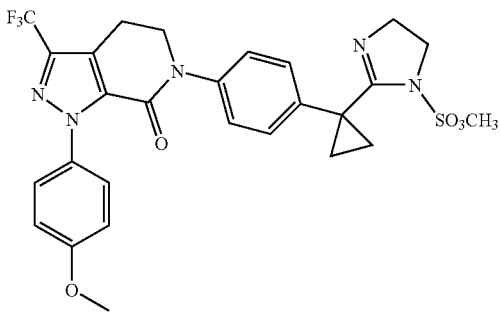

The product from Example 144 (0.017 g, 0.034 mmol) from was dissolved in $CH_2Cl_2$ (0.3 mL). $Et_3N$ (0.1 mL, 0.07 mmol) and MsCl (0.07 mL, 0.09 mmol) were added at rt under $N_2$. The reaction was stirred for 12 h, concentrated to dryness, and purified via flash chromatography (silica, 100% EtOAc then 0.5% $Et_3N$:10% $MeOH:CH_2Cl_2$) to afford the title compound. LC/MS (ESI⁺) 574.4 (M+H)⁺, $t_R$=2.84 min (10–90% $CH_3CN/H_2O$ in a 4-min run). ¹H NMR ($(CD_3)_2CO$, 300 MHz) δ 7.50 (d, J=9.1 Hz, 2H), 7.33 (m, 4H), 6.98 (d, J=9.1 Hz, 2H), 4.16 (t, J=6.6 Hz, 2H), 3.83 (m, 7H), 3.16 (t, J=6.4 Hz, 2H), 2.42 (s, 3H), 1.47 (m, 2H), 1.18 (m, 2H) ppm.

EXAMPLE 147

6-{4-[1-(1H-Imidazol-2-yl)cyclopropyl]phenyl}-1-(4-methoxy-phenyl)-3-trifluoromethyl-1,4,5,6-tetrahydro-pyrazolo[3,4-c]pyridin-7-one

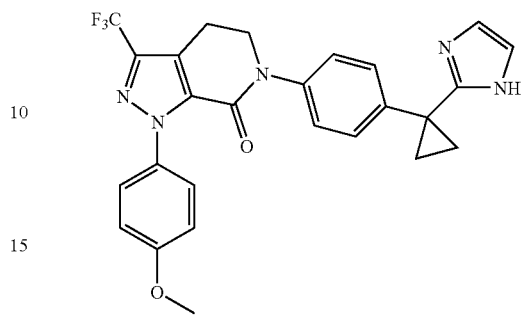

Part A. H-(Boc)-DAP-OMe was dissolved in $CH_2Cl_2$ (2.0 mL) and TFA (1.0 mL) was added. The reaction was allowed to stir for 2 h. The reaction was concentrated and stripped with $CHCl_3$ (10 mL×3). The reaction mixture was re-diluted with MeOH (6.0 mL) and $K_2CO_3$ (spatula tip) added. The product from Part C in Example 142 (0.12 g, 0.234 mmol) was added and the reaction was heated to 65° C. for 2 h. The reaction was concentrated and purified via flash chromatography (silica, EtOAc-10% $MeOH/CH_2Cl_2$) to afford 2-[1-(4-Iodo-phenyl)-cyclopropyl]-4,5-dihydro-3H-imidazole-4-carboxylic acid methyl ester. LC/MS (ESI⁺) 371.0 (M+H)⁺, $t_R$=2.17 min (10–90% $CH_3CN/H_2O$ in a 4-min run).

Part B. 1-(4-Methoxyphenyl)-3-(trifluoromethyl)-1,4,5,6-tetrahydro-7H-pyrazolo[3,4-c]pyridin-7-one (45.0 mg, 0.145 mmol) and product from Part A (36.0 mg, 0.098 mmol) were dissolved in DMSO (0.5 mL). $K_2CO_3$ (10.0 mg, 0.723 mmol) was added followed by 1,10-phenanthroline (spatula tip) and copper iodide (spatula tip). The reaction was heated to 110° C. for 12 h. The reaction was diluted with EtOAc and washed with $H_2O$ (2×) and brine. Organic was dried over $NaSO_4$, filtered, and concentrated. The reaction was purified via flash chromatography (silica, EtOAc-10% MeOH/1% $EtN_3/CH_2Cl_2$). Side product obtained from loss of $CO_2Me$ under the basic conditions to form the title compound. LC/MS (ESI⁺) 494.2 (M+H)⁺, $t_R$=2.21 min (10–90% $CH_3CN/H_2O$ in a 4-min run). ¹H NMR ($(CD_3)_2CO$, 300 MHz) δ 7.50 (d, J=9.2 Hz, 2H), 7.32 (m, 4H), 6.98 (d, J=9.1 Hz, 2H), 6.83 (s, 2H), 4.16 (t, J=6.6 Hz, 2H), 3.83 (s, 3H), 3.16 (t, J=6.2 Hz, 2H), 1.47 (m, 2H), 1.18 (m, 2H) ppm.

EXAMPLE 148

1-(4-Methoxyphenyl)-6-{4-[1-(1-methyl-1H-imidazol-2-yl)-cyclopropyl]phenyl}3-trifluoromethyl-1,4,5,6-tetrahydro-pyrazolo[3,4-c]pyridin-7-one

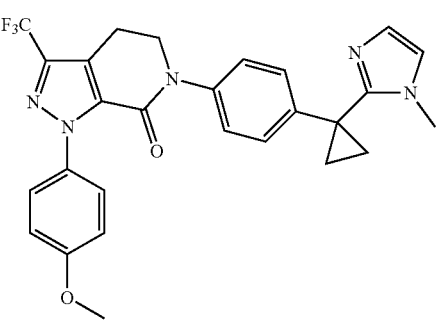

The product from Example 144 (0.08 g, 0.18 mmol) was dissolved in 1,4-dioxane (2.0 mL) and KMnO$_4$ (spatula tip) was added. The reaction was heated to 80° C. for 12 h at rt. The reaction was filtered, concentrated, and purified via flash chromatography (silica, 100% EtOAc then 0.5% Et$_3$N: 10% MeOH/CH$_2$Cl$_2$ then 100% MeOH) to yield the title compound (0.06 g, yield: 72%). $^1$H NMR δ 7.44 (d, J=9.1 Hz, 2H), 7.24 (d, J=8.7 Hz, 2H), 6.98 (m, 4H), 4.07 (dd, J=2.9, 3.7 Hz, 2H), 3.81 (s, 3H), 3.48 (s, 2H), 3.12 (t, J=6.2 Hz, 2H), 1.44 (m, 2H), 1.21 (t, J=7.3 Hz, 2H) ppm.

EXAMPLE 149

2-[(1-{4-[1-(4-Methoxyphenyl)-7-oxo-3-trifluoromethyl-1,4,5,7-tetrahydro-pyrazolo[3,4-c]pyridin-6-yl]phenyl}-cyclopropyl)-methyl-amino]-acetamide

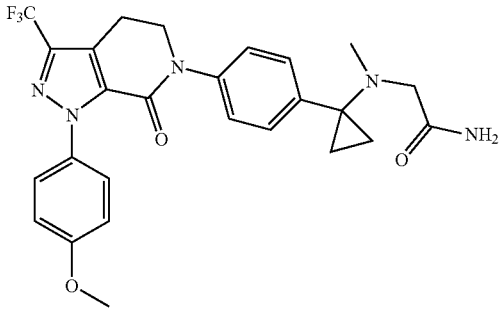

The product of Example 130 (50 mg, 0.11 mmol) was stirred in DMF (0.3 mL). K$_2$CO$_3$ (45 mg, mmol, 0.33 mmol, 3 eq) and chloroacetamide (20 mg, 0.21 mmol, 2 eq) were added. The mixture was stirred at 70° C. for 2 h. EtOAc was added, washed with H$_2$O and brine, dried over MgSO$_4$, filtered, and concentrated. The residue was purified by Silica gel purification to yield the title compound. LC/MS (ESI$^+$) 514.8 (M+H)$^+$, t$_R$=2.00 min (10–90% CH$_3$CN/H$_2$O in a 4-min run). $^1$H NMR (CDCl$_3$) δ 87.46 (d, J=9.2 Hz, 2H), 7.27 (m, 4H), 6.91 (d, J=8.8 Hz, 2H), 4.12 (t, J=6.6 Hz, 2H), 3.81 (s, 3H), 3.15 (m, 4H), 2.29 (m, 3H), 0.97 (m, 2H), 0.87 (m, 2H) ppm.

EXAMPLE 150

6-(4-{1-[(2-Hydroxyethyl)-methylamino]cyclopropyl}phenyl)-1-(4-methoxyphenyl)-3-trifluoromethyl-1,4,5,6-tetrahydro-pyrazolo[3,4-c]pyridin-7-one

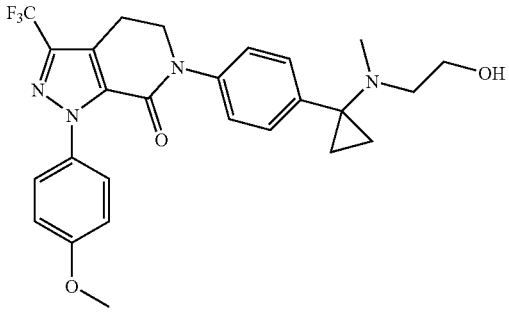

Following a procedure analogous to that used for the preparation of Example 149 but using 2-bromoethanol instead, the title compound was prepared. Silica gel purification yielded the pure desired product. LC/MS (ESI$^+$) 501.8 (M+H)$^+$, t$_R$=2.04 min (10–90% CH$_3$CN/H$_2$O in a 4-min run). $^1$H NMR (CDCl$_3$) δ 7.46 (d, J=9.1 Hz, 2H), 7.29 (m, 4H), 6.92 (d, J=8.8, 2H), 4.14 (t, J=6.6 Hz, 2H), 3.81 (s, 3H), 3.51 (m, 2H), 3.16 (t, J=6.6 Hz, 2H), 2.64 (m, 2H), 2.23 (s, 3H), 0.95 (s, 3H), 0.83 (m, 2H) ppm.

EXAMPLE 151

1-{4-[1-(4-Methoxy-phenyl)-7-oxo-3-trifluoromethyl-1,4,5,7-tetrahydro-pyrazolo[3,4-c]pyridin-6-yl]-phenyl}-cyclopropanecarboxylic acid methoxy-methyl-amide

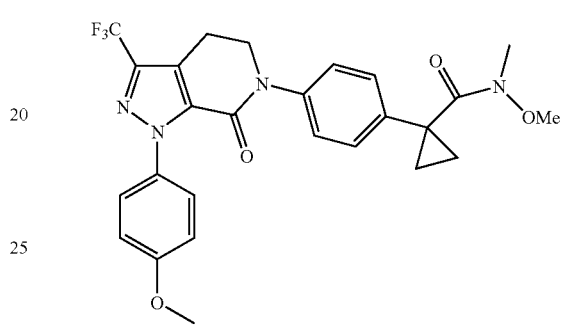

1-{4-[1-(4-Methoxy-phenyl)-7-oxo-3-trifluoromethyl-1,4,5,7-tetrahydro-pyrazolo[3,4-c]pyridin-6-yl]-phenyl}cyclopropane carboxylic acid (1.12 g, 2.37 mmol) and N,O-dimethylhydroxylamine hydrochloride (0.255 g, 2.61 mmol) were dissolved in DMF (20.0 mL) and DIEA (2.0 mL, 11.5 mmol) was added dropwise. 1-[3-(Dimethylamino)propyl]-3-ethylcarbodiimide hydrochloride (0.54 g, 2.8 mmol) was added and the reaction was allowed to proceed under nitrogen at rt for 12 h. The reaction was diluted with EtOAc, washed 1N HCl, brine, dried over Na$_2$SO$_4$, filtered and concentrated. The reaction was purified via flash chromatography (silica, 100% EtOAc, then 10% MeOH/CH$_2$Cl$_2$) to give the title compound. LC/MS (ESI$^+$) 515.6 (M+H).

EXAMPLE 152

6-[4-(1-Hydroxymethylcyclopropyl)phenyl]-1-(4-methoxy-phenyl)-7-oxo-4,5,6,7-tetrahydro-1H-pyrazolo[3,4-c]pyridine-3-carboxylic acid amide

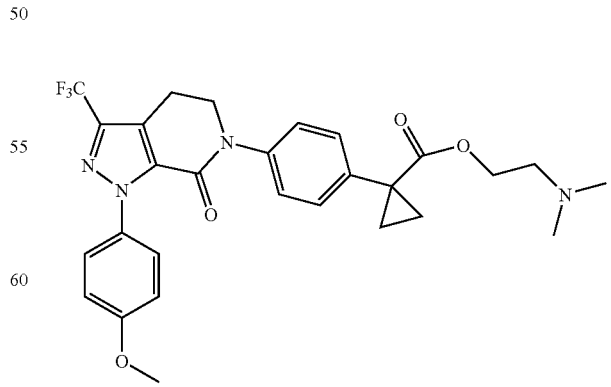

The title compound was obtained as a side product in the reaction from Example 151 (0.55 g, 0.96 mmol) was obtained in 40% yield. LC/MS (ESI+) 556.4 (M+H)+, $t_R$=1.77 min (10–90% $CH_3CN/H_2O$ in a 4-min run). $^1H$ NMR (300 MHz, $(CD_3)_2CO$) δ 7.50 (d, J=8.8 Hz, 2H), 7.39 (AA'BB', J=8.8 Hz, 4H), 7.01 (d, J=8.8 Hz, 2H), 4.19 (t, J=6.6 Hz, 2H), 3.83 (s, 3H), 3.76 (m, 2H), 3.20 (m, 4H), 2.85 (s, 3H), 2.63 (s, 6H), 1.52 (m, 2H), 1.31 (m, 2H), 1.09 (t, J=7.0 Hz, 2H), 0.81 (t, J=6 Hz, 1H) ppm.

EXAMPLE 153

6-[4-(1-Acetyl-cyclopropyl)-phenyl]-1-(4-methoxyphenyl)-7-oxo-4,5,6,7-tetrahydro-1H-pyrazolo[3,4-c]pyridine-3-carboxylic acid amide

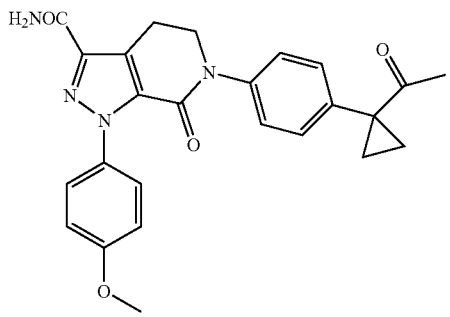

Following a procedure analogous to that used in Example 138, the title compound was prepared. LC/MS (ESI+) 445.6 (M+H).

EXAMPLE 154

6-[4-(1-Aminocyclopropyl)phenyl]-1-(4-methoxyphenyl)-7-oxo-4,5,6,7-tetrahydro-1H-pyrazolo[3,4-c]pyridine-3-carboxylic acid amide, trifluoroacetic acid salt

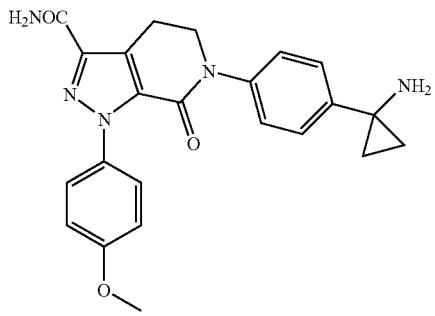

Part A. [1-(4-Iodo-phenyl)-cyclopropyl]-carbamic acid tert-butyl ester (0.34 g, 0.95 mmol) and 1-(4-methoxyphenyl)-7-oxo-4,5,6,7-tetrahydro-1H-pyrazolo[3,4-c]pyridine-3-carboxylic acid ethyl ester (0.30 g, 0.97 mmol) were stirred in DMSO (1 mL). $K_2CO_3$ (0.25 g, 1.81 mmol), CuI (87 mg, 0.46 mmol) and 1,10-phenanthroline (83 mg, 0.46 mmol) were added. The resulting mixture was heated at 120° C. for 2.5 h. After cooling, it was extracted with EtOAc (2×), washed with $H_2O$ and brine, dried over $MgSO_4$, filtered, and concentrated to dryness. The residue was purified by FCC (silica gel, $CH_2Cl_2$:EtOAc=1:1, then EtOAc) to give 6-[4-(1-tert-butoxycarbonylamino-cyclopropyl)-phenyl]-1-(4-methoxy-phenyl)-7-oxo-4,5,6,7-tetrahydro-1H-pyrazolo[3,4-c]pyridine-3-carboxylic acid ethyl ester (0.24 g, yield: 46%).

Part B. The product from Part A underwent the same reaction as used in Part E of Example 67 to yield (1-{4-[3-carbamoyl-1-(4-methoxy-phenyl)-7-oxo-1,4,5,7-tetrahydropyrazolo[3,4-c]pyridin-6-yl]-phenyl}-cyclopropyl)-carbamic acid tert-butyl ester. HRMS $C_{28}H_{32}N_5O_5$ (M+H)+ 518.2388 calcd for 518.2325. $^1H$ NMR ($CDCl_3$) δ 7.47 (d, J=9.2 Hz, 2H), 7.23 (m, 4H), 6.93 (d, J=9.1 Hz, 2H), 6.85 (s, br, 1H), 5.52 (s, br, 1H), 5.26 (s, br, 1H), 4.08 (t, J=6.6 Hz, 2H), 3.81 (s, 3H), 3.36 (t, J=6.6 Hz, 2H), 1.42 (s, br, 9H), 1.24 (m, 2H), 1.18 (m, 2H) ppm.

Part C. The product from Part B (54 mg, 0.104 mmol) was stirred in $CH_2CL_2$ (2 mL) and TFA (1 mL) at rt for 30 min. After evaporation, the residue was purified by reverse phase HPLC to afford the title compound (40 mg, yield: 91.7%). HRMS $C_{23}H_{23}N_5O_3$ (M+H)+ 418.1908 calcd for 418.1879.

EXAMPLE 155

1-(4-Methoxyphenyl)-6-[4-(1-methylaminocyclopropyl)-phenyl]-7-oxo-4,5,6,7-tetrahydro-1H-pyrazolo[3,4-c]pyridine-3-carboxylic acid amide, trifluoroacetic acid salt

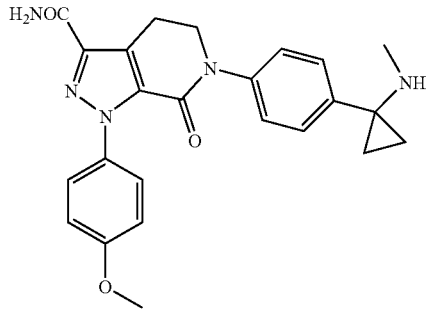

Following a procedure analogous to that used in Example 166, the title compound was prepared. LC/MS (ESI+) 432.6 (M+H)+, $t_R$=1.74 min (10–90% $CH_3CN/H_2O$ in a 4-min run). $^1H$ NMR (acetone-$d_6$) δ 7.65 (d, J=8.5 Hz, 2H), 7.49 (m, 4H), 7.33 (s, br, 1H), 6.97 (d, J=9.2 Hz, 2H), 6.74 (s, br, 1H), 5.69 (s, 1H), 4.15 (t, J=6.6 Hz, 2H), 3.82 (s, 3H), 3.28 (t, J=6.6 Hz, 2H), 2.63 (s, 3H), 1.63 (m, 2H), 1.19 (m, 2H) ppm.

EXAMPLE 156

6-[4-(1-Dimethylaminocyclopropyl)phenyl]-1-(4-methoxyphenyl)-7-oxo-4,5,6,7-tetrahydro-1H-pyrazolo[3,4-c]pyridine-3-carboxylic acid amide, trifluoroacetic acid salt

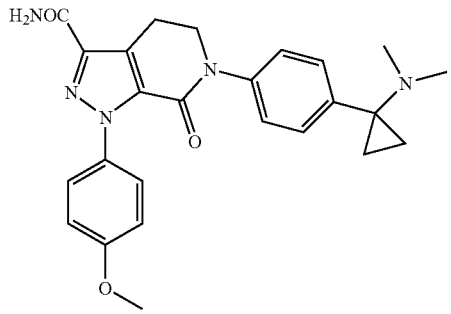

The product of Example 154, HOAc (0.05 mL), and aqueous paraformaldehyde (0.3 mL) were stirred in $CH_3CN$ (1.5 mL) at rt for 15 min. $NaBH_3CN$ (60 mg) was added. The mixture was stirred at rt for 2 h. $H_2O$ was added. The organic solvent was evaporated. The product was purified by RP-prep LC-MS (5–98% $CH_3CN/H_2O$ in a 10-min run). HRMS $C_{25}H_{28}N_5O_3$ (M+H)$^+$ 446.2178 calcd for 446.2193. $^1$H NMR (acetone-d$_6$) δ 7.67 (d, J=8.4 Hz, 2H), 7.51 (AA'BB', J=8.8 Hz, 4H), 6.98 (d, J=9.1 Hz, 2H), 4.17 (t, J=6.6 Hz, 2H), 3.83 (s, 3H), 3.29 (t, J=6.6 Hz, 2H), 2.77 (s, 6H), 1.67 (m, 2H), 1.15 (m, 2H) ppm.

EXAMPLE 157

6-[4-(1-Methylaminomethylcyclopentyl)phenyl]-1-(4-methoxy-phenyl)-7-oxo-4,5,6,7-tetrahydro-1H-pyrazolo[3,4-c]pyridine-3-carboxylic acid amide, trifluoroacetic acid salt

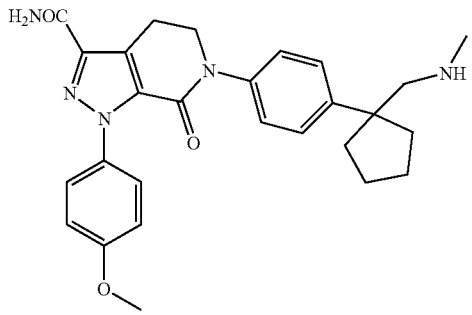

Following an analogous procedures as those used in Examples 27 and 67, the title compound was prepared. HRMS $C_{27}H_{32}N_5O_3$ (M+H)$^+$ 474.2533 calcd for 474.2506.

EXAMPLE 158

6-[4-(1-Dimethylaminomethylcyclopentyl)phenyl]-1-(4-methoxyphenyl)-7-oxo-4,5,6,7-tetrahydro-1H-pyrazolo[3,4-c]pyridine-3-carboxylic acid amide, trifluoroacetic acid salt

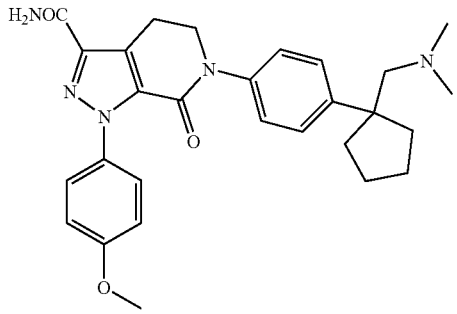

Following an analogous procedures as those used in Examples 28 and 68, the title compound was prepared. LC/MS (ESI$^+$) 488.6 (M+H)$^+$, t$_R$=1.77 min (10–90% $CH_3CN/H_2O$ in a 4-min run).

EXAMPLE 159

6-[4-(1-Dimethylaminomethylcyclopentyl)phenyl]-1-(4-methoxyphenyl)-7-oxo-4,5,6,7-tetrahydro-1H-pyrazolo[3,4-c]pyridine-3-carbonitrile, trifluoroacetic acid salt

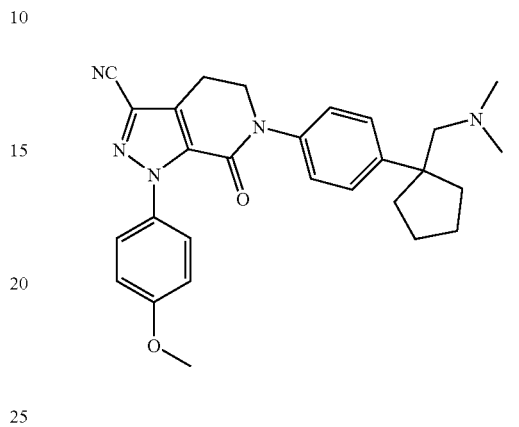

Following an analogous procedures as those used in Examples 28 and 75, the title compound was prepared. HRMS $C_{28}H_{32}N_5O_3$ (M+H)$^+$ 470.2577 calcd for 470.2557.

EXAMPLE 160

6-[4-(1-[(2-Hydroxyethyl)methylaminomethyl]-cyclopentyl)phenyl]-1-(4-methoxy-phenyl)-7-oxo-4,5,6,7-tetrahydro-1H-pyrazolo[3,4-c]pyridine-3-carboxylic acid amide, trifluoroacetic acid salt

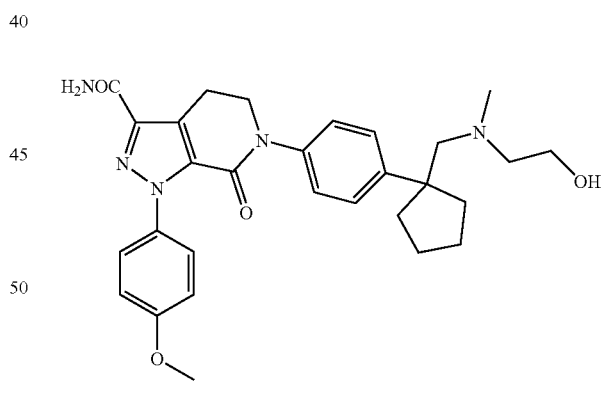

Following a procedure analogous to that used in Example 150 but using the product of Example 157 as the starting material, the title compound was prepared. The product was purified by RP-prep LC-MS (5–98% $CH_3CN/H_2O$ in a 10-min run). LC/MS (ESI$^+$) 518.8 (M+H). $^1$H NMR (acetone-d$_6$) δ 7.56 (d, J=8.8 Hz, 2H), 7.51 (d, J=9.1 Hz, 2H), 7.39 (d, J=8.8 Hz, 2H), 6.97 (d, J=9.2 Hz, 2H), 4.12 (t, J=6.6 Hz, 2H), 3.82 (s, 3H), 3.78 (m, 2H), 3.69 (m, 2H), 3.27 (t, J=6.6 Hz, 2H), 3.15 (t, J=5.0 Hz, 2H), 2.60 (s, 3H), 2.17 (m, 4H), 1.81 (m, 2H), 1.64 (m, 2H) ppm.

EXAMPLE 161

6-[4-(1-Hydroxymethyl-cyclopentyl)-phenyl]-1-(4-methoxy-phenyl)-7-oxo-4,5,6,7-tetrahydro-1H-pyrazolo[3,4-c]pyridine-3-carboxylic acid amide

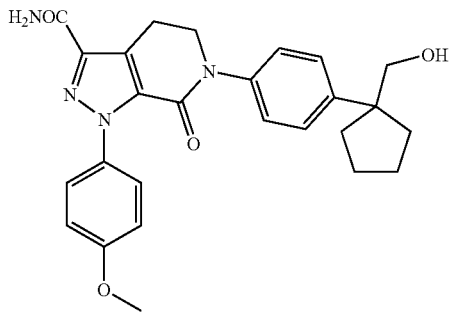

Following a procedure analogous to that used in Example 95, the title compound was prepared. LC/MS (ESI⁺) 461.4.

EXAMPLE 162

6-(4-{1-[(2-Hydroxyethyl)methylamino]cyclopropyl}phenyl)-1-(4-methoxyphenyl)-7-oxo-4,5,6,7-tetrahydro-1H-pyrazolo[3,4-c]pyridine-3-carboxylic acid amide, trifluoroacetic acid salt

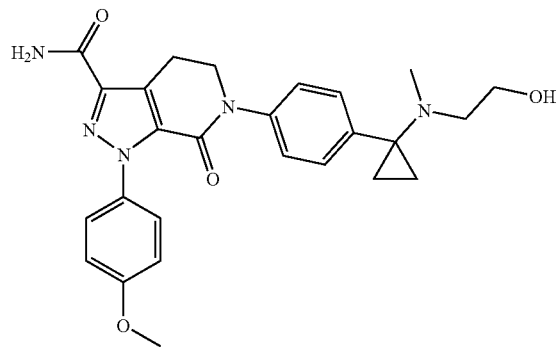

Following a procedure analogous to that used in Example 150 but using the product of Example 155 as the starting material, the title compound was prepared. HRMS $C_{26}H_{30}N_5O_4$ (M+H)⁺ 476.2299 calcd for 476.2319.

EXAMPLE 163

1-(4-Methoxyphenyl)-6-{4-[1-(methyl-prop-2-ynylamino)-cyclopropyl]phenyl}-7-oxo-4,5,6,7-tetrahydro-1H-pyrazolo[3,4-c]pyridine-3-carboxylic acid amide, trifluoroacetic acid salt

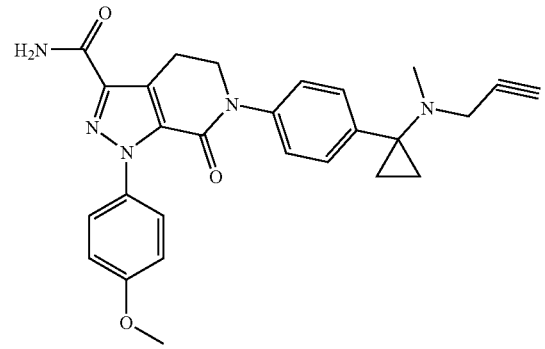

Following a procedure analogous to that used in Example 162 but using 3-bromo-propyne as the starting material instead of 2-bromoethanol, the title compound was prepared. HRMS $C_{27}H_{28}N_5O_3$ (M+H)⁺ 470.2178 calcd for 470.2193.

EXAMPLE 164

3-(1-Hydroxyethyl)-1-(4-methoxyphenyl)-6-[4-(1-methylamino-cyclopropyl)phenyl]-1,4,5,6-tetrahydro-pyrazolo[3,4-c]pyridin-7-one, trifluoroacetic acid salt

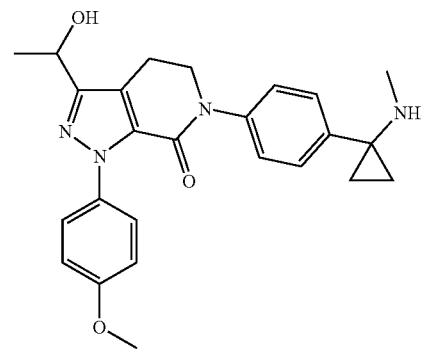

Part A. 6-{4-[1-(tert-Butoxycarbonyl-methyl-amino)-cyclopropyl]-phenyl}-1-(4-methoxy-phenyl)-7-oxo-4,5,6,7-tetrahydro-1H-pyrazolo[3,4-c]pyridine-3-carboxylic acid ethyl ester (0.59 g, 1.79 mmol) was stirred in EtOH (15 mL) and 1N NaOH (3 mL) at rt for 1 h. After evaporation, the mixture was acidified with citric acid. The mixture was extracted with EtOAc (2×), washed with H₂O and brine, dried over MgSO₄, filtered, and concentrated to dryness in vacuo. This acid underwent a series of reactions similar to those used in Part E of Example 1 to afford (1-{4-[3-formyl-1-(4-methoxy-phenyl)-7-oxo-1,4,5,7-tetrahydro-pyrazolo[3,4-c]pyridin-6-yl]-phenyl}-cyclopropyl)-methyl-carbamic acid tert-butyl ester (yield: 99%). LC/MS (ESI⁺) 461.6 (M+H−t-Bu)⁺, $t_R$=1.2.97 min (10–90% CH₃CN/H₂O in a 4-min run).

Part B. The product from Part A (0.38 g, 0.74 mmol) was stirred in CH$_2$Cl$_2$ (6 mL) at −78° C. under N$_2$. ZnMe$_2$ (2M in toluene, 0.74 mL, 1.48 mmol) was added dropwise followed by the addition of TiCl$_4$ (0.16 mL, 1.07 mmol) dropwise. The reaction was stirred at −78° C. for 2 h. Saturated NH$_4$Cl was added. The mixture was extracted with EtOAc, washed with H$_2$O and brine, dried over MgSO$_4$, filtered and concentrated. The residue was purified by FCC (silica gel, CH$_2$Cl$_2$, then 20% EtOAc in CH$_2$Cl$_2$) to yield (1-{4-[3-(1-hydroxy-ethyl)-1-(4-methoxy-phenyl)-7-oxo-1,4,5,7-tetrahydro-pyrazolo[3,4-c]pyridin-6-yl]-phenyl}-cyclopropyl)-methyl-carbamic acid tert-butyl ester (81 mg, yield: 25%). HRMS C$_{26}$H$_{30}$N$_5$O$_4$ (M+H)$^+$ 533.2778 calcd for 533.2765.

Part C. The product from Part B (10 mg) was stirred in CH$_2$Cl$_2$ (1 mL) and TFA (1 mL) at rt for 30 min. After evaporation, the residue was purified by reverse phase HPLC (0–100% CH$_3$CN in H$_2$O) to afford the title compound. HRMS C$_{26}$H$_{30}$N$_5$O$_4$ (M+H)$^+$ 433.2247 calcd for 433.2240. $^1$H NMR (CD$_3$OD) δ 7.59 (d, J=8.4 Hz, 2H), 7.44 (d, J=8.4 Hz, 2H), 7.38 (d, J=8.4 Hz, 2H), 6.94 (d, J=8.4 Hz, 2H), 5.00 (q, J=6.6 Hz, 1H), 4.10 (m, 2H), 3.83 (s, 3H), 3.15 (t, J=6.6 Hz, 2H), 2.58 (s, 3H), 1.56 (d, J=8.4 Hz, 4H), 1.39 (m, 2H), 1.28 (m, 2H) ppm. $^{19}$F NMR (CD$_3$OD) δ −77.49 ppm.

EXAMPLE 165

3-Acetyl-1-(4-methoxyphenyl)-6-[4-(1-methylamino-cyclopropyl)phenyl]-1,4,5,6-tetrahydro-pyrazolo[3,4-c]pyridin-7-one, trifluoroacetic acid salt

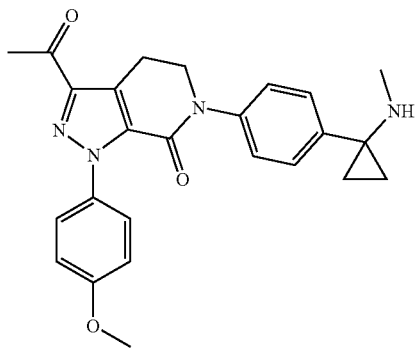

The product from Part B in Example 164 (50 mg, 0.094 mmol), PCC (40 mg, 0.19 mmol), NaOAc (23 mg, 0.28 mmol), and 4 Å MS (50 mg) were stirred in CH$_2$Cl$_2$ (1 mL) for 4 h. The mixture was filtered through Celite®, washed with H$_2$O (2×), dried over MgSO$_4$, filtered and concentrated to dryness. The residue was dissolved in CH$_2$Cl$_2$ (4 mL) and TFA (2 mL) at rt for 30 min. After evaporation, the residue was purified by reverse phase HPLC (0–100% CH$_3$CN in H$_2$O) to afford the title compound. $^1$H NMR (CD$_3$OD) δ 7.59 (d, J=8.1 Hz, 2H), 7.46 (m, 4H), 6.98 (d, J=9.1 Hz, 2H), 4.11 (t, J=6.6 Hz, 2H), 3.82 (m, 5H), 3.29 (m, 2H), 2.59 (m, 3H), 1.39 (m, 2H), 1.28 (m, 2H) ppm. $^{19}$F NMR (CD$_3$OD) δ −77.51 ppm. HRMS C$_{25}$H$_{27}$N$_4$O$_3$ (M+H)$^+$ 431.2102 calcd for 431.2084.

EXAMPLE 166

1-(4-Methoxyphenyl)-6-[4-(1-methylaminocyclopropyl)phenyl]-7-oxo-4,5,6,7-tetrahydro-1H-pyrazolo[3,4-c]pyridine-3-carboxylic acid methylamide, trifluoroacetic acid salt

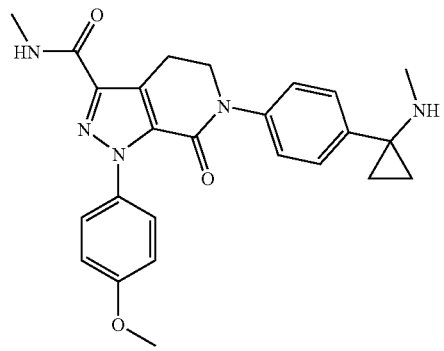

The product from Part A in Example 164 (0.21 g, 0.44 mmol) was stirred in CH$_2$Cl$_2$ (5 mL) at 0° C. (COCl)$_2$ (0.1 mL) was added followed by the addition of 1 drop of DMF. The mixture was stirred at 0° C. for 40 min. The solvents were evaporated in vacuo. Half of the residue was dissolved in CH$_2$Cl$_2$ (1 mL) and MeNH$_2$ (2 M in THF, 0.5 mL) was added. The mixture was stirred at rt for 4 h. The solvents were evaporated. The residue was dissolved in CH$_2$Cl$_2$ (15 mL) and TFA (2 mL). The mixture was stirred at rt for 1 h. The solvents were evaporated. The residue was purified by reverse phase HPLC (0–100% CH$_3$CN in H$_2$O with 0.5% TFA) and lyophilized to dryness. HRMS C$_{25}$H$_{28}$N$_5$O$_3$ (M+H)$^+$ 446.2177 calcd for 446.2193. $^1$H NMR (CD$_3$OD) δ 7.59 (d, J=9.1 Hz, 2H), 7.47 (m, 4H), 6.96 (d, J=9.1 Hz, 2H), 4.17 (t, J=6.6 Hz, 2H), 3.82 (m, 5H), 3.29 (m, 2H), 3.17 (m, 2H), 2.92 (m, 3H), 1.61 (m, 2H), 1.34 (m, 2H) ppm.

EXAMPLE 167

1-(4-Methoxyphenyl)-6-[4-(1-methylaminocyclopropyl)phenyl]-7-oxo-4,5,6,7-tetrahydro-1H-pyrazolo[3,4-c]pyridine-3-carboxylic acid dimethylamide, trifluoroacetic acid salt

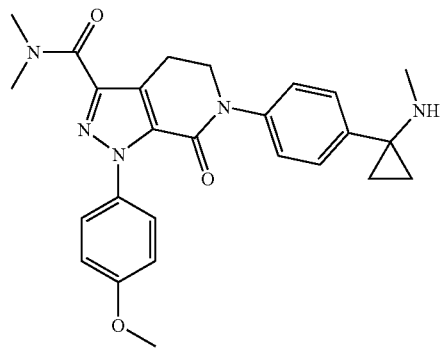

Following a procedure analogous to that used in Example 166 but using dimethylamine as the starting material, the title compound was prepared. The product was purified by reverse phase HPLC (0–100% CH$_3$CN in H$_2$O with 0.5% TFA) and lyophilized to dryness. HRMS C$_{26}$H$_{30}$O$_3$N$_5$ (M+H)$^+$ 460.2319 calcd for 460.2349. $^1$H NMR (CD$_3$OD) δ 7.59 (m, 2H), 7.45 (m, 4H), 6.96 (m, 2H), 4.11 (t, J=6.6 Hz, 2H), 3.37 (s, 3H), 3.17 (t, J=6.6 Hz, 2H), 3.12 (s, 3H), 2.59 (s, 3H), 1.39 (m, 2H), 1.29 (m, 2H) ppm. $^{19}$F NMR (CD$_3$OD) δ −77.56 ppm.

EXAMPLE 168

6-[4-(1-Aminocyclopropyl)phenyl]-1-(4-methoxyphenyl)-7-oxo-4,5,6,7-tetrahydro-1H-pyrazolo[3,4-c]pyridine-3-carbonitrile, trifluoroacetic acid salt

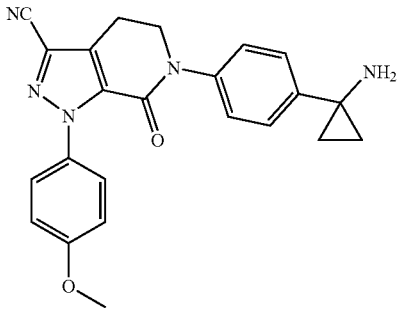

Following a procedure analogous to that used in Example 74 but using the product of Example 154 as the starting material, the title compound was prepared. The product was purified by reverse phase HPLC (0–100% CH$_3$CN in H$_2$O with 0.5% TFA) and lyophilized to dryness. LC/MS(ESI$^+$) 400.4 (M+H)$^+$. $^1$H NMR (acetone-d$_6$) δ 7.52 (d, J=9.1 Hz, 2H), 7.41 (AA'BB', J=8.0 Hz, 4H), 6.98 (d, J=9.1 Hz, 2H), 4.19 (t, J=6.6 Hz, 2H), 3.83 (s, 3H), 3.20 (t, J=6.6 Hz, 2H), 1.69 (m, 2H), 1.51 (m, 2H) ppm.

EXAMPLE 169

1-(4-Methoxyphenyl)-6-[4-(1-methylaminocyclopropyl)phenyl]-7-oxo-4,5,6,7-tetrahydro-1H-pyrazolo[3,4-c]pyridine-3-carbonitrile, trifluoroacetic acid salt

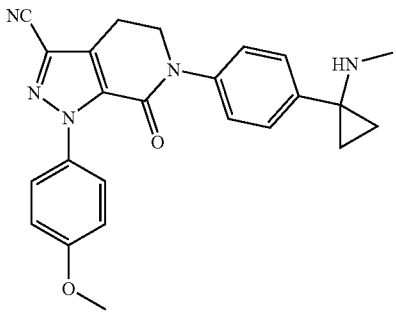

Following a procedure analogous to that used in Example 74 but using the product of Example 155 as the starting material, the title compound was prepared. HRMS C$_{24}$H$_{24}$O$_2$N$_5$ (M+H)$^+$ 414.1900 calcd for 414.1931. $^1$H NMR (acetone-d$_6$) δ 7.68 (d, J=8.4 Hz, 2H), 7.49 (AA'BB', J=9.2 Hz, 4H), 6.98 (d, J=9.1 Hz, 2H), 4.23 (t, J=6.6 Hz, 2H), 3.83 (s, 3H), 3.19 (t, J=6.2 Hz, 2H), 2.62 (s, 3H), 1.64 (t, J=6.6 Hz, 2H), 1.19 (t, J=6.5 Hz, 2H) ppm.

EXAMPLE 170

6-[4-(1-Dimethylaminocyclopropyl)phenyl]-1-(4-methoxyphenyl)-7-oxo-4,5,6,7-tetrahydro-1H-pyrazolo[3,4-c]pyridine-3-carbonitrile, trifluoroacetic acid salt

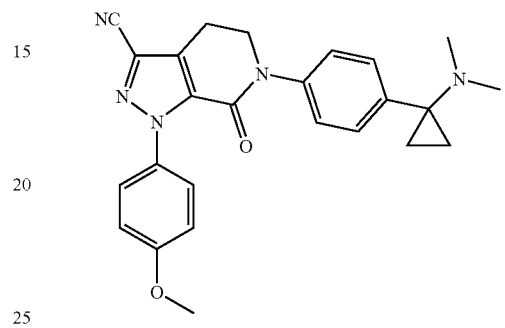

Following a procedure analogous to that used in Example 67 but using the product of Example 156 as the starting material, the title compound was prepared. HRMS C$_{25}$H$_{26}$O$_2$N$_5$ (M+H)$^+$ 428.2104 calcd for 428.2087. $^1$H NMR (acetone-d$_6$) δ 7.70 (d, J=8.4 Hz, 2H), 7.55 (AA'BB', J=9.2 Hz, 4H), 7.00 (d, J=9.1 Hz, 2H), 4.26 (t, J=6.6 Hz, 2H), 3.83 (s, 3H), 3.22 (t, J=6.2 Hz, 2H), 2.79 (s, 6H), 1.70 (t, J=6.1 Hz, 2H), 1.17 (t, J=6.1 Hz, 2H) ppm.

EXAMPLE 171

2-[(1-{4-[3-Cyano-1-(4-methoxyphenyl)-7-oxo-1,4,5,7-tetrahydro-pyrazolo[3,4-c]pyridin-6-yl]phenyl}cyclopropyl)-methylamino]acetamide, trifluoroacetic acid salt

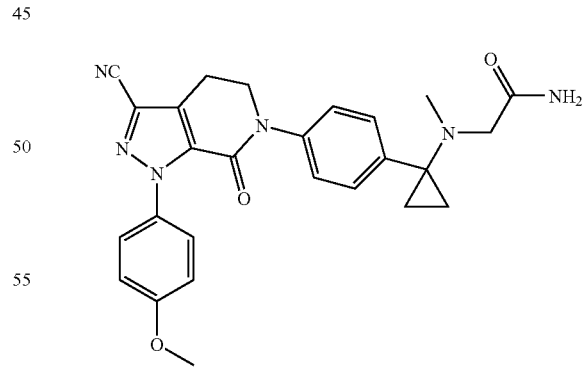

Following a procedure analogous to that used in Example 162 but using the product of Example 169 as the starting material, the title compound was prepared. The product was purified by reverse phase HPLC (0–100% CH$_3$CN in H$_2$O with 0.5% TFA) and lyophilized to dryness. LC/MS (ESI) 471.6 (M+H), t$_R$=2.14 min (10–90% CH$_3$CN in H$_2$O in a 4-min run).

EXAMPLE 172

6-(4-{1-[(2-Hydroxyethyl)methylamino]cyclopropyl}phenyl)-1-(4-methoxyphenyl)-7-oxo-4,5,6,7-tetrahydro-1H-pyrazolo[3,4-c]pyridine-3-carbonitrile, trifluoroacetic acid salt

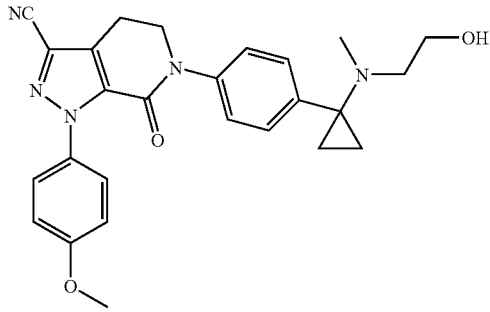

Following a procedure analogous to that used in Example 162 but using the product of Example 169 and 2-bromoethanol as the starting materials, the title compound was prepared. The product was purified by reverse phase HPLC (0–100% $CH_3CN$ in $H_2O$ with 0.5% TFA) and lyophilized to dryness. HRMS $C_{26}H_{28}N_5O_3$ $(M+H)^+$ 458.2196 calcd for 458.2193. $^1$H NMR ($CD_3OD$) δ 7.68 (m, 2H), 7.46 (m, 4H), 6.98 (m, 2H), 4.17 (t, J=6.6 Hz, 2H), 3.82 (m, 5H), 3.29 (m, 2H), 3.17 (m, 2H), 2.92 (m, 3H), 1.61 (m, 2H), 1.34 (m, 2H) ppm. $^{19}$F NMR ($CD_3OD$) δ −77.56 ppm.

EXAMPLE 173

1-(4-Methoxyphenyl)-7-oxo-6-[4-(1-pyrrolidin-1-yl-cyclopropyl)phenyl]-4,5,6,7-tetrahydro-1H-pyrazolo[3,4-c]pyridine-3-carboxylic acid ethyl ester, trifluoroacetic acid salt

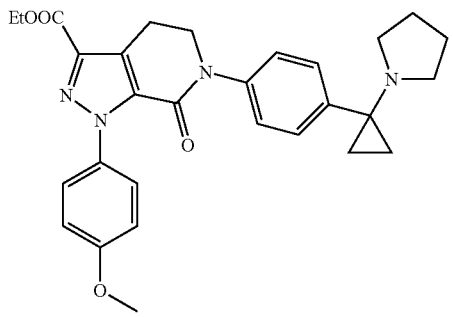

6-[4-(1-Amino-cyclopropyl)-phenyl]-1-(4-methoxy-phenyl)-7-oxo-4,5,6,7-tetrahydro-1H-pyrazolo[3,4-c]pyridine-3-carboxylic acid ethyl ester (95 mg, 0.21 mmol), 1,3-dibromo-propane (0.03 mL, excess), and $K_2CO_3$ (100 mg, excess) were heated in DMF at 80° C. for 24 h. EtOAc was added. The mixture was washed with $H_2O$ and brine, dried over $MgSO_4$, filtered, and concentrated. The residue was purified by FCC (Silica gel, EtOAc, then 15% MeOH in EtOAc) to yield the title compound (89 mg, yield: 83.5%). HRMS $C_{29}H_{33}O_4N_4$ $(M+H)^+$ 501.2489 calcd for 501.2503. $^1$H NMR ($CDCl_3$) δ 7.47 (d, J=8.8 Hz, 2H), 7.27 (AA′BB′, J=8.8 Hz, 4H), 6.90 (d, J=8.9 Hz, 2H), 4.45 (q, J=7.1 Hz, 2H), 4.12 (t, J=6.6 Hz, 2H), 3.80 (s, 3H), 3.31 (t, J=6.6 Hz, 2H), 2.52 (m, 4H), 1.61 (m, 4H), 1.43 (t, J=7.1 Hz, 2H), 0.97 (m, 2H), 0.77 (m, 2H) ppm.

EXAMPLE 174

1-(4-Methoxyphenyl)-7-oxo-6-[4-(1-pyrrolidin-1-yl-cyclopropyl)phenyl]-4,5,6,7-tetrahydro-1H-pyrazolo[3,4-c]pyridine-3-carboxylic acid amide, trifluoroacetic acid salt

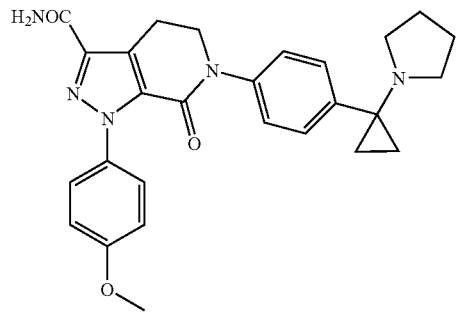

Following a procedure analogous to that used in Example 67 but using the product of Example 173 as the starting material, the title compound was prepared. The product was purified by flash chromatography (silica gel, EtOAc, then 15% MeOH in EtOAc). LC/MS(ESI$^+$) 472.6 $(M+H)^+$, $t_R$=2.02 min (10–90% $CH_3CN$ in $H_2O$ in a 4-min run). $^1$H NMR ($CDCl_3$) δ 7.39 (d, J=8.8 Hz, 2H), 7.21 (AA′BB′, J=8.8 Hz), 6.86 (d, J=9.1 Hz, 2H), 4.04 (t, J=6.9 Hz, 2H), 3.74 (s, 3H), 3.30 (t, J=6.6 Hz, 2H), 2.47 (m, 4H), 1.54 (m, 4H), 0.93 (m, 2H), 0.71 (m, 2H) ppm.

EXAMPLE 175

1-(4-Methoxyphenyl)-7-oxo-6-[4-(1-pyrrolidin-1-yl-cyclopropyl)phenyl]-4,5,6,7-tetrahydro-1H-pyrazolo[3,4-c]pyridine-3-carbonitrile, trifluoroacetic acid salt

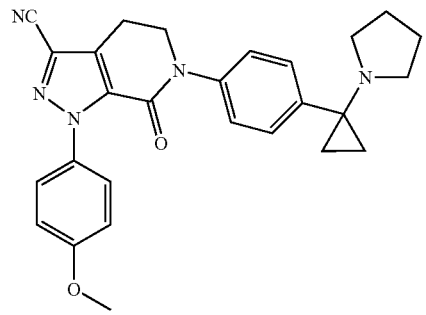

Following a procedure analogous to that used in Example 74 but using the product of Example 174 as the starting material, the title compound was prepared. The product was purified by flash chromatography (silica gel, EtOAc, then 15% MeOH in EtOAc). LC/MS(ESI$^+$) 454.6 $(M+H)^+$, $t_R$=2.27 min (10–90% $CH_3CN$ in $H_2O$ in a 4-min run). $^1$H NMR ($CDCl_3$) δ 7.39 (d, J=8.4 Hz, 2H), 7.28 (d, J=8.4 Hz, 2H), 7.20 (d, J=8.5 Hz), 6.86 (d, J=9.2 Hz, 2H), 4.09 (t, J=6.6 Hz, 2H), 3.75 (s, 3H), 3.10 (t, J=6.6 Hz, 2H), 2.63 (m, 4H), 1.62 (m, 4H), 1.17 (m, 2H), 0.78 (m, 2H) ppm.

EXAMPLE 176

1-(4-Methoxyphenyl)-6-[4-(1-morpholin-4-yl-cyclopropyl)phenyl]-7-oxo-4,5,6,7-tetrahydro-1H-pyrazolo[3,4-c]pyridine-3-carboxylic acid amide, trifluoroacetic acid salt

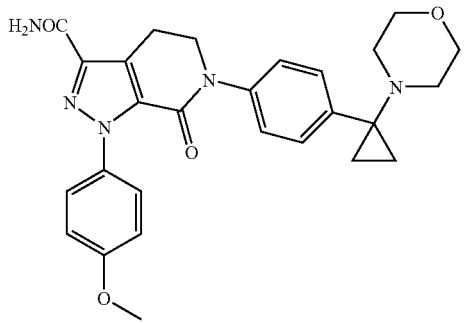

The product of Example 153 (45 mg, 0.108 mmol) and 1-bromo-2-(2-bromo-ethoxy)-ethane (0.25 mL), Et$_3$N (0.25 mL) were heated in DMF (1 mL) at 65° C. for 3 h under N$_2$. The mixture was evaporated, and the residue was purified by reverse phase HPLC (0–100% CH$_3$CN in H$_2$O with 0.5% TFA), and lyophilized to dryness. LC/MS(ESI$^+$) 488.6 (M+H)$^+$, t$_R$=1.97 min (10–90% CH$_3$CN in H$_2$O in a 4-min run). $^1$H NMR (acetone-d$_6$) δ 7.51 (d, J=9.2 Hz, 2H), 7.49 (m, 4H), 6.97 (d, J=8.8 Hz, 2H), 4.12 (t, J=6.6 Hz, 2H), 3.83 (s, 3H), 3.27 (m, 4H), 3.29 (t, J=6.6 Hz, 2H), 2.63 (m, 4H), 1.08 (m, 2H), 0.83 (m, 2H) ppm.

EXAMPLE 177

1-(4-Methoxyphenyl)-6-[4-(1-morpholin-4-yl-cyclopropyl)phenyl]-7-oxo-4,5,6,7-tetrahydro-1H-pyrazolo[3,4-c]pyridine-3-carbonitrile, trifluoroacetic acid salt

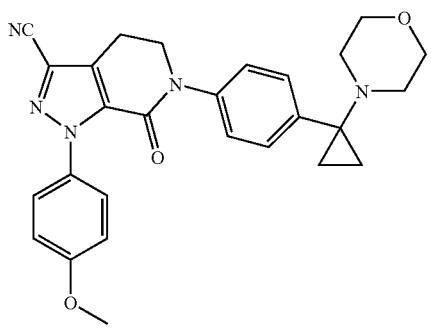

Following a procedure analogous to that used in Example 175 but using the product of Example 168 as the starting material, the title compound was prepared. The product was purified by flash chromatography (silica gel, EtOAc, then 10% MeOH in EtOAc). LC/MS(ESI$^+$) 470.6 (M+H)$^+$. $^1$H NMR (CDCl$_3$) δ 7.46 (d, J=9.2 Hz, 2H), 7.26 (m, 4H), 6.93 (d, J=9.2 Hz, 2H), 4.16 (t, J=6.6 Hz, 2H), 3.82 (s, 3H), 3.75 (m, 2H), 3.65 (m, 4H), 3.50 (t, J=6.3 Hz, 2H), 3.18 (t, J=6.6 Hz, 2H), 0.94 (m, 2H), 0.79 (m, 2H) ppm.

EXAMPLE 178

6-[4-(1-Dimethylaminocyclopropyl)phenyl]-1-(4-methoxyphenyl)-7-oxo-4,5,6,7-tetrahydro-1H-pyrazolo[3,4-c]pyridine-3-carboxylic acid methylamide, trifluoroacetic acid salt

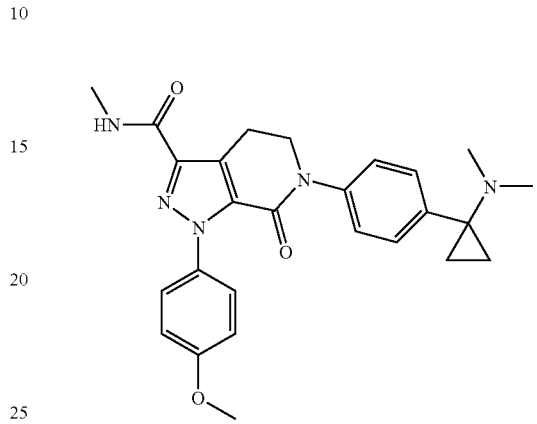

The product was purified by flash chromatography (silica gel, EtOAc, then 10% MeOH in EtOAc. HRMS C$_{26}$H$_{30}$N$_5$O$_3$ (M+H)$^+$ 460.2319 calcd for 460.2349. $^1$H NMR (acetone-d$_6$) δ 7.49 (d, J=9.1 Hz, 2H), 7.30 (m, 4H), 6.95 (d, J=8.8 Hz, 2H), 4.11 (t, J=6.6 Hz, 2H), 3.82 (s, 3H), 3.28 (t, J=6.6 Hz, 2H), 2.90 (d, J=4.7 Hz 3H), 2.15 (s, 6H), 0.83 (m, 2H), 0.73 (m, 2H) ppm.

EXAMPLE 179

6-[4-(1-Dimethylaminocyclopropyl)phenyl]-1-(4-methoxyphenyl)-7-oxo-4,5,6,7-tetrahydro-1H-pyrazolo[3,4-c]pyridine-3-carboxylic acid dimethylamide, trifluoroacetic acid salt

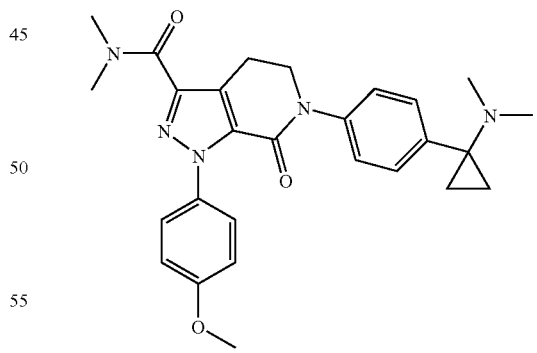

Following a procedure analogous to that used in Example 166, the title compound was prepared. The product was purified by flash chromatography (silica gel, EtOAc, then 10% MeOH in EtOAc). LC/MS(ESI$^+$) 474.6 (M+H)$^+$, t$_R$=6.08 min (10–90% CH$_3$CN in H$_2$O in a 4-min run). $^1$H NMR (acetone-d$_6$) δ 7.50 (d, J=8.8 Hz, 2H), 7.32 (m, 4H), 6.95 (d, J=9.1 Hz, 2H), 4.10 (t, J=6.6 Hz, 2H), 3.82 (s, 3H), 3.38 (s, 3H), 3.18 (t, J=6.6 Hz, 2H), 3.04 (s, 3H), 2.19 (s, 6H), 0.87 (m, 2H), 0.75 (m, 2H) ppm.

EXAMPLE 180

6-{4-[1-(1,1-Dioxo-1λ⁶-thiomorpholin-4-yl)cyclopropyl]phenyl}-1-(4-methoxyphenyl)-7-oxo-4,5,6,7-tetrahydro-1H-pyrazolo[3,4-c]pyridine-3-carboxylic acid amide, trifluoroacetic acid salt

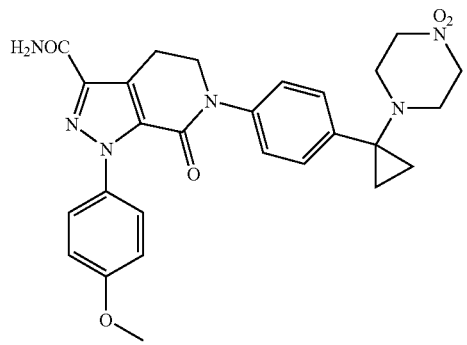

The product from Example 153 (90 mg, 0.22 mmol) was stirred in MeOH (1 mL) in a Pyrex® tube. Vinyl sulfone (0.1 mL) was added followed by the addition of Et₃N (0.2 mL). The tube was capped. The mixture was stirred at rt for 1 h, and heated at 40–50° C. for 1.5 h. After cooling, the solvents were evaporated. The residue was purified by reverse phase HPLC (0–100% CH₃CN in H₂O) and lyophilized to afford the desired product. LC/MS ESI 536.4 (M+H), $t_R$=2.49 (10–90% CH₃CN in H₂O in a 4-min run).

EXAMPLE 181

6-[4-(1-Aminocyclopropylmethyl)phenyl]-1-(4-methoxyphenyl)-7-oxo-4,5,6,7-tetrahydro-1H-pyrazolo[3,4-c]pyridine-3-carboxylic acid amide, trifluoroacetic acid salt

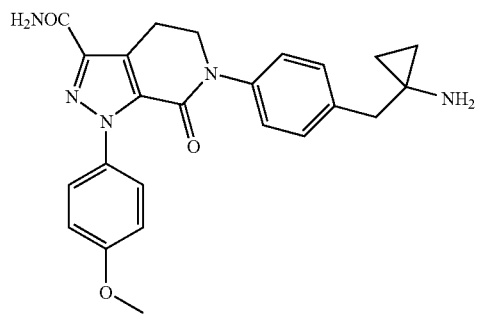

Part A. 4-Iodophenylacetonitrile (0.90 g, 3.70 mmol) was stirred in Et₂O (7 mL) at rt under N₂. Ti(O-iPr)₄ (1.20 ml, 1.1 eq) was added followed by dropwise addition of EtMgBr (2.0 M in Et₂O, 2.5 mL, 2.0 eq) at rt. The reaction mixture was stirred at rt for 0.5 h. BF₃.Et₂O (0.94 ml, 2.0 eq) was added dropwise within 2 mins. The mixture was stirred at rt for 20 min. LC/MS showed one peak corresponding to the desired product. 1N NaOH (ca. 3 mL) was added. It was extracted with Et₂O (2×), washed with H₂O, dried over MgSO₄, filtered, and concentrated to dryness to give 1-(4-iodo-benzyl)-cyclopropylamine (0.60 g, yield: 60%). LC/MS (ESI⁺) 274.2 (M+H), $t_R$=1.61 min (10–90% CH₃CN in H₂O in a 4-min run).

Part B. The product from Part A (0.60 g, 2.2 mmol) was stirred in CH₂Cl₂ (8 mL) at rt under N₂. (BoC)₂O (0.57 g, 1.2 eq) was added followed by the addition of DIEA (0.61 mL, 1.5 eq). The mixture was stirred at rt for 3 h. H₂O was added, the mixture was extracted with EtOAc (2×), washed with H₂O and brine, dried over MgSO₄, and concentrated to dryness to yield [1-(4-iodo-benzyl)-cyclopropyl]-carbamic acid tert-butyl ester (0.61 g, 75%). LC/MS (ESI⁺) 318.0 (M–(t-Bu)+H), $t_R$=2.84 min (10–90% CH₃CN in H₂O in a 4-min run).

Part C. The product of Part B (0.18 g, 0.48 mmol) and 1-(4-methoxy-phenyl)-7-oxo-3a,4,5,6,7,7a-hexahydro-1H-pyrazolo[3,4-c]pyridine-3-carboxylic acid ethyl ester (0.15 g, 0.47 mmol) were stirred in DMSO (1.5 mL) under N₂. K₂CO₃ (0.13 g, 1.0 mmol, 2.1 eq) was added, followed by the addition of CuI (0.050 g, 0.26 mmol) and 1,10-phenanthroline (0.048 g, 0.26 mmol). The mixture was heated at 120° C. for 3 h. After cooling, it was extracted with EtOAc (2×), washed with H₂O and brine, dried over MgSO₄, filtered, and concentrated to dryness. The residue was purified by FCC (silica gel, CH₂Cl₂:EtOAc=1:1, then EtOAc) to give 6-[4-(1-tert-butoxycarbonylamino-cyclopropylmethyl)-phenyl]-1-(4-methoxy-phenyl)-7-oxo-3a,4,5,6,7,7a-hexahydro-1H-pyrazolo[3,4-c]pyridine-3-carboxylic acid ethyl ester (0.11 g, yield: 45%). LC/MS (ESI⁺) 505.2 (M+H–t-Bu), $t_R$=2.75 min (35–98% CH₃CN in H₂O in a 6-min run).

Part D. The product from Part C (90 mg, 0.16 mmol) was stirred in saturated NH₃ in ethylene glycol at 80° C. in a Pyrex® tube for 4 h. The cooled mixture was diluted with H₂O, and extracted with EtOAc (2×). The organics were rinsed with H₂O and brine, dried over MgSO₄, filtered, and concentrated to dryness. The residue was dissolved in CH₂Cl₂ (5 mL), and TFA (3 mL) was added. The mixture was stirred at rt for 20 min. The solvent was evaporated, and the residue was purified by reverse phase HPLC (0–100% CH₃CN in H₂O) to afford pure title compound (45 mg, yield: 65.2%). ¹H NMR (CDCl₃) δ 7.47 (d, J=8.8 Hz, 2H), 7.21 (AA'BB', J=8.4 Hz, 4H), 6.93 (d, J=9.2 Hz, 2H), 4.10 (t, J=6.6 Hz, 2H), 3.82 (s, 3H), 3.37 (t, J=6.6 Hz, 2H), 2.82 (s, br, 2H), 0.75 (s, 4H) ppm. LC/MS (ESI⁺) 432.6 (M+H), $t_R$=0.36 min (35–98% CH₃CN in H₂O in a 6-min run).

EXAMPLE 182

6-[4-(1-Dimethylaminocyclopropylmethyl)phenyl]-1-(4-methoxyphenyl)-7-oxo-4,5,6,7-tetrahydro-1H-pyrazolo[3,4-c]pyridine-3-carboxylic acid amide, trifluoroacetic acid salt

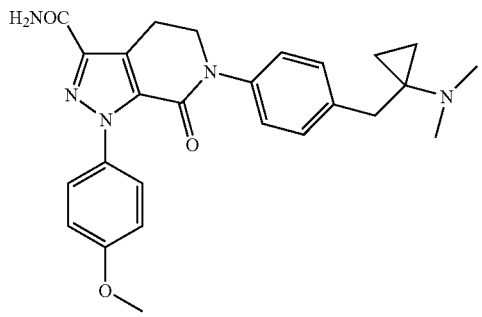

Following the same procedure as shown in Example 155, the title compound was prepared. LC/MS(ESI⁺) 460.6 (M+H)⁺, $t_R$=2.14 min (10–90% CH$_3$CN in H$_2$O in a 4-min run).

EXAMPLE 183

5-Chloro-thiophene-2-carboxylic acid {1-[4-(1-pyrrolidin-1-ylmethyl-cyclopropyl)-benzoyl]-pyrrolidin-3-yl}-amide, trifluoroacetic acid salt

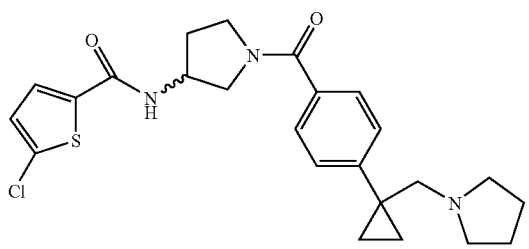

Part A. 1-(4-Chlorocarbonyl-phenyl)-cyclopropanecarboxylic acid methyl ester (0.78 g, 3.28 mmol), pyrrolidin-3-yl-carbamic acid tert-butyl ester (0.60 g, 3.22 mmol) and DIEA (1.18 mL, 6.44 mmol) were stirred in CH$_2$Cl$_2$ (10 mL) at rt under N$_2$ overnight. H$_2$O was added. The mixture was extracted with EtOAc, washed with brine, dried over MgSO$_4$, filtered, dried in vacuo. The residue was dissolved in MeOH (20 mL) and 1N NaOH (10 mL) was added. The reaction was heated at 50° C. for 2.5 h. The solvents were evaporated. The residue was extracted with Et$_2$O, the H$_2$O layer was acidified with citric acid, and extracted with Et$_2$O (2×), washed with brine, dried over MgSO$_4$, filtered, and concentrated to dryness to yield 1-[4-(3-tert-butoxycarbonylamino-pyrrolidine-1-carbonyl)-phenyl]-cyclopropanecarboxylic acid methyl ester (1.08 g, yield: 83.0%).

Part B. The product from Part A was treated with an analogous sequence as used in Part E and Part F of Example 1 but using pyrrolidine as the starting material and {1-[4-(1-pyrrolidin-1-ylmethyl-cyclopropyl)-benzoyl]-pyrrolidin-3-yl}-carbamic acid tert-butyl ester was obtained.

Part C. The product from Part B was stirred in CH$_2$Cl$_2$ (20 mL) and TFA (10 mL) at rt for 1 h. The solvents were evaporated to dryness. Part of the amine (ca. 20 mg) was dissolved in DMF (0.5 mL). 5-Chloro-thiophenecarbocyclic acid (10 mg) was added followed by the addition of HATU (30 mg) and DIEA (0.03 mL). The reaction was stirred at rt overnight. It was purified via preparative LC/MS (5–98% CH$_3$CN in H$_2$O) to afford the desired title compound (12.1 mg, yield: 43.5%). LC/MS(ESI⁺) 458.6 (M+H), $t_R$=2.42 min (10–90% CH$_3$CN in H$_2$O in a 4-min run).

EXAMPLE 184

5-Chloro-thiophene-2-carboxylic acid {1-[4-(1-dimethylaminomethyl-cyclopropyl)-benzoyl]-pyrrolidin-3-yl}-amide, trifluoroacetic acid salt

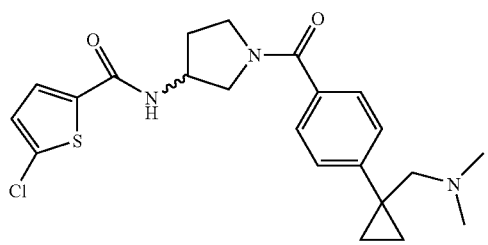

Following a procedure analogous to that used in Example 183, the title compound was prepared. LC/MS(ESI⁺) 405.2 (M+H), $t_R$=2.61 min (10–90% CH$_3$CN in H$_2$O in a 4-min run).

EXAMPLE 185

3-Chloro-1H-indole-6-carboxylic acid {1-[4-(1-pyrrolidin-1-ylmethyl-cyclopropyl)-benzoyl]-pyrrolidin-3-yl}-amide, trifluoroacetic acid salt

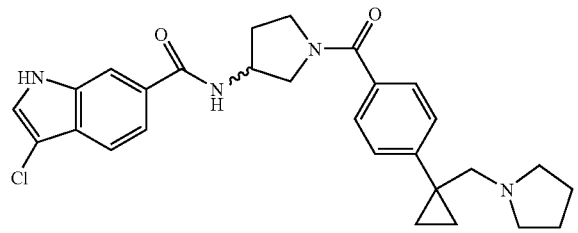

Following a procedure analogous to that used in Example 183, the title compound was prepared. LC/MS (ESI⁺) 491.4 (M+H).

EXAMPLE 186

3-Chloro-1H-indole-6-carboxylic acid {1-[4-(1-dimethylaminomethyl-cyclopropyl)-benzoyl]-pyrrolidin-3-yl}-amide, trifluoroacetic acid salt

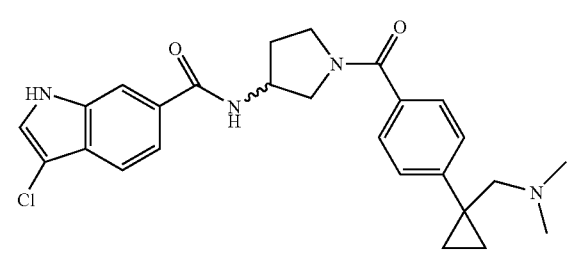

Following a procedure analogous to that used in Example 183, the title compound was prepared. LC/MS (ESI⁺) 465.4 (M+H).

EXAMPLE 187

3-Chloro-1H-indole-6-carboxylic acid {2-[4-(1-pyrrolidin-1-ylmethyl-cyclopropyl)-benzoylamino]-cyclohexyl}-amide, trifluoroacetic acid salt

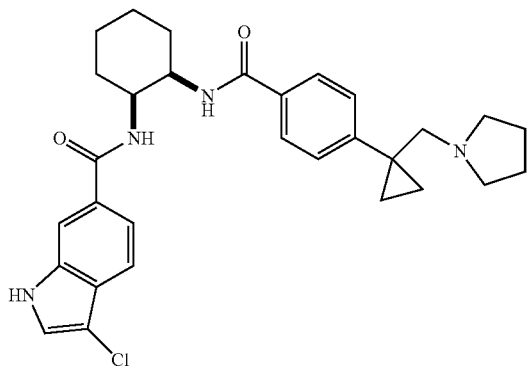

Part A. 1-(4-Chlorocarbonyl-phenyl)-cyclopropanecarboxylic acid methyl ester (0.66 g, 2.77 mmol) was stirred in $CH_2Cl_2$ (10 mL) at rt under $N_2$. 1,2-Cis-diamino-cyclohexane (0.66 mL, 2.0 eq) was added as one portion. The mixture was stirred for 10 min. Diluted HCl was added. The mixture was extracted with EtOAc (2×). The aqueous layer was basified with conc. NaOH, extracted with EtOAc (2×). The organic layers were washed with $H_2O$ and brine, dried over $MgSO_4$, filtered, and concentrated to afford 1-[4-(2-amino-cyclohexylcarbamoyl)-phenyl]-cyclopropanecarboxylic acid methyl ester (0.35 g, yield: 39.8%). LC/MS (ESI$^+$) 317.4 (M+H).

Part B. The product from Part A (0.15 g, 0.47 mmol) was stirred in DMF (1 mL) at rt. 3-Chloro-1H-indole-6-carboxylic acid (0.28 g, 1.36 mmol, 2.9 eq) and HATU (0.36 g, 0.95 mmol, 2.0 eq) were added followed by the addition of DIEA (0.30 mL, 1.71 mmol, 3.6 eq). The mixture was stirred at rt overnight. $H_2O$ was added. The mixture was extracted with EtOAc (2×). The organic layers were washed with brine, dried over $MgSO_4$, and concentrated to dryness to afford 1-(4-{2-[(3-chloro-1H-indole-6-carbonyl)-amino]-cyclohexylcarbamoyl}-phenyl)-cyclopropanecarboxylic acid methyl ester (0.20 g, yield: 85.7%). LC/MS(ESI$^+$) 494.6 (M+H), $t_R$=3.22 min (35–95% $CH_3CN$ in $H_2O$ in a 6-min run).

Part C. The product from Part B was subjected to an analogous sequence as used in Part E and Part F of Example 1 but using pyrrolidine as the starting material to afford 3-chloro-6-{2-[4-(1-pyrrolidin-1-ylmethyl-cyclopropyl)-benzoylamino]-cyclohexylcarbamoyl}-indole-1-carboxylic acid ethyl ester. LC/MS(ESI$^+$) 591.6 (M+H).

Part D. The product from Part C was suspended in 4N HCl (20 mL) and heated at 50° C. for 1 h. The solvent was evaporated. The residue was purified by reverse phase HPLC (0–100% $CH_3CN$ in $H_2O$) to afford the title compound (32 mg, yield: 33% for Part C and Part D). LC/MS (ESI$^+$) 519.4 (M+H), $t_R$=1.85 min (10–90% $CH_3CN$ in $H_2O$ in a 6-min run).

EXAMPLE 188

5-Chloro-thiophene-2-carboxylic acid {2-[4-(1-pyrrolidin-1-ylmethyl-cyclopropyl)-benzoylamino]-cyclohexyl}-amide, trifluoroacetic acid salt

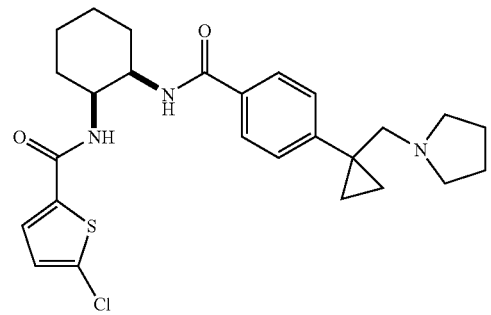

Following a procedure analogous to that used in Example 187, the title compound was prepared. LC/MS (ESI$^+$) 466.4 (M+H).

EXAMPLE 189

1-(3-Chloro-phenyl)-6-{4-[1,1-dimethyl-2-(2-oxo-pyrrolidin-1-yl)-ethyl]-phenyl}-7-oxo-4,5,6,7-tetrahydro-1H-pyrazolo[3,4-c]pyridine-3-carboxylic acid amide

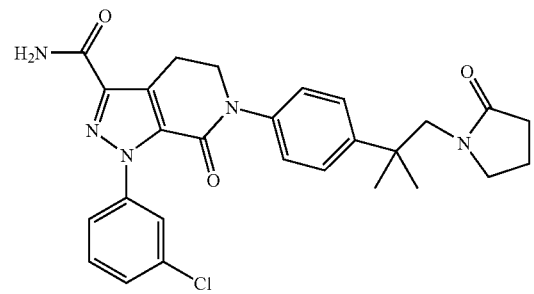

Part A. To crude 2-(4-iodo-phenyl)-2-methyl-propionitrile (see Example 96) (1.5 g, 5.5 mmol) in THF (25 mL) at 0° C. was added 1M Borane in THF (6 mL, 6 mmol) and the reaction was stirred 2 h at rt. The reaction was quenched with water, extracted with ethyl acetate, washed with brine, and dried ($Na_2SO_4$). The crude residue was treated with 1N HCl and extracted with diethyl ether. The aqueous layer was basified and extracted with ethyl acetate and dried to afford 0.38 g (25%) of a light brown oil. $^1$H NMR (CDCl$_3$) δ 7.59 (d, J=8.4 Hz, 2H), 7.04 (d, J=8.4 Hz, 2H), 2.70 (s, 2H), 1.21 (s, 6H) ppm.

Part B. To the product from part A (1 g, 3.6 mmol) in $CH_2Cl_2$ (75 mL) in a separatory funnel were added cold 1N NaOH (25 mL) and 4-chlorobutylchloride (0.53 mL, 4.7 mmol). The reaction was shaken for 15 min, then separated and the organic layer dried. To the crude amide in THF (30 mL) was added KOtBu (1.33 g, 10.9 mmol) at 0° C. and the reaction was stirred 24 h. The reaction was quenched with water, extracted with ethyl acetate, and dried to afford 1.1 g of crude lactam that was carried onto the next step.

Part C. The product from part B (0.26 g, 0.76 mmol), 1-(3-chloro-phenyl)-7-oxo-4,5,6,7-tetrahydro-1H-pyrazolo[3,4-c]pyridine-3-carboxylic acid ethyl ester (0.25 g, 0.76 mmol), and $K_2CO_3$(0.32 g, 2.3 mmol) were combined and degassed DMSO (4 mL) followed by CuI (29 mg, 0.15 mmol) were then added. The reaction was heated to 130° C. for 5 h. The reaction was cooled and partitioned between ethyl acetate and water and extracted with ethyl acetate and dried ($MgSO_4$). Chromatography on silica gel using 0–5% MeOH in $CH_2Cl_2$ afforded ester that was carried onto the next step.

Part D. The ester from part C was placed in 5% $NH_3$ in ethylene glycol (1.5 mL) and heated in a sealed tube at 80° C. for 2 h. The reaction was cooled, poured into water, and filtered. Crystallization from $CH_3CN/H_2O$ afforded 40 mg (10% for 2 steps) of the title compound. High Resolution Mass Spec for $C_{27}H_{29}ClN_5O_3(M+H)^+$ 506.1955.

EXAMPLE 190

6-{4-[1,1-Dimethyl-2-(2-oxo-pyrrolidin-1-yl)-ethyl]-phenyl}-1-(4-methoxy-phenyl)-7-oxo-4,5,6,7-tetrahydro-1H-pyrazolo[3,4-c]pyridine-3-carbonitrile

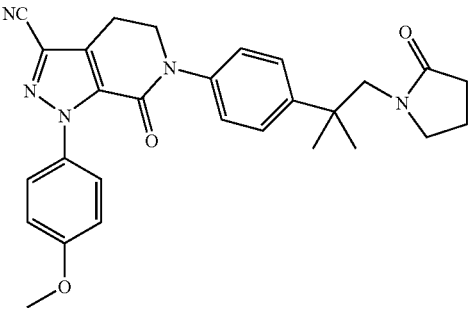

To 1-(4-methoxy-phenyl)-7-oxo-4,5,6,7-tetrahydro-1H-pyrazolo[3,4-c]pyridine-3-carbonitrile (0.149 g, 0.55 mmol), 1-[2-(4-iodo-phenyl)-2-methyl-propyl]-pyrrolidin-2-one (0.19 g, 0.55 mmol), and $K_2CO_3$ (0.23 g, 1.7 mmol) was added degassed DMSO (4 mL) followed by CuI (21 mg, 0.11 mmol). The mixture was heated to 130° C. for 5 h. The reaction was cooled, partitioned between ethyl acetate and water, extracted with ethyl acetate, and dried ($MgSO_4$). Chromatography on silica gel using 0–5% MeOH in $CH_2Cl_2$ followed by further purification by HPLC afforded the title

EXAMPLE 191

1-(4-Methoxy-phenyl)-6-[4-(1-methyl-1-pyrrolidin-1-ylethyl)-phenyl]-7-oxo-4,5,6,7-tetrahydro-1H-pyrazolo[3,4-c]pyridine-3-carboxylic acid amide

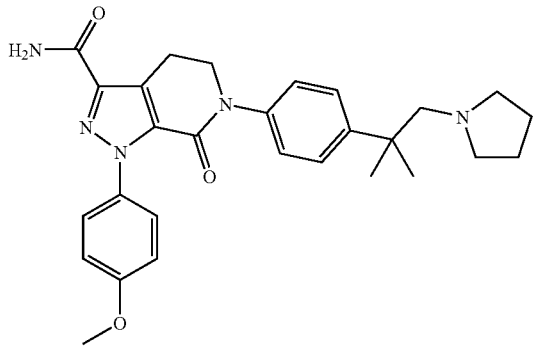

Part A. To pyrrolidine (1.2 g, 0.018 mol) in $CH_2Cl_2$ (50 mL) at 0° C. was added 2M trimethylaluminum in heptane (9 mL, 0.018 mol) and the mixture was stirred 20 min. Ethyl-4-iodobenzoate (1 g, 3.6 mmol) was then added and the reaction was stirred 72 h. The reaction was quenched with ice and 1N HCl, extracted with $CH_2Cl_2$, and dried ($MgSO_4$). To the crude amide was added THF (30 mL) and this solution was cooled to −20° C. To this solution TiCl4.2THF (1.2 g, 3.6 mmol) was added and stirred cold for 0.5 h. A 3M diethyl ether solution of methylmagnesium bromide (7.2 mL, 21.7 mmol) was added and the reaction was stirred 24 h at room temperature. Quenching with 30% NaOH, extracting with ethyl acetate, and drying ($Na_2SO_4$) followed by chromatography on silica gel using 0–5% MeOH in $CH_2Cl_2$ afforded 1-[1-(4-iodo-phenyl)-1-methyl-ethyl]-pyrrolidine (0.1 g, 8.8%); Mass spec $(M+H)^+$ 316.1.

Part B. To the product from part A (100 mg, 0.32 mmol), 1-(4-methoxy-phenyl)-7-oxo-4,5,6,7-tetrahydro-1H-pyrazolo[3,4-c]pyridine-3-carboxylic acid ethyl ester (119 mg, 0.38 mmol), and $K_2CO_3$ (0.11 g, 0.79 mmol) was added DMSO (4 mL) and the mixture was then degassed with $N_2$. CuI (12 mg, 0.063 mmol) was added. The reaction was heated to 130° C. for 6 h. The reaction was quenched with sat'd $NaHCO_3$, extracted with $CH_2Cl_2$, and dried ($MgSO_4$). Chromatography on silica gel using 0–5% MeOH (1% $NH_3$) in $CH_2Cl_2$ afforded 60 mg (37.7%) of ester; Mass Spec $(M+H)^+$ 503.5.

Part C. To the ester (60 mg, 0.12 mmol) was added 5% $NH_3$ in ethylene glycol (1 mL) and the reaction was heated 80° C. in a sealed tube for 2 h. A solid precipitate was collected after dilution with water and the filtrate was extracted with $CH_2Cl_2$. The product was purified by HPLC and freeze-dried to afford the title compound (45 mg, 64%); High Resolution Mass Spectrum for $C_{27}H_{32}N_5O_3$ $(M+H)^+$ 474.2516.

EXAMPLE 192

6-[4-(1-Dimethylamino-1-methyl-ethyl)-phenyl]-1-(4-methoxy-phenyl)-7-oxo-4,5,6,7-tetrahydro-1H-pyrazolo[3,4-c]pyridine-3-carboxylic acid amide

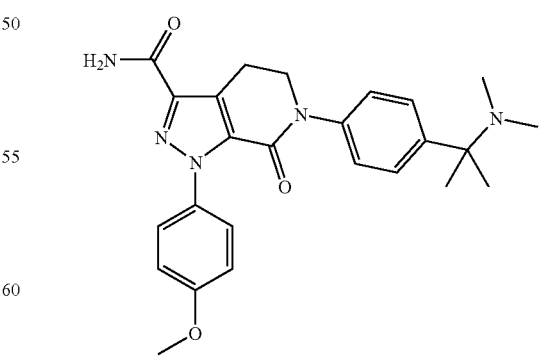

Following a procedure analogous to that used in Example 191, the title compound was prepared. High Resolution Mass Spec $(M+H)^+$ for $C_{25}H_{30}N_5O_3$ 448.2327.

EXAMPLE 193

2-{4-[4-Chloro-2-(5-chloro-pyridin-2-ylcarbamoyl)-phenylcarbamoyl]-phenyl}-2-methyl-propionic acid methyl ester

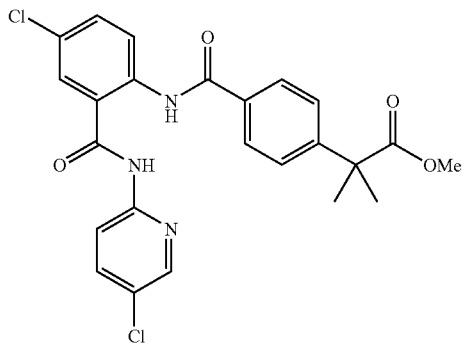

Step A. To a solution of 2-amino-4-chloropyridine (129.0 mg, 1.0 mmol) in anhydrous THF at −78° C. was added KHMDS (4.0 ml, 0.5 M solution in toluene). The mixture was stirred at this temperature under $N_2$ for 30 min. and a solution of 5-chloro-isatoic anhydride (198.0 mg, 1.0 mmol) in THF was added to the above mixture. The resulted mixture was warmed to rt gradually and stirred for 10 hr. The reaction mixture was quenched with sat'd $NH_4Cl$ solution, most of the solvent was evaporated and the residue was diluted with ethyl acetate, washed with brine, and dried over $MgSO_4$. Removal of solvent and chromatography on silica gel (20% ethyl acetate in hexane) yielded the desired product 2-amino-5-chloro-N-(5-chloro-pyridin-2-yl)-benzamide as light brown solid. MS found: $(M+1)^+=282.2$.

Step B. To a mixture of methyl phenylacetate (150.0 mg, 1.0 mmol) in THF at −78° C. was added NaHMDS (2.2 ml, 2.2 mmol). After stirring at this temperature for 15 min, MeI (312.0 mg, 2.2 mmol) was added to the above mixture. The resulted mixture was stirred at −78° C. for 3 hr and rt for 1 hr. The mixture was cooled to −78° C., quenched with sat'd $NH_4Cl$, diluted with EtOAc, washed with aq. $NaHCO_3$ and brine, and dried. Flash chromatography purification (10% EtOAc in hexane) gave 2-methyl-2-phenyl-propionic acid methyl ester as clear oil. MS found: $(M+1)^+=179.1$.

Step C. To a suspension of $AlCl_3$ (500.0 mg, 3.75 mmol) in $CH_2Cl_2$ at −10° C. was added dropwise oxalyl chloride (476.0 mg, 3.75 mmol) in $CH_2Cl_2$. The mixture was stirred at this temperature for 30 min. Then a solution of 2-methyl-2-phenyl-propionic acid methyl ester (178.0 mg, 1.0 mmol) in $CH_2Cl_2$ was added. The resulted mixture was stirred at −10° C. for 1 hr and rt overnight. The mixture was filtered through a pad of celite, the solvent and excess oxalyl chloride was removed under reduced pressure. The residue was dissolved in chlorobenzene and refluxed for 4 hr. Solvent was removed and the residue was dried to give 2-(4-chlorocarbonyl-phenyl)-2-methyl-propionic acid methyl ester.

Step D. To a solution of 2-(4-chlorocarbonyl-phenyl)-2-methyl-propionic acid methyl ester (240.0 mg, 1.0 mmol) in $CH_2Cl_2$ at 0° C. was added TEA (3.0 mmol) followed by addition of 2-amino-5-chloro-N-(5-chloro-pyridin-2-yl)-benzamide (281 mg, 1.0 mmol) and DMAP (cat. 10 mg). The resulted mixture was stirred at 0° C. for 1 hr and rt over night. Solvent was evaporated and HPLC purification gave 2{4-[4-Chloro-2-(5-chloro-pyridin-2-ylcarbamoyl)-phenylcarbamoyl]-phenyl}-2-methyl-propionic acid methyl ester as white solid. MS found: $(M+1)^+=486.2$.

EXAMPLE 194

2{4-[4-Chloro-2-(5-chloro-pyridin-2-ylcarbamoyl)-phenylcarbamoyl]-phenyl}-2-methyl-propyl alcohol

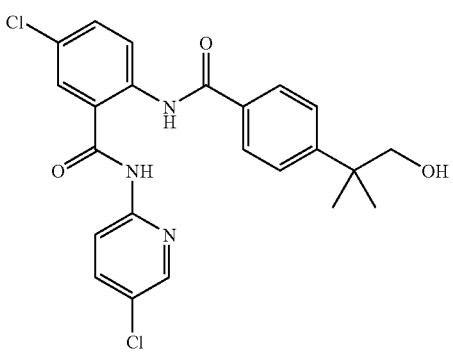

To a solution of 2{4-[4-Chloro-2-(5-chloro-pyridin-2-ylcarbamoyl)-phenylcarbamoyl]-phenyl}-2-methyl-propionic acid methyl ester (485.0 mg, 1 mmol) in THF was added $LiBH_4$ (2.0 ml, 2.0 M solution in THF). The mixture was stirred at 60° C. over night. The reaction mixture was cooled, and quenched with sat'd $NH_4Cl$. HPLC purification gave 2{4-[4-Chloro-2-(5-chloro-pyridin-2-ylcarbamoyl)-phenylcarbamoyl]-phenyl}-2-methyl-propyl alcohol as white solid. MS found: $(M+1)^+=457.9$.

EXAMPLE 195

5-chloro-N-(5-chloropyridin-2-yl)-2-({4-[2-(ethylamino)-1,1-dimethylethyl]benzoyl}amino)benzamide

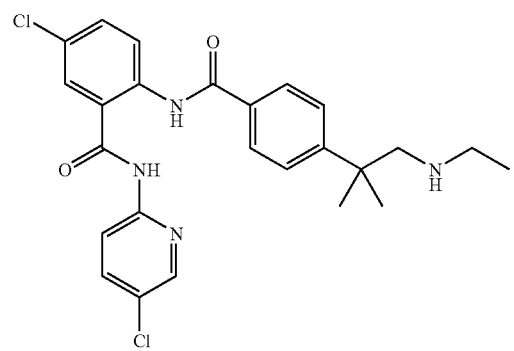

Step A. To a solution of the product obtained from Example 194 (457.0 mg, 1.0 mmol) in $CH_2Cl_2$ was added Dess-Martin reagent (636.0 mg, 1.5 mmol). The mixture was stirred at rt for 2.5 hr. The mixture was filtered and solvent was removed to give the desired aldehyde that was used for next step.

Step B. To a solution of the above aldehyde (46.0 mg, 0.1 mmol) in $CH_2Cl_2$ was added diethylamine (0.2 mmol) and $NaBH_3CN$ (10.0 mg). The mixture was stirred at rt over night. The reaction mixture was filtered and HPLC purification gave the desired product as white solid. MS found: (M+1)⁺=485.0.

EXAMPLE 196

5-chloro-N-(5-chloropyridin-2-yl)-2-{[4-(1,1-dimethyl-2-pyrrolidin-1-ylethyl)benzoyl]amino}benzamide

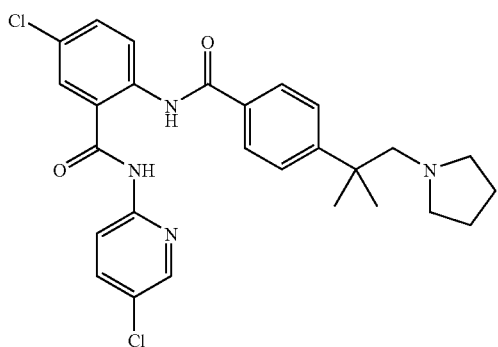

Following a procedure analogous to Example 195, the desired compound was obtained as white solid. MS found: (M+1)⁺=511.3.

EXAMPLE 197

5-chloro-N-(5-chloropyridin-2-yl)-2-{[4-(1,1-dimethyl-2-morpholin-4-ylethyl)benzoyl]amino}benzamide

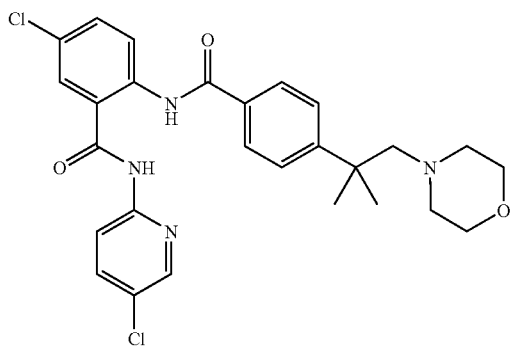

Following a procedure analogous to Example 195, the desired compound was obtained as white solid. MS found: (M+1)⁺=527.3.

EXAMPLE 198

2-{4-[2-(5-chloro-pyridin-2-ylcarbamoyl)-phenylcarbamoyl]-phenyl}-2-methyl-propionic acid methyl ester

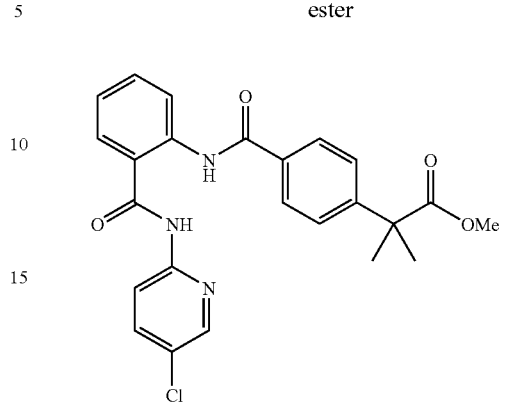

Following a procedure analogous to Example 193, the desired compound was obtained as white solid. MS found: (M+1)⁺=452.1.

EXAMPLE 199

2-{4-[2-(5-chloro-pyridin-2-ylcarbamoyl)-4-methoxy-phenylcarbamoyl]-phenyl}-2-methyl-propionic acid methyl ester

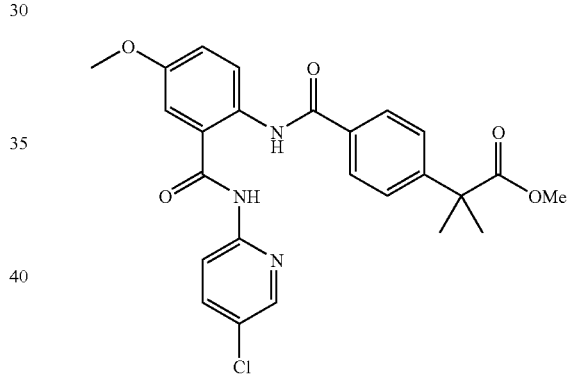

Following a procedure analogous to Example 193, the desired compound was obtained as white solid. MS found: (M+1)⁺=482.1.

EXAMPLE 200

N-(5-chloropyridin-2-yl)-2-{[4-(2-hydroxy-1,1-dimethylethyl)benzoyl]amino}benzamide

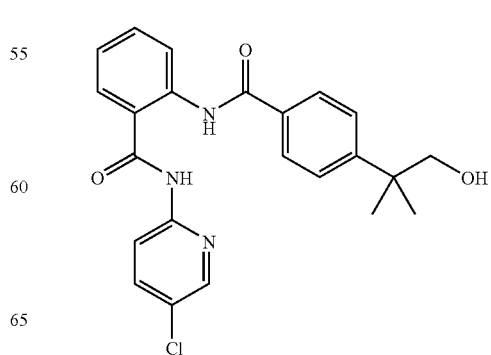

Following a procedure analogous to Example 2, the desired compound was obtained as white solid. MS found: (M+1)$^+$=424.1.

EXAMPLE 201

N-(5-chloropyridin-2-yl)-2-{[4-(2-hydroxy-1,1-dimethylethyl)benzoyl]amino}-5-methoxybenzamide

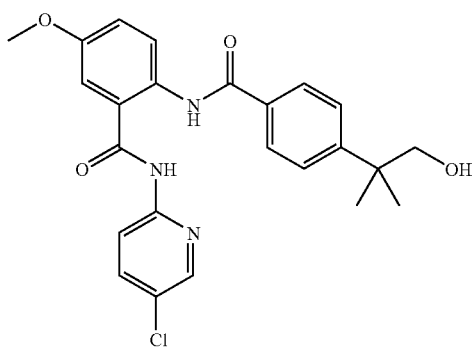

Following a procedure analogous to Example 194, the desired compound was obtained as white solid. MS found: (M+1)$^+$=454.1.

EXAMPLE 202

N-(5-chloropyridin-2-yl)-2-{[4-(1,1-dimethyl-2-pyrrolidin-1-ylethyl)benzoyl]amino}benzamide

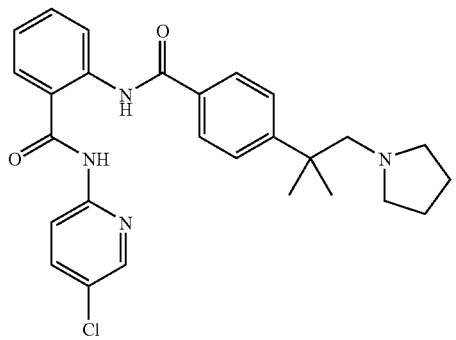

Following a procedure analogous to Example 195, the desired compound was obtained as white solid. MS found: (M+1)$^+$=577.1.

EXAMPLE 203

N-(5-chloropyridin-2-yl)-2-{[4-(1,1-dimethyl-2-morpholin-4-ylethyl)benzoyl]amino}benzamide

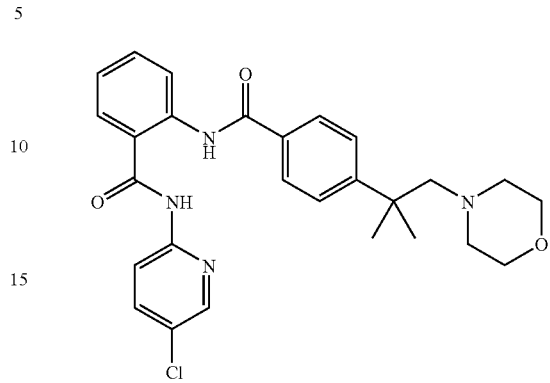

Following a procedure analogous to Example 195, the desired compound was obtained as white solid. MS found: (M+1)$^+$=493.1.

EXAMPLE 204

N-(5-chloropyridin-2-yl)-2-{[4-(1,1-dimethyl-2-pyrrolidin-1-ylethyl)benzoyl]amino}-5-methoxybenzamide

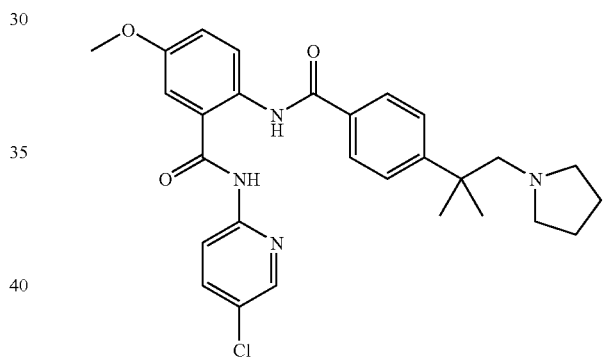

Following a procedure analogous to Example 195, the desired compound was obtained as white solid. MS found: (M+1)$^+$=507.1.

EXAMPLE 205

2-[(4-{2-[acetyl(methyl)amino]-1,1-dimethylethyl}benzoyl)amino]-N-(5-chloropyridin-2-yl)benzamide

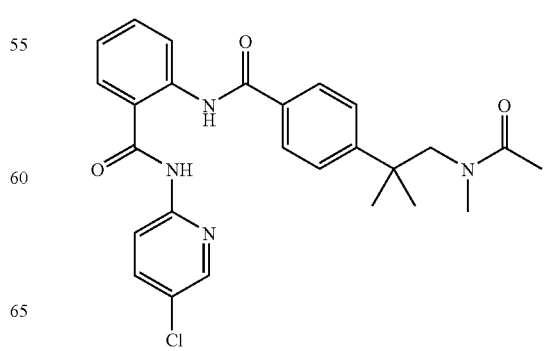

Step A. Following a procedure analogous to Example 195, the desired amine N-(5-chloropyridin-2-yl)-2-({4-[1,1-dimethyl-2-(methylamino)ethyl]benzoyl}-amino)benzamide was obtained as white solid.

Step B. To a solution of the above amine (10.0 mg, 0.018 mmol) in CH$_2$Cl$_2$ at 0° C. was added Ac$_2$O (10 μl) and TEA (50 μl). The mixture was stirred at 0° C. for 4 hr. Solvent was removed and the residue was purified with reverse phase HPLC. MS found: (M+1)$^+$=479.2.

EXAMPLE 206

2-(4-{[2-(5-chloro-pyridin-2-ylcarbamoyl)-phenylamino]methyl}-phenyl)-2-methyl-propionic acid methyl ester

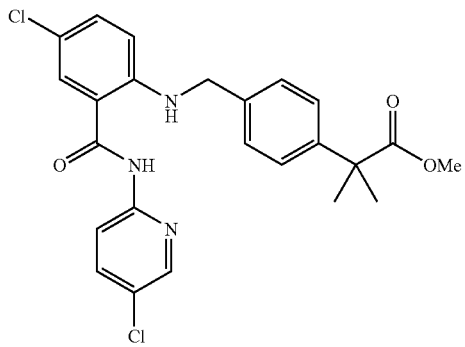

Step A. The product obtained from Example 193, Step C (240.0 mg, 1.0 mmol) was treated with THF/H$_2$O (1:1, 10 ml). The mixture was stirred at 60° C. for 2 hr. The reaction mixture was extracted with EtOAc, washed with 1N HCl, H$_2$O and brine. Reverse phase HPLC purification provided 4-(1-methoxycarbonyl-1-methyl-ethyl)-benzoic acid as white solid. MS found: (M+1)$^+$=223.1.

Step B. To a solution of the product obtained above (222.0 mg, 1.0 mmol) in THF was added BH$_3$-THF (0.75 ml, 1.0 M solution in THF). The mixture was stirred at 65° C. for 7 hr. Then the reaction mixture was cooled to rt and quenched with H$_2$O. After removal of solvent, the residue was purified with reverse phase to give 2-(4-hydroxymethyl-phenyl)-2-methyl-propionic acid methyl ester as clear oil. MS found: (M+1)$^+$=209.2.

Step C. To a solution of the product obtained above (83.0 mg, 0.399 mmol) in CH$_2$Cl$_2$ was added Dess-Martin reagent (203.0 mg, 0.48 mmol). The mixture was stirred at rt for 4 hr. The mixture was filtered, solvent was evaporated and the residue was dried to give the corresponding aldehyde, which was directly used in the next step.

Step D. A mixture of the product from above (66.0 mg, 0.32 mmol) and 2-amino-5-chloro-N-(5-chloro-pyridin-2-yl)-benzamide (90.0 mg, 0.32 mmol) in ethanol was refluxed under N$_2$ for 2 hr. After the mixture was cooled to room temperature, NaBH$_4$ (100.0 mg) was added, and the resulted mixture was stirred at rt over night. The reaction mixture was quenched with H$_2$O, and solvent was evaporated. The residue was purified with reverse phase HPLC to give desired product as white solid. MS found: (M+1)$^+$=472.0.

EXAMPLE 207

5-chloro-N-(5-chloropyridin-2-yl)-2-{[4-(2-hydroxy-1,1-dimethylethyl)benzyl]amino}benzamide

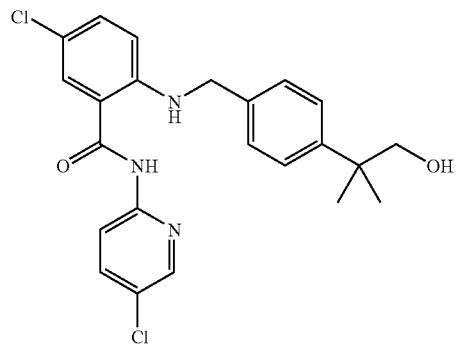

Following a procedure analogous to Example 194, the desired compound was obtained as white solid. MS found: (M+1)$^+$=444.1.

EXAMPLE 208

5-Chloro-N-(5-chloro-pyridin-2-yl)-2-[4-(2-dimethylamino-1,1-dimethyl-ethyl)-benzylamino]-benzamide

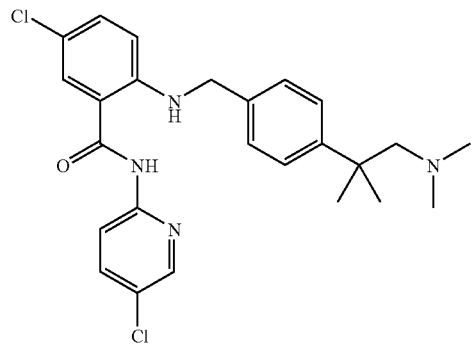

Step A. To a solution of 2-methyl-2-phenylpropionic acid (5.0 g, 30.49 mmol) in CH$_2$Cl$_2$ at 0° C. was added oxalyl chloride (4.0 ml, 45.7 mmol). The mixture was stirred at 0° C. for 3 hr. Solvent was evaporated and the residue was dried.

The above residue was dissolved in CH$_2$Cl$_2$, and dimethylamine was purged for 20 min. or until saturated. The mixture was stirred rt for 1 hr. The reaction mixture was washed with water, 1N HCl, sat'd NaHCO$_3$, and brine. Chromatography purification gave N,N-dimethyl-2-phenylisobutyramide as white solid. MS found: (M+1)$^+$=192.2.

Step B. Following a procedure analogous to Example 193, Step C, 4-(1-dimethylcarbamoyl-1-methyl-ethyl)-benzoyl chloride was obtained as colorless oil.

A solution of the product obtained above (2.45 g, 9.7 mmol) in MeOH at 0° C. was added Et$_3$N (40 ml) and DMAP (20 mg). The resulted mixture was stirred at 0° C. for 1 hr and rt over night. Then most of the solvent was removed, the residue was diluted with EtOAc. The resulted mixture was washed with 1N HCl, water and brine. Chromatography purification (30% EtOAc in hexane) provided 4-(1-dimethylcarbamoyl-1-methyl-ethyl)-benzoic acid methyl ester as white solid. MS found: $(M+1)^+=250.1$.

Step C. To a solution of the product obtained above (35.0 mg, 0.14 mmol) in THF at 0° C. was added LAH (0.7 ml, 1.0 M solution in THF). The mixture was stirred at 0° C. for 1 hr and rt over night. Then the reaction mixture was quenched with sat'd potassium sodium tartrate solution. Solvent was evaporated and the residue was purified with reverse phase HPLC. The desired [4-(2-dimethylamino-1,1-dimethyl-ethyl)-phenyl]-methanol was obtained as clear oil. MS found: $(M+1)^+=208.2$.

Step D. Following a procedure analogous to Example 195, Step A, the above alcohol was oxidized to 4-(2-dimethylamino-1,1-dimethyl-ethyl)-benzaldehyde. MS found: $(M+1)^+=206.2$.

Step E. Following a procedure analogous to Example 206, Step D, the desired compound was obtained as light yellow solid. MS found: $(M+1)^+=471.1$.

EXAMPLE 209

N-(5-chloropyridin-2-yl)-2-({4-[1-(hydroxymethyl)cyclopropyl]benzoyl}amino)-5-methoxybenzamide

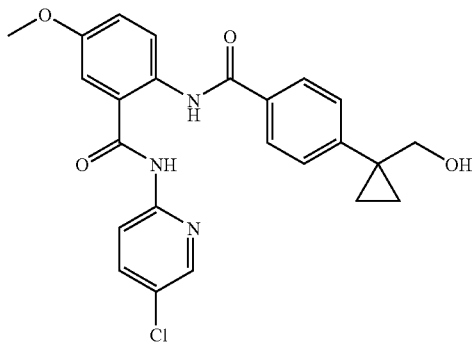

Step A. Following a procedure analogous to Example 193, Step C, 1-phenyl-cyclopropanecarboxylic acid methyl ester was converted to the desired 1-(4-chlorocarbonyl)-cyclopropanecarboxylic acid methyl ester.

Step B. Following a procedure analogous to Example 193, Step D, the desired 1-{4-[2-(5-chloro-pyridin-2-ylcarbamoyl)-4-methoxy-phenylcarbamoyl]-phenyl}-cyclopropanecarboxylic acid methyl ester was obtained as white solid. MS found: $(M+1)^+=480.1$.

Step C. Following a procedure analogous to Example 194, the desired product was obtained as yellow solid. MS found: $(M+1)^+=452.1$.

EXAMPLE 210

N-(5-chloropyridin-2-yl)-5-methoxy-2-({4-[1-(pyrrolidin-1-ylmethyl)cyclopropyl]benzoyl}amino)benzamide

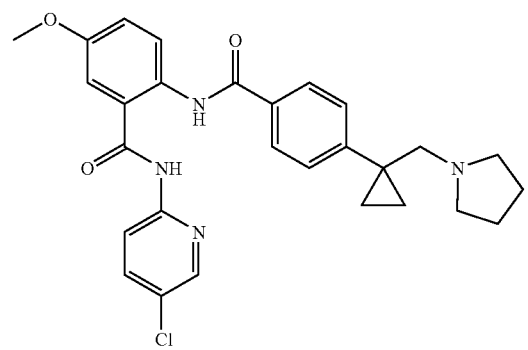

Step A. To a solution of the product obtained from Example 209 (20 mg, 0.044 mmol) in $CH_2Cl_2$ was added Dess-Martin reagent (28.0 mg, 0.066 mmol). The mixture was stirred at rt for 2.5 hr. Then the reaction mixture was filtered, the solvent was removed and the residue was dried to give the corresponding aldehyde.

Step B. To a solution of the aldehyde from above (15.0 mg, 0.033 mmol) in 1,2-dichloroethane at 0° C. was added pyrrolidine (1.0 mL) and 2 drops of AcOH. The mixture was stirred at 0° C. for 10 min, and $NaBH(OAc)_3$ (35 mg, 0.16 mmol) was added. The resulted mixture was warmed to rt slowly and stirred for 3 hr. After quenching with $H_2O$, the mixture was concentrated and the residue was purified with reverse phase HPLC to give the desired product as white solid. MS found: $(M+1)^+=505.2$.

EXAMPLE 211

N-(5-chloropyridin-2-yl)-2-({4-[1-(pyrrolidin-1-ylmethyl)cyclopropyl]benzoyl}amino)benzamide

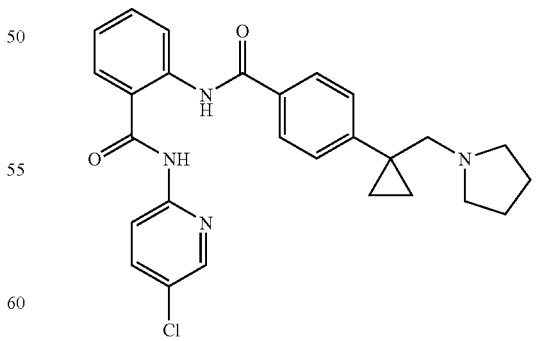

Following a procedure analogous to Example 210, the desired product was obtained as white solid. MS found: $(M+1)^+=475.2$.

EXAMPLE 212

1-{4-[2-(5-chloro-pyridin-2-ylcarbamoyl)-phenyl-carbamoyl]-phenyl}-cyclopropanecarboxylic acid methyl ester

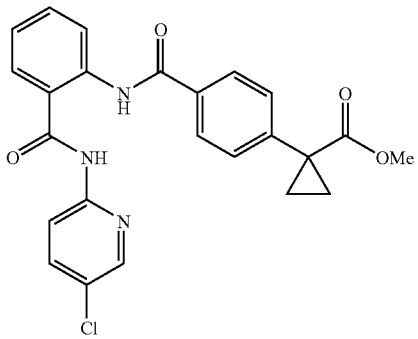

Following a procedure analogous to Example 209, Step A, the desired product was obtained as white solid. MS found: $(M+1)^+=450.1$.

EXAMPLE 213

N-(5-chloropyridin-2-yl)-2-({4-[1-(hydroxymethyl)cyclopropyl]benzoyl}amino)benzamide

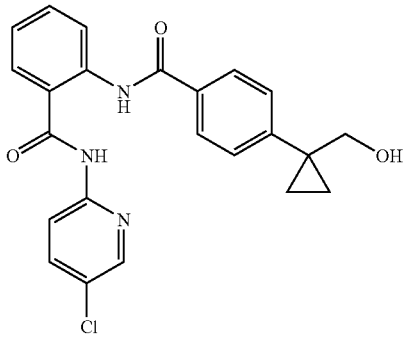

Following a procedure analogous to Example 209, the desired product was obtained as white solid. MS found: $(M+1)^+=422.1$.

EXAMPLE 214

6-chloro-3-(5-chloropyridin-2-yl)-2-[4-(1,1-dimethyl-2-morpholin-4-ylethyl)phenyl]quinazolin-4(3H)-one

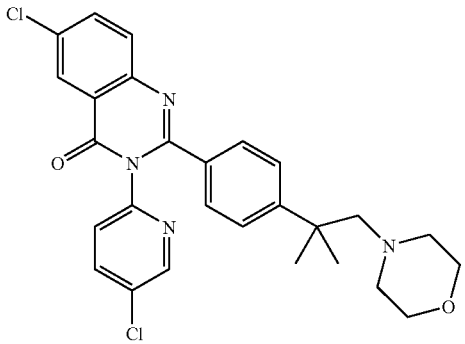

A solution of the product from Example 197 (15.0 mg, 0.028 mmol) in 5 ml of 4N HCl in dioxane and 0.5 mL of THF was refluxed for 6 hr. The mixture was cooled to rt and purified with reverse phase HPLC to give the desired product as white solid. MS found: $(M+1)^+=509.1$.

EXAMPLE 215

3-(5-chloropyridin-2-yl)-2-{4-[1-(pyrrolidin-1-ylmethyl)cyclopropyl]phenyl}quinazolin-4(3H)-one

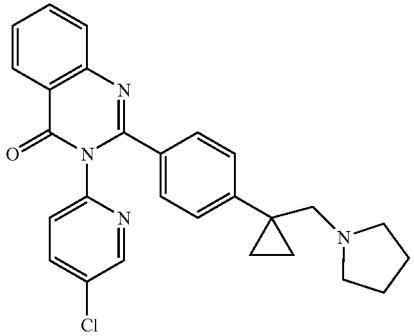

Following a procedure analogous to Example 214, the desired product was obtained as a white solid. MS found: $(M+1)^+=457.1$.

EXAMPLE 216

6-[4-(1-Methoxymethyl-cyclopropyl)-phenyl]-1-(4-methoxy-phenyl)-7-oxo-4,5,6,7-tetrahydro-1H-pyrazolo[3,4-c]pyridine-3-carboxylic acid amide

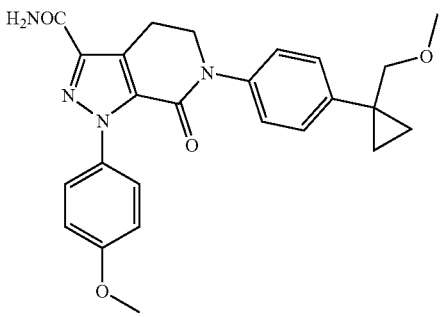

Following a procedure analogous to that used in Example 140, the title compound was prepared. LC/MS (ESI$^+$) 447.4 (M+H).

EXAMPLE 217

6-{4-[1-(4,4-Dimethyl-4,5-dihydro-oxazol-2-yl)-cyclopropyl]-phenyl}-1-(4-methoxy-phenyl)-3-trifluoromethyl-1,4,5,6-tetrahydro-pyrazolo[3,4-c]pyridin-7-one

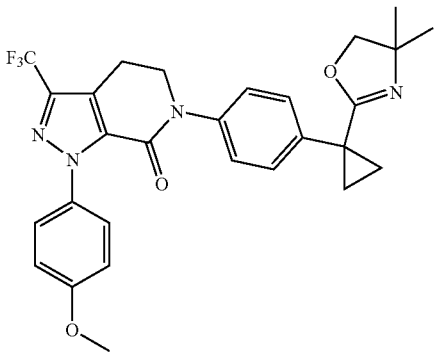

EXAMPLE 218

6-[4-(1-Methanesulfonyl-1-methyl-ethyl)-phenyl]-1-(4-methoxy-phenyl)-7-oxo-4,5,6,7-tetrahydro-1H-pyrazolo[3,4-c]pyridine-3-carboxylic acid amide

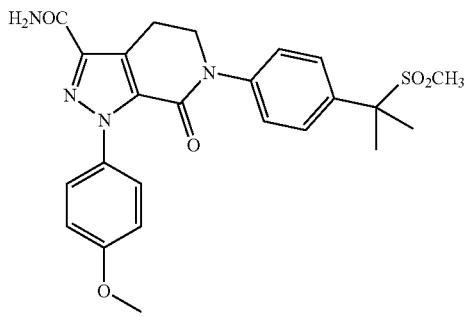

Following a procedure analogous to that used in Example 140, the title compound was prepared. LC/MS (ESI+) 525.6 (M+H), $t_R$=2.05 min (10%-90% AcCN/H$_2$O in a 4-min run).

Part A. To 4-iodobenzyl bromide (5 g, 0.018 mol) in DMF (15 mL) cooled to 0° C. was added sodium thiomethoxide (1.2 g, 0.017 mol). The reaction was stirred 18 h at room temperature. The reaction was partitioned between ethyl acetate and water. The aqueous layer was extracted, washed with water and brine, and dried (Na$_2$SO$_4$). The crude oil obtained was carried onto the next step.

Part B. The product of Part A (0.6 g, 2.3 mmol), 1-(4-methoxy-phenyl)-7-oxo-4,5,6,7-tetrahydro-1H-pyrazolo[3,4-c]pyridine-3-carboxylic acid ethyl ester (0.6 g, 1.9 mmol), K$_2$CO$_3$ (0.66 g, 4.7 mmol), and dimethylsulfoxide (5 mL) were combined and degassed with N$_2$. Copper(I) iodide (72 mg, 0.38 mmol) was added and the reaction was heated to 130° C. for 5 h. The reaction was quenched with sat'd NaHCO$_3$, extracted with CH$_2$Cl$_2$, and dried (MgSO$_4$). Purification by chromatography using 1:1 hexanes/ethyl acetate afforded 0.55 g (64%) of product; High Resolution Mass Spec for C$_{24}$H$_{26}$N$_3$O$_4$S (M+H)$^+$ 452.1652.

Part C. To the product of Part B (0.27 g, 0.59 mmol) in CH$_2$Cl$_2$ (15 mL) at 0° C. was added 3-chloroperbenzoic acid (0.4 g) and the reaction was stirred for 72 h. The reaction was washed with sat'd NaHCO$_3$, and dried (MgSO$_4$) to afford impure product. The product was dissolved in ethyl acetate washed twice with sat'd NaHCO$_3$, dried (MgSO$_4$), filtered, and concentrated to afford 0.3 g of a yellow foam; High Resolution Mass Spec for C$_{24}$H$_{26}$N$_3$O$_6$S (M+H)$^+$ 484.1541.

Part D. To the product of Part C (0.24 g, 4.9 mmol) in DMF (5 mL) at 0° C. was added NaH (60 mg, 14.7 mmol) and iodomethane (0.09 mL, 14.7 mmol). The reaction was stirred 24 h, then quenched with water, extracted with ethyl acetate, and dried (MgSO$_4$). To the crude ester 5% NH$_3$ in ethylene glycol (2 mL) was added and the reaction was heated in a sealed tube at 80° C. for 2 h. The reaction was quenched with water and the resulting precipitate collected. Purification of the solid by HPLC and freeze-drying afforded 15 mg (6%) of the title compound; High Resolution Mass Spec for C$_{24}$H$_{27}$N$_4$O$_5$S (M+H)$^+$ 483.1694.

EXAMPLE 219

6-[4-(1-Hydroxy-1-methyl-ethyl)-phenyl]-1-(4-methoxy-phenyl)-7-oxo-4,5,6,7-tetrahydro-1H-pyrazolo[3,4-c]pyridine-3-carboxylic acid amide

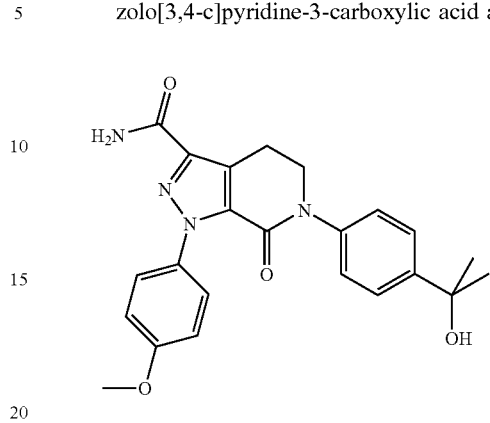

Part A. To ethyl 4-iodobenzoate (1 g, 3.6 mmol) in THF (20 mL) at 0° C. was added 3M methyl magnesium bromide (3 mL, 9 mmol). The reaction was stirred for 72 h, quenched with 1N HCl, extracted with ethyl acetate, and dried (Na$_2$SO$_4$) to afford 0.94 g (100%) of the alcohol; $^1$H NMR (CDCl$_3$) δ 7.67 (d, J=8.8 Hz, 2H), 7.25 (d, J=8.8 Hz, 2H), 1.56 (s, 6H) ppm.

Part B. The product of Part A (0.9 g, 3.4 mmol), 1-(4-methoxy-phenyl)-7-oxo-4,5,6,7-tetrahydro-1H-pyrazolo[3,4-c]pyridine-3-carboxylic acid ethyl ester (1 g, 3.4 mmol), K$_2$CO$_3$ (1.2 g, 8.5 mmol), and DMSO (10 mL) were combined and degassed with N$_2$. Copper (I) iodide (130 mg, 0.68 mmol) was added, and the reaction was heated to 130° C. for 18 h. The reaction was quenched with sat'd NaHCO$_3$, extracted with CH$_2$Cl$_2$, and dried (MgSO$_4$). Purification by chromatography using 1:1 hexanes/ethyl acetate afforded an impure product; Mass Spec (M+H)$^+$ 450.6.

Part C. To the impure product of Part B (0.8 g) was added 5% NH$_3$ in ethylene glycol (8 mL), and the reaction was heated in a sealed tube at 80° C. for 2 h. The reaction was quenched with water and extracted with ethyl acetate. Purification of the solid by HPLC and freeze-drying afforded 120 mg of the title compound; High Resolution Mass Spec for C$_{23}$H$_{25}$N$_4$O$_4$ (M+H)$^+$ 421.1862.

EXAMPLE 220

(1-{4-[1-(4-Methoxy-phenyl)-7-oxo-3-trifluoromethyl-1,4,5,7-tetrahydro-pyrazolo[3,4-c]pyridin-6-yl]-phenyl}-cyclopropyl)-acetic acid

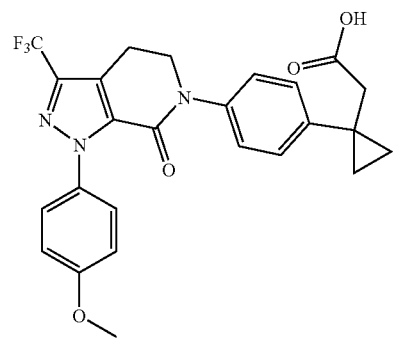

Part A. 1-(4-Iodophenyl)-cyclopropanecarbonyl chloride (1.74 g, 5.69 mmol) was stirred in CH₃CN and THF (1:1 v/v, 20 mL total) at 0° C. under N₂. TMSCHN₂ (2M in hexanes, 4.3 mL, 1.5 eq) was added dropwise. The mixture was stirred at room temperature for 4 h. It was evaporated; sat'd NaHCO₃ was added. It was extracted with EtOAc. The organic layer was washed with brine, dried over MgSO₄, filtered, and concentrated to dryness. The residue was stirred in t-BuOH (20 mL) at gentle reflux. A mixture of silver benzoate (0.7 g, 3.07 mmol) and Et₃N (5 mL) was added over 1 min.

The reaction was stirred at reflux for 1 h, and the hot mixture was filtered through Celite®. H₂O was added to the filtrate; the mixture was extracted with EtOAc (3×). The organics were washed with sat'd NaHCO₃, H₂O, 1M HCl, sat'd NaHCO₃, H₂O, brine, dried over MgSO₄, filtered, and concentrated to dryness. The residue was purified by FCC (silica gel, hexanes:CH₂Cl₂=1:0 to 1:1 to 0:1 then 10% EtOAc in CH₂Cl₂) to give [1-(4-iodo-phenyl)-cyclopropyl]-acetic acid tert-butyl ester (0.69 g, yield: 35%). $^1$H NMR (CDCl₃): δ 7.49 (d, J=8.8 Hz, 2H), 6.98 (d, J=8.8 Hz, 2H), 2.39 (s, 2H), 1.27 (s, 9H), 0.81 (s, 4H) ppm. LC/MS(ESI⁺) 359.4 (M+H).

Part B. The product from Part A (0.34 g, 0.95 mmol) and 1-(4-methoxyphenyl)-3-(trifluoromethyl)-1,4,5,6-tetrahydro-7H-pyrazolo[3,4-c]pyridin-7-one (0.31 g, 0.99 mmol) were stirred in DMSO (1 mL) in a Pyrex® tube under N₂. K₂CO₃ (0.33 g, 2.39 mmol) was added, followed by the addition of CuI (95 mg, 0.50 mmol) and 1,10-phenanthroline (90 mg, 0.50 mmol). The mixture was stirred at 120° C. for 3 h. LC/MS showed 70% conversion. The cooled mixture was extracted with EtOAc (3×), washed with H₂O, brine, dried over MgSO₄, filtered, and concentrated to dryness. The residue was purified by FCC (silica gel, hexanes:CH₂Cl₂=1:0 to 1:1 to 0:1, then EtOAc:CH₂Cl₂=1:10 to 1:2) to give (1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-acetic acid tert-butyl ester (0.35 g, yield: 67%). $^1$H NMR (CDCl₃) δ 7.48 (d, J=8.8 Hz, 2H), 7.35 (d, J=8.8 Hz, 2H), 7.21 (d, J=8.5 Hz, 2H), 6.93 (d, J=8.8 Hz, 2H), 4.12 (t, J=6.6 Hz, 2H), 3.82 (s, 3H), 3.16 (t, J=6.6 Hz, 2H), 2.51 (s, 2H), 1.39 (s, 9H), 0.91 (s, 4H) ppm. LC/MS(ESI) 542.4 (M+H).

Part C. The product from Part B (300 mg, 0.55 mmol) was stirred in CH₂CH₂ (10 mL) and TFA (5 mL) at rt for 4 h. It was purified by FCC (silica gel, EtOAc, then 10% MeOH in CH₂Cl₂) to give the desired title compound (235 mg, yield: 87.4%). $^1$H NMR (CDCl₃) δ 7.43 (d, J=8.8 Hz, 2H), 7.34 (d, J=8.4 Hz, 2H), 7.19 (d, J=8.4 Hz, 2H), 6.91 (d, J=8.7 Hz, 2H), 5.23 (s, 2H), 4.11 (t, J=6.8 Hz, 2H), 3.81 (s, 3H), 3.16 (t, J=6.6 Hz, 2H), 2.63 (s, 2H), 0.95 (m, 2H), 0.91 (m, 2H) ppm. LC/MS(ESI) 486.6 (M+H). HRMS (ESI), C₂₅H₂₃N₃O₄F₃, calcd for 486.1641, found 486.1649.

EXAMPLE 221

2-(1-{4-[1-(4-Methoxy-phenyl)-7-oxo-3-trifluoromethyl-1,4,5,7-tetrahydro-pyrazolo[3,4-c]pyridin-6-yl]-phenyl}-cyclopropyl)-acetamide

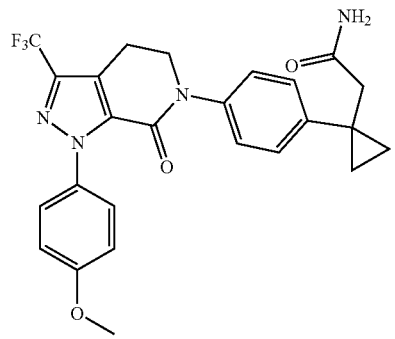

The acid chloride product from Example 210 (12.5 mg, 0.03 mmol) was stirred in THF (0.5 mL) at rt. Concentrated aqueous NH₃ (0.5 mL) was added. The mixture was stirred at rt for 4 h. LC/MS showed completion of the reaction. The mixture was purified by RP HPLC to give the title compound (9.0 mg, yield: 71.5%). $^1$H NMR (CDCl₃) δ 7.38 (d, J=8.8 Hz, 2H), 7.26 (m, 4H), 6.84 (d, J=8.8 Hz, 2H), 5.23 (s, 2H), 4.04 (m, 2H), 3.74 (s, 3H), 3.08 (m, 2H), 2.48 (s, 2H), 0.91 (m, 4H) ppm. LC/MS(ESI) 485.6 (M+H).

Using the same procedure as that described for Example 221, Examples 222–224 were prepared.

EXAMPLE 222

2-(1-{4-[1-(4-Methoxy-phenyl)-7-oxo-3-trifluoromethyl-1,4,5,7-tetrahydro-pyrazolo[3,4-c]pyridin-6-yl]-phenyl}-cyclopropyl)-N-methyl-acetamide

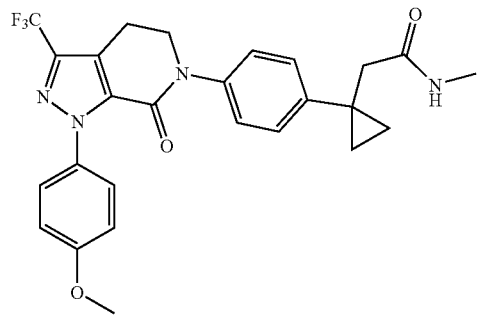

$^1$H NMR (CDCl₃) δ 7.46 (d, J=8.8 Hz, 2H), 7.26 (m, 4H), 6.92 (d, J=8.8 Hz, 2H), 4.11 (t, J=6.3 Hz, 2H), 3.81 (s, 3H), 3.15 (t, J=6.3 Hz, 2H), 2.69 (m, 3H), 2.52 (s, 2H), 1.78 (m, 4H), 0.95 (m, 4H) ppm. HRMS (ESI) calcd. 499.1958; found 499.1970 for C₂₆H₂₆F₃N₄O₃ (M+H). LC/MS (10–90% CH₃CN in H₂O in a 4-min run, t$_R$=2.30 min), 499.6 (M+H).

EXAMPLE 223

2-(1-{4-[1-(4-Methoxy-phenyl)-7-oxo-3-trifluoromethyl-1,4,5,7-tetrahydro-pyrazolo[3,4-c]pyridin-6-yl]-phenyl}-cyclopropyl)-N,N-dimethyl-acetamide

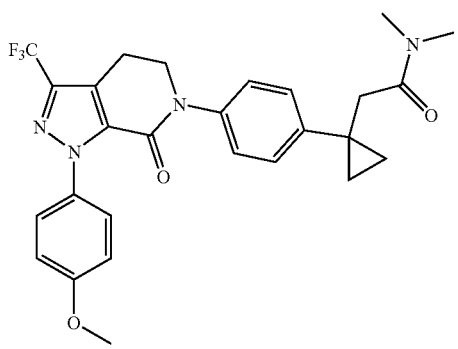

$^1$H NMR (CDCl$_3$) δ 7.46 (d, J=8.8 Hz, 2H), 7.38 (d, J=8.5 Hz, 2H), 7.19 (d, J=8.4 Hz, 2H), 6.91 (d, J=8.8 Hz, 2H), 4.10 (t, J=6.6 Hz, 2H), 3.81 (s, 3H), 3.13 (t, J=6.6 Hz, 2H), 2.86 (s, 3H), 2.76 (s, 3), 2.64 (s, 3H), 0.89 (m, 4H) ppm. HRMS (ESI), calcd. 513.2114; found 513.2113 for C$_{27}$H$_{28}$F$_3$N$_4$O$_3$ (M+H). LC/MS (10–90% CH$_3$CN in H$_2$O in a 4-min run, t$_R$=2.46 min), 513.6 (M+H).

EXAMPLE 224

1-(4-Methoxy-phenyl)-6-{4-[1-(2-oxo-2-pyrrolidin-1-yl-ethyl)-cyclopropyl]-phenyl}-3-trifluoromethyl-1,4,5,6-tetrahydro-pyrazolo[3,4-c]pyridin-7-one

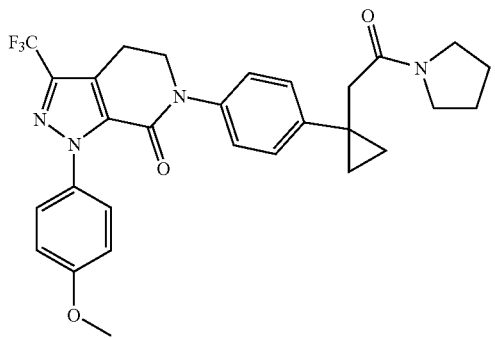

$^1$H NMR (CDCl$_3$) δ 7.46 (d, J=8.8 Hz, 2H), 7.41 (d, J=8.4 Hz, 2H), 7.18 (d, J=8.4 Hz, 2H), 6.91 (d, J=8.8 Hz, 2H), 4.10 (t, J=6.6 Hz, 2H), 3.81 (s, 3H), 3.38 (t, J=6.4 Hz, 2H), 3.13 (m, 4H), 2.56 (s, 2H), 1.78 (m, 4H), 0.92 (m, 2H), 0.88 (m, 2H) ppm. HRMS(ESI) calcd. 539.2271; found 539.2214 for C$_{28}$H$_{30}$F$_3$N$_3$O$_3$ (M+H). LC/MS (ESI) (10–90% CH$_3$CN in H$_2$O in a 4-min run, t$_R$=2.52 min) 539.6 (M+H).

EXAMPLE 225

6-{4-[1-(2-Hydroxy-ethyl)-cyclopropyl]-phenyl}-1-(4-methoxy-phenyl)-3-trifluoromethyl-1,4,5,6-tetrahydro-pyrazolo[3,4-c]pyridin-7-one

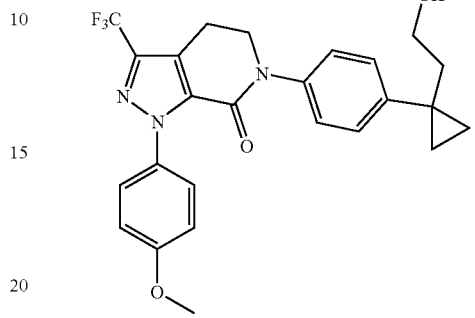

Using the similar sequence for the preparation of Part E in Example 1 but using the product of Example 220 as the starting material, the title compound was prepared. $^1$H NMR (CDCl$_3$) δ 7.46 (d, J=8.8 Hz, 2H), 7.31 (d, J=8.8 Hz, 2H), 7.21 (d, J=8.5 Hz, 2H), 6.92 (d, J=9.2 Hz, 2H), 5.23 (s, 2H), 4.11 (t, J=6.6 Hz, 2H), 3.80 (s, 3H), 3.59 (t, J=7.0 Hz, 2H), 3.14 (t, J=6.6 Hz, 2H), 1.82 (t, J=7.0 Hz, 2H), 0.78 (m, 2H), 0.74 (m, 2H) ppm. LC/MS (ESI) 472.4 (M+H).

Following procedures analogous to that used for Part E and Part F of Example 1, but using the product of Example 225 as one of the starting materials, Examples 226–229 were prepared.

EXAMPLE 226

1-(4-Methoxy-phenyl)-6-{4-[1-(2-methylamino-ethyl)cyclopropyl]-phenyl}-3-trifluoromethyl-1,4,5,6-tetrahydro-pyrazolo[3,4-c]pyridin-7-one, trifluoroacetic acid salt

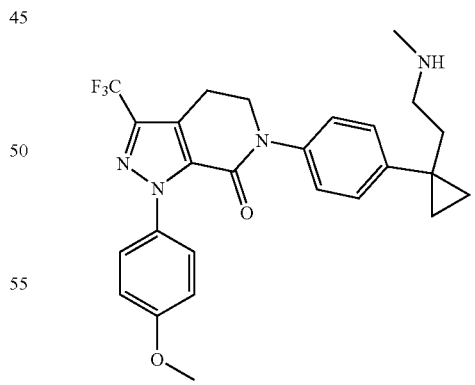

$^1$H NMR (CDCl$_3$) δ 7.45 (d, J=8.8 Hz, 2H), 7.26 (m, 4H), 6.91 (d, J=8.8 Hz, 2H), 4.12 (t, J=6.6 Hz, 2H), 3.81 (s, 3H), 3.16 (t, J=6.6 Hz, 2H), 2.98 (m, 2H), 2.75 (m, 6H), 1.97 (m, 2H), 0.86 (m, 2H), 0.79 (m, 2H) ppm. HRMS (ESI) calcd. 485.2165; found 485.2153 for C$_{26}$H$_{28}$F$_3$N$_4$O$_2$ (M+H). LC/MS (10–90% CH$_3$CN in H$_2$O in a 4-min run, t$_R$=2.10 min) 485.6 (M+H).

EXAMPLE 227

6-{4-[1-(2-Dimethylamino-ethyl)-cyclopropyl]-phenyl}-1-(4-methoxy-phenyl)-3-trifluoromethyl-1,4,5,6-tetrahydro-pyrazolo[3,4-c]pyridin-7-one, trifluoroacetic acid salt

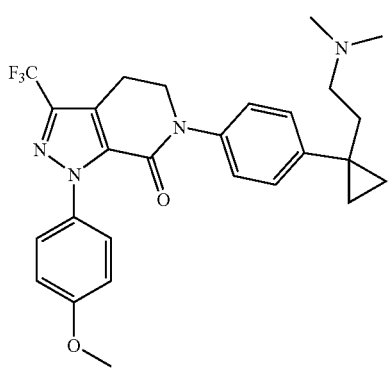

$^1$H NMR (CDCl$_3$) δ 7.45 (d, J=8.8 Hz, 2H), 7.26 (m, 4H), 6.91 (d, J=8.8 Hz, 2H), 4.12 (t, J=6.6 Hz, 2H), 3.81 (s, 3H), 3.16 (t, J=6.6 Hz, 2H), 2.98 (m, 2H), 2.75 (m, 6H), 1.97 (m, 2H), 0.86 (m, 2H), 0.79 (m, 2H) ppm. HRMS (ESI) calcd. 499.2322; found 499.2318 for C$_{27}$H$_{30}$F$_3$N$_4$O$_2$ (M+H). LC/MS (10–90% CH$_3$CN in H$_2$O in a 4-min run, t$_R$=2.10 min) 499.6 (M+H).

EXAMPLE 228

1-(4-Methoxy-phenyl)-6-{4-[1-(2-pyrrolidin-1-yl-ethyl)-cyclopropyl]-phenyl}-3-trifluoromethyl-1,4,5,6-tetrahydro-pyrazolo[3,4-c]pyridin-7-one, trifluoroacetic acid salt

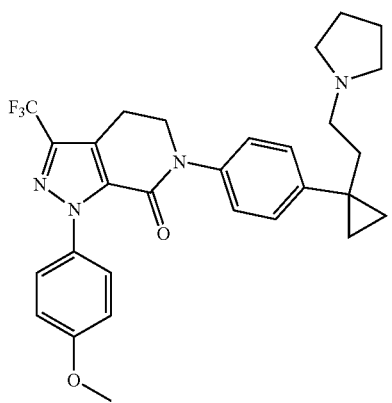

$^1$H NMR (CDCl$_3$) δ 7.46 (d, J=8.8 Hz, 2H), 7.26 (m, 4H), 6.92 (d, J=8.8 Hz, 2H), 4.12 (t, J=6.6 Hz, 2H), 3.81 (s, 3H), 3.77 (m, 2H), 3.16 (t, J=6.6 Hz, 2H), 3.02 (m, 2H), 2.65 (m, 2H), 2.02 (m, 6H), 0.84 (m, 2H), 0.77 (m, 2H). HRMS(ESI) calcd. 525.2478, found 525.2483 for C$_{29}$H$_{32}$F$_3$N$_4$O$_2$ (M+H). LC/MS (10–90% CH$_3$CN in H$_2$O in 4-min run, t$_R$=2.18 min) 525.6 (M+H).

EXAMPLE 229

1-(4-Methoxy-phenyl)-6-{4-[1-(2-morpholin-4-yl-ethyl)-cyclopropyl]-phenyl}-3-trifluoromethyl-1,4,5,6-tetrahydro-pyrazolo[3,4-c]pyridin-7-one, trifluoroacetic acid salt

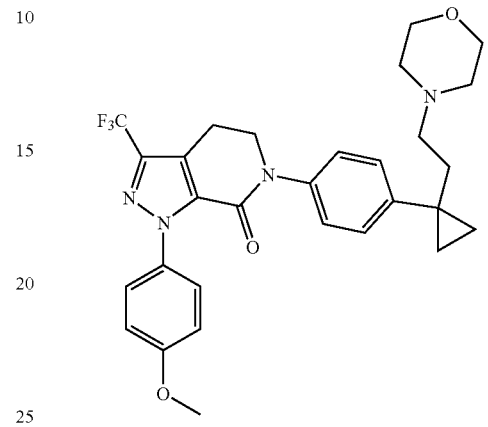

$^1$H NMR (CDCl$_3$) δ 7.45 (d, J=8.8 Hz, 2H), 7.26 (m, 4H), 6.92 (d, J=8.8 Hz, 2H), 4.12 (t, J=6.6 Hz, 2H), 3.93 (m, 4H), 3.81 (s, 3H), 3.47 (m, 2H), 3.16 (t, J=6.6 Hz, 2H), 2.98 (m, 2H), 2.72 (m, 2H), 1.99 (m, 2H), 0.85 (m, 2H), 0.76 (m, 2H) ppm. HRMS(ESI) calcd. 541.2427, found 541.2413 for C$_{29}$H$_{32}$F$_3$N$_4$O$_3$ (M+H). LC/MS (ESI) (10–90% CH$_3$CN in H$_2$O in a 4-min run, t$_R$=2.11 min), 541.6 (M+H).

EXAMPLE 230

1-(4-Methoxy-phenyl)-6-{4-[1-(2-pyrrolidin-1-yl-acetyl)-cyclopropyl]-phenyl}-3-trifluoromethyl-1,4,5,6-tetrahydro-pyrazolo[3,4-c]pyridin-7-one

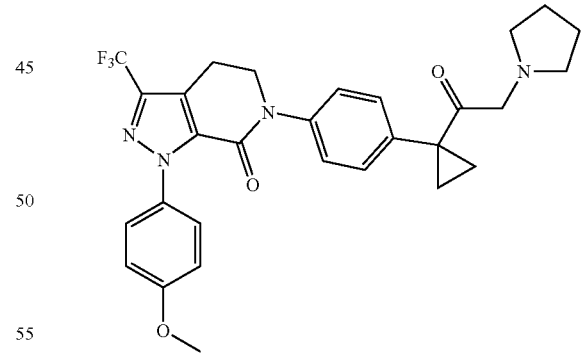

Part A. 1-(4-Iodophenyl)-cyclopropanecarbonyl chloride (1.74 g, 5.69 mmol) was stirred in CH$_3$CN and THF (1:1 v/v, 20 mL) total at 0° C. under N$_2$. TMSCHN$_2$ (2M in hexanes, 4.3 mL) was added dropwise. The mixture was stirred at 0° C. to rt for 2 h. It was partitioned between EtOAc and sat'd NaHCO$_3$. The organics were washed with brine, dried over MgSO$_4$, filtered, and concentrated to dryness. HBr/HOAc (30%, 8 mL) was added dropwise to the residue at 0° C. The mixture was stirred at 0° C. for 30 min, and EtOAc was added; it was washed with 15% citric acid, sat'd NaHCO$_3$, H₂O, brine, dried over MgSO₄, filtered, and concentrated to dryness to give crude 2-bromo-1-[1-(4-iodo-phenyl)-cyclopropyl]-ethanone (0.5 g).

Part B. The product from Part A (0.5 g, 1.37 mmol) was dissolved in DMF (1.8 mL), a spatula tip of the K₂CO₃ and pyrrolidine (0.2 mL) were added. The mixture was heated at 80° C. for 1.5 h. The cooled mixture was partitioned between EtOAc and H₂O. The organics were washed with brine, dried over MgSO₄, filtered, and concentrated to dryness. The residue was purified by FCC (silica gel, EtOAc:CH₂Cl₂=0:1 to 1:0, then 10% MeOH in EtOAc) to give 1-[1-(4-iodo-phenyl)-cyclopropyl]-2-pyrrolidin-1-yl-ethanone (85 mg, yield: 17% for 2 steps). ¹H NMR (CDCl₃) δ 7.68 (d, J=8.4 Hz, 2H), 7.13 (d, J=8.4 Hz, 2H), 3.30 (s, 2H), 2.51 (m, 4H), 1.75 (m, 4H), 1.63 (m, 2H) 1.10 (m, 2H) ppm. LC/MS (ESI) 356.4 (M+H).

Part C. The product of part B (50 mg, 0.14 mmol) and 1-(4-methoxyphenyl)-3-(trifluoromethyl)-1,4,5,6-tetrahydro-7H-pyrazolo[3,4-c]pyridin-7-one (52.5 mg, 0.17 mmol) were stirred in DMSO (0.2 mL) in a Pyrex tube under N₂. K₂CO₃ (39 mg) was added followed by the addition of CuI (20 mg) and 9,10-phenantholine (20 mg). The mixture was stirred at 120° C. for 2 h. The cooled mixture was purified by reverse phase HPLC to give the title compound (9.6 mg, yield: 12.7%). LC/MS (ESI) 539.6 (M+H).

EXAMPLE 231

6-[4-(1-Carbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid ethyl ester

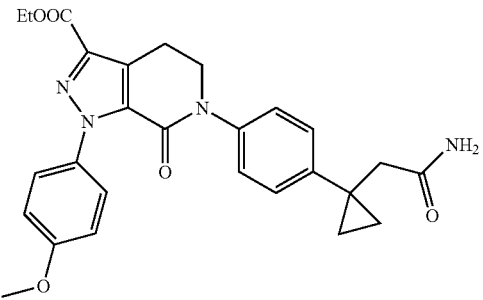

Part A. Following procedure similar to that of Part C in Example 220 but using 1-(4-methoxy-phenyl)-7-oxo-4,5,6,7-tetrahydro-1H-pyrazolo[3,4-c]pyridine-3-carboxylic acid ethyl ester and [1-(4-iodo-phenyl)-cyclopropyl]-acetic acid tert-butyl ester as starting materials, 6-[4-(1-tert-butoxycarbonylmethyl-cyclopropyl)-phenyl]-1-(4-methoxy-phenyl)-7-oxo-4,5,6,7-tetrahydro-1H-pyrazolo[3,4-c]pyridine-3-carboxylic acid ethyl ester was obtained (406.29 mg, yield: 86%). ¹H NMR (CDCl₃) δ 7.48 (d, J=8.9 Hz, 2H), 7.33 (d, J=8.5 Hz, 2H), 7.22 (d, J=8.5 Hz, 2H), 6.91 (d, J=8.9 Hz, 2H), 4.47 (q, J=7.1 Hz, 2H), 4.12 (m, 2H), 3.81 (s, 3H), 3.32 (t, J=6.6 Hz, 2H), 2.50 (s, 2H), 1.44 (t, J=7.1 Hz, 3H), 1.38 (s, 9H), 0.90 (s, 4H) ppm. LRMS (ESI) 546.2 (M+H).

Part B. The product from Part A (450 mg) was stirred in a mixture of CH₂Cl₂ (10 mL) and TFA (15 mL) at rt for 4 h. The solvents were evaporated. The residue was dried in vacuo to give 6-[4-(1-carboxymethyl-cyclopropyl)-phenyl]-1-(4-methoxy-phenyl)-7-oxo-4,5,6,7-tetrahydro-1H-pyrazolo[3,4-c]pyridine-3-carboxylic acid ethyl ester (386 mg, yield: 95.6%). ¹H NMR (CDCl₃) δ 7.45 (d, J=8.7 Hz, 2H), 7.35 (d, J=8.3 Hz, 2H), 7.21 (d, J=8.3 Hz, 2H), 6.91 (d, J=8.7 Hz, 2H), 4.47 (q, J=7.1 Hz, 2H), 4.14 (t, J=6.6 Hz, 2H), 3.82 (s, 3H), 3.34 (t, J=6.5 Hz, 2H), 2.65 (s, 2H), 1.43 (t, J=7.1 Hz, 3H), 0.97 (m, 2H), 0.91 (m, 2H) ppm. LRMS (ESI) 490.1 (M+H).

Part C. The product from Part B (150 mg, 0.31 mmol) was stirred in CH₂Cl₂ (5 mL). Oxalyl chloride (2M solution in CH₂Cl₂, 0.3 mL. ca. 2 eq) was added, followed by the addition of 1 drop of DMF. The mixture was stirred at rt for 1 h. The solvents were evapoarated. The residue was dried in vaco. One third of the residue (0.1 mmol) was dissolved in THF (2.0 mL), concentrated NH₃H₂O (2.0 mL) was added. The mixture was stirred at rt for 2 h. EtOAc was added. It was washed with H₂O, brine, dried over MgSO₄, filtered, and concentrated to dryness. The residue was purified by FCC (silica gel, CH₂Cl₂, then EtOAc) to give pure title compound. ¹H NMR (CDCl₃) δ 7.39 (d, J=8.9 Hz, 2H), 7.22 (d, J=8.4 Hz, 2H), 7.15 (d, J=8.5 Hz, 2H), 6.82 (d, J=8.9 Hz, 2H), 5.46 (s, br, 1H), 5.30 (s, br, 1H), 4.38 (t, J=7.1 Hz, 2H), 4.03 (t, J=6.6 Hz, 2H), 3.73 (s, 3H), 3.23 (t, J=6.7 Hz, 2H), 2.45 (s, 2H), 1.36 (t, J=7.1 Hz, 2H), 0.88 (m, 4H) ppm. HRMS (ESI) C₂₇H₂₉N₄O₅ calcd for 489.2138, found 489.2152.

Following procedures analogous to that used for Example 231, Examples 232–238 were prepared.

EXAMPLE 232

6-[4-(1-Carbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid amide

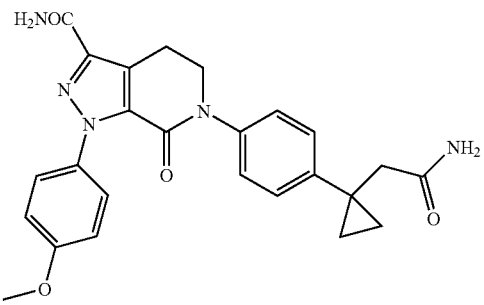

¹H NMR (methanol-d₄) δ 7.50 (d, J=8.9 Hz, 2H), 7.40 (d, J=8.5 Hz, 2H), 7.27 (d, J=8.5 Hz, 2H), 7.00 (d, J=8.9 Hz, 2H), 4.10 (t, J=6.6 Hz, 2H), 3.86 (s, 3H), 3.33 (m, 2H), 2.54 (s, 2H), 0.99 (m, 2H), 0.94 (m, 2H) ppm. LC/MS (ESI) t_R=2.66 min (10–90% MeOH in H₂O with 10 mM NH₄OAc in a 4-min gradient), 460.10 (M+H, 100%), 492.11 (M+H+MeOH, 70%).

EXAMPLE 233

1-(4-Methoxy-phenyl)-6-[4-(1-methylcarbamoylmethyl-cyclopropyl)-phenyl]-7-oxo-4,5,6,7-tetrahydro-1H-pyrazolo[3,4-c]pyridine-3-carboxylic acid ethyl ester

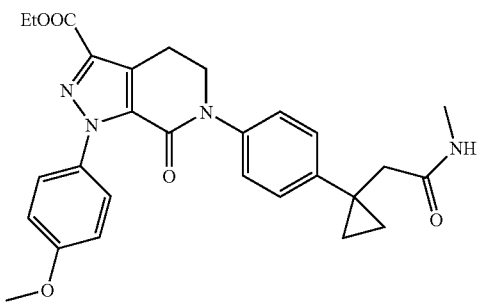

$^1$H NMR (CDCl$_3$) δ 7.39 (d, J=9.0 Hz, 2H), 7.17 (m, 4H), 6.82 (d, J=9.0 Hz, 2H), 5.46 (m, 1H), 4.38 (q, J=6.8 Hz, 2H), 4.02 (t, J=6.8 Hz, 2H), 3.73 (s, 3H), 3.23 (t, J=6.6 Hz, 2H), 2.61 (d, J=4.8 Hz, 3H), 2.43 (s, 2H), 1.36 (t, J=7.2 Hz, 3H), 0.87 (s, 4H) ppm. HRMS (ESI) C$_{28}$H$_{31}$N$_4$O$_5$, calcd for 503.2294, found 503.2281.

EXAMPLE 234

1-(4-Methoxy-phenyl)-6-[4-(1-methylcarbamoylmethyl-cyclopropyl)-phenyl]-7-oxo-4,5,6,7-tetrahydro-1H-pyrazolo[3,4-c]pyridine-3-carboxylic acid amide

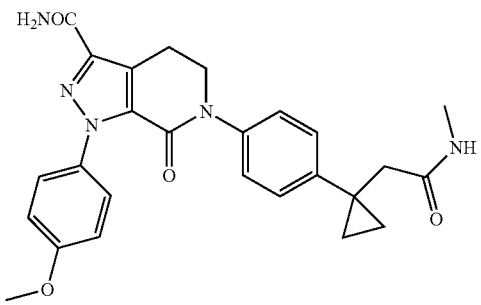

$^1$H NMR (methanol-d$_4$) δ 7.38 (d, J=8.8 Hz, 2H), 7.23 (d, J=8.8 Hz, 2H), 7.12 (d, J=8.8 Hz, 2H), 6.85 (d, J=8.8 Hz, 2H), 3.94 (t, J=6.6 Hz, 2H), 3.71 (s, 3H), 3.18 (t, J=6.6 Hz, 2H), 2.48 (s, 3H), 2.35 (s, 2H), 0.84 (m, 2H), 0.77 (m, 2H) ppm. LC/MS (ESI) t$_R$=2.76 min (10–90% MeOH in H$_2$O with 10 mM NH$_4$OAc in a 4-min gradient), 474.09 (M+H, 100%), 506.12 (M+H+MeOH, 100%).

EXAMPLE 235

6-[4-(1-Dimethylcarbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid ethyl ester

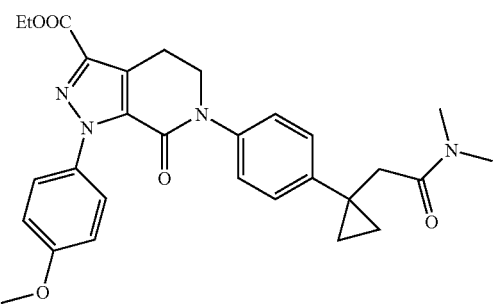

$^1$H NMR (CDCl$_3$) δ 7.40 (d, J=8.9 Hz, 2H), 7.30 (d, J=8.4 Hz, 2H), 7.13 (d, J=8.4 Hz, 2H), 6.82 (d, J=9.0 Hz, 2H), 4.38 (q, J=7.1 Hz, 2H), 4.03 (t, J=6.6 Hz, 2H), 3.73 (s, 3H), 3.22 (t, J=6.6 Hz, 2H), 2.78 (s, 3H), 2.68 (s, 3H), 2.57 (s, 2H), 1.36 (t, J=7.1 Hz, 3H), 0.82 (m, 2H), 0.81 (m, 2H) ppm. HRMS (ESI) C$_{29}$H$_{33}$N$_4$O$_5$, calcd for 517.2451, found 517.2439

EXAMPLE 236

6-[4-(1-Dimethylcarbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid amide

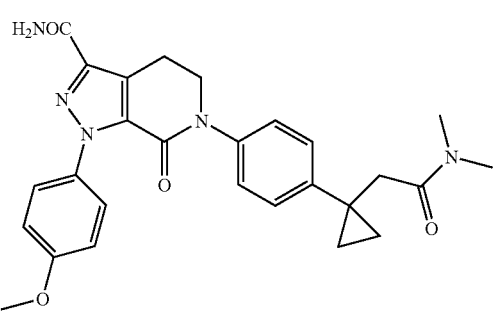

$^1$H NMR (methanol-d$_4$) δ 7.50 (d, J=9.0 Hz, 2H), 7.38 (d, J=8.5 Hz, 2H), 7.26 (d, J=8.5 Hz, 2H), 6.99 (d, J=9.0 Hz, 2H), 4.08 (t, J=6.6 Hz, 2H), 3.85 (s, 3H), 3.33 (m, 2H), 2.83 (s, 3H), 2.75 (s, 3H), 2.72 (s, 2H), 0.95 (m, 2H), 0.90 (m, 2H) ppm. LC/MS (ESI) t$_R$=2.90 min (10–90% MeOH in H$_2$O with 10 mM NH$_4$OAc in a 4-min gradient), 488.10 (M+H, 100%), 520.13 (M+H+MeOH, 60%).

EXAMPLE 237

6-{4-[1-(2-Hydroxy-ethyl)-cyclopropyl]-phenyl}-1-(4-methoxy-phenyl)-7-oxo-4,5,6,7-tetrahydro-1H-pyrazolo[3,4-c]pyridine-3-carboxylic acid amide

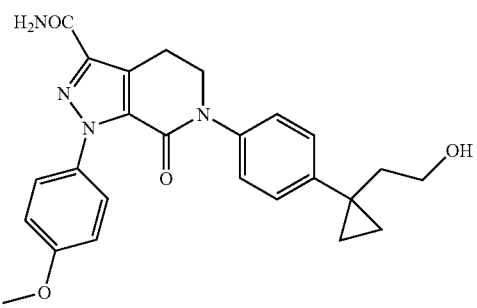

$^1$H NMR (methanol-d$_4$) δ 7.43 (d, J=8.8 Hz, 2H), 7.29 (d, J=8.4 Hz, 2H), 7.21 (d, J=8.5 Hz, 2H), 6.92 (d, J=8.9 Hz, 2H), 4.03 (m, 4H), 3.78 (s, 3H), 3.43 (t, J=6.6 Hz, 2H), 1.78 (t, J=7.0 Hz, 2H), 0.72 (m, 2H), 0.70 (m, 2H) ppm. LC/MS (ESI) t$_R$=2.62 min (10–90% MeOH in H$_2$O with 10 mM NH$_4$OAc in a 4-min gradient), 474.11 (M+H, 100%).

EXAMPLE 238

1-(4-Methoxy-phenyl)-6-{4-[1-(2-morpholin-4-yl-ethyl)-cyclopropyl]-phenyl}-7-oxo-4,5,6,7-tetrahydro-1H-pyrazolo[3,4-c]pyridine-3-carboxylic acid amide

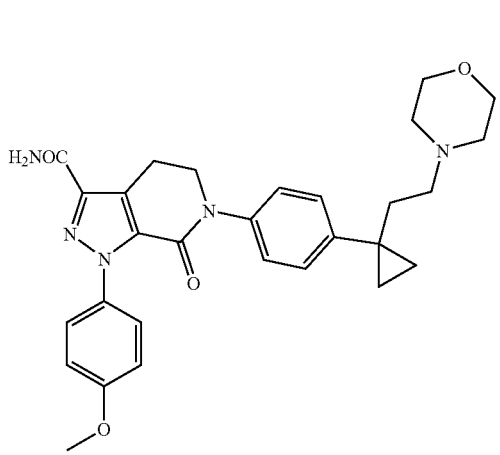

$^1$H NMR (methanol-d$_4$) δ 7.38 (d, J=9.0 Hz, 2H), 7.24 (d, J=8.5 Hz, 2H), 7.15 (d, J=8.5 Hz, 2H), 6.87 (d, J=9.0 Hz, 2H), 3.97 (t, J=6.6 Hz, 2H), 3.73 (s, 3H), 3.52 (m, 4H), 3.20 (m, 2H), 2.25 (m, 6H), 1.70 (m, 2H), 0.70 (m, 2H), 0.65 (m, 2H) ppm. LC/MS (ESI) t$_R$=3.18 min (10–90% MeOH in H$_2$O with 10 mM NH$_4$OAc in a 4-min gradient), 516.13 (M+H, 100%).

EXAMPLE 239

1-(4-Methoxy-phenyl)-6-{4-[1-(2-morpholin-4-yl-ethyl)-cyclopropyl]-phenyl}-7-oxo-4,5,6,7-tetrahydro-1H-pyrazolo[3,4-c]pyridine-3-carbonitrile, trifluoroacetic acid salt

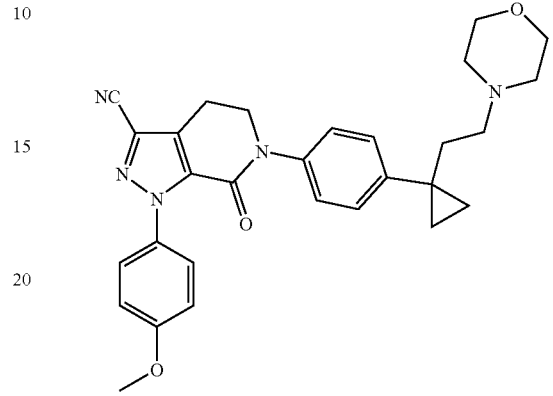

Following the procedure as Example 74 but using the product of Example 238 as the starting material, the titled compound was prepared. LRMS (ESI) 498.2 (M+H).

EXAMPLE 240

(1R,2S)-5-Chloro-thiophene-2-carboxylic acid {2-[4-(1-pyrrolidin-1-ylmethyl-cyclopropyl)-benzoylamino]-cyclopentyl}-amide, trifluoroacetic acid salt

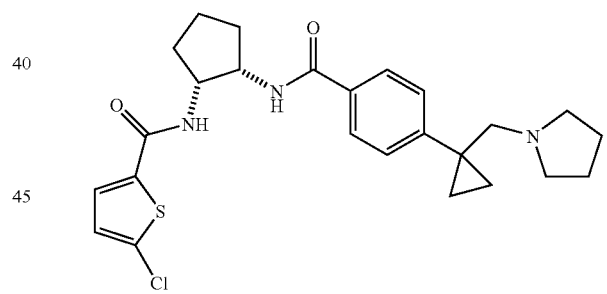

Part A. To a solution of (1S,2S)-2-benzyloxy-cyclopentylamine (9.8 g, 51.2 mmol) in THF (150 mL) were sequentially added Et$_3$N (13.6 mL, 0.10 mol) and (Boc)$_2$O (12.30 g, 56.4 mmol) at 0° C. The reaction mixture was stirred overnight at room temperature, and diluted with EtOAc (200 mL). The organic phase was washed with H$_2$O, brine, and dried (Na$_2$SO$_4$). The solvent was evaporated to afford (1S,2S)-(2-benzyloxy-cyclopentyl)-carbamic acid tert-butyl ester (14.90 g, 100%) as a slight yellow solid. MS m/z 293.0 ([M+H]$^+$).

Part B. The product from Part A (10.0 mg, 34.2 mmol) was dissolved in ethanol (100 mL), Pd/C (800 mg, 5%) was then added. The reaction mixture was hydrogenated at 25 psi with stirring for 4 h, and filtered through a pad of Celite®. The filtrate was evaporated to afford (1S,2S)-(2-hydroxy-cyclopentyl)-carbamic acid tert-butyl ester (6.84 g, 99%) as a white solid. MS m/z 202.0 ([M+H]$^+$).

Part C. To a solution of the product from Part B (4.95 g, 24.6 mmol) in CH₂Cl₂ (50 mL) were sequentially added Et₃N (4.11 mL, 29.51 mol) and MsCl (2.09 g, 27.05 mmol) at 0° C. The reaction mixture was stirred for 2 h at 0° C., then quenched with H₂O and extracted with EtOAc (3×50 mL). The organic phase was washed with H₂O, brine, and dried (Na₂SO₄). The solvent was evaporated to afford (1S,2S)-methanesulfonic acid 2-tert-butoxycarbonylamino-cyclopentyl ester (6.35 g, 92%) as a white solid. MS m/z 297.0 ([M+NH₄]⁺).

Part D. NaN₃ (4.40 g, 67.7 mmol) was added to a solution of the product from Part C (6.30 g, 22.6 mmol) in DMF (50 mL), and the reaction mixture was heated at 80° C. for 12 h with vigorous stirring. The reaction was cooled to room temperature, poured into water, and extracted with EtOAc (4×100 mL). The extracts were combined and washed with H₂O, aqueous LiCl (10%), brine, and dried (Na₂SO₄). The solvent was evaporated, and the residue was taken to next step without purification. The residue from above reaction was then dissolved in ethanol (200 mL), and Pd/C (300 mg, 5%) was added. The reaction mixture was hydrogenated at 1 atm with stirring for 24 h, and filtered through a pad of Celite®. The filtrate was evaporated to afford (1S,2R)-(2-amino-cyclopentyl)-carbamic acid tert-butyl ester (6.84 g, 99%) as a white solid. MS m/z 201.0 ([M+H]⁺).

Part E. The product from Part D (150 mg, 0.75 mmol) and 5-chloro-thiophene-2-carboxylic acid (101 mg, 0.62 mmol) were dissolved in DMF (2 mL) and cooled to 0° C. To this solution was added HATU (354 mg, 0.93 mmol), DIEA (0.22 mL, 1.24 mmol). The mixture was stirred overnight. It was diluted with ethyl acetate, washed with water, aqueous LiCl (10%), brine, and dried (MgSO₄). After evaporation of the solvent, the residue was purified on silica gel using 50% EtOAc-Hexane to afford (1S,2R)-{2-[(5-chloro-thiophene-2-carbonyl)-amino]-cyclopentyl}-carbamic acid tert-butyl ester (115 mg, 54%) as a white solid. MS m/z 367.6 ([M+Na]⁺).

Part F. The product from Part E (115 mg, 0.33 mmol) was suspended in CH₂Cl₂ (1 mL) and TFA (1 mL) was added. A clear solution was obtained and stirred for 2 h at ambient temperature. The resulting solution was concentrated, and the residue was partitioned between EtOAc and aqueous Na₂CO₃. The aqueous was extracted with EtOAc (3×10 mL). The extracts were combined and washed with brine and dried (Na₂SO₄). Evaporation of the solvent afforded (1R,2S)-5-chloro-thiophene-2-carboxylic acid (2-amino-cyclopentyl)-amide (80 mg, 98%) as a white solid that was taken to next step without purification. MS m/z 245.0 ([M+H]⁺).

Part G. The product from Part F (40 mg, 0.16 mmol) and excess 4-(1-pyrrolidin-1-ylmethyl-cyclopropyl)-benzoyl chloride (Example 1) and DIEA (0.05 mL) were stirred in CH₂Cl₂ (1 mL) at 0° C. The above solution was added Et₃N (0.05 mL) and stirred overnight. The reaction mixture was diluted with ethyl acetate, washed with water, aqueous LiCl (10%), brine, and dried (MgSO₄). After evaporation of the solvent, the residue was purified on reverse-phase HPLC to afford the title compound as a white solid. LRMS (ESI) 472.2 (M+H).

Using the same procedure as that described for Example 240, Examples 241–243 were prepared:

EXAMPLE 241

(1R,2S)-3-Chloro-1H-indole-6-carboxylic acid {2-[4-(1-pyrrolidin-1-ylmethyl-cyclopropyl)-benzoylamino]-cyclopentyl}-amide, trifluoroacetic acid salt

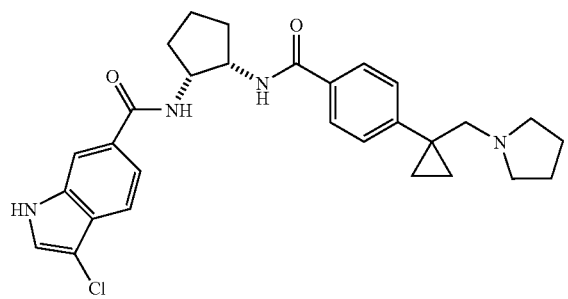

LC/MS (ESI) 505.2 (M+H).

EXAMPLE 242

(1R,2S)-5-Chloro-thiophene-2-carboxylic acid {2-[4-(1-pyrrolidin-1-ylmethyl-cyclopropyl)-benzoylamino]-cyclohexyl}-amide, trifluoroacetic acid salt

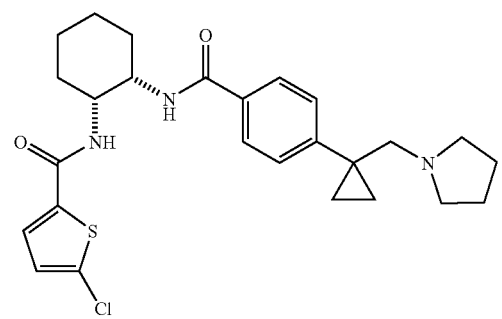

LC/MS (ESI) 486.2 (M+H)

EXAMPLE 243

Cis-3-Chloro-1H-indole-6-carboxylic acid {2-[4-(1-pyrrolidin-1-ylmethyl-cyclopropyl)-phenylcarbamoyl]-cyclohexyl}-amide, trifluoroacetic acid salt

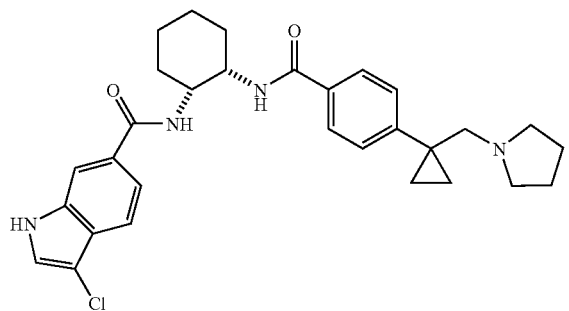

LRMS (ESI) 519.2 (M+H).

Numerous modifications and variations of the present invention are possible in light of the above teachings. It is therefore to be understood that within the scope of the

What is claimed is:
1. A compound of formula I:

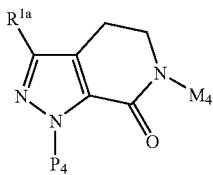

I or a stereoisomer or pharmaceutically acceptable salt thereof, wherein;

$P_4$ is -$G_1$-G;
$M_4$ is -A-B;
G is a group of formula IIa:

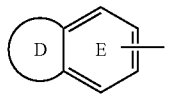

IIa ring D, including the two atoms of Ring E to which it is attached, is a 5–6 membered ring consisting of carbon atoms and 0–2 heteroatoms selected from the group consisting of N, O, and $S(O)_p$;
ring D is substituted with 0–2 R and there are 0–3 ring double bonds;
E is phenyl substituted with 1–3 R;
alternatively, ring D is absent and ring E is phenyl substituted with 1–3 R;
alternatively, ring D is absent and ring E is phenyl and is substituted with 1 R and with a 5–6 membered heterocycle consisting of: carbon atoms and 1–4 heteroatoms selected from the group consisting of N, O, and $S(O)_p$, wherein the 5–6 membered heterocycle is substituted with 0–2 carbonyls and 1–3 R and there are 0–3 ring double bonds;
R is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, ONHC$(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_rC(O)H$, $(CR^8R^9)_rC(O)R^{2c}$, $(CR^8R^9)_rNR^7R^8$, $(CR^8R^9)_rC(O)NR^7R^8$, $(CR^8R^9)_rNR^7C(O)R^7$, $(CR^8R^9)_r$ $OR^3$, $(CR^8R^9)_rS(O)_pNR^7R^8$, $(CR^8R^9)_rNR^7S(O)_pR^7$, $(CR^8R^9)_rSR^3$, $(CR^8R^9)_rS(O)R^3$, $(CR^8R^9)_rS(O)_2R^3$, and $OCF_3$, provided that $S(O)_pR^7$ forms other than $S(O)_2H$ or $S(O)H$;
alternatively, when 2 R groups are attached to adjacent atoms, they combine to form methylenedioxy or ethylenedioxy;
A is selected from phenyl, pyridyl, and pyrimidyl, and is substituted with 0–2 $R^4$;
B is Y—$R^{4a}$, provided that A and $R^{4a}$ are attached to the same atom on Y;
Y is a $C_{3-10}$ carbocycle further comprising 0–4 double bonds and 0–2 carbonyl groups, and the carbocycle is substituted with 0–2 $R^4$;
alternatively, Y is $CY^1Y^2$, and $Y^1$ and $Y^2$ are independently $C_{1-4}$ alkyl substituted with 0–2 $R^4$;
$G_1$ is absent;
$R^{1a}$, at each occurrence, is selected from H, —($CR^3$ $R^{3a})_r$—$R^{1b}$, —($CR^3R^{3a})_r$—$CR^3R^{1b}R^{1b}$, —($CR^3$ $R^{3a})_r$—O—($CR^3R^{3a})_r$—$R^{1b}$, —($CR^3R^{3a})_r$—$NR^2$— ($CR^3R^{3a})_r$—$R^{1b}$, —($CR^3R^{3a})_r$—$S(O)_p$—($CR^3R^{3a})_r$— $R^{1b}$, —($CR^3R^{3a})_r$—$CO_2$—($CR^3R^{3a})_r$—$R^{1b}$, —($CR^3R^{3a})_r$—$C(O)NR^2$—($CR^3R^{3a})_r$—$R^{1b}$, —($CR^3R^{3a})_r$—$C(O)$—($CR^3R^{3a})_r$—$R^{1b}$, —$C_{2-6}$ alkenylene-$R^{1b}$, —$C_{2-6}$ alkynylene-$R^{1b}$, and —($CR^3$ $R^{3a})_r$—$C(=NR^{1b})NR^3R^{1b}$, provided that $R^{1a}$ forms other than an N-halo, N—S, O—O, or N—CN bond;
$R^{1b}$ is selected from H, $C_{1-3}$ alkyl, F, Cl, Br, I, —CN, —$NO_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $CH(CH_2OR^2)_2$, $(CF_2)_r$ $CO_2R^{2a}$, $S(O)_pR^{2b}$, $NR^2(CH_2)_rOR^2$, $C(=NR^{2c})$ $NR^2R^{2a}$, $NR^2C(O)R^{2b}$, $NR^2C(O)NR^2R^{2a}$, $NR^2C(O)_2$ $R^{2a}$, $OC(O)NR^2R^{2a}$, $C(O)NR^2R^{2a}$, $C(O)NR^2(CH_2)_r$ $OR^2$, $SO_2NR^2R^{2a}$, $NR^2SO_2R^2$, $C(O)NR^2SO_2R^2$, $C_{3-6}$ carbocycle substituted with 0–2 $R^{4b}$, and 5–10 membered heterocycle substituted with 0–2 $R^{4b}$ and consisting of carbon atoms and from 1–4 heteroatoms selected from the group consisting of N, O, and $S(O)_p$, provided that $R^{1b}$ forms other than an O—O, N-halo, N—S, or N—CN bond and provided that $S(O)_pR^2$ forms other than $S(O)_2H$ or $S(O)H$;
$R^2$, at each occurrence, is selected from H, $CF_3$, $C_{1-6}$ alkyl, benzyl, —$(CH_2)_r$—$C_{3-10}$ carbocycle substituted with 0–2 $R^{4b}$, and —$(CH_2)_r$-5–10 membered heterocycle substituted with 0–2 $R^{4b}$ and consisting of: carbon atoms and 1–4 heteroatoms selected from the group consisting of N, O, and $S(O)_p$;
$R^{2a}$, at each occurrence, is selected from H, $CF_3$, $C_{1-6}$ alkyl, benzyl, —$(CH_2)_r$—$C_{3-10}$ carbocycle substituted with 0–2 $R^{4b}$, and —$(CH_2)_r$-5–10 membered heterocycle substituted with 0–2 $R^{4b}$ and consisting of: carbon atoms and 1–4 heteroatoms selected from the group consisting of N, O, and $S(O)_p$;
alternatively, $R^2$ and $R^{2a}$, together with the nitrogen atom to which they are attached, combine to form a 3–6 membered saturated, partially saturated or unsaturated ring substituted with 0–2 $R^{4b}$ and consisting of: 0–1 additional heteroatoms selected from the group consisting of N, O, and $S(O)_p$;
$R^{2b}$, at each occurrence, is selected from $CF_3$, $C_{1-4}$ alkoxy substituted with 0–2 $R^{4b}$, $C_{1-6}$ alkyl substituted with 0–3 $R^{4b}$, —$(CH_2)_r$—$C_{3-10}$ carbocycle substituted with 0–2 $R^{4b}$, and —$(CH_2)_r$-5–10 membered heterocycle substituted with 0–2 $R^{4b}$ and consisting of: carbon atoms and 1–4 heteroatoms selected from the group consisting of N, O, and $S(O)_p$;
$R^{2c}$, at each occurrence, is selected from $CF_3$, OH, $C_{1-4}$ alkoxy, $C_{1-6}$ alkyl, —$(CH_2)_r$—$C_{3-10}$ carbocycle substituted with 0–2 $R^{4b}$, and —$(CH_2)_r$-5–10 membered heterocycle substituted with 0–2 $R^{4b}$ and consisting of carbon atoms and from 1–4 heteroatoms selected from the group consisting of N, O, and $S(O)_p$;
$R^{2d}$, at each occurrence, is selected from H, $R^{4c}$, $C_{1-6}$ alkyl substituted with 0–2 $R^{4c}$, —$(CR^3R^{3a})_r$—$C_{3-10}$ carbocycle substituted with 0–2 $R^{4c}$, and —$(CR^3R^{3a})_r$-5–10 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, when two $R^{2d}$'s are attached to the same nitrogen atom, then $R^{2d}$ and $R^{2d}$, together with the nitrogen atom to which they are attached, combine to form a 5–10 membered saturated, partially saturated or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-6}$ alkyl substituted with 0–2 $R^{4c}$, —$(CR^3R^{3a})_r$—$C_{3-10}$ carbocycle substituted with 0–2 $R^{4c}$, and —$(CR^3R^{3a})_r$-5–10 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—S(O)$_p$ moiety;

$R^3$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms, the nitrogen atom to which $R^3$ and $R^{3a}$ are attached, and 0–1 additional heteroatoms selected from the group consisting of N, O, and $S(O)_p$;

$R^{3b}$, at each occurrence, is selected from H, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —$(C_{0-4}$ alkyl)-5–10 membered carbocycle substituted with 0–3 $R^{1a}$, and —$(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{3e}$, at each occurrence, is selected from H, $S(O)_2NHR^3$, $C(O)R^3$, $C(O)NHR^3$, $C(O)OR^{3f}$, $S(O)R^{3f}$, $S(O)_2R^{3f}$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —$(C_{0-4}$ alkyl)-5–10 membered carbocycle substituted with 0–3 $R^{1a}$, and —$(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3f}$, at each occurrence, is selected from: $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —$(C_{0-4}$ alkyl)-5–10 membered carbocycle substituted with 0–3 $R^{1a}$, and —$(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3g}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_r$-3–6 membered carbocycle, and —$(CH_2)_r$-5–6 membered heterocycle consisting of: carbon atoms and 1–4 heteroatoms selected from the group consisting of N, O, and $S(O)_p$;

alternatively, when $R^3$ and $R^{3g}$ are attached to the same carbon atom, they combine with the attached carbon atom to form a cyclopropyl group;

$R^4$, at each occurrence, is selected from H, =O, $(CR^3R^{3a})_rOR^2$, F, Cl, Br, I, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rC(=NS(O)_2R^{5a})NR^2R^{2a}$, $(CR^3R^{3a})_rNR^2C(=NR^2)NR^2R^{2a}$, $(CR^3R^{3a})_rC(O)NR^2C(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2$—$C_{1-4}$ alkyl, $(CR^3R^{3a})_rNR^2SO_2R^{5a}$, $(CR^3R^{3a})_rS(O)_pR^{5a}$, $(CR^3R^{3a})_r(CF_2)_rCF_3$, $N(CH_2)_rR^{1b}$, $O(CH_2)_rR^{1b}$, $S(CH_2)_rR^{1b}$, $(CR^3R^{3a})_r$-5–6 membered carbocycle substituted with 0–1 $R^5$, and a $(CR^3R^{3a})_r$-5–6 membered heterocycle substituted with 0–1 $R^5$ and consisting of: carbon atoms and 1–4 heteroatoms selected from the group consisting of N, O, and $S(O)_p$;

$R^{4a}$ is selected from $C_{1-6}$ alkyl substituted with 0–2 $R^{4c}$, $C_{2-6}$ alkenyl substituted with 0–2 $R^{4c}$, $C_{2-6}$ alkynyl substituted with 0–2 $R^{4c}$, —$(CR^3R^{3g})_r$—$C_{5-10}$ membered carbocycle substituted with 0–3 $R^{4c}$, —$(CR^3R^{3g})_r$-5–10 membered heterocycle substituted with 0–3 $R^{4c}$ and consisting of: carbon atoms and 1–4 heteroatoms selected from the group consisting of N, O, and $S(O)_p$, $(CR^3R^{3g})_rCN$, $(CR^3R^{3g})_rC(=NR^{2d})NR^{2d}R^{2d}$, $(CR^3R^{3g})_rNR^{2d}C(=NR^{2d})NR^{2d}R^{2d}$, $(CR^3R^{3g})_rNR^{2d}C(R^{2e})(=NR^{2d})$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r$—$NR^{2d}C(O)R^{2e}$, $(CR^3R^{3g})_r$—$C(O)R^{2e}$, $(CR^3R^{3g})_r$—$OC(O)R^{2e}$, $(CR^3R^{3g})_r$—$C(O)NR^{2d}R^{2d}$, $(CR^3R^{3g})_r$—$C(O)OR^{2d}$, $(CR^3R^{3g})_r$—$NR^{2d}C(O)NR^{2d}R^{2d}$, $(CR^3R^{3g})_r$—$OC(O)NR^{2d}R^{2d}$, $(CR^3R^{3g})_r$—$NR^{2d}C(O)OR^{2d}$, $(CR^3R^{3g})_r$—$SO_2NR^{2d}R^{2d}$, $(CR^3R^{3g})_r$—$NR^{2d}SO_2NR^{2d}R^{2d}$, $(CR^3R^{3g})_r$—$C(O)NR^{2d}SO_2R^{2d}$, $(CR^3R^{3g})_r$—$NR^{2d}SO_2R^{2d}$, and $(CR^3R^{3g})_r$—$S(O)_pR^{2d}$, provided that $S(O)_pR^{2d}$ forms other than $S(O)_2H$ or $S(O)H$ and further provided that $R^{4a}$ is other than a hydroxamic acid;

$R^{4b}$, at each occurrence, is selected from H, =O, $(CH_2)_rOR^3$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_r$—$C(O)NR^3R^{3a}$, $(CH_2)_rNR^3C(O)NR^3R^{3a}$, $(CH_2)_r$—$C(=NR^3)NR^3R^{3a}$, $(CH_2)_rNR^3C(=NR^3)NR^3R^{3a}$, $(CH_2)_rSO_2NR^3R^{3a}$, $(CH_2)_rNR^3SO_2NR^3R^{3a}$, $(CH_2)_rNR^3SO_2$—$C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_p$—$C_{1-4}$ alkyl, $(CH_2)_rS(O)_p$-phenyl, and $(CH_2)_r(CF_2)_rCF_3$;

$R^{4c}$, at each occurrence, is selected from =O, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $C_{2-6}$ alkenyl, $C_{2-6}$ alkynyl, $(CR^3R^{3a})_rCN$, $(CR^3R^{3a})_rNO_2$, $(CR^3R^{3a})_rNR^2R^{2a}$, $(CR^3R^{3a})_rN(\rightarrow O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rN=CHOR^3$, $(CR^3R^{3a})_rC(O)NR^2(CH_2)_2NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rNR^2C(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rC(O)NR^2SO_2$—$C_{1-4}$ alkyl, $(CR^3R^{3a})_rNR^2SO_2R^{5a}$, $(CR^3R^{3a})_rS(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$4–10 membered heterocycle substituted with 0–2 $R^{4b}$ and consisting of carbon atoms and from 1–4 heteroatoms selected from the group consisting of N, O, and $S(O)_p$;

$R^5$, at each occurrence, is selected from H, $C_{1-6}$ alkyl, =O, $(CH_2)_rOR^3$, F, Cl, Br, I, —CN, $NO_2$, $(CH_2)_r$ $NR^3R^{3a}$, $(CH_2)_rC(O)R^3$, $(CH_2)_rC(O)OR^{3c}$, $(CH_2)_r$ $NR^3C(O)R^{3a}$, $(CH_2)_rC(O)NR^3R^{3a}$, $(CH_2)_rNR^3C(O)$ $NR^3R^{3a}$, $(CH_2)_rCH(=NOR^{3d})$, $(CH_2)_rC(=NR^3)$ $NR^3R^{3a}$, $(CH_2)_rNR^3C(=NR^3)NR^3R^{3a}$, $(CH_2)_r$ $SO_2NR^3R^{3a}$, $(CH_2)_rNR^3SO_2NR^3R^{3a}$, $(CH_2)_r$ $NR^3SO_2$—$C_{1-4}$ alkyl, $(CH_2)_rNR^3SO_2CF_3$, $(CH_2)_r$ $NR^3SO_2$-phenyl, $(CH_2)_rS(O)_pCF_3$, $(CH_2)_rS(O)_p$—$C_{1-4}$ alkyl, $(CH_2)_rS(O)_p$-phenyl, $(CF_2)_rCF_3$, phenyl substituted with 0–2 $R^6$, naphthyl substituted with 0–2 $R^6$, and benzyl substituted with 0–2 $R^6$;

$R^{5a}$, at each occurrence, is selected from $C_{1-6}$ alkyl, $(CH_2)_rOR^3$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CF_2)_rCF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—C(O) bond;

$R^6$, at each occurrence, is selected from H, OH, $(CH_2)_r$ $OR^2$, halo, $C_{1-4}$ alkyl, —CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, C(=NH)NH_2, NHC(=NH)NH_2, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkyl-C(O)—, $C_{1-6}$ alkyl-O—, $(CH_2)_n$-phenyl, $C_{1-4}$ alkyl-OC(O)—, $C_{6-10}$ aryl-O—, $C_{6-10}$ aryl-OC(O)—, $C_{6-10}$ aryl-CH_2—C(O)—, $C_{1-4}$ alkyl-C(O)O—$C_{1-4}$ alkyl-OC(O)—, $C_{6-10}$ aryl-C(O)O—$C_{1-4}$ alkyl-OC(O)—, $C_{1-6}$ alkyl-NH_2—C(O)—, phenyl-NH_2—C(O)—, and phenyl $C_{1-4}$ alkyl-C(O)—;

$R^8$, at each occurrence, is selected from H, $C_{1-6}$ alkyl, and $(CH_2)_n$-phenyl;

alternatively, $R^7$ and $R^8$, when attached to the same nitrogen, combine to form a 5–10 membered heterocyclic ring consisting of carbon atoms and 0–2 additional heteroatoms selected from the group consisting of N, O, and $S(O)_p$;

$R^9$, at each occurrence, is selected from H, $C_{1-6}$ alkyl, and $(CH_2)_n$-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6; and, t, at each occurrence, is selected from 0, 1, 2, and 3.

2. A compound according to claim 1, wherein:

G is a group of Formula IIa:

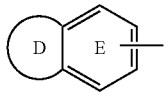

IIa ring D, including the two atoms of Ring E to which it is attached, is a 5–6 membered ring consisting of carbon atoms and 0–2 heteroatoms selected from the group consisting of N, O, and $S(O)_p$;

ring D is substituted with 0–2 R and there are 0–3 ring double bonds;

E is phenyl substituted with 1–3 R;

alternatively, ring D is absent, and ring E is phenyl substituted with 1–3 R;

alternatively, ring D is absent, ring E is phenyl and ring E is substituted with 1 R and substituted with a 5–6 membered heterocycle consisting of: carbon atoms and 1–4 heteroatoms selected from the group consisting of N, O, and $S(O)_p$, wherein the 5–6 membered heterocycle is substituted with 0–2 carbonyls and 1–3 R and there are 0–3 ring double bonds;

R is selected from H, $C_{1-4}$ alkyl, F, Cl, OH, $OCH_3$, $OCH_2CH_3$, $OCH(CH_3)_2$, CN, $C(=NH)NH_2$, $C(=NH)$ NHOH, $C(=NH)NHOCH_3$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $(CR^8R^9)_rNR^7R^8$, C(O) $NR^7R^8$, $CH_2C(O)NR^7R^8$, $S(O)_pNR^7R^8$, $CH_2S(O)_p$ $NR^7R^8$, $SO_2R^3$, and $OCF_3$;

alternatively, when 2 R groups are attached to adjacent atoms, they combine to form methylenedioxy or ethylenedioxy;

Y is a $C_{3-7}$ monocyclic carbocycle further comprising 0–2 double bonds and 0–2 carbonyl groups, and the carbocycle is substituted with 0–2 $R^4$;

alternatively, Y is $CY^1Y^2$, and $Y^1$ and $Y^2$ are independently $C_{1-3}$ alkyl substituted with 0–1 $R^4$;

$R^{1a}$, at each occurrence, is selected from H, —$(CH_2)_r$— $R^{1b}$, —$(CH(CH_3))_r$—$R^{1b}$, —$(C(CH_3)_2)_r$—$R^{1b}$, —O— $(CR^3R^{3a})_r$—$R^{1b}$, —$NR^2$—$(CR^3R^{3a})_r$—$R^{1b}$, and —S—$(CR^3R^{3a})_r$—$R^{1b}$, provided that $R^{1a}$ forms other than an N-halo, N—S, O—O, or N—CN bond;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_p$ $R^{2b}$, $NR^2(CH_2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)$ $NR^2(CH_2)_rOR^2$, $SO_2NR^2R^{2a}$, $NR^2SO_2R^2$, $C_{5-6}$ carbocycle substituted with 0–2 $R^{4b}$, and 5–6 membered heterocycle substituted with 0–2 $R^{4b}$ and consisting of carbon atoms and from 1–4 heteroatoms selected from the group consisting of N, O, and $S(O)_p$, provided that $R^{1b}$ forms other than an O—O, N-halo, N—S, or N—CN bond and provided that $S(O)_pR^2$ forms other than $S(O)_2H$ or $S(O)H$;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, a $C_{5-6}$ carbocycle-$CH_2$-substituted with 0–2 $R^{4b}$, and 5–6 membered heterocycle substituted with 0–2 $R^{4b}$ and consisting of: carbon atoms and 1–4 heteroatoms selected from the group consisting of N, O, and $S(O)_p$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle substituted with 0–2 $R^{4b}$ and consisting of: carbon atoms and 1–4 heteroatoms selected from the group consisting of N, O, and $S(O)_p$;

alternatively, $R^2$ and $R^{2a}$, together with the nitrogen atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle substituted with 0–2 $R^{4b}$ and consisting of: carbon atoms and 1–4 heteroatoms selected from the group consisting of N, O, and $S(O)_p$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle substituted with 0–2 $R^{4b}$ and consisting of carbon atoms and from 1–4 heteroatoms selected from the group consisting of N, O, and $S(O)_p$;

$R^{2d}$, at each occurrence, is selected from H, $R^{4c}$, $C_{1-4}$ alkyl substituted with 0–2 $R^{4c}$, $-(CR^3R^{3a})_r-C_{3-6}$ carbocycle substituted with 0–2 $R^{4c}$, and $-(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, when two $R^{2d}$'s are attached to the same nitrogen atom, then $R^{2d}$ and $R^{2d}$, together with the nitrogen atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-4}$ alkyl substituted with 0–2 $R^{4c}$, $-(CR^3R^{3a})_r-C_{3-6}$ carbocycle substituted with 0–2 $R^{4c}$, and $-(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^{3g}$, at each occurrence, is selected from H, $CH_3$, $CH_2CH_3$, $CH_2CH_2CH_3$, $CH(CH_3)_2$, cyclopropyl, cyclopropyl-methyl, benzyl, and phenyl;

alternatively, when $R^3$ and $R^{3g}$ are attached to the same carbon atom, they combine with the attached carbon atom to form a cyclopropyl group;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^{5a}$, $CF_3$, $CF_2CF_3$, 5–6 membered carbocycle substituted with 0–1 $R^5$, and a 5–6 membered heterocycle substituted with 0–1 $R^5$ and consisting of: carbon atoms and 1–4 heteroatoms selected from the group consisting of N, O, and $S(O)_p$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2$—$C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, $CF_3$, and $CH_2$—$CF_3$;

$R^{4c}$, at each occurrence, is selected from =O, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $C_{2-4}$ alkenyl, $C_{2-4}$ alkynyl, $(CR^3R^{3a})_rCN$, $(CR^3R^{3a})_rNO_2$, $(CR^3R^{3a})_rNR^2R^{2a}$, $(CR^3R^{3a})_rN(\rightarrow O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2R^{5a}$, $(CR^3R^{3a})_rS(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$5–10 membered heterocycle substituted with 0–2 $R^{4b}$ and consisting of carbon atoms and from 1–4 heteroatoms selected from the group consisting of N, O, and $S(O)_p$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl; and, r, at each occurrence, is selected from 0, 1, 2, and 3.

3. A compound according to claim 2, wherein:

G is selected from the group:

phenyl; 2,5-bis-aminomethyl-phenyl; 2-amido-4-methoxy-phenyl; 2-amido-5-chloro-phenyl; 2-amido-phenyl; 2-aminomethyl-3-fluoro-phenyl; 2-aminomethyl-3-methoxy-phenyl; 2-aminomethyl-4-fluoro-phenyl; 2-aminomethyl-4-methoxy-phenyl; 2-aminomethyl-5-fluoro-phenyl; 2-aminomethyl-5-methoxy-phenyl; 2-aminomethyl-6-fluoro-phenyl; 2-aminomethyl-phenyl; 2-aminosulfonyl-4-methoxy-phenyl; 2-aminosulfonyl-phenyl; 2-aminomethyl-4-ethyl-phenyl; 2-aminosulfonyl-4-ethyl-phenyl; 2-amido-4-ethyl-phenyl; 2-hydroxy-4-methoxy-phenyl; 2-methylsulfonyl-phenyl; 3-(N,N-dimethylamino)-4-chloro-phenyl; 3-(N,N-dimethylamino)-phenyl; 3-(N-hydroxy-amidino)-phenyl; 3-(N-methoxy-amidino)-phenyl; 3-(N-methylamino)-4-chloro-phenyl; 3-(N-methylamino)-phenyl; 3-amidino-phenyl; 3-amido-6-hydroxy-phenyl; 3-amido-phenyl; 3-amino-4- chloro-phenyl; 3-aminomethyl-phenyl; 3-amino-phenyl; 3-chloro-4-fluoro-phenyl; 3-chloro-phenyl; 3-hydroxy-4-methoxy-phenyl; 4-chloro-3-fluoro-phenyl; 4-chloro-phenyl; 4-ethyl-phenyl; 4-ethyl-2-methylsulfonyl-phenyl; 4-ethyl-2-methoxy-phenyl; 4-methoxy-2-methylsulfonyl-phenyl; 4-methoxy-phenyl; 5-chloro-2-aminosulfonyl-phenyl; 5-chloro-2-methylsulfonyl-phenyl;
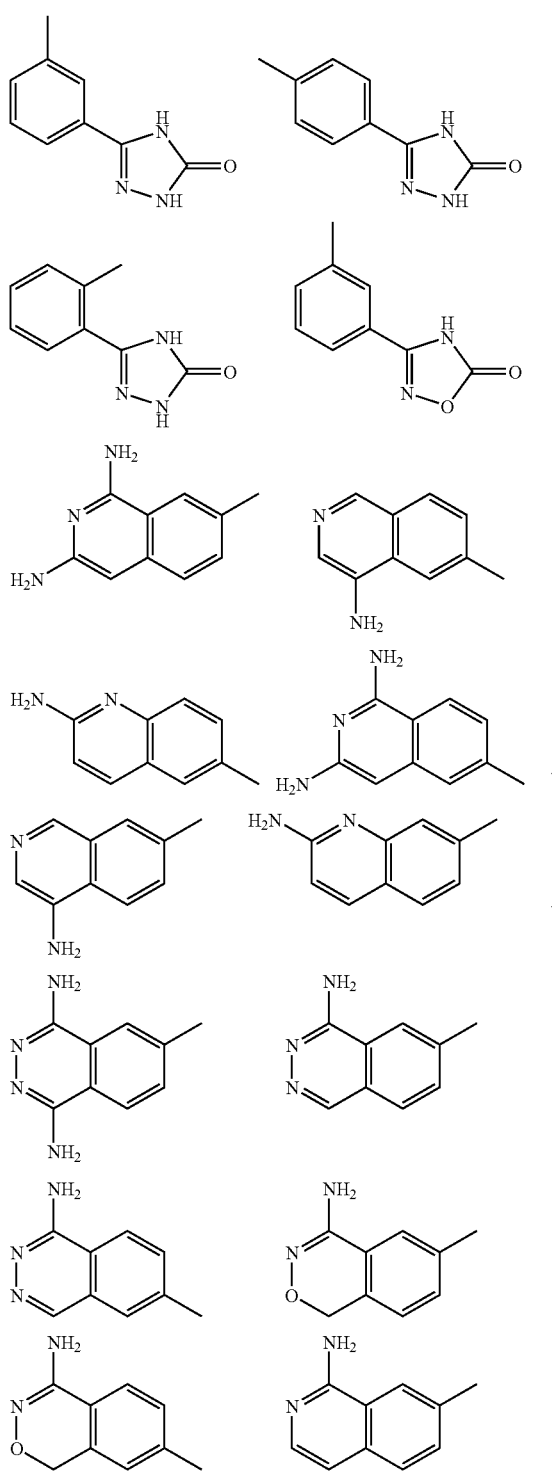
-continued
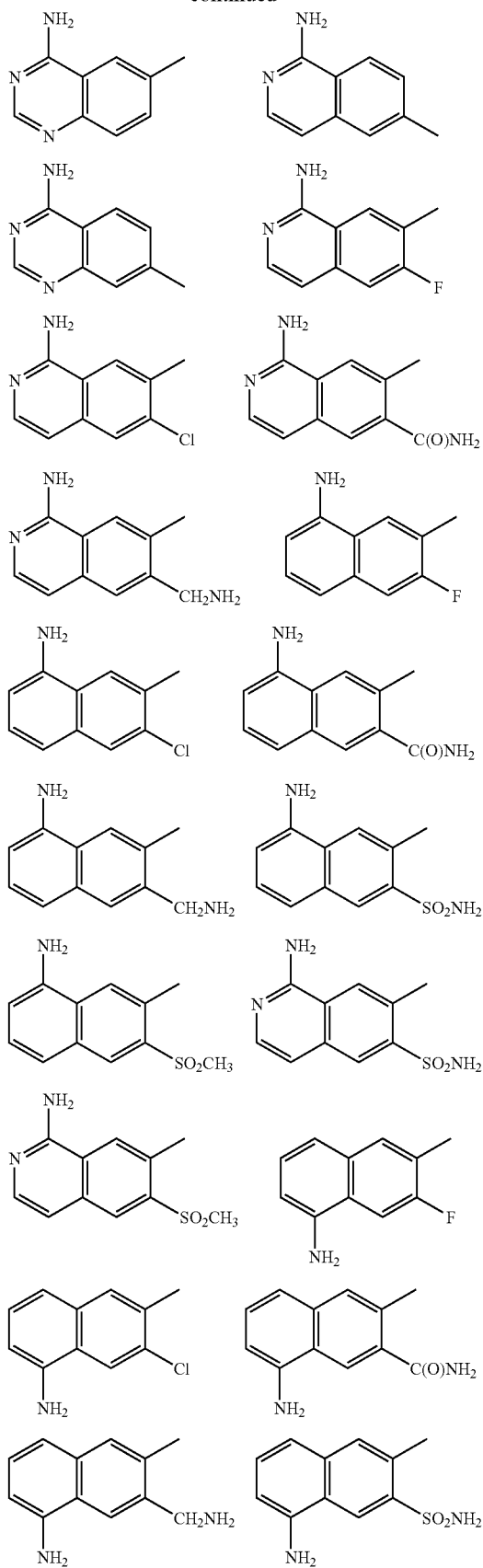

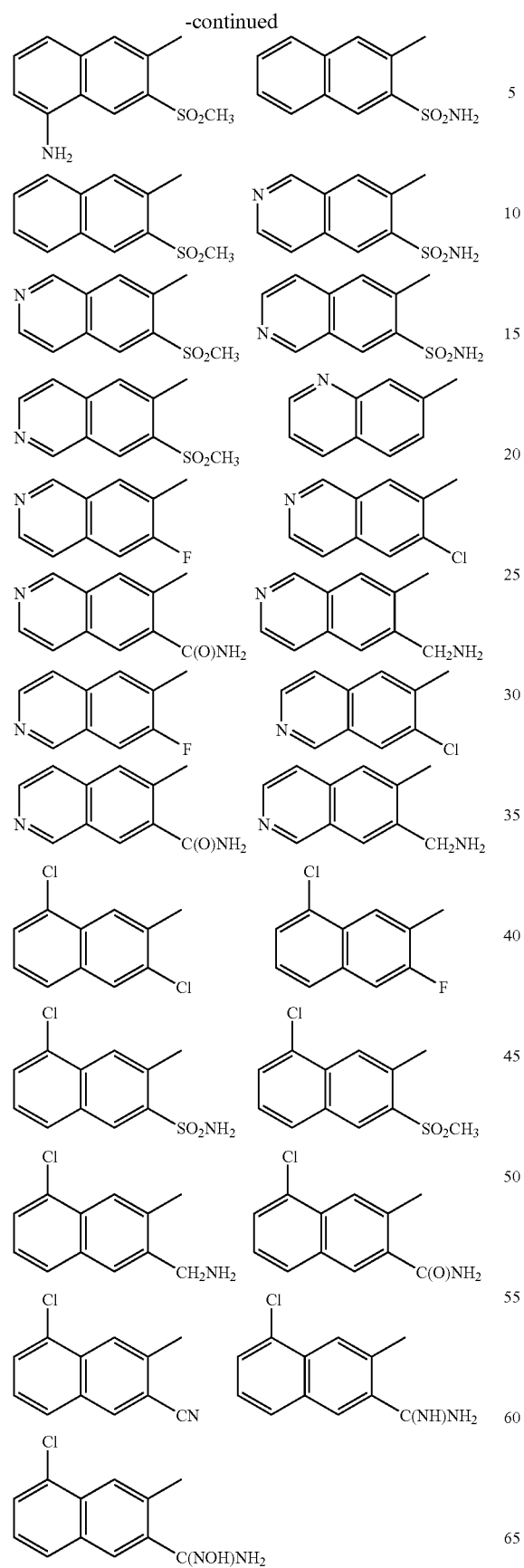
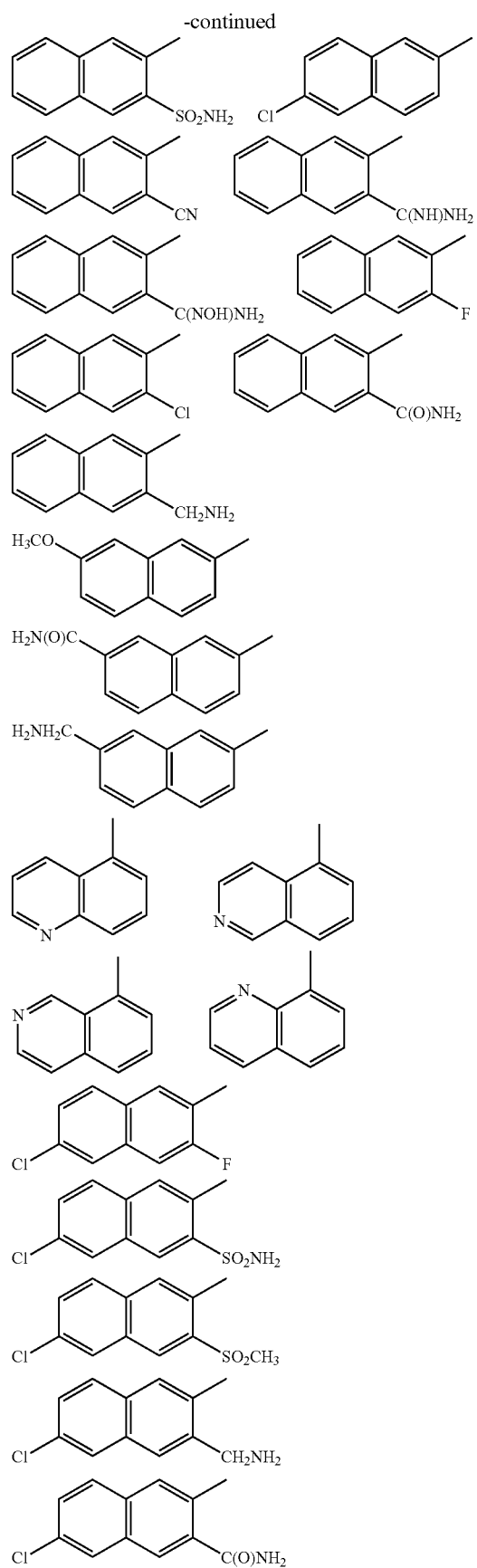

-continued

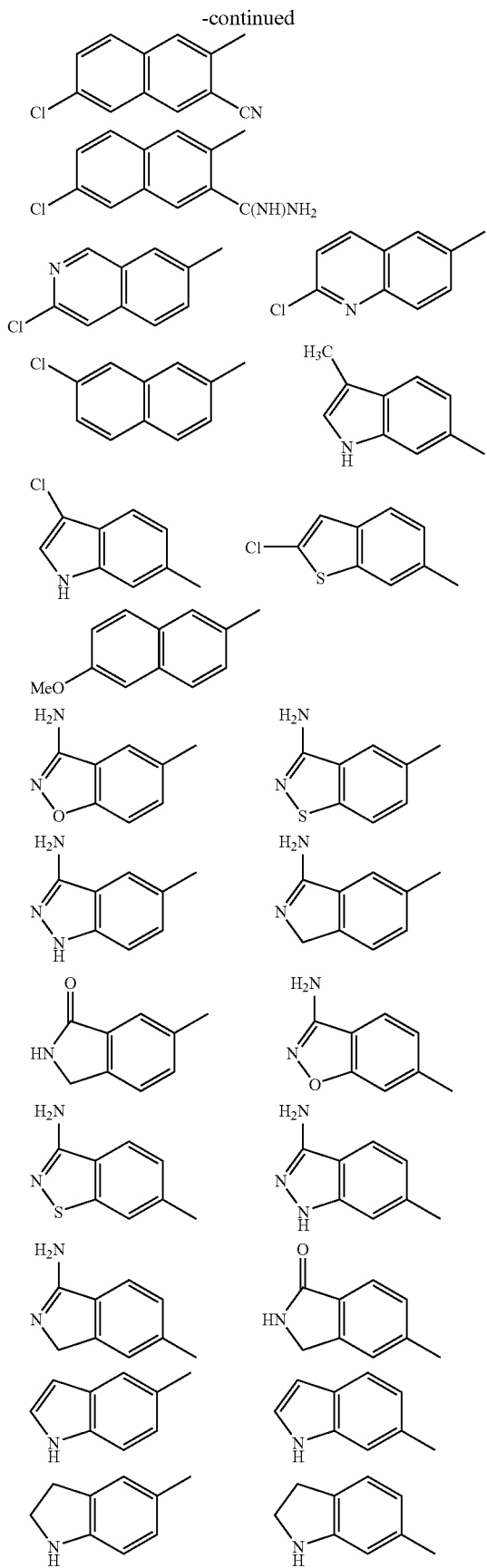

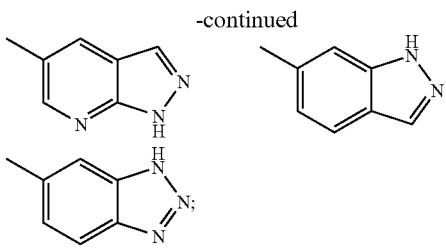

Y is a $C_{3-6}$ monocyclic carbocycle further comprising 0–1 double bonds and 0–1 carbonyl groups, and the carbocycle is substituted with 0–2 $R^4$;

alternatively, Y is $CY^1Y^2$, and $Y^1$ and $Y^2$ are independently $C_{1-2}$ alkyl substituted with 0–1 $R^4$;

$R^{1a}$, at each occurrence, is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

$R^{1b}$ is selected from H, $CH_3$, $CH_2CH_3$, F, Cl, Br, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $C(O)NR^2R^{2a}$, $SO_2NR^2R^{2a}$, $NR^2SO_2R^2$, phenyl substituted with 0–2 $R^{4b}$, and 5–6 membered aromatic heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, phenyl substituted with 0–2 $R^{4b}$, benzyl substituted with 0–2 $R^{4b}$, and 5–6 membered aromatic heterocycle substituted with 0–2 $R^{4b}$ and consisting of: carbon atoms and 1–4 heteroatoms selected from the group consisting of N, O, and $S(O)_p$;

$R^{2a}$, at each occurrence, is selected from H, $CF_3$, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle substituted with 0–2 $R^{4b}$ and consisting of: carbon atoms and 1–4 heteroatoms selected from the group consisting of N, O, and $S(O)_p$;

alternatively, $R^2$ and $R^{2a}$, together with the nitrogen atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle substituted with 0–2 $R^{4b}$ and consisting of: carbon atoms and 1–4 heteroatoms selected from the group consisting of N, O, and $S(O)_p$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle substituted with 0–2 $R^{4b}$ and consisting of carbon atoms and from 1–4 heteroatoms selected from the group consisting of N, O, and $S(O)_p$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^4$, at each occurrence, is selected from H, $(CH_2)_2OR^2$, $CH_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$ is selected from —$(CR^3R^{3g})_r$-5–6 membered carbocycle substituted with 0–3 $R^{4c}$, —$(CR^3R^{3g})_r$-5–6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3g})_rN(\to O)R^{2d}R^{2d}$, $(CR^3R^{3g})_rOR^{2d}$, $(CR^3R^{3g})_r—NR^{2d}C(O)R^{2e}$, $(CR^3R^{3g})_r—C(O)R^{2e}$, $(CR^3R^{3g})_r—OC(O)R^{2e}$, $(CR^3R^{3g})_r—C(O)NR^{2d}R^{2d}$, $(CR^3R^{3g})_r—C(O)OR^{2d}$, $(CR^3R^{3g})_r—NR^{2d}C(O)NR^{2d}R^{2d}$, $(CR^3R^{3g})_r—NR^{2d}C(O)OR^{2d}$, $(CR^3R^{3g})_r—SO_2NR^{2d}R^{2d}$, $(CR^3R^{3g})_r—NR^{2d}SO_2R^{2d}$, and $(CR^3R^{3g})_r—S(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2—C(O)R^3$, $C(O)OR^{3c}$, $CH_2—C(O)OR^{3c}$, $NR^3C(O)R^{3a}$, $CH_2NR^3C(O)R^{3a}$, $C(O)NR^3R^{3a}$, $CH_2—C(O)NR^3R^{3a}$, $SO_2NR^3R^{3a}$, $CH_2SO_2NR^3R^{3a}$, $NR_3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})F$, Br, $(CR^3R^{3a})Br$, Cl, $(CR^3R^{3a})Cl$, $CF_3$, $(CR^3R^{3a})CF_3$, $C_{1-4}$ alkyl, $C_{2-3}$ alkenyl, $C_{2-3}$ alkynyl, —CN, $(CR^3R^{3a})CN$, $NO_2$, $(CR^3R^{3a})NO_2$, $NR^2R^{2a}$, $(CR^3R^{3a})NR^2R^{2a}$, $N(\to O)R^2R^{2a}$, $(CR^3R^{3a})N(\to O)R^2R^{2a}$, $C(O)R^{2c}$, $(CR^3R^{3a})C(O)R^{2c}$, $NR^2C(O)R^{2b}$, $(CR^3R^{3a})NR^2C(O)R^{2b}$, $C(O)NR^2R^{2a}$, $(CR^3R^{3a})C(O)NR^2R^{2a}$, $NR^2C(O)NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})NR^2SO_2NR^2R^{2a}$, $NR^2SO_2R^{5a}$, $(CR^3R^{3a})NR^2SO_2R^{5a}$, $S(O)_pR^{5a}$, $(CR^3R^{3a})S(O)_pR^{5a}$, $CF_3$, $CF_2CF_3$, $C_{3-10}$ carbocycle substituted with 0–2 $R^{4b}$, $(CR^3R^{3a})$—$C_{3-10}$ carbocycle substituted with 0–2 $R^{4b}$, 5–10 membered heterocycle substituted with 0–2 $R^{4b}$ and consisting of: carbon atoms and from 1–4 heteroatoms selected from the group consisting of N, O, and $S(O)_p$, and $(CR^3R^{3a})$-5–10 membered heterocycle substituted with 0–2 $R^{4b}$ and consisting of carbon atoms and from 1–4 heteroatoms selected from the group consisting of N, O, and $S(O)_p$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.

4. A compound according to claim 3, wherein:

G is selected from the group:

phenyl; 2-amido-4-methoxy-phenyl; 2-amido-phenyl; 2-aminomethyl-3-fluoro-phenyl; 2-aminomethyl-4-fluoro-phenyl; 2-aminomethyl-4-methoxy-phenyl; 2-aminomethyl-5-fluoro-phenyl; 2-aminomethyl-5-methoxy-phenyl; 2-aminomethyl-6-fluoro-phenyl; 2-aminomethyl-phenyl; 2-aminosulfonyl-4-methoxy-phenyl; 2-aminosulfonyl-phenyl; 2-methylsulfonyl-phenyl; 2-aminomethyl-4-ethyl-phenyl; 2-aminosulfonyl-4-ethyl-phenyl; 2-amido-4-ethyl-phenyl; 3-(N,N-dimethylamino)-4-chloro-phenyl; 3-(N,N-dimethylamino)-phenyl; 3-(N-methylamino)-4-chloro-phenyl; 3-(N-methylamino)-phenyl; 3-amido-phenyl; 3-amino-4-chloro-phenyl; 3-aminomethyl-phenyl; 3-amino-phenyl; 3-chloro-phenyl; 4-chloro-phenyl; 4-ethyl-phenyl; 4-ethyl-2-methylsulfonyl-phenyl; 4-ethyl-2-methoxy-phenyl; 4-methoxy-2-methylsulfonyl-phenyl; 4-methoxy-phenyl;

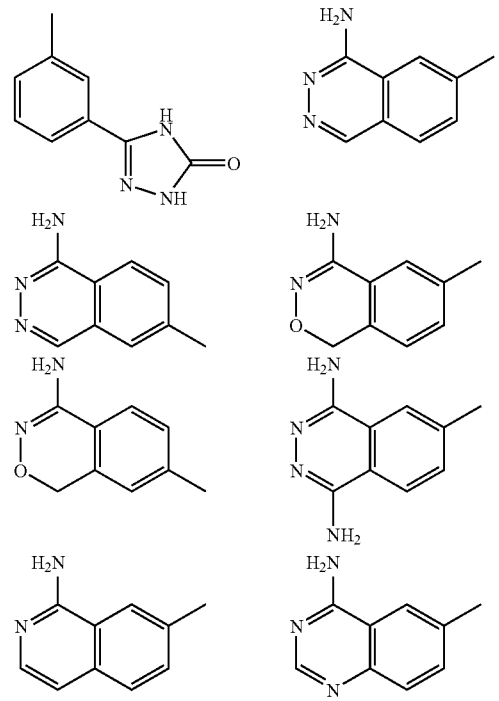

-continued
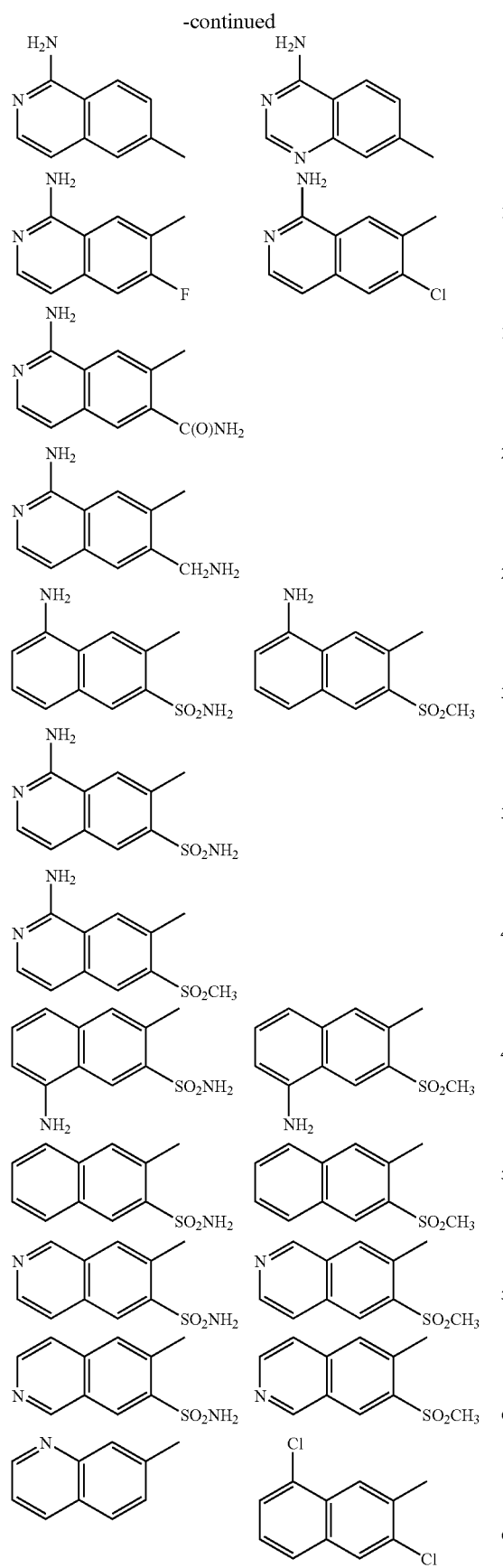
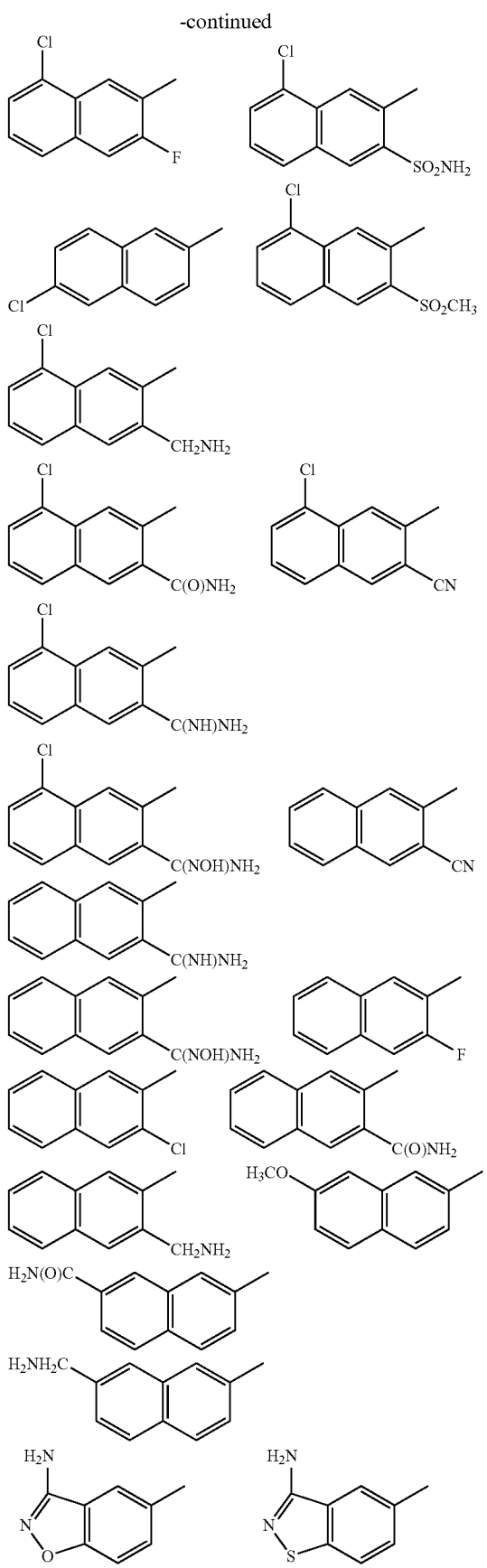

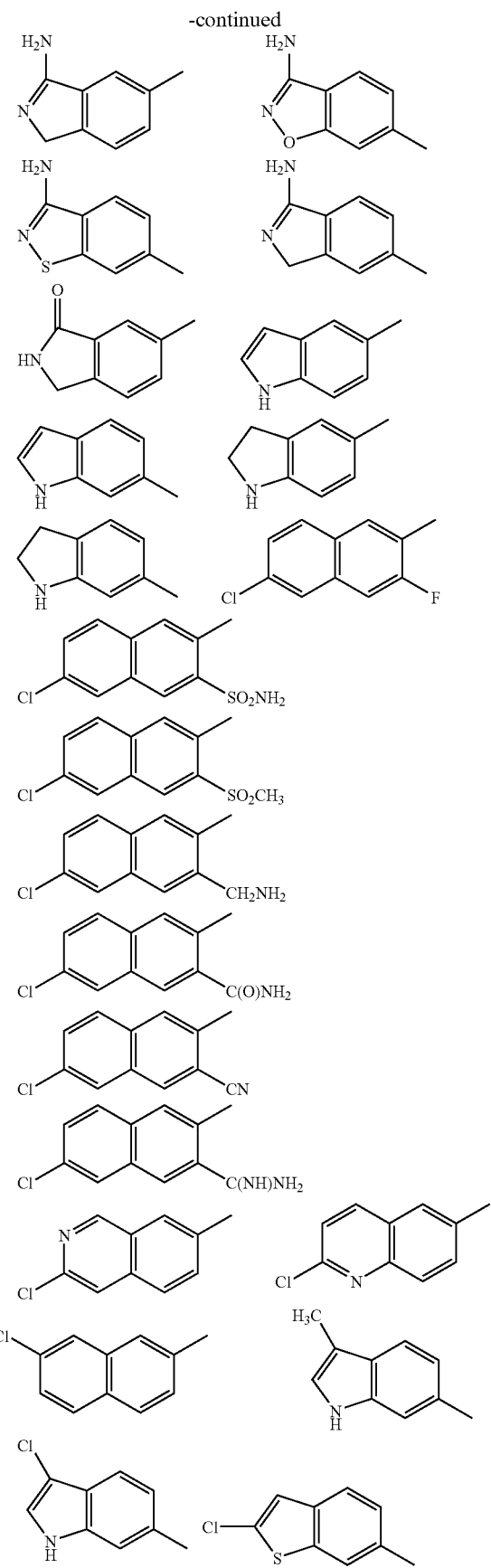

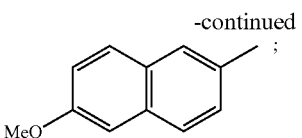

Y is selected from $C(CH_3)_2$, $C(CH_2CH_3)_2$, cyclopropyl, cyclobutyl, cyclopentyl, cyclopentanonyl, cyclohexyl, and cyclohexanonyl, and, when Y is a ring, Y is substituted with 0–1 $R^4$;

$R^{1a}$, at each occurrence, is selected from H, $R^{1b}$, $CH(CH_3)R^{1b}$, $C(CH_3)_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^2$, $C(O)NR^2R^{2a}$, $SO_2NR^2R^{2a}$, $NR^2SO_2R^2$, and 5–6 membered aromatic heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5–6 membered aromatic heterocycle substituted with 0–1 $R^{4b}$ and consisting of: carbon atoms and 1–4 heteroatoms selected from the group consisting of N, O, and $S(O)_p$;

$R^{2a}$, at each occurrence, is selected from H, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle substituted with 0–1 $R^{4b}$ and consisting of: carbon atoms and 1–4 heteroatoms selected from the group consisting of N, O, and $S(O)_p$;

alternatively, $R^2$ and $R^{2a}$, together with the nitrogen atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle substituted with 0–1 $R^{4b}$ and consisting of: carbon atoms and 1–4 heteroatoms selected from the group consisting of N, O, and $S(O)_p$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle substituted with 0–1 $R^{4b}$ and consisting of carbon atoms and from 1–4 heteroatoms selected from the group consisting of N, O, and $S(O)_p$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^4$, at each occurrence, is selected from OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $CF_3$, and $CF_2CF_3$;

$R^{4a}$ is selected from —$(CR^3R^{3g})_r$-5–6 membered carbocycle substituted with 0–3 $R^{4c}$, —$(CR^3R^{3g})_r$-5–6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})_r$—$C(O)NR^{2d}R^{2d}$, $(CR^3R^{3g})_r$—$NR^{2d}C(O)R^{2e}$, $(CR^3R^{3g})_r$—$C(O)R^{2e}$, $(CR^3R^{3g})_r$—$NR^{2d}C(O)NR^{2d}R^{2d}$, $(CR^3R^{3g})_r$—$NR^{2d}C(O)OR^{2d}$, $(CR^3R^{3g})_r$—$NR^{2d}SO_2R^{2d}$, and $(CR^3R^{3g})_r$—$S(O)_pR^{2d}$, provided that $S(O)_pR^{2d}$ forms other than $S(O)_2H$ or S(O)H;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, and $CF_3$;

$R^{4c}$, at each occurrence, is selected from =O, $OR^2$, $CH_2OR^2$, F, Br, Cl, $CF_3$, $CH_3$, $CH_2CH_3$, $CH_2CH_2CH_3$, $CH(CH_3)_2$, $C_{2-3}$ alkenyl, $C_{2-3}$ alkynyl, —CN, $NO_2$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, $CF_2CF_3$, $C_{3-6}$ carbocycle substituted with 0–2 $R^{4b}$, $(CH_2)$—$C_{3-6}$ carbocycle substituted with 0–2 $R^{4b}$, 5–6 membered heterocycle substituted with 0–2 $R^{4b}$ and consisting of carbon atoms and from 1–4 heteroatoms selected from the group consisting of N, O, and $S(O)_p$, and $(CH_2)$-5–6 membered heterocycle substituted with 0–2 $R^{4b}$ and consisting of carbon atoms and from 1–4 heteroatoms selected from the group consisting of N, O, and $S(O)_p$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR_3SO_2$—$C_{1-4}$ alkyl, $NR^3SO_2$-phenyl, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$; and, r, at each occurrence, is selected from 0, 1, and 2.

5. A compound according to claim 4, wherein:

-G is selected from:

2-amido-4-methoxy-phenyl; 2-amido-phenyl; 2-aminomethyl-3-fluoro-phenyl; 2-aminomethyl-4-fluoro-phenyl; 2-aminomethyl-5-fluoro-phenyl; 2-aminomethyl-6-fluoro-phenyl; 2-aminomethyl-phenyl; 2-aminosulfonyl-4-methoxy-phenyl; 2-aminosulfonyl-phenyl; 3-amido-phenyl; 3-amino-4-chloro-phenyl; 3-aminomethyl-phenyl; 3-chloro-phenyl; 4-chloro-phenyl; 4-ethyl-phenyl; 4-methoxy-phenyl;

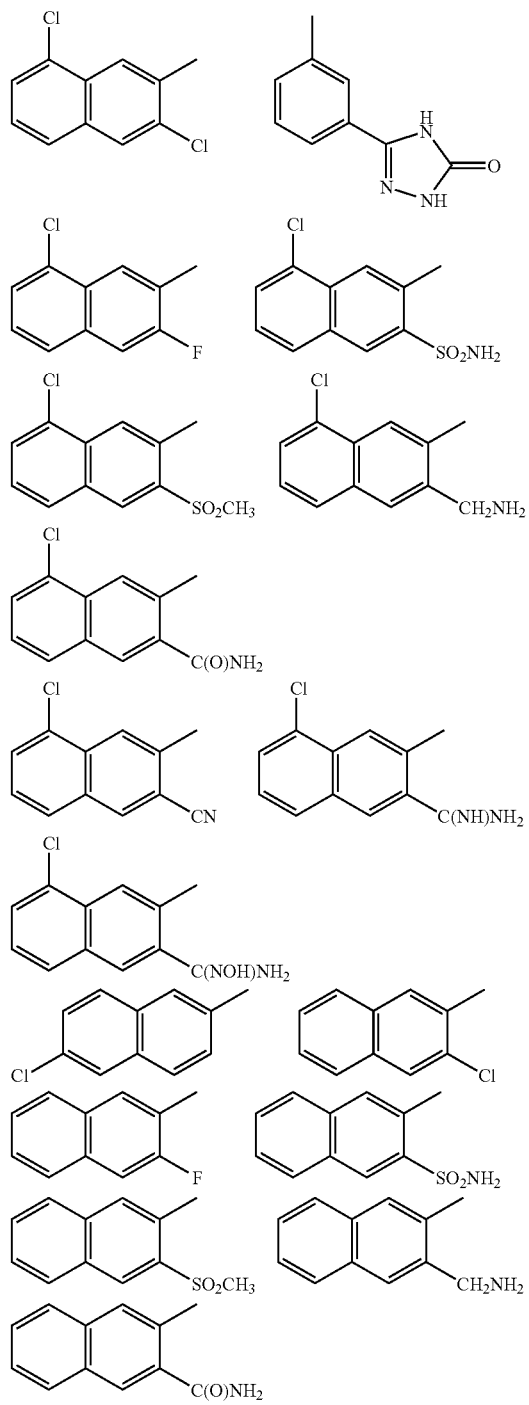

-continued

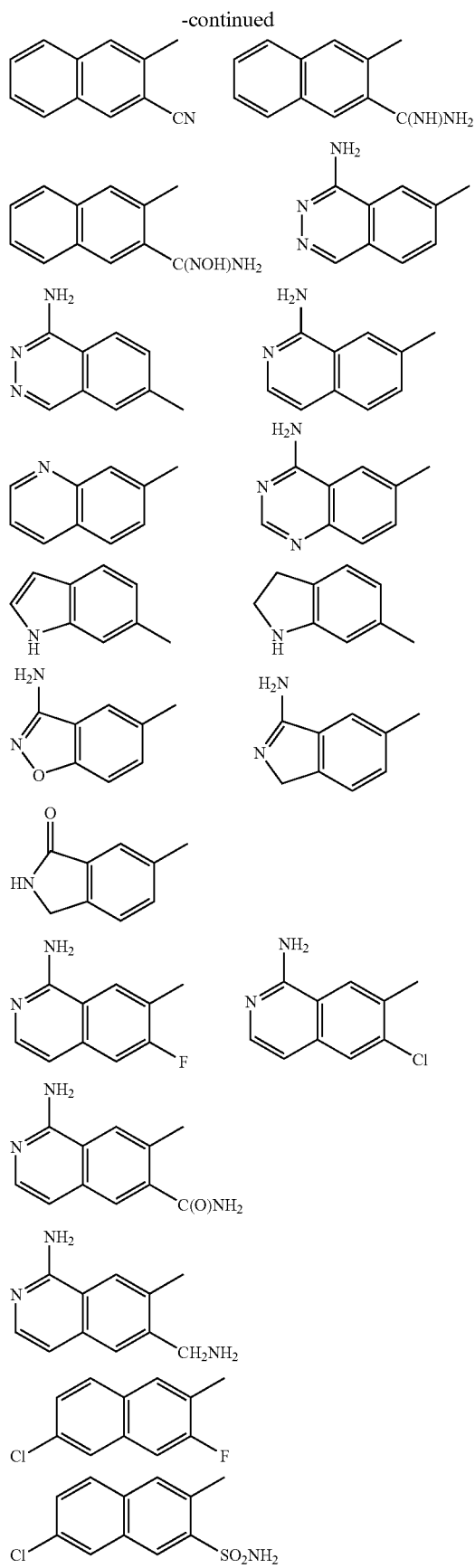

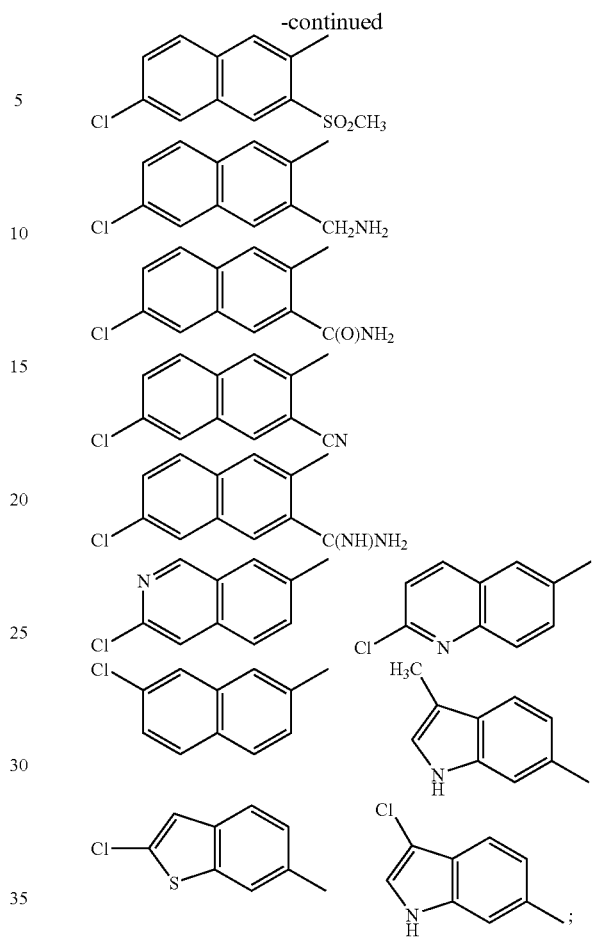

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

Y is selected from $C(CH_3)_2$, $C(CH_2CH_3)_2$, cyclopropyl, cyclobutyl, cyclopentyl, 2-cyclopentanonyl, cyclohexyl, and 2-cyclohexanonyl;

$R^{1a}$, at each occurrence, is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5 membered aromatic heterocycle substituted with 0–1 $R^{4b}$ and consisting of: carbon atoms and 1–4 heteroatoms selected from the group consisting of N, O, and $S(O)_p$;

$R^{2a}$, at each occurrence, is selected from H, $CH_3$, and $CH_2CH_3$;

alternatively, $R^2$ and $R^{2a}$, together with the nitrogen atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from OH, $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from —$(CH_2)_r$-5–6 membered carbocycle substituted with 0–3 $R^{4c}$, —$(CH_2)_r$-5–6 membered heterocycle substituted with 0–3 $R^{4c}$ and consisting of: carbon atoms and 1–4 heteroatoms selected from the group consisting of N, O, and $S(O)_p$, $(CH_2)_rNR^{2d}R^{2d}$, $(CH_2)_rN(\rightarrow O)R^{2d}R^{2d}$, $(CH_2)_rOR^{2d}$, $(CH_2)_r$—C(O)$NR^{2d}R^{2d}$, $(CH_2)_r$—$NR^{2d}C(O)R^{2e}$, $(CH_2)_r$—C(O)$R^{2e}$, $(CH_2)_r$—$NR^{2d}C(O)NR^{2d}R^{2d}$, $(CH_2)_r$—$NR^{2d}C(O)OR^{2d}$, $(CH_2)_r$—$NR^{2d}SO_2R^{2d}$, and $(CH_2)_r$—$S(O)_pR^{2d}$, provided that $S(O)_pR^{2d}$ forms other than $S(O)_2H$ or S(O)H;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$;

$R^{4c}$, at each occurrence, is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $C_{2-3}$ alkenyl, $C_{2-3}$ alkynyl, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, cyclopropyl substituted with 0–1 $R^{4b}$, cyclobutyl substituted with 0–1 $R^{4b}$, cyclopentyl substituted with 0–1 $R^{4b}$, phenyl substituted with 0–1 $R^{4b}$, —$CH_2$-cyclopropyl substituted with 0–1 $R^{4b}$, —$CH_2$-cyclobutyl substituted with 0–1 $R^{4b}$, —$CH_2$-cyclopentyl substituted with 0–1 $R^{4b}$, benzyl substituted with 0–2 $R^{4b}$, 5–6 membered aromatic heterocycle substituted with 0–2 $R^{4b}$ and consisting of carbon atoms and from 1–4 heteroatoms selected from the group consisting of N, O, and $S(O)_p$, and $(CH_2)$5–6 membered aromatic heterocycle substituted with 0–2 $R^{4b}$ and consisting of carbon atoms and from 1–4 heteroatoms selected from the group consisting of N, O, and $S(O)_p$;

$R^5$, at each occurrence, is selected from H, =O, $CH_3$, $CH_2CH_3$, $OR^3$, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_2$—$CH_3$, $S(O)_2$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

6. A compound according to claim 5, wherein:

-G is selected from:

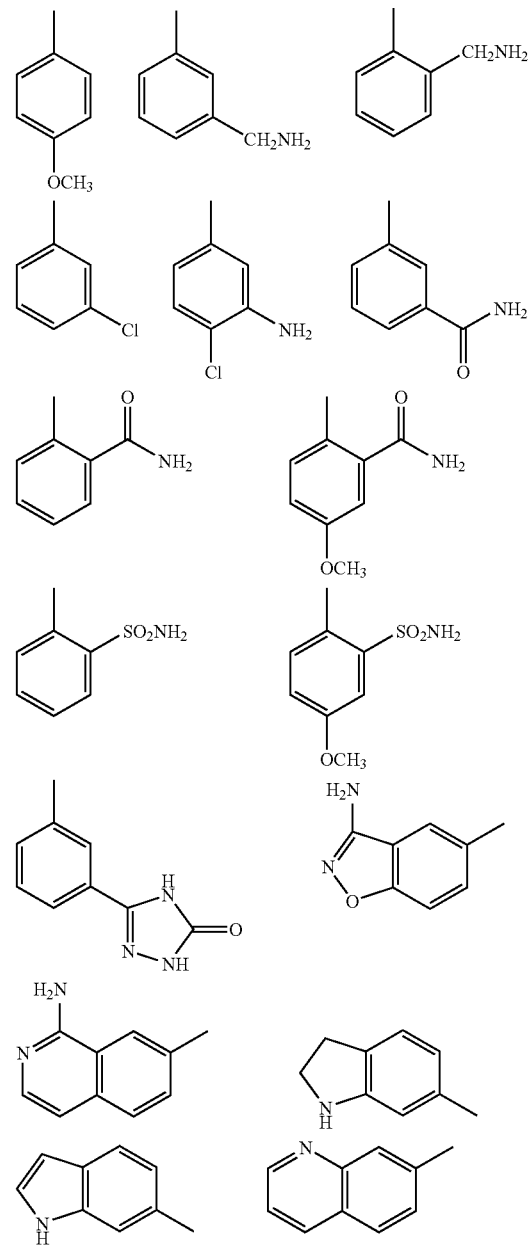

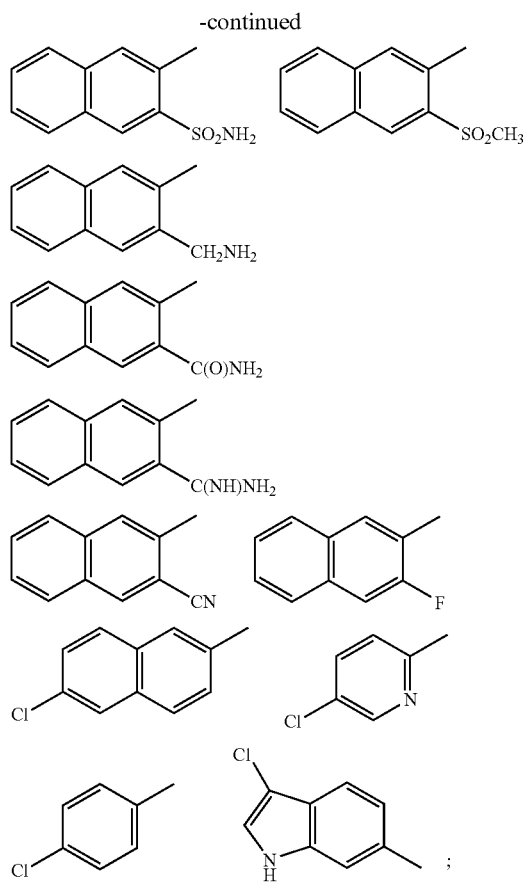

A-B is selected from:

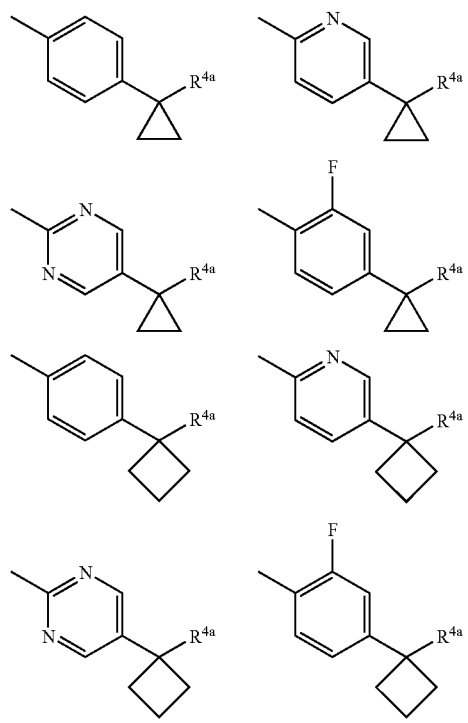

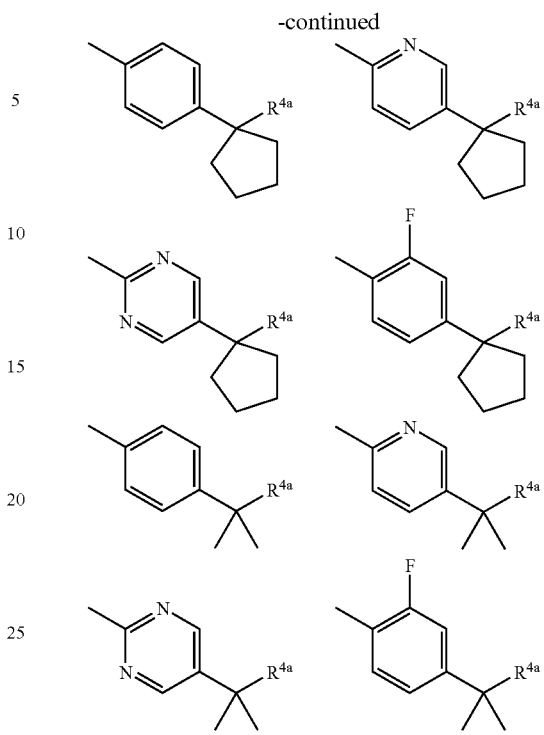

$R^{2d}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from $NR^{2d}R^{2d}$, $CH_2NR^{2d}R^{2d}$, $CH_2CH_2NR^{2d}R^{2d}$, $N(\to O)R^{2d}R^{2d}$, $CH_2N(\to O)R^{2d}R^{2d}$, $CH_2OR^{2d}$, $C(O)R^{2e}$, $C(O)NR^{2d}R^{2d}$, $CH_2C(O)NR^{2d}R^{2d}$, $NR^{2d}C(O)R^{2e}$, $CH_2NR^{2d}C(O)R^{2e}$, $NR^{2d}C(O)NR^{2d}R^{2d}$, $CH_2NR^{2d}C(O)NR^{2d}R^{2d}$, $NR^{2d}C(O)OR^{2d}$, $CH_2NR^{2d}C(O)OR^{2d}$, $NR^{2d}SO_2R^{2d}$, $CH_2NR^{2d}SO_2R^{2d}$, $S(O)_pR^{2d}$, $CH_2S(O)_pR^{2d}$, 5–6 membered carbocycle substituted with 0–2 $R^{4c}$, —($CH_2$)-5–6 membered carbocycle substituted with 0–2 $R^{4c}$, —($CH_2$)$_2$-5–6 membered carbocycle substituted with 0-2 $R^4C$, 5-6 membered heterocycle substituted with 0–2 $R^{4c}$ and consisting of: carbon atoms and 1–4 heteroatoms selected from the group consisting of N, O, and $S(O)_p$, —($CH_2$)-5–6 membered heterocycle substituted with 0–2 $R^{4c}$ and consisting of: carbon atoms and 1–4 heteroatoms selected from the group consisting of N, O, and $S(O)_p$, and —($CH_2$)$_2$-5–6 membered heterocycle substituted with 0–2 $R^{4c}$ and consisting of: carbon atoms and 1–4 heteroatoms selected from the group consisting of N, O, and S(O)$_p$ provided that S(O)$_p$R$^{2d}$ forms other than S(O)$_2$H or S(O)H; and, R$^{4c}$ is selected from =O, OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, CH=CH$_2$, CH≡CH, CH$_2$OH, CH$_2$OCH$_3$, CH$_2$OCH$_2$CH$_3$, CH$_2$OCH$_2$CH$_2$CH$_3$, CH$_2$OCH(CH$_3$)$_2$, F, Br, Cl, CF$_3$, NR$^2$R$^{2a}$, CH$_2$NR$^2$R$^{2a}$, C(O)R$^{2c}$, CH$_2$C(O)R$^{2c}$, NR$^2$C(O)R$^{2b}$, CH$_2$NR$^2$C(O)R$^{2b}$, C(O)NR$^2$R$^{2a}$, CH$_2$C(O)NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, and CH$_2$S(O)$_p$R$^{5a}$.

7. A compound according to claim 6, wherein:

A-B is selected from:

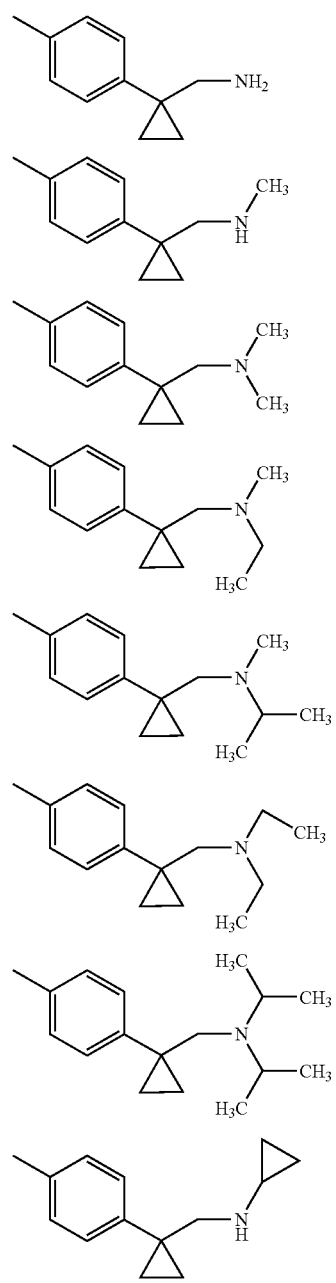

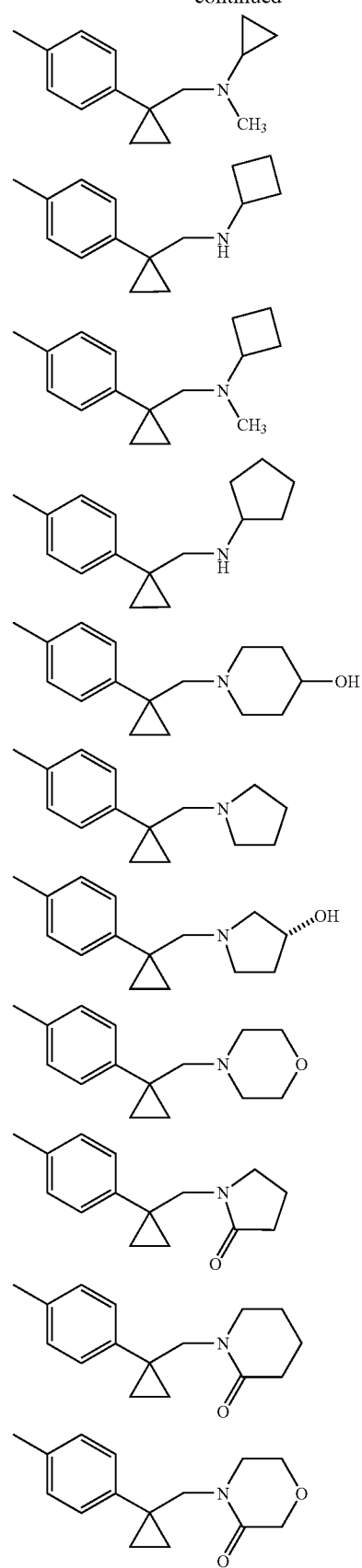

-continued

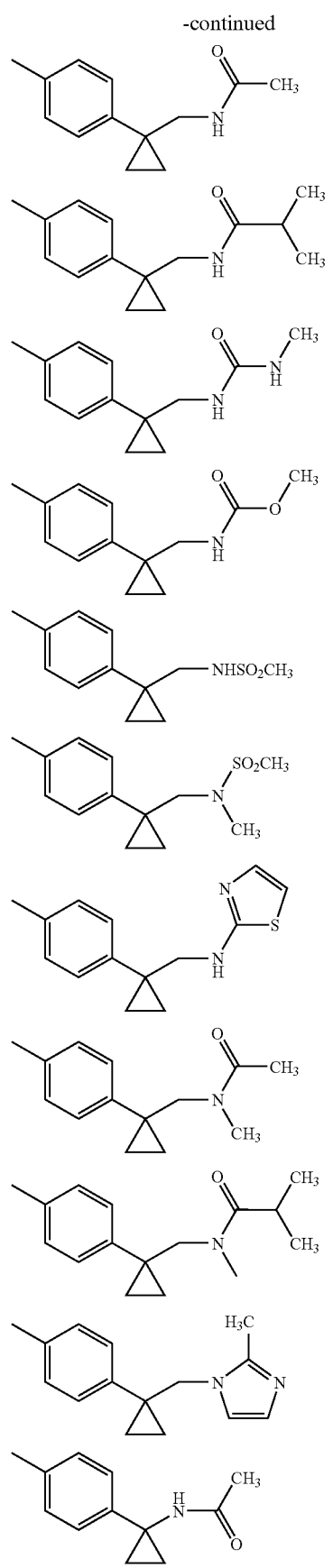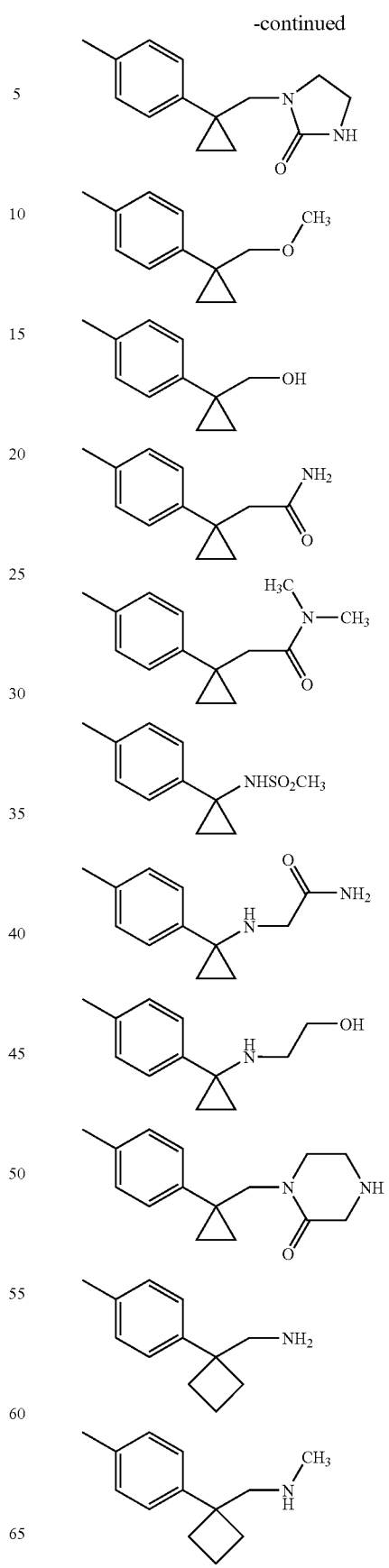

-continued
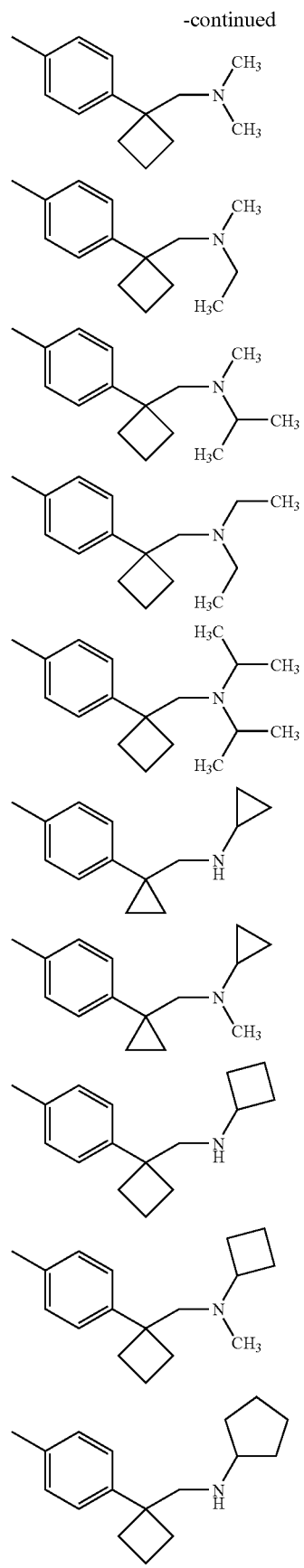
-continued
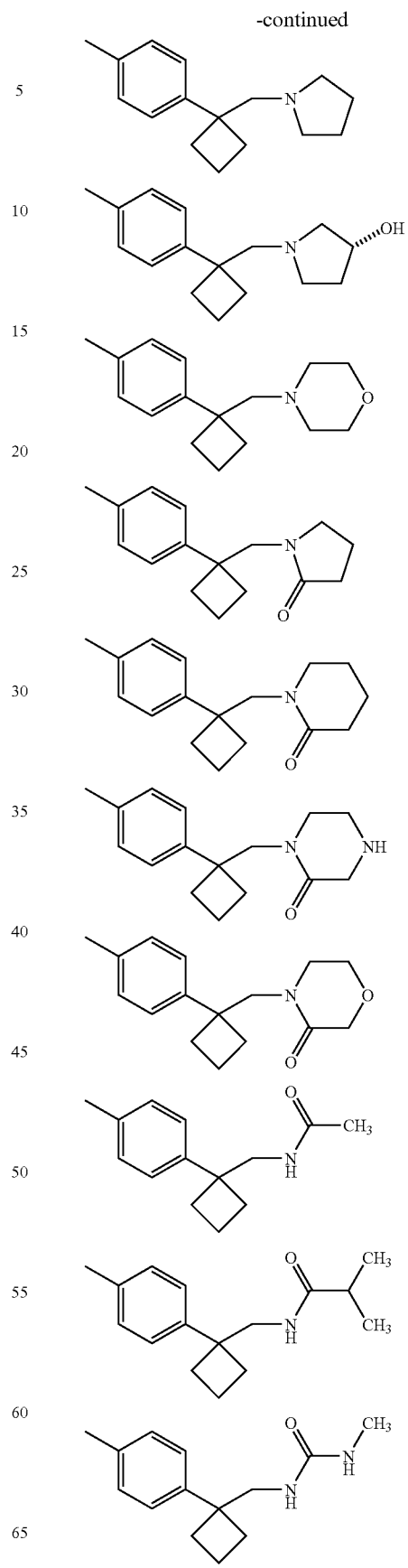

-continued
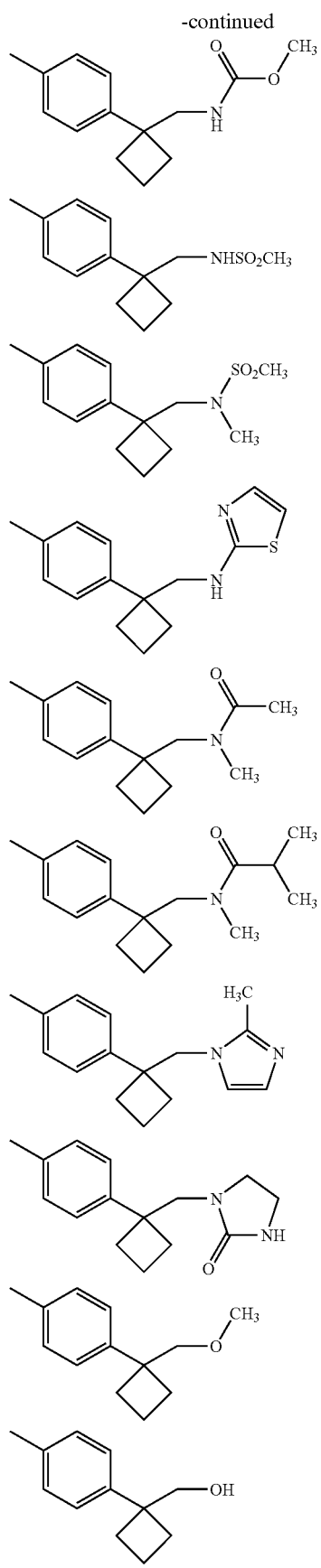
-continued
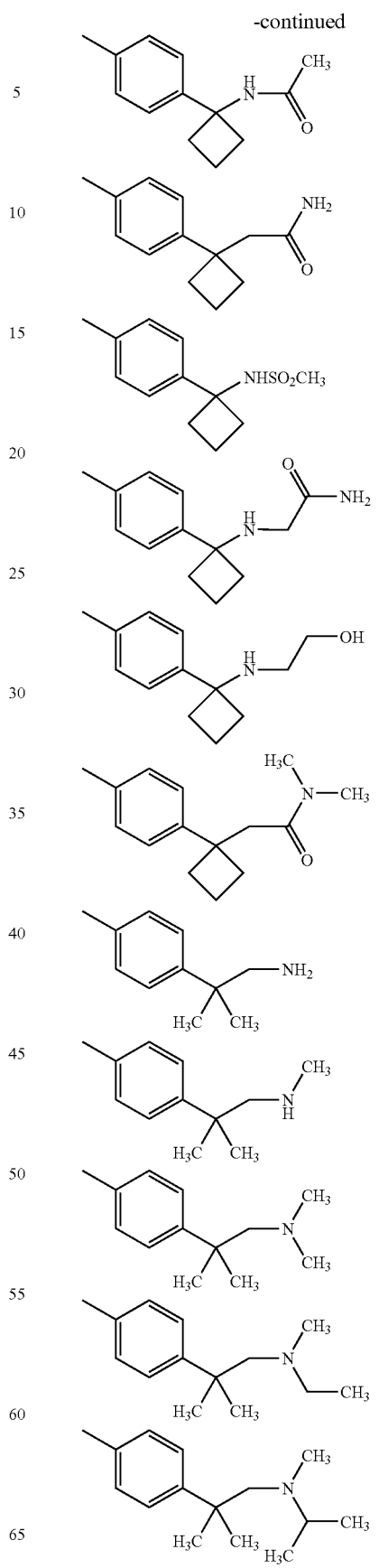

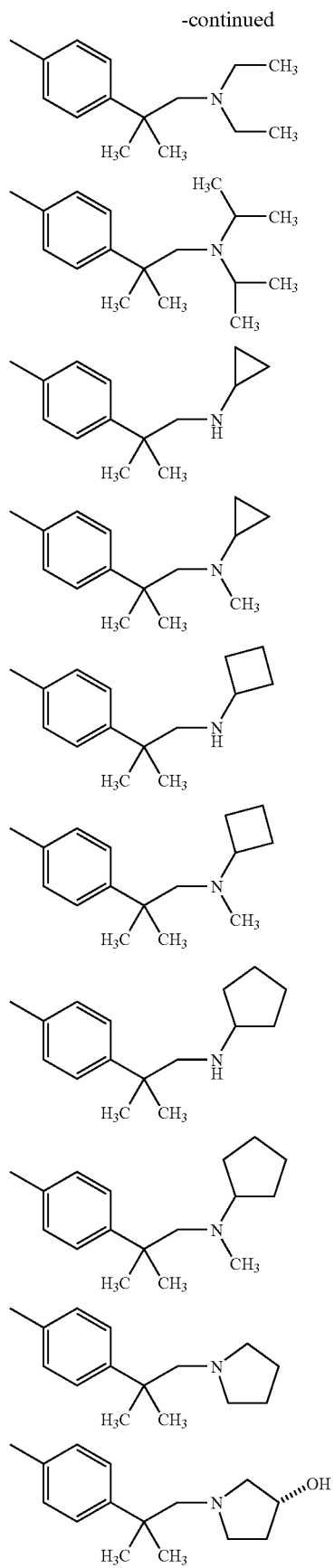
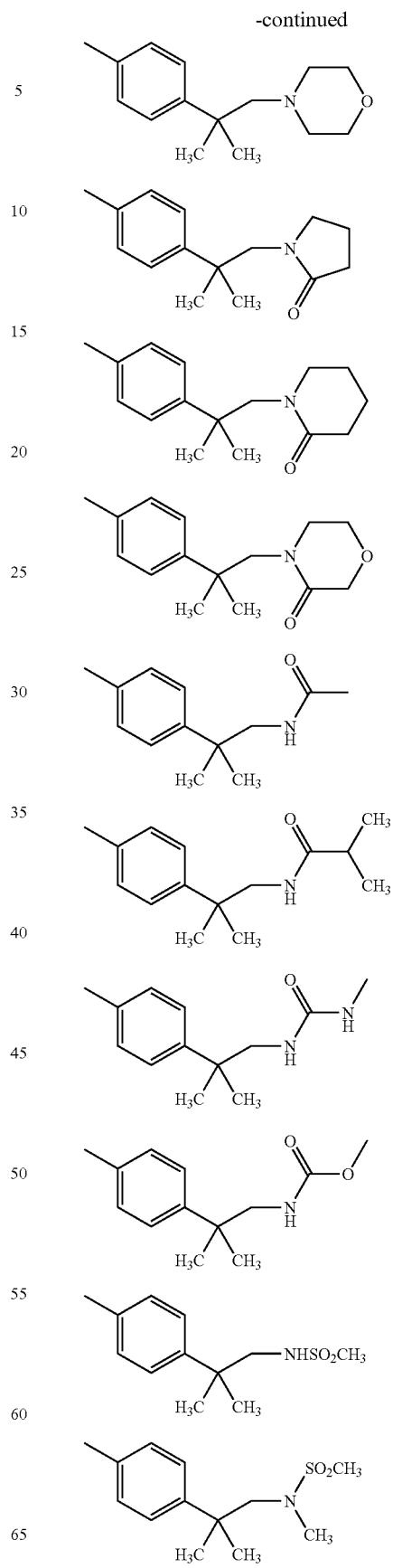

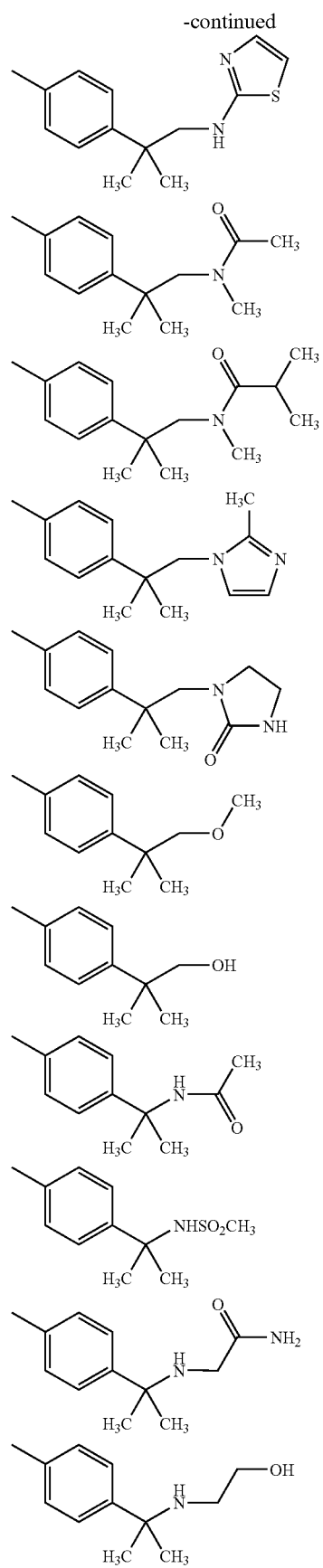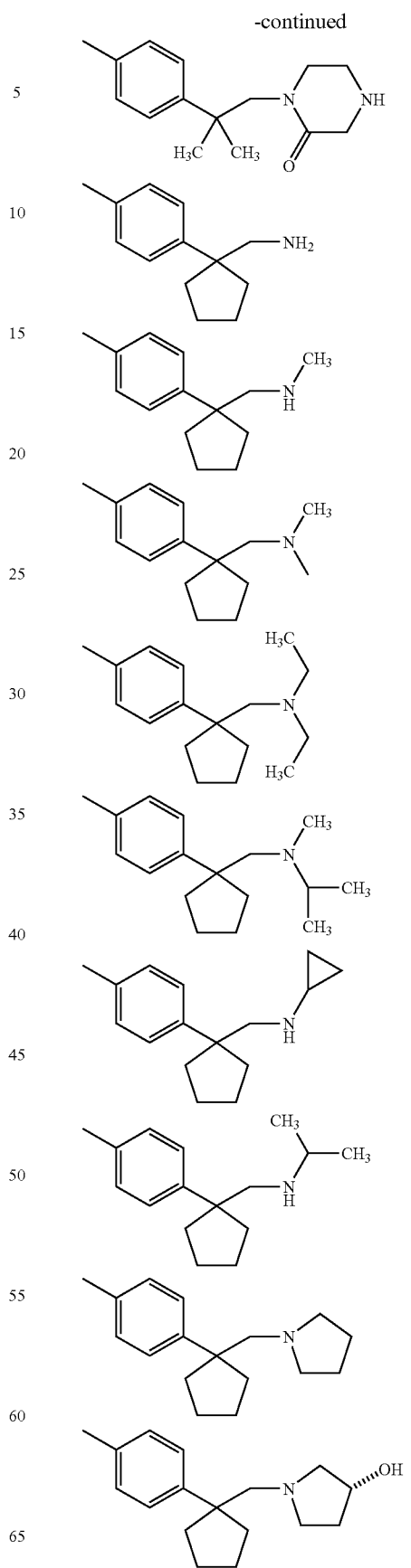

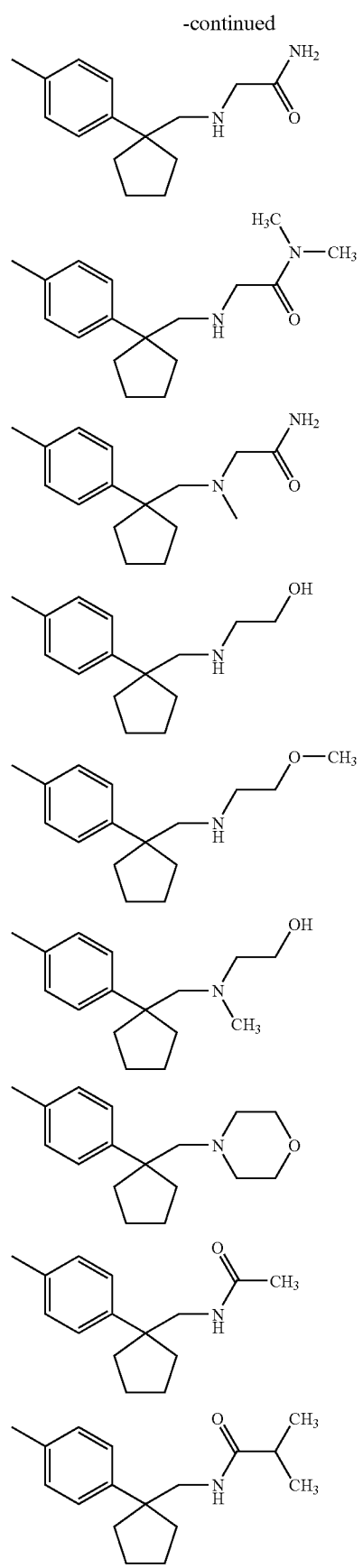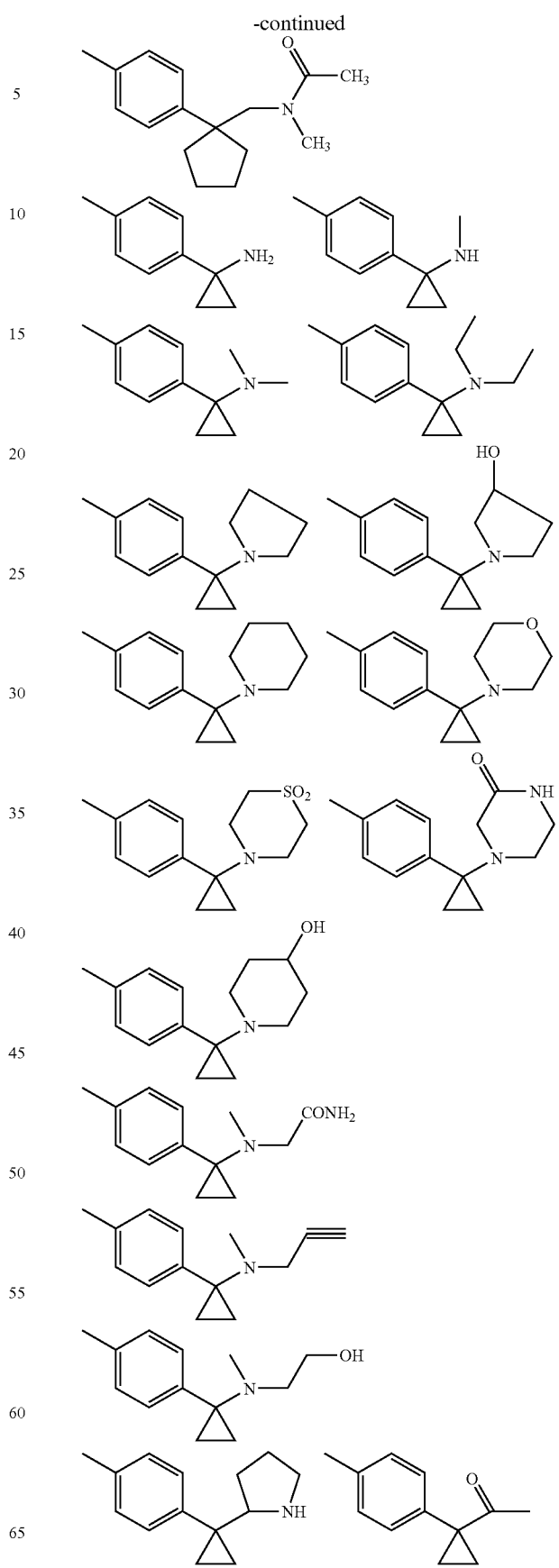

-continued
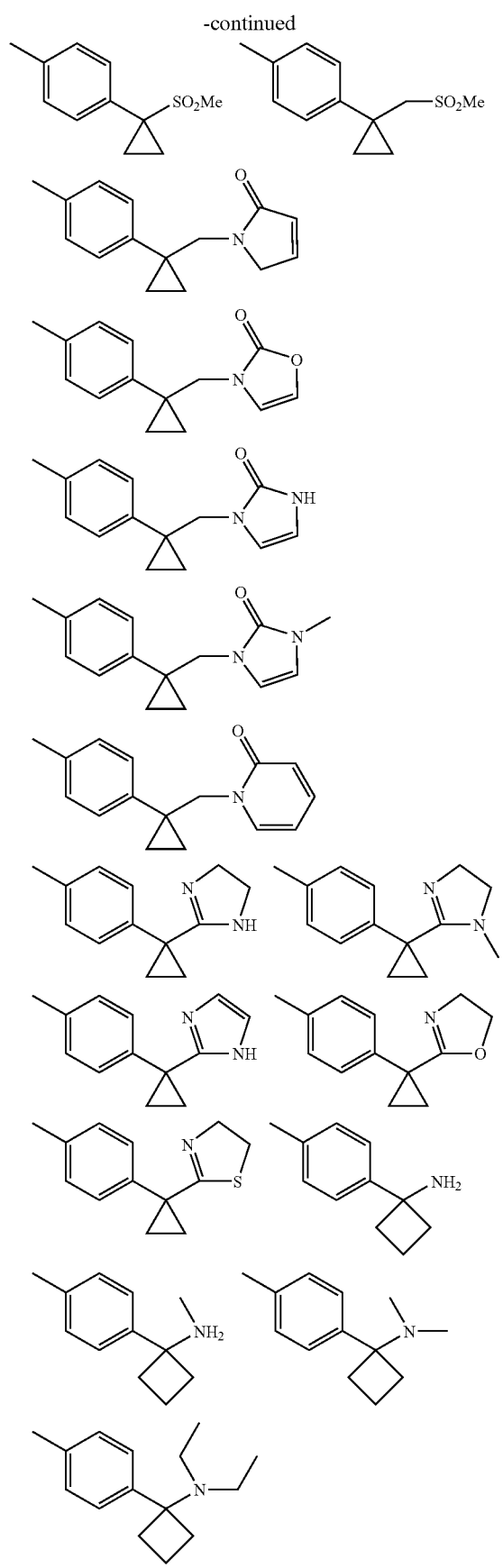
-continued
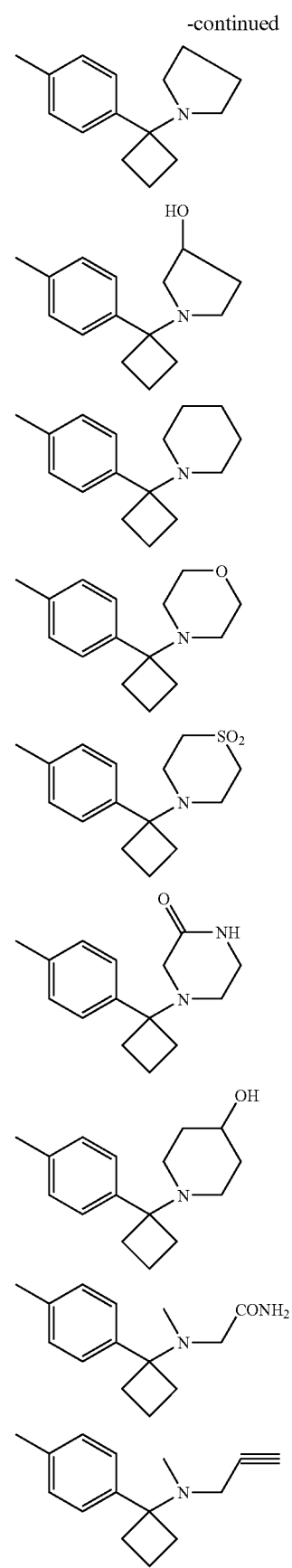

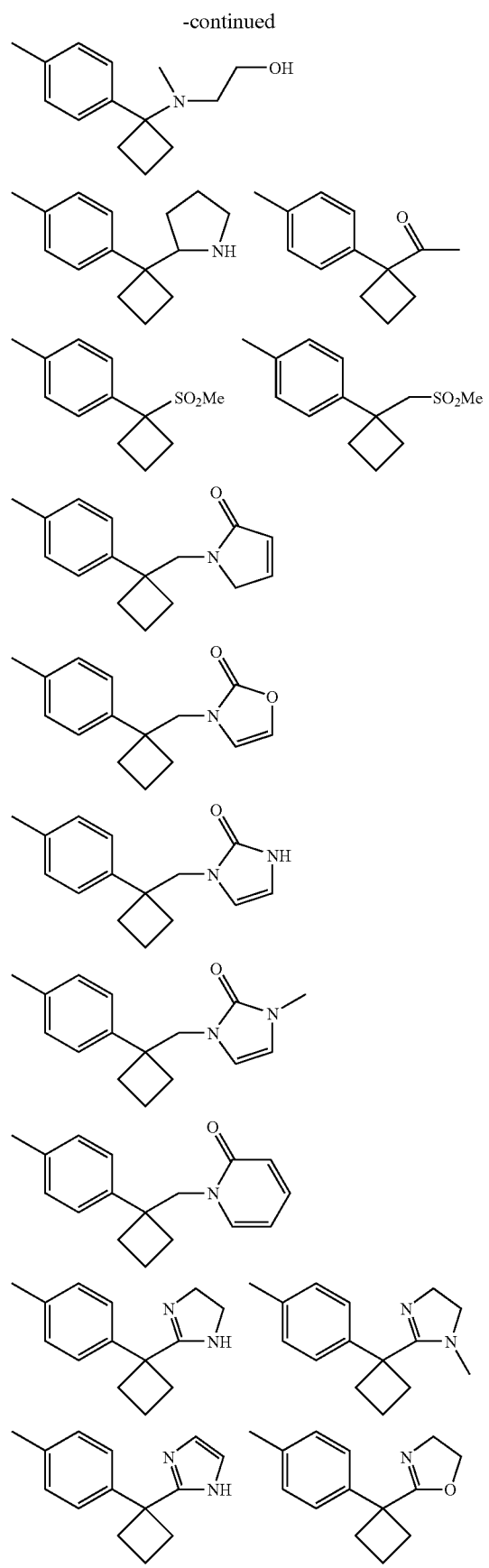
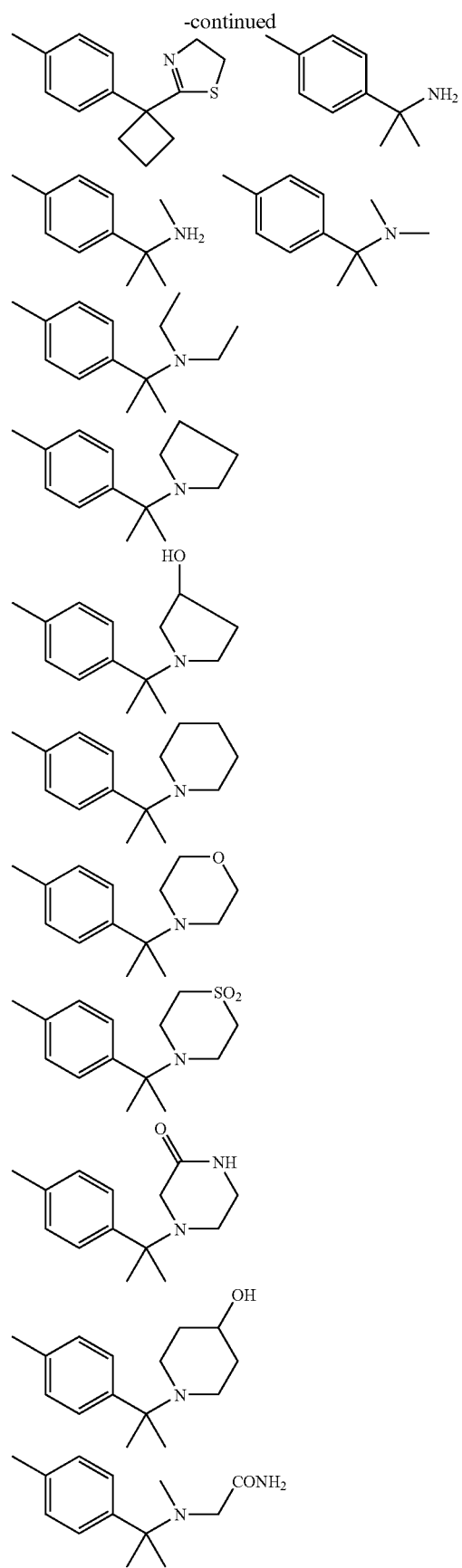

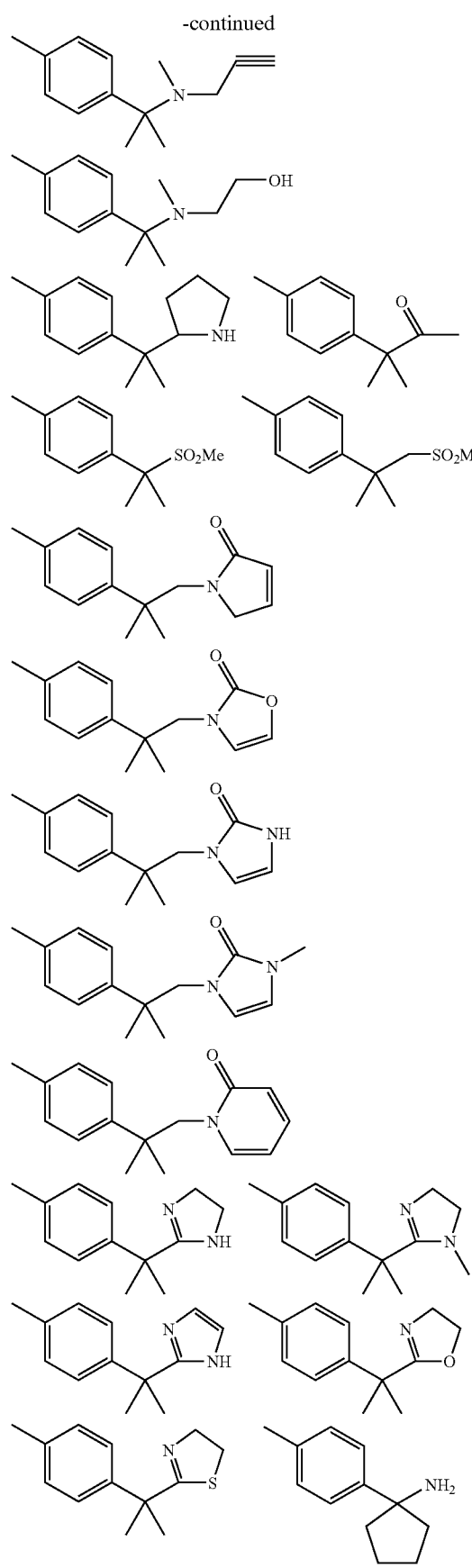
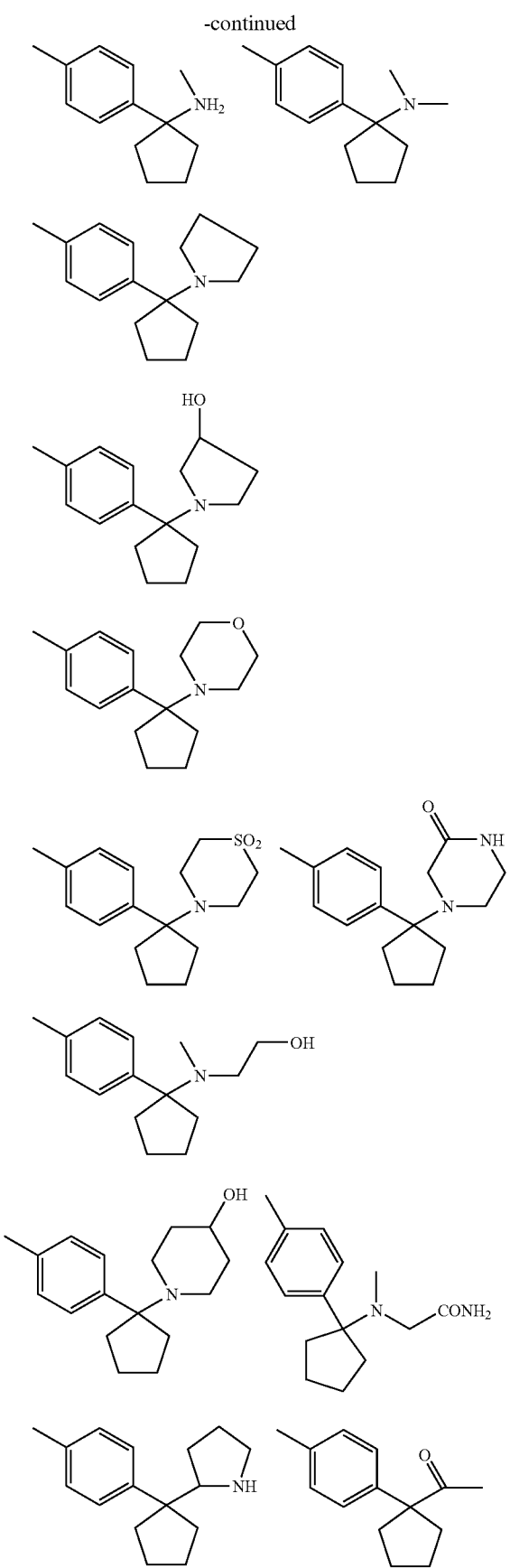

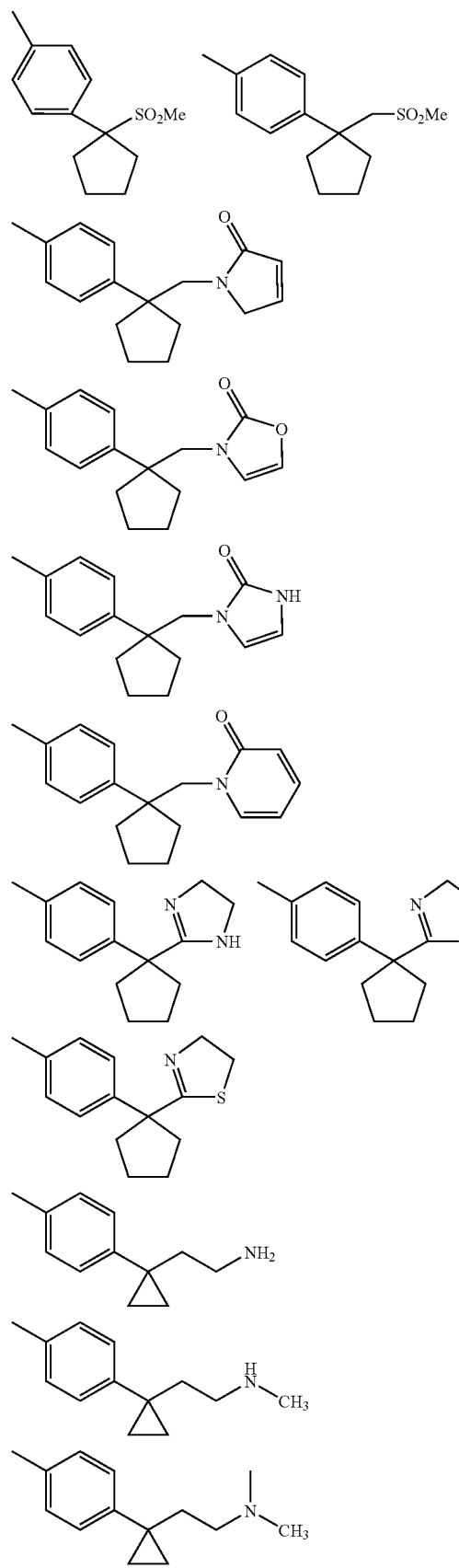
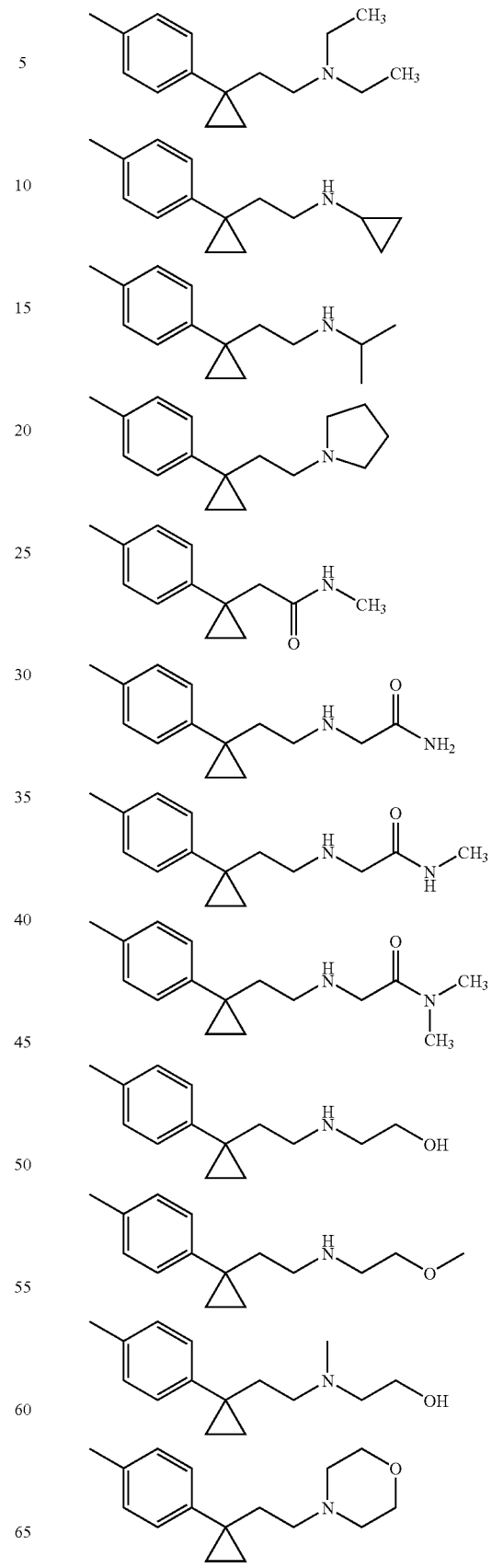

-continued
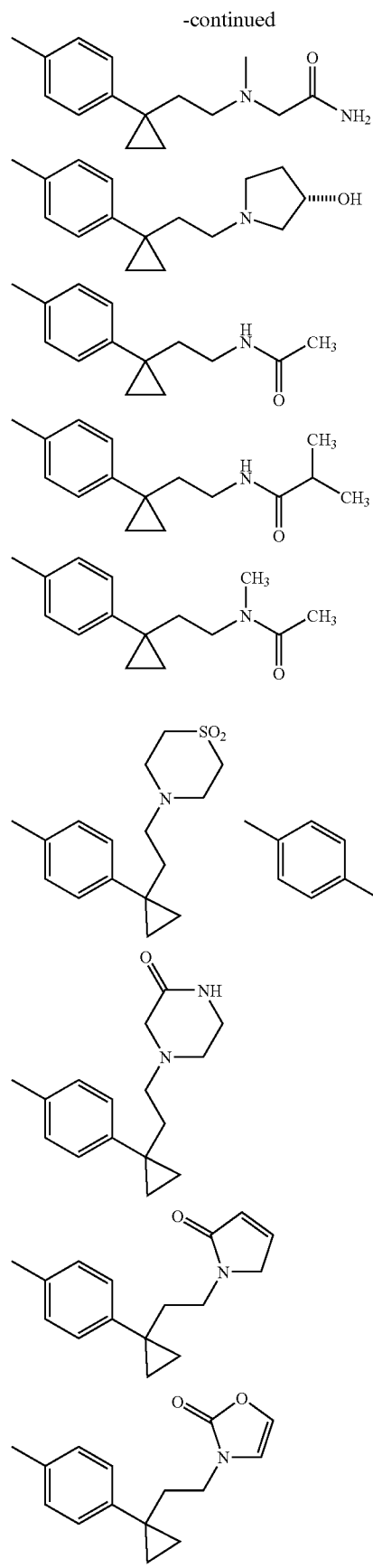
-continued
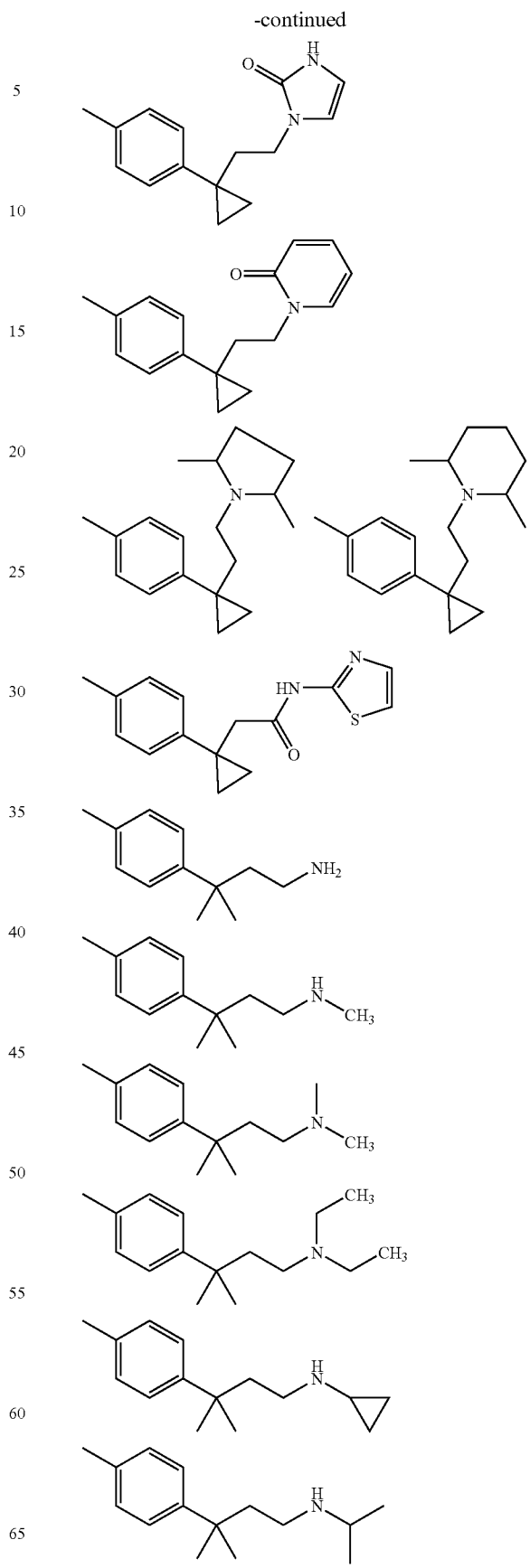

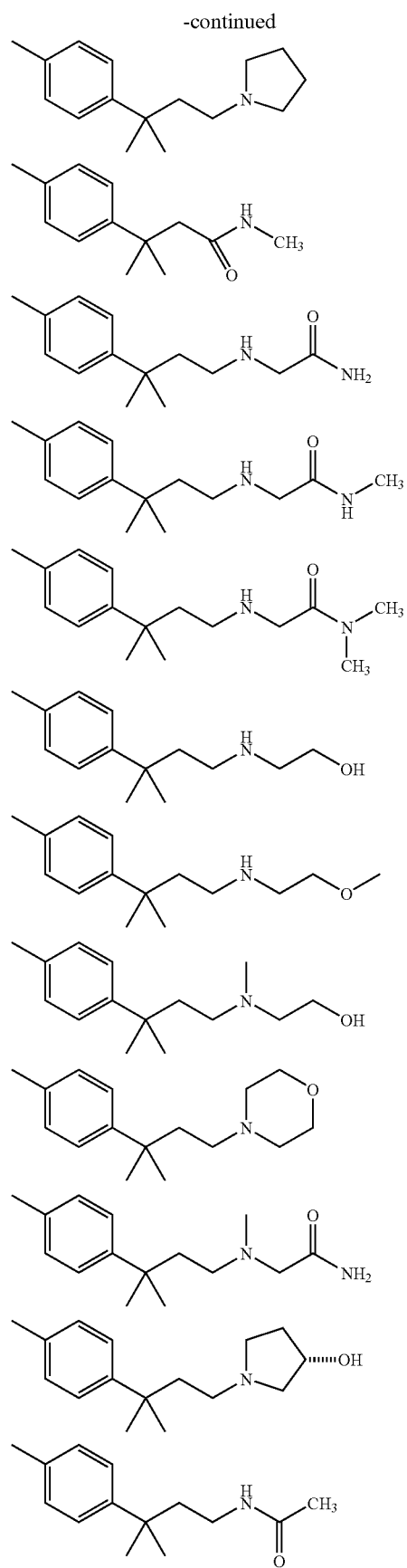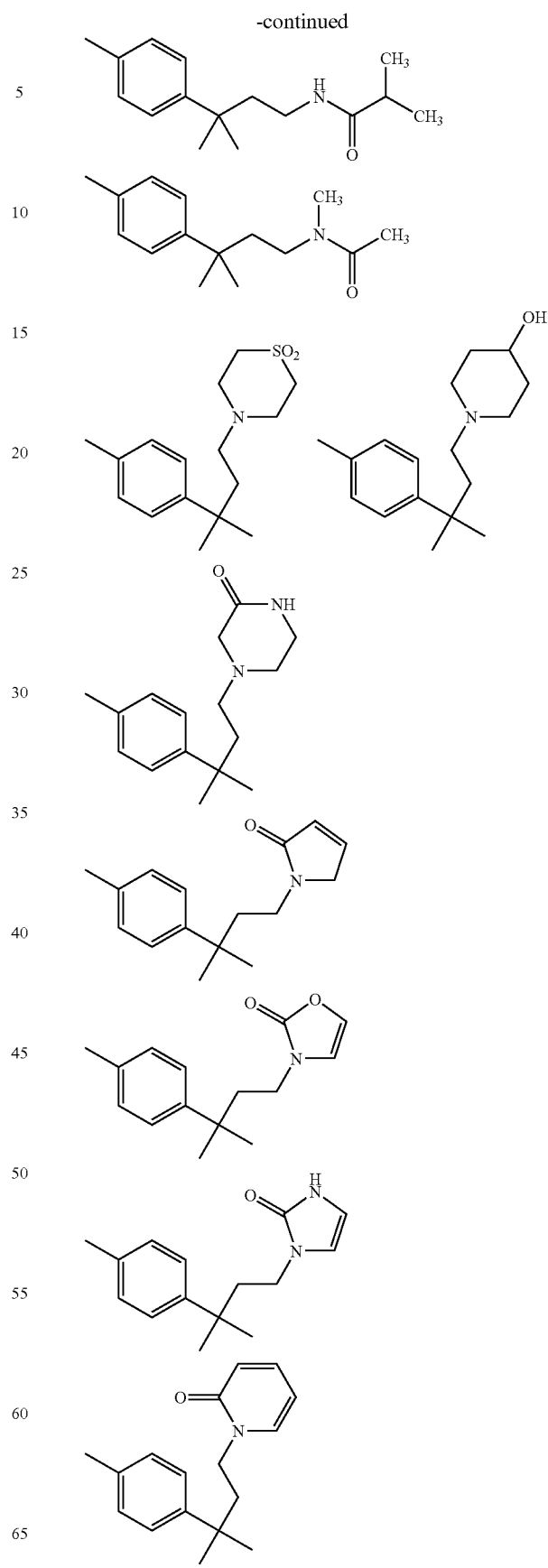

-continued
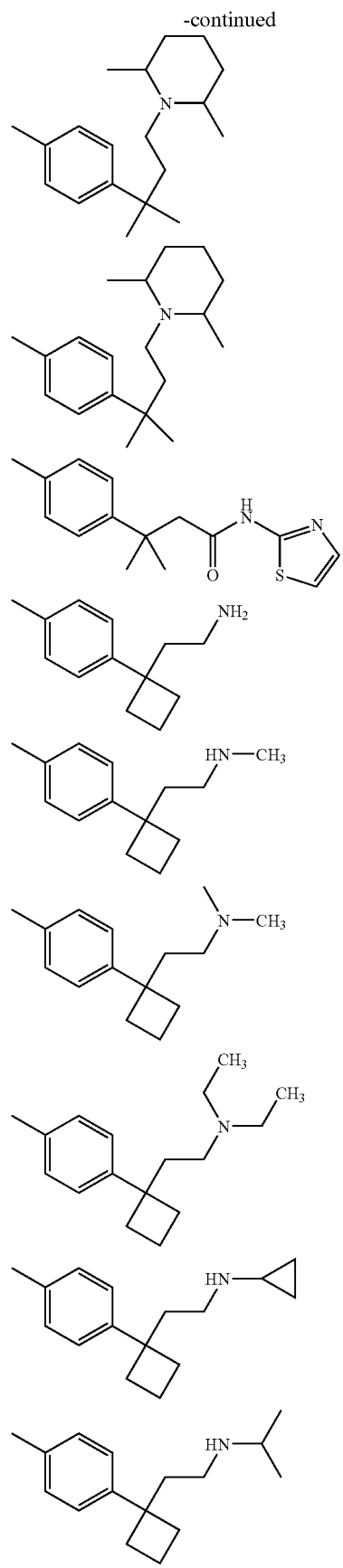
-continued
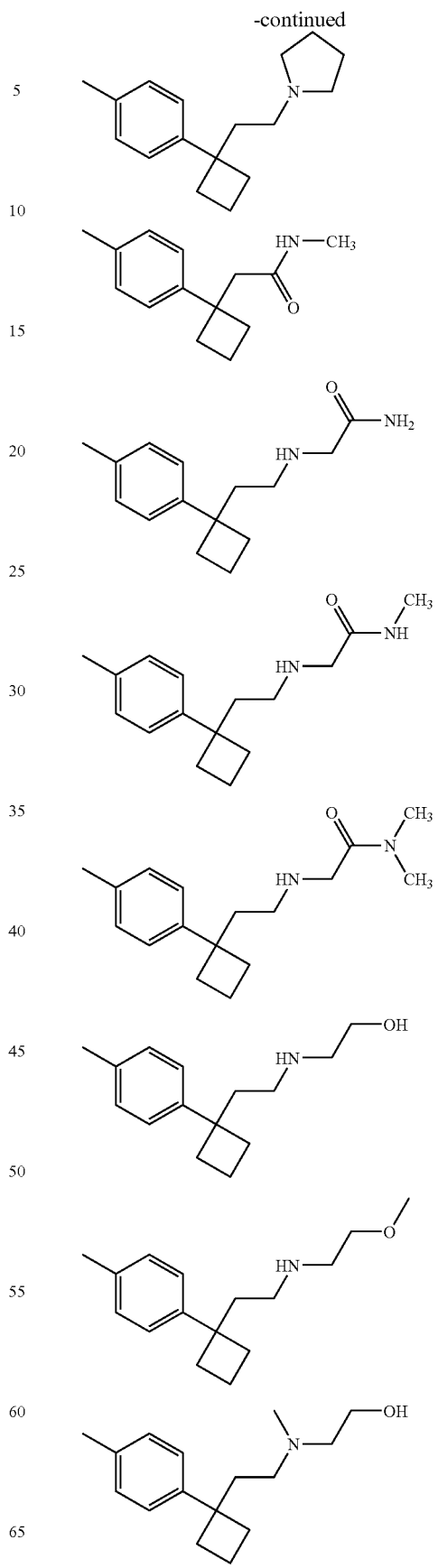

-continued
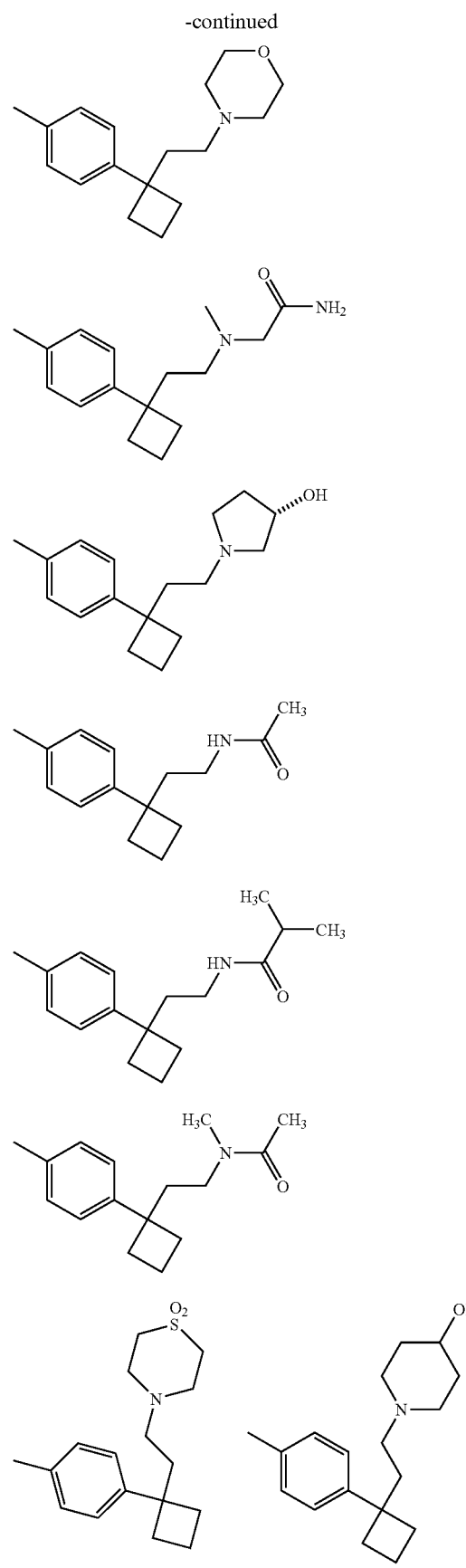
-continued
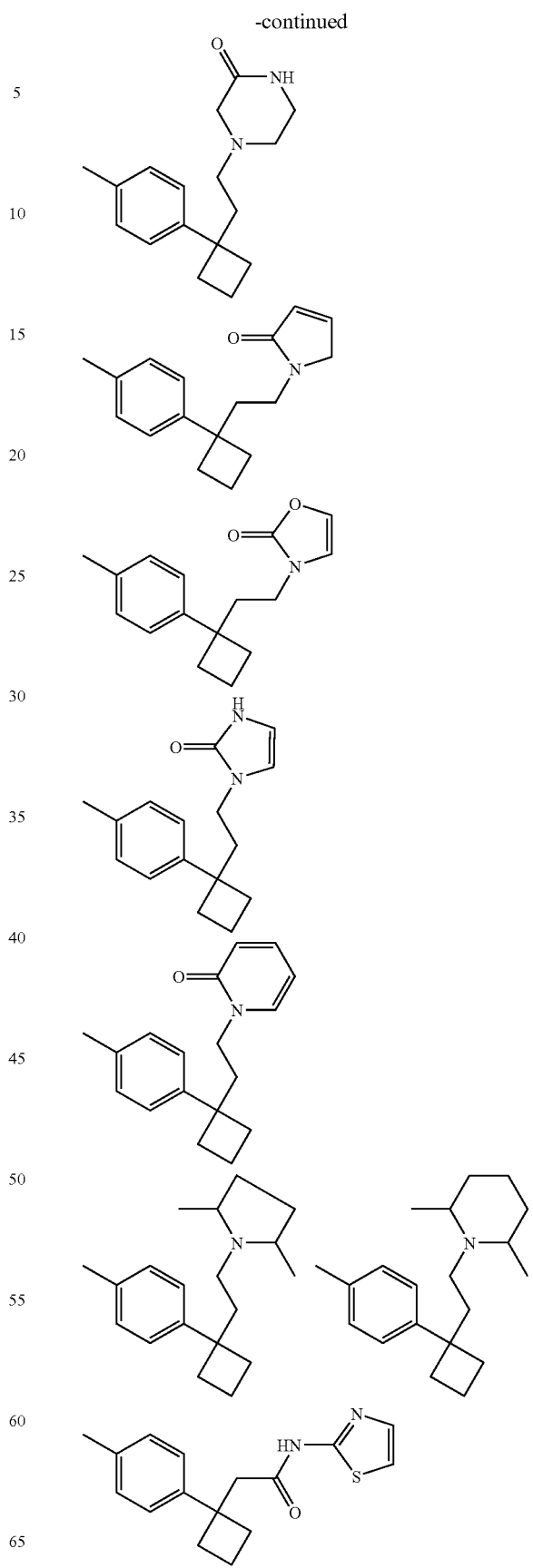

-continued
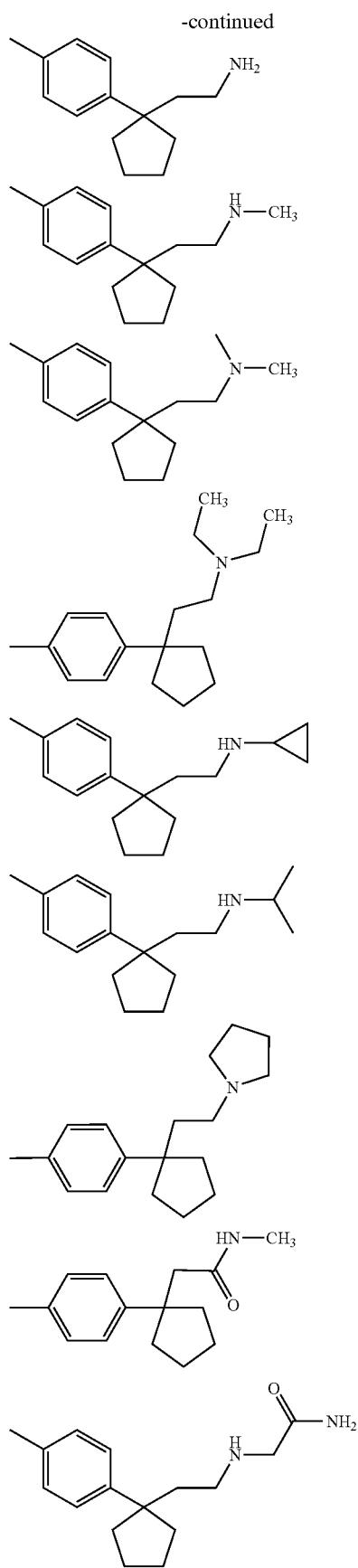
-continued
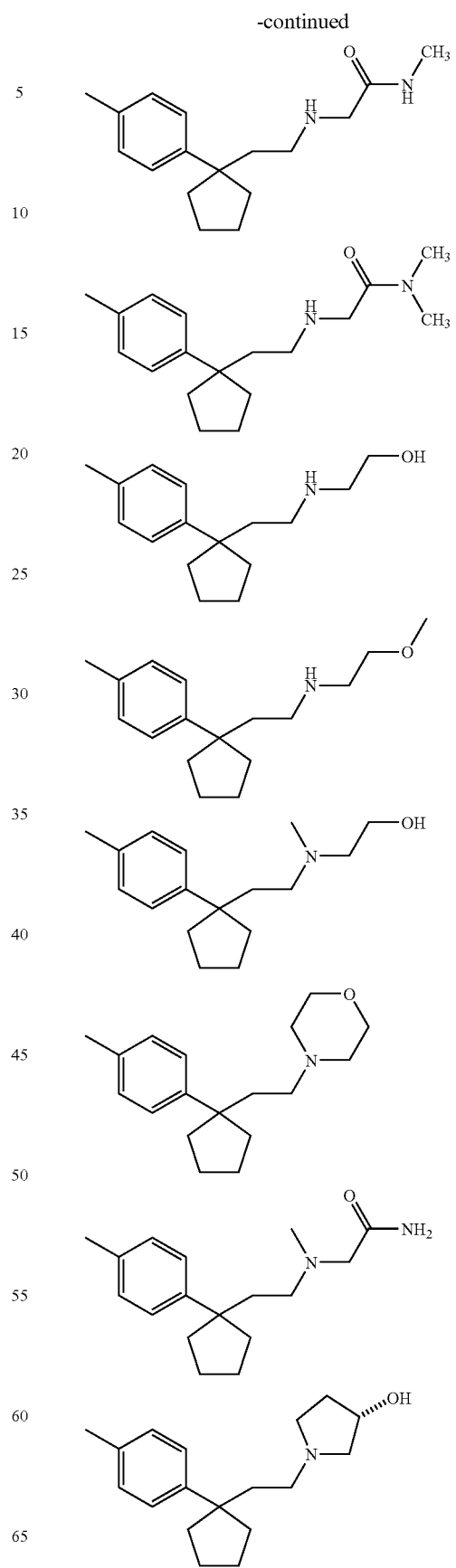

-continued
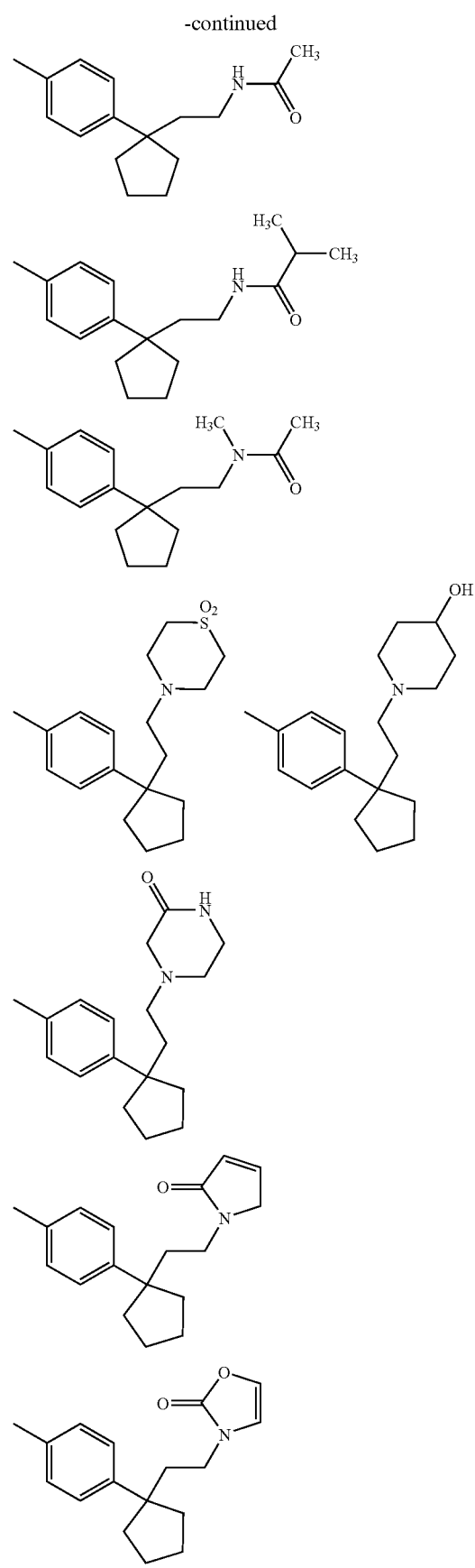
-continued
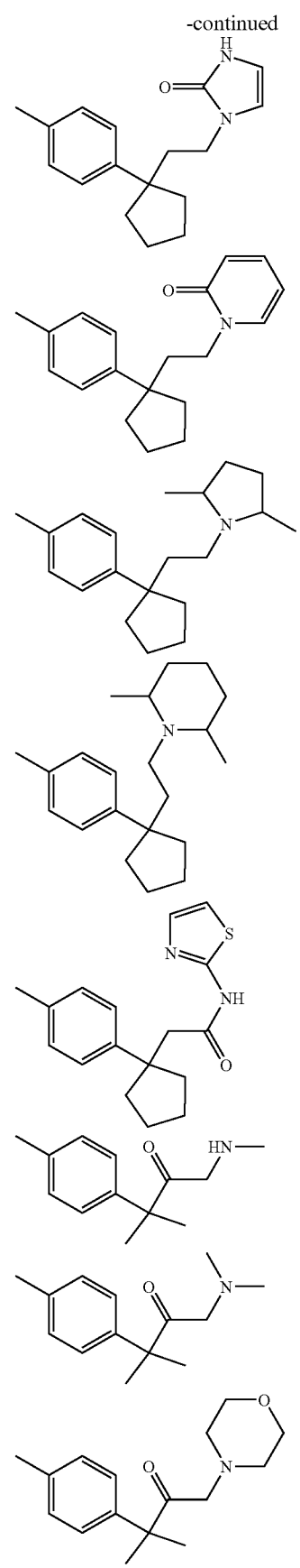

503
-continued
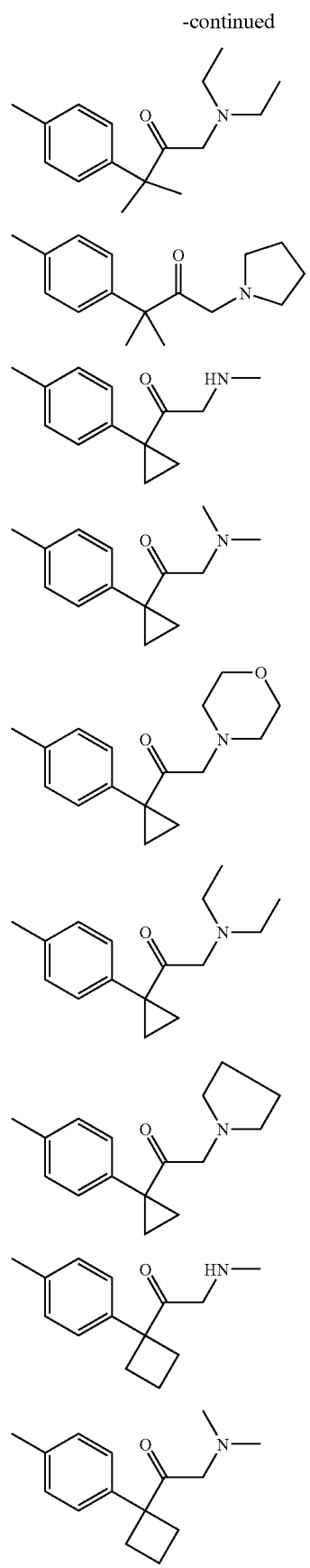
504
-continued
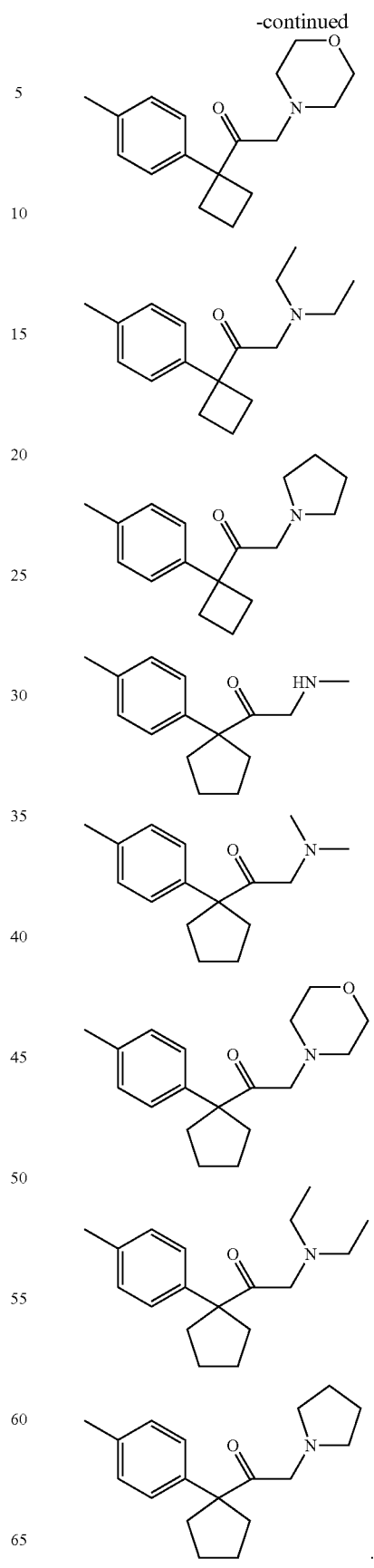

8. A compound according to claim 1, wherein the compound is the compound is selected from the group:

1-(4-methoxyphenyl)-6-(4-{1-[(methylamino)methyl]cyclopropyl}phenyl)-3-(trifluoromethyl)-1,4,5,6-tetrahydro-7H-pyrazolo[3,4-c]pyridin-7-one;

6-(4-{1-[(dimethylamino)methyl]cyclopropyl}phenyl)-1-(4-methoxyphenyl)-3-(trifluoromethyl)-1,4,5,6-tetrahydro-7H-pyrazolo[3,4-c]pyridin-7-one;

6-(4-{1-[(diethylamino)methyl]cyclopropyl}phenyl)-1-(4-methoxyphenyl)-3-(trifluoromethyl)-1,4,5,6-tetrahydro-7H-pyrazolo[3,4-c]pyridin-7-one;

6-(4-{1-[(isopropylamino)methyl]cyclopropyl}phenyl)-1-(4-methoxyphenyl)-3-(trifluoromethyl)-1,4,5,6-tetrahydro-7H-pyrazolo[3,4-c]pyridin-7-one;

6-(4-{1-[(cyclopentylamino)methyl]cyclopropyl}phenyl)-1-(4-methoxyphenyl)-3-(trifluoromethyl)-1,4,5,6-tetrahydro-7H-pyrazolo[3,4-c]pyridin-7-one;

1-(4-methoxyphenyl)-6-{4-[1-(1-pyrrolidinylmethyl)cyclopropyl]phenyl}-3-(trifluoromethyl)-1,4,5,6-tetrahydro-7H-pyrazolo[3,4-c]pyridin-7-one;

6-[4-(1-{[(3R)-3-hydroxy-1-pyrrolidinyl]methyl}cyclopropyl)phenyl]-1-(4-methoxyphenyl)-3-(trifluoromethyl)-1,4,5,6-tetrahydro-7H-pyrazolo[3,4-c]pyridin-7-one;

6-(4-{1-[(4-hydroxy-1-piperidinyl)methyl]cyclopropyl}phenyl)-1-(4-methoxyphenyl)-3-(trifluoromethyl)-1,4,5,6-tetrahydro-7H-pyrazolo[3,4-c]pyridin-7-one;

1-(4-methoxyphenyl)-6-{4-[1-(4-morpholinylmethyl)cyclopropyl]phenyl}-3-(trifluoromethyl)-1,4,5,6-tetrahydro-7H-pyrazolo[3,4-c]pyridin-7-one;

1-(4-methoxyphenyl)-6-{4-[1-(1-pyrrolidinylcarbonyl)cyclopropyl]phenyl}-3-(trifluoromethyl)-1,4,5,6-tetrahydro-7H-pyrazolo[3,4-c]pyridin-7-one;

1-{4-[1-(4-methoxyphenyl)-7-oxo-3-(trifluoromethyl)-1,4,5,7-tetrahydro-6H-pyrazolo[3,4-c]pyridin-6-yl]phenyl}-N,N-dimethylcyclopropanecarboxamide;

1-(4-methoxyphenyl)-6-(4-{1-[(4-methyl-1-piperazinyl)carbonyl]cyclopropyl}phenyl)-3-(trifluoromethyl)-1,4,5,6-tetrahydro-7H-pyrazolo[3,4-c]pyridin-7-one;

6-{4-[1-(4-hydroxypiperidine-1-carbonyl)cyclopropyl]phenyl}-1-(4-methoxyphenyl)-3-(trifluoromethyl)-1,4,5,6-tetrahydro-7H-pyrazolo[3,4-c]pyridin-7-one;

1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropanecarboxamide;

1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropanecarboxylic acid cyclopentylamide;

1-{4-[1-(4-methoxyphenyl)-7-oxo-3-(trifluoromethyl)-1,4,5,7-tetrahydro-6H-pyrazolo[3,4-c]pyridin-6-yl]phenyl}-N-(1,3,4-thiadiazol-2-yl)cyclopropanecarboxamide;

1-{4-[1-(4-methoxyphenyl)-7-oxo-3-(trifluoromethyl)-1,4,5,7-tetrahydro-6H-pyrazolo[3,4-c]pyridin-6-yl]phenyl}-N-(1H-tetrazol-5-yl)cyclopropanecarboxamide;

methyl 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropanecarboxylate;

1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropanecarbonitrile;

6-{4-[1-(aminomethyl)cyclopropyl]phenyl}-1-(4-methoxyphenyl)-3-(trifluoromethyl)-1,4,5,6-tetrahydro-7H-pyrazolo[3,4-c]pyridin-7-one;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropyl)methyl]-N-methylacetamide;

N'-ethyl-N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropyl)methyl]-N-methylurea;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopropyl)methyl]-N-methylmethanesulfonamide;

1-(4-methoxyphenyl)-6-{4-[1-(2-methylimidazol-1-ylmethyl)cyclopropyl]phenyl}-3-trifluoromethyl-1,4,5,6-tetrahydro-pyrazolo[3,4-c]pyridin-7-one;

1-(4-methoxyphenyl)-6-{4-[1-(thiazol-2-ylaminomethyl)-cyclopropyl]phenyl}-3-trifluoromethyl-1,4,5,6-tetrahydro-pyrazolo[3,4-c]pyridin-7-one;

methyl 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopentanecarboxylate;

1-(4-methoxyphenyl)-6-(4-{1-[(methylamino)methyl]cyclopentyl}phenyl)-3-(trifluoromethyl)-1,4,5,6-tetrahydro-7H-pyrazolo[3,4-c]pyridin-7-one;

6-(4-{1-[(dimethylamino)methyl]cyclopentyl}phenyl)-1-(4-methoxyphenyl)-3-(trifluoromethyl)-1,4,5,6-tetrahydro-7H-pyrazolo[3,4-c]pyridin-7-one;

1-(4-methoxyphenyl)-6-{4-[1-(1-pyrrolidinylmethyl)cyclopentyl]phenyl}-3-(trifluoromethyl)-1,4,5,6-tetrahydro-7H-pyrazolo[3,4-c]pyridin-7-one;

6-[4-(1-{[(3R)-3-hydroxy-1-pyrrolidinyl]methyl}cyclopentyl)phenyl]-1-(4-methoxyphenyl)-3-(trifluoromethyl)-1,4,5,6-tetrahydro-7H-pyrazolo[3,4-c]pyridin-7-one;

1-(4-methoxyphenyl)-6-{4-[1-(4-morpholinylmethyl)cyclopentyl]phenyl}-3-(trifluoromethyl)-1,4,5,6-tetrahydro-7H-pyrazolo[3,4-c]pyridin-7-one;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopentyl)methyl]-N-methylacetamide;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclopentyl)methyl]-N-methylmethanesulfonamide;

methyl 1-{4-[1-(4-methoxyphenyl)-7-oxo-3-(trifluoromethyl)-1,4,5,7-tetrahydro-6H-pyrazolo[3,4-c]pyridin-6-yl]phenyl}cyclobutanecarboxylate;

1-(4-methoxyphenyl)-6-(4-{1-[(methylamino)methyl]cyclobutyl}phenyl)-3-(trifluoromethyl)-1,4,5,6-tetrahydro-7H-pyrazolo[3,4-c]pyridin-7-one;

6-(4-{1-[(dimethylamino)methyl]cyclobutyl}phenyl)-1-(4-methoxyphenyl)-3-(trifluoromethyl)-1,4,5,6-tetrahydro-7H-pyrazolo[3,4-c]pyridin-7-one;

6-(4-{1-[(diethylamino)methyl]cyclobutyl}phenyl)-1-(4-methoxyphenyl)-3-(trifluoromethyl)-1,4,5,6-tetrahydro-7H-pyrazolo[3,4-c]pyridin-7-one;

1-(4-methoxyphenyl)-6-{4-[1-(1-pyrrolidinylmethyl)cyclobutyl]phenyl}-3-(trifluoromethyl)-1,4,5,6-tetrahydro-7H-pyrazolo[3,4-c]pyridin-7-one;

6-[4-(1-{[(3R)-3-hydroxy-1-pyrrolidinyl]methyl}cyclobutyl)phenyl]-1-(4-methoxyphenyl)-3-(trifluoromethyl)-1,4,5,6-tetrahydro-7H-pyrazolo[3,4-c]pyridin-7-one;

1-(4-methoxyphenyl)-6-{4-[1-(4-morpholinylmethyl)cyclobutyl]phenyl}-3-(trifluoromethyl)-1,4,5,6-tetrahydro-7H-pyrazolo[3,4-c]pyridin-7-one;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclobutyl)methyl]-N-methylacetamide;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclobutyl)methyl]-N-methylmethanesulfonamide;

1-{4-[1-(4-Methoxyphenyl)-7-oxo-3-trifluoromethyl-1,4,5,7-tetrahydro-pyrazolo[3,4-c]pyridin-6-yl]-phenyl}cyclohexanecarboxylic acid methyl ester;

1-(4-methoxyphenyl)-6-(4-{1-[(methylamino)methyl]cyclohexyl}phenyl)-3-(trifluoromethyl)-1,4,5,6-tetrahydro-7H-pyrazolo[3,4-c]pyridin-7-one;

6-(4-{1-[(dimethylamino)methyl]cyclohexyl}phenyl)-1-(4-methoxyphenyl)-3-(trifluoromethyl)-1,4,5,6-tetrahydro-7H-pyrazolo[3,4-c]pyridin-7-one;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclohexyl)methyl]-N-methylacetamide;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}cyclohexyl)methyl]-N-methylmethanesulfonamide;

1-(4-methoxyphenyl)-6-(4-{1-[(methylamino)methyl]cyclopropyl}phenyl)-3-(methylsulfonyl)-1,4,5,6-tetrahydro 7H-pyrazolo[3,4-c]pyridin-7-one;

6-(4-{1-[(dimethylamino)methyl]cyclopropyl}phenyl)-1-(4-methoxyphenyl)-3-(methylsulfonyl)-1,4,5,6-tetrahydro-7H-pyrazolo[3,4-c]pyridin-7-one;

6-(4-{1-[(isopropylamino)methyl]cyclopropyl}phenyl)-1-(4-methoxyphenyl)-3-(methylsulfonyl)-1,4,5,6-tetrahydro-7H-pyrazolo[3,4-c]pyridin-7-one;

6-(4-{1-[(cyclopentylamino)methyl]cyclopropyl}phenyl)-1-(4-methoxyphenyl)-3-(methylsulfonyl)-1,4,5,6-tetrahydro-7H-pyrazolo[3,4-c]pyridin-7-one;

1-(4-methoxyphenyl)-3-(methylsulfonyl)-6-{4-[1-(1-pyrrolidinylmethyl)cyclopropyl]phenyl}-1,4,5,6-tetrahydro-7H-pyrazolo[3,4-c]pyridin-7-one;

6-[4-(1-{[(3R)-3-hydroxy-1-pyrrolidinyl]methyl}cyclopropyl)phenyl]-1-(4-methoxyphenyl)-3-(methylsulfonyl)-1,4,5,6-tetrahydro-7H-pyrazolo[3,4-c]pyridin-7-one;

6-(4-{1-[(diethylamino)methyl]cyclopropyl}phenyl)-1-(4-methoxyphenyl)-3-(methylsulfonyl)-1,4,5,6-tetrahydro-7H-pyrazolo[3,4-c]pyridin-7-one;

1-(4-methoxyphenyl)-3-(methylsulfonyl)-6-{4-[1-(4-morpholinylmethyl)cyclopropyl]phenyl}-1,4,5,6-tetrahydro-7H-pyrazolo[3,4-c]pyridin-7-one;

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}cyclopropyl)methyl]-N-methylacetamide;

3-methanesulfonyl-1-(4-methoxyphenyl)-6-{4-[1-(2-methylimidazol-1-ylmethyl)cyclopropyl]phenyl}-1,4,5,6-tetrahydro-pyrazolo[3,4-c]pyridin-7-one;

3-methanesulfonyl-1-(4-methoxyphenyl)-6-{4-[1-(thiazol-2-ylaminomethyl)cyclopropyl]phenyl}-1,4,5,6-tetrahydro-pyrazolo[3,4-c]pyridin-7-one;

1-(4-methoxyphenyl)-6-(4-{1-[(methylamino)methyl]cyclobutyl}phenyl)-3-(methylsulfonyl)-1,4,5,6-tetrahydro 7H-pyrazolo[3,4-c]pyridin-7-one;

6-(4-{1-[(dimethylamino)methyl]cyclobutyl}phenyl)-1-(4-methoxyphenyl)-3-(methylsulfonyl)-1,4,5,6-tetrahydro-7H-pyrazolo[3,4-c]pyridin-7-one;

6-(4-{1-[(isopropylamino)methyl]cyclobutyl}phenyl)-1-(4-methoxyphenyl)-3-(methylsulfonyl)-1,4,5,6-tetrahydro-7H-pyrazolo[3,4-c]pyridin-7-one;

1-(4-methoxyphenyl)-3-(methylsulfonyl)-6-{4-[1-(1-pyrrolidinylmethyl)cyclobutyl]phenyl}-1,4,5,6-tetrahydro-7H-pyrazolo[3,4-c]pyridin-7-one;

6-[4-(1-{[(3R)-3-hydroxy-1-pyrrolidinyl]methyl}cyclobutyl)phenyl]-1-(4-methoxyphenyl)-3-(methylsulfonyl)-1,4,5,6-tetrahydro-7H-pyrazolo[3,4-c]pyridin-7-one;

6-(4-{1-[(diethylamino)methyl]cyclobutyl}phenyl)-1-(4-methoxyphenyl)-3-(methylsulfonyl)-1,4,5,6-tetrahydro-7H-pyrazolo[3,4-c]pyridin-7-one;

1-(4-methoxyphenyl)-3-(methylsulfonyl)-6-{4-[1-(4-morpholinylmethyl)cyclobutyl]phenyl}-1,4,5,6-tetrahydro-7H-pyrazolo[3,4-c]pyridin-7-one;

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}cyclopropyl)methyl]-N-methylacetamide;

1-(4-methoxyphenyl)-6-(4-{1-[(methylamino)methyl]cyclopropyl}phenyl)-7-oxo-4,5,6,7-tetrahydro-1H-pyrazolo[3,4-c]pyridine-3-carboxamide;

6-(4-{1-[(dimethylamino)methyl]cyclopropyl}phenyl)-1-(4-methoxyphenyl)-7-oxo-4,5,6,7-tetrahydro-1H-pyrazolo[3,4-c]pyridine-3-carboxamide;

6-(4-{1-[(diethylamino)methyl]cyclopropyl}phenyl)-1-(4-methoxyphenyl)-7-oxo-4,5,6,7-tetrahydro-1H-pyrazolo[3,4-c]pyridine-3-carboxamide;

1-(4-methoxyphenyl)-7-oxo-6-{4-[1-(1-pyrrolidinylmethyl)cyclopropyl]phenyl}-4,5,6,7-tetrahydro-1H-pyrazolo[3,4-c]pyridine-3-carboxamide;

1-(4-methoxyphenyl)-6-{4-[1-(4-morpholinylmethyl)cyclopropyl]phenyl}-7-oxo-4,5,6,7-tetrahydro-1H-pyrazolo[3,4-c]pyridine-3-carboxamide;

6-(4-{1-[(isopropylamino)methyl]cyclopropyl}phenyl)-1-(4-methoxyphenyl)-7-oxo-4,5,6,7-tetrahydro-1H-pyrazolo[3,4-c]pyridine-3-carboxamide;

6-[4-(1-{[(3R)-3-hydroxy-1-pyrrolidinyl]methyl}cyclopropyl)phenyl]-1-(4-methoxyphenyl)-7-oxo-4,5,6,7-tetrahydro-1H-pyrazolo[3,4-c]pyridine-3-carboxamide;

1-(4-methoxyphenyl)-6-(4-{1-[(methylamino)methyl]cyclopropyl}phenyl)-7-oxo-4,5,6,7-tetrahydro-1H-pyrazolo[3,4-c]pyridine-3-carbonitrile;

6-(4-{1-[(dimethylamino)methyl]cyclopropyl}phenyl)-1-(4-methoxyphenyl)-7-oxo-4,5,6,7-tetrahydro-1H-pyrazolo[3,4-c]pyridine-3-carbonitrile;

6-(4-{1-[(diethylamino)methyl]cyclopropyl}phenyl)-1-(4-methoxyphenyl)-7-oxo-4,5,6,7-tetrahydro-1H-pyrazolo[3,4-c]pyridine-3-carbonitrile;

1-(4-methoxyphenyl)-7-oxo-6-{4-[1-(1-pyrrolidinylmethyl)cyclopropyl]phenyl}-4,5,6,7-tetrahydro-1H-pyrazolo[3,4-c]pyridine-3-carbonitrile;

6-(4-{1-[(isopropylamino)methyl]cyclopropyl}phenyl)-1-(4-methoxyphenyl)-7-oxo-4,5,6,7-tetrahydro-1H-pyrazolo[3,4-c]pyridine-3-carbonitrile;

6-[4-(1-{[(3R)-3-hydroxy-1-pyrrolidinyl]methyl}cyclopropyl)phenyl]-1-(4-methoxyphenyl)-7-oxo-4,5,6,7-tetrahydro-1H-pyrazolo[3,4-c]pyridine-3-carbonitrile;

1-(4-methoxyphenyl)-6-{4-[1-(4-morpholinylmethyl)cyclopropyl]phenyl}-7-oxo-4,5,6,7-tetrahydro-1H-pyrazolo[3,4-c]pyridine-3-carbonitrile;

1-(3-chlorophenyl)-6-{4-[1-(isopropylamino)methyl)cyclopropyl]phenyl}-7-oxo-4,5,6,7-tetrahydro-1H-pyrazolo[3,4-c]pyridine-3-carboxamide;

1-(3-chlorophenyl)-6-{4-[1-(4-morpholinylmethyl)cyclopropyl]phenyl}-7-oxo-4,5,6,7-tetrahydro-1H-pyrazolo[3,4-c]pyridine-3-carboxamide;

6-(4-{1-[(isopropylamino)methyl]cyclopropyl}phenyl)-1-(4-methoxyphenyl)-7-oxo-4,5,6,7-tetrahydro-1H-pyrazolo[3,4-c]pyridine-3-carbonitrile;

1-(4-methoxyphenyl)-6-{4-[1-(4-morpholinylmethyl)cyclopropyl]phenyl}-7-oxo-4,5,6,7-tetrahydro-1H-pyrazolo[3,4-c]pyridine-3-carbonitrile;

1-(3-chlorophenyl)-6-(4-{1-[(methylamino)methyl]cyclopropyl}phenyl)-7-oxo-4,5,6,7-tetrahydro-1H-pyrazolo[3,4-c]pyridine-3-carboxamide;

1-(3-chlorophenyl)-6-(4-{1-[(dimethylamino)methyl]cyclopropyl}phenyl)-7-oxo-4,5,6,7-tetrahydro-1H-pyrazolo[3,4-c]pyridine-3-carboxamide;

1-(3-chlorophenyl)-6-(4-{1-[(diethylamino)methyl]cyclopropyl}phenyl)-7-oxo-4,5,6,7-tetrahydro-1H-pyrazolo[3,4-c]pyridine-3-carboxamide;

1-(3-chlorophenyl)-6-(4-{1-[(diisopropylamino)methyl]cyclopropyl}phenyl)-7-oxo-4,5,6,7-tetrahydro-1H-pyrazolo[3,4-c]pyridine-3-carboxamide;

1-(3-chlorophenyl)-6-(4-{1-[(cyclopropylamino)methyl]cyclopropyl}phenyl)-7-oxo-4,5,6,7-tetrahydro-1H-pyrazolo[3,4-c]pyridine-3-carboxamide;

1-(3-chlorophenyl)-6-(4-{1-[(cyclobutylamino)methyl]cyclopropyl}phenyl)-7-oxo-4,5,6,7-tetrahydro-1H-pyrazolo[3,4-c]pyridine-3-carboxamide;

1-(3-chlorophenyl)-7-oxo-6-(4-{1-[(2-oxo-1-pyrrolidinyl)methyl]cyclopropyl}phenyl)-4,5,6,7-tetrahydro-1H-pyrazolo[3,4-c]pyridine-3-carboxamide;

1-(3-chlorophenyl)-6-[4-(1-{[(2-hydroxyethyl)(methyl)amino]methyl}cyclopropyl)phenyl]-7-oxo-4,5,6,7-tetrahydro-1H-pyrazolo[3,4-c]pyridine-3-carboxamide;

1-(3-chlorophenyl)-6-(4-{1-[2-(dimethylamino)-2-oxoethyl]cyclopropyl}phenyl)-7-oxo-4,5,6,7-tetrahydro-1H-pyrazolo[3,4-c]pyridine-3-carboxamide;

1-(3-chlorophenyl)-6-{4-[1-(methoxymethyl)cyclopropyl]phenyl}-7-oxo-4,5,6,7-tetrahydro-1H-pyrazolo[3,4-c]pyridine-3-carboxamide;

1-(3-chlorophenyl)-6-{4-[1-(methoxymethyl)cyclopropyl]phenyl}-7-oxo-4,5,6,7-tetrahydro-1H-pyrazolo[3,4-c]pyridine-3-carbonitrile;

1-(3-chlorophenyl)-6-(4-{1-[(methylamino)methyl]cyclopropyl}phenyl)-7-oxo-4,5,6,7-tetrahydro-1H-pyrazolo[3,4-c]pyridine-3-carbonitrile;

1-(3-chlorophenyl)-6-(4-{1-[(dimethylamino)methyl]cyclopropyl}phenyl)-7-oxo-4,5,6,7-tetrahydro-1H-pyrazolo[3,4-c]pyridine-3-carbonitrile;

1-(3-chlorophenyl)-6-[4-(1-{[(2-hydroxyethyl)(methyl)amino]methyl}cyclopropyl)phenyl]-7-oxo-4,5,6,7-tetrahydro-1H-pyrazolo[3,4-c]pyridine-3-carbonitrile;

1-(4-methoxyphenyl)-7-oxo-6-(4-{1-[(2-oxo-1-pyrrolidinyl)methyl]cyclopropyl}phenyl)-4,5,6,7-tetrahydro-1H-pyrazolo[3,4-c]pyridine-3-carbonitrile;

N-[(1-{4-[3-cyano-1-(4-methoxyphenyl)-7-oxo-1,4,5,7-tetrahydro-6H-pyrazolo[3,4-c]pyridin-6-yl]phenyl}cyclopropyl)methyl]-N-methylacetamide;

6-(4-{1-[(cyclopropylamino)methyl]cyclopropyl}phenyl)-1-(4-methoxyphenyl)-7-oxo-4,5,6,7-tetrahydro-1H-pyrazolo[3,4-c]pyridine-3-carbonitrile;

6-(4-{1-[(cyclobutylamino)methyl]cyclopropyl}phenyl)-1-(4-methoxyphenyl)-7-oxo-4,5,6,7-tetrahydro-1H-pyrazolo[3,4-c]pyridine-3-carbonitrile;

6-[4-(1-{[(2-hydroxyethyl)amino]methyl}cyclopropyl)phenyl]-1-(4-methoxyphenyl)-7-oxo-4,5,6,7-tetrahydro-1H-pyrazolo[3,4-c]pyridine-3-carbonitrile;

6-[4-(1-{[(2-hydroxyethyl)(methyl)amino]methyl}cyclopropyl)phenyl]-1-(4-methoxyphenyl)-7-oxo-4,5,6,7-tetrahydro-1H-pyrazolo[3,4-c]pyridine-3-carbonitrile;

6-(4-{1-[(diisopropylamino)methyl]cyclopropyl}phenyl)-1-(4-methoxyphenyl)-7-oxo-4,5,6,7-tetrahydro-1H-pyrazolo[3,4-c]pyridine-3-carbonitrile;

6-[4-(1-{[(2-hydroxyethyl)(methyl)amino]methyl}cyclopropyl)phenyl]-1-(4-methoxyphenyl)-7-oxo-4,5,6,7-tetrahydro-1H-pyrazolo[3,4-c]pyridine-3-carboxamide;

6-{4-[1-(dimethylamino)cyclopropyl]phenyl}-1-(4-methoxyphenyl)-7-oxo-4,5,6,7-tetrahydro-1H-pyrazolo[3,4-c]pyridine-3-carboxamide;

6-(4-{1-[(2-hydroxyethyl)(methyl)amino]cyclopropyl}phenyl)-1-(4-methoxyphenyl)-7-oxo-4,5,6,7-tetrahydro-1H-pyrazolo[3,4-c]pyridine-3-carboxamide;

2-(1-{4-[1-(4-methoxyphenyl)-3-(methylsulfonyl)-7-oxo-1,4,5,7-tetrahydro-6H-pyrazolo[3,4-c]pyridin-6-yl]phenyl}cyclopropyl)-N,N-dimethylacetamide;

6-(4-{1-[2-(dimethylamino)-2-oxoethyl]cyclopropyl}phenyl)-1-(4-methoxyphenyl)-7-oxo-4,5,6,7-tetrahydro-1H-pyrazolo[3,4-c]pyridine-3-carboxamide;

2-(1-{4-[3-cyano-1-(4-methoxyphenyl)-7-oxo-1,4,5,7-tetrahydro-6H-pyrazolo[3,4-c]pyridin-6-yl]phenyl}cyclopropyl)-N,N-dimethylacetamide;

2-(1-{4-[3-cyano-1-(4-methoxyphenyl)-7-oxo-1,4,5,7-tetrahydro-6H-pyrazolo[3,4-c]pyridin-6-yl]phenyl}cyclopropyl)acetamide;

2-(1-{4-[1-(3-chlorophenyl)-3-cyano-7-oxo-1,4,5,7-tetrahydro-6H-pyrazolo[3,4-c]pyridin-6-yl]phenyl}cyclopropyl)acetamide;

1-(3-chlorophenyl)-6-(4-{1-[2-(dimethylamino)-2-oxoethyl]cyclopropyl}phenyl)-7-oxo-4,5,6,7-tetrahydro-1H-pyrazolo[3,4-c]pyridine-3-carboxamide;

2-(1-{4-[1-(3-chlorophenyl)-3-(methylsulfonyl)-7-oxo-1,4,5,7-tetrahydro-6H-pyrazolo[3,4-c]pyridin-6-yl]phenyl}cyclopropyl)-N,N-dimethylacetamide;

1-(4-methoxyphenyl)-7-oxo-6-(4-{1-[(2-oxo-1-imidazolidinyl)methyl]cyclopropyl}phenyl)-4,5,6,7-tetrahydro-1H-pyrazolo[3,4-c]pyridine-3-carbonitrile;

1-(4-methoxyphenyl)-7-oxo-6-(4-{1-[(2-oxo-1-piperazinyl)methyl]cyclopropyl}phenyl)-4,5,6,7-tetrahydro-1H-pyrazolo[3,4-c]pyridine-3-carbonitrile;

1-(4-methoxyphenyl)-7-oxo-6-(4-{1-[(3-oxo-4-morpholinyl)methyl]cyclopropyl}phenyl)-4,5,6,7-tetrahydro-1H-pyrazolo[3,4-c]pyridine-3-carbonitrile;

1-(4-methoxyphenyl)-7-oxo-6-(4-{1-[(2-oxo-1-piperidinyl)methyl]cyclopropyl}phenyl)-4,5,6,7-tetrahydro-1H-pyrazolo[3,4-c]pyridine-3-carbonitrile;

2-[(1-{4-[3-cyano-1-(4-methoxyphenyl)-7-oxo-1,4,5,7-tetrahydro-6H-pyrazolo[3,4-c]pyridin-6-yl]phenyl}cyclopropyl)oxy]acetamide;

1-[4-{3-cyano-1-(4-methoxyphenyl)-7-oxo-1,4,5,7-tetrahydro-6H-pyrazolo[3,4-c]pyridin-6-yl]phenyl}cyclopropyl carbamate;

2-(1-{4-[3-cyano-1-(4-methoxyphenyl)-7-oxo-1,4,5,7-tetrahydro-6H-pyrazolo[3,4-c]pyridin-6-yl]phenyl}cyclopropyl)acetamide;

2-(1-{4-[3-cyano-1-(4-methoxyphenyl)-7-oxo-1,4,5,7-tetrahydro-6H-pyrazolo[3,4-c]pyridin-6-yl]phenyl}cyclopropyl)-N,N-dimethylacetamide;

1-(4-methoxyphenyl)-6-{4-[1-(methylamino)cyclopropyl]phenyl}-7-oxo-4,5,6,7-tetrahydro-1H-pyrazolo[3,4-c]pyridine-3-carbonitrile;

6-{4-[1-(dimethylamino)cyclopropyl]phenyl}-1-(4-methoxyphenyl)-7-oxo-4,5,6,7-tetrahydro-1H-pyrazolo[3,4-c]pyridine-3-carbonitrile;

1-(4-methoxyphenyl)-7-oxo-6-{4-[1-(1,3-thiazol-2-ylamino)cyclopropyl]phenyl}-4,5,6,7-tetrahydro-1H-pyrazolo[3,4-c]pyridine-3-carbonitrile;

N-(1-{4-[3-cyano-1-(4-methoxyphenyl)-7-oxo-1,4,5,7-tetrahydro-6H-pyrazolo[3,4-c]pyridin-6-yl]phenyl}cyclopropyl)urea;

N-(1-{4-[3-cyano-1-(4-methoxyphenyl)-7-oxo-1,4,5,7-tetrahydro-6H-pyrazolo[3,4-c]pyridin-6-yl]phenyl}cyclopropyl)-N'-methylurea;

N-(1-{4-[3-cyano-1-(4-methoxyphenyl)-7-oxo-1,4,5,7-tetrahydro-6H-pyrazolo[3,4-c]pyridin-6-yl]phenyl}cyclopropyl)-2-methylpropanamide;

6-(4-{1-[(4-hydroxy-1-piperidinyl)methyl]cyclopropyl}phenyl)-1-(4-methoxyphenyl)-7-oxo-4,5,6,7-tetrahydro-1H-pyrazolo[3,4-c]pyridine-3-carbonitrile;

1-(4-methoxyphenyl)-6-(4-{1-[(2-methyl-5,6-dihydro-1(4H)-pyrimidinyl)methyl]cyclopropyl}phenyl)-7-oxo-4,5,6,7-tetrahydro-1H-pyrazolo[3,4-c]pyridine-3-carbonitrile;

1-(4-methoxyphenyl)-6-(4-{1-[(2-methyl-4,5-dihydro-1H-imidazol-1-yl)methyl]cyclopropyl}phenyl)-7-oxo-4,5,6,7-tetrahydro-1H-pyrazolo[3,4-c]pyridine-3-carbonitrile;

6-{4-[1-(4,5-dihydro-1,3-oxazol-2-ylmethyl)cyclopropyl]phenyl}-1-(4-methoxyphenyl)-7-oxo-4,5,6,7-tetrahydro-1H-pyrazolo[3,4-c]pyridine-3-carbonitrile;

6-{4-[1-(4,5-dihydro-1H-imidazol-2-ylmethyl)cyclopropyl]phenyl}-1-(4-methoxyphenyl)-7-oxo-4,5,6,7-tetrahydro-1H-pyrazolo[3,4-c]pyridine-3-carbonitrile;

1-(4-methoxyphenyl)-6-(4-{1-[(1-methyl-4,5-dihydro-1H-imidazol-2-yl)methyl]cyclopropyl}phenyl)-7-oxo-4,5,6,7-tetrahydro-1H-pyrazolo[3,4-c]pyridine-3-carbonitrile;

1-(4-methoxyphenyl)-7-oxo-6-(4-{1-[(1,3-thiazol-2-ylamino)methyl]cyclopropyl}phenyl)-4,5,6,7-tetrahydro-1H-pyrazolo[3,4-c]pyridine-3-carbonitrile;

1-(4-methoxyphenyl)-6-(4-{1-[(2-methyl-1H-imidazol-1-yl)methyl]cyclopropyl}phenyl)-7-oxo-4,5,6,7-tetrahydro-1H-pyrazolo[3,4-c]pyridine-3-carbonitrile;

1-(4-methoxyphenyl)-6-{4-[1-methyl-1-(2-oxo-1-pyrrolidinyl)ethyl]phenyl}-7-oxo-4,5,6,7-tetrahydro-1H-pyrazolo[3,4-c]pyridine-3-carboxamide;

1-(4-methoxyphenyl)-6-{4-[1-methyl-1-(2-oxo-1-piperidinyl)ethyl]phenyl}-7-oxo-4,5,6,7-tetrahydro-1H-pyrazolo[3,4-c]pyridine-3-carboxamide;

6-{4-[1,1-dimethyl-2-(2-oxo-1-piperidinyl)ethyl]phenyl}-1-(4-methoxyphenyl)-7-oxo-4,5,6,7-tetrahydro-1H-pyrazolo[3,4-c]pyridine-3-carboxamide;

6-{4-[1,1-dimethyl-2-(2-oxo-1-pyrrolidinyl)ethyl]phenyl}-1-(4-methoxyphenyl)-7-oxo-4,5,6,7-tetrahydro-1H-pyrazolo[3,4-c]pyridine-3-carboxamide;

6-{4-[1,1-dimethyl-2-(3-oxo-4-morpholinyl)ethyl]phenyl}-1-(4-methoxyphenyl)-7-oxo-4,5,6,7-tetrahydro-1H-pyrazolo[3,4-c]pyridine-3-carboxamide;

6-{4-[1,1-dimethyl-2-(2-oxo-1-piperazinyl)ethyl]phenyl}-1-(4-methoxyphenyl)-7-oxo-4,5,6,7-tetrahydro-1H-pyrazolo[3,4-c]pyridine-3-carboxamide;

6-{4-[1,1-dimethyl-2-(2-oxotetrahydro-1(2H)-pyrimidinyl)ethyl]phenyl}-1-(4-methoxyphenyl)-7-oxo-4,5,6,7-tetrahydro-1H-pyrazolo[3,4-c]pyridine-3-carboxamide;

6-{4-[1,1-dimethyl-2-(2-oxodihydro-2H-1,3-oxazin-3(4H)-yl)ethyl]phenyl}-1-(4-methoxyphenyl)-7-oxo-4,5,6,7-tetrahydro-1H-pyrazolo[3,4-c]pyridine-3-carboxamide;

1-{4-[3-(aminocarbonyl)-1-(4-methoxyphenyl)-7-oxo-1,4,5,7-tetrahydro-6H-pyrazolo[3,4-c]pyridin-6-yl]phenyl}-1-methylethyl methylcarbamate;

1-{4-[3-(aminocarbonyl)-1-(4-methoxyphenyl)-7-oxo-1,4,5,7-tetrahydro-6H-pyrazolo[3,4-c]pyridin-6-yl]phenyl}-1-methylethyl 3-pyrrolidinylcarbamate;

6-{4-[1-ethyl-1-(1-pyrrolidinylmethyl)propyl]phenyl}-1-(4-methoxyphenyl)-7-oxo-4,5,6,7-tetrahydro-1H-pyrazolo[3,4-c]pyridine-3-carboxamide;

6-(4-{1-[(dimethylamino)methyl]-1-ethylpropyl}phenyl)-1-(4-methoxyphenyl)-7-oxo-4,5,6,7-tetrahydro-1H-pyrazolo[3,4-c]pyridine-3-carboxamide;

1-[3-(aminomethyl)phenyl]-6-{4-[1,1-dimethyl-2-(1-pyrrolidinyl)ethyl]phenyl}-7-oxo-4,5,6,7-tetrahydro-1H-pyrazolo[3,4-c]pyridine-3-carboxamide;

1-[3-(aminomethyl)phenyl]-6-{4-[2-(dimethylamino)-1,1-dimethylethyl]phenyl}-7-oxo-4,5,6,7-tetrahydro-1H-pyrazolo[3,4-c]pyridine-3-carboxamide;

1-[3-(aminocarbonyl)phenyl]-6-{4-[2-(dimethylamino)-1,1-dimethylethyl]phenyl}-7-oxo-4,5,6,7-tetrahydro-1H-pyrazolo[3,4-c]pyridine-3-carboxamide;

1-[3-(aminocarbonyl)phenyl]-6-{4-[1,1-dimethyl-2-(1-pyrrolidinyl)ethyl]phenyl}-7-oxo-4,5,6,7-tetrahydro-1H-pyrazolo[3,4-c]pyridine-3-carboxamide;

1-(3-amino-1,2-benzisoxazol-5-yl)-6-{4-[1,1-dimethyl-2-(1-pyrrolidinyl)ethyl]phenyl}-7-oxo-4,5,6,7-tetrahydro-1H-pyrazolo[3,4-c]pyridine-3-carboxamide;

1-(3-amino-1,2-benzisoxazol-5-yl)-6-{4-[1,1-dimethyl-2-(1-pyrrolidinyl)ethyl]phenyl}-3-(trifluoromethyl)-1,4,5,6-tetrahydro-7H-pyrazolo[3,4-c]pyridin-7-one;

1-(1-amino-7-isoquinolinyl)-6-{4-[1,1-dimethyl-2-(1-pyrrolidinyl)ethyl]phenyl}-7-oxo-4,5,6,7-tetrahydro-1H-pyrazolo[3,4-c]pyridine-3-carboxamide;

1-(1-amino-7-isoquinolinyl)-6-{4-[2-(dimethylamino)-1,1-dimethylethyl]phenyl}-7-oxo-4,5,6,7-tetrahydro-1H-pyrazolo[3,4-c]pyridine-3-carboxamide;

1-(1-amino-7-isoquinolinyl)-6-(4-{1-[(dimethylamino)methyl]cyclopropyl}phenyl)-7-oxo-4,5,6,7-tetrahydro-1H-pyrazolo[3,4-c]pyridine-3-carboxamide;

1-(1-amino-7-isoquinolinyl)-7-oxo-6-{4-[1-(1-pyrrolidinylmethyl)cyclopropyl]phenyl}-4,5,6,7-tetrahydro-1H-pyrazolo[3,4-c]pyridine-3-carboxamide;

1-(3-amino-1,2-benzisoxazol-5-yl)-7-oxo-6-{4-[1-(1-pyrrolidinylmethyl)cyclopropyl]phenyl}-4,5,6,7-tetrahydro-1H-pyrazolo[3,4-c]pyridine-3-carboxamide;

1-(3-amino-1,2-benzisoxazol-5-yl)-6-{4-[1-(1-pyrrolidinylmethyl)cyclopropyl]phenyl}-3-(trifluoromethyl)-1,4,5,6-tetrahydro-7H-pyrazolo[3,4-c]pyridin-7-one;

1-(3-amino-1,2-benzisoxazol-5-yl)-7-oxo-6-{4-[1-(1-pyrrolidinylmethyl)cyclopropyl]phenyl}-4,5,6,7-tetrahydro-1H-pyrazolo[3,4-c]pyridine-3-carbonitrile;

1-[3-(aminomethyl)phenyl]-7-oxo-6-(4-{1-[(2-oxo-1-pyrrolidinyl)methyl]cyclopropyl}phenyl)-4,5,6,7-tetrahydro-1H-pyrazolo[3,4-c]pyridine-3-carboxamide;

6-(4-(1-{[acetyl(methyl)amino]methyl}cyclopropyl)phenyl)-1-[3-(aminomethyl)phenyl]-7-oxo-4,5,6,7-tetrahydro-1H-pyrazolo[3,4-c]pyridine-3-carboxamide;

1-[3-(aminocarbonyl)phenyl]-6-(4-{1-[(dimethylamino)methyl]cyclopropyl}phenyl)-7-oxo-4,5,6,7-tetrahydro-1H-pyrazolo[3,4-c]pyridine-3-carboxamide;

3-[3-cyano-6-(4-{1-[(dimethylamino)methyl]cyclopropyl}phenyl)-7-oxo-4,5,6,7-tetrahydro-1H-pyrazolo[3,4-c]pyridin-1-yl]benzamide;

1-(2,3-dihydro-1H-indol-6-yl)-6-(4-{1-[(dimethylamino)methyl]cyclopropyl}phenyl)-7-oxo-4,5,6,7-tetrahydro-1H-pyrazolo[3,4-c]pyridine-3-carboxamide;

1-(2,3-dihydro-1H-indol-6-yl)-7-oxo-6-{4-[1-(1-pyrrolidinylmethyl)cyclopropyl]phenyl}-4,5,6,7-tetrahydro-1H-pyrazolo[3,4-c]pyridine-3-carboxamide;

1-(2,3-dihydro-1H-indol-6-yl)-7-oxo-6-(4-{1-[(2-oxo-1-pyrrolidinyl)methyl]cyclopropyl}phenyl)-4,5,6,7-tetrahydro-1H-pyrazolo[3,4-c]pyridine-3-carboxamide;

6-(4-{1-[(dimethylamino)methyl]cyclobutyl}phenyl)-1-(4-methoxyphenyl)-7-oxo-4,5,6,7-tetrahydro-1H-pyrazolo[3,4-c]pyridine-3-carboxamide;

1-(4-methoxyphenyl)-6-{4-[1-(4-morpholinylmethyl)cyclobutyl]phenyl}-7-oxo-4,5,6,7-tetrahydro-1H-pyrazolo[3,4-c]pyridine-3-carboxamide;

1-(4-methoxyphenyl)-6-{4-[1-(4-morpholinylmethyl)cyclopentyl]phenyl}-7-oxo-4,5,6,7-tetrahydro-1H-pyrazolo[3,4-c]pyridine-3-carboxamide;

6-(4-{1-[(dimethylamino)methyl]cyclopentyl}phenyl)-1-(4-methoxyphenyl)-7-oxo-4,5,6,7-tetrahydro-1H-pyrazolo[3,4-c]pyridine-3-carboxamide;

1-(4-methoxyphenyl)-6-{4-[1-(2-oxo-pyrrolidin-1-yl)-cyclopropyl]phenyl}-3-trifluoromethyl-1,4,5,6-tetrahydro-pyrazolo[3,4-c]pyridin-7-one;

1-(4-methoxyphenyl)-6-{4-[1-(2-oxo-piperidin-1-yl)-cyclopropyl]phenyl}-3-trifluoromethyl-1,4,5,6-tetrahydro-pyrazolo[3,4-c]pyridin-7-one;

1-(4-methoxyphenyl)-6-[4-(1-methylaminocyclopropyl)-phenyl]-3-trifluoromethyl-1,4,5,6-tetrahydro-pyrazolo[3,4-c]pyridin-7-one;

6-[4-(1-dimethylaminocyclopropyl)phenyl]-1-(4-methoxyphenyl)-3-trifluoromethyl-1,4,5,6-tetrahydro-pyrazolo[3,4-c]pyridin-7-one;

N-(1-{4-[1-(4-methoxyphenyl)-7-oxo-3-trifluoromethyl-1,4,5,7-tetrahydro-pyrazolo[3,4-c]pyridin-6-yl]phenyl}-cyclopropyl)-N-methyl-acetamide;

N-(1-{4-[1-(4-methoxyphenyl)-7-oxo-3-trifluoromethyl-1,4,5,7-tetrahydro-pyrazolo[3,4-c]pyridin-6-yl]phenyl}-cyclopropyl)-N-methyl-methanesulfonamide;

N-(1-{4-[1-(4-methoxyphenyl)-7-oxo-3-trifluoromethyl-1,4,5,7-tetrahydro-pyrazolo[3,4-c]pyridin-6-yl]phenyl}-cyclopropyl)-N-methyl-2-methylaminoacetamide;

2-dimethylamino-N-(1-{4-[1-(4-methoxyphenyl)-7-oxo-3-trifluoromethyl-1,4,5,7-tetrahydro-pyrazolo[3,4-c]pyridin-6-yl]phenyl}cyclopropyl)-N-methylacetamide;

N-(1-{4-[1-(4-methoxyphenyl)-7-oxo-3-trifluoromethyl-1,4,5,7-tetrahydro-pyrazolo[3,4-c]pyridin-6-yl]phenyl}-cyclopropyl)-N-methyl-2-morpholin-4-yl-acetamide;

6-{4-[1-(1-hydroxyethyl)cyclopropyl]phenyl}-1-(4-methoxyphenyl)-3-trifluoromethyl-1,4,5,6-tetrahydro-pyrazolo[3,4-c]pyridin-7-one;

6-[4-(1-acetylcyclopropyl)phenyl]-1-(4-methoxyphenyl)-3-trifluoromethyl-1,4,5,6-tetrahydro-pyrazolo[3,4-c]pyridin-7-one;

6-{4-[1-(1-hydroxy-1-methyl-ethyl)cyclopropyl]phenyl}-1-(4-methoxyphenyl)-3-trifluoromethyl-1,4,5,6-tetrahydro-pyrazolo[3,4-c]pyridin-7-one;

6-[4-(1-methoxymethylcyclopropyl)phenyl]-1-(4-methoxyphenyl)-3-trifluoromethyl-1,4,5,6-tetrahydro-pyrazolo[3,4-c]pyridin-7-one;

6-{4-[1-(4,5-dihydro-oxazol-2-yl)cyclopropyl]phenyl}-1-(4-methoxyphenyl)-3-trifluoromethyl-1,4,5,6-tetrahydro-pyrazolo[3,4-c]pyridin-7-one;

1-{4-[1-(4-methoxy-phenyl)-7-oxo-3-trifluoromethyl-1,4,5,7-tetrahydro-pyrazolo[3,4-c]pyridin-6-yl]-phenyl}-cyclopropanecarboxylic acid 2-amino-ethyl ester;

6-{4-[1-(4,5-dihydro-oxazol-2-yl)-cyclopropyl]-phenyl}-1-(4-methoxy-phenyl)-7-oxo-4,5,6,7-tetrahydro-1H-pyrazolo[3,4-c]pyridine-3-carboxylic acid amide;

6-{4-[1-(4,5-dihydro-1H-imidazol-2-yl)cyclopropyl]phenyl}-1-(4-methoxyphenyl)-3-trifluoromethyl-1,4,5,6-tetrahydro-pyrazolo[3,4-c]pyridin-7-one;

1-(4-methoxyphenyl)-6-{4-[1-(1-methyl-4,5-dihydro-1H-imidazol-2-yl)cyclopropyl]phenyl}-3-trifluoromethyl-1,4,5,6-tetrahydro-pyrazolo[3,4-c]pyridin-7-one;

6-{4-[1-(1-methanesulfonyl-4,5-dihydro-1H-imidazol-2-yl)-cyclopropyl]phenyl}-1-(4-methoxyphenyl)-3-trifluoromethyl-1,4,5,6-tetrahydro-pyrazolo[3,4-c]pyridin-7-one;

6-{4-[1-(1H-imidazol-2-yl)cyclopropyl]phenyl}-1-(4-methoxy-phenyl)-3-trifluoromethyl-1,4,5,6-tetrahydro-pyrazolo[3,4-c]pyridin-7-one;

1-(4-methoxyphenyl)-6-{4-[1-(1-methyl-1H-imidazol-2-yl)-cyclopropyl]phenyl}-3-trifluoromethyl-1,4,5,6-tetrahydro-pyrazolo[3,4-c]pyridin-7-one;

2-[(1-{4-[1-(4-methoxyphenyl)-7-oxo-3-trifluoromethyl-1,4,5,7-tetrahydro-pyrazolo[3,4-c]pyridin-6-yl]phenyl}-cyclopropyl)-methyl-amino]-acetamide;

6-(4-{1-[(2-hydroxyethyl)-methylamino]cyclopropyl}phenyl)-1-(4-methoxyphenyl)-3-trifluoromethyl-1,4,5,6-tetrahydro-pyrazolo[3,4-c]pyridin-7-one;

1-{4-[1-(4-methoxy-phenyl)-7-oxo-3-trifluoromethyl-1,4,5,7-tetrahydro-pyrazolo[3,4-c]pyridin-6-yl]-phenyl}-cyclopropanecarboxylic acid methoxy-methyl-amide;

6-[4-(1-hydroxymethylcyclopropyl)phenyl]-1-(4-methoxy-phenyl)-7-oxo-4,5,6,7-tetrahydro-1H-pyrazolo[3,4-c]pyridine-3-carboxylic acid amide;

6-[4-(1-acetyl-cyclopropyl)-phenyl]-1-(4-methoxy-phenyl)-7-oxo-4,5,6,7-tetrahydro-1H-pyrazolo[3,4-c]pyridine-3-carboxylic acid amide;

6-[4-(1-aminocyclopropyl)phenyl]-1-(4-methoxyphenyl)-7-oxo-4,5,6,7-tetrahydro-1H-pyrazolo[3,4-c]pyridine-3-carboxylic acid amide;

1-(4-methoxyphenyl)-6-[4-(1-methylaminocyclopropyl)-phenyl]-7-oxo-4,5,6,7-tetrahydro-1H-pyrazolo[3,4-c]pyridine-3-carboxylic acid amid;

6-[4-(1-dimethylaminocyclopropyl)phenyl]-1-(4-methoxyphenyl)-7-oxo-4,5,6,7-tetrahydro-1H-pyrazolo[3,4-c]pyridine-3-carboxylic acid amide;

6-[4-(1-methylaminomethylcyclopentyl)phenyl]-1-(4-methoxy-phenyl)-7-oxo-4,5,6,7-tetrahydro-1H-pyrazolo[3,4-c]pyridine-3-carboxylic acid amide;

6-[4-(1-dimethylaminomethylcyclopentyl)phenyl]-1-(4-methoxyphenyl)-7-oxo-4,5,6,7-tetrahydro-1H-pyrazolo[3,4-c]pyridine-3-carboxylic acid amide;

6-[4-(1-dimethylaminomethylcyclopentyl)phenyl]-1-(4-methoxyphenyl)-7-oxo-4,5,6,7-tetrahydro-1H-pyrazolo[3,4-c]pyridine-3-carbonitrile;

6-[4-(1-[(2-hydroxyethyl)methylaminomethyl]-cyclopentyl)phenyl]-1-(4-methoxy-phenyl)-7-oxo-4,5,6,7-tetrahydro-1H-pyrazolo[3,4-c]pyridine-3-carboxylic acid amide;

6-[4-(1-hydroxymethyl-cyclopentyl)-phenyl]-1-(4-methoxy-phenyl)-7-oxo-4,5,6,7-tetrahydro-1H-pyrazolo[3,4-c]pyridine-3-carboxylic acid amide;

6-(4-{1-[(2-hydroxyethyl)methylamino]cyclopropyl}phenyl)-1-(4-methoxyphenyl)-7-oxo-4,5,6,7-tetrahydro-1H-pyrazolo[3,4-c]pyridine-3-carboxylic acid amide;

1-(4-methoxyphenyl)-6-{4-[1-(methyl-prop-2-ynylamino)-cyclopropyl]phenyl}-7-oxo-4,5,6,7-tetrahydro-1H-pyrazolo[3,4-c]pyridine-3-carboxylic acid amide;

3-(1-hydroxyethyl)-1-(4-methoxyphenyl)-6-[4-(1-methylamino-cyclopropyl)phenyl]-1,4,5,6-tetrahydro-pyrazolo[3,4-c]pyridin-7-one;

3-acetyl-1-(4-methoxyphenyl)-6-[4-(1-methylamino-cyclopropyl)phenyl]-1,4,5,6-tetrahydro-pyrazolo[3,4-c]pyridin-7-one;

1-(4-methoxyphenyl)-6-[4-(1-methylaminocyclopropyl)phenyl]-7-oxo-4,5,6,7-tetrahydro-1H-pyrazolo[3,4-c]pyridine-3-carboxylic acid methylamide;

1-(4-methoxyphenyl)-6-[4-(1-methylaminocyclopropyl)phenyl]-7-oxo-4,5,6,7-tetrahydro-1H-pyrazolo[3,4-c]pyridine-3-carboxylic acid dimethylamide;

6-[4-(1-aminocyclopropyl)phenyl]-1-(4-methoxyphenyl)-7-oxo-4,5,6,7-tetrahydro-1H-pyrazolo[3,4-c]pyridine-3-carbonitrile;

1-(4-methoxyphenyl)-6-[4-(1-methylaminocyclopropyl)phenyl]-7-oxo-4,5,6,7-tetrahydro-1H-pyrazolo[3,4-c]pyridine-3-carbonitrile;

6-[4-(1-dimethylaminocyclopropyl)phenyl]-1-(4-methoxyphenyl)-7-oxo-4,5,6,7-tetrahydro-1H-pyrazolo[3,4-c]pyridine-3-carbonitrile;

2-[(1-{4-[3-cyano-1-(4-methoxyphenyl)-7-oxo-1,4,5,7-tetrahydro-pyrazolo[3,4-c]pyridin-6-yl]phenyl}cyclopropyl)-methylamino]acetamide;

6-(4-{1-[(2-hydroxyethyl)methylamino]cyclopropyl}phenyl)-1-(4-methoxyphenyl)-7-oxo-4,5,6,7-tetrahydro-1H-pyrazolo[3,4-c]pyridine-3-carbonitrile;

1-(4-methoxyphenyl)-7-oxo-6-[4-(1-pyrrolidin-1-yl-cyclopropyl)phenyl]-4,5,6,7-tetrahydro-1H-pyrazolo[3,4-c]pyridine-3-carboxylic acid ethyl ester;

1-(4-methoxyphenyl)-7-oxo-6-[4-(1-pyrrolidin-1-yl-cyclopropyl)phenyl]-4,5,6,7-tetrahydro-1H-pyrazolo[3,4-c]pyridine-3-carboxylic acid amide;

1-(4-methoxyphenyl)-7-oxo-6-[4-(1-pyrrolidin-1-yl-cyclopropyl)phenyl]-4,5,6,7-tetrahydro-1H-pyrazolo[3,4-c]pyridine-3-carbonitrile;

1-(4-methoxyphenyl)-6-[4-(1-morpholin-4-yl-cyclopropyl)phenyl]-7-oxo-4,5,6,7-tetrahydro-1H-pyrazolo[3,4-c]pyridine-3-carboxylic acid amide;

1-(4-methoxyphenyl)-6-[4-(1-morpholin-4-yl-cyclopropyl)phenyl]-7-oxo-4,5,6,7-tetrahydro-1H-pyrazolo[3,4-c]pyridine-3-carbonitrile;

6-[4-(1-dimethylaminocyclopropyl)phenyl]-1-(4-methoxyphenyl)-7-oxo-4,5,6,7-tetrahydro-1H-pyrazolo[3,4-c]pyridine-3-carboxylic acid methylamide;

6-[4-(1-dimethylaminocyclopropyl)phenyl]-1-(4-methoxyphenyl)-7-oxo-4,5,6,7-tetrahydro-1H-pyrazolo[3,4-c]pyridine-3-carboxylic acid dimethylamide;

6-{4-[1-(1,1-dioxo-1λ$^6$-thiomorpholin-4-yl)cyclopropyl]phenyl}-1-(4-methoxyphenyl)-7-oxo-4,5,6,7-tetrahydro-1H-pyrazolo[3,4-c]pyridine-3-carboxylic acid amide;

6-[4-(1-aminocyclopropylmethyl)phenyl]-1-(4-methoxyphenyl)-7-oxo-4,5,6,7-tetrahydro-1H-pyrazolo[3,4-c]pyridine-3-carboxylic acid amide;

6-[4-(1-dimethylaminocyclopropylmethyl)phenyl]-1-(4-methoxyphenyl)-7-oxo-4,5,6,7-tetrahydro-1H-pyrazolo[3,4-c]pyridine-3-carboxylic acid amide;

1-(3-chloro-phenyl)-6-{4-[1,1-dimethyl-2-(2-oxo-pyrrolidin-1-yl)-ethyl]-phenyl}-7-oxo-4,5,6,7-tetrahydro-1H pyrazolo[3,4-c]pyridine-3-carboxylic acid amide;

6-{4-[1,1-dimethyl-2-(2-oxo-pyrrolidin-1-yl)-ethyl]-phenyl}-1-(4-methoxy-phenyl)-7-oxo-4,5,6,7-tetrahydro-1H-pyrazolo[3,4-c]pyridine-3-carbonitrile;

1-(4-methoxy-phenyl)-6-[4-(1-methyl-1-pyrrolidin-1-yl-ethyl)-phenyl]-7-oxo-4,5,6,7-tetrahydro-1H-pyrazolo[3,4-c]pyridine-3-carboxylic acid amide;

6-[4-(1-dimethylamino-1-methyl-ethyl)-phenyl]-1-(4-methoxy-phenyl)-7-oxo-4,5,6,7-tetrahydro-1H-pyrazolo[3,4-c]pyridine-3-carboxylic acid amide;

6-[4-(1-methoxymethyl-cyclopropyl)-phenyl]-1-(4-methoxy-phenyl)-7-oxo-4,5,6,7-tetrahydro-1H-pyrazolo[3,4-c]pyridine-3-carboxylic acid amide;

6-{4-[1-(4,4-dimethyl-4,5-dihydro-oxazol-2-yl)-cyclopropyl]-phenyl}-1-(4-methoxy-phenyl)-3-trifluoromethyl-1,4,5,6-tetrahydro-pyrazolo[3,4-c]pyridin-7-one;

6-[4-(1-methanesulfonyl-1-methyl-ethyl)-phenyl]-1-(4-methoxy-phenyl)-7-oxo-4,5,6,7-tetrahydro-1H-pyrazolo[3,4-c]pyridine-3-carboxylic acid amide;

6-[4-(1-hydroxy-1-methyl-ethyl)-phenyl]-1-(4-methoxy-phenyl)-7-oxo-4,5,6,7-tetrahydro-1H-pyrazolo[3,4-c]pyridine-3-carboxylic acid amide;

1-(4-methoxy-phenyl)-6-(4-{1-[2-(2-oxo-2H-pyridin-1-yl)-ethyl]-cyclopropyl}-phenyl)-3-trifluoromethyl-1,4,5,6-tetrahydro-pyrazolo[3,4-c]pyridin-7-one;

2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-acetamide;

2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-N-methyl-acetamide;

2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-N,N-dimethyl-acetamide;

1-(4-methoxy-phenyl)-6-{4-[1-(2-oxo-2-pyrrolidin-1-yl-ethyl)-cyclopropyl]-phenyl}-3-trifluoromethyl-1,4,5,6-tetrahydro-pyrazolo[3,4-c]pyridin-7-one;

6-{4-[1-(2-hydroxy-ethyl)-cyclopropyl]-phenyl}-1-(4-methoxy-phenyl)-3-trifluoromethyl-1,4,5,6-tetrahydro-pyrazolo[3,4-c]pyridin-7-one;

1-(4-methoxy-phenyl)-6-{4-[1-(2-methylamino-ethyl)-cyclopropyl]-phenyl}-3-trifluoromethyl-1,4,5,6-tetrahydro-pyrazolo[3,4-c]pyridin-7-one;

6-{4-[1-(2-dimethylamino-ethyl)-cyclopropyl]-phenyl}-1-(4-methoxy-phenyl)-3-trifluoromethyl-1,4,5,6-tetrahydro-pyrazolo[3,4-c]pyridin-7-one;

1-(4-methoxy-phenyl)-6-{4-[1-(2-pyrrolidin-1-yl-ethyl)-cyclopropyl]-phenyl}-3-trifluoromethyl-1,4,5,6-tetrahydro-pyrazolo[3,4-c]pyridin-7-one;

1-(4-methoxy-phenyl)-6-{4-[1-(2-morpholin-4-yl-ethyl)-cyclopropyl]-phenyl}-3-trifluoromethyl-1,4,5,6-tetrahydro-pyrazolo[3,4-c]pyridin-7-one;

1-(4-methoxy-phenyl)-6-{4-[1-(2-pyrrolidin-1-yl-acetyl)-cyclopropyl]-phenyl}-3-trifluoromethyl-1,4,5,6-tetrahydro-pyrazolo[3,4-c]pyridin-7-one;

6-[4-(1-carbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid ethyl ester;

6-[4-(1-carbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid amide;

1-(4-methoxy-phenyl)-6-[4-(1-methylcarbamoylmethyl-cyclopropyl)-phenyl]-7-oxo-4,5,6,7-tetrahydro-1H-pyrazolo[3,4-c]pyridine-3-carboxylic acid ethyl ester;

1-(4-methoxy-phenyl)-6-[4-(1-methylcarbamoylmethyl-cyclopropyl)-phenyl]-7-oxo-4,5,6,7-tetrahydro-1H-pyrazolo[3,4-c]pyridine-3-carboxylic acid amide;

6-[4-(1-dimethylcarbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid ethyl ester;

6-[4-(1-dimethylcarbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid amide;

6-{4-[1-(2-hydroxy-ethyl)-cyclopropyl]-phenyl}-1-(4-methoxy-phenyl)-7-oxo-4,5,6,7-tetrahydro-1H-pyrazolo[3,4-c]pyridine-3-carboxylic acid amide;

1-(4-methoxy-phenyl)-6-{4-[1-(2-morpholin-4-yl-ethyl)-cyclopropyl]-phenyl}-7-oxo-4,5,6,7-tetrahydro-1H-pyrazolo[3,4-c]pyridine-3-carboxylic acid amide;

1-(4-methoxy-phenyl)-7-oxo-6-(4-{1-[2-(2-oxo-pyrrolidin-1-yl)-ethyl]-cyclopropyl}-phenyl)-4,5,6,7-tetrahydro-1H-pyrazolo[3,4-c]pyridine-3-carboxylic acid amide;

1-(4-methoxy-phenyl)-6-{4-[1-(2-methylamino-ethyl)-cyclopropyl]-phenyl}-7-oxo-4,5,6,7-tetrahydro-1H-pyrazolo[3,4-c]pyridine-3-carboxylic acid amide;

6-{4-[1-(2-dimethylamino-ethyl)-cyclopropyl]-phenyl}-1-(4-methoxy-phenyl)-7-oxo-4,5,6,7-tetrahydro-1H-pyrazolo[3,4-c]pyridine-3-carboxylic acid amide;

6-{4-[1-(2-diethylamino-ethyl)-cyclopropyl]-phenyl}-1-(4-methoxy-phenyl)-7-oxo-4,5,6,7-tetrahydro-1H-pyrazolo[3,4-c]pyridine-3-carboxylic acid amide;

1-(4-methoxy-phenyl)-7-oxo-6-{4-[1-(2-pyrrolidin-1-yl-ethyl)-cyclopropyl]-phenyl}-4,5,6,7-tetrahydro-1H-pyrazolo[3,4-c]pyridine-3-carboxylic acid amide;

6-(4-{1-[2-(2,5-dimethyl-pyrrolidin-1-yl)-ethyl]-cyclopropyl}-phenyl)-1-(4-methoxy-phenyl)-7-oxo-4,5,6,7-tetrahydro-1H-pyrazolo[3,4-c]pyridine-3-carboxylic acid amide;

6-(4-{1-[2-(3-hydroxy-pyrrolidin-1-yl)-ethyl]-cyclopropyl}-phenyl)-1-(4-methoxy-phenyl)-7-oxo-4,5,6,7-tetrahydro-1H-pyrazolo[3,4-c]pyridine-3-carboxylic acid amide;

6-(4-{1-[2-(2,5-dimethyl-pyrrolidin-1-yl)-ethyl]-cyclopropyl}-phenyl)-1-(4-methoxy-phenyl)-7-oxo-4,5,6,7-tetrahydro-1H-pyrazolo[3,4-c]pyridine-3-carboxylic acid amide;

1-(4-methoxy-phenyl)-7-oxo-6-(4-{1-[2-(2-oxo-piperidin-1-yl)-ethyl]-cyclopropyl}-phenyl)-4,5,6,7-tetrahydro-1H-pyrazolo[3,4-c]pyridine-3-carboxylic acid amide;

1-(4-methoxy-phenyl)-7-oxo-6-(4-{1-[2-(2-oxo-2H-pyridin-1-yl)-ethyl]-cyclopropyl}-phenyl)-4,5,6,7-tetrahydro-1H-pyrazolo[3,4-c]pyridine-3-carboxylic acid amide;

1-(4-methoxy-phenyl)-6-(4-{1-[2-(methyl-thiazol-2-yl-amino)-ethyl]-cyclopropyl}-phenyl)-7-oxo-4,5,6,7-tetrahydro-1H-pyrazolo[3,4-c]pyridine-3-carboxylic acid amide;

6-[4-(1-{2-[(2-hydroxy-ethyl)-methyl-amino]-ethyl}-cyclopropyl)-phenyl]-1-(4-methoxy-phenyl)-7-oxo-4,5,6,7-tetrahydro-1H-pyrazolo[3,4-c]pyridine-3-carboxylic acid amide;

1-(4-methoxy-phenyl)-6-(4-{1-[2-(2-methyl-imidazol-1-yl)-ethyl]-cyclopropyl}-phenyl)-7-oxo-4,5,6,7-tetrahydro-1H-pyrazolo[3,4-c]pyridine-3-carboxylic acid amide;

6-(4-{1-[2-(2,6-dimethyl-piperidin-1-yl)-ethyl]-cyclopropyl}-phenyl)-1-(4-methoxy-phenyl)-7-oxo-4,5,6,7-tetrahydro-1H-pyrazolo[3,4-c]pyridine-3-carboxylic acid amide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopropyl)-N,N-dimethyl-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopropyl)-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopropyl)-N-methyl-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopropyl)-N,N-dimethyl-acetamide;

6-{4-[1-(2-hydroxy-ethyl)-cyclopropyl]-phenyl}-3-methanesulfonyl-1-(4-methoxy-phenyl)-1,4,5,6-tetrahydro-pyrazolo[3,4-c]pyridin-7-one;

3-methanesulfonyl-6-{4-[1-(2-methoxy-ethyl)-cyclopropyl]-phenyl}-1-(4-methoxy-phenyl)-1,4,5,6-tetrahydro-pyrazolo[3,4-c]pyridin-7-one;

3-methanesulfonyl-1-(4-methoxy-phenyl)-6-{4-[1-(2-methylamino-ethyl)-cyclopropyl]-phenyl}-1,4,5,6-tetrahydro-pyrazolo[3,4-c]pyridin-7-one;

6-{4-[1-(2-dimethylamino-ethyl)-cyclopropyl]-phenyl}-3-methanesulfonyl-1-(4-methoxy-phenyl)-1,4,5,6-tetrahydro-pyrazolo[3,4-c]pyridin-7-one;

6-{4-[1-(2-diethylamino-ethyl)-cyclopropyl]-phenyl}-3-methanesulfonyl-1-(4-methoxy-phenyl)-1,4,5,6-tetrahydro-pyrazolo[3,4-c]pyridin-7-one;

6-{4-[1-(2-isopropylamino-ethyl)-cyclopropyl]-phenyl}-3-methanesulfonyl-1-(4-methoxy-phenyl)-1,4,5,6-tetrahydro-pyrazolo[3,4-c]pyridin-7-one;

3-methanesulfonyl-1-(4-methoxy-phenyl)-6-{4-[1-(2-pyrrolidin-1-yl-ethyl)-cyclopropyl]-phenyl}-1,4,5,6-tetrahydro-pyrazolo[3,4-c]pyridin-7-one;

3-methanesulfonyl-1-(4-methoxy-phenyl)-6-(4-{1-[2-(2-oxo-pyrrolidin-1-yl)-ethyl]-cyclopropyl}-phenyl)-1,4,5,6-tetrahydro-pyrazolo[3,4-c]pyridin-7-one;

6-(4-{1-[2-(2,5-dimethyl-pyrrolidin-1-yl)-ethyl]-cyclopropyl}-phenyl)-3-methanesulfonyl-1-(4-methoxy-phenyl)-1,4,5,6-tetrahydro-pyrazolo[3,4-c]pyridin-7-one;

6-(4-{1-[2-(3-hydroxy-pyrrolidin-1-yl)-ethyl]-cyclopropyl}-phenyl)-3-methanesulfonyl-1-(4-methoxy-phenyl)-1,4,5,6-tetrahydro-pyrazolo[3,4-c]pyridin-7-one;

3-methanesulfonyl-1-(4-methoxy-phenyl)-6-(4-{1-[2-(2-oxo-piperidin-1-yl)-ethyl]-cyclopropyl}-phenyl)-1,4,5,6-tetrahydro-pyrazolo[3,4-c]pyridin-7-one;

3-methanesulfonyl-1-(4-methoxy-phenyl)-6-{4-[1-(2-morpholin-4-yl-ethyl)-cyclopropyl]-phenyl}-1,4,5,6-tetrahydro-pyrazolo[3,4-c]pyridin-7-one;

6-[4-(1-{2-[(2-hydroxy-ethyl)-methyl-amino]-ethyl}-cyclopropyl)-phenyl]-3-methanesulfonyl-1-(4-methoxy-phenyl)-1,4,5,6-tetrahydro-pyrazolo[3,4-c]pyridin-7-one;

2-{[2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopropyl)-ethyl]-methyl-amino}-acetamide;

2-[2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopropyl)-ethylamino]-acetamide;

6-(4-{1-[2-(2-hydroxy-ethylamino)-ethyl]-cyclopropyl}-phenyl)-3-methanesulfonyl-1-(4-methoxy-phenyl)-1,4,5,6-tetrahydro-pyrazolo[3,4-c]pyridin-7-one;

3-methanesulfonyl-1-(4-methoxy-phenyl)-6-(4-{1-[2-(2-methyl-imidazol-1-yl)-ethyl]-cyclopropyl}-phenyl)-1,4,5,6-tetrahydro-pyrazolo[3,4-c]pyridin-7-one;

3-methanesulfonyl-1-(4-methoxy-phenyl)-6-(4-{1-[2-(thiazol-2-ylamino)-ethyl]-cyclopropyl}-phenyl)-1,4,5,6-tetrahydro-pyrazolo[3,4-c]pyridin-7-one;

3-methanesulfonyl-1-(4-methoxy-phenyl)-6-(4-{1-[2-(2-oxo-2H-pyridin-1-yl)-ethyl]-cyclopropyl}-phenyl)-1,4,5,6-tetrahydro-pyrazolo[3,4-c]pyridin-7-one;

2-(1-{4-[3-cyano-1-(4-methoxy-phenyl)-7-oxo-1,4,5,7-tetrahydro-pyrazolo[3,4-c]pyridin-6-yl]-phenyl}-cyclopropyl)-acetamide;

2-(1-{4-[3-cyano-1-(4-methoxy-phenyl)-7-oxo-1,4,5,7-tetrahydro-pyrazolo[3,4-c]pyridin-6-yl]-phenyl}-cyclopropyl)-N-methyl-acetamide;

2-(1-{4-[3-cyano-1-(4-methoxy-phenyl)-7-oxo-1,4,5,7-tetrahydro-pyrazolo[3,4-c]pyridin-6-yl]-phenyl}-cyclopropyl)-N,N-dimethyl-acetamide;

6-{4-[1-(2-hydroxy-ethyl)-cyclopropyl]-phenyl}-1-(4-methoxy-phenyl)-7-oxo-4,5,6,7-tetrahydro-1H-pyrazolo[3,4-c]pyridine-3-carbonitrile;

1-(4-methoxy-phenyl)-6-{4-[1-(2-methylamino-ethyl)-cyclopropyl]-phenyl}-7-oxo-4,5,6,7-tetrahydro-1H-pyrazolo[3,4-c]pyridine-3-carbonitrile;

6-{4-[1-(2-dimethylamino-ethyl)-cyclopropyl]-phenyl}-1-(4-methoxy-phenyl)-7-oxo-4,5,6,7-tetrahydro-1H-pyrazolo[3,4-c]pyridine-3-carbonitrile;

1-(4-methoxy-phenyl)-7-oxo-6-{4-[1-(2-pyrrolidin-1-yl-ethyl)-cyclopropyl]-phenyl}-4,5,6,7-tetrahydro-1H-pyrazolo[3,4-c]pyridine-3-carbonitrile;

1-(4-methoxy-phenyl)-6-{4-[1-(2-morpholin-4-yl-ethyl)-cyclopropyl]-phenyl}-7-oxo-4,5,6,7-tetrahydro-1H-pyrazolo[3,4-c]pyridine-3-carbonitrile;

6-(4-{1-[2-(1,1-dioxo-1l6-thiomorpholin-4-yl)-ethyl]-cyclopropyl}-phenyl)-1-(4-methoxy-phenyl)-7-oxo-4,5,6,7-tetrahydro-1H-pyrazolo[3,4-c]pyridine-3-carbonitrile;

6-(4-{1-[2-(2-hydroxy-ethylamino)-ethyl]-cyclopropyl}-phenyl)-1-(4-methoxy-phenyl)-7-oxo-4,5,6,7-tetrahydro-1H-pyrazolo[3,4-c]pyridine-3-carbonitrile;

2-[2-(1-{4-[3-cyano-1-(4-methoxy-phenyl)-7-oxo-1,4,5,7-tetrahydro-pyrazolo[3,4-c]pyridin-6-yl]-phenyl}-cyclopropyl)-ethylamino]-acetamide;

2-{[2-(1-{4-[3-cyano-1-(4-methoxy-phenyl)-7-oxo-1,4,5,7-tetrahydro-pyrazolo[3,4-c]pyridin-6-yl]-phenyl}-cyclopropyl)-ethyl]-methyl-amino}-acetamide;

6-[4-(1-{2-[(2-hydroxy-ethyl)-methyl-amino]-ethyl}-cyclopropyl)-phenyl]-1-(4-methoxy-phenyl)-7-oxo-4,5,6,7-tetrahydro-1H-pyrazolo[3,4-c]pyridine-3-carbonitrile;

N-[2-(1-{4-[3-cyano-1-(4-methoxy-phenyl)-7-oxo-1,4,5,7-tetrahydro-pyrazolo[3,4-c]pyridin-6-yl]-phenyl}-cyclopropyl)-ethyl]-N-methyl-methanesulfonamide;

N-[2-(1-{4-[3-cyano-1-(4-methoxy-phenyl)-7-oxo-1,4,5,7-tetrahydro-pyrazolo[3,4-c]pyridin-6-yl]-phenyl}-cyclopropyl)-ethyl]-N-methyl-acetamide;

1-(4-methoxy-phenyl)-7-oxo-6-(4-{1-[2-(2-oxo-pyrrolidin-1-yl)-ethyl]-cyclopropyl}-phenyl)-4,5,6,7-tetrahydro-1H-pyrazolo[3,4-c]pyridine-3-carbonitrile;

1-(4-methoxy-phenyl)-7-oxo-6-(4-{1-[2-(2-oxo-2H-pyridin-1-yl)-ethyl]-cyclopropyl}-phenyl)-4,5,6,7-tetrahydro-1H-pyrazolo[3,4-c]pyridine-3-carbonitrile;

6-{4-[1-(2-dimethylamino-ethyl)-cyclopropyl]-phenyl}-1-(4-methoxy-phenyl)-3-methyl-1,4,5,6-tetrahydro-pyrazolo[3,4-c]pyridin-7-one;

6-{4-[1-(2-dimethylamino-ethyl)-cyclopropyl]-phenyl}-1-(4-methoxy-phenyl)-1,4,5,6-tetrahydro-pyrazolo[3,4-c]pyridin-7-one;

6-{4-[1-(2-dimethylamino-ethyl)-cyclobutyl]-phenyl}-1-(4-methoxy-phenyl)-1,4,5,6-tetrahydro-pyrazolo[3,4-c]pyridin-7-one;

6-{4-[1-(2-dimethylamino-ethyl)-cyclobutyl]-phenyl}-1-(4-methoxy-phenyl)-3-methyl-1,4,5,6-tetrahydro-pyrazolo[3,4-c]pyridin-7-one;

6-{4-[1-(2-dimethylamino-ethyl)-cyclobutyl]-phenyl}-1-(4-methoxy-phenyl)-3-trifluoromethyl-1,4,5,6-tetrahydro-pyrazolo[3,4-c]pyridin-7-one;

6-{4-[1-(2-dimethylamino-ethyl)-cyclobutyl]-phenyl}-1-(4-methoxy-phenyl)-7-oxo-4,5,6,7-tetrahydro-1H-pyrazolo[3,4-c]pyridine-3-carbonitrile;

6-{4-[1-(2-dimethylamino-ethyl)-cyclobutyl]-phenyl}-1-(4-methoxy-phenyl)-7-oxo-4,5,6,7-tetrahydro-1H-pyrazolo[3,4-c]pyridine-3-carboxylic acid amide;

6-{4-[1-(2-dimethylamino-ethyl)-cyclobutyl]-phenyl}-3-methanesulfonyl-1-(4-methoxy-phenyl)-1,4,5,6-tetrahydro-pyrazolo[3,4-c]pyridin-7-one;

6-{4-[1-(2-dimethylamino-ethyl)-cyclopentyl]-phenyl}-3-methanesulfonyl-1-(4-methoxy-phenyl)-1,4,5,6-tetrahydro-pyrazolo[3,4-c]pyridin-7-one;

6-{4-[1-(2-dimethylamino-ethyl)-cyclopentyl]-phenyl}-1-(4-methoxy-phenyl)-7-oxo-4,5,6,7-tetrahydro-1H-pyrazolo[3,4-c]pyridine-3-carbonitrile;

6-{4-[1-(2-dimethylamino-ethyl)-cyclopentyl]-phenyl}-1-(4-methoxy-phenyl)-7-oxo-4,5,6,7-tetrahydro-1H-pyrazolo[3,4-c]pyridine-3-carboxylic acid amide;

6-{4-[1-(2-dimethylamino-ethyl)-cyclopentyl]-phenyl}-1-(4-methoxy-phenyl)-3-trifluoromethyl-1,4,5,6-tetrahydro-pyrazolo[3,4-c]pyridin-7-one;

6-{4-[1-(2-dimethylamino-ethyl)-cyclopentyl]-phenyl}-1-(4-methoxy-phenyl)-3-methyl-1,4,5,6-tetrahydro-pyrazolo[3,4-c]pyridin-7-one;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopentyl)-acetamide;

6-[4-(1-carbamoylmethyl-cyclopentyl)-phenyl]-1-(4-methoxy-phenyl)-7-oxo-4,5,6,7-tetrahydro-1H-pyrazolo[3,4-c]pyridine-3-carboxylic acid amide;

1-(4-methoxy-phenyl)-6-[4-(1-methylcarbamoylmethyl-cyclopentyl)-phenyl]-7-oxo-4,5,6,7-tetrahydro-1H-pyrazolo[3,4-c]pyridine-3-carboxylic acid amide;

6-[4-(1-dimethylcarbamoylmethyl-cyclopentyl)-phenyl]-1-(4-methoxy-phenyl)-7-oxo-4,5,6,7-tetrahydro-1H-pyrazolo[3,4-c]pyridine-3-carboxylic acid amide;

2-(1-{4-[3-cyano-1-(4-methoxy-phenyl)-7-oxo-1,4,5,7-tetrahydro-pyrazolo[3,4-c]pyridin-6-yl]-phenyl}-cyclopentyl)-N,N-dimethyl-acetamide;

2-(1-{4-[3-cyano-1-(4-methoxy-phenyl)-7-oxo-1,4,5,7-tetrahydro-pyrazolo[3,4-c]pyridin-6-yl]-phenyl}-cyclopentyl)-N-methyl-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopentyl)-N-methyl-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopentyl)-N,N-dimethyl-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclopentyl)-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclobutyl)-acetamide;

2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclobutyl)-N-methyl-acetamide;
2-(1-{4-[3-methanesulfonyl-1-(4-methoxy-phenyl)-7-oxo-1,4,5,7-tetrahydro-pyrazolo[3,4-c]pyridin-6-yl]-phenyl}-cyclobutyl)-N,N-dimethyl-acetamide;
2-(1-{4-[3-cyano-1-(4-methoxy-phenyl)-7-oxo-1,4,5,7-tetrahydro-pyrazolo[3,4-c]pyridin-6-yl]-phenyl}-cyclobutyl)-N,N-dimethyl-acetamide;
2-(1-{4-[3-cyano-1-(4-methoxy-phenyl)-7-oxo-1,4,5,7-tetrahydro-pyrazolo[3,4-c]pyridin-6-yl]-phenyl}-cyclobutyl)-N-methyl-acetamide;
2-(1-{4-[3-cyano-1-(4-methoxy-phenyl)-7-oxo-1,4,5,7-tetrahydro-pyrazolo[3,4-c]pyridin-6-yl]-phenyl}-cyclobutyl)-acetamide;
2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclobutyl)-acetamide;
2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclobutyl)-N-methyl-acetamide;
2-(1-{4-[1-(4-methoxy-phenyl)-3-methyl-7-oxo-1,4,5,7-tetrahydro-pyrazolo[3,4-c]pyridin-6-yl]-phenyl}-cyclobutyl)-N-methyl-acetamide;
2-(1-{4-[1-(4-methoxy-phenyl)-3-methyl-7-oxo-1,4,5,7-tetrahydro-pyrazolo[3,4-c]pyridin-6-yl]-phenyl}-cyclobutyl)-acetamide;
2-(1-{4-[1-(4-methoxy-phenyl)-7-oxo-1,4,5,7-tetrahydro-pyrazolo[3,4-c]pyridin-6-yl]-phenyl}-cyclobutyl)-acetamide;
2-(1-{4-[1-(4-methoxy-phenyl)-7-oxo-1,4,5,7-tetrahydro-pyrazolo[3,4-c]pyridin-6-yl]-phenyl}-cyclobutyl)-N-methyl-acetamide;
2-(1-{4-[1-(4-methoxy-phenyl)-7-oxo-1,4,5,7-tetrahydro-pyrazolo[3,4-c]pyridin-6-yl]-phenyl}-cyclobutyl)-N,N-dimethyl-acetamide;
(1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-acetic acid;
2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-acetamide;
2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-N-methyl-acetamide;
2-(1-{4-[1-(4-methoxy-phenyl)-7-oxo-3-trifluoromethyl-1,4,5,7-tetrahydro-pyrazolo[3,4-c]pyridin-6-yl]-phenyl}-cyclopropyl)-N,N-dimethyl-acetamide;
1-(4-methoxy-phenyl)-6-{4-[1-(2-oxo-2-pyrrolidin-1-yl-ethyl)-cyclopropyl]-phenyl}-3-trifluoromethyl-1,4,5,6-tetrahydro-pyrazolo[3,4-c]pyridin-7-one;
6-{4-[1-(2-hydroxy-ethyl)-cyclopropyl]-phenyl}-1-(4-methoxy-phenyl)-3-trifluoromethyl-1,4,5,6-tetrahydro-pyrazolo[3,4-c]pyridin-7-one;
1-(4-methoxy-phenyl)-6-{4-[1-(2-methylamino-ethyl)cyclopropyl]-phenyl}-3-trifluoromethyl-1,4,5,6-tetrahydro-pyrazolo[3,4-c]pyridin-7-one;
6-{4-[1-(2-dimethylamino-ethyl)-cyclopropyl]-phenyl}-1-(4-methoxy-phenyl)-3-trifluoromethyl-1,4,5,6-tetrahydro-pyrazolo[3,4-c]pyridin-7-one;
1-(4-methoxy-phenyl)-6-{4-[1-(2-pyrrolidin-1-yl-ethyl)-cyclopropyl]-phenyl}-3-trifluoromethyl-1,4,5,6-tetrahydro-pyrazolo[3,4-c]pyridin-7-one;
1-(4-methoxy-phenyl)-6-{4-[1-(2-morpholin-4-yl-ethyl)-cyclopropyl]-phenyl}-3-trifluoromethyl-1,4,5,6-tetrahydro-pyrazolo[3,4-c]pyridin-7-one
1-(4-methoxy-phenyl)-6-{4-[1-(2-pyrrolidin-1-yl-acetyl)-cyclopropyl]-phenyl}-3-trifluoromethyl-1,4,5,6-tetrahydro-pyrazolo[3,4-c]pyridin-7-one;
6-[4-(1-carbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid ethyl ester;
6-[4-(1-carbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid amide;
1-(4-methoxy-phenyl)-6-[4-(1-methylcarbamoylmethyl-cyclopropyl)-phenyl]-7-oxo-4,5,6,7-tetrahydro-1H-pyrazolo[3,4-c]pyridine-3-carboxylic acid ethyl ester;
1-(4-Methoxy-phenyl)-6-[4-(1-methylcarbamoylmethyl-cyclopropyl)-phenyl]-7-oxo-4,5,6,7-tetrahydro-1H-pyrazolo[3,4-c]pyridine-3-carboxylic acid amide;
6-[4-(1-dimethylcarbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid ethyl ester;
6-[4-(1-dimethylcarbamoylmethyl-cyclopropyl)-phenyl]-1-(4-methoxy-phenyl)-7-oxo-4,5,6,7-tetrahydro-1H-pyrazolo[3,4-c]pyridine-3-carboxylic acid amide;
6-{4-[1-(2-hydroxy-ethyl)-cyclopropyl]-phenyl}-1-(4-methoxy-phenyl)-7-oxo-4,5,6,7-tetrahydro-1H-pyrazolo[3,4-c]pyridine-3-carboxylic acid amide;
1-(4-methoxy-phenyl)-6-{4-[1-(2-morpholin-4-yl-ethyl)-cyclopropyl]-phenyl}-7-oxo-4,5,6,7-tetrahydro-1H-pyrazolo[3,4-c]pyridine-3-carboxylic acid amide; and,
1-(4-methoxy-phenyl)-6-{4-[1-(2-morpholin-4-yl-ethyl)-cyclopropyl]-phenyl}-7-oxo-4,5,6,7-tetrahydro-1H-pyrazolo[3,4-c]pyridine-3-carbonitrile;
or a pharmaceutically acceptable salt form thereof.

9. A pharmaceutical composition, comprising: a pharmaceutically acceptable carrier and a therapeutically effective amount of a compound of claim 1 or a pharmaceutically acceptable salt thereof.

10. A pharmaceutical composition, comprising: a pharmaceutically acceptable carrier and a therapeutically effective amount of a compound of claim 2 or a pharmaceutically acceptable salt thereof.

11. A pharmaceutical composition, comprising: a pharmaceutically acceptable carrier and a therapeutically effective amount of a compound of claim 3 or a pharmaceutically acceptable salt thereof.

12. A pharmaceutical composition, comprising: a pharmaceutically acceptable carrier and a therapeutically effective amount of a compound of claim 4 or a pharmaceutically acceptable salt thereof.

13. A pharmaceutical composition, comprising: a pharmaceutically acceptable carrier and a therapeutically effective amount of a compound of claim 5 or a pharmaceutically acceptable salt thereof.

14. A pharmaceutical composition, comprising: a pharmaceutically acceptable carrier and a therapeutically effective amount of a compound of claim 6 or a pharmaceutically acceptable salt thereof.

15. A pharmaceutical composition, comprising: a pharmaceutically acceptable carrier and a therapeutically effective amount of a compound of claim 7 or a pharmaceutically acceptable salt thereof.

16. A pharmaceutical composition, comprising: a pharmaceutically acceptable carrier and a therapeutically effective amount of a compound of claim 8 or a pharmaceutically acceptable salt thereof.

17. A pharmaceutical composition, comprising: a pharmaceutically acceptable carrier and a therapeutically effective amount of a compound of claim 6 or a pharmaceutically acceptable salt thereof.

18. A pharmaceutical composition, comprising: a pharmaceutically acceptable carrier and a therapeutically effective amount of a compound of claim 7 or a pharmaceutically acceptable salt thereof.

19. A pharmaceutical composition, comprising: a pharmaceutically acceptable carrier and a therapeutically effective amount of a compound of claim 8 or a pharmaceutically acceptable salt thereof.

20. A method for treating a thromboembolic disorder, comprising: administering to a patient in need thereof a therapeutically effective amount of a compound of claim 2 or a pharmaceutically acceptable salt form thereof.

21. A method according to claim 20 wherein the thromboembolic disorder is selected from the group consisting of arterial cardiovascular thromboembolic disorders, venous cardiovascular thromboembolic disorders, and thromboembolic disorders in the chambers of the heart.

22. A method according to claim 20 wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

23. A method for treating a thromboembolic disorder, comprising: administering to a patient in need thereof a therapeutically effective amount of a compound of claim 4 or a pharmaceutically acceptable salt form thereof.

24. A method according to claim 23 wherein the thromboembolic disorder is selected from the group consisting of arterial cardiovascular thromboembolic disorders, venous cardiovascular thromboembolic disorders, and thromboembolic disorders in the chambers of the heart.

25. A method according to claim 23 wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

26. A method for treating a thromboembolic disorder, comprising: administering to a patient in need thereof a therapeutically effective amount of a compound of claim 6 or a pharmaceutically acceptable salt form thereof.

27. A method according to claim 26 wherein the thromboembolic disorder is selected from the group consisting of arterial cardiovascular thromboembolic disorders, venous cardiovascular thromboembolic disorders, and thromboembolic disorders in the chambers of the heart.

28. A method according to claim 26 wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

29. A method for treating a thromboembolic disorder, comprising: administering to a patient in need thereof a therapeutically effective amount of a compound of claim 8 or a pharmaceutically acceptable salt form thereof.

30. A method according to claim 29 wherein the thromboembolic disorder is selected from the group consisting of arterial cardiovascular thromboembolic disorders, venous cardiovascular thromboembolic disorders, and thromboembolic disorders in the chambers of the heart.

31. A method according to claim 29 wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

* * * * *

UNITED STATES PATENT AND TRADEMARK OFFICE
CERTIFICATE OF CORRECTION

PATENT NO. : 7,312,214 B2
APPLICATION NO. : 10/430024
DATED : December 25, 2007
INVENTOR(S) : Jennifer X. Qiao et al.

It is certified that error appears in the above-identified patent and that said Letters Patent is hereby corrected as shown below:

In the Claims:

Col. 446, line 5, change "heterocyle" to -- heterocycle --.

Col. 467, lines 25 to 28, change "  " to --  --.

Col. 467, lines 30 to 34, between "  " and "  ", insert --  --.

Col. 468, line 54, change "$NR^{2d}SO_{22}R^{2d}$" to -- $NR^{2d}SO_2R^{2d}$ --.

Col. 468, line 59, change "O-2" to -- 0-2 --.

Col. 483, lines 54 to 59, change " " to -- " --.

Col. 486, lines 9 to 13, change " " to -- " --.

Col. 488, lines 4 to 9, change " " to -- " --.

Col. 522, lines 64 to 67, Claim 17 should be deleted.

Col. 523, lines 1 to 8, Claims 18 and 19 should be deleted.

Col. 524, line 48, add Claims 32 to 34 as follows:

-- 32. A method for treating a thromboembolic disorder, comprising: administering to a patient in need thereof a therapeutically effective amount of a compound of Claim 1 or a pharmaceutically acceptable salt form thereof.

UNITED STATES PATENT AND TRADEMARK OFFICE
CERTIFICATE OF CORRECTION

PATENT NO. : 7,312,214 B2
APPLICATION NO. : 10/430024
DATED : December 25, 2007
INVENTOR(S) : Jennifer X. Qiao et al.

It is certified that error appears in the above-identified patent and that said Letters Patent is hereby corrected as shown below:

33. A method according to Claim 32 wherein the thromboembolic disorder is selected from the group consisting of arterial cardiovascular thromboembolic disorders, venous cardiovascular thromboembolic disorders, and thromboembolic disorders in the chambers of the heart.

34. A method according to Claim 32, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. --.

Signed and Sealed this

Twenty-second Day of July, 2008

JON W. DUDAS
*Director of the United States Patent and Trademark Office*